US011149018B2

(12) United States Patent
Beck et al.

(10) Patent No.: US 11,149,018 B2
(45) Date of Patent: Oct. 19, 2021

(54) SUBSTITUTED N-ARYLETHYL-2-AMINOQUINOLINE-4-CARBOXAMIDES AND USE THEREOF

(71) Applicants: Bayer Aktiengesellschaft, Leverkusen (DE); Bayer Pharma Aktiengesellschaft, Berlin (DE)

(72) Inventors: Hartmut Beck, Wuppertal (DE); Raimund Kast, Wuppertal (DE); Mark Meininghaus, Wuppertal (DE); Chantal Fuerstner, Muelheim/Ruhr (DE); Timo Stellfeld, Berlin (DE); Clemens-Jeremias Von Buehler, Neuss (DE); Lisa Dietz, Wuppertal (DE); Michaela Bairlein, Wuppertal (DE); Johanna Anlahr, Dortmund (DE); Hannah Joerissen, Heiligenhaus (DE); Peter Hauff, Berlin (DE); Joerg Mueller, Berlin (DE); Karoline Droebner, Velbert (DE); Jens Nagel, Daxweiler (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 99 days.

(21) Appl. No.: 16/604,157

(22) PCT Filed: Apr. 4, 2018

(86) PCT No.: PCT/EP2018/058613
§ 371 (c)(1),
(2) Date: Oct. 9, 2019

(87) PCT Pub. No.: WO2018/189012
PCT Pub. Date: Oct. 18, 2018

(65) Prior Publication Data
US 2020/0157073 A1    May 21, 2020

(30) Foreign Application Priority Data
Apr. 10, 2017 (EP) .................................. 17165674

(51) Int. Cl.
| | | |
|---|---|---|
| *C07D 401/04* | (2006.01) | |
| *A61P 1/16* | (2006.01) | |
| *A61P 13/12* | (2006.01) | |
| *A61P 11/00* | (2006.01) | |
| *C07D 215/50* | (2006.01) | |
| *C07D 417/04* | (2006.01) | |
| *A61K 45/06* | (2006.01) | |
| *C07D 413/04* | (2006.01) | |

(52) U.S. Cl.
CPC .............. *C07D 401/04* (2013.01); *A61P 1/16* (2018.01); *A61P 11/00* (2018.01); *A61P 13/12* (2018.01); *C07D 215/50* (2013.01); *C07D 413/04* (2013.01); *C07D 417/04* (2013.01); *A61K 45/06* (2013.01)

(58) Field of Classification Search
CPC .. C07D 401/04; C07D 215/50; C07D 413/04; C07D 417/04; A61P 1/16; A61P 13/12; A61P 11/00; A61K 45/06
See application file for complete search history.

(56) References Cited

U.S. PATENT DOCUMENTS 8,058,300 B2 * 11/2011 Hutchinson ............. A61P 13/12
514/380

FOREIGN PATENT DOCUMENTS

| | | |
|---|---|---|
| EP | 2 415 755 A1 | 2/2012 |
| WO | 95/32948 A1 | 12/1995 |
| WO | 96/02509 A1 | 2/1996 |
| WO | 97/19926 A1 | 6/1997 |
| WO | 2000/031038 A1 | 6/2000 |
| WO | 00/64877 A1 | 11/2000 |
| WO | 2004/045614 A1 | 6/2004 |
| WO | 2006/094237 A2 | 9/2006 |
| WO | 2011/153553 A2 | 12/2011 |
| WO | 2012/122370 A2 | 9/2012 |
| WO | 2013/074059 A2 | 5/2013 |
| WO | 2013/164326 A1 | 11/2013 |
| WO | 2014/117090 A1 | 7/2014 |
| WO | 2015/094912 A1 | 6/2015 |
| WO | 2016/004035 A1 | 1/2016 |
| WO | 2016/061280 A1 | 4/2016 |

OTHER PUBLICATIONS

Giardina et al Journal of Medicinal Chemistry 1999, 42, 1053-1065. (Year: 1999).*
Zhang et al Frontiers in Pharmacology Oct. 2010, vol. 1, pp. 1-7. (Year: 2010).*
Abramovitz, Mark, et al. "Cloning and Expression of a cDNA for the Human Prostanoid FP Receptor," The Journal of Biological Chemistry, (1994), vol. 269, No. 4: 2632-2636.
Agas, Dimitrios, et al. "Prostaglandin F2α: A Bone Remodeling Mediator," Journal of Cellular Physiology, (2013), vol. 228: 25-29.
Aihara, Kensaku, et al. "Clinical Relevance of Plasma Prostaglandin F2α Metabolite Concentrations in Patients with Idiopathic Pulmonary Fibrosis," PLOS ONE, (2013), vol. 8, No. 6: 1-7.
Barnes, Peter J. "Chronic Obstructive Pulmonary Disease," New England Journal of Medicine, (2000), vol. 343, No. 4: 269-280.
Bastiaansen-Jenniskens, Yvonne M., et al. "Stimulation of Fibrotic Processes by the Infrapatellar Fat Pad in Cultured Synoviocytes From Patients with Osteoarthritis," Arthritis & Rheumatism, (2013), vol. 65, No. 8: 2070-2080.

(Continued)

*Primary Examiner* — John Mabry
(74) *Attorney, Agent, or Firm* — McBee Moore & Vanik IP, LLC

(57) ABSTRACT

The present application relates to novel substituted N-arylethyl-2-aminoquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

12 Claims, No Drawings

(56) References Cited

OTHER PUBLICATIONS

Basu, Samar, et al. "Type 1 Diabetes is Associated with Increased Cyclooxyenase- and Cytokine-Mediated Inflammation," Diabetes Care, (2005), vol. 28, No. 6: 1371-1375.
Basu, Samar, et al. "Presence of a 15-Ketoprostaglandin Delta13-Reductase in Porcine Cornea," Acta Chemica Scandinavica, (1992), vol. 46: 108-110.
Basu, Samar. "Bioactive Eicosanoids: Role of Prostaglandin F2α and F2-Isoprostanes in Inflammation and Oxidative Stress Related Pathology," Mol. Cells, (2010), vol. 30: 383-391.
Behr, J. et al. "Pulmonary hypertension in interstitial lung disease," Eur Respir J, (2008), vol. 31: 1357-1367.
Blanco, Isabel, et al. "Hemodynamic and Gas Exchange Effects of Sildenafil in Patients with Chronic Obstructive Pulmonary Disease and Pulmonary Hypertension," American Journal of Respiratory and Critical Care Medicine, (2010), vol. 181: 270-278.
Carlson, N.G., et al. "Vulnerability of oligodendrocyte precursor cells to death is modulated by key prostaglandins," Multiple Sclerosis Journal, (2015), vol. 21 (S11): 467-468.
Catrina, Anca I., et al. "Lungs, joints and immunity against citrullinated proteins in rheumatoid arthritis," Nat. Rev. Rheumatol., (2014), vol. 10: 645-653.
Dawood, M. Yusoff, et al. "Clinical efficacy and differential inhibition of menstrual fluid prostaglandin F2α in a randomized, double-blind, crossover treatment with placebo, acetaminophen, and ibuprofen in primary dysmenorrhea," American Journal of Obstetrics & Gynecology, (2007), vol. 196: 35.e1-35.e5.
Ding, Wen-yuan, et al. "Prostaglandin F2α facilitates collagen synthesis in cardiac fibroblasts via an F-prostanoid receptor/protein kinase C/ Rho kinase pathway independent of transforming growth factor β1," International Journal of Biochemistry & Cell Biology, (2012), vol. 44: 1031-1039.
Ding, Wen-yuan, et al. "FP-receptor gene silencing ameliorates myocardial fibrosis and protects from diabetic cardiomyopathy," J. Mol. Med., (2014), vol. 92: 629-640.
Doyle, Tracy J., et al. "A Roadmap to Promote Clinical and Translational Research in Rheumatoid Arthritis-Associated Interstitial Lung Disease," Chest, (2014), vol. 145, No. 3: 454-463.
Rosenzweig, Erika B. "Emerging treatments for pulmonary arterial hypertension," Expert Opinion on Emerging Drugs, (2006), vol. 11, No. 4: 609-619.
Estenne, Marc, et al. "Bronchiolitis Obliterans after Human Lung Transplantation," Am. J. Respir. Crit. Care Med., (2002), vol. 166: 440-444.
Ghofrani, Hossein Ardeschir, et al. "Neue Therapieoptionen in der Behandlung der pulmonalarteriellen Hypertonie," Herz, (2005), vol. 30: 296-302.
Helmersson, J., et al. "Active smoking and a history of smoking are associated with enhanced prostaglandin F2α, interleukin-6 and F2-isoprostane formation in elderly men," Atherosclerosis, (2005), vol. 181: 201-207.
Helmersson, J., et al. "Association of Type 2 Diabetes With Cyclooxygenase-Mediated Inflammation and Oxidative Stress in an Elderly Population," Circulation, (2004), vol. 109: 1729-1734.
Helmersson-Karlqvist, Johanna, et al. "Prostaglandin F2α formation is associated with mortality in a Swedish community-based cohort of older males," European Heart Journal, (2015), vol. 36: 238-243.
Montani, David, et al. "Updated clinical classification of pulmonary hypertension," Pulmonary Circulation: Diseases and their treatment, Hodder Arnold Publishing (2011), Third Edition, 197-206.
Hoeper, Marius M., et al. "Diagnosis, Assessment, and Treatment of Non-Pulmonary Arterial Hypertension Pulmonary Hypertension," Journal of the American College of Cardiology, (2009), vol. 54, No. 1: S85-96.
Hsia, Shih-Min, et al. "Effects of Resveratrol, a Grape Polyphenol, on Uterine Contraction and Ca2+ Mobilization in Rats in Vivo and in Vitro," Endocrinology, (2011), vol. 152: 2090-2099.

Kanno, Yosuke, et al. "Alpha 2-Antiplasmin Regulates the Development of Dermal Fibrosis in Mice by Prostaglandin F2α Synthesis Through Adipose Triglyceride Lipase/Calcium-Independent Phospholipase A2," Arthritis & Rheumatism, (2013), vol. 65, No. 2: 492-502.
Khidhir, K.G., et al. "Human scalp hair follicles express the genes for prostanoid FP receptor (Abstract 607)," J. Invest. Dermatol., (2009), vol. 129: S102.
Kim, Yun Tai, et al. "Prostaglandin FP receptor inhibitor reduces ischemic brain damage and neurotoxicity," Neurobiology of Disease, (2012), vol. 48: 58-65.
Kim, Joohwee, et al."Prostaglandin F2α receptor (FP) signaling regulates Bmp signaling and promotes chondrocyte differenhation," Biochimica et Biophysica Act, (2015), vol. 1853: 500-512.
Kitanaka, Jun-ichi, et al. "Cloning and Expression of a cDNA for Rat Prostaglandin F2α Receptor," Prostaglandins, (1994), vol. 48: 31-41.
Lettieri, Christopher J., et al. "Prevalence and Outcomes of Pulmonary Arterial Hypertension in Advanced Idiopathic Pulmonary Fibrosis," Chest, (2006), vol. 129: 746-752.
Ley, Brett, et al. "Clinical Course and Prediction of Survival in Idiopathic Pulmonary Fibrosis," Am. J. Respir. Crit. Care Med., (2011), vol. 183: 431-440.
Humbert, Marc, et al. "Cellular and Molecular Pathobiology of Pulmonary Arterial Hypertension," Journal of the American College of Cardiology, (2004), vol. 43, No. 12: 13S-24S.
Naeije, Robert in: A. J. Peacock et al. "Pulmonary vascular function," Pulmonary Circulation. Diseases and their treatment, 3rd Edition, Hodder Arnold Publishing, (2011), 3-15.
Oga, Toru, et al. "Prostaglandin F2α receptor signaling facilitates bleomycin-induced pulmonary fibrosis independently of transforming growth factor-β," Nature Medicine, (2009), vol. 15, No. 12: 1426-1431.
Olman, Mitchell a. "Beyond TGF-β: a prostaglandin promotes fibrosis," Nature Medicine, (2009), vol. 15, No. 12: 1360-1361.
Olson, Amy L., et al. "Rheumatoid Arthritis-Interstitial Lung Disease-associated Mortality," Am. J. Respir. Crit. Care Med., (2011), vol. 183: 372-378.
O'Reilly, Katherine M.A., et al. "Crystalline and amorphous silica differentially regulate the cyclooxygenase-prostaglandin pathway in pulmonary fibroblasts: implications for pulmonary fibrosis," Am. J. Physiol. Lung Cell Mol. Physiol., (2005), vol. 288: L1010-L1016.
Powell, Andrea M., et al. "Menstrual-PGF2α, PGE2 and TXA2 in Normal and Dysmenorrheic Women and Their Temporal Relationship to Dysmenorrhea," Prostaglandins, (1985), vol. 29, No. 2: 273-289.
Sales, Kurt J., et al. "F-Prostanoid Receptor Regulation of Fibroblast Growth Factor 2 Signaling in Endometrial Adenocarcinoma Cells," Endocrinology, (2007), vol. 148, No. 8: 3635-3644.
Sinaiko, Alan R., et al. "Relation of Body Mass Index and Insulin Resistance to Cardiovascular Risk Factors, Inflammatory Factors, and Oxidative Stress During Adolescence," Circulation, (2005), vol. 111: 1985-1991.
Soldan, M. Mateo Paz, et al. "Relapses and disability accumulation in progressive multiple sclerosis," Neurology, (2015), vol. 84: 81-88.
Stolz, D., et al. "A randomised, controlled trial of bosentan in severe COPD," Eur. Respir. J., (2008), vol. 32: 619-628.
Strieter, Robert M., et al. "New Mechanisms of Pulmonary Fibrosis," Chest, (2009), vol. 136: 1364-1370.
Sugimoto, Yukihiko, et al. "Cloning and Expression of a cDNA for Mouse Prostaglandin F Receptor," The Journal of Biological Chemistry, (1994), vol. 269, No. 2: 1356-1360.
Ito, Takayuki, et al. "Current Drug Targets and Future Therapy of Pulmonary Arterial Hypertension," Current Medical Chemistry, (2007), vol. 14: 719-733.
Von Der Beck, D., et al. "Die Therapie der idiopathischen pulmonalen Fibrose," Pneumologe, (2013), vol. 10: 105-111.
Watanabe, Kikuko, et al. "Enzymatic Formation of Prostaglandin F2α from Prostaglandin H2 and D2," The Journal of Biological Chemistry, (1985), vol. 260, No. 11: 7035-7041.

(56) References Cited

OTHER PUBLICATIONS

Wells, Athol U., et al. "Interstitial lung disease in connective tissue disease—mechanisms and management," Nature Reviews: Rheumatology, (2014), vol. 10: 728-739.
International Search Report of PCT/EP2018/058613 dated Jun. 25, 2018.
Woodward, D.F., et al. "International Union of Basic and Clinical Pharmacology. LXXXIII: Classification of Prostanoid Receptors, Updating 15 Years of Progress," Pharmacological Reviews, (2011), vol. 63, No. 3: 471-538.
Xiao, Bing, et al. "Rare SNP rs12731181 in the miR-590-3p Target Site of the Prostaglandin F2$\alpha$ Receptor Gene Confers Risk for Essential Hypertension in the Han Chinese Population," Arterioscler Thromb Vasc. Biol., (2015), vol. 35: 1687-1695.
Yang, Yang, et al. "Prostanoids receptors signaling in different diseases/cancers progression," Journal of Receptors and Signal Transduction, (2013), vol. 33, No. 1: 14-27.
Zhang, Jian, et al. "PG F2$\alpha$ receptor: a promising therapeutic target for cardiovascular disease," Frontiers in Pharmacology, (2010), vol. 1: 1-7.

\* cited by examiner

SUBSTITUTED N-ARYLETHYL-2-AMINOQUINOLINE-4-CARBOXAMIDES AND USE THEREOF

CROSS-REFERENCE TO RELATED APPLICATIONS

This application is the National Stage entry of International Application No. PCT/EP2018/058613, filed 4 Apr. 2018, which claims priority to European Patent Application No. 17165674.7, filed 10 Apr. 2017.

BACKGROUND

Field

The present application relates to novel substituted N-arylethyl-2-aminoquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

Description of Related Art

Prostaglandin F2alpha (PGF2α) is part of the family of bioactive prostaglandins, which are derivatives of arachidonic acid. After release from membrane phospholipids by A2 phospholipases, arachidonic acid is oxidized by cyclooxygenases to prostaglandin H2 (PGH2), which is converted further by PGF synthase to PGF2α. PGF2α can also be formed enzymatically in a much smaller proportion from other prostaglandins such as PGE2 or PGD2 [Watanabe et al., *J. Biol. Chem.* 1985, 260, 7035-7041]. PGF2α is not stored, but is released immediately after synthesis, as a result of which it displays its effects locally. PGF2α is an unstable molecule ($t_{1/2} < 1$ minute), which is rearranged rapidly by enzymatic means in the lung, liver and kidney to give an inactive metabolite, 15-ketodihydro-PGF2α [Basu et al., *Acta Chem. Scand.* 1992, 46, 108-110]. 15-Ketodihydro-PGF2α is detectable in relatively large amounts in the plasma and later also in the urine, both under physiological and pathophysiological conditions.

The biological effects of PGF2α come about through the binding and activation of a receptor on the membrane, of the PGF2α receptor or else of what is called the FP receptor. The FP receptor is one of the G protein-coupled receptors characterized by seven transmembrane domains. As well as the human FP receptor, it is also possible to clone the FP receptors of mice and rats [Abramovitz et al., *J. Biol. Chem.* 1994, 269, 2632-2636; Sugimoto et al., *J. Biol. Chem.* 1994, 269, 1356-1360; Kitanaka et al., *Prostaglandins* 1994, 48, 31-41]. In humans there exist two isoforms of the FP receptor, FPA and FPB. The FP receptor is the least selective of the prostanoid receptors, since not only PGF2α but also PGD2 and PGE2 bind to it with nanomolar affinities [Woodward et al., *Pharmacol. Rev.* 2011, 63, 471-538]. Stimulation of the FP receptor leads primarily to Gq-dependent activation of phospholipase C, which results in release of calcium and activation of the diacylglycerol-dependent protein kinase C (PKC). The elevated intracellular calcium level leads to calmodulin-mediated stimulation of myosin light-chain kinase (MLCK). As well as coupling to the G protein Gq, the FP receptor, via G12/G13, can also stimulate the Rho/Rho kinase signal transduction cascade and, via Gi coupling, can alternatively stimulate the Raf/MEK/MAP signaling pathway [Woodward et al., *Pharmacol. Rev.* 2011, 63, 471-538].

PGF2α is involved in the regulation of numerous physiological functions, for example ovarian functions, embryonal development, changes in the endometrium, uterine contraction and luteolysis, and in the induction of contractions and birth. PGF2α is also synthesized in epithelial cells in the endometrium, where it stimulates cellular proliferation [Woodward et al., *Pharmacol. Rev.* 2011, 63, 471-538]. In addition, PGF2α is a potent stimulator of smooth muscle constriction, vascular constriction and bronchoconstriction, and is involved in acute and chronic inflammatory processes [Basu, *Mol. Cells* 2010, 30, 383-391]. It has thus been shown that 15-keto-dihydro-PGF2α, a stable metabolite of PGF2α, was systemically detectable in patients having rheumatoid arthritis, psoriatic arthrosis and osteoarthrosis. In the kidney, PGF2α is involved in water absorption, natriuresis and diuresis. In the eyes, PGF2α regulates intraocular pressure. PGF2α also plays an important role in bone metabolism: Prostaglandin stimulates the sodium-dependent transport of inorganic phosphate into osteoblasts and it promotes the release of interleukin-6 and vascular endothelial growth factor (VEGF) in osteoblasts; in addition, PGF2α is a strong mitogen and a survival factor for osteoblasts [Agas et al., *J. Cell Physiol.* 2013, 228, 25-29].

Elevated PGF2α/FP receptor activity also led to upregulation of tumourigenic and angiogenic genes such as COX-2 [Sales et al., 2007, *Endocrinology* 148:3635-44], FGF-2 and VEGF [Sales et al., 2010 *Am J Pathol* 176:431], which indicates that the FP receptor stimulates endometrial tumour growth by regulation of vascular functions. In addition, the FP receptor is involved in the regulation of the proliferation of endometrial epithelial cells and can affect their adhesion to the extracellular matrix and motility. The findings suggest that PGF2α/FP receptor plays a multifactorial role in endometrial adenocarcinomas [Yang et al., 2013 *J Recept Signal Transduct*, 33(1): 14-27].

Elevated expression of the FP receptor in precursor cells of oligodendrocytes (OPCs) could be a marker for damage to oligodendrocytes and active myelin [Soldan et al., *Neurology* 2015, 84]. After autopsy, the expression of the FP receptor on OPCs in the vicinity of the edges of MS plaques was observed in tissue from patients having multiple sclerosis (MS). No FP receptor expression was found in control samples of white brain matter. This indicates that the FP receptor plays a role in the aetiology of multiple sclerosis [Carlson et al., 2015, *Mult. Sclerosis.* 23 (11) 467-468].

Brain injuries lead to upregulation of prostaglandins, in particular of the proinflammatory PGF2α, and to overactivation of the FP receptor. For instance, with FP receptor-deficient mice, and by treatment with the FP antagonist AL-8810, significant neuroprotective effects were shown after occlusion of the cerebral artery [Kim et al., 2012, *Neurobiol Disease* 48, 58-65].

In addition, it was shown that PGF2α-FP receptor activation is involved in various cardiovascular dysfunctions such as myocardial fibrosis, myocardial infarction and hypertension [Zhang et al., *Frontiers in Pharmacol.* 2010, 1, 1-7; Ding et al., *Int. J. Biochem. Cell. Biol.*, 2012, 44, 1031-1039; Ding et al., *J. Mol. Med.*, 2014, 6, 629-640].

Thus, the main metabolite of PGF2α, 15-keto-dihydro-PGF2α, is elevated in humans with living conditions having elevated cardiovascular risk [Helmersson-Karlquist et al., Eur Heart J 2015, 36, 238-243], for example also in the case of smokers [Helmersson et al., 2005 *Atherosclerosis* 181, 201-207), Fettleibigkeit [Sinaiko et al., 2005 *Circulation*

111, 1985-1991], type I diabetes [Basu et al., 2005, 28, 1371-1375] and type II diabetes [Helmersson et al., 2004, *Circulation* 109, 1729-1734]. [Zhang et al., *Frontiers in Pharmacol* 2010, 1:1-7]. It has also been shown that genetic polymorphism in a Chinese subpopulation leads to elevated transcription of the FP gene and elevated vasocontractility [Xiao et al., 2015, *Arterioscler Thromb Vasc Biol.* 35:1687-1695].

Moreover, the PGF2α receptor (FP) is involved in joint disorders and the regulation of the signal cascade of the bone morphogenetic protein (BMP) and promotes differentiation of chondrocytes [Kim et al., *Biochim. Biophys. Acta,* 2015, 1853, 500-512]. More stable analogues of PGF2α have been developed for oestrus synchronization and for influencing human reproductive functions, and also for reduction of intraocular pressure for treatment of glaucoma [Basu, *Mol. Cells* 2010, 30, 383-391]. In the latter application, a side-effect that was observed was the stimulation of hair growth, for example of eyelashes, by the more chemically stable PGF2α analogues, for example latanoprost. [Johnston et al., *Am J Ophthalmol* 1997, 124-544-547]. The genes of the FP receptor are also expressed in human hair follicles on the scalp [Khidhir et al., *J Invest Dermatol,* 2009, Abstr 607]. These findings suggest that the FP receptor is involved in the regulation of hair growth and may also be involved in disorders such as hirsutism, for example.

There is also a good description of the role of the FP receptor in the signal cascade in the aetiology of visceral pain (dysmenorrhoea). Thus, dysmenorrhoeic pain best correlates with the rate of PGF release during menstruation (cf. Powell et al., *Prostaglandins* 1985, 29, 273-290; Dawood and Khan-Dawood, *Am. J. Obstet. Gynecol.* 2007, 196, 35.e1-35.e5; Hsia et al., *Endocrinology* 2011, 152, 2090-2099). There has been no description of a connection of the FP receptor signalling pathway in peripheral mediated inflammatory pain to date. The data submitted herewith show this surprising connection for the first time.

In patients having idiopathic pulmonary fibrosis (IPF), it has been shown that the stable PGF2α metabolite 15-ketodihydro-PGF2α is significantly elevated in the plasma and that the level of 15-ketodihydro-PGF2α correlates with functional parameters, for example forced vital capacity (FVC), the diffusion distance of carbon monoxide in the lung (DLCO) and the 6-minute walk test. In addition, a relationship between elevated plasma 15-ketodihydro-PGF2α and the mortality of patients has been detected [Aihara et al., *PLoS One* 2013, 8, 1-6]. In accordance with this, it has also been shown that stimulation of human lung fibroblasts with naturally occurring silica dusts, which in humans can lead to silicosis in the event of chronic inhalation and as a result to pulmonary fibrosis, brings about significant upregulation of PGF2α synthesis [O'Reilly et al., *Am. J. Physiol. Lung Cell. Mol. Physiol.* 2005, 288, L1010-L1016]. In bleomycin-induced pulmonary fibrosis in mice, the elimination of the FP receptor by knockdown (FP −/−) led to a distinct reduction in pulmonary fibrosis compared to wild-type mice [Oga et al., *Nat. Med.* 2009, 15, 1426-1430]. In FP −/− mice, after administration of bleomycin, a significant reduction in the hydroxyproline content and reduced induction of profibrotic genes in the pulmonary tissue was observed. Moreover, lung function was distinctly improved in FP −/− mice compared to the wild-type mice. In human pulmonary fibroblasts, PGF2α stimulates proliferation and collagen production via the FP receptor. Since this occurs independently of the profibrotic mediator TGFβ, the PGF2α/FP receptor signalling cascade constitutes an independent route in the onset of pulmonary fibrosis [Oga et al., *Nat. Med.* 2009, 15, 1426-1430]. These findings show that the FP receptor is a therapeutic target protein for treatment of IPF [Olman, *Nat. Med.* 2009, 15, 1360-1361]. The involvement of PGF2α in the induction of fibrotic lesions has also been shown in cardiac mouse fibroblasts [Ding et al., *Int. J. Biochem. & Cell Biol.* 2012, 44, 1031-1039], in an animal model of scleroderma [Kanno et al., *Arthritis Rheum.* 2013, 65, 492-502] and in synoviocytes from patients with gonioarthrosis [Bastiaansen et al. *Arthritis Rheum.* 2013, 65, 2070-2080].

It is therefore assumed that the FP receptor plays an important role in many disorders, injuries and pathological lesions whose aetiology and/or progression is associated with inflammatory events and/or proliferative and fibroproliferative tissue and vessel remodelling. These may especially be disorders of and/or damage to the lung, the cardiovascular system or the kidney, or the disorder may be a blood disorder, a neoplastic disease or another inflammatory disorder.

Inflammatory and fibrotic disorders of and damage to the lung which should be mentioned in this context are in particular idiopathic pulmonary fibrosis, interstitial pulmonary disorders associated with rheumatoid arthritis, pulmonary hypertension, bronchiolitis obliterans syndrome (BOS), chronic-obstructive pulmonary disease (COPD), asthma and cystic fibrosis. Disorders of and damage to the cardiovascular system in which the FP receptor is involved are, for example, tissue lesions following myocardial infarction and associated with heart failure. Renal disorders are, for example, renal insufficiency and kidney failure. An example of a blood disorder is sickle cell anaemia. Examples of tissue degradation and remodelling in the event of neoplastic processes are the invasion of cancer cells into healthy tissue (formation of metastases) and neovascularization (neoangiogenesis). Other inflammatory diseases where the FP receptor plays a role are, for example, arthrosis and multiple sclerosis.

Idiopathic fibrosis of the lung or idiopathic pulmonary fibrosis (IPF) is a progressive lung disease which, left untreated, results in death within an average of 2.5 to 3.5 years after diagnosis. At the time of diagnosis, patients are usually more than 60 years old, men being slightly more frequently affected than women. Onset of IPF is insidious and characterized by increasing shortness of breath and a dry tickly cough. IPF is one of the group of idiopathic interstitial pneumonias (IIP), a heterogeneous group of pulmonary disorders which are characterized by fibrosis and inflammation of varying severity which can be distinguished using clinical, imaging and fine tissue criteria. Within this group, idiopathic pulmonary fibrosis is of particular significance owing to its frequency and aggressive progression [Ley et al., *Am. J. Respir. Crit. Care Med.* 2011, 183, 431-440]. IPF may either occur sporadically or be hereditary. As yet, the causes are unknown. However, in recent years there have been numerous indications that chronic damage of the alveolar epithelium leads to the release of profibrotic cytokines/mediators followed by increased fibroblast proliferation and increased collagen fibre formation, resulting in a patchy fibrosis and the typical honeycomb structure of the lung [Strieter et al., *Chest* 2009, 136, 1364-1370]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonary hypertension [von der Beck et al., *Der Pneumologe* 2013, 10(2), 105-111]. The prevalence of pulmonary hypertension in interstitial pulmonary disorders is 10-40% [Lettieri et al., *Chest* 2006, 129, 746-752; Behr et al., *Eur. Respir. J.* 2008, 31, 1357-1367]. Currently, there is no curative treatment for IPF—except for lung transplantation.

Rheumatoid arthritis (RA) is a progressive systemic autoimmune disorder which is characterized by chronic erosive synovitis. Interstitial lung disorder (ILD) is one of the most common extra-articular manifestations of RA [Wells et al. *Nat Rev Rheumatol* 2014, 10, 728-739]. About 10% of patients having RA have a clinically proven interstitial pulmonary disorder (RA-ILD); a further third show subclinical ILD in CT scans of the chest. The mortality rate for patients with RA-ILD is three times as high as for patients with RA without ILD, with an average life expectation of only 2.6 years after diagnosis of ILD [Olson et al. *Am J Respir Crit Care Med* 2011 183, 372-378; Doyle et al. *Chest* 2014, 145(3), 454-463].

The inflammatory and autoimmune disorders of the lung together with various environmental triggers (e.g. smoke, fine dust, chemical irritants) and a genetic disposition play an important role in the development and progression of RA-ILD [Catrina et al. *Nat Rev Rheumatol* 2014, 10(11), 645-653].

Pulmonary hypertension (PH) is a progressive lung disease which, left untreated, results in death within an average of 2.8 years after diagnosis. By definition, the mean pulmonary arterial pressure (mPAP) in case of chronic pulmonary hypertension is >25 mmHg at rest or >30 mmHg under exertion (normal value<20 mmHg). The pathophysiology of pulmonary hypertension is characterized by vasoconstriction and remodelling of the pulmonary vessels. In chronic PH, there is a neomuscularization of primarily unmuscularized lung vessels, and the circumference of the vascular musculature of the vessels already muscularized increases. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), *Pulmonary Circulation. Diseases and their treatment*, 3$^{rd}$ edition, Hodder Arnold Publ., 2011, 3]. Since 2008, pulmonary hypertension is classified in accordance with the Dana Point classification into various sub-groups according to the respective aetiology [D. Montana and G. Simonneau, in: A. J. Peacock et al. (Eds.), *Pulmonary Circulation. Diseases and their treatment*, 3$^{rd}$ edition, Hodder Arnold Publ., 2011, 197-206].

Despite all the advances in the therapy of PH there is as yet no prospect of cure of this serious disorder. Standard therapies available on the market (for example prostacyclin analogues, endothelin receptor antagonists, phosphodiesterase inhibitors) are able to improve the quality of life, the exercise tolerance and the prognosis of the patients. These are therapeutic principles which are administered systemically and act primarily haemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilation, they lead to a reduction (desaturation) of the arterial oxygen content in the patients. The probable reason for this is an unfavourable effect on the ventilation-perfusion adaptation in the lung in heterogeneous lung disorders owing to the systemic administration of non-selective vasodilators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular, such novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective aetiology [D. Montana and G. Simonneau, in: A. J. Peacock et al. (Eds.), *Pulmonary Circulation. Diseases and their treatment*, 3$^{rd}$ edition, Hodder Arnold Publ., 2011, 197-206; Hoeper et al., *J. Am. Coll. Cardiol.*, 2009, 54 (1), Suppl. S, S85-S96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoea syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

Bronchiolitis obliterans syndrome (BOS) is a chronic rejection reaction after a lung transplant. Within the first five years after a lung transplant about 50-60% of all patients are affected, and within the first nine years more than 90% of patients [Estenne et al., *Am. J. Respir. Crit. Care Med.* 2003, 166, 440-444]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages. Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements under intensified immunosuppression; patients not showing any response experience persistent deterioration, such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade of life. In the subsequent years of life, shortness of breath frequently becomes worse, and there are instances of coughing combined with copious and purulent sputum, and stenotic respiration extending as far as breathlessness (dyspnea). COPD is primarily a smokers' disease: smoking is the cause of 90% of all cases of COPD and of 80-90% of all COPD-related deaths. COPD is a big medical problem and constitutes the sixth most frequent cause of death worldwide. Of people over the age of 45, about 4-6% are affected. Although the obstruction of the respiratory flow may only be partial and temporal, COPD cannot be cured. Accordingly, the aim of treatment is to improve the quality of life, to alleviate the symptoms, to prevent acute worsening and to slow the progressive impairment of lung function. Existing pharmacotherapies, which have hardly changed over the last two or three decades, are the use of bronchodilators to open blocked respiratory passages, and in certain situations corticosteroids to control the inflammation of the lung [P. J. Barnes, *N. Engl. J. Med.* 2000, 343, 269-280]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodelling of the bronchi.

It is an object of the present invention to identify and provide novel substances that are potent, chemically and metabolically stable, non-prostanoid antagonists of the FP receptor, and are suitable as such for treatment and/or prevention particularly of fibrotic and inflammatory disorders.

WO 95/32948-A1, WO 96/02509-A1, WO 97/19926-A1 and WO 2000/031038-A1, inter alia, disclose 2-arylquinoline-4-carboxamides as $NK_3$ or dual $NK_2/NK_3$ antagonists suitable for treatment of disorders of the lung and central nervous system. WO 2016/004035 discloses 2-arylquinoline-4-carboxamides as TSH receptor agonists which can serve for treatment of functional disorders and malignant thyroid lesions. WO 2000/064877 claims quinoline-4-carboxamide derivatives which can be used as $NK_3$ antagonists for the treatment of various disorders, inter alia of the lung and the central nervous system. WO 2004/045614-A1 describes particular quinolinecarboxamides as glucokinase ligands for the treatment of diabetes. WO 2006/094237-A2 discloses quinoline derivatives as sirtuin modulators which can be used for treatment of various kinds of disorders. WO 2011/153553-A2 claims various bicyclic heteroaryl compounds as kinase inhibitors for the treatment of neoplastic disorders in particular. EP 2 415 755-A1 describes, inter alia, quinoline derivatives suitable for treatment of disorders associated with the activity of plasminogen activator inhibitor 1 (PAI-1). WO 2013/074059-A2 details various quinoline-4-carboxamide derivatives which can serve as inhibitors of cytosine deaminases for boosting DNA transfection of cells. WO 2013/164326-A1 discloses N,3-diphenylnaphthalene-1-carboxamides as agonists of the EP2 prostaglandin receptor for treatment of respiratory pathway disorders. WO 2014/117090-A1 describes various 2-arylquinoline derivatives as inhibitors of metalloenzymes. WO 2012/122370-A2 discloses quinoline-4-carboxamide derivatives which can be used for the treatment of autoimmune and neoplastic disorders. WO 2015/094912-A1 discloses, inter alia, substituted N,2-diphenylquinoline-4-carboxamide derivatives that are suitable as antagonists of the prostaglandin EP4 receptor for treatment of arthritis and associated states of pain. WO 2016/061280 discloses protein tyrosine phosphatase modulators having a 4-amino-2-arylquinoline base structure, which can be used inter alia for treatment of metabolic disorders, diabetes and cardiovascular disorders.

The present invention relates to compounds of the general formula (I)

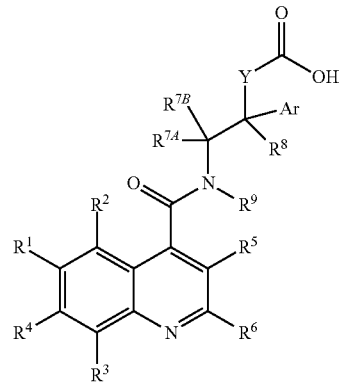

in which
Ar is phenyl or is pyridyl,
where phenyl may be up to tetrasubstituted and pyridyl up to disubstituted, in each case identically or differently, by fluorine, chlorine, by up to tri-fluorine-substituted $(C_1-C_4)$-alkyl, up to tetra-fluorine-substituted $(C_3-C_4)$- cycloalkyl, up to tri-fluorine-substituted $(C_1-C_2)$-alkoxy, or up to tri-fluorine-substituted $(C_1-C_2)$-alkylsulfanyl, or where two substituents of the phenyl or pyridyl group, if they are bonded to adjacent ring atoms, are optionally bonded to one another in such a way that they together form a methylenedioxy or ethylenedioxy group, or where phenyl may be up to pentasubstituted by fluorine, Y is a bond or a group of the formula

where $\#^1$ is the attachment site to the carbon atom, $\#^2$ is the attachment site to the carboxyl group, X is a bond, $-CH_2-$, $-O-$, $-S(=O)_m-$ or $-N(R^{11})-$, in which m is 0, 1 or 2 and $R^{11}$ is hydrogen or methyl, $R^{10A}$ and $R^{10B}$ are independently hydrogen, fluorine or methyl, or $R^{10A}$ and $R^{10B}$ together with the carbon atom to which they are bonded form a cyclopropyl group, k is 1, 2, 3 or 4, $R^1$ is halogen, up to penta-fluorine-substituted $(C_1-C_4)$-alkyl, up to tri-fluorine-substituted methoxy, (trifluoromethyl)sulfanyl, pentafluorosulfanyl, trimethylsilyl, ethynyl, cyclopropyl or cyclobutyl, where cyclopropyl and cyclobutyl may be up to tetrasubstituted by fluorine, $R^2$, $R^3$ and $R^4$ are independently hydrogen, halogen or up to tri-fluorine-substituted methyl, $R^5$ is halogen, up to penta-fluorine-substituted $(C_1-C_4)$-alkyl, up to tri-fluorine-substituted methoxy, hydroxyl, methylsulfanyl, (trifluoromethyl)sulfanyl, cyano, ethenyl, cyclopropyl or cyclobutyl, where cyclopropyl and cyclobutyl may be up to tetrasubstituted by fluorine, $R^6$ is $-NR^{12}R^{13}$ in which $R^{12}$ is hydrogen or $(C_1-C_3)$-alkyl, and $R^{13}$ is $(C_1-C_4)$-alkyl or $(C_3-C_7)$-cycloalkyl, in which $(C_3-C_7)$-cycloalkyl may be up to tetrasubstituted by fluorine and $(C_1-C_4)$-alkyl may be up to pentasubstituted by fluorine or monosubstituted by $(C_3-C_6)$-cycloalkyl, methoxy, trifluoromethoxy or phenyl, in which phenyl may be up to trisubstituted by fluorine, or is a saturated or partially unsaturated, 4- to 8-membered monocyclic or 6- to 10-membered bicyclic heterocycle which is attached via a nitrogen atom and may contain one further, identical or different heteroatom from the group of N, O, S, SO and $SO_2$ as ring member, where the 4- to 8-membered monocyclic and 6- to 10-membered bicyclic heterocycle may each be substituted by 1 to 3 substituents independently selected from the group of $(C_1-C_4)$alkyl, hydroxyl, oxo, $(C_1-C_3)$-alkoxy, difluoromethoxy, trifluoromethoxy, cyano, amino, monomethylamino, dimethylamino, aminocarbonyl, monomethylaminocarbonyl, dimethylaminocarbonyl, and additionally up to tetrasubstituted by fluorine, in which $(C_1-C_4)$-alkyl may be up to pentasubstituted by fluorine or monosubstituted by hydroxyl or methoxy, $R^{7A}$ and $R^{7B}$ are independently hydrogen or methyl, or $R^{7A}$ and $R^{7B}$ together with the carbon atom to which they are bonded form a cyclopropyl group, $R^8$ is hydrogen, fluorine, methyl, trifluoromethyl, ethyl or hydroxyl, $R^9$ is hydrogen or methyl, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds of the invention are likewise N-oxides of the compounds of the formula (I) and the salts, solvates and solvates of the salts thereof.

DETAILED DESCRIPTION OF A PREFERRED EMBODIMENT

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention especially include the salts derived from conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 16 carbon atoms, by way of example and with preference ethylamine, diethylamine, triethylamine, DIPEA, monoethanolamine, diethanolamine, triethanolamine, dimethylaminoethanol, diethylaminoethanol, tris (hydroxymethyl)aminomethane, choline (2-hydroxy-N,N,N-trimethylethanaminium), procaine, dicyclohexylamine, dibenzylamine, N-methylmorpholine, N-methylpiperidine, arginine, lysine and 1,2-ethylenediamine.

In addition, physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

In the context of the present invention, the term "enantiomerically pure" is understood to the effect that the compound in question with respect to the absolute configuration of the chiral centres is present in an enantiomeric excess of more than 95%, preferably more than 98%. The enantiomeric excess, ee, is calculated here by evaluating an HPLC analysis chromatogram on a chiral phase using the formula below:

$$ee = \left|\frac{\text{Enantiomer 1 (area percent)} - \text{Enantiomer 2 (area percent)}}{\text{Enantiomer 1 (area percent)} + \text{Enantiomer 2 (area percent)}}\right| \times 100\%$$

If the compounds of the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, such as, in particular, those in which one or more radioactive isotopes have been incorporated, may be beneficial, for example, for the examination of the mechanism of action or of the active compound distribution in the body; because of their comparative ease of preparability and detectability, particularly compounds labelled with $^{3}H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds according to the invention. The term "prodrugs" refers here to compounds which may themselves be biologically active or inactive, but are converted while present in the body, for example by a metabolic or hydrolytic route, to compounds of the invention.

The present invention comprises as prodrugs in particular hydrolysable ester derivatives of the inventive carboxylic acids of the formula (I). These are understood to mean esters which can be hydrolysed to the free carboxylic acids, as the main biologically active compounds, in physiological media under the conditions of the biological tests described hereinbelow and in particular in vivo by an enzymatic or chemical route. Preferred esters of this kind are $(C_1\text{-}C_4)$-alkyl esters of the formula (IV) in which the alkyl group may be straight-chain or branched. Particular preference is given to methyl, ethyl or tert-butyl esters.

In the context of the present invention, unless specified otherwise, the substituents are defined as follows:

The expression "halogen" or "halogen atom" denotes, for example, a fluorine, chlorine, bromine or iodine atom.

The expression "$C_1\text{-}C_4$-alkyl" denotes a straight-chain or branched monounsaturated monovalent hydrocarbyl group having 1, 2, 3 or 4 carbon atoms, for example a methyl, ethyl, propyl, isopropyl, butyl, sec-butyl, isobutyl or tert-butyl group or an isomer thereof.

The expression "$C_3\text{-}C_7$-cycloalkyl" relates to a saturated monovalent mono- or bicyclic hydrocarbyl ring having 3, 4, 5, 6 or 7 carbon atoms ("$C_3\text{-}C_7$-cycloalkyl"). The $C_3\text{-}C_7$-cycloalkyl group is, for example, a monocyclic hydrocarbyl ring, for example a cyclopropyl, cyclobutyl, cyclopentyl, cyclohexyl or cycloheptyl group.

The expression "$C_1\text{-}C_3$-alkoxy" denotes a straight-chain or branched saturated monovalent group of the formula $(C_1\text{-}C_3\text{-alkyl})\text{-}O\text{—}$, in which the expression "$C_1\text{-}C_3$-alkyl" is as defined above, e.g. a methoxy, ethoxy, n-propoxy or isopropoxy group, or an isomer thereof.

The expression "4- to 8-membered monocyclic heterocycle" in the context of the invention represents a monocyclic saturated or partially unsaturated heterocycle which has a total of 4 to 8 ring atoms and may contain one further ring heteroatom from the group of N, O, S, SO and $SO_2$, and which may be bonded via a ring nitrogen atom. Preference is given to 5- to 7-membered heterocycloalkyl having one ring nitrogen atom and optionally one further ring heteroatom from the group of N, O and S. Particular preference is given to 5-, 6- or 7-membered heterocycloalkyl having one ring nitrogen atom. For example, the following may be mentioned: azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, 1,4-oxazepanyl, 2,5-dihydro-1H-pyrrol-1-yl, 3,6-dihydropyridin-1(2H)-yl and 3,6-dihydro-2H-1,2-oxazin-2-yl. Preference is given to azetidinyl, pyrrolidinyl, imidazolidinyl, 1,2-oxazolidinyl, piperidinyl, piperazinyl, 1,2-oxazinanyl, morpholinyl, thiomorpholinyl, 2,5-dihydro-1H-pyrrol-1-yl, 3,6-dihydropyridin-1(2H)-yl and 3,6-dihydro-2H-1,2-oxazin-2-yl. Particular preference is given to pyrrolidinyl, piperidinyl and azepanyl.

The expression "6- to 10-membered bicyclic heterocycle" in the context of the present invention represents a bicyclic saturated or partially unsaturated heterocycle which has a total of 6 to 10 ring atoms and may contain one further ring heteroatom from the group of N, O, S, SO and $SO_2$, and which may be bonded via a ring nitrogen atom. Preference is given to 7- to 10-membered heterocycloalkyl having one ring nitrogen atom and optionally one further ring heteroatom from the group of N, O and S. Bicyclic spirocyclic heterocyclyl radicals in the context of the present invention shall be embraced by the "bicyclic heterocycle" definition. Preferred examples include the following: azabicyclo[3.1.1]hept-3-yl, 3-azabicyclo[3.2.1]oct-3-yl, 3,4-dihydroisoquinolin-2(1H)-yl, octahydro-2H-isoindol-2-yl and 5-azaspiro[2.5]oct-5-yl.

The expression "$C_1$-$C_2$-alkylsulfanyl" denotes a straight-chain or branched saturated monovalent group of the formula ($C_1$-$C_2$-alkyl)-S— in which the expression "$C_1$-$C_2$-alkyl" is as defined above, e.g. a methylsulfanyl or ethylsulfanyl group.

An oxo substituent in the context of the invention is an oxygen atom bonded to a carbon atom via a double bond.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which Ar is phenyl,
where phenyl may be up to tetrasubstituted by fluorine or up to trisubstituted, identically or differently, by fluorine, chlorine, methyl, trifluoromethyl, difluoromethyl, methoxy, difluoromethoxy or trifluoromethoxy, Y is a bond or a group of the formula $\#^1$—(CH$_2$)$_n$-$\#^2$ where
$\#^1$ is the attachment site to the carbon atom,
$\#^2$ is the attachment site to the carboxyl group,
n is 1, 2 or 3,
$R^1$ is bromine or ethynyl,
$R^2$, $R^3$ and $R^4$ are each hydrogen,
$R^5$ is chlorine or methyl,
and
$R^6$ is —$NR^{12}R^{13}$
in which
$R^{12}$ is hydrogen or methyl, and
$R^{13}$ is ($C_1$-$C_4$)-alkyl,
in which ($C_1$-$C_4$)-alkyl may be up to trisubstituted by fluorine or monosubstituted by phenyl,
or
is a saturated or partially unsaturated, 5- to 7-membered monocyclic or 7- to 10-membered bicyclic heterocycle which is attached via a nitrogen atom and may contain one further, identical or different heteroatom from the group of N, O and S as ring member,
where the 5- to 7-membered monocyclic and 7- to 10-membered bicyclic heterocycle may each be substituted by 1 or 2 substituents independently selected from the group of methyl, difluoromethyl, trifluoromethyl, ethyl, 2,2,2-trifluoroethyl, 2,2-difluoroethyl, isopropyl, and additionally up to tetrasubstituted by fluorine, $R^{7A}$, $R^{7B}$, $R^8$ and $R^9$ are each hydrogen,
and the salts, solvates and solvates of the salts thereof.

In the context of the present invention, particular preference is given to compounds of the formula (I) in which
Ar is phenyl,
where phenyl may be up to trisubstituted, identically or differently, by fluorine, chlorine, methyl, trifluoromethyl, difluoromethoxy or trifluoromethoxy, Y is a group of the formula $\#^1$—CH$_2$CH$_2$-$\#^2$ where
$\#^1$ is the attachment site to the carbon atom,
$\#^2$ is the attachment site to the carboxyl group,
$R^1$ is bromine,
$R^2$, $R^3$, $R^4$ are each hydrogen,
$R^5$ is methyl,
$R^6$ is a group of the formula

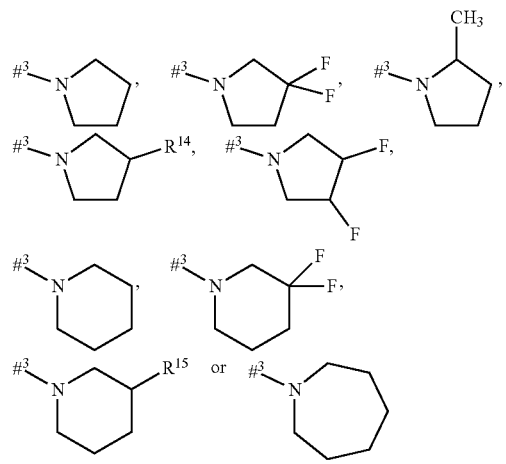

where
$\#^3$ is the attachment site to the rest of the molecule,
$R^{14}$ is fluorine or methyl,
$R^{15}$ is fluorine, methyl or ethyl,
$R^{7A}$, $R^{7B}$, $R^8$ and $R^9$ are each hydrogen,
and the salts, solvates and solvates of the salts thereof.

A particular embodiment of the present invention comprises compounds of the formula (I) in which
$R^1$ is bromine, and
$R^2$, $R^3$ and $R^4$ are each hydrogen,
and the N-oxides, salts, solvates, salts of the N-oxides and solvates of the N-oxides or salts thereof.

A further particular embodiment of the present invention encompasses compounds of the formula (I) in which
$R^5$ is methyl,
and the N-oxides, salts, solvates, salts of the N-oxides and solvates of the N-oxides or salts thereof.

A further particular embodiment of the present invention encompasses compounds of the formula (I) in which
$R^6$ is a group of the formula

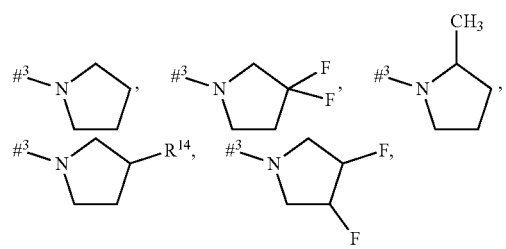

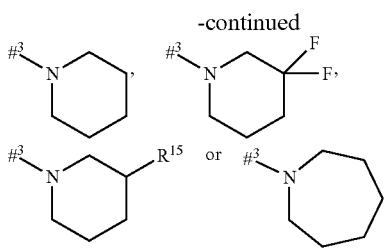

where
³ is the attachment site to the rest of the molecule,
R¹⁴ is fluorine or methyl,
R¹⁵ is fluorine, methyl or ethyl,
and the N-oxides, salts, solvates, salts of the N-oxides and solvates of the N-oxides or salts thereof.

A further particular embodiment of the present invention encompasses compounds of the formula (I) in which
R⁶ is pyrrolidine,
and the N-oxides, salts, solvates, salts of the N-oxides and solvates of the N-oxides or salts thereof.

A further particular embodiment of the present invention encompasses compounds of the formula (I) in which
Y is a group of the formula

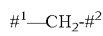
¹—CH₂-#² where
¹ is the attachment site to the carbon atom,
² is the attachment site to the carboxyl group,
and the N-oxides, salts, solvates, salts of the N-oxides and solvates of the N-oxides or salts thereof.

A further particular embodiment of the present invention encompasses compounds of the formula (I) in which
Y is a group of the formula

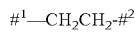
¹—CH₂CH₂-#² where
¹ is the attachment site to the carbon atom,
² is the attachment site to the carboxyl group,
and the N-oxides, salts, solvates, salts of the N-oxides and solvates of the N-oxides or salts thereof.

A further particular embodiment of the present invention encompasses compounds of the formula (I) in which
Ar is phenyl,
where phenyl may be up to trisubstituted, identically or differently, by fluorine, chlorine, methyl, trifluoromethyl, difluoromethoxy or trifluoromethoxy,
and the N-oxides, salts, solvates, salts of the N-oxides and solvates of the N-oxides or salts thereof.

A further particular embodiment of the present invention encompasses compounds of the formula (I) in which
R¹ is bromine,
R², R³, R⁴ are each hydrogen,
R⁵ is methyl,
and the N-oxides, salts, solvates, salts of the N-oxides and solvates of the N-oxides or salts thereof.

A further particular embodiment of the present invention encompasses compounds of the formula (I) in which
R⁷ᴬ, R⁷ᴮ, R⁸ and R⁹ are each hydrogen,
and the N-oxides, salts, solvates, salts of the N-oxides and solvates of the N-oxides or salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges.

The radical definitions specified as preferred, particularly preferred and very particularly preferred apply both to the compounds of the formula (I) and correspondingly toward all intermediates.

The invention further provides a process for preparing the inventive compounds of the formula (I), characterized in that a compound of the formula (II)

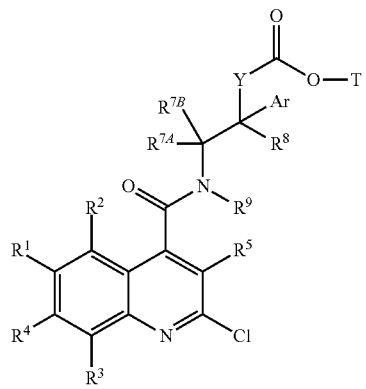

(II)

in which R¹, R², R³, R⁴, R⁵, R⁷ᴬ, R⁷ᴮ, R⁸, R⁹ and Ar have the definitions given above,
and
T is an ester protecting group, especially (C₁-C₄)-alkyl,
in a first step
[A] is reacted with an amine compound of the formula (III)

R⁶—H (III)

in which R⁶ has the definition given above,
and in a subsequent step
[B] the ester radical T of a compound of the formula (IV) obtained from step [A] after reaction with an amine compound (III)

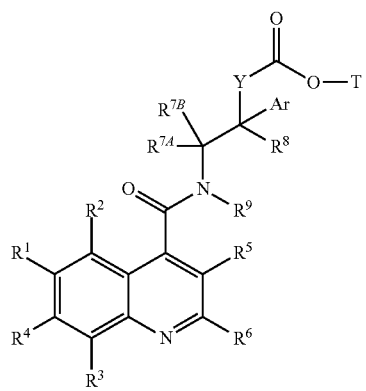

(IV)

in which R¹, R², R³, R⁴, R⁵, R⁶, R⁷ᴬ, R⁷ᴮ, R⁸, R⁹ and Ar have the definitions given above, and
T is an ester protecting group, especially (C$_1$-C$_4$)-alkyl,
is detached,
and the compounds of the formula (I) thus obtained

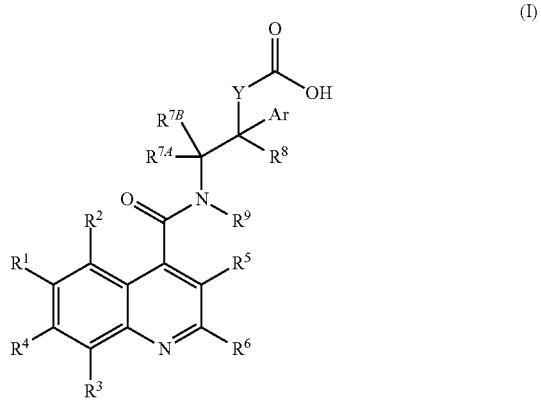

(I)

in which R$^1$, R$^2$, R$^3$, R$^4$, R$^5$, R$^6$, R$^{7A}$, R$^{7B}$, R$^8$, R$^9$ and Ar have the definitions given above,
are optionally separated into their enantiomers and/or diastereomers and/or converted with the appropriate (i) solvents and/or (ii) bases or acids to the solvates, salts and/or solvates of the salts thereof.

The reaction in step [A]: (II)+(III)→(IV) can be effected via a nucleophilic substitution reaction.

The nucleophilic substitution reaction is preferably conducted with an excess of the amine compound and optionally in the presence of a base. Suitable bases are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate or caesium carbonate, alkali metal alkoxides such as lithium tert-butoxide, sodium tert-butoxide or potassium tert-butoxide, alkali metal hydrides such as sodium hydride or potassium hydride, or organic amines such as N,N-diisopropylethylamine (DIPEA), 1,5-diazabicyclo[4.3.0]non-5-ene (DBN) and 1,8-diazabicycle-[5.4.0]undec-7-ene (DBU). Preference is given to using N,N-diisopropylethylamine (DIPEA). The reaction is conducted generally within a temperature range from 30° C. to +130° C., preferably at +90° C. to +110° C.

Inert solvents for process step [A] are, for example, ethers such as diethyl ether, dioxane, tetrahydrofuran, glycol dimethyl ether or diethylene glycol dimethyl ether, alcohols such as methanol, ethanol, propanol, butanol, isopropyl alcohol and tert-butanol, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide (DMF), N,N'-dimethylpropyleneurea (DMPU) or N-methylpyrrolidone (NMP). It is likewise possible to use mixtures of the solvents mentioned. Preference is given to using butanol or N-methylpyrrolidone (NMP).

The detachment of the ester protecting group T in process step [B]: (IV)→(I) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Methyl and ethyl ester are preferably cleaved using a base. Benzyl esters can alternatively also be cleaved by hydrogenation (hydrogenolysis) in the presence of a suitable catalyst, for example palladium on activated carbon. Silyl esters can be cleaved by treatment with acids or fluorides, e.g. tetrabutylammonium fluoride.

Suitable inert solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran, 1,4-dioxane, methanol and/or ethanol. Preference is given to using dichloromethane in the case of the reaction with trifluoroacetic acid, and 1,4-dioxane in the case of the reaction with hydrogen chloride, in each case under anhydrous conditions.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using aqueous lithium hydroxide solution or sodium hydroxide solution.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, optionally with addition of water. Preference is given to using hydrogen chloride or trifluoroacetic acid.

The ester cleavage is generally conducted within a temperature range from –20° C. to +100° C., preferably at 0° C. to +80° C.

Compounds of the formula (I) can be converted by customary methods to their corresponding salts, derived either from bases or from acids. Acidic salts (acid addition salts) can be converted to the corresponding acid addition salts, for example, by addition of strong acids, such as the mineral acids hydrochloric acid or sulfuric acid, to compounds of the formula (I). Preferred acidic salts are the salts of hydrochloric acid. Preference is given to using solutions of hydrochloric acid in dioxane. The acidic salt in question can also be prepared by addition of strong acids, such as the mineral acids hydrochloric acid or sulfuric acid, to ester compounds of the formula (IV), by first detaching the ester group T and directly forming the salt in question in situ, i.e. without isolation of the free carboxylic acid. The preferred ester group T with regard to detachment by acids is the tert-butyl group.

Salts of compounds of the formula (I) that have been derived from customary bases can be prepared, for example, by addition of bases, such as alkali metal and alkaline earth metal hydroxide solutions, to compounds of the formula (I). Preference is given to using aqueous hydroxide solutions (e.g. sodium hydroxide solution). The aqueous hydroxide solutions (e.g. potassium hydroxide solution) can also be generated in situ, by mixing an organometallic compound dissolved in an organic solvent (e.g. potassium tert-butoxide solution in THF) with water or an aqueous solution. The base-derived salts in question can also be prepared by addition of bases, such as alkali metal and alkaline earth metal hydroxide solutions, to ester compounds of the formula (IV), by first detaching the ester group T and directly forming the salt in question in situ, i.e. without isolation of the free carboxylic acid. Preferred ester groups T with regard to detachment by bases are the methyl and ethyl group.

The compounds of the formula (II) can be prepared by reacting a carbonyl chloride of the formula (V)

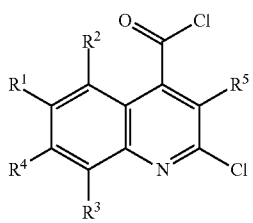

(V)

in which $R^1$, $R^2$, $R^3$, $R^4$ and $R^5$ have the definitions given above
with an amine compound of the formula (VI)

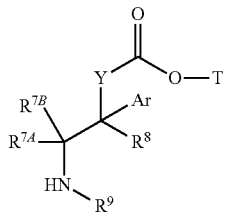

(IV)

in which $R^{7A}$, $R^{7B}$, $R^8$, $R^9$ and Ar have the definitions given above
and
T is an ester protecting group, especially ($C_1$-$C_4$)-alkyl,
and optionally using an auxiliary base, to give an inventive compound of the formula (II)

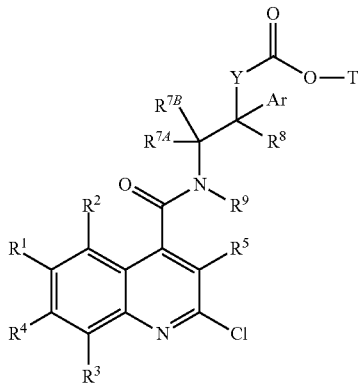

(II)

in which $R^1$, $R^2$, $R^3$, $R^4$, $R^5$, $R^{7A}$, $R^{7B}$, $R^8$, $R^9$ and Ar have the definitions given above,
and
T is an ester protecting group, especially ($C_1$-$C_4$)-alkyl.

The reaction (V)+(VI)→(II) is preferably conducted in the presence of a customary auxiliary base, for example sodium carbonate or potassium carbonate, sodium hydrogencarbonate or potassium hydrogencarbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, sodium hydride or potassium hydride or sodium hydrogencarbonate or potassium hydrogencarbonate. Preference is given to using DIPEA as base.

Inert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP), or alcohols such as methanol, ethanol and isopropyl alcohol. It is also possible to use mixtures of such solvents. Preference is given to using dichloromethane. The couplings are generally conducted within a temperature range from 0° C. to +130° C., preferably at +20° C. to +80° C.

Suitable ester protecting groups T are, in general, all protecting groups known to the person skilled in the art, for example suitably substituted methyl, such as methylthiomethyl (MTM), tetrahydropyranyl (THP), 2-(trimethylsilyl)ethoxymethyl (SEM), benzyloxymethyl (BOM), phenacyl and N-phthalimidomethyl, suitably 2-substituted ethyl, such as 4-methylphenylsulfonylethyl (TSE), 2,2,2-trichloroethyl, 2-(trimethylsilyl)ethyl and 2-(2'-pyridyl)ethyl (PET), allyl, benzyl, suitably substituted benzyl, such as diphenylmethyl (DPM), bis(ortho-nitrophenyl)methyl, 9-anthrylmethyl, 2,4,6-trimethylbenzyl, 4-bromobenzyl, 4-methoxybenzyl (PMB), piperonyl and suitably substituted silyl, such as triethylsilyl (TES), tert-butyldimethylsilyl (TBDMS) and di-tert-butylmethylsilyl (DTBMS); the ester protecting group T used in the process according to the invention is especially and with preference ($C_1$-$C_4$)-alkyl.

The compounds of the formula (V), depending on the respective substitution pattern, can be prepared by, in analogy to methods known from the literature (*J. Med. Chem.* 2005, 48 (10), 3564-3575), reacting an isatin derivative of the formula (VII) in an acylation reaction with an acid anhydride (VIII) to give the compound of the formula (IX) and then reacting the latter in a rearrangement reaction with sodium hydroxide solution to give the carboxylic acid of the formula (X). Alternatively, the isatin derivative of the formula (VII) can also be converted directly to the carboxylic acid of the formula (X) by reaction with the acid anhydride (VIII), without isolation of the intermediate (IX). The acid chlorides of the formula (XI) can then be obtained from the carboxylic acids of the formula (X) by methods known to those skilled in the art, for example by reaction with phosphorus oxychloride or thionyl chloride (Scheme 1).

Scheme 1

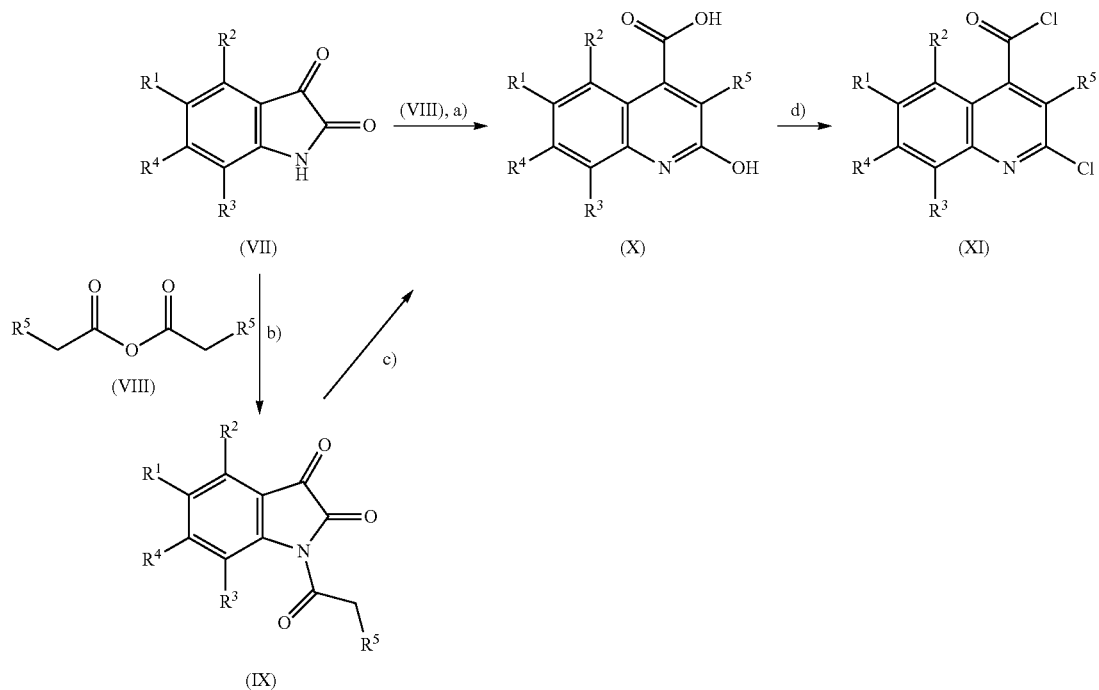

[$R^1$, $R^2$, $R^3$, $R^4$ and $R^5$ as specified above; a) ΔT, e.g. overnight; b) ΔT, e.g. 1-3 h; c) NaOH, ΔT; d) POCl$_3$ or SOCl$_2$, ΔT].

The compounds of the formula (VI), depending on the respective substitution pattern, can be prepared, for example, by the synthesis routes described in Schemes 2 to 8 below and in the Experimental in the respective examples, and in analogy to synthesis methods known from the literature:

Scheme 1
(when Y = #$^1$—(CH$_2$)$_n$—#$^2$ with n = 0, 1, 2, 3 (VI-1)).

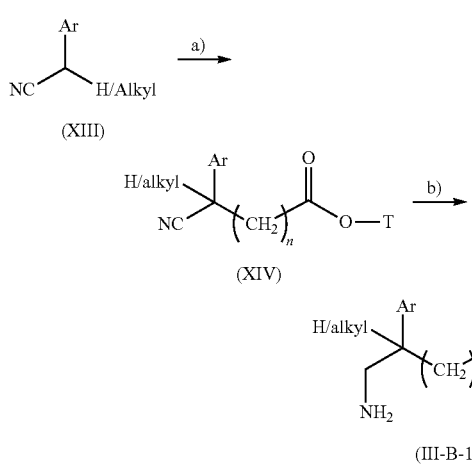

[alkyl = methyl, ethyl; Ar = subst. phenyl, subst. pyridyl; T = ester protecting group, e.g. methyl, ethyl, tert-butyl; n = 0, 1, 2, 3, a): when n = 0: di-tert-butyl dicarbonate, LDA, -78° C.; when n = 1: tert-butyl bromoacetate, LDA or LiHMDS, -78° C.; when n = 2: tert-butyl 3-bromopropanoate, LDA or LiHMDS, -78° C.; or tert-butyl acrylate, potassium carbonate or sodium hydride; when n = 3: tert-butyl 4-bromobutanoate, LDA, -78° C. b): H$_2$, Raney nickel or PtO$_2$. LDA = lithium diisopropylamide; LiHMDS = lithium bis(trimethylsilyl)amide].

Scheme 3
(when R$^8$ = fluorine (VI-2), hydroxyl (VI-3)).

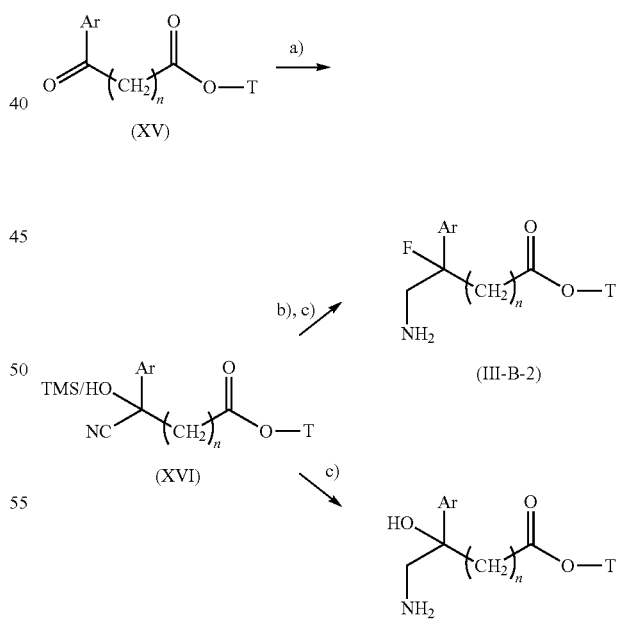

[Ar = subst. phenyl, subst. pyridyl; T = ester protecting group, e.g. methyl, ethyl, tert-butyl; n = 0, 1, 2, 3; a): e.g. KCN or TMSCN; b) DAST; c): H$_2$, catalyst, e.g. Raney nickel or PtO$_2$. DAST = di-ethylaminosulfur trifluoride].

Scheme 4
(when R$^{7A}$/R$^{7B}$ = H, Me (VI-4)).

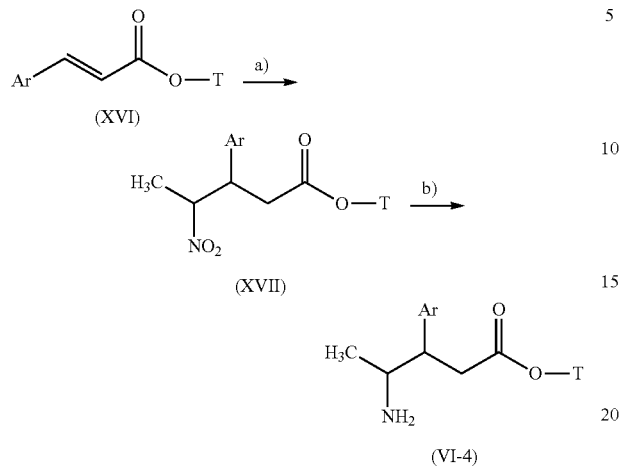

[Ar = subst. phenyl, subst. pyridyl; T = ester protecting group, e.g. methyl, ethyl, tert-butyl; a): nitroethane, base, e.g. 2-tert-butyl-1,1,3,3-tetramethylguanidine; b) zinc dust, hydrochloric acid].

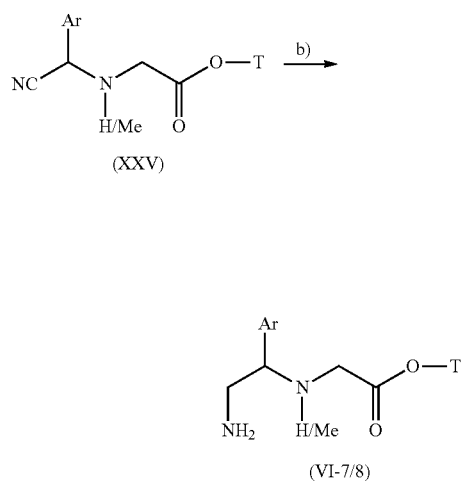

[Ar = subst. phenyl, subst. pyridyl; T = ester protecting group, e.g. methyl, ethyl, tert-butyl; a): TMS—CN; b) H$_2$, Raney nickel].

Scheme 5
(when R$^{10A}$R$^{10B}$ = Me, Me(VI-5) or F, F (VI-6)).

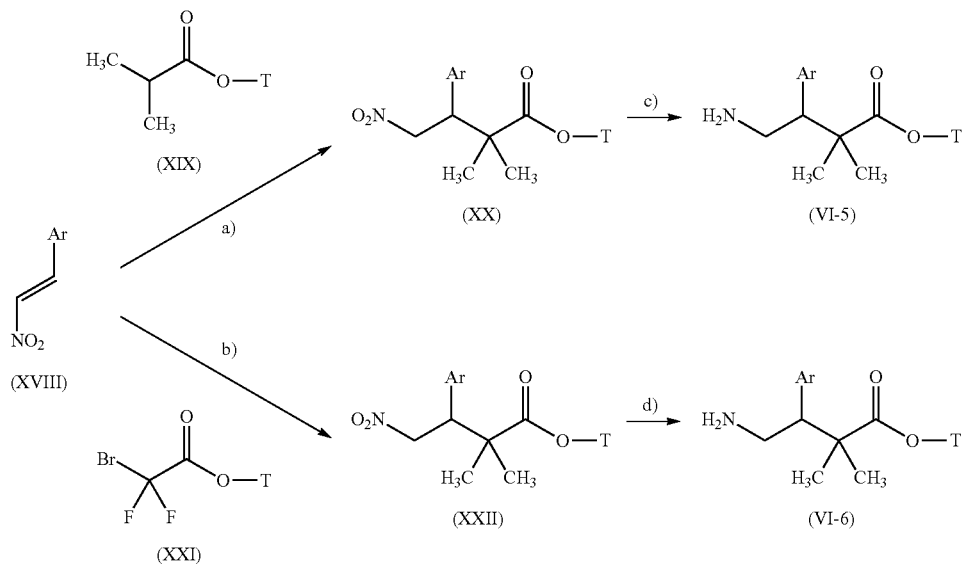

[Ar = subst. phenyl, subst. pyridyl; T = ester protecting group, e.g. methyl, ethyl, tert-butyl; a) LDA, -78° C.; b) zinc; c) H$_2$. Raney nickel; d) H$_2$, PtO$_2$. LDA = lithium diisopropylamide].

Scheme 6
(when X = NH (VI-7) or NMe (VI-8)).

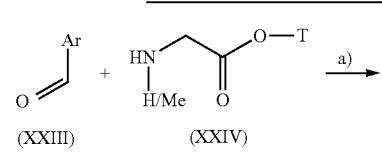

Scheme 7
(when X = S (VI-9) or SO2 (VI-10)).

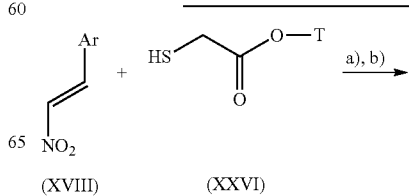

-continued

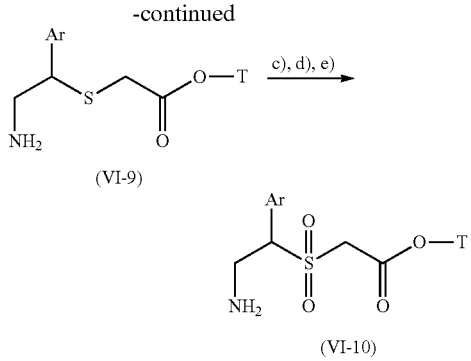

(VI-9)

(VI-10)

[Ar = subst. phenyl, subst. pyridyl; T = ester protecting group, e.g. methyl, ethyl, tert-butyl; a) e.g. in DCM; b) SnCl₂; c) protection of amino functionality, e.g. as NH-Boc: di-tert-butyl dicarbonate, triethylamine; d) mCPBA; e) deprotection of amino functionality, e.g. HCl/dioxane. Boc = tert-butylocycarbonyl; DCM = dischloromethane].

Scheme 8
(when X = O (VI-11)).

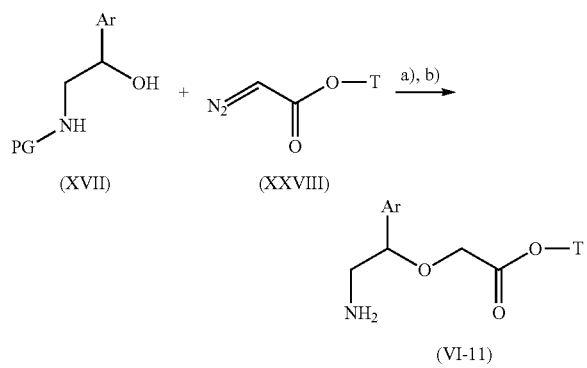

(XVII)   (XXVIII)

(VI-11)

[Ar = subst. phenyl, subst, pyridyl; T = ester protecting group, e.g. methyl, ethyl, tert-butyl; PG = protecting group, e.g. Boc; a) Rh₂(OAc)₄; b) deprotection of amino gunctionality, e.g. HCl/dioxane. Boc - tert-butylocyarconyl].

Separation of the compounds according to the invention into the corresponding enantiomers and/or diastereomers can, if appropriate, also be conducted at the early stage of the intermediates (II), (IV) or (VIII), which are then reacted further in separated form in accordance with the reaction sequence described above. It may be appropriate to provide the amine functionality of the intermediates (III-A) and (III-B) with a protecting group, e.g. Boc, prior to such a separation and then to deprotect it again after the separation. For such a separation of the stereoisomers of intermediates, preference is likewise given to employing chromatographic methods on achiral or chiral separation phases.

The compounds of the formulae (VII), (VIII), (XII), (XIV), (XVI), (XVIII), (XIX), (XXI), (XXIII), (XXIV), (XXVI), (XVII) and (XXVIII) are likewise commercially available or described as such in the literature, or they can be prepared in a simple manner proceeding from other commercially available compounds in analogy to methods known from the literature.

Detailed procedures and further literature references can also be found in the experimental section, in the section on the preparation of the starting compounds and intermediates.

Further inventive compounds of the formula (I) can, if appropriate, also be prepared by transformations of functional groups of individual radicals or substituents, especially those listed under $R^1$ and $R^5$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulfonamides, ester cleavage and hydrolysis, and the introduction and removal of temporary protecting groups.

The compounds of the invention have valuable pharmacological properties and can be used for treatment and/or prophylaxis of disorders in humans and animals.

The compounds of the invention are potent, chemically and metabolically stable antagonists of the FP receptor ("FP antagonists") and are therefore suitable for treatment and/or prevention of disorders and pathological processes, especially those where the FP receptor is involved in the course of an inflammatory event and/or tissue or vessel reconstruction.

In the context of the present invention, these especially include disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, and also granulomatous interstitial lung diseases, rheumatoid arthritis with interstitial pulmonary disease, interstitial lung diseases of known aetiology and other interstitial lung diseases of unknown aetiology, pulmonary arterial hypertension (PAH) and other forms of pulmonary hypertension (PH), bronchiolitis obliterans syndrome (BOS), chronic-obstructive pulmonary disease (COPD), pulmonary sarcoidosis, acute respiratory distress syndrome (ARDS), acute lung injury (ALl), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anaemia and inflammatory and fibrotic eye disorders.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention can additionally be used for treatment and/or prevention of cardiovascular disorders, for example high blood pressure (hypertension), heart failure, coronary heart disorders, stable and unstable angina pectoris, renal hypertension, peripheral and cardiovascular disorders, arrhythmias, rhythm disorders of the atria and ventricles, and conduction disorders, for example atrioventricular blocks of degrees I-III, supraventricular tachycardia, atrial fibrillation, atrial flutter, ventricular fibrillation, ventricular flutter, ventricular tachycardia, Torsade de pointes tachycardia, atrial and ventricular extrasystoles, AV-junctional extrasystoles, sick sinus syndrome, syncopes, AV nodal reentrant tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, and also for treatment and/or prevention of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, diabetic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhoea and premature contractions, and also periphally mediated inflammatory pain (for example in the case of symptomatic endometriosis). In addition, they are suitable for prophylaxis or treatment of hirsutism or hypertrichosis.

In addition, the compounds of the invention have antiinflammatory action and can therefore be used as antiinflammatory agents for the treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammatory disorders of the central nervous system, multiple sclerosis, inflammatory skin disorders and inflammatory eye disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphoea, keloids, hypertrophic scarring, naevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for aging or keratinized skin.

The compounds of the invention can also be used for treatment and/or prevention of anaemias such as haemolytic anaemias, in particular haemoglobinopathies such as sickle cell anaemia and thalassamias, megaloblastic anaemias, iron deficiency anaemias, anaemias owing to acute blood loss, displacement anaemias and aplastic anaemias.

Moreover, the compounds of the invention are suitable for treatment of cancers, for example skin cancer, brain tumours, breast cancer, bone marrow tumours, leukaemias, liposarcomas, carcinomas of the gastrointestinal tract, of the liver, the pancreas, the lung, the kidney, the ureter, the prostate and the genital tract and also of malignant tumours of the lymphoproliferative system, for example Hodgkin's and non-Hodgkin's lymphoma.

In addition, the compounds of the invention can be used for treatment and/or prevention of arteriosclerosis, impaired lipid metabolism and dyslipidaemias (hypolipoproteinaemia, hypertriglyceridaemias, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinemia, insulin resistance, glucose intolerance and diabetic sequelae, such as retinopathy, nephropathy and neuropathy), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, for example dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, for example HPV, HCMV, HIV, SARS), of disorders of the skeletal bone and the joints and also the skeletal muscle (various forms of arthritis, for example arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, and also Still syndrome, Felty syndrome, Sjbrgen syndrome, Clutton syndrome, Poncet syndrome, Pott syndrome and Reiter syndrome, various forms of arthropathy, for example arthropathia deformans, arthropathia neuropathica, arthropathia ovaripriva, arthropathia psoriatica and arthropathia tabica, systemic scleroses, various forms of inflammatory myopathies, for example myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also Günther syndrome and Münchmeyer syndrome), of inflammatory changes to the arteries (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, lepra, Sezary syndrome and paraneoplastic syndrome, in the event of rejection reactions after organ transplants and for wound healing and angiogenesis particularly in the case of chronic wounds.

Owing to their profile of biochemical and pharmacological properties, the compounds of the invention are particularly suitable for treatment and/or prevention of interstitial lung diseases, especially idiopathic pulmonary fibrosis (IPF), and also of pulmonary hypertension (PH), bronchiolitis obliterans syndrome (BOS), inflammatory and fibrotic skin and eye disorders and fibrotic disorders of the internal organs.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
- NO- and haem-independent activators of soluble guanylate cyclase (sGC), such as in particular the compounds described in WO 01/19355, WO 01/19776, WO 01/19778, WO 01/19780, WO 02/070462 and WO 02/070510;
- NO-independent but haem-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;
- prostacyclin analogues and IP receptor agonists, by way of example and with preference iloprost, beraprost, treprostinil, epoprostenol or selexipag;
- endothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
- compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
- compounds which block the binding of serotonin to its receptors, by way of example and with preference antagonists of the 5-$HT_{2B}$ receptor such as PRX-08066;
- antagonists of growth factors, cytokines and chemokines, by way of example and with preference antagonists of TGF-β, CTGF, IL-1, IL-4, IL-5, IL-6, IL-8, IL-13 and integrins;
- Rho kinase-inhibiting compounds, by way of example and with preference fasudil, Y-27632, SLx-2119, BF-66851, BF-66852, BF-66853, KI-23095 or BA-1049;
- compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;
- compounds which influence the energy metabolism of the heart, by way of example and with preference etomoxir, dichloroacetate, ranolazine or trimetazidine;
- anti-obstructive agents as used, for example, for treatment of chronic obstructive pulmonary disease (COPD) or bronchial asthma, by way of example and with preference from the group of the inhalatively or systemically administered agonists of the β-adrenergic receptor (β-mimetics) and the inhalatively administered antimuscarinergic substances;
- antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;
- antifibrotic agents, byway of example and with preference the multikinase inhibitor nintedanib, adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-4 antagonists, IL-13 antagonists, $\alpha_v\beta_6$-integrin antagonists, TGF-β antagonists, inhibitors of the Wnt signalling pathway or CCR2 antagonists;
- antithrombotic agents, by way of example and with preference from the group of platelet aggregation inhibitors, the anticoagulants and the profibrinolytic substances;
- hypotensive active compounds, by way of example and with preference from the group of the calcium antagonists, angiotensin AII antagonists, ACE inhibitors, vasopeptidase inhibitors, endothelin antagonists, renin inhibitors, α-receptor blockers, β-receptor blockers, mineralocorticoid receptor antagonists and also the diuretics;
- lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-α, PPAR-γ and/or PPAR-δ agonists, cholesterol absorption inhibitors, lipase inhibitors, polymeric bile acid adsorbents, bile acid reabsorption inhibitors and lipoprotein(a) antagonists; and/or
- chemotherapeutics as used, for example, for treatment of neoplasms in the lung or other organs.

In a preferred embodiment of the invention, the compounds of the invention are administered in combination with a β-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, α-receptor blockers, β-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an $α_1$-receptor blocker, by way of example and with preference prazosin.

In a preferred embodiment of the invention, the compounds of the invention are administered in combination with a β-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS201038, R-103757 or JTT-130.

In a preferred embodiment of the invention, the compounds of the invention are administered in combination with a PPAR-γ agonist, by way of example and with preference pioglitazone or rosiglitazone.

In a preferred embodiment of the invention, the compounds of the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogues, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, vaginal, dermal, transdermal, conjunctival or otic route, or as an implant or stent.

The compounds according to the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous, intravitreal or intraperitoneal route). Administration forms suitable for parenteral administration include inter alia preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, eye drops, eye ointments, eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (for example patches), milk, pastes, foams, dusting powders, implants or stents.

Oral and parenteral administration are preferred, especially oral, intravenous and intrapulmonary (inhalative) administration.

The compounds according to the invention can be converted to the administration forms mentioned. This can be accomplished in a manner known per se by mixing with pharmaceutically suitable excipients. These excipients include fillers and carriers (for example cellulose, microcrystalline cellulose, for example Avicel®, lactose, mannitol, starch, calcium phosphates, for example Di-Cafos®), ointment bases (for example vaseline, paraffins, triglycerides, waxes, wool wax, wool wax alcohols, lanolin, hydrophilic ointment, polyethylene glycols), suppository bases (for example polyethylene glycols, cocoa butter, hard fat), solvents (e.g. water, ethanol, isopropanol, glycerol, propylene glycol, mid-chain triglycerides fatty oils, liquid polyethylene glycols, paraffins), surfactants, emulsifiers, dispersants or wetting agents (for example sodium dodecylsulfate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®), buffer substances, and also acids and bases (for example phosphates, carbonates, citric acid, acetic acid, hydrochloric acid, sodium hydroxide, ammonium carbonate, trometamol, triethanolamine), isotonizing agents (for example glucose, sodium chloride), adsorbents (for example finely divided silicas), viscosity-increasing agents, gel formers, thickeners or binders (for example polyvinylpyrrolidone, methyl cellulose, hydroxypropyl methyl cellulose, hydroxypropyl cellulose, carboxymethyl cellulose-sodium, starch, carbomers, polyacrylic acids, for example Carbopol®, alginates, gelatins), disintegrants (for example modified starch, carboxymethyl cellulose-sodium, sodium starch glycolate, for example Explotab®, crosslinked polyvinylpyrrolidone, croscarmellose-sodium, for example AcDiSol®), flow regulators, lubricants, glidants and mould release agents (for example magnesium stearate, stearic acid, talc, finely divided silicas, for example Aerosil®), coating agents (for example sugar, shellac) and film formers for films or diffusion membranes with fast or modified dissolution (for example polyvinylpyrrolidones, for example Kollidon®, polyvinyl alcohol, hydroxypropyl methyl cellulose, hydroxypropyl cellulose, ethyl cellulose, hydroxypropyl methyl cellulose phthalate, cellulose acetate, cellulose acetate phthalate, polyacrylates, polymethacrylates, for example Eudragit®), capsule materials (e.g. gelatins, hydroxypropyl methyl cellulose), synthetic polymers (for example polylactides, polyglycolides, polyacrylates, polymethacrylates, for example Eudragit®, polyvinylpyrrolidones, for example Kollidon®, polyvinyl alcohols, polyvinyl acetate, polyethylene oxides, polyethylene glycols and the copolymers and block copolymers thereof), plasticizers (for example polyethylene glycols, propylene glycol, glycerol, triacetin, triacetyl citrate, dibutyl phthalate), penetration enhancers, stabilizers (e.g. antioxidants, for example ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), dyes (e.g. inorganic pigments, for example iron oxides, titanium dioxide), aromas, sweeteners, flavour and/or odour correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight. In the case of intrapulmonary administration, the amount is generally about 0.1 to 50 mg per inhalation.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The present invention further provides pharmaceutical compositions comprising at least one compound according to the invention, typically together with one or more pharmaceutically suitable excipients, and the use thereof according to the present invention.

The working examples which follow illustrate the invention. The invention is not restricted to the examples.

A. EXAMPLES

Abbreviations and Acronyms $[\alpha]_D^{20}$ specific angle of rotation (in polarimetry)
atm atmosphere; unit of pressure
br. broad (in NMR)
c concentration
ca. circa
d doublet (in NMR)
DAD diode array detector (in HPLC)
DBU 1,8-diazabicyclo[5.4.0]undec-7-ene
dd doublet of doublets (in NMR)
DIPEA N,N-diisopropylethylamine
DMF N,N-dimethylformamide
DMSO dimethyl sulfoxide
ΔT heating, temperature increase (in reaction schemes)
ee enantiomeric excess
EI electron impact ionization (in MS)
eq. equivalent
ESI electrospray ionization (in MS)
Et ethyl
wt % percent by weight
h hour(s)
HPLC high-pressure, high-performance liquid chromatography
IPr isopropyl
LC liquid chromatography
LC-MS liquid chromatography-coupled mass spectrometry
LDA lithium diisopropylamide
m multiplet (in NMR)
M molar
Me methyl
min minute(s)
MS mass spectrometry
MWD multiple wavelength detector (in HPLC, UV detector)
NMP N-methyl-2-pyrrolidone
NMR nuclear magnetic resonance spectrometry
MTB ether tert-butyl methyl ether
MTP multititre plate
q quartet (in NMR)
qd quartet of doublets (in NMR)
RP reverse phase (in HPLC)
RT room temperature
$R_t$ retention time (in HPLC, LC/MS)
s singlet (in NMR)
SFC supercritical fluid chromatography
t triplet (in NMR)
td triplet of doublets (in NMR)
TFA trifluoroacetic acid
tert tertiary
THF tetrahydrofuran
ULC Ultra Liquid Chromatography
UPLC ultra-performance liquid chromatography
UV ultraviolet spectrometry
% by vol. percent by volume Other abbreviations have their meanings as familiar to the person skilled in the art.

HPLC and LC/MS Methods:

Method 1 (LC-MS):

MS instrument type Thermo Scientific FT-MS; UHPLC+ instrument type Thermo Scientific UltiMate 3000; column Waters, HSST3, 2.1×75 mm, C18 1.8 μm; eluent A 1 l of water+0.01% formic acid; eluent B 1 l of acetonitrile+0.01% formic acid; gradient 0.0 min 10% B→2.5 min 95% B→3.5 min 95% B; oven 50° C.; flow rate 0.90 ml/min; UV detection 210 nm/optimum integration path 210-300 nm Method 2 (LC-MS):

Instrument: Waters ACQUITY SQD UPLC System; column: Waters Acquity UPLC HSS T3 1.8 μm 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 3 (LC-MS):

Instrument: Waters Single Quad MS System; Instrument: Waters UPLC Acquity; column: Waters BEH C18 1.7 μm 50×2.1 mm; eluent A: 1 l water+1.0 ml (25% ammonia)/l eluent B: 1 l acetonitrile; gradient: 0.0 min 92% A→0.1 min 92% A→1.8 min 5% A→3.5 min 5% A; oven: 50° C.; flow rate: 0.45 ml/min; UV detection: 210 nm (208-400 nm).
Method 4 (LC-MS):
    Instrument: Agilent MS Quad 6150; HPLC: Agilent 1290; column: Waters Acquity UPLC HSS T3 1.8 μm 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.
Method 5 (GC-MS):
    Instrument: Thermo Scientific DSQII, Thermo Scientific Trace GC Ultra; column: Restek RTX-35MS, 15 m×200 μm×0.33 am; constant flow rate of helium: 1.20 ml/min; oven: 60° C.; inlet: 220° C.; gradient: 60° C., 30° C./min→300° C. (hold for 3.33 min).
Method 6 (Preparative HPLC):
    Column: Chromatorex C18, 10 m, 250×40 mm; eluent A: water, eluent B: acetonitrile; injection at 3 min; gradient: 0.0 min 30% B→6.0 min 30% B→27 min 95% B→38 min 95% B→39 min 30% B→40.2 min 30% B; flow rate: 50 ml/min, UV detection: 210 nm.
Method 7 (Preparative HPLC):
    Column: Chromatorex C18, 10 μm, 125×30 mm; eluent A: water, eluent B: acetonitrile; injection at 3 min; gradient: 0.0 min 30% B→5.5 min 30% B→17.65 min 95% B→19.48 min 95% B→19.66 min 30% B→20.51 min 30% B; flow rate: 75 ml/min, UV detection: 210 nm.
Method 8 (Preparative HPLC):
    Column: Chromatorex C18, 10 μm, 250×40 mm; eluent A: water, eluent B: acetonitrile; injection at 3 min; gradient: 0.0 min 10% B→6.0 min 10% B→27 min 95% B→38 min 95% B→39 min 10% B→40.2 min 10% B; flow rate: 50 ml/min, UV detection: 210 nm.
Method 9 (Preparative HPLC):
    Column: Chromatorex C18, 10 μm, 250×40 mm; eluent A: water+0.1% TFA, eluent B: acetonitrile; injection at 3 min; gradient: 0.0 min 10% B→6.0 min 10% B→27 min 95% B→38 min 95% B→39 min 10% B→40.2 min 10% B; flow rate: 50 ml/min, UV detection: 210 nm.
Method 10 (Preparative HPLC):
    Column: Chromatorex C18, 10 μm, 125×30 mm; eluent A: water+0.1% TFA, eluent B: acetonitrile; injection at 3 min; gradient: 0.0 min 10% B→5.5 min 10% B→17.65 min 95% B→19.48 min 95% B→19.66 min 10% B→20.51 min 10% B; flow rate: 75 ml/min, UV detection: 210 nm.
Method 11 (Preparative HPLC):
    Column: Chromatorex C18, 10 μm, 125×30 mm; eluent A: water, eluent B: acetonitrile; injection at 3 min; gradient: 0.0 min 10% B→5.5 min 10% B→17.65 min 95% B→19.48 min 95% B→19.66 min 10% B→20.51 min 10% B; flow rate: 75 ml/min, UV detection: 210 nm.
Method 12 (Preparative HPLC):
    Column: Chromatorex C18, 10 μm, 250×40 mm; eluent A: water+0.1% TFA, eluent B: acetonitrile; injection at 3 min; gradient: 0.0 min 30% B→6.0 min 30% B→27 min 95% B→38 min 95% B→39 min 30% B→40.2 min 30% B; flow rate: 50 ml/min, UV detection: 210 nm.
Method 13 (Preparative HPLC):
    Column: Chromatorex C18, 10 am, 125 mm×30 mm; eluent A: water+0.1% formic acid, eluent B: acetonitrile+0.1% formic acid; injection at 3 min; gradient: 0.0 min 10% B→6.0 min 10% B→27 min 95% B→38 min 95% B→39 min 10% B→40 min 10% B; flow rate: 75 ml/min, UV detection: 210 nm.
Method 14 (Preparative HPLC):
    Column: Chromatorex C18, 10 m, 250 mm×40 mm; eluent A: water+0.1% formic acid, eluent B: acetonitrile+0.1% formic acid; gradient: 0.0 min 10% B→6.0 min 10% B→27 min 95% B→38 min 95% B→39 min 10% B→40 min 10% B; flow rate: 75 ml/min, UV detection: 210 nm.
Method 15 (Preparative HPLC):
    Column: Chromatorex C18, 10 μm, 250 mm×40 mm; eluent A: water+0.1% formic acid, eluent B: methanol+formic acid; gradient: 0.0 min 20% B→6.2 min 20% B→6.5 min 40% B→15.5 min 60% B→16 min 100% B→23 min 100% B→23.6 min 20% B→25.8 min 20% B; flow rate: 75 ml/min, UV detection: 210 nm.
Method 16 (Preparative HPLC-MS):
    Instrument MS: Waters SQD; Instrument HPLC: Waters UPLC; column: Zorbax SB-Aq (Agilent), 50 mm×2.1 mm, 1.8 am; eluent A: water+0.025% formic acid, eluent B: acetonitrile (ULC)+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.600 ml/min; UV detection: DAD; 210 nm.
Method 17 (Preparative HPLC-MS):
    MS instrument: Waters; HPLC instrument: Waters (column: Phenomenex, Luna, 5 am, C18(2) 100 Å, AXIA Tech. 50×21.2 mm), eluent A: water+0.0375% formic acid, eluent B: acetonitrile (ULC)+0.0375% formic acid, with gradient; flow rate: 40 ml/min; UV detection: DAD; 210-400 nm.
Method 18 (Preparative HPLC):
    Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 20% B→2 min 20% B→7 min 92% B→9 min 92% B→20% B; UV detection: 210 nm.
Method 19 (Preparative HPLC):
    Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 30% B→2 min 30% B→2.2 min 50% B→7 min 90% B→7.5 min 92% B→9 min 92% B→30% B; UV detection: 200-400 nm.
Method 20 (Preparative HPLC):
    Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 10% B→2 min 10% B→2.2 min 30% B→7 min 70% B→7.5 min 92% B→9 min 92% B→10% B; UV detection: 200-400 nm.
Method 21 (Preparative HPLC):
    Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 10% B→2 min 10% B→2.2 min 20% B→7 min 60% B→7.5 min 92% B→9 min 92% B→10% B; UV detection: 200-400 nm.
Method 22 (Preparative HPLC):
    Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 7.5% B→2 min 7.5% B→7 min 35% B→7.5 min 92% B→9 min 92% B→10% B; UV detection: 200-400 nm.

Method 23 (Preparative HPLC):

Instrument: Waters Prep LC/MS system, column: Phenomenex Kinetex, C18, 5 μm, 100×30 mm; at-column injection (complete injection); eluent A: water, eluent B: acetonitrile, eluent C: 2% formic acid in water; flow rate for eluent (A+B): 65 ml/min, flow rate for eluent C: constant 5 ml/min; gradient (A/B): 0.0 min 50% B→2 min 50% B→2.2 min 70% B→7 min 92% B→9 min 92% B→10% B; UV detection: 200-400 nm.

Method 24 (Preparative HPLC):

Column: Chromatorex C18, 10 μm, 125 mm×30 mm; eluent A: water, eluent B: acetonitrile; injection at 3 min; gradient: 0.0 min 10% B→6 min 10% B→27 min 95% B→38 min 95% B→39 min 10% B→40 min 10% B; flow rate: 75 ml/min, UV detection: 210 nm.

Method 25 (LC-MS):

Instrument: Waters Acquity UPLCMS SingleQuad; column: Acquity UPLC BEH C18 1.7 μm 50×2.1 mm; eluent A: water+0.1% by vol. of formic acid (99%), eluent B: acetonitrile; gradient: 0-1.6 min 1-99% B, 1.6-2.0 min 99% B; flow rate: 0.8 ml/min; temperature: 60° C.; DAD scan: 210-400 nm.

Method 26 (LC-MS):

Instrument: Waters Acquity UPLCMS SingleQuad; column: Acquity UPLC BEH C18 1.7 μm 50×2.1 mm; eluent A: water+0.2% by vol. of aqueous ammonia (32%), eluent B: acetonitrile; gradient: 0-1.6 min 1-99% B, 1.6-2.0 min 99% B; flow rate: 0.8 ml/min; temperature: 60° C.; DAD scan: 210-400 nm.

Method 27 (Preparative HPLC):

Instrument: Waters Autopurification MS SingleQuad; column: Waters XBrigde C18 5 μm 100×30 mm; eluent A: water+0.2% by vol. of aqueous ammonia (32%), eluent B: acetonitrile; gradient: 0-5.5 min 5-100% B; flow 70 ml/min; temperature: 25° C.; DAD scan: 210-400 nm.

Method 28 (Preparative HPLC):

Waters XBridge C18 5 μm 100×30 mm; eluent A: water+0.1% formic acid, eluent B: acetonitrile; gradient: 0 min 5% B→5.5 min 100% B; flow rate 70 ml/min; DAD detection: 210-400 nm.

Method 29 (preparative HPLC):

Column: Reprosil C18 10 μm; 250 mm×40 mm, flow rate: 75 ml/min, detection at 210 nm; eluent A: water, eluent B: acetonitrile; 0-6 min 10% B; 6-27 min: gradient to 95% B; 27-38 min 95% B; 38-39 min gradient to 10% B; 39-40 min 10% B.

Method 30 (preparative HPLC):

Column: Reprosil C18 10 μm, 250 mm×40 mm; eluent A: water+0.1% formic acid, eluent B: acetonitrile+0.1% formic acid; 0-6 min 10% B; 6-27 min: gradient to 95% B; 27-38 min 95% B; 38-39 min gradient to 10% B; 39-40 min 10% B; flow rate: 75 ml/min, UV detection: 210 nm.

Method 31 (Preparative HPLC):

Column: Chromatorex C18 10 μm; 125 mm×30 mm, flow rate: 75 ml/min, detection at 210 nm; eluent A: water+0.1% formic acid, eluent B: methanol+formic acid; 0-7.2 min 5% B; 7.2-7.45 min: gradient to 20% B; 7.45-14.5 min gradient to 40% B; 14.5-15 min gradient to 100% B; 15-24.3 min 100% B; 24.2-24.5 min gradient to 5% B; 24.5-27.3 min 5% B.

Method 32 (Preparative HPLC):

Reprosil C18, 10 m, 205×50 mm; eluent A: water, eluent B: acetonitrile; injection at 3 min; gradient: 0.0 min 30% B→5.5 min 30% B→17.65 min 95% B→20.79 min 95% B→20.97 min 30% B→22.65 min 30% B; flow rate: 150 ml/min, UV detection: 210 nm.

Method 33 (Preparative HPLC):

Reprosil C18, 10 m, 205×50 mm; eluent A: water, eluent B: acetonitrile; injection at 3 min; gradient: 0.0 min 10% B→5.5 min 10% B→17.65 min 95% B→20.79 min 95% B→20.97 min 10% B→22.65 min 10% B; flow rate: 150 ml/min, UV detection: 210 nm.

Method 34 (quantitative ion chromatography):

Determination of ions with external standards; instrument: Thermo Scientific ICS 5000+; capillary IC columns: IonPac AS11-HC and IonPac CS16; eluent: eluent gradient $[H]^+[OH]^-$; detector: conductivity detection Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the $^1$H NMR spectrum. Compounds may still contain residues of solvent which have not normally been taken into account in the reporting of the purity. If no purity is indicated, either the purity is 100% according to automated peak integration in the LC/MS chromatogram or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals which follow have in some cases been taken directly from the suggestions of the ACD SpecManager (ACD/Labs Release 12.00, Product version 12.5) or ACD/Spectrus Processor 2014 (File Version S20S41, Build 72444, 21 Aug. 2014) or ACD/Spektrus Processor 2015 Pack 2 (File Version S40S41, Build 79720, 30 Jul. 2015) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured or partly obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

The $^1$H NMR data of selected examples are in some cases stated in the form of $^1$H NMR peak lists. For each signal peak, first the δ value in ppm and then the signal intensity in round brackets are listed. The δ value/signal intensity number pairs for different signal peaks are listed with separation from one another by commas. The peak list for an example therefore takes the following form: $δ_1$ (intensity$_1$), $δ_2$ (intensity$_2$), ..., $δ_i$ (intensity$_i$), ..., $δ_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation.

A detailed description of the presentation of NMR data in the form of peak lists can be found in the publication "Citation of NMR Peaklist Data within Patent Applications" (cf. Research Disclosure Database Number 605005, 2014, 1 Aug. 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "Minimum Height" to values of <1%.

Melting points and melting point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates

Example 1A

5-Bromo-1-propionyl-1H-indole-2,3-dione

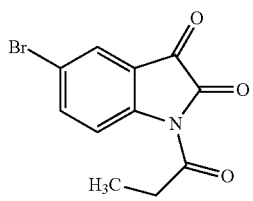

A mixture of 5-bromo-1H-indole-2,3-dione (35.0 g, 155 mmol) and propanoic anhydride (150 ml, 1.2 mol) was heated to reflux while stirring for 3 h. After cooling to RT, the solids present were filtered off, washed with tert-butyl methyl ether and dried under reduced pressure. 16.20 g (60% purity by $^1$H NMR, 22% of theory) of the title compound were obtained in the product mixture. According to $^1$H NMR of the product mixture, some of the title compound had already rearranged to give the 6-bromo-2-hydroxy-3-methylquinoline-4-carboxylic acid conversion product.

$^1$H-NMR (400 MHz, DMSO-d6) δ [ppm]: 8.23 (d, 1H), 8.03-7.86 (m, 2H), 3.01 (q, 2H), 1.14 (t, 3H).

Example 2A

6-Bromo-2-hydroxy-3-methylquinoline-4-carboxylic acid

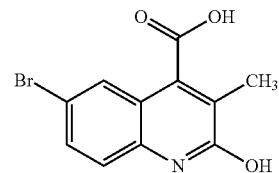 [SMILES: Cc1c(O)nc2ccc(Br)cc2c1C(=O)O]

Method A:

To a mixture of 5-bromo-1-propionyl-1H-indole-2,3-dione (16.2 g, 57.4 mmol, not corrected for purity, Example 1A) in water (100 ml) was added, at RT, sodium hydroxide (13.8 g, 345 mmol), and the mixture was stirred under reflux for 2 h. After cooling to RT, the mixture was acidified with 3 M hydrochloric acid and the solids formed were filtered off. The solids were dissolved in 1 M sodium hydroxide solution (400 ml), and the solution was washed five times with ethyl acetate (200 ml each time). Subsequently, the aqueous solution was acidified with concentrated hydrochloric acid, and the solids formed were filtered off, washed with water and dried under reduced pressure. 8.30 g (95% purity, 49% of theory) of the title compound were obtained.

LC-MS (Method 1): $R_t$=0.65 min; MS (ESIpos): m/z=282/284 [M+H]$^+$ $^1$H-NMR (400 MHz, DMSO-d6) δ [ppm]: 14.28 (br. s, 1H), 12.13 (br. s, 1H), 7.85-7.07 (m, 3H), 2.09 (br. s, 3H).

Purification by Means of Preparative HPLC:

From a similarly conducted preliminary experiment, a batch purified by means of preparative HPLC was obtained as follows: The crude product (4.4 g, 9% purity by LC-S) was dissolved in 50 ml of a mixture of methanol, DMSO and THF while heating, and purified by means of preparative HPLC [column: Chromatorex Spring Column, C18, 10 μm, 290 mm×100 mm; flow rate: 250 ml/min; detection: 210 nm; temperature: 22° C.; injection: 30 ml; acetonitrile/water gradient 0:100→9:1; run time 41 min]. 248 mg (100% purity) of the title compound were obtained.

$^1$H-NMR (400 MHz, DMSO-d6) δ [ppm]: 14.26 (br. s, 1H), 12.13 (s, 1H), 7.67 (dd, 1H), 7.50 (d, 1H), 7.30 (d, 1H), 2.09 (s, 3H).

Method B:

A mixture of 5-bromo-1-propionyl-1H-indole-2,3-dione (99.3 g, 352 mmol, Example 1A), water (615 ml) and sodium hydroxide (84.5 g, 2.11 mol) was stirred at 100° C. for 2 h. After cooling to RT, the mixture was admixed with water (1400 ml) and washed with ethyl acetate (1400 ml).

The aqueous phase was solidified with concentrated hydrochloric acid, and the solids formed were filtered off with suction and dried under reduced pressure. 74.4 g (100% purity by LC-MS, 75% of theory) of the title compound were obtained.

LC-MS (Method 1): $R_t$=0.65 min; MS (ESIpos): m/z=282/284 [M+H]$^+$.

Method C:

A mixture of 5-bromo-1H-indole-2,3-dione (58.8 g, 260.2 mmol) and propanoic anhydride (250 ml, 1.95 mol) under argon was heated to reflux (internal temperature: 160° C.) while stirring overnight. Subsequently, the mixture was cooled to 0° C., MTB ether (500 ml) was added and the mixture was dried at 0° C. for 1 h. The solids present were filtered off, washed with MTB ether and dried under air. 43.0 g (100% purity, 59% of theory) of the title compound were obtained.

LC-MS (Method 1): $R_t$=0.69 min; MS (ESIpos): m/z=282/284 [M+H]$^+$ $^1$H-NMR (400 MHz, DMSO-d6) δ [ppm]: 14.26 (br. s, 1H), 12.13 (s, 1H), 7.67 (dd, 1H), 7.50 (d, 1H), 7.30 (d, 1H), 2.09 (s, 3H).

Example 3A

6-Bromo-2-chloro-3-methylquinoline-4-carbonyl chloride

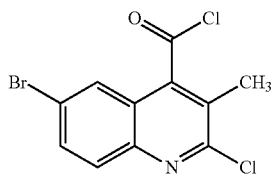 [SMILES: Cc1c(Cl)nc2ccc(Br)cc2c1C(=O)Cl]

Method A:

A mixture of 6-bromo-2-hydroxy-3-methylquinoline-4-carboxylic acid (8.30 g, 29.4 mmol, Example 2A) and phosphorus oxychloride (60 ml, 641 mmol) under argon was heated under reflux for 3 h. After cooling to RT, the mixture was poured gradually onto ice-water (600 ml). The solution obtained was extracted three times with dichloromethane (300 ml each time). The combined organic phases were dried over sodium sulfate, filtered and concentrated, and the residue was purified by means of flash column chromatography (320 g of silica gel, first cyclohexane, then cyclohexane/ethyl acetate 98:2, then cyclohexane/ethyl acetate 96:4, Isolera). The combined target fractions were concentrated and the residue was dried under reduced pressure. 3.74 g (83% purity, 33% of theory) of a first batch of the title compound and 1.90 g (88% purity, 18% of theory, see analysis) of a second batch of the title compound were obtained.

LC-MS (Method 2): $R_t$=1.35 min; MS (ESIpos): m/z=320 [M+H]$^+$

Method B:

To a mixture of 6-bromo-2-hydroxy-3-methylquinoline-4-carboxylic acid (20.0 g, 70.9 mmol) in acetonitrile (400 ml) under argon were added, at RT, thionyl chloride (52 ml, 710 mmol) and DMF (11 ml, 140 mmol). The mixture was gradually heated to reflux under reduced pressure, in the course of which evolution of gas was observed. After stirring under reflux for about 1 hour, the mixture was allowed to cool down to RT, and volatile constituents were removed on a rotary evaporator. The residue obtained was purified by means of flash column chromatography (200 g of silica gel, dichloromethane). The combined target fractions were concentrated and the residue was dried under reduced pressure. 16.4 g (97% purity, 70% of theory) of the title compound were obtained.

LC-MS (Method 4): $R_t$=1.66 min; MS (ESIpos): m/z=320 [M+H]$^+$

Example 4A (6-Chloro-2,3-difluorophenyl)methanol

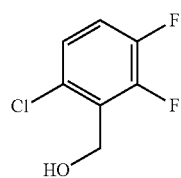 [SMILES: OCc1c(Cl)ccc(F)c1F]

To a solution of 6-chloro-2,3-difluorobenzaldehyde (5.00 g, 28.3 mmol) in THF (20 ml) was added in portions, at RT, sodium borohydride (1.39 g, 36.8 mmol) (evolution of gas). Subsequently, a further 20 ml of THF were added, and the mixture was stirred at RT for 45 min. Thereafter, dichloromethane (100 ml), water (100 ml) and saturated aqueous ammonium chloride solution (50 ml) were added to the mixture, which was agitated. The aqueous phase was acidified in between with concentrated acetic acid. After phase separation, the organic phase was washed once with saturated aqueous sodium chloride solution, dried over sodium sulfate, filtered and concentrated, and the residue was dried briefly under reduced pressure. 5.35 g (100% purity, ">106% of theory", not entirely dry) of the title compound were obtained.

GC-MS (Method 5): $R_t$=3.23 min, MS (EIpos): m/z=178 [M]$^+$ $^1$H-NMR (400 MHz, DMSO-d6) δ [ppm]: 7.45 (dd, 1H), 7.36 (ddd, 1H), 5.36 (t, 1H), 4.59 (dd, 3H).

Example 5A 2-(Bromomethyl)-1-chloro-3,4-difluorobenzene

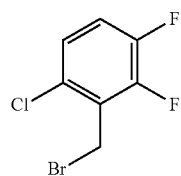 [SMILES: Fc1ccc(Cl)c(CBr)c1F]

To a solution of (6-chloro-2,3-difluorophenyl)methanol (5.34 g, 29.9 mmol, Example 4A) in dichloromethane (30 ml) were added dropwise while stirring, at −15° C., phosphorus tribromide (1.6 ml, 16 mmol). Subsequently, the cooling bath was removed and the mixture was stirred at RT for a further 2 h. Thereafter, saturated aqueous sodium hydrogencarbonate solution, water and dichloromethane (50 ml of each) were added gradually to the mixture, which was agitated. After phase separation, the organic phase was washed with saturated aqueous sodium chloride solution (100 ml), dried over sodium sulfate, filtered and concentrated, and the residue was dried briefly under reduced pressure. 3.88 g (94% purity by GC-MS, 51% of theory) of the title compound were obtained.

GC-MS (Method 5): $R_t$=3.57 min, MS (EIpos): m/z=240 [M]$^+$ $^1$H-NMR (400 MHz, DMSO-d6) δ [ppm]: 7.55 (dd, 1H), 7.45 (ddd, 1H), 4.71 (d, 3H).

Example 6A 2-(Bromomethyl)-1-(difluoromethoxy)-3-fluorobenzene

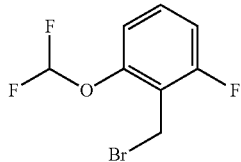

To a solution of [2-(difluoromethoxy)-6-fluorophenyl]methanol (9.90 g, 51.5 mmol, preparable according to WO 2016/168633 A1, p. 71) in dichloromethane (60 ml) was added dropwise while stirring, at −15° C., a solution of phosphorus tribromide (1.6 ml, 16 mmol) in dichloromethane (20 ml). Subsequently, the cooling bath was removed and the mixture was stirred at RT for a further 2 h. Thereafter, saturated aqueous sodium hydrogencarbonate solution, water and dichloromethane (100 ml of each) were added gradually to the mixture, which was agitated. After phase separation, the organic phase was washed with saturated aqueous sodium chloride solution (200 ml), dried over sodium sulfate, filtered and concentrated, and the residue was dried briefly under reduced pressure. 9.60 g (95% purity, 69% of theory) of the title compound were obtained.

GC-MS (Method 5): $R_t$=3.38 min, MS (EIpos): m/z=254/256 [M]$^+$ $^1$H-NMR (400 MHz, DMSO-d6) δ [ppm]: 1.238 (0.57), 1.255 (1.12), 1.273 (0.58), 4.610 (15.58), 4.614 (16.00), 7.105 (3.32), 7.126 (3.80), 7.161 (2.02), 7.184 (8.39), 7.205 (2.57), 7.366 (8.46), 7.470 (2.03), 7.487 (2.27), 7.491 (3.74), 7.508 (3.68), 7.512 (2.00), 7.529 (1.66), 7.549 (4.14).

$^1$H-NMR (400 MHz, DMSO-d6) δ [ppm]: 7.60-7.03 (m, 4H), 4.61 (d, 2H).

Example 7A (2-Chloro-3-fluorophenyl)acetonitrile

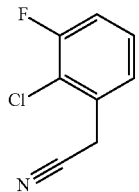

To a solution of 1-(bromomethyl)-2-chloro-3-fluorobenzene (6.96 g, 31.1 mmol) in dichloromethane (60 ml) were added, while stirring, water (60 ml) and tetrabutylammonium bromide (1.00 g, 3.11 mmol). Subsequently, a solution of potassium cyanide (6.08 g, 93.4 mmol) in water (60 ml) was added, and the mixture was stirred at RT for 2.5 h. Subsequently, the phases were separated, and the organic phase was washed three times with saturated aqueous sodium hydrogencarbonate solution, dried over sodium sulfate, filtered and concentrated, and the residue was dried briefly under reduced pressure. 4.98 g (100% purity, 94% of theory) of the title compound were obtained.

GC-MS (Method 5): $R_t$=4.03 min, MS (EIpos): m/z=169 [M]$^+$ $^1$H-NMR (400 MHz, DMSO-d6) δ [ppm]: 4.175 (16.00), 7.400 (0.90), 7.408 (1.10), 7.414 (1.15), 7.417 (1.13), 7.424 (2.60), 7.440 (2.84), 7.443 (2.99), 7.459 (5.37), 7.468 (1.52), 7.474 (1.39).

$^1$H-NMR (400 MHz, DMSO-d6) δ [ppm]: 7.50-7.37 (m, 3H), 4.18 (s, 2H).

Example 8A (6-Chloro-2,3-difluorophenyl)acetonitrile

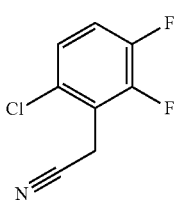 [SMILES: N#CCc1c(Cl)ccc(F)c1F]

To a solution of 2-(bromomethyl)-1-chloro-3,4-difluorobenzene (3.87 g, 16.0 mmol, Example 5A) in acetonitrile (48 ml) were added, while stirring, trimethylsilyl cyanide (2.5 ml, 18 mmol) and a 1 M solution of tetrabutylammonium fluoride in THF (19 ml, 19 mmol), and the mixture was stirred at 80° C. for 30 min. After cooling to RT, the solvent was removed on a rotary evaporator. The residue was taken up in ethyl acetate (80 ml), and the solution was washed with water and saturated aqueous sodium chloride solution (80 ml each time), dried over sodium sulfate, filtered and concentrated. The residue was taken up in dichloromethane and purified by means of flash chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. 2.24 g (71% purity by GC-MS, 96% of theory) of the title compound were obtained.

GC-MS (Method 5): $R_t$=3.92 min, MS (EIpos): m/z=187 [M]$^+$

LC-MS (Method 1): $R_t$=1.57 min; MS (ESIneg): m/z=186 [M−H]

$^1$H-NMR (400 MHz, DMSO-d6) δ [ppm]: 7.58 (dd, 1H), 7.49 (ddd, 1H), 4.16 (d, 2H).

Example 9A (2-Chloro-3,6-difluorophenyl)acetonitrile

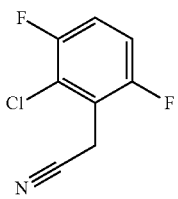 [SMILES: N#CCc1c(F)ccc(F)c1Cl]

To a solution of 2-(bromomethyl)-3-chloro-1,4-difluorobenzene (4.80 g, 19.9 mmol, CAS-RN 90292-67-4, commercially available) in dichloromethane (40 ml) were added, while stirring, water (40 ml) and tetrabutylammonium bromide (641 mg, 1.99 mmol). Subsequently, a solution of potassium cyanide (3.88 g, 59.6 mmol) in water (40 ml) was added, and the mixture was stirred at RT for 2.5 h. Subsequently, the phases were separated, and the organic phase was washed three times with saturated aqueous sodium hydrogencarbonate solution, dried over sodium sulfate, filtered and concentrated, and the residue was dried briefly under reduced pressure. 3.80 g (94% purity, 96% of theory) of the title compound were obtained.

LC-MS (Method 1): $R_t$=1.59 min; MS (ESIneg): m/z=186 [M−H]⁻

¹H-NMR (400 MHz, DMSO-d6) δ [ppm]: 7.57 (td, 1H), 7.44 (td, 1H), 4.15 (d, 2H).

Example 10A

[2-(Difluoromethoxy)-6-fluorophenyl]acetonitrile

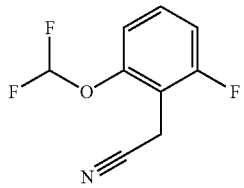

To a solution of 2-(bromomethyl)-1-(difluoromethoxy)-3-fluorobenzene (9.60 g, 37.6 mmol, Example 6A) in dichloromethane (60 ml) were added, while stirring, water (60 ml) and tetrabutylammonium bromide (1.21 g, 3.76 mmol). Subsequently, a solution of potassium cyanide (7.35 g, 113 mmol) in water (120 ml) was added, and the mixture was stirred at RT for 2.5 h. Subsequently, the phases were separated, and the organic phase was washed twice with saturated aqueous sodium hydrogencarbonate solution (100 ml each time), dried over sodium sulfate, filtered and concentrated, and the residue was dried briefly under reduced pressure. 7.26 g (98% purity, 94% of theory) of the title compound were obtained.

GC-MS (Method 5): $R_t$=3.70 min, MS (EIpos): m/z=201 [M]⁺

LC-MS (Method 1): $R_t$=1.56 min

¹H-NMR (400 MHz, DMSO-d6) δ [ppm]: 0.937 (0.68), 3.164 (0.78), 3.177 (0.77), 3.952 (16.00), 7.152 (3.20), 7.171 (6.16), 7.215 (2.00), 7.237 (3.89), 7.259 (2.35), 7.353 (6.55), 7.489 (1.60), 7.509 (2.98), 7.526 (3.04), 7.531 (1.93), 7.535 (3.48), 7.547 (1.32).

¹H-NMR (400 MHz, DMSO-d6) δ [ppm]: 7.58-7.43 (m, 1H), 7.39-7.05 (m, 3H), 3.95 (s, 2H).

Example 11A (+/−)-tert-Butyl 3-(2-chloro-6-fluorophenyl)-3-cyanopropanoate (Racemate)

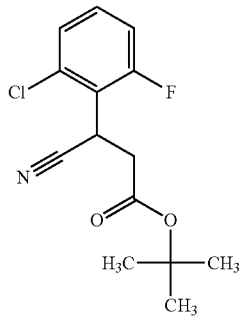 [SMILES: CC(C)(C)OC(=O)CC(C#N)c1c(F)cccc1Cl]

To a solution of (2-chloro-5-fluorophenyl)acetonitrile (25.0 g, 147 mmol) in THF (200 ml) under argon was added gradually while stirring, at −78° C., a 2 M solution of LDA in THF (110 ml, 220 mmol). The mixture was allowed to come to 0° C. and, after 15 min, cooled back down again to −78° C. Subsequently, tert-butyl bromoacetate (33 ml, 220 mmol) was slowly added dropwise thereto at −78° C. while stirring. The mixture was allowed to come to RT within 3 h, then water (100 ml) was added and the mixture was stirred at RT for 10 min. Water (200 ml) was added again, followed by ethyl acetate (200 ml), and the phases were separated. The aqueous phase was extracted with ethyl acetate (200 ml). The combined organic phases were washed once with saturated aqueous sodium chloride solution (300 ml), dried over sodium sulfate, filtered and concentrated, and the residue was taken up in dichloromethane and purified by means of flash column chromatography (1 kg of silica gel, cyclohexane/ethyl acetate 9:1). The combined target fractions were concentrated, and the residue was dried under reduced pressure. 15.2 g (64% purity, 23% of theory) of a first batch of the title compound and 28.6 g (87% purity, 59% of theory, see analysis) of a second batch of the title compound were obtained.

LC-MS (Method 2): $R_t$=1.09 min; MS (ESIpos): m/z=284 [M+H]⁺

¹H-NMR (500 MHz, DMSO-d6) δ [ppm]: 0.934 (1.18), 0.947 (1.27), 1.343 (16.00), 1.392 (1.87), 1.401 (1.18), 2.976 (0.49), 2.991 (0.48), 3.081 (0.60), 3.316 (0.94), 4.854 (0.42), 7.452 (0.69), 7.500 (0.48), 7.512 (0.47).

¹H-NMR (400 MHz, DMSO-d6) δ [ppm]: 7.55-7.47 (m, 1H), 7.47-7.42 (m, 1H), 7.40-7.33 (m, 1H), 4.85 (td, 1H), 3.10 (dd, 1H), 2.97 (dd, 1H), 1.34 (s, 9H).

Example 12A (+/−)-tert-Butyl 4-(2-chloro-5-fluorophenyl)-4-cyanobutanoate (Racemate)

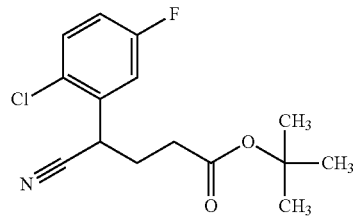

To a solution of (2-chloro-5-fluorophenyl)acetonitrile (10.0 g, 59.0 mmol) in THF (75 ml) under argon was added gradually while stirring, at −78° C., a 2 M solution of LDA in THF (44 ml, 88 mmol). The mixture was allowed to come to 0° C. and, after 15 min, cooled back down again to −78° C. Subsequently, tert-butyl 3-bromopropanoate (11 ml, 71 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by means of flash column chromatography (340 g silica gel Biotage Snap-Cartridge KP-Sil, cyclohexane/ethyl acetate gradient 93:7→3:7, Isolera One). The combined target fractions were concentrated and the residue was dried under reduced pressure. 14.8 g (93% purity, 78% of theory) of the title compound were obtained.

LC-MS (Method 1): $R_t$=2.22 min; MS (ESIpos): m/z=298 [M+H]⁺

Example 13A (+/−)-tert-Butyl 4-(2-chlorophenyl)-4-cyanobutanoate (Racemate)

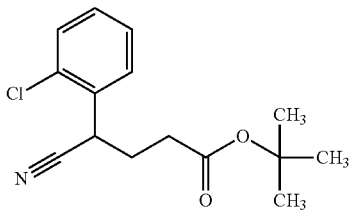 [SMILES: CC(C)(C)OC(=O)CCC(C#N)c1ccccc1Cl]

To a solution of (2-chlorophenyl)acetonitrile (5.00 g, 33.0 mmol) in THF (46 ml) under argon was added gradually while stirring, at −78° C., a 2 M solution of LDA in THF (25 ml, 49 mmol). The mixture was allowed to come to 0° C. and, after 15 min, cooled back down again to −78° C. Subsequently, tert-butyl 3-bromopropanoate (8.28 g, 39.6 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by preparative HPLC (Method 8). The combined target fractions were concentrated and the residue was dried under reduced pressure. 5.20 g (75% purity, 42% of theory) of the title compound were obtained.

LC-MS (Method 1): $R_t$=2.22 min; MS (ESIpos): m/z=280 [M+H]$^+$

Example 14A (+/−)-tert-Butyl 4-cyano-4-[2-(trifluoromethyl)phenyl]butanoate (Racemate)

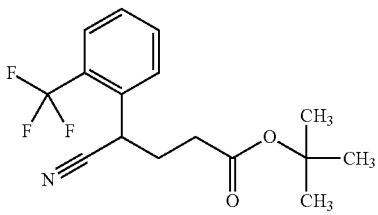 [SMILES: CC(C)(C)OC(=O)CCC(C#N)c1ccccc1C(F)(F)F]

To a solution of [2-(trifluoromethyl)phenyl]acetonitrile (14.8 g, 79.8 mmol, CAS-RN 3038-47-9, commercially available) in THF (100 ml) under argon was slowly added while stirring a 2 M solution of LDA in THF (48 ml, 96 mmol), in the course of which the internal temperature was kept between −70° C. and −60° C. The mixture was allowed to come to 0° C. and, after 15 min, cooled back down again to −70° C. Subsequently, a solution of tert-butyl 3-bromopropanoate (15 ml, 96 mmol) in THF (70 ml) was slowly added dropwise thereto at −70° C. while stirring. Stirring of the mixture was continued overnight, in the course of which the cooling bath (dry ice/acetone) was allowed to come gradually to RT. Subsequently, water (200 ml) and ethyl acetate (250 ml) were gradually added at about 0° C. to the mixture, which was agitated. After phase separation, the aqueous phase was extracted once with ethyl acetate (150 ml). The combined organic phases were washed once with saturated aqueous sodium chloride solution (250 ml), dried over sodium sulfate, filtered and concentrated, and the residue was taken up in dichloromethane and purified by means of flash column chromatography (400 g of silica gel, cyclohexane/ethyl acetate 9:1). The combined target fractions were concentrated, and the residue was dried under reduced pressure. 18.7 g (100% purity, 75% of theory) of the title compound were obtained.

LC-MS (Method 1): $R_t$=2.26 min; MS (ESIpos): m/z=314 [M+H]$^+$ $^1$H-NMR (400 MHz, DMSO-d6) δ [ppm]: 7.91-7.75 (m, 3H), 7.62 (t, 1H), 4.35 (dd, 1H), 2.44-2.33 (m, 2H), 2.31-2.19 (m, 1H), 2.18-2.06 (m, 1H), 1.39 (s, 9H).

Example 15A (+/−)-tert-Butyl 4-cyano-4-[2-(trifluoromethoxy)phenyl]butanoate (Racemate)

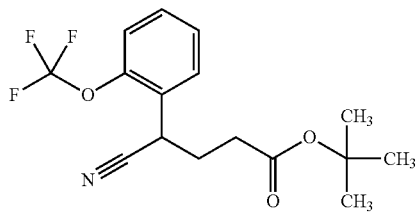 [SMILES: CC(C)(C)OC(=O)CCC(C#N)c1ccccc1OC(F)(F)F]

To a solution of [2-(trifluoromethoxy)phenyl]acetonitrile (5.00 g, 24.9 mmol) in THF (65 ml) under argon was added gradually while stirring, at −78° C., a 2 M solution of LDA in THF (15 ml, 30 mmol). The mixture was allowed to come to 0° C. and, after 15 min, cooled back down again to −78° C. Subsequently, a solution of tert-butyl 3-bromopropanoate (4.7 ml, 30 mmol) in THF (45 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7 7:3, Isolera One). The combined target fractions were concentrated and the residue was dried under reduced pressure. 3.13 g (80% purity, 31% of theory) of the title compound were obtained.

LC-MS (Method 1): $R_t$=2.27 min; MS (ESIpos): m/z=330 [M+H]$^+$

Example 16A (+/−)-tert-Butyl 4-(2-chloro-3-fluorophenyl)-4-cyanobutanoate (Racemate)

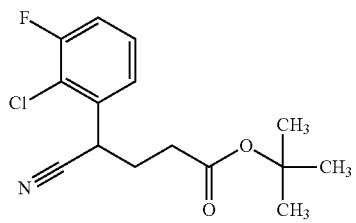

To a solution of (2-chloro-3-fluorophenyl)acetonitrile (4.00 g, 23.6 mmol, Example 7A) in THF (30 ml) under argon was added gradually while stirring, at −78° C., a 2 M solution of LDA in THF (14 ml, 28 mmol). The mixture was allowed to come to 0° C. and, after 15 min, cooled back down again to −78° C. Subsequently, a solution of tert-butyl 3-bromopropanoate (4.5 ml, 28 mmol) in THF (20 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. 4.36 g (95% purity, 59% of theory) of the title compound were obtained.

LC-MS (Method 1): $R_t$=2.24 min; MS (ESIpos): m/z=298 [M+H]$^+$ $^1$H-NMR (400 MHz, DMSO-d6) δ [ppm]: 0.007 (0.14), 1.174 (0.02), 1.222 (0.06), 1.342 (0.84), 1.346 (0.35), 1.382 (16.00), 1.429 (0.05), 1.539 (0.06), 1.987 (0.03), 2.071 (0.04), 2.090 (0.09), 2.106 (0.20), 2.125 (0.45), 2.142 (0.53), 2.162 (0.44), 2.182 (0.23), 2.196 (0.08), 2.217 (0.06), 2.252 (0.02), 2.302 (0.07), 2.317 (0.08), 2.343 (0.38), 2.358 (0.60), 2.362 (0.45), 2.376 (0.75), 2.395 (0.29), 2.417 (0.12), 2.436 (0.04), 2.669 (0.03), 2.709 (0.02), 3.730 (0.02), 4.174 (0.10), 4.566 (0.34), 4.586 (0.43), 4.603 (0.33), 7.426 (0.24), 7.431 (0.29), 7.444 (0.48), 7.449 (0.60), 7.460 (0.54), 7.466 (0.30), 7.476 (0.47), 7.482 (0.52), 7.491 (0.55), 7.508 (0.28), 7.529 (0.09).

$^1$H-NMR (400 MHz, DMSO-d6) δ [ppm]: 7.55-7.40 (m, 3H), 4.59 (dd, 1H), 2.45-2.29 (m, 2H), 2.23-2.06 (m, 2H), 1.38 (s, 9H).

Example 17A (+/−)-tert-Butyl 4-(6-chloro-2,3-difluorophenyl)-4-cyanobutanoate (Racemate)

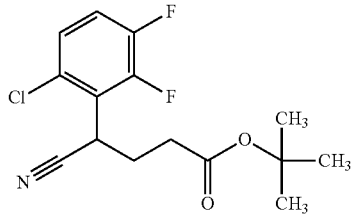 [SMILES: CC(C)(C)OC(=O)CCC(C#N)c1c(Cl)ccc(F)c1F]

To a solution of (6-chloro-2,3-difluorophenyl)acetonitrile (2.23 g, 11.9 mmol, not corrected for purity, Example 8A) in THF (15 ml) under argon was added gradually while stirring, at −78° C., a 2 M solution of LDA in THF (7.1 ml, 14 mmol). The mixture was allowed to come to 0° C. and, after 15 min, cooled back down again to −78° C. Subsequently, a solution of tert-butyl 3-bromopropanoate (4.5 ml, 28 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water (50 ml) and ethyl acetate (100 ml) were gradually added at about 0° C. to the mixture, which was agitated. After phase separation, the aqueous phase was extracted once with ethyl acetate (50 ml). The combined organic phases were washed once with saturated aqueous sodium chloride solution (80 ml), dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 93:7→7:3, Isolera One). The combined target fractions were concentrated and the residue was dried under reduced pressure. 2.29 g (83% purity, 51% of theory) of the title compound were obtained.

LC-MS (Method 1): $R_t$=2.17 min; MS (ESIpos): m/z=316 [M+H]$^+$ $^1$H-NMR (400 MHz, DMSO-d6) δ [ppm]: 7.73-7.53 (m, 1H), 7.52-7.41 (m, 1H), 4.68 (t, 1H), 2.43-2.32 (m, 2H), 2.32-2.18 (m, 1H), 2.18-2.04 (m, 1H), 1.37 (s, 9H).

Example 18A (+/−)-tert-Butyl 4-cyano-4-(5-fluoro-2-methylphenyl)butanoate (Racemate)

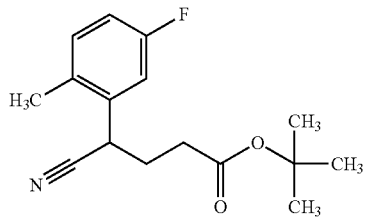 [SMILES: Cc1ccc(F)cc1C(C#N)CCC(=O)OC(C)(C)C]

To a solution of (5-fluoro-2-methylphenyl)acetonitrile (4.00 g, 26.8 mmol) in THF (30 ml) under argon was added gradually while stirring, at −78° C., a 2 M solution of LDA in THF (16 ml, 32 mmol). The mixture was allowed to come to 0° C. and, after 15 min, cooled back down again to −78° C. Subsequently, a solution of tert-butyl 3-bromopropanoate (5.1 ml, 32 mmol) in THF (20 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. 4.94 g (100% purity, 66% of theory) of the title compound were obtained.

LC-MS (Method 1): $R_t$=2.18 min; MS (ESIpos): m/z=278 [M+H]$^+$ $^1$H-NMR (400 MHz, DMSO-d6) δ [ppm]: 7.29 (dd, 1H), 7.23 (dd, 1H), 7.11 (td, 1H), 4.34 (dd, 1H), 2.42-2.34 (m, 2H), 2.30 (s, 3H), 2.17-1.96 (m, 2H), 1.40 (s, 9H).

Example 19A

(+/−)-tert-Butyl 4-(2-chloro-3,6-difluorophenyl)-4-cyanobutanoate (Racemate)

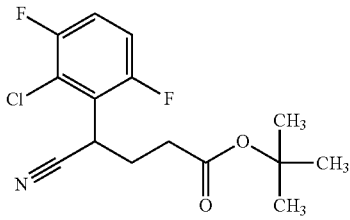 [SMILES: CC(C)(C)OC(=O)CCC(C#N)c1c(F)ccc(F)c1Cl]

To a solution of (2-chloro-3,6-difluorophenyl)acetonitrile (3.84 g, 20.5 mmol, Example 9A) in THF (15 ml) under argon was added gradually while stirring, at −78° C., a 2 M solution of LDA in THF (12 ml, 25 mmol). The mixture was allowed to come to 0° C. and, after 15 min, cooled back down again to −78° C. Subsequently, a solution of tert-butyl 3-bromopropanoate (2.6 ml, 16 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. 4.14 g (95% purity, 61% of theory) of the title compound were obtained.

LC-MS (Method 1): $R_t$=2.17 min; MS (ESIpos): m/z=338 [M+Na]$^+$ $^1$H-NMR (400 MHz, DMSO-d6) δ [ppm]: 7.58 (td, 1H), 7.45 (td, 1H), 4.68 (t, 1H), 2.39-2.32 (m, 2H), 2.29-2.17 (m, 1H), 2.17-2.05 (m, 1H), 1.37 (s, 9H).

Example 20A

(+/−)-tert-Butyl 4-cyano-4-[2-fluoro-6-(trifluoromethyl)phenyl]butanoate (Racemate)

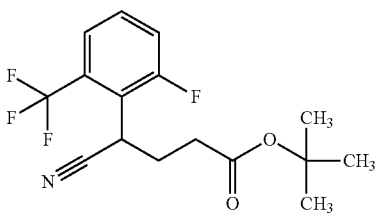

The reaction was conducted under argon. To prepare an LDA solution, butyllithium (1.6 M solution in hexane, 27 ml, 43 mmol) was added gradually at −15° C. to a solution of diisopropylamine (6.2 ml, 44 mmol) in THF (27 ml), and the mixture was stirred at 0° C. for a further 10 min. This solution was slowly added dropwise to a solution, cooled to −78° C., of [2-fluoro-6-(trifluoromethyl)phenyl]acetonitrile (8.01 g, 98% purity, 38.7 mmol, CAS-RN 179946-34-0, commercially available) in 74 ml of THF. On completion of addition, the cooling bath was removed, the mixture was allowed to come to 0° C. and, after 15 min, was cooled again to −78° C. Subsequently, a solution of tert-butyl 3-bromopropanoate (8.0 ml, 97% purity, 46 mmol) in 27 ml of THF was slowly added dropwise and the mixture was stirred at −78° C. for a further 1 h. The cooling bath was removed, and stirring of the reaction mixture at RT was continued overnight. For workup, an ammonium chloride solution (10% in water, 300 ml) was added, and the mixture was stirred vigorously for 5 min and then extracted twice with ethyl acetate. The combined organic phases were washed successively, twice each time, with 1 M hydrochloric acid, a saturated aqueous sodium hydrogencarbonate solution and a saturated aqueous sodium chloride solution, then dried over sodium sulfate and concentrated under reduced pressure. The residue was dissolved in a mixture of cyclohexane, a little ethyl acetate and dichloromethane, and purified by means of flash chromatography on silica gel (cyclohexane/ethyl acetate gradient 100:0 to 70:30). The combined target fractions were concentrated, and the residue was dried under reduced pressure and then purified further by means of preparative HPLC (Method 24). The product-containing fractions were concentrated, and the residue was dried under reduced pressure. 4.52 g (100% purity, 35% of theory) of the title compound were obtained.

LC-MS (Method 1): $R_t$=2.23 min; MS (ESIpos): m/z=332 [M+H]$^+$ $^1$H-NMR (400 MHz, DMSO-d6) δ [ppm]: 1.219 (0.06), 1.379 (16.00), 1.536 (0.07), 2.073 (0.16), 2.091 (0.22), 2.107 (0.28), 2.125 (0.26), 2.144 (0.10), 2.213 (0.07), 2.231 (0.19), 2.250 (0.22), 2.267 (0.18), 2.285 (0.13), 2.302 (0.08), 2.327 (0.07), 2.365 (0.07), 2.384 (0.36), 2.393 (0.38), 2.402 (0.59), 2.410 (0.56), 2.420 (0.29), 2.428 (0.27), 2.452 (0.06), 2.669 (0.06), 4.373 (0.20), 4.390 (0.39), 4.407 (0.19), 7.698 (0.31), 7.711 (1.11), 7.722 (0.54), 7.748 (0.35), 7.766 (0.11).

Example 21A

(+/−)-tert-Butyl 4-cyano-4-(2,3,6-trichlorophenyl)butanoate (Racemate)

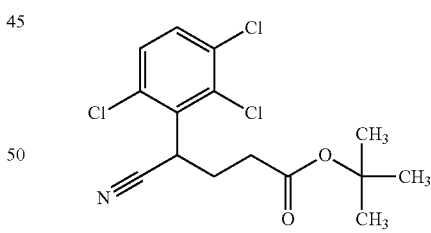

The reaction was conducted under argon. To prepare an LDA solution, butyllithium (1.6 M solution in hexane, 30 ml, 48 mmol) was added gradually at −15° C. to a solution of diisopropylamine (7.1 ml, 51 mmol) in THF (30 ml), and the mixture was stirred at 0° C. for a further 10 min. This solution was slowly added dropwise to a solution, cooled to −78° C., of (2,3,6-trichlorophenyl)acetonitrile (10.0 g, 97% purity, 44.0 mmol, CAS-RN 3215-65-4, commercially available) in THF (84 ml). On completion of addition, the cooling bath was removed, the mixture was allowed to come to 0° C. and, after 15 min, was cooled again to −78° C. Subsequently, a solution of tert-butyl 3-bromopropanoate (9.1 ml, 97% purity, 53 mmol) in THF (30 ml) was slowly added dropwise and the mixture was stirred at −78° C. for a further 1 h. The cooling bath was removed, and stirring of the reaction mixture at RT was continued overnight. For workup, an ammonium chloride solution (10% in 300 ml of water) was added, and the mixture was stirred vigorously for 5 min and then extracted twice with ethyl acetate.

The combined organic phases were washed successively, twice each time, with 1 M hydrochloric acid, a saturated aqueous sodium hydrogencarbonate solution and a saturated aqueous sodium chloride solution, and then dried over sodium sulfate and concentrated under reduced pressure. The residue was purified by preparative HPLC (Method 24). The combined target fractions were concentrated, and the residue was dried under reduced pressure. 10.2 g (95% purity, 63% of theory) of the title compound were obtained.

LC-MS (Method 1): $R_t$=2.41 min; MS (ESIpos): m/z=348 [M+H]$^+$ $^1$H-NMR (500 MHz, DMSO-d6) δ [ppm]: 1.382 (16.00), 1.997 (0.45), 2.316 (0.42), 2.367 (0.45), 2.381 (0.71), 2.403 (0.63), 3.322 (0.80), 5.002 (0.48), 7.620 (0.69), 7.637 (0.90), 7.746 (0.92), 7.763 (0.70).

Example 22A (+/−)-tert-Butyl 4-cyano-4-[2-(difluoromethoxy)-6-fluorophenyl]butanoate (Racemate)

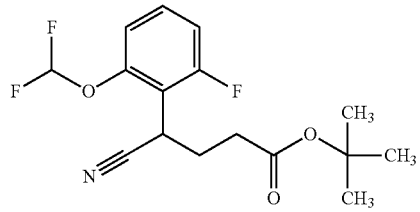 [SMILES: CC(C)(C)OC(=O)CCC(C#N)c1c(F)cccc1OC(F)F]

To a solution of [2-(difluoromethoxy)-6-fluorophenyl] acetonitrile (7.24 g, 36.0 mmol, Example 10A) in THF (30 ml) under argon was added gradually while stirring, at about −70 to −60° C., a 2 M solution of LDA in THF (22 ml, 43 mmol). The mixture was allowed to come to 0° C. and, after 15 min, cooled back down again to −70° C. Subsequently, a solution of tert-butyl 3-bromopropanoate (6.8 ml, 43 mmol) in THF (15 ml) was slowly added dropwise thereto at about −70 to −60° C. while stirring. Stirring of the mixture was continued overnight, in the course of which the cooling bath (dry ice/isopropanol) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by means of flash column chromatography (400 g of silica gel, cyclohexane/ethyl acetate gradient 10:1). The combined target fractions were concentrated, and the residue was dried under reduced pressure. 7.11 g (74% purity, 45% of theory) of the title compound were obtained.

LC-MS (Method 2): $R_t$=1.10 min; MS (ESIpos): m/z=330 [M+H]$^+$

Example 23A (+/−)-tert-Butyl 4-amino-3-(2-chloro-6-fluorophenyl)butanoate (Racemate)

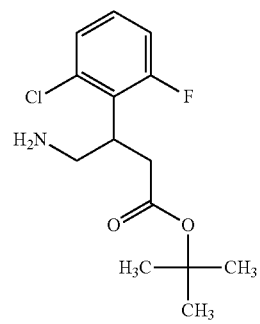 [SMILES: CC(C)(C)OC(=O)CC(CN)c1c(F)cccc1Cl]

To a solution of (+/−)-tert-butyl 3-(2-chloro-6-fluorophenyl)-3-cyanopropanoate (43.9 g, 79% purity, 122 mmol, Example 11A) in tert-butanol (500 ml) was added Raney nickel (7.15 g, 122 mmol), and hydrogenation was effected at standard pressure (1 atm) for four days. Subsequently, Raney nickel (7.15 g, 122 mmol) was again added to the mixture and hydrogenation was effected at standard pressure (1 atm) for a further 24 h. Thereafter, the catalyst was filtered off through kieselguhr, which was washed through twice with tert-butanol (15 ml each time). The filtrate was concentrated and the residue was taken up in ethyl acetate (300 ml) and extracted twice with 1 M hydrochloric acid (250 ml each time). Subsequently, the aqueous phase was adjusted to pH 8-9 with saturated aqueous sodium hydrogencarbonate solution and extracted twice with ethyl acetate (200 ml each time). The combined organic phases were dried over sodium sulfate, filtered and concentrated, and the residue was dried under reduced pressure. 20.11 g (99% purity, 57% of theory) of the title compound were obtained.

LC-MS (Method 2): $R_t$=0.55 min; MS (ESIpos): m/z=288 [M+H]$^+$

Example 24A (+/−)-tert-Butyl 5-amino-4-(2-chloro-5-fluorophenyl)pentanoate (Racemate)

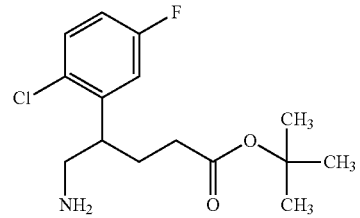

To a solution of (+/−)-tert-butyl 4-(2-chloro-5-fluorophenyl)-4-cyanobutanoate (14.0 g, 93% purity, 43.7 mmol, Example 12A) in tert-butanol (260 ml) was added Raney nickel (2.57 g, 43.7 mmol), and hydrogenation was effected at standard pressure (1 atm) overnight. Subsequently, Raney nickel (2.57 g, 43.7 mmol) was again added to the mixture and hydrogenation was effected at standard pressure (1 atm) for a further 24 h. Subsequently, Raney nickel (2.57 g, 43.7 mmol) was once more added to the mixture and hydrogenation was effected at standard pressure (1 atm) for a further 24 h. Thereafter, the catalyst was filtered off through kieselguhr and the mother liquor was concentrated. 14.4 g (60% purity, 65% of theory) of the title compound were obtained.

LC-MS (Method 1): $R_t$=1.14 min; MS (ESIpos): m/z=302 [M+H]$^+$

Example 25A (+/−)-tert-Butyl 5-amino-4-(2-chlorophenyl)pentanoate (Racemate)

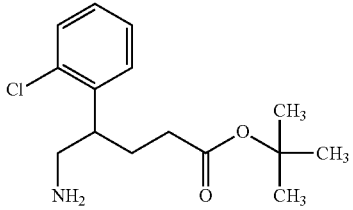 [SMILES: CC(C)(C)OC(=O)CCC(CN)c1ccccc1Cl]

To a solution of (+/−)-tert-butyl 4-(2-chlorophenyl)-4-cyanobutanoate (4.50 g, 16.1 mmol, Example 13A) in tert-butanol (90 ml) was added Raney nickel (944 mg, 16.1 mmol), and hydrogenation was effected at standard pressure (1 atm) overnight. Subsequently, Raney nickel (944 mg, 16.1 mmol) was again added to the mixture and hydrogenation was effected at standard pressure (1 atm) for a further 24 h. Thereafter, the catalyst was filtered off through kieselguhr and the mother liquor was concentrated. The residue was taken up in dichloromethane and purified by means of flash chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. 1.62 g (91% purity, 32% of theory) of the title compound were obtained.

LC-MS (Method 3): $R_t$=1.70 min; MS (ESIpos): m/z=284 [M+H]$^+$

Example 26A (+/−)-tert-Butyl 5-amino-4-[2-(trifluoromethyl)phenyl]pentanoate (Racemate)

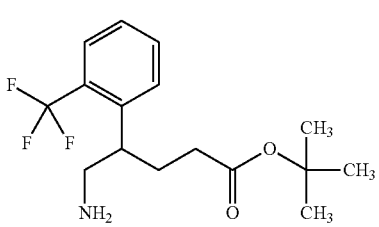 [SMILES: CC(C)(C)OC(=O)CCC(CN)c1ccccc1C(F)(F)F]

To a solution of (+/−)-tert-butyl 4-cyano-4-[2-(trifluoromethyl)phenyl]butanoate (18.6 g, 59.5 mmol, Example 14A) in tert-butanol (200 ml) was added Raney nickel (3.49 g, 59.5 mmol), and hydrogenation was effected at standard pressure (1 atm) for 24 h. Thereafter, the catalyst was filtered off through kieselguhr, which was washed through twice with tert-butanol (50 ml each time). The filtrate was concentrated, and the residue was dried under reduced pressure. 17.8 g (82% purity, 77% of theory) of the title compound were obtained.

LC-MS (Method 1): $R_t$=1.23 min; MS (ESIpos): m/z=318 [M+H]$^+$

Example 27A (+/−)-tert-Butyl 5-amino-4-[2-(trifluoromethoxy)phenyl]pentanoate (Racemate)

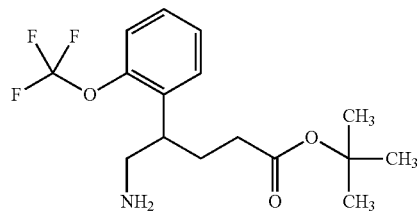 [SMILES: CC(C)(C)OC(=O)CCC(CN)c1ccccc1OC(F)(F)F]

To a solution of (+/−)-tert-butyl 4-cyano-4-[2-(trifluoromethoxy)phenyl]butanoate (3.13 g, 80% purity, 7.59 mmol, Example 15A) in tert-butanol (45 ml) was added Raney nickel (446 mg, 7.59 mmol), and hydrogenation was effected at standard pressure (1 atm) overnight. Subsequently, Raney nickel (446 mg, 7.59 mmol) was added again, and the mixture was hydrogenated at standard pressure (1 atm) for a further 24 h. Thereafter, the catalyst was filtered off through kieselguhr and the filtrate was concentrated and dried under reduced pressure. 3.00 g (83% purity, 98% of theory) of the title compound were obtained.

LC-MS (Method 1): $R_t$=1.29 min; MS (ESIpos): m/z=334 [M+H]$^+$

Example 28A (+/−)-tert-Butyl 5-amino-4-(2-chloro-3-fluorophenyl)pentanoate (Racemate)

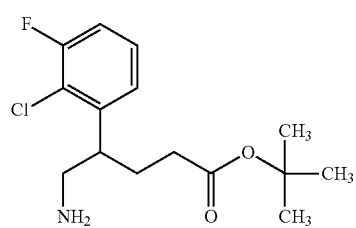

To a solution of (+/−)-tert-butyl 4-(2-chloro-3-fluorophenyl)-4-cyanobutanoate (4.32 g, 14.5 mmol, Example 16A) in tert-butanol (85 ml) was added Raney nickel (852 mg, 14.5 mmol), and hydrogenation was effected at standard pressure (1 atm) overnight. Subsequently, the catalyst was filtered off through kieselguhr, which was washed through twice with tert-butanol (15 ml), and the mother liquor was concentrated. The residue was taken up in ethyl acetate (80 ml) and extracted successively with 1 M hydrochloric acid and water (80 ml each time). The combined aqueous phases were adjusted to pH 8-9 with saturated aqueous sodium hydrogencarbonate solution and extracted twice with ethyl acetate (80 ml). The combined organic phases were dried over sodium sulfate, filtered and concentrated, and the residue was dried under reduced pressure. 2.43 g (85% purity, 47% of theory) of the title compound were obtained.

LC-MS (Method 1): $R_t$=1.28 min; MS (ESIpos): m/z=302 [M+H]$^+$

Example 29A (+/−)-tert-Butyl 5-amino-4-(6-chloro-2,3-difluorophenyl)pentanoate (Racemate)

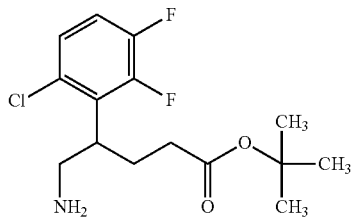 [SMILES: CC(C)(C)OC(=O)CCC(CN)c1c(Cl)ccc(F)c1F]

To a solution of (+/−)-tert-butyl 4-(6-chloro-2,3-difluorophenyl)-4-cyanobutanoate (2.26 g, 83% purity, 5.95 mmol, Example 17A) in tert-butanol (35 ml) was added Raney nickel (349 mg, 5.95 mmol), and hydrogenation was effected at standard pressure (1 atm) overnight. Subsequently, the catalyst was filtered off through kieselguhr, which was washed through twice with tert-butanol (10 ml), and the filtrate was concentrated. The residue was taken up in ethyl acetate (50 ml) and extracted successively with 1 M hydrochloric acid and water (50 ml each time). The combined aqueous phases were adjusted to pH 8-9 with saturated aqueous sodium hydrogencarbonate solution and extracted twice with ethyl acetate (50 ml). The combined organic phases were dried over sodium sulfate, filtered and concentrated, and the residue was dried under reduced pressure. 1.05 g (97% purity, 53% of theory) of the title compound were obtained.

LC-MS (Method 4): $R_t$=1.82 min; MS (ESIpos): m/z=320 [M+H]$^+$

Example 30A (+/−)-tert-Butyl 5-amino-4-(5-fluoro-2-methylphenyl)pentanoate (Racemate)

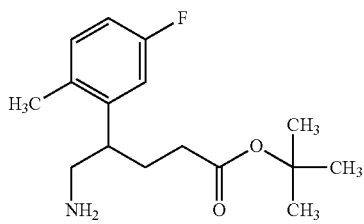

To a solution of (+/−)-tert-butyl 4-cyano-4-(5-fluoro-2-methylphenyl)butanoate (4.92 g, 17.7 mmol, Example 18A) in tert-butanol (100 ml) was added Raney nickel (1.04 g, 17.7 mmol), and hydrogenation was effected at standard pressure (1 atm) for 24 h. Subsequently, the catalyst was filtered off through kieselguhr, which was washed through twice with tert-butanol (15 ml), and the filtrate was concentrated. The residue was taken up in ethyl acetate (80 ml) and extracted successively with 1 M hydrochloric acid and water (80 ml each time). The combined aqueous phases were adjusted to pH 8-9 with saturated aqueous sodium hydrogencarbonate solution and extracted twice with ethyl acetate (80 ml). The combined organic phases were dried over sodium sulfate, filtered and concentrated, and the residue was dried under reduced pressure. 2.04 g (92% purity, 38% of theory) of the title compound were obtained.

LC-MS (Method 4): $R_t$=1.94 min; MS (ESIpos): m/z=282 [M+H]$^+$ $^1$H-NMR (400 MHz, DMSO-d6) δ [ppm]: 1.109 (0.34), 1.197 (0.07), 1.293 (0.03), 1.357 (16.00), 1.394 (0.15), 1.513 (0.24), 1.609 (0.11), 1.621 (0.11), 1.638 (0.25), 1.648 (0.17), 1.663 (0.22), 1.681 (0.14), 1.709 (0.06), 1.927 (0.05), 1.943 (0.10), 1.950 (0.13), 1.964 (0.28), 1.986 (1.50), 1.995 (1.06), 2.011 (0.26), 2.018 (0.20), 2.072 (0.03), 2.232 (3.57), 2.303 (0.20), 2.366 (0.03), 2.641 (0.07), 2.659 (0.11), 2.672 (0.57), 2.681 (0.59), 2.690 (0.75), 2.696 (0.71), 2.711 (0.09), 2.728 (0.08), 2.851 (0.21), 2.863 (0.20), 3.172 (0.05), 3.312 (0.65), 6.866 (0.17), 6.873 (0.21), 6.887 (0.37), 6.894 (0.43), 6.909 (0.20), 6.916 (0.23), 6.968 (0.43), 6.974 (0.37), 6.994 (0.42), 7.001 (0.36), 7.105 (0.03), 7.150 (0.35), 7.166 (0.40), 7.187 (0.30).

$^1$H-NMR (400 MHz, DMSO-d6) δ [ppm]: 7.17 (dd, 1H), 6.99 (dd, 1H), 6.89 (td, 1H), 2.93-2.80 (m, 1H), 2.74-2.62 (m, 2H), 2.23 (s, 3H), 2.06-1.87 (m, 3H), 1.74-1.60 (m, 1H), 1.50 (br. s, 2H), 1.36 (s, 9H).

Example 31A (+/−)-tert-Butyl 5-amino-4-(2-chloro-3,6-difluorophenyl)pentanoate (Racemate)

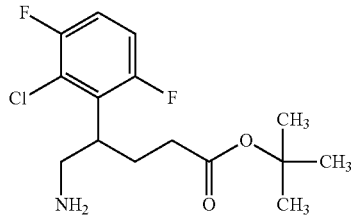 [SMILES: CC(C)(C)OC(=O)CCC(CN)c1c(F)ccc(F)c1Cl]

To a solution of (+/−)-tert-butyl 4-(2-chloro-3,6-difluorophenyl)-4-cyanobutanoate (4.10 g, 13.0 mmol, Example 19A) in tert-butanol (75 ml) was added Raney nickel (762 mg, 13.0 mmol), and hydrogenation was effected at standard pressure (1 atm) for 24 h. Subsequently, the catalyst was filtered off through kieselguhr, which was washed through twice with tert-butanol (15 ml), and the mother liquor was concentrated. The residue was taken up in ethyl acetate (80 ml) and the solution was extracted successively with 1 M hydrochloric acid and water (80 ml each time). The combined aqueous phases were adjusted to pH 8-9 with saturated aqueous sodium hydrogencarbonate solution and extracted twice with ethyl acetate (100 ml each time). The combined organic phases were dried over sodium sulfate, filtered and concentrated, and the residue was dried under reduced pressure. 1.76 g (100% purity, 42% of theory) of the title compound were obtained.

LC-MS (Method 1): $R_t$=1.21 min; MS (ESIpos): m/z=320 [M+H]$^+$

Example 32A (+/−)-tert-Butyl 5-amino-4-[2-fluoro-6-(trifluoromethyl)phenyl]pentanoate (Racemate)

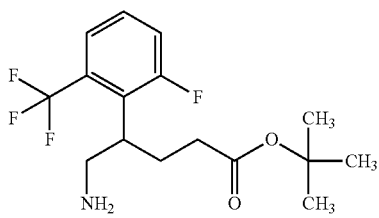

To a solution of (+/−)-tert-butyl 4-cyano-4-[2-fluoro-6-(trifluoromethyl)phenyl]butanoate (4.52 g, 13.6 mmol, Example 20A) in tert-butanol (100 ml) and methanol (15 ml) was added Raney nickel (801 mg, 13.6 mmol), and the mixture was hydrogenated at standard pressure (1 atm) overnight. Raney nickel (2 g, 34.0 mmol) was added once again to the reaction mixture, which was stirred vigorously with hydrogen under standard pressure (1 atm) for 40 h. Subsequently, the catalyst was filtered off through kieselguhr, which was washed through three times with methanol (30 ml each time), and the filtrate was concentrated under reduced pressure. The residue was taken up in 200 ml of ethyl acetate. This organic phase was extracted twice with 200 ml of 1 M hydrochloric acid. The combined aqueous phases were brought to pH 8-9 by gradual addition of sodium hydrogencarbonate, then extracted twice with 200 ml each time of ethyl acetate. The combined organic phases were dried over sodium sulfate and concentrated on a rotary evaporator. The residue was dried under reduced pressure. 3.32 g (92% purity, 67% of theory) of the title compound were obtained.

LC-MS (Method 1): $R_t$=1.21 min; MS (ESIpos): m/z=336 [M+H]$^+$ $^1$H-NMR (400 MHz, DMSO-d6) δ [ppm]: 1.109 (0.25), 1.156 (0.06), 1.167 (0.07), 1.174 (0.12), 1.191 (0.06), 1.327 (16.00), 1.390 (0.40), 1.484 (0.07), 1.882 (0.09), 1.905 (0.14), 1.930 (0.25), 1.946 (0.23), 1.965 (0.29), 1.979 (0.15), 1.987 (0.45), 2.006 (0.19), 2.034 (0.10), 2.055 (0.30), 2.074 (0.35), 2.093 (0.31), 2.118 (0.16), 2.129 (0.11), 2.150 (0.04), 2.310 (0.07), 2.365 (0.02), 2.669 (0.02), 2.782 (0.10), 2.799 (0.17), 2.812 (0.24), 2.828 (0.25), 2.872 (0.18), 2.876 (0.18), 2.890 (0.29), 2.895 (0.30), 2.920 (0.37), 3.494 (0.02), 3.522 (0.03), 4.019 (0.05), 4.037 (0.05), 7.476 (0.66), 7.485 (0.49), 7.489 (0.49), 7.501 (0.31), 7.509 (0.87), 7.521 (0.09), 7.550 (0.51), 7.557 (0.32), 7.564 (0.37), 7.573 (0.26), 7.614 (0.04), 7.637 (0.04).

Example 33A (+/−)-tert-Butyl 5-amino-4-(2,3,6-trichlorophenyl)pentanoate (Racemate)

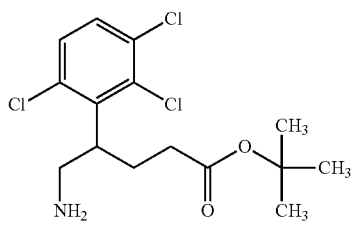 [SMILES: CC(C)(C)OC(=O)CCC(CN)c1c(Cl)ccc(Cl)c1Cl]

To a solution of (+/−)-tert-butyl 4-cyano-4-(2,3,6-trichlorophenyl)butanoate (10.2 g, 95% purity, 27.9 mmol, Example 21A) in tert-butanol (210 ml) and methanol (9.1 ml) was added Raney nickel (1.64 g, 27.9 mmol), and the mixture was hydrogenated at standard pressure (1 atm) overnight while stirring. An additional amount of Raney nickel (2.0 g, 34.0 mmol) was added, and the mixture was hydrogenated at standard pressure (1 atm) while stirring for three further days. Subsequently, the catalyst was filtered off through kieselguhr, which was washed through three times with methanol (30 ml each time), and the filtrate was concentrated. The residue was taken up in ethyl acetate (400 ml). This organic phase was extracted twice with 1 M hydrochloric acid (300 ml). The combined aqueous phases were brought to pH 8-9 by gradual addition of sodium hydrogencarbonate and then extracted twice with ethyl acetate (300 ml each time). The combined organic phases were dried over sodium sulfate and concentrated on a rotary evaporator. Drying under reduced pressure gave 2.54 g (89% purity, 23% of theory) of the title compound.

LC-MS (Method 1): $R_t$=1.30 min; MS (ESIpos): m/z=352 [M+H]$^+$ $^1$H-NMR (400 MHz, DMSO-d6) δ [ppm]: 1.336 (16.00), 1.352 (1.85), 1.492 (0.42), 2.013 (0.65), 2.022 (0.61), 2.030 (0.63), 2.042 (0.89), 2.055 (0.81), 2.070 (0.42), 2.082 (0.42), 2.097 (0.43), 3.049 (0.54), 3.069 (0.57), 7.426 (0.52), 7.506 (0.64), 7.532 (0.56), 7.544 (0.61), 7.553 (0.41).

Example 34A (+/−)-tert-Butyl 5-amino-4-[2-(difluoromethoxy)-6-fluorophenyl]pentanoate (Racemate)

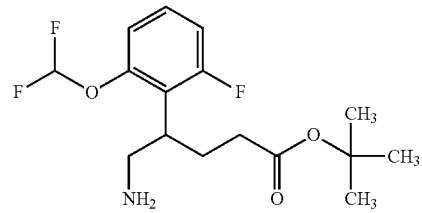 [SMILES: CC(C)(C)OC(=O)CCC(CN)c1c(F)cccc1OC(F)F]

To a solution of (+/−)-tert-butyl 4-cyano-4-[2-(difluoromethoxy)-6-fluorophenyl]butanoate (7.07 g, 74% purity, 16.0 mmol, Example 22A) in tert-butanol (97 ml) was added Raney nickel (937 mg, 16.0 mmol), and hydrogenation was effected at standard pressure (1 atm) for three days. Subsequently, the catalyst was filtered off through kieselguhr, which was washed through twice with tert-butanol (30 ml each time). The filtrate was concentrated, and the residue was dried under reduced pressure. 6.21 g (65% purity, 76% of theory) of the title compound were obtained.

LC-MS (Method 1): $R_t$=1.16 min; MS (ESIpos): m/z=334 [M+H]$^+$

Example 35A (+/−)-tert-Butyl 4-{[(6-bromo-2-chloro-3-methylquinolin-4-yl)carbonyl]amino}-3-(2-chloro-6-fluorophenyl)butanoate (Racemate)

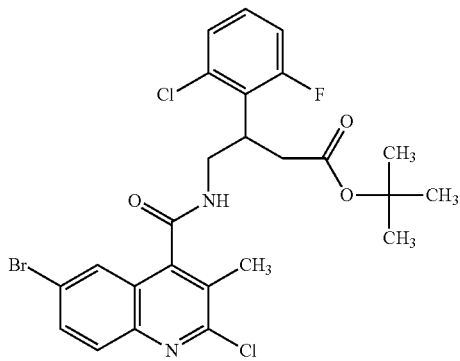 [SMILES: Cc1c(Cl)nc2ccc(Br)cc2c1C(=O)NCC(CC(=O)OC(C)(C)C)c1c(F)cccc1Cl]

To a suspension of (+/−)-tert-butyl 4-amino-3-(2-chloro-6-fluorophenyl)butanoate (541 mg, 1.88 mmol, Example 23A) in dichloromethane (10 ml) at RT was added DIPEA (820 µl, 4.7 mmol). Subsequently, a suspension of 6-bromo-2-chloro-3-methylquinoline-4-carbonyl chloride (500 mg, 1.57 mmol, Example 3A) in dichloromethane (5 ml) was added, and the mixture was stirred at RT for 16 h. Subsequently, dichloromethane and water (30 ml of each) were added to the mixture, which was agitated. After phase separation, the aqueous phase was extracted once with dichloromethane (30 ml). The combined organic phases were dried over sodium sulfate, filtered and concentrated, and the residue was taken up in dichloromethane and purified by means of flash column chromatography (50 g silica gel Biotage Snap-Cartridge KP-Sil, cyclohexane/ethyl acetate gradient 93:7→7:3, Isolera One). The combined target fractions were concentrated and the residue was dried under reduced pressure. 804 mg (96% purity, 86% of theory) of the title compound were obtained.

LC-MS (Method 2): $R_t$=1.30 min; MS (ESIpos): m/z=569/571 [M+H]$^+$ $^1$H-NMR (400 MHz, DMSO-d6) δ [ppm]: 1.241 (16.00), 1.397 (0.24), 2.250 (0.33), 2.755 (0.40), 2.770 (0.37), 3.730 (0.13), 4.051 (0.16), 7.206 (0.19), 7.219 (0.23), 7.246 (0.21), 7.340 (0.65), 7.882 (0.19), 7.905 (1.60), 7.934 (0.13), 8.968 (0.22), 8.983 (0.44), 8.998 (0.22).

$^1$H-NMR (400 MHz, DMSO-d6) δ [ppm]: 8.98 (t, 1H), 7.97-7.86 (m, 2H), 7.86-7.43 (br., 1H), 7.38-7.31 (m, 2H), 7.26-7.17 (m, 1H), 4.16-3.92 (m, 1H), 3.91-3.55 (m, 2H), 2.85-2.62 (m, 2H), 2.25 (br. s, 3H), 1.24 (s, 9H).

Example 36A (+/−)-tert-Butyl 5-{[(6-bromo-2-chloro-3-methylquinolin-4-yl)carbonyl]amino}-4-(2-chloro-5-fluorophenyl)pentanoate (Racemate)

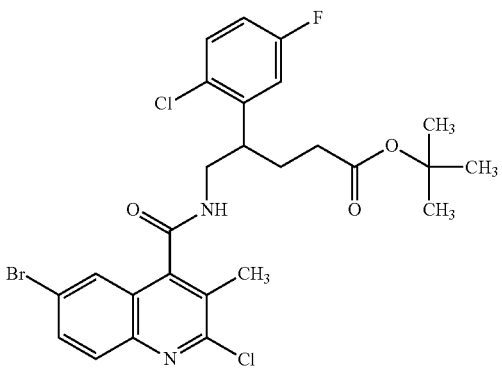 [SMILES: Cc1c(Cl)nc2ccc(Br)cc2c1C(=O)NCC(CCC(=O)OC(C)(C)C)c1cc(F)ccc1Cl]

To a suspension of (+/−)-tert-butyl 5-amino-4-(2-chloro-5-fluorophenyl)pentanoate (2.73 g, 9.03 mmol, Example 24A) in dichloromethane (50 ml) at RT was added DIPEA (3.9 ml, 23 mmol). Subsequently, a suspension of 6-bromo-2-chloro-3-methylquinoline-4-carbonyl chloride (2.45 g, 98% purity, 7.53 mmol, Example 3A) in dichloromethane (35 ml) was added, and the mixture was stirred at RT overnight. Subsequently, the mixture was stirred at 50° C. for a further 20 h. After cooling to RT, dichloromethane and water (50 ml of each) were added to the mixture, which was agitated. After phase separation, the aqueous phase was extracted once with dichloromethane (50 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7→6:4, Isolera One). The combined target fractions were concentrated and the residue was dried under reduced pressure. 1.49 g (98% purity, 33% of theory) of the title compound were obtained.

LC-MS (Method 1): $R_t$=2.58 min; MS (ESIpos): m/z=583/585 [M+H]$^+$ $^1$H-NMR (400 MHz, DMSO-d6) δ [ppm]: 8.87 (t, 1H), 7.93-7.86 (m, 2H), 7.65 (br. m, 1H, partially hidden), 7.51 (dd, 1H), 7.43 (dd, 1H), 7.19-7.11 (m, 1H), 3.73 (br. s, 2H), 3.58 (br. s, 1H), 2.23 (br. s, 3H), 2.14-2.07 (m, 2H), 2.06-1.96 (m, 1H), 1.88-1.73 (m, 1H), 1.37 (s, 9H).

Example 37A (+/−)-tert-Butyl 5-{[(6-bromo-2-chloro-3-methylquinolin-4-yl)carbonyl]amino}-4-(2-chlorophenyl)pentanoate (Racemate)

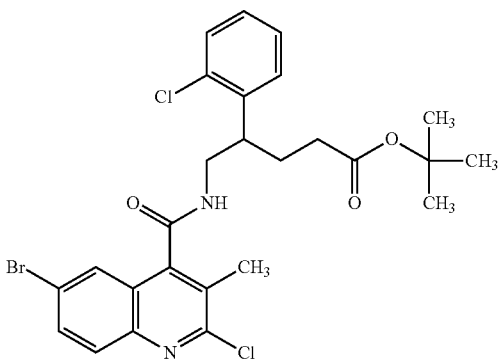 [SMILES: Cc1c(Cl)nc2ccc(Br)cc2c1C(=O)NCC(CCC(=O)OC(C)(C)C)c1ccccc1Cl]

To a suspension of (+/−)-tert-butyl 5-amino-4-(2-chlorophenyl)pentanoate (800 g, 80% purity, 22.6 mmol, Example 25A) in dichloromethane (200 ml) at RT was added DIPEA (9.8 ml, 56 mmol). Subsequently, a suspension of 6-bromo-2-chloro-3-methylquinoline-4-carbonyl chloride (5.99 g, 18.8 mmol, Example 3A) in dichloromethane (30 ml) was added, and the mixture was stirred at RT overnight. Subsequently, dichloromethane and water (50 ml of each) were added to the mixture, which was agitated. After phase separation, the aqueous phase was extracted once with dichloromethane (50 ml). The combined organic phases were dried over sodium sulfate, filtered and concentrated, and the residue was taken up in dichloromethane and purified by means of flash column chromatography (340 g silica gel Biotage Snap-Cartridge, cyclohexane/ethyl acetate gradient 97:3→7:3, Isolera One). The combined target fractions were concentrated to obtain two product fractions, and the residues were dried under reduced pressure. 2.52 g (92% purity, 22% of theory, see analysis) of a first batch of the title compound were obtained. The second product fraction from the chromatography was taken up again in dichloromethane and repurified by means of flash chromatography (100 g silica gel Biotage Snap-Cartridge KP-Sil, cyclohexane/ethyl acetate gradient 97:3→7:3, Isolera One). 1.35 g (88% purity, 11% of theory) of a second batch of the title compound were obtained.

LC-MS (Method 1): $R_f$=2.54 min; MS (ESIpos): m/z=565/567 [M+H]$^+$

Example 38A (+/−)-tert-Butyl 5-{[(6-bromo-2-chloro-3-methylquinolin-4-yl)carbonyl]amino}-4-[2-(trifluoromethyl)phenyl]pentanoate (Racemate)

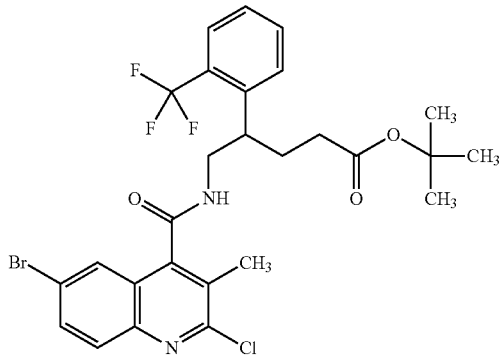 [SMILES: Cc1c(Cl)nc2ccc(Br)cc2c1C(=O)NCC(CCC(=O)OC(C)(C)C)c1ccccc1C(F)(F)F]

To a suspension of (+/−)-tert-butyl 5-amino-4-[2-(trifluoromethyl)phenyl]pentanoate (12.0 g, 82% purity, 30.9 mmol, Example 26A) in dichloromethane (250 ml) at RT was added DIPEA (13 ml, 77 mmol). Subsequently, a suspension of 6-bromo-2-chloro-3-methylquinoline-4-carbonyl chloride (8.22 g, 25.8 mmol, Example 3A) in dichloromethane (50 ml) was added, and the mixture was stirred at RT for 18 h. Subsequently, water (400 ml) was added to the mixture, which was agitated. After phase separation, the aqueous phase was extracted once with dichloromethane (200 ml). The combined organic phases were washed with saturated aqueous sodium chloride solution, dried over sodium sulfate, filtered and concentrated, and the residue was purified by means of flash column chromatography (100 g silica gel Biotage Snap-Cartridge Ultra, cyclohexane/ethyl acetate gradient 97:3→75:25, Isolera One). The combined target fractions were concentrated, and the residue was dried under reduced pressure. 11.7 g (100% purity, 76% of theory) of the title compound were obtained.

LC-MS (Method 1): $R_f$=2.60 min; MS (ESIpos): m/z=599/601 [M+H]$^+$ $^1$H-NMR (400 MHz, DMSO-d6) δ [ppm]: 1.188 (0.07), 1.318 (0.14), 1.349 (16.00), 1.398 (0.94), 1.505 (0.07), 1.871 (0.13), 1.894 (0.17), 1.909 (0.20), 2.004 (0.25), 2.024 (0.50), 2.039 (0.49), 2.058 (0.33), 2.087 (0.27), 2.240 (0.18), 2.366 (0.11), 2.670 (0.06), 3.670 (0.14), 3.752 (0.17), 5.754 (0.11), 7.487 (0.36), 7.505 (0.24), 7.692 (0.19), 7.712 (0.44), 7.728 (0.81), 7.747 (0.98), 7.765 (0.28), 7.904 (2.33), 7.930 (0.08), 8.907 (0.34).

Separation of the Enantiomers:

The title compound (7.0 g) was dissolved in isopropanol (140 ml) and separated into the enantiomers by means of preparative SFC on chiral phase (see Examples 39A and 40A) [column: Daicel Chiralcel OD-H, 5 μm, 250 mm×50 mm; flow rate: 175 ml/min; injection: 1.2 ml; eluent: 17% isopropanol/83% carbon dioxide; run time 15 min, isocratic, UV detection 210 nm, temperature 38° C.]. The combined target fractions were each concentrated, and the respective residue was lyophilized.

Example 39A (−)-tert-Butyl 5-{[(6-bromo-2-chloro-3-methylquinolin-4-yl)carbonyl]amino}-4-[2-(trifluoromethyl)phenyl]pentanoate (Enantiomer 1)

In the enantiomer separation described in Example 38A, 3.37 g (100% purity, ee>99%) of the title compound were obtained as the enantiomer that eluted earlier.

$[α]_D^{20}$=−19.3°, 589 nm, c=0.38 g/100 ml, methanol

LC-MS (Method 1): $R_f$=2.60 min; MS (ESIpos): m/z=599/601 [M+H]$^+$ $^1$H-NMR (400 MHz, DMSO-d6) δ [ppm]: −0.009 (0.17), 0.007 (0.15), 1.029 (2.07), 1.044 (2.09), 1.187 (0.07), 1.310 (0.10), 1.317 (0.13), 1.348 (16.00), 1.503 (0.06), 1.871 (0.11), 1.894 (0.15), 1.908 (0.18), 1.918 (0.15), 1.941 (0.10), 1.963 (0.05), 1.984 (0.07), 2.003 (0.23), 2.023 (0.46), 2.038 (0.45), 2.057 (0.31), 2.080 (0.22), 2.087 (0.25), 2.100 (0.18), 2.117 (0.18), 2.130 (0.14), 2.151 (0.11), 2.239 (0.15), 2.365 (0.07), 2.669 (0.04), 3.669 (0.13), 3.751 (0.22), 3.762 (0.20), 3.766 (0.22), 3.777 (0.19), 3.782 (0.16), 3.792 (0.14), 4.323 (0.26), 4.334 (0.26), 7.467 (0.17), 7.485 (0.32), 7.503 (0.21), 7.691 (0.18), 7.710 (0.40), 7.727 (0.74), 7.745 (0.90), 7.764 (0.24), 7.881 (0.08), 7.902 (2.20), 7.929 (0.06), 8.907 (0.31).

Example 40A (+)-tert-Butyl 5-{[(6-bromo-2-chloro-3-methylquinolin-4-yl)carbonyl]amino}-4-[2-(trifluoromethyl)phenyl]pentanoate (Enantiomer 2)

In the enantiomer separation described in Example 38A, 3.32 g (100% purity, ee 99%) of the title compound were obtained as the enantiomer that eluted later.

$[α]_D^{20}$=+18.0°, 589 nm, c=0.33 g/100 ml, methanol

LC-MS (Method 1): $R_f$=2.60 min; MS (ESIpos): m/z=599/601 [M+H]$^+$ $^1$H-NMR (400 MHz, DMSO-d6) δ [ppm]: 1.029 (2.26), 1.044 (2.27), 1.187 (0.07), 1.317 (0.13), 1.347 (16.00), 1.503 (0.06), 1.870 (0.12), 1.894 (0.16), 1.908 (0.19), 1.941 (0.10), 2.003 (0.24), 2.023 (0.48), 2.038 (0.47), 2.057 (0.32), 2.086 (0.26), 2.117 (0.18), 2.222 (0.16), 2.365 (0.08), 2.669 (0.05), 3.669 (0.13), 3.751 (0.24), 3.762 (0.22), 3.766 (0.24), 3.777 (0.21), 3.792 (0.15), 4.323 (0.32), 4.333 (0.31), 7.466 (0.17), 7.484 (0.34), 7.503 (0.23), 7.691 (0.18), 7.710 (0.42), 7.727 (0.77), 7.745 (0.94), 7.764 (0.25), 7.881 (0.08), 7.902 (2.28), 7.929 (0.07), 8.906 (0.32).

Example 41A (+/−)-tert-Butyl 5-{[(6-bromo-2-chloro-3-methylquinolin-4-yl)carbonyl]amino}-4-[2-(trifluoromethoxy)phenyl]pentanoate (Racemate)

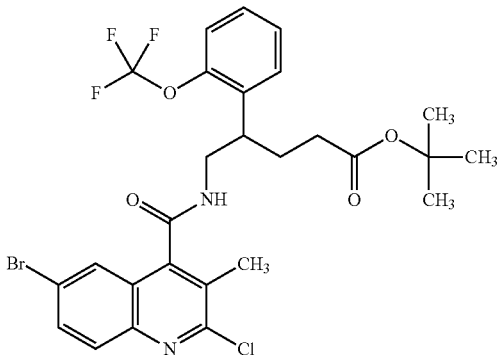 [SMILES: Cc1c(Cl)nc2ccc(Br)cc2c1C(=O)NCC(CCC(=O)OC(C)(C)C)c1ccccc1OC(F)(F)F]

To a suspension of (+/−)-tert-butyl 5-amino-4-[2-(trifluoromethoxy)phenyl]pentanoate (10.0 g, 78% purity, 23.4 mmol, Example 27A) in dichloromethane (250 ml) at RT was added DIPEA (10 ml, 58 mmol). Subsequently, a suspension of 6-bromo-2-chloro-3-methylquinoline-4-carbonyl chloride (6.21 g, 19.5 mmol, Example 3A) in dichloromethane (50 ml) was added, and the mixture was stirred at RT for 18 h. Subsequently, water (400 ml) was added to the mixture, which was agitated. After phase separation, the aqueous phase was extracted once with dichloromethane (200 ml). The combined organic phases were washed with saturated aqueous sodium chloride solution, dried over sodium sulfate, filtered and concentrated, and the residue was purified by means of flash column chromatography (100 g silica gel Biotage Snap-Cartridge Ultra, cyclohexane/ethyl acetate gradient 97:3→75:25, Isolera One). The combined target fractions were concentrated, and the residue was dried under reduced pressure. 9.91 g (92% purity, 76% of theory) of the title compound were obtained.

LC-MS (Method 1): $R_t$=2.63 min; MS (ESIpos): m/z=615/617 [M+H]$^+$ $^1$H-NMR (400 MHz, DMSO-d6) δ [ppm]: 1.202 (0.07), 1.300 (0.34), 1.361 (16.00), 1.787 (0.09), 1.807 (0.20), 1.830 (0.19), 2.038 (0.28), 2.062 (0.92), 2.069 (1.14), 2.096 (0.23), 2.219 (0.18), 2.308 (0.23), 2.365 (0.08), 3.385 (0.19), 3.632 (0.13), 3.650 (0.24), 3.665 (0.31), 3.683 (0.28), 3.702 (0.29), 3.720 (0.24), 7.370 (0.40), 7.405 (0.64), 7.428 (0.48), 7.554 (0.40), 7.567 (0.37), 7.578 (0.29), 7.879 (0.11), 7.901 (1.98), 8.882 (0.34).

Separation of the Enantiomers:

The title compound (5.26 g) was taken up in isopropanol (120 ml). This was followed by filtration, the filter residue was washed through with 12 ml of isopropanol, and the solution was separated into the enantiomers by means of preparative SFC on chiral phase (see Examples 42A and 43A) [column: Daicel Chiralcel OD-H, 5 µm, 250 mm×50 mm; flow rate: 175 ml/min; injection: 0.8 ml; eluent: 15% isopropanol/85% carbon dioxide; run time 14.5 min, isocratic, UV detection 210 nm, temperature 40° C.]. The combined target fractions were concentrated, and the respective residue was lyophilized.

Example 42A (+)-tert-Butyl 5-{[(6-bromo-2-chloro-3-methylquinolin-4-yl)carbonyl]amino}-4-[2-(trifluoromethoxy)phenyl]pentanoate (Enantiomer 1)

In the enantiomer separation described in Example 41A, 2.37 g (100% purity, ee 100%) of the title compound were obtained as the enantiomer that eluted earlier.

$[α]_D^{20}$=+16.3°, 589 nm, c=0.45 g/100 ml, methanol

LC-MS (Method 1): $R_t$=2.64 min; MS (ESIpos): m/z=615/617 [M+H]$^+$ $^1$H-NMR (400 MHz, DMSO-d6) δ [ppm]: 1.029 (0.18), 1.044 (0.18), 1.201 (0.07), 1.300 (0.06), 1.317 (0.07), 1.325 (0.09), 1.361 (16.00), 1.517 (0.07), 1.788 (0.10), 1.807 (0.21), 1.830 (0.21), 1.877 (0.06), 2.038 (0.31), 2.063 (1.04), 2.069 (1.28), 2.096 (0.25), 2.223 (0.20), 2.365 (0.06), 2.669 (0.05), 3.384 (0.22), 3.617 (0.08), 3.632 (0.14), 3.650 (0.27), 3.665 (0.35), 3.683 (0.32), 3.702 (0.31), 3.720 (0.26), 3.735 (0.13), 3.754 (0.08), 7.370 (0.43), 7.405 (0.68), 7.422 (0.54), 7.428 (0.52), 7.554 (0.44), 7.567 (0.41), 7.577 (0.32), 7.879 (0.11), 7.901 (2.03), 7.928 (0.08), 8.882 (0.39).

Example 43A (−)-tert-Butyl 5-{[(6-bromo-2-chloro-3-methylquinolin-4-yl)carbonyl]amino}-4-[2-(trifluoromethoxy)phenyl]pentanoate (Enantiomer 2)

In the enantiomer separation described in Example 41A, 2.40 g (100% purity, ee 99%) of the title compound were obtained as the enantiomer that eluted later.

$[α]_D^{20}$=−15.9°, 589 nm, c=0.44 g/100 ml, methanol

LC-MS (Method 1): $R_t$=2.63 min; MS (ESIpos): m/z=615/617 [M+H]$^+$ $^1$H-NMR (400 MHz, DMSO-d6) δ [ppm]: 1.029 (0.50), 1.044 (0.50), 1.201 (0.07), 1.316 (0.07), 1.325 (0.09), 1.361 (16.00), 1.517 (0.06), 1.788 (0.09), 1.807 (0.20), 1.830 (0.20), 2.038 (0.28), 2.063 (0.96), 2.069 (1.20), 2.096 (0.22), 2.222 (0.17), 2.308 (0.19), 2.365 (0.06), 2.669 (0.05), 3.384 (0.20), 3.617 (0.08), 3.632 (0.13), 3.650 (0.25), 3.666 (0.32), 3.683 (0.29), 3.702 (0.29), 3.720 (0.24), 3.736 (0.12), 3.754 (0.08), 4.323 (0.07), 4.333 (0.07), 7.369 (0.40), 7.405 (0.64), 7.421 (0.50), 7.428 (0.50), 7.554 (0.40), 7.567 (0.37), 7.577 (0.31), 7.879 (0.11), 7.901 (1.97), 8.882 (0.36).

Example 44A (+/−)-tert-Butyl 5-{[(6-bromo-2-chloro-3-methylquinolin-4-yl)carbonyl]amino}-4-(2-chloro-3-fluorophenyl)pentanoate (Racemate)

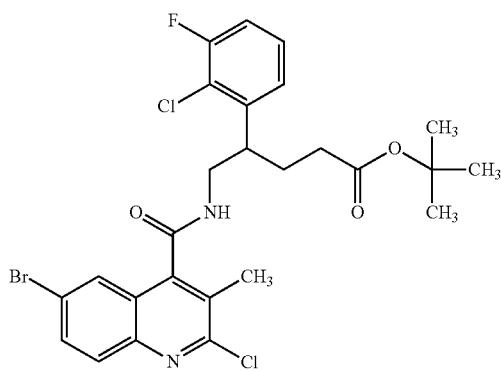 [SMILES: Cc1c(Cl)nc2ccc(Br)cc2c1C(=O)NCC(CCC(=O)OC(C)(C)C)c1cccc(F)c1Cl]

To a solution of (+/−)-tert-butyl 5-amino-4-(2-chloro-3-fluorophenyl)pentanoate (1.40 g, 85% purity, 3.94 mmol, Example 28A) in dichloromethane (45 ml) at RT was added DIPEA (1.7 ml, 9.9 mmol). Subsequently, 6-bromo-2-chloro-3-methylquinoline-4-carbonyl chloride (1.07 g, 98% purity, 3.29 mmol, Example 3A) was added, and the mixture was stirred at RT for 20 h. Subsequently, water and dichloromethane (150 ml of each) were added to the mixture, which was agitated. After phase separation, the aqueous phase was extracted once with dichloromethane (150 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 206 mg (100% purity, 11% of theory) of the title compound were obtained.

LC-MS (Method 2): $R_t$=1.32 min; MS (ESIpos): m/z=583/585 [M−H]⁻

¹H-NMR (400 MHz, DMSO-d6) δ [ppm]: 1.210 (0.08), 1.370 (16.00), 1.397 (2.57), 1.828 (0.24), 2.035 (0.25), 2.052 (0.26), 2.071 (0.32), 2.090 (1.00), 2.106 (1.01), 2.126 (0.40), 2.218 (0.37), 3.603 (0.25), 3.733 (0.32), 7.313 (0.33), 7.335 (0.25), 7.355 (0.33), 7.374 (0.52), 7.419 (0.29), 7.896 (2.22), 7.923 (0.14), 8.855 (0.29), 8.870 (0.52).

Example 45A (+/−)-tert-Butyl 5-{[(6-bromo-2-chloro-3-methylquinolin-4-yl)carbonyl]amino}-4-(6-chloro-2,3-difluorophenyl)pentanoate (Racemate)

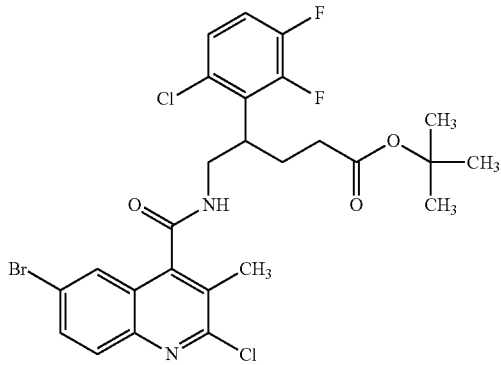 [SMILES: Cc1c(Cl)nc2ccc(Br)cc2c1C(=O)NCC(CCC(=O)OC(C)(C)C)c1c(Cl)ccc(F)c1F]

To a solution of (+/−)-tert-butyl 5-amino-4-(6-chloro-2,3-difluorophenyl)pentanoate (400 mg, 96% purity, 1.20 mmol, Example 29A) in dichloromethane (12 ml) at RT was added DIPEA (520 µl, 3.0 mmol). Subsequently, 6-bromo-2-chloro-3-methylquinoline-4-carbonyl chloride (326 mg, 98% purity, 1.00 mmol, Example 3A) was added, and the mixture was stirred at RT for 20 h. Subsequently, water and dichloromethane (10 ml of each) were added to the mixture, which was agitated. After phase separation, the aqueous phase was extracted once with dichloromethane (100 ml). The combined organic phases were dried over sodium sulfate, filtered and concentrated, and the residue was taken up in dichloromethane and purified by means of flash column chromatography (25 g silica gel Biotage Snap-Cartridge Ultra, cyclohexane/ethyl acetate gradient 97:3→7:3, Isolera One). The combined target fractions were concentrated, and the residue was dried under reduced pressure. 156 mg (87% purity, 23% of theory) of the title compound were obtained.

LC-MS (Method 2): $R_t$=1.34 min; MS (ESIpos): m/z=601/603 [M+H]⁺

¹H-NMR (400 MHz, DMSO-d6) δ [ppm]: 0.007 (0.31), 1.203 (0.08), 1.260 (0.09), 1.309 (0.11), 1.363 (16.00), 1.397 (2.44), 1.970 (0.12), 2.056 (0.23), 2.075 (0.22), 2.159 (0.48), 2.176 (0.70), 2.242 (1.02), 2.351 (0.88), 2.365 (0.11), 2.669 (0.08), 2.709 (0.08), 3.097 (0.10), 3.702 (0.26), 3.804 (0.30), 7.402 (0.45), 7.737 (0.19), 7.878 (0.19), 7.901 (1.91), 7.908 (1.10), 7.929 (0.48), 8.965 (0.37).

Example 46A (+/−)-tert-Butyl 5-{[(6-bromo-2-chloro-3-methylquinolin-4-yl)carbonyl]amino}-4-(5-fluoro-2-methylphenyl)pentanoate (Racemate)

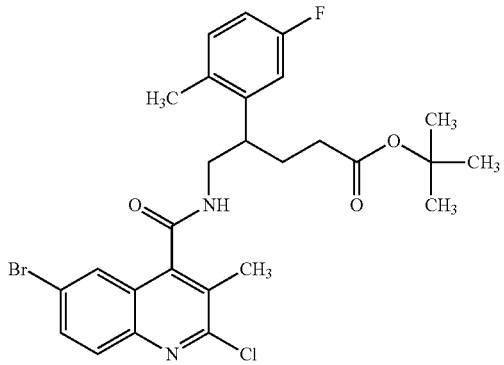 [SMILES: Cc1ccc(F)cc1C(CCC(=O)OC(C)(C)C)CNC(=O)c1c(C)c(Cl)nc2ccc(Br)cc12]

To a solution of (+/−)-tert-butyl 5-amino-4-(5-fluoro-2-methylphenyl)pentanoate (1.40 g, 92% purity, 4.58 mmol, Example 30A) in dichloromethane (45 ml) at RT was added DIPEA (2.0 ml, 11 mmol). Subsequently, 6-bromo-2-chloro-3-methylquinoline-4-carbonyl chloride (1.25 g, 97% purity, 3.81 mmol, Example 3A) was added, and the mixture was stirred at RT for 20 h. Subsequently, water and dichloromethane (150 ml of each) were added to the mixture, which was agitated. After phase separation, the aqueous phase was extracted once with dichloromethane (100 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 538 mg (100% purity, 25% of theory) of the title compound were obtained.

LC-MS (Method 2): $R_t$=1.34 min; MS (ESIpos): m/z=563/565 [M+H]⁺

¹H-NMR (400 MHz, DMSO-d6) δ [ppm]: 0.007 (0.21), 1.211 (0.07), 1.300 (0.11), 1.332 (0.11), 1.372 (16.00), 1.397 (2.79), 1.755 (0.12), 1.789 (0.19), 1.812 (0.17), 1.969 (0.16), 1.982 (0.20), 1.999 (0.20), 2.019 (0.15), 2.032 (0.13), 2.067 (0.69), 2.084 (0.98), 2.103 (0.46), 2.283 (1.44), 3.504 (0.12), 3.517 (0.18), 3.537 (0.20), 3.551 (0.24), 3.565 (0.15), 3.706 (0.13), 3.724 (0.19), 3.744 (0.16), 3.758 (0.14), 6.957 (0.24), 7.156 (0.31), 7.162 (0.31), 7.183 (0.32), 7.206 (0.36), 7.221 (0.40), 7.242 (0.31), 7.876 (0.11), 7.898 (2.22), 7.925 (0.09), 8.851 (0.31).

Example 47A (+/−)-tert-Butyl 5-{[(6-bromo-2-chloro-3-methylquinolin-4-yl)carbonyl]amino}-4-(2-chloro-3,6-difluorophenyl)pentanoate (Racemate)

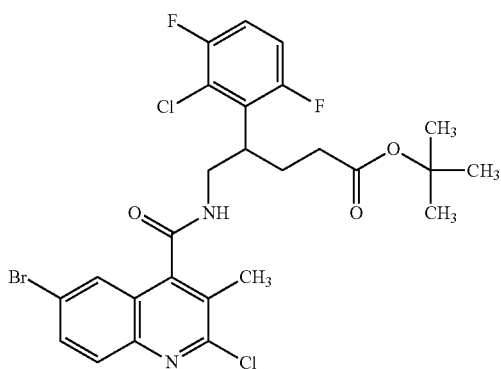 [SMILES: Cc1c(Cl)nc2ccc(Br)cc2c1C(=O)NCC(CCC(=O)OC(C)(C)C)c1c(F)ccc(F)c1Cl]

To a solution of (+/−)-tert-butyl 5-amino-4-(2-chloro-3,6-difluorophenyl)pentanoate (9.53 g, 81% purity, 24.0 mmol, Example 31A) in dichloromethane (200 ml) at RT was added DIPEA (10 ml, 60 mmol). Subsequently, 6-bromo-2-chloro-3-methylquinoline-4-carbonyl chloride (6.38 g, 20.0 mmol, Example 3A) was added, and the mixture was stirred at RT for 20 h. Subsequently, water and dichloromethane (150 ml of each) were added to the mixture, which was agitated. After phase separation, the aqueous phase was extracted once with dichloromethane (150 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 8.40 g (90% purity, 63% of theory) of the title compound were obtained.

LC-MS (Method 1): $R_t$=2.54 min; MS (ESIpos): m/z=601/603 [M+H]$^+$ $^1$H-NMR (400 MHz, DMSO-d6) δ [ppm]: 1.157 (0.23), 1.175 (0.45), 1.193 (0.24), 1.202 (0.08), 1.268 (0.07), 1.311 (0.35), 1.321 (0.40), 1.363 (16.00), 1.380 (0.76), 1.407 (0.25), 1.519 (0.07), 1.989 (0.95), 2.046 (0.21), 2.060 (0.26), 2.077 (0.24), 2.097 (0.18), 2.143 (0.58), 2.161 (0.76), 2.237 (0.60), 2.351 (0.07), 2.366 (0.05), 2.670 (0.04), 2.711 (0.03), 3.697 (0.24), 3.800 (0.28), 4.003 (0.08), 4.021 (0.21), 4.039 (0.21), 4.057 (0.08), 7.312 (0.25), 7.327 (0.19), 7.417 (0.21), 7.750 (0.05), 7.882 (0.18), 7.905 (2.10), 7.934 (0.14), 8.950 (0.24), 8.964 (0.43).

Separation of the Enantiomers:

The title compound (4.8 g) was dissolved in acetonitrile and separated into the enantiomers by means of preparative HPLC on chiral phase (see Examples 48A and 49A) [column: Daicel Chiralcel OX-H, 5 μm, 250 mm×20 mm; flow rate: 20 ml/min; detection: 220 nm; temperature: 30° C.; injection: 30 ml; eluent: 20% isopropanol/80% heptane; run time 18 min, isocratic]. The combined target fractions were each concentrated, and the respective residue was dried under reduced pressure.

Example 48A (+)-tert-Butyl 4-{[(6-bromo-2-chloro-3-methylquinolin-5-yl)carbonyl]amino}-4-(2-chloro-3,6-difluorophenyl)pentanoate (Enantiomer 1)

In the enantiomer separation described in Example 47A, 1.52 g (81% purity, ee 100%) of the title compound were obtained as the enantiomer that eluted earlier.

$[α]_D^{20}$=+31.9°, 589 nm, c=0.31 g/100 ml, methanol
LC-MS (Method 1): $R_t$=2.56 min; MS (ESIpos): m/z=601/603 [M+H]$^+$ $^1$H-NMR (400 MHz, DMSO-d6) δ [ppm]: −0.151 (0.03), 1.009 (0.23), 1.029 (3.00), 1.044 (3.00), 1.105 (0.49), 1.108 (0.83), 1.120 (0.35), 1.139 (0.06), 1.201 (0.08), 1.267 (0.07), 1.309 (0.32), 1.362 (16.00), 1.406 (0.23), 1.518 (0.07), 1.595 (0.04), 1.681 (0.12), 1.979 (0.14), 2.045 (0.23), 2.059 (0.28), 2.075 (0.27), 2.096 (0.21), 2.142 (0.65), 2.160 (0.82), 2.236 (0.67), 2.350 (0.12), 2.417 (0.04), 2.669 (0.04), 3.533 (0.53), 3.696 (0.29), 3.741 (0.21), 3.756 (0.35), 3.772 (0.47), 3.787 (0.49), 3.802 (0.40), 7.311 (0.29), 7.326 (0.21), 7.417 (0.25), 7.748 (0.07), 7.881 (0.20), 7.904 (2.30), 7.928 (0.16), 8.963 (0.48).

Example 49A (−)-tert-Butyl 5-{[(6-bromo-2-chloro-3-methylquinolin-4-yl)carbonyl]amino}-4-(2-chloro-3,6-difluorophenyl)pentanoate (Enantiomer 2)

In the enantiomer separation described in Example 47A, 1.46 g (82% purity, ee 97%) of the title compound were obtained as the enantiomer that eluted later.

$[α]_D^{20}$=−32.3°, 589 nm, c=0.36 g/100 ml, methanol
LC-MS (Method 1): $R_t$=2.56 min; MS (ESIpos): m/z=601/603 [M+H]$^+$ $^1$H-NMR (400 MHz, DMSO-d6) δ [ppm]: 0.850 (0.05), 1.009 (0.34), 1.029 (2.07), 1.044 (2.03), 1.104 (0.77), 1.108 (1.13), 1.120 (0.64), 1.139 (0.11), 1.155 (0.06), 1.201 (0.08), 1.267 (0.10), 1.309 (0.37), 1.320 (0.47), 1.362 (16.00), 1.378 (0.57), 1.406 (0.24), 1.518 (0.07), 1.681 (0.09), 1.974 (0.16), 2.044 (0.25), 2.061 (0.32), 2.075 (0.30), 2.095 (0.24), 2.142 (0.72), 2.159 (0.86), 2.236 (0.75), 2.669 (0.05), 3.533 (0.56), 3.567 (0.54), 3.697 (0.34), 3.756 (0.32), 3.771 (0.43), 3.787 (0.47), 3.802 (0.41), 4.270 (0.05), 7.311 (0.32), 7.326 (0.22), 7.417 (0.28), 7.763 (0.07), 7.881 (0.28), 7.904 (2.52), 7.932 (0.15), 8.963 (0.51).

Example 50A (+/−)-tert-Butyl 5-{[(6-bromo-2-chloro-3-methylquinolin-4-yl)carbonyl]amino}-4-[2-fluoro-6-(trifluoromethyl)phenyl]pentanoate (Racemate)

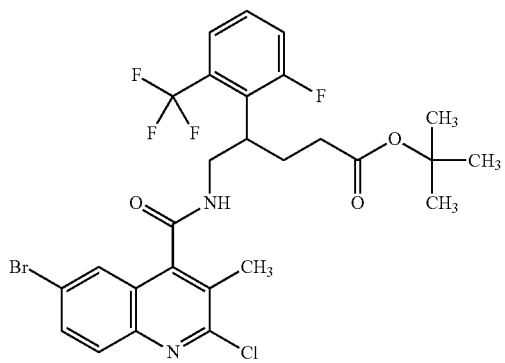 [SMILES: Cc1c(Cl)nc2ccc(Br)cc2c1C(=O)NCC(CCC(=O)OC(C)(C)C)c1c(F)cccc1C(F)(F)F]

To a solution of (+/−)-tert-butyl 5-amino-4-[2-fluoro-6-(trifluoromethyl)phenyl]pentanoate (2.15 g, 92% purity, 5.91 mmol, Example 32A) and DIPEA (2.6 ml, 15 mmol) in dichloromethane (57 ml) at RT was added a solution of 6-bromo-2-chloro-3-methylquinoline-4-carbonyl chloride (1.57 g, 4.92 mmol, Example 3A) in a little dichloromethane. The mixture was stirred at RT overnight. For workup, water and dichloromethane (200 ml of each) were added.

The phases were separated. The aqueous phase was extracted once with dichloromethane (200 ml). The combined organic phases were washed with saturated aqueous sodium chloride solution (200 ml), dried over sodium sulfate, filtered and concentrated under reduced pressure. The residue was dissolved in a little cyclohexane and ethyl acetate and purified by means of column chromatography (Biotage, 100 g of silica gel, Snap-Cartridge Ultra, eluent: cyclohexane/ethyl acetate 8:2). The product fraction obtained was concentrated under reduced pressure, and the residue was dried under reduced pressure. 2.20 g (97% purity, 70% of theory) of the title compound were obtained.

LC-MS (Method 1): $R_t$=2.57 min; MS (ESIpos): m/z=617 [M+H]$^+$ $^1$H-NMR (400 MHz, DMSO-d6) δ [ppm]: 8.96 (t, 1H), 7.94-7.86 (m, 2H) 7.87-7.25 (m, 4H), 3.93 (br. s, 1H), 3.73 (br. s, 1H), 3.34-3.24 (1H, concealed), 2.45-1.99 (m, 7H), 1.34 (s, 9H).

Example 51A (+/−)-tert-Butyl 5-{[(6-bromo-2-chloro-3-methylquinolin-4-yl)carbonyl]amino}-4-(2,3,6-trichlorophenyl)pentanoate (Racemate)

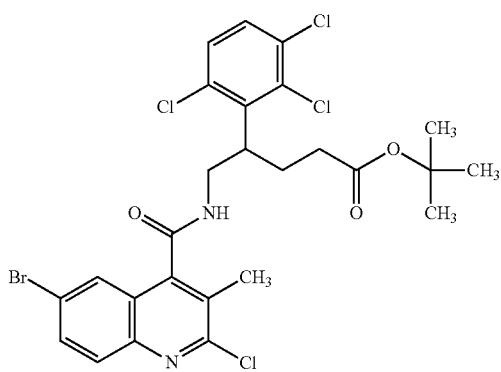 [SMILES: Cc1c(Cl)nc2ccc(Br)cc2c1C(=O)NCC(CCC(=O)OC(C)(C)C)c1c(Cl)ccc(Cl)c1Cl]

To a solution of (+/−)-tert-butyl 5-amino-4-(2,3,6-trichlorophenyl)pentanoate (1.84 g, 89% purity, 4.64 mmol, Example 33A) and DIPEA (2.0 ml, 12 mmol) in dichloromethane (45 ml) at RT was added a solution of 6-bromo-2-chloro-3-methylquinoline-4-carbonyl chloride (1.23 g, 3.87 mmol, Example 3A) in a little dichloromethane. The mixture was stirred at RT for 2 h. For workup, water and dichloromethane (200 ml of each) were added. The phases were separated. The aqueous phase was extracted once with dichloromethane (200 ml). The combined organic phases were washed with saturated aqueous sodium chloride solution (200 ml), dried over sodium sulfate, filtered and concentrated under reduced pressure. The residue was dissolved in a little DMSO and purified by means of preparative HPLC (Method 13). The product fraction obtained was concentrated under reduced pressure, and the residue was dried under reduced pressure. 2.03 g (93% purity, 77% of theory) of the title compound were obtained.

LC-MS (Method 4): $R_t$=1.75 min; ionization without detection of the target mass $^1$H-NMR (500 MHz, DMSO-d$_6$): δ [ppm]=8.98-8.88 (m, 1H), 7.97-7.34 (m, 5H), 4.22-3.95 (m, 2H), 3.95-3.79 (m, 1H), 2.35-1.99 (m, 7H), 1.37-1.34 (m, 9H).

Example 52A (+/−)-tert-Butyl 5-{[(6-bromo-2-chloro-3-methylquinolin-4-yl)carbonyl]amino}-4-[2-(difluoromethoxy)-6-fluorophenyl]pentanoate (Racemate)

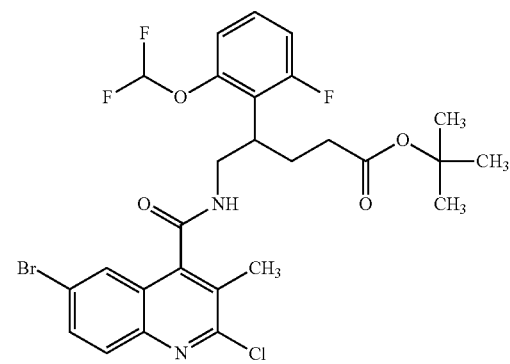 [SMILES: Cc1c(Cl)nc2ccc(Br)cc2c1C(=O)NCC(CCC(=O)OC(C)(C)C)c1c(F)cccc1OC(F)F]

To a solution of (+/−)-tert-butyl 5-amino-4-[2-(difluoromethoxy)-6-fluorophenyl]pentanoate (5.51 g, 65% purity, 10.7 mmol, Example 34A) in dichloromethane (100 ml) at RT was added DIPEA (4.7 ml, 27 mmol). Subsequently, 6-bromo-2-chloro-3-methylquinoline-4-carbonyl chloride (2.85 g, 8.94 mmol, Example 3A) was added, and the mixture was stirred at RT for 20 h. Subsequently, water and dichloromethane (150 ml of each) were added to the mixture, which was agitated. After phase separation, the aqueous phase was extracted once with dichloromethane (150 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 4.78 g (91% purity, 79% of theory) of the title compound were obtained.

LC-MS (Method 1): $R_t$=2.49 min; MS (ESIpos): m/z=615/617 [M+H]$^+$ $^1$H-NMR (400 MHz, DMSO-d6) δ [ppm]: 1.158 (0.05), 1.175 (0.11), 1.199 (0.07), 1.292 (0.08), 1.308 (0.28), 1.320 (0.37), 1.337 (1.76), 1.360 (16.00), 1.372 (0.72), 1.394 (0.28), 1.516 (0.07), 1.957 (0.22), 1.989 (0.32), 1.998 (0.30), 2.011 (0.25), 2.031 (0.28), 2.047 (0.23), 2.067 (0.18), 2.086 (0.80), 2.103 (0.80), 2.120 (0.32), 2.224 (0.28), 2.343 (0.12), 2.635 (0.07), 2.672 (0.09), 2.848 (0.04), 3.522 (0.22), 3.741 (0.20), 3.797 (0.16), 4.021 (0.05), 4.039 (0.05), 6.965 (0.07), 6.985 (0.12), 7.028 (0.46), 7.048 (0.53), 7.069 (0.41), 7.097 (0.32), 7.120 (0.46), 7.144 (0.34), 7.161 (0.08), 7.179 (0.10), 7.253 (0.70), 7.288 (0.09), 7.305 (0.11), 7.323 (0.07), 7.364 (0.17), 7.385 (0.25), 7.402 (0.24), 7.436 (0.37), 7.751 (0.07), 7.878 (0.17), 7.901 (1.98), 7.930 (0.15), 8.918 (0.25), 8.933 (0.50), 8.948 (0.26).

Example 53A (+/−)-tert-Butyl 4-({[6-bromo-3-methyl-2-(piperidin-1-yl)quinolin-4-yl]carbonyl}amino)-3-(2-chloro-6-fluorophenyl)butanoate (Racemate)

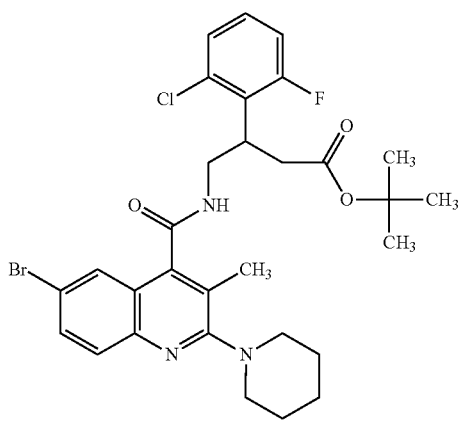 [SMILES: Cc1c(N2CCCCC2)nc2ccc(Br)cc2c1C(=O)NCC(CC(=O)OC(C)(C)C)c1c(F)cccc1Cl]

To a suspension of (+/−)-tert-butyl 4-{[(6-bromo-2-chloro-3-methylquinolin-4-yl)carbonyl]amino}-3-(2-chloro-6-fluorophenyl)butanoate (300 mg, 526 µmol, Example 35A) in 1-butanol (3.8 ml) was added piperidine (160 µl, 1.6 mmol), and the mixture was stirred at 100° C. for 16 h. After cooling to RT, water and ethyl acetate (50 ml of each) were added to the mixture, which was agitated. After phase separation, the aqueous phase was extracted once with ethyl acetate (50 ml). The combined organic phases were dried over sodium sulfate, filtered and concentrated, and the residue was taken up in dichloromethane and prepurified by means of flash column chromatography (25 g silica gel Biotage Snap-Cartridge KP-Sil, cyclohexane/ethyl acetate gradient 93:7→6:4, Isolera One). This was followed by repurification by means of preparative HPLC (Method 9). The combined target fractions were concentrated and the residue was dried under reduced pressure. 184 mg (98% purity, 55% of theory) of the title compound were obtained.

LC-MS (Method 1): $R_t$=2.74 min; MS (ESIpos): m/z=618/620 [M+H]$^+$ $^1$H-NMR (400 MHz, DMSO-d6) δ [ppm]: 1.236 (16.00), 1.613 (0.55), 1.678 (1.07), 2.169 (1.96), 2.758 (0.44), 2.772 (0.40), 3.161 (1.37), 3.704 (0.19), 4.052 (0.23), 7.213 (0.31), 7.239 (0.27), 7.326 (1.03), 7.333 (0.91), 7.354 (0.27), 7.647 (0.36), 7.669 (1.51), 7.678 (0.99), 7.683 (0.88), 7.705 (0.21), 8.825 (0.26), 8.840 (0.53), 8.855 (0.26).

$^1$H-NMR (400 MHz, DMSO-d6) δ [ppm]: 8.84 (t, 1H), 7.72-7.63 (m, 2H), 7.50 (br. s, 1H), 7.39-7.30 (m, 2H), 7.25-7.17 (m, 1H), 4.13-3.96 (m, 1H), 3.87-3.57 (m, 2H), 3.16 (br. s, 4H), 2.86-2.60 (m, 2H), 2.17 (s, 3H), 1.79-1.55 (m, 6H), 1.24 (s, 9H).

Example 54A (+/−)-tert-Butyl 4-[({6-bromo-3-methyl-2-[(2-phenylethyl)amino]quinolin-4-yl}carbonyl)amino]-3-(2-chloro-6-fluorophenyl)butanoate (Racemate)

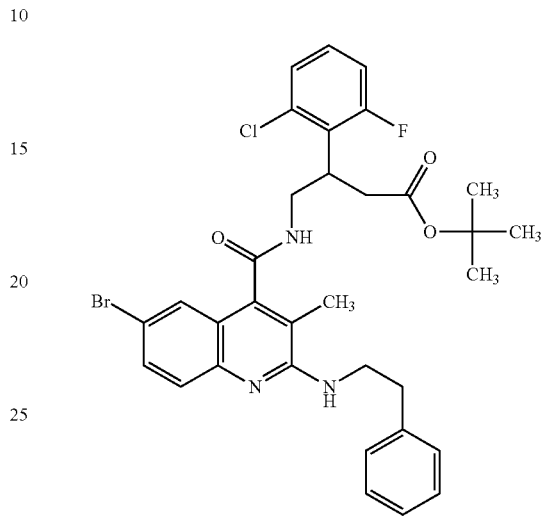

To a suspension of (+/−)-tert-butyl 4-{[(6-bromo-2-chloro-3-methylquinolin-4-yl)carbonyl]amino}-3-(2-chloro-6-fluorophenyl)butanoate (300 mg, 526 µmol, Example 35A) in 1-butanol (3.8 ml) was added 2-phenylethanamine (200 µl, 1.6 mmol), and the mixture was stirred at 100° C. overnight. Subsequently, the mixture was stirred at 130° C. for a further 24 h. After cooling to RT, water and ethyl acetate (50 ml of each) were added to the mixture, which was agitated. After phase separation, the aqueous phase was extracted once with ethyl acetate (50 ml). The combined organic phases were dried over sodium sulfate, filtered and concentrated, and the residue was taken up in dichloromethane and prepurified by means of flash column chromatography (25 g silica gel Biotage Snap-Cartridge KP-Sil, cyclohexane/ethyl acetate gradient 93:7→6:4, Isolera One). This was followed by repurification by means of preparative HPLC (Method 9). The combined target fractions were concentrated and the residue was dried under reduced pressure. 162 mg (98% purity, 46% of theory) of the title compound were obtained.

LC-MS (Method 1): $R_t$=2.41 min; MS (ESIpos): m/z=654/656 [M+H]$^+$ $^1$H-NMR (400 MHz, DMSO-d6) δ [ppm]: 8.88 (br. s, 1H), 7.68 (br. s, 1H), 7.41-7.15 (m, 11H), 4.04 (br. s, 1H), 3.90-3.62 (m, 4H), 2.97 (br. t, 2H), 2.82-2.66 (m, 2H), 2.10-1.88 (m, 3H), 1.24 (s, 9H).

Example 55A (+/−)-tert-Butyl 5-({[6-bromo-3-methyl-2-(piperidin-1-yl)quinolin-4-yl]carbonyl}amino)-4-(2-chloro-5-fluorophenyl)pentanoate (Racemate)

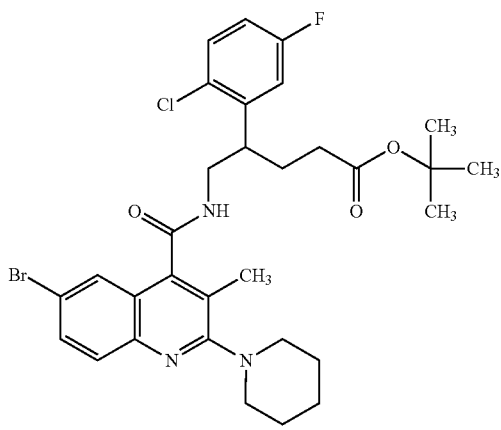 [SMILES: Cc1c(N2CCCCC2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (1.10 g, 1.88 mmol, Example 36A) in 1-butanol (14 ml) was added piperidine (560 µl, 5.6 mmol), and the mixture was stirred at 100° C. for three days. After cooling to RT, water and ethyl acetate (50 ml of each) were added to the mixture, which was agitated. After phase separation, the aqueous phase was extracted once with ethyl acetate (50 ml). The combined organic phases were dried over sodium sulfate, filtered and concentrated, and the residue was taken up in dichloromethane and purified by means of flash column chromatography (100 g silica gel Biotage Snap-Cartridge KP-Sil, cyclohexane/ethyl acetate gradient 93:7→6:4, Isolera One). The combined target fractions were concentrated and the residue was dried under reduced pressure. 676 mg (98% purity, 56% of theory) of the title compound were obtained.

LC-MS (Method 1): $R_t$=2.83 min; MS (ESIpos): m/z=632/634 [M+H]$^+$ $^1$H-NMR (400 MHz, DMSO-d6) δ [ppm]: 8.72 (t, 1H), 7.69-7.61 (m, 2H), 7.50 (dd, 1H), 7.47 (br. s, 1H, partially hidden), 7.41 (dd, 1H), 7.14 (td, 1H), 3.74-3.64 (m, 2H), 3.63-3.53 (m, 1H), 3.17-3.10 (m, 4H), 2.17-1.94 (m, 6H), 1.86-1.74 (m, 1H), 1.72-1.55 (m, 6H), 1.37 (s, 9H).

Separation of the Enantiomers:

The title compound (675 mg) was dissolved in ethanol (7 ml) and separated into the enantiomers by means of preparative HPLC on chiral phase (see Examples 56A and 57A) [column: Daicel Chiralcel OX-H, 5 µm, 250 mm×20 mm; flow rate: 40 ml/min; injection: 0.1 ml; eluent: 20% ethanol/80% heptane; run time 10 min, isocratic]. The combined target fractions were concentrated and the residue was lyophilized.

Example 56A (−)-tert-Butyl 5-({[6-bromo-3-methyl-2-(piperidin-1-yl)quinolin-4-yl]carbonyl}amino)-4-(2-chloro-5-fluorophenyl)pentanoate (Enantiomer 1)

In the enantiomer separation described in Example 55A, 237 mg (98% purity, ee 99%) of the title compound were obtained as the enantiomer that eluted earlier.

$[α]_D^{20}$=−12.8°, 589 nm, c=0.34 g/100 ml, methanol

LC-MS (Method 1): $R_t$=2.83 min; MS (ESIpos): m/z=632/634 [M+H]$^+$ $^1$H-NMR (400 MHz, DMSO-d6) δ [ppm]: 8.72 (t, 1H), 7.69-7.61 (m, 2H), 7.50 (dd, 1H), 7.47 (br. s, 1H, partially hidden), 7.41 (dd, 1H), 7.14 (td, 1H), 3.74-3.64 (m, 2H), 3.63-3.53 (m, 1H), 3.17-3.09 (m, 4H), 2.16-1.97 (m, 6H), 1.87-1.74 (m, 1H), 1.72-1.55 (m, 6H), 1.37 (s, 9H).

Example 57A (+)-tert-Butyl 5-({[6-bromo-3-methyl-2-(piperidin-1-yl)quinolin-4-yl]carbonyl}amino)-4-(2-chloro-5-fluorophenyl)pentanoate (Enantiomer 2)

In the enantiomer separation described in Example 55A, 207 mg (98% purity, ee 99%) of the title compound were obtained as the enantiomer that eluted later.

$[α]_D^{20}$=+13.1°, 589 nm, c=0.38 g/100 ml, methanol

LC-MS (Method 1): $R_t$=2.83 min; MS (ESIpos): m/z=632/634 [M+H]$^+$ $^1$H-NMR (400 MHz, DMSO-d6) δ [ppm]: 8.72 (t, 1H), 7.70-7.60 (m, 2H), 7.50 (dd, 1H), 7.47 (br. s, 1H, partially hidden), 7.41 (dd, 1H), 7.14 (td, 1H), 3.74-3.64 (m, 2H), 3.63-3.53 (m, 1H), 3.17-3.10 (m, 4H), 2.16-1.96 (m, 6H), 1.87-1.74 (m, 1H), 1.73-1.54 (m, 6H), 1.37 (s, 9H).

Example 58A (+/−)-tert-Butyl 5-({[6-bromo-2-(4,4-difluoropiperidin-1-yl)-3-methylquinolin-4-yl]carbonyl}amino)-4-(2-chloro-5-fluorophenyl)pentanoate (Racemate)

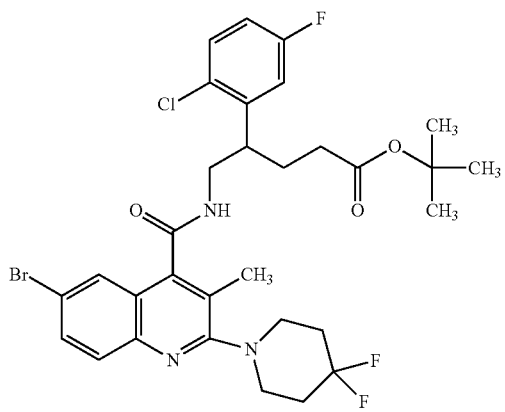 [SMILES: Cc1c(N2CCC(F)(F)CC2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (135 mg, 231 µmol, Example 36A) in 1-butanol (1.7 ml) was added 4,4-difluoropiperidine (84 mg, 693 µmol), and the mixture was stirred at 100° C. for four days. After cooling to RT, water and ethyl acetate (20 ml of each) were added to the mixture, which was agitated. After phase separation, the aqueous phase was extracted once with ethyl acetate (20 ml). The combined organic phases were dried over sodium sulfate, filtered and concentrated, and the residue was taken up in dichloromethane and prepurified by means of flash column chromatography (25 g silica gel Biotage Snap-Cartridge KP-Sil, cyclohexane/ethyl acetate gradient 93:7→5:5, Isolera One). This was followed by repurification by means of preparative HPLC (Method 9). The combined target fractions were concentrated, and the residue was dried under reduced pressure. 19 mg (72% purity, 9% of theory) of the title compound were obtained.

LC-MS (Method 1): $R_t$=2.72 min; MS (ESIpos): m/z=668/670 [M+H]$^+$

Example 59A (+/−)-tert-Butyl 5-({[6-bromo-3-methyl-2-(morpholin-4-yl)quinolin-4-yl]carbonyl}amino)-4-(2-chloro-5-fluorophenyl)pentanoate (Racemate)

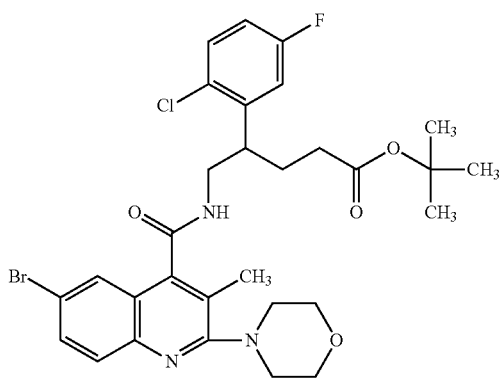

To a suspension of (+/−)-tert-butyl 5-{[(6-bromo-2-chloro-3-methylquinolin-4-yl)carbonyl]amino}-4-(2-chloro-5-fluorophenyl)pentanoate (135 mg, 231 µmol, Example 36A) in 1-butanol (1.7 ml) was added morpholine (60 µl, 690 µmol), and the mixture was stirred at 100° C. for four days. After cooling to RT, water and ethyl acetate (20 ml of each) were added to the mixture, which was agitated. After phase separation, the aqueous phase was extracted once with ethyl acetate (20 ml). The combined organic phases were dried over sodium sulfate, filtered and concentrated, and the residue was taken up in dichloromethane and prepurified by means of flash column chromatography (25 g silica gel Biotage Snap-Cartridge KP-Sil, cyclohexane/ethyl acetate gradient 93:7→6:4, Isolera One). This was followed by repurification by means of preparative HPLC (Method 9). The combined target fractions were concentrated, and the residue was dried under reduced pressure. 61 mg (98% purity, 41% of theory) of the title compound were obtained.

LC-MS (Method 1): $R_t$=2.55 min; MS (ESIpos): m/z=634/636 [M+H]$^+$ $^1$H-NMR (400 MHz, DMSO-d6) δ [ppm]: −0.009 (0.21), 0.007 (0.19), 1.211 (0.06), 1.296 (0.07), 1.328 (0.09), 1.371 (16.00), 1.527 (0.06), 1.773 (0.12), 1.790 (0.14), 1.808 (0.16), 1.829 (0.13), 1.999 (0.14), 2.011 (0.18), 2.029 (0.18), 2.050 (0.15), 2.063 (0.12), 2.085 (0.65), 2.102 (0.88), 2.122 (0.35), 2.147 (1.79), 2.327 (0.04), 2.365 (0.04), 2.669 (0.04), 2.709 (0.04), 3.172 (1.20), 3.177 (1.21), 3.185 (0.93), 3.587 (0.21), 3.692 (0.46), 3.753 (1.33), 3.764 (1.83), 3.775 (1.35), 3.838 (0.55), 7.115 (0.13), 7.123 (0.15), 7.137 (0.24), 7.143 (0.26), 7.157 (0.15), 7.165 (0.15), 7.395 (0.34), 7.402 (0.35), 7.420 (0.36), 7.428 (0.34), 7.483 (0.48), 7.496 (0.50), 7.505 (0.47), 7.518 (0.43), 7.661 (0.18), 7.683 (1.46), 7.691 (0.90), 7.708 (0.11), 7.713 (0.13), 8.731 (0.20), 8.746 (0.40), 8.760 (0.19).

$^1$H-NMR (400 MHz, DMSO-d6) δ [ppm]: 8.75 (t, 1H), 7.73-7.65 (m, 2H), 7.50 (dd, 1H), 7.46 (br. s, 1H, concealed), 7.41 (dd, 1H), 7.14 (td, 1H), 3.80-3.65 (m, 6H, partially hidden), 3.59 (br. s, 1H), 3.25-3.12 (m, 4H), 2.20-1.95 (m, 6H), 1.87-1.73 (m, 1H), 1.37 (s, 9H).

Example 60A (+/−)-tert-Butyl 5-({[6-bromo-2-(3,6-dihydropyridin-1(2H)-yl)-3-methylquinolin-4-yl]carbonyl}amino)-4-(2-chloro-5-fluorophenyl)pentanoate (Racemate)

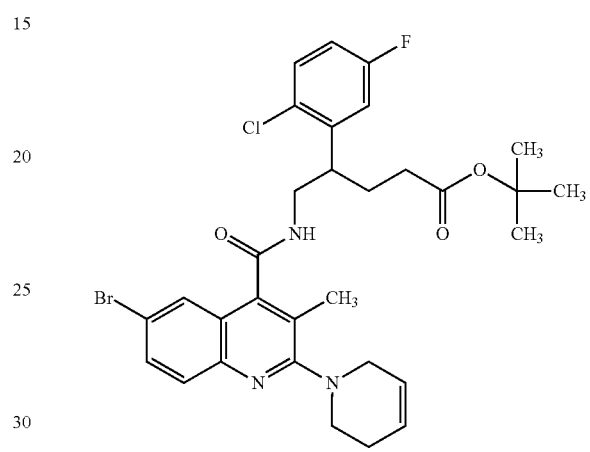

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added 1,2,3,6-tetrahydropyridine (43 mg, 513 µmol), and the mixture was stirred at 100° C. for three days. After cooling to RT, the mixture was purified directly (without further workup) by preparative HPLC (Method 18). The combined target fractions were concentrated, and the residue was lyophilized. 50 mg (98% purity, 45% of theory) of the title compound were obtained.

LC-MS (Method 1): $R_t$=2.73 min; MS (ESIpos): m/z=630/632 [M+H]$^+$ $^1$H-NMR (400 MHz, DMSO-d6) δ [ppm]: −0.150 (0.07), −0.009 (0.56), 0.007 (0.62), 0.146 (0.07), 1.213 (0.06), 1.297 (0.06), 1.331 (0.09), 1.373 (16.00), 1.529 (0.07), 1.780 (0.12), 1.814 (0.18), 1.836 (0.14), 2.007 (0.15), 2.019 (0.18), 2.037 (0.18), 2.057 (0.17), 2.070 (0.16), 2.086 (0.71), 2.103 (0.93), 2.124 (0.46), 2.140 (2.18), 2.302 (0.44), 2.365 (0.07), 2.669 (0.07), 2.709 (0.06), 3.274 (0.31), 3.587 (0.19), 3.689 (0.35), 3.795 (0.79), 5.817 (0.15), 5.843 (0.49), 5.863 (0.45), 5.888 (0.14), 7.123 (0.16), 7.144 (0.28), 7.158 (0.16), 7.165 (0.16), 7.397 (0.35), 7.404 (0.37), 7.422 (0.38), 7.429 (0.37), 7.482 (0.48), 7.496 (0.48), 7.504 (0.45), 7.517 (0.41), 7.619 (0.38), 7.641 (1.32), 7.654 (0.81), 7.659 (0.75), 7.677 (0.22), 7.682 (0.24), 8.720 (0.21), 8.734 (0.41), 8.748 (0.20).

$^1$H-NMR (400 MHz, DMSO-d6) δ [ppm]: 8.73 (t, 1H), 7.69-7.61 (m, 2H), 7.50 (dd, 1H), 7.47 (br. s, 1H), 7.41 (dd, 1H), 7.14 (td, 1H), 5.91-5.79 (m, 2H), 3.80 (br. s, 2H), 3.69 (br. s, 2H), 3.59 (br. s, 1H), 3.27 (br. s, 2H, partially hidden), 2.30 (br. s, 2H), 2.18-1.97 (m, 6H), 1.88-1.74 (m, 1H), 1.37 (s, 9H).

Example 61A (+/−)-tert-Butyl 5-({[6-bromo-3-methyl-2-(thiomorpholin-4-yl)quinolin-4-yl]carbonyl}amino)-4-(2-chloro-5-fluorophenyl)pentanoate (Racemate)

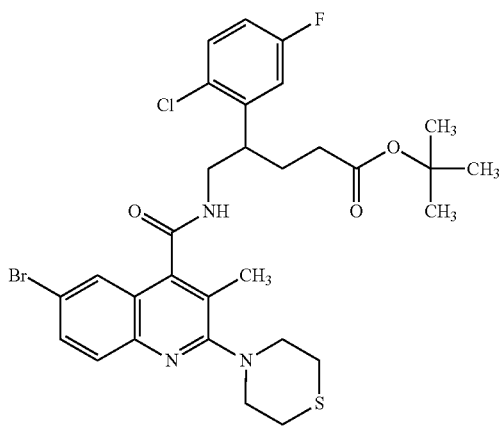

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added thiomorpholine (53 mg, 513 µmol), and the mixture was stirred at 100° C. for 18 h. Subsequently, thiomorpholine (53 mg, 513 µmol) was added again, and the mixture was stirred at 100° C. for a further four days. After cooling to RT, the mixture was purified directly (without further workup) by preparative HPLC (Method 18). The combined target fractions were concentrated, and the residue was lyophilized. 55 mg (98% purity, 48% of theory) of the title compound were obtained.

LC-MS (Method 1): $R_t$=2.69 min; MS (ESIpos): m/z=650/652 [M+H]$^+$ $^1$H-NMR (400 MHz, DMSO-d6) δ [ppm]: −0.150 (0.07), −0.009 (0.65), 0.007 (0.57), 0.145 (0.08), 1.212 (0.06), 1.298 (0.07), 1.329 (0.09), 1.372 (16.00), 1.528 (0.07), 1.775 (0.12), 1.809 (0.18), 1.830 (0.15), 2.000 (0.15), 2.013 (0.19), 2.030 (0.19), 2.051 (0.16), 2.064 (0.14), 2.084 (0.71), 2.101 (0.99), 2.128 (2.24), 2.327 (0.06), 2.365 (0.05), 2.669 (0.07), 2.709 (0.06), 2.785 (1.20), 2.797 (1.13), 3.424 (1.18), 3.583 (0.20), 3.687 (0.35), 7.124 (0.16), 7.144 (0.28), 7.165 (0.17), 7.395 (0.35), 7.402 (0.36), 7.420 (0.37), 7.427 (0.36), 7.482 (0.49), 7.495 (0.51), 7.504 (0.48), 7.517 (0.44), 7.656 (0.22), 7.678 (1.47), 7.683 (1.07), 7.688 (0.88), 7.706 (0.15), 7.710 (0.17), 8.714 (0.22), 8.728 (0.43), 8.742 (0.21).

$^1$H-NMR (400 MHz, DMSO-d6) δ [ppm]: 8.73 (t, 1H), 7.72-7.65 (m, 2H), 7.50 (dd, 1H), 7.46 (br. s, 1H, partially hidden), 7.41 (dd, 1H), 7.14 (td, 1H), 3.69 (br. s, 2H), 3.58 (br. s, 1H), 3.46-3.39 (m, 4H), 2.82-2.75 (m, 4H), 2.17-1.97 (m, 6H), 1.88-1.74 (m, 1H), 1.37 (s, 9H).

Example 62A (+/−)-tert-Butyl 5-[({6-bromo-2-[cis-2,6-dimethylmorpholin-4-yl]-3-methylquinolin-4-yl}carbonyl)amino]-4-(2-chloro-5-fluorophenyl)pentanoate (Racemate)

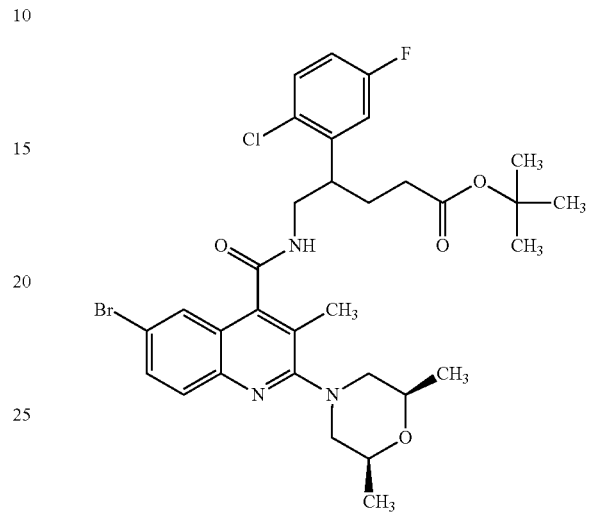

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added cis-2,6-dimethylmorpholine (59 mg, 513 µmol), and the mixture was stirred at 100° C. for three days. After cooling to RT, the mixture was purified directly (without further workup) by preparative HPLC (Method 18). The combined target fractions were concentrated, and the residue was lyophilized. 70 mg (98% purity, 60% of theory) of the title compound were obtained.

LC-MS (Method 1): $R_t$=2.71 min; MS (ESIpos): m/z=662/664 [M+H]$^+$ $^1$H-NMR (400 MHz, DMSO-d6) δ [ppm]: −0.149 (0.06), 0.007 (0.42), 0.146 (0.06), 1.133 (3.52), 1.148 (3.54), 1.212 (0.07), 1.299 (0.08), 1.330 (0.09), 1.372 (16.00), 1.528 (0.07), 1.813 (0.18), 2.017 (0.18), 2.035 (0.17), 2.055 (0.15), 2.067 (0.15), 2.085 (0.69), 2.101 (0.90), 2.121 (0.34), 2.156 (2.32), 2.327 (0.08), 2.366 (0.07), 2.669 (0.09), 2.709 (0.08), 3.431 (0.58), 3.461 (0.54), 3.581 (0.19), 3.685 (0.31), 3.777 (0.41), 7.124 (0.16), 7.145 (0.28), 7.159 (0.16), 7.393 (0.35), 7.400 (0.35), 7.418 (0.36), 7.425 (0.35), 7.483 (0.49), 7.496 (0.50), 7.505 (0.46), 7.518 (0.42), 7.655 (0.08), 7.676 (2.30), 8.707 (0.22), 8.721 (0.42).

$^1$H-NMR (400 MHz, DMSO-d6) δ [ppm]: 8.72 (t, 1H), 7.71-7.64 (m, 2H), 7.50 (dd, 1H), 7.46 (br. s, 1H, partially hidden), 7.41 (dd, 1H), 7.14 (td, 1H), 3.84-3.73 (m, 2H), 3.69 (br. s, 2H), 3.58 (br. s, 1H), 3.45 (br. d, 2H), 2.54-2.48 (concealed, 2H), 2.16 (s, 3H), 2.13-1.96 (m, 3H), 1.87-1.75 (m, 1H), 1.37 (s, 9H), 1.15 (s, 3H), 1.13 (s, 3H).

Example 63A (+/−)-tert-Butyl 5-({[6-bromo-3-methyl-2-(pyrrolidin-1-yl)quinolin-4-yl]carbonyl}amino)-4-(2-chloro-5-fluorophenyl)pentanoate (Racemate)

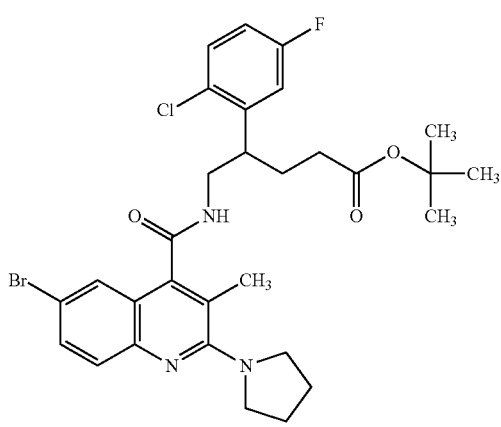 [SMILES: Cc1c(N2CCCC2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added pyrrolidine (43 μl, 510 μmol), and the mixture was stirred at 100° C. for three days. After cooling to RT, the mixture was purified directly (without further workup) by preparative HPLC (Method 20). The combined target fractions were concentrated, and the residue was lyophilized. 63 mg (98% purity, 58% of theory) of the title compound were obtained.

LC-MS (Method 1): $R_t$=2.28 min; MS (ESIpos): m/z=618/620 [M+H]$^+$ $^1$H-NMR (400 MHz, DMSO-d6) δ [ppm]: −0.150 (0.06), −0.008 (0.54), 0.007 (0.50), 0.146 (0.06), 1.211 (0.06), 1.299 (0.08), 1.332 (0.11), 1.343 (0.12), 1.371 (16.00), 1.527 (0.07), 1.775 (0.13), 1.791 (0.16), 1.809 (0.20), 1.831 (0.21), 1.870 (1.32), 1.999 (0.16), 2.012 (0.20), 2.030 (0.20), 2.050 (0.18), 2.083 (0.71), 2.100 (0.91), 2.120 (0.36), 2.155 (1.44), 2.327 (0.05), 2.366 (0.05), 2.669 (0.06), 2.709 (0.06), 3.567 (1.08), 3.670 (0.36), 7.118 (0.15), 7.138 (0.27), 7.152 (0.16), 7.385 (0.41), 7.392 (0.43), 7.410 (0.41), 7.418 (0.40), 7.466 (0.74), 7.474 (0.45), 7.488 (1.61), 7.496 (0.45), 7.510 (0.39), 7.544 (0.66), 7.549 (0.62), 7.566 (0.39), 7.572 (0.38), 8.674 (0.39).

$^1$H-NMR (400 MHz, DMSO-d6) δ [ppm]: 8.67 (t, 1H), 7.56 (dd, 1H), 7.52-7.46 (m, 2H), 7.40 (dd, 1H), 7.37 (br. s, 1H, concealed), 7.14 (td, 1H), 3.67 (br. s, 2H), 3.57 (br. s, 5H), 2.20-1.96 (m, 6H), 1.91-1.74 (m, 5H).

Example 64A (+/−)-tert-Butyl 5-({[6-bromo-3-methyl-2-(1,2-oxazolidin-2-yl)quinolin-4-yl]carbonyl}amino)-4-(2-chloro-5-fluorophenyl)pentanoate (Racemate)

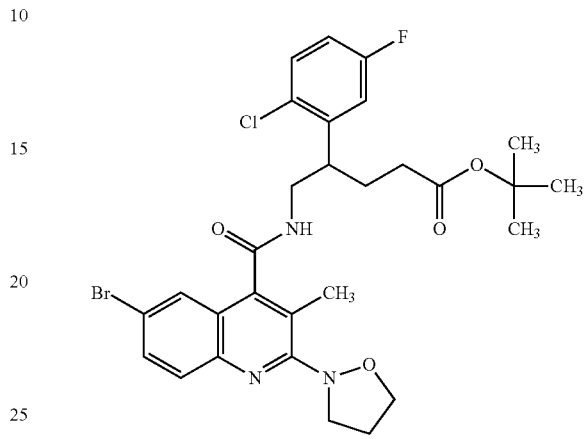

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added 1,2-oxazolidine (37.5 mg, 513 μmol), and the mixture was stirred at 100° C. for three days.

After cooling to RT, the mixture was purified directly (without further workup) by preparative HPLC (Method 23). The combined target fractions were concentrated, and the residue was lyophilized. 35 mg (98% purity, 32% of theory) of the title compound were obtained.

LC-MS (Method 1): $R_t$=2.57 min; MS (ESIpos): m/z=620/622 [M+H]$^+$ $^1$H-NMR (400 MHz, DMSO-d6) δ [ppm]: −0.150 (0.04), −0.009 (0.31), 0.145 (0.04), 1.212 (0.06), 1.288 (0.06), 1.324 (0.09), 1.373 (16.00), 1.529 (0.07), 1.757 (0.05), 1.775 (0.13), 1.792 (0.16), 1.810 (0.19), 1.831 (0.15), 2.000 (0.16), 2.013 (0.20), 2.031 (0.20), 2.051 (0.18), 2.062 (0.13), 2.087 (0.71), 2.104 (0.92), 2.122 (0.32), 2.210 (1.47), 2.239 (0.64), 2.257 (0.85), 2.275 (0.62), 2.293 (0.19), 2.331 (0.05), 2.365 (0.04), 2.669 (0.04), 2.709 (0.04), 3.590 (0.20), 3.686 (0.39), 3.700 (0.53), 3.773 (0.37), 3.819 (0.64), 3.837 (1.08), 3.856 (0.58), 7.124 (0.15), 7.145 (0.27), 7.159 (0.16), 7.394 (0.36), 7.401 (0.36), 7.419 (0.36), 7.426 (0.35), 7.486 (0.43), 7.499 (0.46), 7.508 (0.45), 7.521 (0.43), 7.709 (0.11), 7.731 (2.33), 7.757 (0.09), 8.772 (0.22), 8.787 (0.42), 8.800 (0.21).

1H-NMR (400 MHz, DMSO-d6): δ [ppm]=8.79 (t, 1H), 7.77-7.69 (m, 2H), 7.53 (br. s, 1H, concealed), 7.50 (dd, 1H), 7.41 (dd, 1H), 7.14 (td, 1H), 3.84 (t, 2H), 3.77 (br. s, 2H), 3.74-3.65 (m, 2H), 3.65-3.54 (m, 1H), 2.31-2.17 (m, 5H), 2.15-2.07 (m, 2H), 2.07-1.97 (m, 1H), 1.88-1.73 (m, 1H), 1.37 (s, 9H).

Example 65A (+/−)-tert-Butyl 5-({[6-bromo-2-(2,5-dihydro-1H-pyrrol-1-yl)-3-methylquinolin-4-yl]carbonyl}amino)-4-(2-chloro-5-fluorophenyl)pentanoate (Racemate)

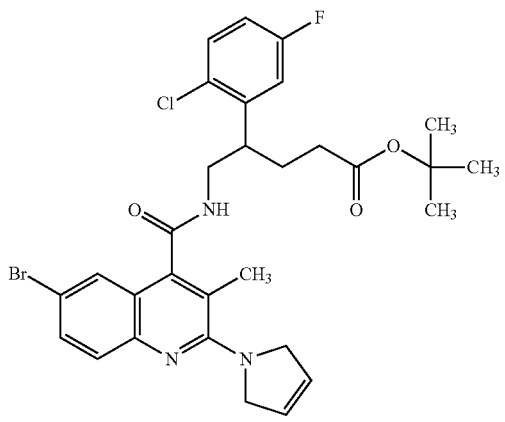 [SMILES: Cc1c(N2CC=CC2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added 2,5-dihydro-1H-pyrrole (36 mg, 513 µmol), and the mixture was stirred at 100° C. for three days. After cooling to RT, the mixture was purified directly (without further workup) by preparative HPLC (Method 23). The combined target fractions were concentrated, and the residue was lyophilized. 32 mg (81% purity, 25% of theory) of the title compound were obtained.

LC-MS (Method 1): $R_t$=2.55 min; MS (ESIpos): m/z=616/618 [M+H]$^+$ 1H-NMR (400 MHz, DMSO-d6): δ [ppm]=8.69 (t, 1H), 7.57 (dd, 1H), 7.52-7.46 (m, 2H), 7.40 (dd, 1H), 7.36 (broad, concealed, 1H), 7.17-7.10 (m, 1H), 5.96 (s, 2H), 4.53 (br. s, 4H), 3.77-3.52 (m, 3H), 2.25 (br. s, 3H), 2.14-1.95 (m, 3H), 1.87-1.74 (m, 1H), 1.37 (s, 9H).

Example 66A tert-Butyl 5-[({6-bromo-2-[3-hydroxypyrrolidin-1-yl]-3-methylquinolin-4-yl}carbonyl)amino]-4-(2-chloro-5-fluorophenyl)pentanoate (Diastereomer Mixture)

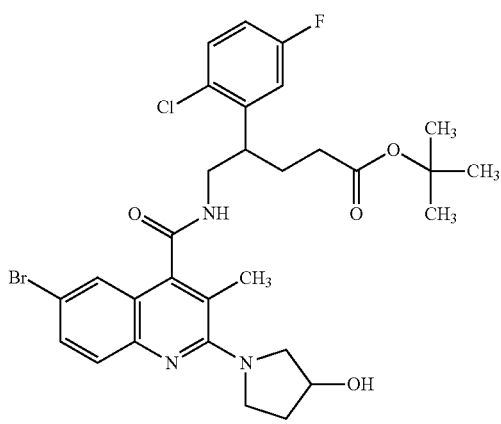 [SMILES: Cc1c(N2CCC(O)C2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added (+/−)-pyrrolidin-3-ol (45 mg, 513 µmol), and the mixture was stirred at 100° C. for three days. After cooling to RT, the mixture was purified directly (without further workup) by preparative HPLC (Method 20). The combined target fractions were concentrated, and the residue was lyophilized. 60 mg (98% purity, 54% of theory) of the title compound were obtained.

LC-MS (Method 1): $R_t$=2.02 min; MS (ESIpos): m/z=634/636 [M+H]$^+$ $^1$H-NMR (400 MHz, DMSO-d6) δ [ppm]: −0.008 (0.82), 0.008 (0.78), 1.371 (16.00), 1.832 (0.42), 2.084 (0.90), 2.101 (1.17), 2.122 (0.54), 2.146 (1.73), 3.669 (0.41), 4.331 (0.42), 4.897 (0.43), 4.905 (0.74), 4.912 (0.46), 7.390 (0.51), 7.416 (0.50), 7.466 (0.85), 7.478 (0.44), 7.488 (1.75), 7.497 (0.43), 7.500 (0.41), 7.545 (0.70), 7.548 (0.65), 7.567 (0.41), 8.696 (0.44).

$^1$H-NMR (400 MHz, DMSO-d6) δ [ppm]: 8.70 (br. t, 1H), 7.59-7.53 (m, 1H), 7.52-7.46 (m, 2H), 7.43-7.38 (m, 1H), 7.36 (br. s, partly concealed, 1H), 7.18-7.09 (m, 1H), 4.90 (t, 1H), 4.33 (br. s, 1H), 3.90-3.46 (m, 7H), 2.19-1.72 (m, 9H), 1.37 (s, 9H).

Example 67A tert-Butyl 5-[({6-bromo-3-methyl-2-[3-methylpiperidin-1-yl]quinolin-4-yl}carbonyl)amino]-4-(2-chloro-5-fluorophenyl)pentanoate (Diastereomer Mixture)

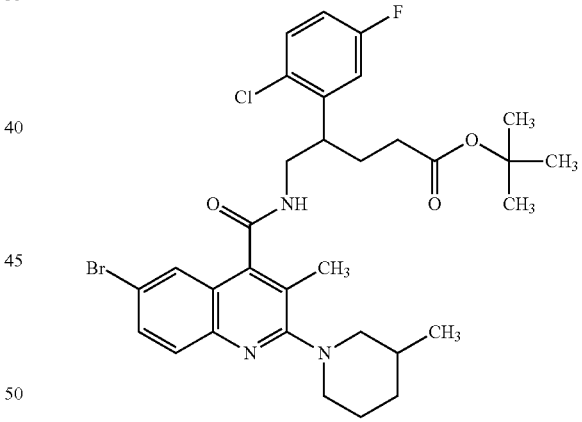

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 µmol, Example 36A) in 1-butanol (1.2 ml) was added (+/−)-3-methylpiperidine (51 mg, 513 µmol), and the mixture was stirred at 100° C. for two days. After cooling to RT, the mixture was purified directly (without further workup) by preparative HPLC (Method 18). The combined target fractions were concentrated, and the residue was lyophilized. 78 mg (98% purity, 69% of theory) of the title compound were obtained.

LC-MS (Method 1): $R_t$=2.89 min; MS (ESIpos): m/z=646/648 [M+H]$^+$ $^1$H-NMR (400 MHz, DMSO-d6) δ [ppm]: 0.008 (0.63), 0.919 (1.45), 0.936 (1.34), 1.373 (16.00), 1.794 (0.50), 2.084 (0.80), 2.101 (1.03), 2.132 (2.37), 3.459 (0.49), 3.678 (0.42), 7.483 (0.57), 7.496 (0.55), 7.505 (0.51), 7.518 (0.42), 7.648 (1.52), 7.656 (0.95), 8.717 (0.41).

$^1$H-NMR (400 MHz, DMSO-d6) δ [ppm]: 8.72 (t, 1H), 7.68-7.62 (m, 2H), 7.50 (dd, 1H), 7.46 (br. s, partly concealed, 1H), 7.41 (dd, 1H), 7.19-7.10 (m, 1H), 3.78-3.39 (m, 5H), 2.69 (br. d, 1H), 2.45-2.41 (concealed, 1H), 2.18-1.94 (m, 6H), 1.86-1.58 (m, 5H), 1.37 (s, 9H), 1.17-1.01 (m, 1H), 0.93 (d, 3H).

Example 68A (+/−)-tert-Butyl 5-({[(6-bromo-3-methyl-2-(4-methylpiperidin-1-yl)quinolin-4-yl]carbonyl}amino)-4-(2-chloro-5-fluorophenyl)pentanoate (Racemate)

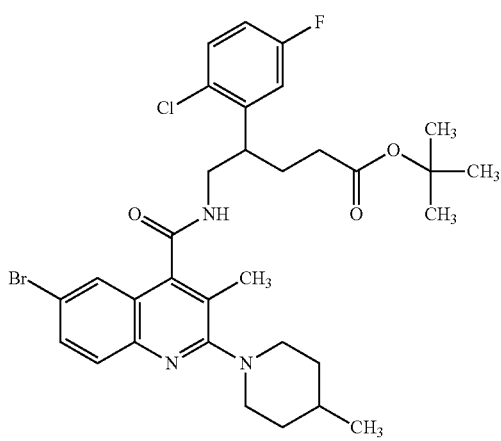 [SMILES: Cc1c(N2CCC(C)CC2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added 4-methylpiperidine (51 mg, 513 μmol), and the mixture was stirred at 100° C. for two days.

After cooling to RT, the mixture was purified directly (without further workup) by preparative HPLC (Method 18). The combined target fractions were concentrated, and the residue was lyophilized. 72 mg (98% purity, 64% of theory) of the title compound were obtained.

LC-MS (Method 1): $R_t$=2.88 min; MS (ESIpos): m/z=646/648 [M+H]$^+$ $^1$H-NMR (400 MHz, DMSO-d6) δ [ppm]: −0.009 (0.32), 0.007 (0.30), 0.865 (0.06), 0.964 (1.71), 0.980 (1.80), 1.212 (0.06), 1.285 (0.31), 1.314 (0.35), 1.372 (16.00), 1.562 (0.16), 1.717 (0.43), 1.747 (0.39), 1.774 (0.14), 1.809 (0.17), 1.829 (0.14), 2.001 (0.14), 2.014 (0.18), 2.031 (0.18), 2.051 (0.17), 2.065 (0.15), 2.084 (0.69), 2.100 (0.98), 2.119 (2.48), 2.327 (0.06), 2.365 (0.07), 2.669 (0.07), 2.709 (0.10), 2.756 (0.29), 2.777 (0.32), 2.805 (0.16), 3.508 (0.47), 3.540 (0.46), 3.580 (0.20), 3.683 (0.41), 7.123 (0.16), 7.144 (0.28), 7.157 (0.17), 7.165 (0.17), 7.391 (0.36), 7.398 (0.37), 7.416 (0.38), 7.424 (0.36), 7.481 (0.49), 7.495 (0.48), 7.503 (0.44), 7.517 (0.40), 7.618 (0.33), 7.640 (1.38), 7.650 (0.88), 7.655 (0.78), 7.673 (0.19), 7.678 (0.21), 8.704 (0.21), 8.719 (0.42), 8.733 (0.21).

$^1$H-NMR (400 MHz, DMSO-d6) δ [ppm]: 8.72 (t, 1H), 7.69-7.61 (m, 2H), 7.50 (dd, 1H), 7.47 (br. s, partially hidden, 1H), 7.41 (dd, 1H), 7.14 (td, 1H), 3.74-3.64 (m, 2H), 3.63-3.56 (m, 1H), 3.52 (br. d, 2H), 2.83-2.70 (m, 2H), 2.15-1.97 (m, 6H), 1.86-1.76 (m, 1H), 1.73 (br. d, 2H), 1.62-1.50 (m, 1H), 1.37 (s, 9H), 1.36-1.22 (m, 2H), 0.97 (d, 3H).

Example 69A tert-Butyl 5-[({6-bromo-2-[3-methoxypiperidin-1-yl]-3-methylquinolin-4-yl}carbonyl)amino]-4-(2-chloro-5-fluorophenyl)pentanoate (Diastereomer Mixture)

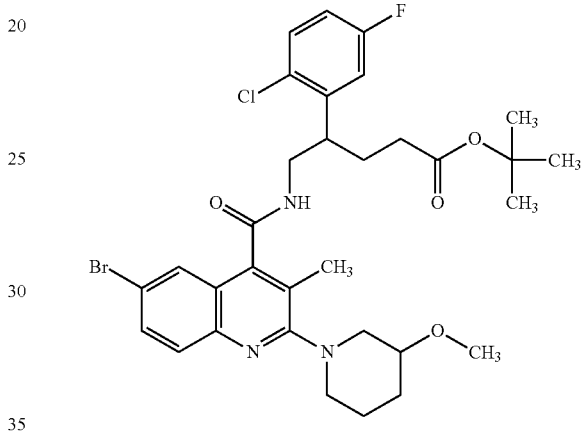

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added (+/−)-3-methoxypiperidine (59.1 mg, 513 μmol), and the mixture was stirred at 100° C. for two days. After cooling to RT, the mixture was purified directly (without further workup) by preparative HPLC (Method 18). The combined target fractions were concentrated, and the residue was lyophilized. 68 mg (98% purity, 58% of theory) of the title compound were obtained.

LC-MS (Method 1): $R_t$=2.66 min; MS (ESIpos): m/z=662/664 [M+H]$^+$ $^1$H-NMR (400 MHz, DMSO-d6) δ [ppm]: 0.007 (0.53), 1.233 (0.14), 1.373 (16.00), 1.573 (0.15), 1.794 (0.35), 2.035 (0.36), 2.085 (0.75), 2.102 (0.96), 2.133 (2.46), 2.731 (0.18), 2.840 (0.18), 3.301 (6.14), 3.425 (0.25), 3.585 (0.45), 3.614 (0.33), 3.687 (0.47), 7.122 (0.18), 7.143 (0.30), 7.156 (0.18), 7.395 (0.37), 7.402 (0.37), 7.420 (0.38), 7.428 (0.36), 7.479 (0.54), 7.493 (0.55), 7.502 (0.49), 7.515 (0.43), 7.635 (0.30), 7.657 (1.46), 7.664 (1.01), 7.669 (0.84), 7.691 (0.18), 8.721 (0.43).

$^1$H-NMR (400 MHz, DMSO-d6) δ [ppm]: 8.72 (t, 1H), 7.70-7.62 (m, 2H), 7.50 (dd, 1H), 7.46 (br. s, partially hidden, 1H), 7.41 (dd, 1H), 7.14 (td, 1H), 3.76-3.64 (m, 2H), 3.64-3.54 (m, 1H), 3.47-3.38 (m, 1H), 3.30 (s, partially hidden, 3H), 2.92-2.79 (m, 1H), 2.78-2.67 (m, 1H), 2.18-1.95 (m, 7H), 1.87-1.74 (m, 2H), 1.65-1.52 (m, 1H), 1.46-1.32 (m, partially hidden, 1H), 1.37 (s, 9H).

Example 70A tert-Butyl 5-[({6-bromo-2-[2-(hydroxymethyl)morpholin-4-yl]-3-methylquinolin-4-yl}carbonyl)amino]-4-(2-chloro-5-fluorophenyl)pentanoate (Diastereomer Mixture)

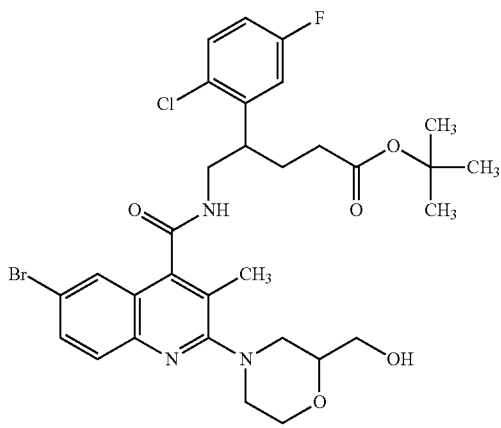 [SMILES: Cc1c(N2CCOC(CO)C2)nc2ccc(Br)cc2c1C(=O)NCC(CCC(=O)OC(C)(C)C)c1cc(F)ccc1Cl]

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added (+/−)-morpholin-2-ylmethanol (60 mg, 513 μmol), and the mixture was stirred at 100° C. for two days. After cooling to RT, the mixture was purified directly (without further workup) by preparative HPLC (Method 23). The combined target fractions were concentrated, and the residue was lyophilized. 35 mg (98% purity, 30% of theory) of the title compound were obtained.

LC-MS (Method 1): $R_t$=2.28 min; MS (ESIpos): m/z=664/666 $[M+H]^+$ $^1$H-NMR (400 MHz, DMSO-d6) δ [ppm]: −0.009 (0.40), 0.007 (0.40), 1.213 (0.06), 1.329 (0.08), 1.372 (16.00), 1.529 (0.06), 1.776 (0.12), 1.810 (0.17), 1.832 (0.14), 2.000 (0.14), 2.013 (0.18), 2.031 (0.17), 2.051 (0.15), 2.086 (0.66), 2.103 (0.89), 2.123 (0.35), 2.153 (1.90), 2.327 (0.08), 2.366 (0.07), 2.669 (0.23), 2.692 (0.17), 2.710 (0.12), 2.898 (0.16), 3.380 (0.32), 3.417 (0.42), 3.481 (0.21), 3.494 (0.42), 3.508 (0.51), 3.522 (0.45), 3.535 (0.25), 3.549 (0.29), 3.618 (0.29), 3.680 (0.41), 3.708 (0.52), 3.737 (0.22), 3.908 (0.32), 3.935 (0.26), 4.748 (0.34), 4.762 (0.68), 4.776 (0.32), 7.123 (0.15), 7.144 (0.27), 7.158 (0.15), 7.396 (0.30), 7.403 (0.31), 7.421 (0.32), 7.428 (0.30), 7.482 (0.48), 7.496 (0.50), 7.504 (0.47), 7.517 (0.43), 7.661 (0.14), 7.683 (1.97), 7.689 (0.99), 7.711 (0.12), 8.749 (0.37).

$^1$H-NMR (400 MHz, DMSO-d6) δ [ppm]: 8.75 (t, 1H), 7.72-7.65 (m, 2H), 7.50 (dd, 1H), 7.47 (br s, 1H), 7.41 (dd, 1H), 7.14 (td, 1H), 4.76 (t, 1H), 3.92 (br d, 1H), 3.77-3.47 (m, 7H), 3.46-3.35 (m, 2H), 2.96-2.82 (m, 1H), 2.74-2.60 (m, 1H), 2.15 (s, 3H), 2.13-2.07 (m, 2H), 2.07-1.96 (m, 1H), 1.88-1.73 (m, 1H), 1.37 (s, 9H).

Example 71A tert-Butyl 5-[({6-bromo-2-[3-(hydroxymethyl)piperidin-1-yl]-3-methylquinolin-4-yl}carbonyl)amino]-4-(2-chloro-5-fluorophenyl)pentanoate (Diastereomer Mixture)

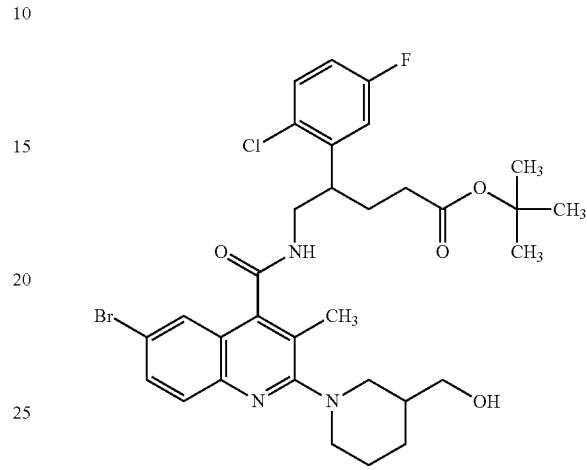

To a suspension of (+/−)-tert-butyl 5-{[(6-bromo-2-chloro-3-methylquinolin-4-yl)carbonyl]amino}-4-(2-chloro-5-fluorophenyl)pentanoate (100 mg, 171 μmol, Example 36A) in 1-butanol (1.2 ml) was added (+/−)-piperidin-3-ylmethanol (59 mg, 513 μmol), and the mixture was stirred at 100° C. for three days. After cooling to RT, the mixture was purified directly (without further workup) by preparative HPLC (Method 23). The combined target fractions were concentrated, and the residue was lyophilized. 63 mg (98% purity, 54% of theory) of the title compound were obtained.

LC-MS (Method 1): $R_t$=2.43 min; MS (ESIpos): m/z=662/664 $[M+H]^+$ $^1$H-NMR (400 MHz, DMSO-d6) δ [ppm]: −0.154 (0.04), 0.142 (0.04), 1.118 (0.19), 1.141 (0.21), 1.209 (0.07), 1.295 (0.07), 1.326 (0.10), 1.369 (16.00), 1.525 (0.07), 1.640 (0.17), 1.747 (0.56), 1.773 (0.71), 1.807 (0.34), 1.999 (0.16), 2.011 (0.20), 2.029 (0.20), 2.049 (0.18), 2.062 (0.16), 2.081 (0.76), 2.098 (1.02), 2.128 (2.35), 2.323 (0.05), 2.362 (0.04), 2.665 (0.06), 2.721 (0.17), 2.741 (0.19), 3.356 (0.20), 3.368 (0.37), 3.381 (0.33), 3.394 (0.23), 3.407 (0.13), 3.438 (0.24), 3.468 (0.21), 3.585 (0.48), 3.613 (0.36), 3.680 (0.34), 4.505 (0.34), 4.517 (0.69), 4.530 (0.33), 7.118 (0.17), 7.139 (0.31), 7.153 (0.18), 7.160 (0.18), 7.388 (0.36), 7.395 (0.37), 7.413 (0.38), 7.421 (0.37), 7.477 (0.50), 7.490 (0.50), 7.499 (0.45), 7.513 (0.41), 7.623 (0.21), 7.645 (1.52), 7.654 (0.92), 7.676 (0.15), 8.728 (0.41).

$^1$H-NMR (400 MHz, DMSO-d6) δ [ppm]: 8.73 (t, 1H), 7.69-7.62 (m, 2H), 7.50 (dd, 1H), 7.47 (br. s, partially hidden, 1H), 7.41 (dd, 1H), 7.14 (td, 1H), 4.52 (t, 1H), 3.75-3.53 (m, 4H), 3.46 (br. d, 1H), 3.42-3.35 (m, 1H), 3.33-3.26 (m, concealed, 2H), 2.81-2.64 (m, 1H), 2.18-1.96 (m, 6H), 1.87-1.71 (m, 4H), 1.69-1.57 (m, 1H), 1.37 (s, 9H), 1.21-1.05 (m, 1H).

Example 72A (+/−)-tert-Butyl 5-({[6-bromo-3-methyl-2-(piperidin-1-yl)quinolin-4-yl]carbonyl}amino)-4-(2-chlorophenyl)pentanoate (Racemate)

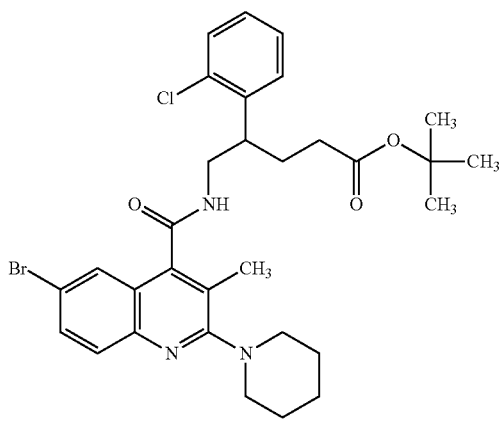

To a suspension of (+/−)-tert-butyl 5-{[(6-bromo-2-chloro-3-methylquinolin-4-yl)carbonyl]amino}-4-(2-chlorophenyl)pentanoate (1.10 g, 1.94 mmol, Example 37A) in 1-butanol (14 ml) was added piperidine (580 µl, 5.8 mmol), and the mixture was stirred at 100° C. for three days. After cooling to RT, water and ethyl acetate (50 ml of each) were added to the mixture, which was agitated. After phase separation, the aqueous phase was extracted once with ethyl acetate (50 ml). The combined organic phases were dried over sodium sulfate, filtered and concentrated, and the residue was taken up in dichloromethane and purified by means of flash column chromatography (100 g silica gel Biotage Snap-Cartridge KP-Sil, cyclohexane/ethyl acetate gradient 93:7→6:4, Isolera One). The combined target fractions were concentrated, and the residue was dried under reduced pressure. 557 mg (84% purity, 39% of theory) of the title compound were obtained.

LC-MS (Method 1): $R_t$=2.82 min; MS (ESIpos): m/z=614/616 [M+H]$^+$ $^1$H-NMR (400 MHz, DMSO-d6) δ [ppm]: 8.72 (t, 1H), 7.69-7.61 (m, 2H), 7.51-7.43 (m, 2H), 7.49 (br., 1H), 7.40-7.34 (m, 1H), 7.30-7.24 (m, 1H), 3.73-3.53 (m, 3H), 3.13 (br s, 4H), 2.17-2.00 (m, 6H), 1.87-1.75 (m, 1H), 1.71-1.55 (m, 6H), 1.37 (s, 9H).

Separation of the Enantiomers:

The title compound (550 mg) was dissolved in methanol (20 ml) and separated into the enantiomers by means of preparative SFC on chiral phase (see Examples 73A and 74A) [column: Daicel Chiralpak OX-H, 5 µm, 250 mm×20 mm; flow rate: 80 ml/min; detection: 210 nm; temperature: 40° C.; injection: 0.3 ml; eluent: 15% isopropanol/85% heptane; run time 16 min, isocratic]. The combined target fractions were concentrated and the residue was dried under reduced pressure.

Example 73A (−)-tert-Butyl 5-({[6-bromo-3-methyl-2-(piperidin-1-yl)quinolin-4-yl]carbonyl}amino)-4-(2-chlorophenyl)pentanoate (Enantiomer 1)

In the enantiomer separation described in Example 72A, the prepurified title compound was obtained as the enantiomer that eluted earlier (ee 99%). This was followed by repurification by means of preparative HPLC (Method 6). The combined target fractions were concentrated, and the residue was dried under reduced pressure. 150 mg (95% purity) of the repurified title compound were obtained.

$[α]_D^{20}$=−8.4°, 589 nm, c=0.31 g/100 ml, methanol

LC-MS (Method 2): $R_t$=1.51 min; MS (ESIpos): m/z=614/616 [M+H]$^+$ $^1$H-NMR (400 MHz, DMSO-d6) δ [ppm]: 1.208 (0.07), 1.312 (0.09), 1.333 (0.12), 1.368 (16.00), 1.525 (0.09), 1.604 (0.60), 1.668 (1.18), 1.814 (0.26), 2.045 (0.27), 2.074 (1.54), 2.085 (0.84), 2.108 (0.38), 2.131 (1.97), 3.132 (1.52), 3.584 (0.27), 3.671 (0.49), 7.251 (0.23), 7.270 (0.53), 7.289 (0.37), 7.351 (0.32), 7.370 (0.57), 7.388 (0.30), 7.438 (0.79), 7.458 (0.67), 7.479 (0.73), 7.497 (0.64), 7.623 (0.30), 7.645 (1.58), 7.652 (1.07), 7.675 (0.20), 8.705 (0.28), 8.720 (0.54), 8.733 (0.26).

$^1$H-NMR (400 MHz, DMSO-d6) δ [ppm]: 8.72 (t, 1H), 7.69-7.61 (m, 2H), 7.47 (dd, 2H), 7.49 (br., concealed, 1H), 7.37 (t, 1H), 7.27 (t, 1H), 3.74-3.50 (m, 3H), 3.13 (br. s, 4H), 2.17-1.98 (m, 6H), 1.89-1.74 (m, 1H), 1.72-1.55 (m, 6H), 1.37 (s, 9H).

Example 74A (+)-tert-Butyl 5-({[6-bromo-3-methyl-2-(piperidin-1-yl)quinolin-4-yl]carbonyl}amino)-4-(2-chlorophenyl)pentanoate (Enantiomer 2)

In the enantiomer separation described in Example 72A, the prepurified title compound was obtained as the enantiomer that eluted later (ee 98%). This was followed by repurification by means of preparative HPLC (Method 6). The combined target fractions were concentrated, and the residue was dried under reduced pressure. 141 mg (98% purity) of the repurified title compound were obtained.

$[α]_D^{20}$=+8.0°, 589 nm, c=0.26 g/100 ml, methanol

LC-MS (Method 2): $R_t$=1.51 min; MS (ESIpos): m/z=614/616 [M+H]$^+$ $^1$H-NMR (400 MHz, DMSO-d6) δ [ppm]: 1.368 (16.00), 1.604 (0.61), 1.669 (1.21), 1.814 (0.27), 2.073 (1.61), 2.085 (0.85), 2.107 (0.39), 2.131 (2.06), 3.132 (1.57), 3.584 (0.28), 3.672 (0.51), 7.251 (0.24), 7.270 (0.55), 7.289 (0.39), 7.351 (0.33), 7.370 (0.60), 7.388 (0.31), 7.438 (0.83), 7.458 (0.71), 7.479 (0.78), 7.498 (0.66), 7.622 (0.31), 7.645 (1.57), 7.653 (1.05), 7.675 (0.20), 8.720 (0.56).

$^1$H-NMR (400 MHz, DMSO-d6) δ [ppm]: 8.72 (t, 1H), 7.70-7.61 (m, 2H), 7.47 (dd, 2H), 7.49 (br., 1H), 7.37 (t, 1H), 7.27 (t, 1H), 3.74-3.52 (m, 3H), 3.13 (br. s, 4H), 2.18-1.99 (m, 6H), 1.88-1.74 (m, 1H), 1.72-1.54 (m, 6H), 1.37 (s, 9H).

Example 75A (+/−)-tert-Butyl 5-({[6-bromo-3-methyl-2-(thiomorpholin-4-yl)quinolin-4-yl]carbonyl}amino)-4-(2-chlorophenyl)pentanoate (Racemate)

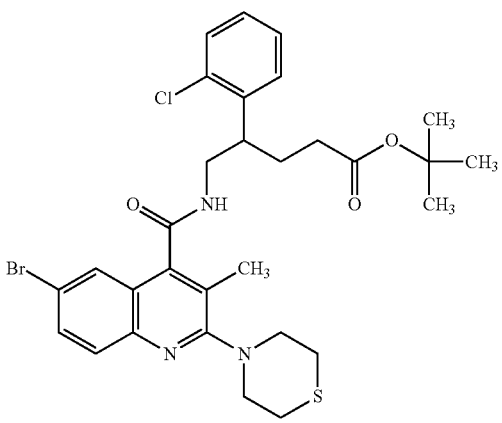

To a suspension of (+/−)-tert-butyl 5-{[(6-bromo-2-chloro-3-methylquinolin-4-yl)carbonyl]amino}-4-(2-chlorophenyl)pentanoate (250 mg, 91% purity, 402 µmol, Example 37A) in 1-butanol (2.9 ml) was added thiomorpholine (124 mg, 1.21 mmol), and the mixture was stirred at 100° C. for two days. After cooling to RT, the mixture was purified directly (without further workup) by preparative HPLC (Method 6). The combined target fractions were concentrated, and the residue was dried under reduced pressure. 77 mg (98% purity, 30% of theory) of the title compound were obtained.

LC-MS (Method 2): $R_t$=1.42 min; MS (ESIpos): m/z=632/634 [M+H]$^+$ $^1$H-NMR (400 MHz, DMSO-d6) δ [ppm]: −0.008 (0.51), 0.008 (0.46), 1.369 (16.00), 2.073 (1.08), 2.086 (0.66), 2.132 (1.34), 2.774 (0.88), 2.786 (1.01), 2.798 (0.95), 3.413 (0.94), 3.419 (0.94), 3.426 (0.99), 3.437 (0.86), 7.372 (0.41), 7.438 (0.61), 7.441 (0.57), 7.458 (0.51), 7.461 (0.48), 7.479 (0.49), 7.482 (0.49), 7.499 (0.41), 7.678 (1.34), 7.684 (0.99), 7.688 (0.81).

$^1$H-NMR (400 MHz, DMSO-d6) δ [ppm]: 8.72 (t, 1H), 7.74-7.62 (m, 2H), 7.60-7.42 (m, 3H), 7.37 (t, 1H), 7.31-7.23 (m, 1H), 3.67 (br. s, 2H), 3.62-3.53 (m, 1H), 3.46-3.38 (m, 4H), 2.83-2.74 (m, 4H), 2.19-1.97 (m, 6H), 1.88-1.73 (m, 1H), 1.37 (s, 9H).

Example 76A (+/−)-tert-Butyl 5-({[6-bromo-2-(4,4-difluoropiperidin-1-yl)-3-methylquinolin-4-yl]carbonyl}amino)-4-(2-chlorophenyl)pentanoate (Racemate)

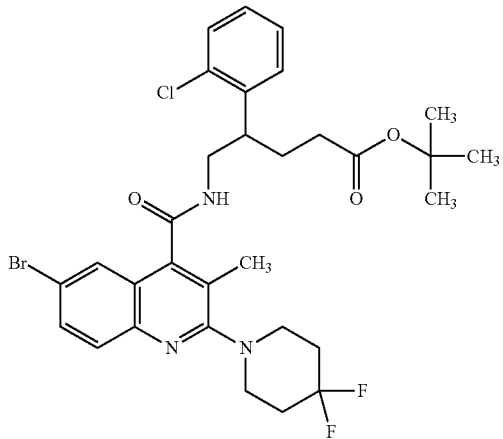 [SMILES: Cc1c(N2CCC(F)(F)CC2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (100 mg, 88% purity, 155 µmol, Example 37A) in 1-butanol (1.1 ml) was added 4,4-difluoropiperidine (94 mg, 777 µmol), and the mixture was stirred at 100° C. for two days. After cooling to RT, the mixture was purified by preparative HPLC (Method 18). The combined target fractions were concentrated, and the residue was dried under reduced pressure. 28 mg (98% purity, 27% of theory) of the title compound were obtained.

LC-MS (Method 1): $R_t$=2.71 min; MS (ESIpos): m/z=650/652 [M+H]$^+$ $^1$H-NMR (400 MHz, DMSO-d6) δ [ppm]: −0.008 (0.67), 1.369 (16.00), 2.075 (1.36), 2.088 (0.85), 2.111 (0.57), 2.167 (1.98), 2.523 (0.67), 7.272 (0.44), 7.373 (0.48), 7.439 (0.66), 7.459 (0.57), 7.486 (0.59), 7.503 (0.48), 7.682 (1.32), 7.691 (0.87), 7.695 (0.76), 8.738 (0.45).

$^1$H-NMR (400 MHz, DMSO-d6) δ [ppm]: 8.74 (t, 1H), 7.74-7.64 (m, 2H), 7.59-7.42 (m, 3H), 7.37 (t, 1H), 7.30-7.23 (m, 1H), 3.68 (br. s, 2H), 3.62-3.53 (m, 1H), 2.23-1.94 (m, 11H), 1.89-1.70 (m, 1H), 1.37 (s, 9H).

Example 77A (+/−)-tert-Butyl 5-({[6-bromo-2-(3,6-dihydropyridin-1(2H)-yl)-3-methylquinolin-4-yl]carbonyl}amino)-4-(2-chlorophenyl)pentanoate (Racemate)

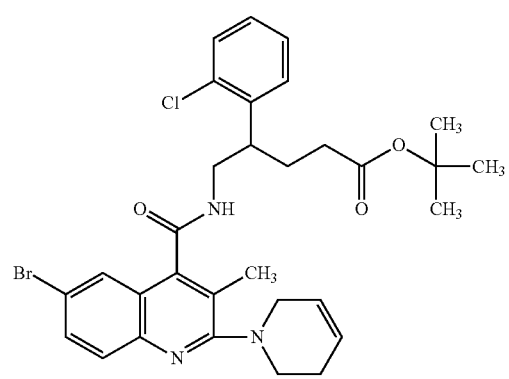 [SMILES: Cc1c(N2CC=CCC2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (250 mg, 91% purity, 402 µmol, Example 37A) in 1-butanol (2.9 ml) was added 1,2,3,6-tetrahydropyridine (100 mg, 1.21 mmol), and the mixture was stirred at 100° C. for two days. After cooling to RT, the mixture was purified directly (without further workup) by preparative HPLC (Method 6). The combined target fractions were concentrated, and the residue was dried under reduced pressure. 158 mg (98% purity, 63% of theory) of the title compound were obtained.

LC-MS (Method 1): $R_t$=2.75 min; MS (ESIpos): m/z=612/614 [M+H]$^+$ $^1$H-NMR (400 MHz, DMSO-d6) δ [ppm]: 1.370 (16.00), 2.077 (1.26), 2.089 (0.70), 2.144 (1.50), 2.303 (0.46), 3.797 (0.80), 5.844 (0.51), 5.864 (0.46), 7.273 (0.41), 7.374 (0.45), 7.439 (0.61), 7.441 (0.64), 7.458 (0.53), 7.461 (0.54), 7.485 (0.60), 7.502 (0.47), 7.642 (1.32), 7.655 (0.81), 7.660 (0.74), 8.732 (0.44).

$^1$H-NMR (400 MHz, DMSO-d6) δ [ppm]: 8.73 (t, 1H), 7.70-7.60 (m, 2H), 7.58-7.41 (m, 3H), 7.37 (t, 1H), 7.31-7.23 (m, 1H), 5.95-5.77 (m, 2H), 3.80 (br. s, 2H), 3.68 (br. s, 2H), 3.63-3.53 (m, 1H), 3.28 (br. s, 2H), 2.30 (br. s, 2H), 2.18-1.98 (m, 6H), 1.87-1.74 (m, 1H), 1.37 (s, 9H).

Example 78A (+/−)-tert-Butyl 5-({[6-bromo-3-methyl-2-(1,2-oxazinan-2-yl)quinolin-4-yl]carbonyl}amino)-4-(2-chlorophenyl)pentanoate (Racemate)

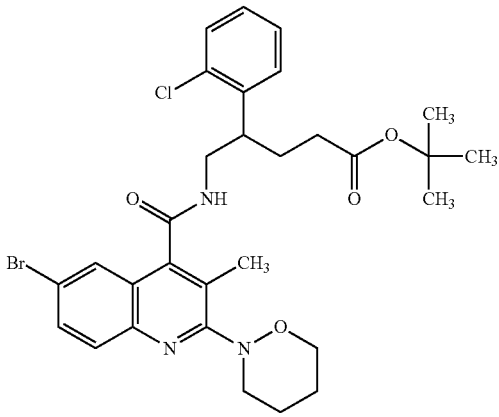 [SMILES: Cc1c(N2CCCCO2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (100 mg, 88% purity, 155 µmol, Example 37A) in 1-butanol (1.1 ml) were added 1,2-oxazinane (67.7 mg, 777 µmol) and DIPEA (140 µl, 780 µmol), and the mixture was stirred at 100° C. for two days. After cooling to RT, the mixture was purified by preparative HPLC (Method 18). The combined target fractions were concentrated, and the residue was dried under reduced pressure. 24 mg (98% purity, 25% of theory) of the title compound were obtained.

LC-MS (Method 1): $R_t$=2.75 min; MS (ESIpos): m/z=616/618 [M+H]$^+$ $^1$H-NMR (400 MHz, DMSO-d6) δ [ppm]: 1.369 (16.00), 1.697 (0.63), 1.870 (0.56), 1.884 (0.67), 1.898 (0.45), 2.075 (1.56), 2.086 (0.82), 2.145 (1.44), 3.573 (0.69), 3.680 (0.54), 4.041 (0.59), 4.053 (0.94), 4.065 (0.59), 7.274 (0.52), 7.371 (0.56), 7.444 (0.75), 7.464 (0.65), 7.479 (0.65), 7.498 (0.50), 7.731 (2.67), 8.805 (0.54).

$^1$H-NMR (400 MHz, DMSO-d6) δ [ppm]: 8.81 (t, 1H), 7.73 (s, 2H), 7.55 (br. s, 1H), 7.47 (dd, 2H), 7.37 (m, 2H), 7.31-7.24 (m, 1H), 4.05 (t, 2H), 3.77-3.48 (m, 5H), 2.20-1.98 (m, 6H), 1.93-1.75 (m, 3H), 1.74-1.64 (m, 2H), 1.37 (s, 9H).

Example 79A (+/−)-tert-Butyl 5-({[6-bromo-3-methyl-2-(pyrrolidin-1-yl)quinolin-4-yl]carbonyl}amino)-4-(2-chlorophenyl)pentanoate (Racemate)

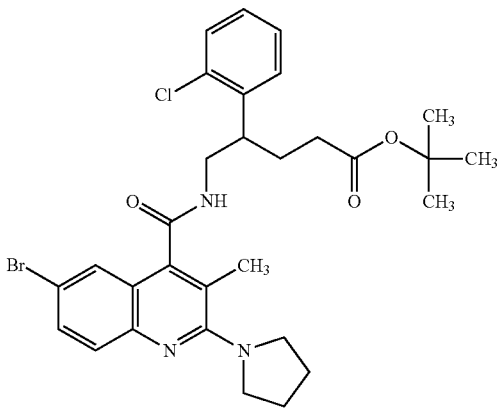 [SMILES: Cc1c(N2CCCC2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (500 mg, 91% purity, 803 µmol, Example 37A) in 1-butanol (5.8 ml) was added pyrrolidine (200 µl, 2.4 mmol), and the mixture was stirred at 100° C. for two days. After cooling to RT, the mixture was purified by preparative HPLC (Method 6). The combined target fractions were concentrated, and the residue was dried under reduced pressure. 450 mg (96% purity, 89% of theory) of the title compound were obtained.

LC-MS (Method 2): $R_t$=1.08 min; MS (ESIpos): m/z=600/602 [M+H]$^+$ $^1$H-NMR (400 MHz, DMSO-d6) δ [ppm]: 8.67 (t, 1H), 7.56 (dd, 1H), 7.52-7.40 (m, 4H), 7.37 (t, 1H), 7.30-7.23 (m, 1H), 3.76-3.47 (m, 7H), 2.23-1.98 (m, 6H), 1.92-1.73 (m, 5H), 1.37 (s, 9H).

Example 80A tert-Butyl 5-[({6-bromo-3-methyl-2-[3-methylpyrrolidin-1-yl]quinolin-4-yl}carbonyl)amino]-4-(2-chlorophenyl)pentanoate (Diastereomer Mixture)

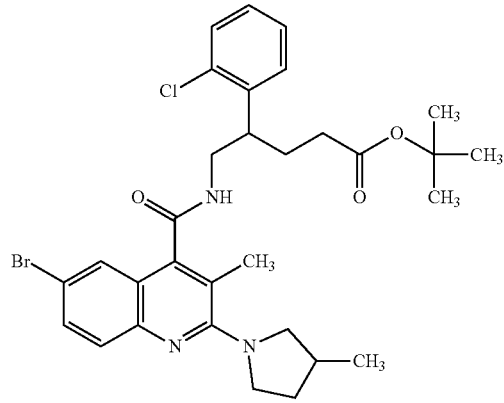 [SMILES: Cc1c(N2CCC(C)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (100 mg, 88% purity, 155 µmol, Example 37A) in 1-butanol (1.1 ml) were added (+/−)-3-methylpyrrolidine hydrochloride (95 mg, 777 µmol) and DIPEA (140 µl, 780 µmol), and the mixture was stirred at 100° C. for two days. After cooling to RT, the mixture was purified by preparative HPLC (Method 19). The combined target fractions were concentrated, and the residue was dried under reduced pressure. 27 mg (98% purity by LC-MS, 28% of theory) of the title compound were obtained in a mixture with the corresponding n-butyl ester.

LC-MS (Method 1): $R_t$=2.41 min; MS (ESIpos): m/z=614/616 [M+H]$^+$

Example 81A (+/−)-tert-Butyl 5-({[6-bromo-2-(3,3-difluoropyrrolidin-1-yl)-3-methylquinolin-4-yl]carbonyl}amino)-4-(2-chlorophenyl)pentanoate (Racemate)

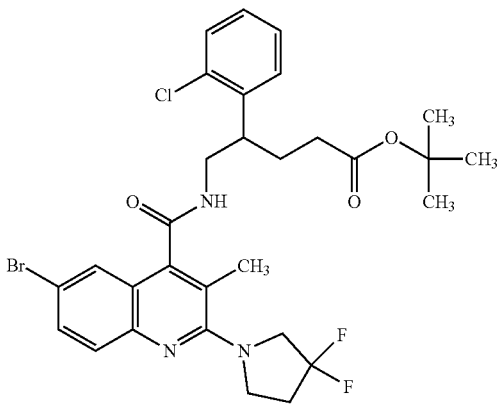 [SMILES: Cc1c(N2CCC(F)(F)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (100 mg, 88% purity, 155 µmol, Example 37A) in 1-butanol (1.1 ml) were added difluoropyrrolidine hydrochloride (112 mg, 777 µmol) and DIPEA (140 µl, 780 µmol), and the mixture was stirred at 100° C. for two days. After cooling to RT, the mixture was purified by preparative HPLC (Method 18). The combined target fractions were concentrated, and the residue was dried under reduced pressure. 32 mg (98% purity by LC-MS, 32% of theory) of the title compound were obtained in a mixture with the corresponding n-butyl ester.

LC-MS (Method 1): $R_t$=2.66 min; MS (ESIpos): m/z=636/638 [M+H]$^+$

Example 82A (+/−)-tert-Butyl 5-({[6-bromo-3-methyl-2-(1,2-oxazolidin-2-yl)quinolin-4-yl]carbonyl}amino)-4-(2-chlorophenyl)pentanoate (Racemate)

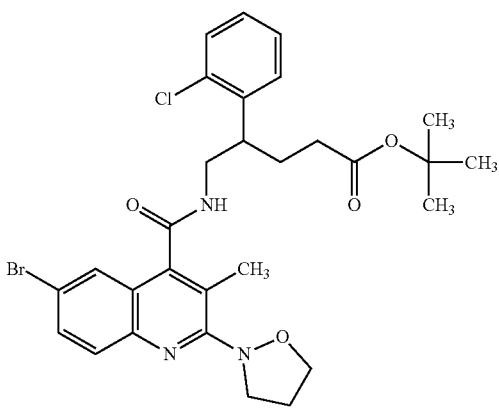 [SMILES: Cc1c(N2CCCO2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (250 mg, 91% purity, 402 µmol, Example 37A) in 1-butanol (2.9 ml) was added 1,2-oxazolidine (88 mg, 1.21 mmol), and the mixture was stirred at 100° C. for two days. After cooling to RT, the mixture was purified by preparative HPLC (Method 6). The combined target fractions were concentrated, and the residue was dried under reduced pressure. 137 mg (98% purity, 55% of theory) of the title compound were obtained.

LC-MS (Method 2): $R_t$=1.31 min; MS (ESIpos): m/z=602/604 [M+H]$^+$ $^1$H-NMR (400 MHz, DMSO-d6) δ [ppm]: 1.326 (0.11), 1.345 (0.22), 1.368 (16.00), 1.812 (0.20), 2.051 (0.20), 2.073 (1.19), 2.085 (0.63), 2.102 (0.25), 2.212 (0.90), 2.239 (0.67), 2.257 (0.83), 2.275 (0.61), 2.293 (0.19), 3.594 (0.21), 3.681 (0.40), 3.773 (0.40), 3.819 (0.60), 3.838 (1.03), 3.856 (0.56), 7.253 (0.18), 7.272 (0.41), 7.291 (0.29), 7.352 (0.24), 7.371 (0.44), 7.390 (0.23), 7.443 (0.65), 7.461 (0.53), 7.483 (0.54), 7.501 (0.42), 7.708 (0.11), 7.730 (2.34), 8.783 (0.42), 8.797 (0.22).

$^1$H-NMR (400 MHz, DMSO-d6) δ [ppm]: 8.78 (t, 1H), 7.79-7.69 (m, 2H), 7.55 (br. s, 1H), 7.51-7.43 (m, 2H), 7.37 (t, 1H), 7.31-7.23 (m, 1H), 3.84 (t, 2H), 3.80-3.52 (m, 5H), 2.31-2.15 (m, 5H), 2.12-1.98 (m, 3H), 1.89-1.74 (m, 1H), 1.37 (s, 9H).

Example 83A

Butyl 5-({[6-bromo-2-(3-methoxypyrrolidin-1-yl)-3-methylquinolin-4-yl]carbonyl}amino)-4-(2-chlorophenyl)pentanoate (Diastereomer Mixture)

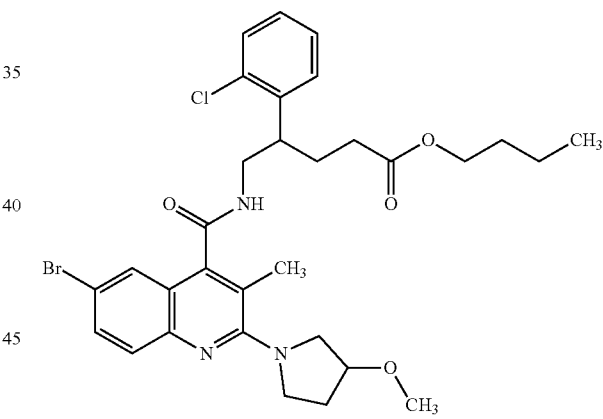

To a suspension of (+/−)-tert-butyl 5-{[(6-bromo-2-chloro-3-methylquinolin-4-yl)carbonyl]amino}-4-(2-chlorophenyl)pentanoate (100 mg, 88% purity, 155 µmol, Example 37A) in 1-butanol (1.1 ml) were added (+/−)-3-methoxypyrrolidine hydrochloride (107 mg, 777 µmol) and DIPEA (140 µl, 780 µmol), and the mixture was stirred at 100° C. for two days. After cooling to RT, the mixture was purified by preparative HPLC (Method 19). The combined target fractions were concentrated, and the residue was dried under reduced pressure. 36 mg (98% purity, 36% of theory) of the title compound were obtained.

LC-MS (Method 1): $R_t$=2.38 min; MS (ESIpos): m/z=630/632 [M+H]$^+$ $^1$H-NMR (400 MHz, DMSO-d6) δ [ppm]: 0.841 (6.92), 0.859 (16.00), 0.878 (8.20), 1.242 (0.62), 1.260 (2.27), 1.279 (3.99), 1.297 (4.01), 1.316 (2.45), 1.335 (0.68), 1.472 (1.34), 1.488 (3.43), 1.508 (4.15), 1.525 (3.19), 1.542 (0.92), 1.836 (0.66), 1.849 (0.86), 1.870 (1.04), 1.884 (0.78), 1.904

(0.42), 2.050 (0.40), 2.070 (1.08), 2.082 (1.26), 2.101 (1.32), 2.123 (1.34), 2.132 (1.26), 2.170 (7.46), 2.190 (4.09), 2.209 (1.68), 2.229 (0.50), 2.327 (0.46), 2.422 (0.74), 2.440 (1.52), 2.458 (2.17), 2.476 (3.21), 2.669 (0.40), 3.585 (1.18), 3.675 (1.62), 3.783 (2.51), 3.910 (0.72), 3.926 (1.48), 3.937 (3.09), 3.944 (3.49), 3.953 (5.65), 3.961 (5.89), 3.970 (3.85), 3.978 (3.23), 3.988 (1.62), 4.004 (1.04), 7.252 (0.96), 7.271 (2.27), 7.289 (1.70), 7.351 (1.40), 7.369 (2.51), 7.388 (1.38), 7.436 (4.09), 7.455 (3.47), 7.480 (3.31), 7.500 (2.49), 7.570 (3.37), 7.592 (6.68), 7.630 (3.79), 7.636 (3.45), 7.653 (1.86), 7.658 (1.76), 8.693 (1.22), 8.706 (2.39), 8.720 (1.20).

Example 84A (+/−)-tert-Butyl 5-({[6-bromo-2-(3,3-dimethylpiperidin-1-yl)-3-methylquinolin-4-yl]carbonyl}amino)-4-(2-chlorophenyl)pentanoate (Racemate)

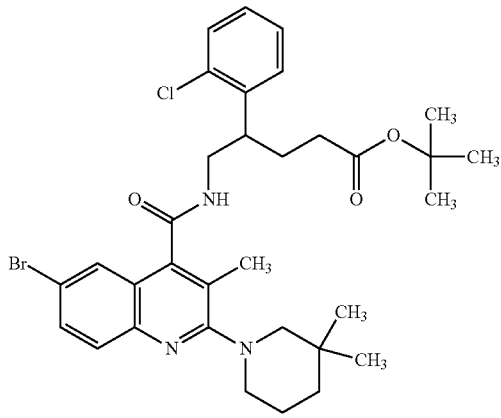 [SMILES: Cc1c(N2CCCC(C)(C)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (500 mg, 883 µmol, Example 37A) in 1-butanol (6.4 ml) was added 3,3-dimethylpiperidine (370 µl, 2.6 mmol), and the mixture was stirred at 100° C. for two days. Subsequently, 3,3-dimethylpiperidine (370 µl, 2.6 mmol) was added again, and the mixture was stirred at 100° C. for a further three days. After cooling to RT, the mixture was concentrated and the residue was taken up in dichloromethane and purified by means of flash column chromatography (50 g silica gel Biotage Snap-Cartridge Ultra, cyclohexane/ethyl acetate gradient 93:7→7:3, Isolera One). The combined target fractions were concentrated, and the residue was dried under reduced pressure. 420 mg (94% purity, 69% of theory) of the title compound were obtained.

LC-MS (Method 2): $R_t$=1.58 min; MS (ESIpos): m/z=642/644 [M+H]$^+$ $^1$H-NMR (400 MHz, DMSO-d6) δ [ppm]: 8.72 (t, 1H), 7.70-7.61 (m, 2H), 7.59-7.42 (m, 3H), 7.37 (t, 1H), 7.30-7.24 (m, 1H), 3.75-3.62 (m, 2H), 3.62-3.53 (m, 1H), 3.05 (br. s, 2H), 2.86 (s, 2H), 2.17 (s, 3H), 2.13-1.99 (m, 3H), 1.92-1.75 (m, 1H), 1.75-1.65 (m, 2H), 1.44-1.35 (m, 2H, partially hidden), 1.37 (s, 9H), 1.00 (s, 6H).

Example 85A tert-Butyl 5-[({6-bromo-3-methyl-2-[3-methylpiperidin-1-yl]quinolin-4-yl}carbonyl)amino]-4-(2-chlorophenyl)pentanoate (Diastereomer Mixture)

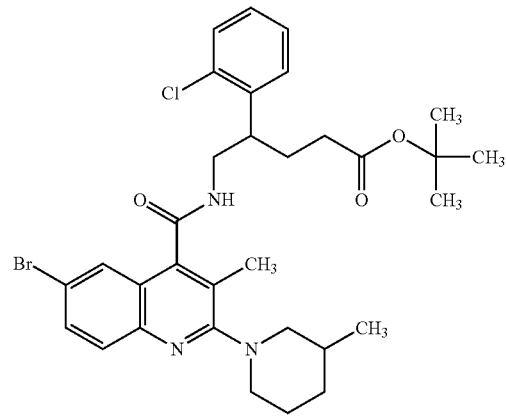 [SMILES: Cc1c(N2CCCC(C)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (1.10 g, 1.94 mmol, Example 37A) in 1-butanol (14 ml) was added (+/−)-3-methylpiperidine (680 µl, 5.8 mmol), and the mixture was stirred at 100° C. for two days. After cooling to RT, the mixture was concentrated and the residue was taken up in dichloromethane and purified by means of flash column chromatography (50 g silica gel Biotage Snap-Cartridge Ultra, cyclohexane/ethyl acetate gradient 93:7→7:3, Isolera One). The combined target fractions were concentrated, and the residue was dried under reduced pressure. 982 mg (96% purity, 77% of theory) of the title compound were obtained.

LC-MS (Method 2): $R_t$=1.54 min; MS (ESIpos): m/z=628/630 [M+H]$^+$ $^1$H-NMR (400 MHz, DMSO-d6) δ [ppm]: 8.72 (t, 1H), 7.71-7.60 (m, 2H), 7.59-7.41 (m, 3H), 7.37 (t, 1H), 7.31-7.23 (m, 1H), 3.67 (br. s, 2H), 3.62-3.54 (m, 1H), 3.46 (br. t, 2H), 2.78-2.64 (m, 1H), 2.48-2.39 (m, 1H), 2.19-2.00 (m, 6H), 1.89-1.57 (m, 5H), 1.37 (s, 9H), 1.15-1.02 (m, 1H), 0.93 (d, 3H).

Separation of the Diastereomers/Enantiomers:

The title compound (850 mg) was dissolved in a mixture of isopropanol (5 ml) and heptane (6 ml), and first subjected to preliminary separation by means of preparative HPLC on chiral phase [column: Daicel Chiralcel OX-H, 5 µm, 250 mm×20 mm; flow rate: 15 ml/min; injection: 0.13 ml; eluent: 20% isopropanol/80% heptane; run time 16 min, isocratic]. One sufficiently clean fraction (peak 1, see Example 86A) and two mixed fractions were obtained. The first mixed fraction (peak 2 and peak 3) was purified by means of preparative HPLC on chiral phase [column: Daicel Chiralcel OZ-H, 5 am, 250 mm×20 mm; flow rate: 15 ml/min; eluent: 15% isopropanol/85% heptane] (see Examples 87A and 88A). The second mixed fraction (predominantly peak 4) was likewise purified by means of preparative HPLC on chiral phase [column: Daicel Chiralcel OZ-H, 5 am, 250 mm×20 mm; flow rate: 15 ml/min; eluent: 10% isopropanol/90% heptane] (see Example 89A). The combined target fractions were each concentrated, and each residue was lyophilized.

Example 86A (−)-tert-Butyl 5-[({6-bromo-3-methyl-2-[3-methylpiperidin-1-yl]quinolin-4-yl}carbonyl)amino]-4-(2-chlorophenyl)pentanoate (Diastereomer 1)

In the diastereomer separation described in Example 85A, 194 mg (96% purity, ee 99%) of the title compound were obtained as the diastereomer (peak 1) that eluted first.

$[\alpha]_D^{20}$=−16.2°, 589 nm, c=0.38 g/100 ml, methanol
LC-MS (Method 1): $R_t$=2.90 min; MS (ESIpos): m/z=628/630 [M+H]$^+$ $^1$H-NMR (400 MHz, DMSO-d6) δ [ppm]: 0.945 (1.66), 0.961 (1.68), 1.103 (0.18), 1.131 (0.20), 1.159 (0.16), 1.177 (0.21), 1.195 (0.10), 1.235 (0.07), 1.340 (0.34), 1.359 (0.12), 1.395 (16.00), 1.420 (0.31), 1.551 (0.07), 1.645 (0.16), 1.676 (0.19), 1.755 (0.33), 1.790 (0.37), 1.817 (0.52), 1.846 (0.44), 2.056 (0.20), 2.073 (0.25), 2.082 (0.22), 2.100 (1.31), 2.111 (0.75), 2.127 (0.30), 2.134 (0.28), 2.162 (1.64), 2.353 (0.03), 2.392 (0.03), 2.443 (0.15), 2.472 (0.24), 2.711 (0.14), 2.737 (0.26), 2.768 (0.14), 2.928 (0.08), 2.947 (0.08), 3.463 (0.27), 3.486 (0.45), 3.514 (0.24), 3.610 (0.23), 3.698 (0.40), 7.280 (0.20), 7.296 (0.45), 7.314 (0.35), 7.351 (0.07), 7.379 (0.28), 7.397 (0.47), 7.415 (0.24), 7.464 (0.64), 7.466 (0.61), 7.483 (0.54), 7.507 (0.60), 7.523 (0.51), 7.652 (0.18), 7.674 (1.58), 7.682 (0.94), 7.699 (0.12), 7.704 (0.14), 8.727 (0.22), 8.741 (0.43), 8.755 (0.20).

Example 87A (+)-tert-Butyl 5-[({6-bromo-3-methyl-2-[3-methylpiperidin-1-yl]quinolin-4-yl}carbonyl)amino]-4-(2-chlorophenyl)pentanoate (Diastereomer 2)

In the diastereomer separation described in Example 85A, 157 mg (100% purity, ee 99%) of the title compound were obtained as the diastereomer (peak 2) that eluted second.

$[\alpha]_D^{20}$=+15.5°, 589 nm, c=0.37 g/100 ml, methanol
LC-MS (Method 1): $R_t$=2.90 min; MS (ESIpos): m/z=628/630 [M+H]$^+$ $^1$H-NMR (400 MHz, DMSO-d6) δ [ppm]: 0.919 (1.60), 0.935 (1.63), 1.077 (0.18), 1.101 (0.19), 1.139 (0.11), 1.157 (0.10), 1.176 (0.05), 1.208 (0.07), 1.311 (0.08), 1.333 (0.11), 1.368 (16.00), 1.525 (0.07), 1.619 (0.15), 1.649 (0.18), 1.729 (0.31), 1.764 (0.36), 1.791 (0.51), 1.820 (0.43), 2.046 (0.24), 2.056 (0.21), 2.074 (1.34), 2.085 (0.75), 2.101 (0.29), 2.107 (0.27), 2.136 (1.68), 2.327 (0.04), 2.365 (0.04), 2.417 (0.15), 2.446 (0.24), 2.475 (0.18), 2.685 (0.14), 2.710 (0.26), 2.741 (0.13), 3.437 (0.27), 3.461 (0.45), 3.488 (0.24), 3.584 (0.23), 3.672 (0.40), 7.253 (0.19), 7.271 (0.44), 7.288 (0.31), 7.353 (0.27), 7.371 (0.48), 7.389 (0.25), 7.440 (0.63), 7.457 (0.54), 7.480 (0.62), 7.497 (0.52), 7.625 (0.20), 7.648 (1.58), 7.655 (0.94), 7.673 (0.12), 7.678 (0.14), 8.701 (0.23), 8.715 (0.44), 8.729 (0.21).

Example 88A (+)-tert-Butyl 5-[({6-bromo-3-methyl-2-[3-methylpiperidin-1-yl]quinolin-4-yl}carbonyl)amino]-4-(2-chlorophenyl)pentanoate (Diastereomer 3)

In the diastereomer separation described in Example 85A, 169 mg (100% purity, ee 99%) of the title compound were obtained as the diastereomer (peak 3) that eluted third.

$[\alpha]_D^{20}$=+9.6°, 436 nm, c=0.42 g/100 ml, methanol
LC-MS (Method 1): $R_t$=2.91 min; MS (ESIpos): m/z=628/630 [M+H]$^+$ $^1$H-NMR (400 MHz, DMSO-d6) δ [ppm]: 0.920 (1.65), 0.936 (1.68), 1.078 (0.18), 1.101 (0.19), 1.139 (0.15), 1.157 (0.18), 1.176 (0.09), 1.208 (0.07), 1.314 (0.08), 1.331 (0.10), 1.369 (16.00), 1.525 (0.07), 1.626 (0.16), 1.656 (0.19), 1.728 (0.33), 1.760 (0.36), 1.794 (0.49), 1.820 (0.43), 2.047 (0.23), 2.056 (0.21), 2.074 (1.37), 2.085 (0.79), 2.102 (0.29), 2.137 (1.81), 2.327 (0.04), 2.365 (0.04), 2.431 (0.17), 2.459 (0.27), 2.669 (0.16), 2.699 (0.24), 2.728 (0.13), 2.923 (0.03), 3.434 (0.28), 3.462 (0.49), 3.492 (0.23), 3.583 (0.23), 3.668 (0.37), 7.253 (0.19), 7.272 (0.44), 7.292 (0.31), 7.353 (0.27), 7.372 (0.49), 7.390 (0.26), 7.440 (0.66), 7.460 (0.56), 7.481 (0.65), 7.498 (0.52), 7.626 (0.18), 7.649 (1.66), 7.655 (0.96), 7.677 (0.14), 8.702 (0.25), 8.716 (0.49), 8.730 (0.24).

Example 89A (−)-tert-Butyl 5-[({6-bromo-3-methyl-2-[3-methylpiperidin-1-yl]quinolin-4-yl}carbonyl)amino]-4-(2-chlorophenyl)pentanoate (Enantiomer 4)

In the diastereomer separation described in Example 85A, 158 mg (96% purity, ee 99%) of the title compound were obtained as the diastereomer (peak 4) that eluted last.

$[\alpha]_D^{20}$=−10.4°, 436 nm, c=0.44 g/1 00 ml, methanol
LC-MS (Method 1): $R_t$=2.90 min; MS (ESIpos): m/z=628/630 [M+H]$^+$ $^1$H-NMR (400 MHz, DMSO-d6) δ [ppm]: 0.920 (1.61), 0.936 (1.63), 1.077 (0.17), 1.100 (0.18), 1.139 (0.09), 1.157 (0.06), 1.208 (0.06), 1.314 (0.10), 1.331 (0.09), 1.369 (16.00), 1.525 (0.06), 1.626 (0.15), 1.657 (0.18), 1.728 (0.32), 1.761 (0.34), 1.794 (0.46), 1.820 (0.40), 2.047 (0.22), 2.056 (0.20), 2.074 (1.27), 2.086 (0.74), 2.102 (0.28), 2.137 (1.67), 2.327 (0.04), 2.365 (0.04), 2.431 (0.16), 2.460 (0.25), 2.669 (0.16), 2.699 (0.22), 2.728 (0.12), 3.433 (0.26), 3.462 (0.46), 3.493 (0.21), 3.583 (0.21), 3.667 (0.34), 7.254 (0.18), 7.272 (0.43), 7.288 (0.33), 7.325 (0.05), 7.353 (0.26), 7.372 (0.46), 7.390 (0.24), 7.437 (0.63), 7.440 (0.64), 7.457 (0.54), 7.460 (0.54), 7.481 (0.60), 7.498 (0.48), 7.626 (0.18), 7.649 (1.60), 7.655 (0.94), 7.678 (0.14), 8.702 (0.23), 8.716 (0.45), 8.730 (0.22).

Example 90A (+/−)-tert-Butyl 5-({[6-bromo-2-(3,3-difluoropiperidin-1-yl)-3-methylquinolin-4-yl]carbonyl}amino)-4-(2-chlorophenyl)pentanoate (Racemate)

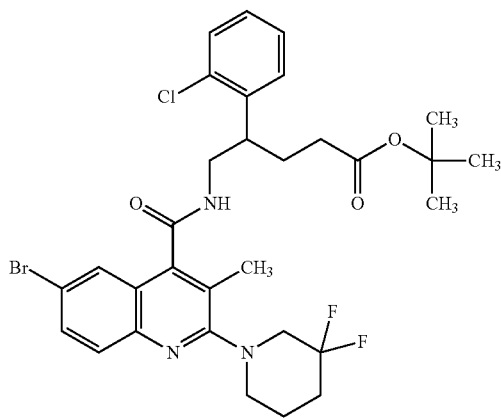 [SMILES: Cc1c(N2CCCC(F)(F)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (1.50 g, 98% purity, 2.60 mmol, Example 37A) in NMP (24 ml) were added 3,3-difluoropiperidine hydrochloride (3.27 g, 20.8 mmol) and DIPEA (5.42 ml, 31.15 mmol), and the mixture was stirred at 120° C. for 18 h. After cooling to RT, water (200 ml) and ethyl acetate (100 ml) were added to the mixture, which was agitated. After phase separation, the aqueous phase was extracted repeatedly with ethyl acetate (100 ml each time). The combined organic phases were dried over sodium sulfate, filtered and concentrated, and the residue was purified by means of flash column chromatography (100 g silica gel Biotage Snap-Cartridge Ultra, cyclohexane/ethyl acetate gradient 97:3→9:1, Isolera One). The combined target fractions were concentrated, and the residue was dried under reduced pressure. 933 mg (96% purity, 53% of theory) of the title compound were obtained.

LC-MS (Method 1): $R_t$=2.70 min; MS (ESIpos): m/z=650/652 [M+H]$^+$ $^1$H-NMR (400 MHz, DMSO-d6) δ [ppm]: −0.149 (0.04), 0.146 (0.04), 1.210 (0.08), 1.234 (0.04), 1.311 (0.07), 1.333 (0.09), 1.370 (16.00), 1.398 (3.71), 1.526 (0.08), 1.764 (0.07), 1.797 (0.17), 1.817 (0.23), 1.880 (0.52), 2.046 (0.34), 2.056 (0.38), 2.076 (1.68), 2.088 (1.06), 2.110 (0.55), 2.152 (1.68), 2.327 (0.05), 2.366 (0.05), 2.670 (0.04), 2.710 (0.04), 3.167 (0.60), 3.447 (0.40), 3.476 (0.76), 3.505 (0.38), 3.587 (0.24), 3.683 (0.40), 7.254 (0.20), 7.273 (0.48), 7.291 (0.35), 7.355 (0.28), 7.374 (0.51), 7.392 (0.26), 7.441 (0.69), 7.461 (0.57), 7.485 (0.60), 7.504 (0.47), 7.674 (0.26), 7.696 (1.50), 7.703 (0.97), 7.707 (0.83), 7.729 (0.17), 8.718 (0.24), 8.732 (0.49), 8.746 (0.24).

Separation of the Enantiomers:

The title compound (1.51 g) was dissolved in methanol (40 ml) and separated into the enantiomers by means of preparative SFC on chiral phase (see Examples 91A and 92A) [column: Daicel Chiralcel OZ-H, 5 μm, 250 mm×30 mm; flow rate: 114 ml/min; injection: 0.40 ml; eluent: 22% methanol/78% carbon dioxide; run time 9 min, isocratic]. The combined target fractions were concentrated, and the respective residue was dried under reduced pressure.

Example 91A tert-Butyl 5-({[6-bromo-2-(3,3-difluoropiperidin-1-yl)-3-methylquinolin-4-yl]carbonyl}amino)-4-(2-chlorophenyl)pentanoate (Enantiomer 1)

In the enantiomer separation described in Example 90A, 672 mg (97% purity, ee 98%) of the title compound were obtained as the enantiomer that eluted earlier.

$R_t$=2.35 min (chiral analytical SFC; Agilent Phenyl Cellulose-2 column, 3 μm, 50 mm×4.6 mm, eluent: carbon dioxide/methanol 95:5→4:6; flow rate 3 ml/min; temperature 40° C.; detection 220 nm)

LC-MS (Method 1): $R_t$=2.70 min; MS (ESIpos): m/z=650/652 [M+H]$^+$ $^1$H-NMR (400 MHz, DMSO-d6) δ [ppm]: −0.009 (0.28), 0.007 (0.29), 1.038 (0.05), 1.055 (0.10), 1.073 (0.05), 1.209 (0.06), 1.310 (0.07), 1.332 (0.10), 1.369 (16.00), 1.525 (0.06), 1.795 (0.14), 1.816 (0.18), 1.879 (0.44), 2.045 (0.28), 2.075 (1.41), 2.087 (0.90), 2.109 (0.46), 2.151 (1.41), 2.327 (0.05), 2.669 (0.06), 2.709 (0.04), 3.162 (0.52), 3.446 (0.34), 3.475 (0.65), 3.504 (0.32), 3.586 (0.20), 3.681 (0.34), 7.255 (0.17), 7.273 (0.40), 7.290 (0.30), 7.355 (0.24), 7.373 (0.43), 7.391 (0.22), 7.439 (0.60), 7.442 (0.58), 7.459 (0.50), 7.462 (0.48), 7.486 (0.50), 7.502 (0.40), 7.674 (0.24), 7.696 (1.37), 7.702 (0.97), 7.707 (0.83), 7.724 (0.15), 7.729 (0.17), 8.716 (0.21), 8.731 (0.43), 8.745 (0.21).

Example 92A tert-Butyl 5-({[6-bromo-2-(3,3-difluoropiperidin-1-yl)-3-methylquinolin-4-yl]carbonyl}amino)-4-(2-chlorophenyl)pentanoate (Enantiomer 2)

In the enantiomer separation described in Example 90A, 634 mg (98% purity, ee 98%) of the title compound were obtained as the enantiomer that eluted later.

$R_t$=2.67 min (chiral analytical SFC; Agilent Phenyl Cellulose-2 column, 3 μm, 50 mm×4.6 mm, eluent: carbon dioxide/methanol 95:5→4:6; flow rate 3 ml/min; temperature 40° C.; detection 220 nm)

LC-MS (Method 1): $R_t$=2.70 min; MS (ESIpos): m/z=650/652 [M+H]$^+$ $^1$H-NMR (400 MHz, DMSO-d6) δ [ppm]: 1.038 (0.09), 1.055 (0.18), 1.073 (0.09), 1.208 (0.06), 1.310 (0.06), 1.332 (0.09), 1.369 (16.00), 1.525 (0.07), 1.796 (0.15), 1.816 (0.20), 1.878 (0.45), 2.045 (0.28), 2.075 (1.47), 2.087 (0.94), 2.110 (0.47), 2.151 (1.50), 2.327 (0.05), 2.669 (0.06), 3.162 (0.54), 3.446 (0.36), 3.475 (0.67), 3.504 (0.33), 3.587 (0.21), 3.681 (0.36), 4.335 (0.06), 7.254 (0.17), 7.273 (0.41), 7.290 (0.29), 7.355 (0.24), 7.373 (0.45), 7.391 (0.23), 7.439 (0.64), 7.459 (0.53), 7.483 (0.52), 7.502 (0.42), 7.674 (0.24), 7.696 (1.40), 7.702 (0.97), 7.707 (0.82), 7.724 (0.15), 7.729 (0.17), 8.717 (0.22), 8.731 (0.45), 8.745 (0.22).

Example 93A tert-Butyl 5-[({6-bromo-3-methyl-2-[3-(trifluoromethyl)piperidin-1-yl]quinolin-4-yl}carbonyl)amino]-4-(2-chlorophenyl)pentanoate (Diastereomer Mixture)

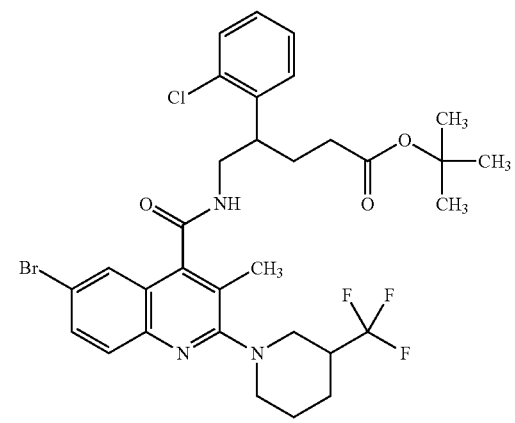 [SMILES: Cc1c(N2CCCC(C(F)(F)F)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (250 mg, 98% purity, 433 μmol, Example 37A) in NMP (4 ml) were added (+/−)-3-(trifluoromethyl)piperidine (530 mg, 3.46 mmol) and DIPEA (602 μl, 3.46 mmol), and the mixture was stirred at 120° C. for two days. After cooling to RT, the mixture was concentrated and the residue was dissolved in acetonitrile and purified by means of preparative HPLC (Method 6). The combined target fractions were concentrated, and the residue was dried under reduced pressure. 156 mg (98% purity, 52% of theory) of the title compound were obtained.

LC-MS (Method 1): R$_t$=2.85 min; MS (ESIpos): m/z=682/684 [M+H]$^+$ $^1$H-NMR (400 MHz, DMSO-d6) δ [ppm]: 1.153 (3.05), 1.181 (2.46), 1.268 (0.43), 1.284 (0.44), 1.308 (0.41), 1.370 (16.00), 1.504 (0.40), 1.521 (0.50), 2.076 (1.13), 2.089 (0.66), 2.144 (1.11), 7.271 (0.44), 7.373 (0.43), 7.436 (0.60), 7.456 (0.49), 7.484 (0.58), 7.488 (0.55), 7.503 (0.47), 7.689 (2.18).

Example 94A (+/−)-tert-Butyl 5-({[6-bromo-3-methyl-2-(4-methylpiperazin-1-yl)quinolin-4-yl]carbonyl}amino)-4-(2-chlorophenyl)pentanoate (Racemate)

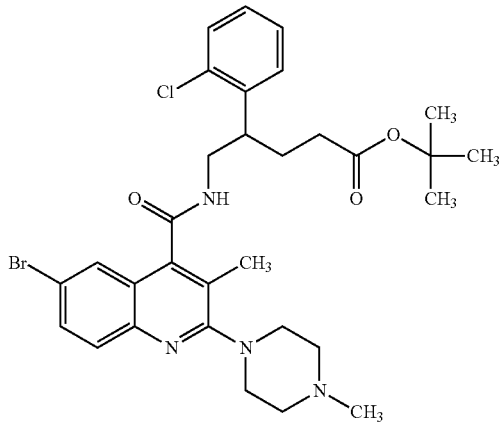 [SMILES: Cc1c(N2CCN(C)CC2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (200 mg, 98% purity, 346 μmol, Example 37A) in NMP (4 ml) were added 1-methylpiperazine (277 mg, 2.77 mmol) and DIPEA (482 μl, 2.77 mmol), and the mixture was stirred at 120° C. for two days. After cooling to RT, the mixture was concentrated and the residue was dissolved in acetonitrile and purified by means of preparative HPLC (Method 6). The combined target fractions were concentrated, and the residue was dried under reduced pressure. 135 mg (98% purity, 61% of theory) of the title compound were obtained.

LC-MS (Method 1): R$_t$=1.72 min; MS (ESIpos): m/z=629/631 [M+H]$^+$ $^1$H-NMR (400 MHz, DMSO-d6) δ [ppm]: −0.023 (0.08), −0.008 (0.22), 0.008 (0.24), 1.027 (0.04), 1.208 (0.06), 1.234 (0.21), 1.312 (0.07), 1.333 (0.09), 1.368 (16.00), 1.525 (0.06), 1.793 (0.13), 1.813 (0.17), 2.052 (0.17), 2.073 (1.11), 2.085 (0.60), 2.102 (0.29), 2.108 (0.28), 2.132 (1.31), 2.242 (3.22), 2.327 (0.06), 2.366 (0.06), 2.670 (0.06), 2.710 (0.06), 3.178 (1.02), 3.584 (0.19), 3.672 (0.32), 7.253 (0.17), 7.272 (0.37), 7.289 (0.27), 7.353 (0.23), 7.371 (0.42), 7.388 (0.21), 7.438 (0.59), 7.441 (0.57), 7.458 (0.50), 7.461 (0.48), 7.481 (0.52), 7.497 (0.44), 7.640 (0.20), 7.662 (1.35), 7.666 (1.05), 7.671 (0.81), 7.688 (0.12), 7.693 (0.14), 8.712 (0.20), 8.727 (0.40), 8.741 (0.19).

Example 95A tert-Butyl 5-[({6-bromo-2-[3-hydroxypiperidin-1-yl]-3-methylquinolin-4-yl}carbonyl)amino]-4-(2-chlorophenyl)pentanoate (Diastereomer Mixture)

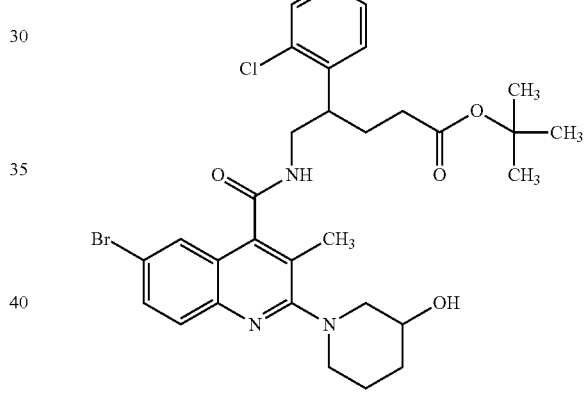

To a suspension of (+/−)-tert-butyl 5-{[(6-bromo-2-chloro-3-methylquinolin-4-yl)carbonyl]amino}-4-(2-chlorophenyl)pentanoate (200 mg, 98% purity, 346 μmol, Example 37A) in NMP (3 ml) were added (+/−)-piperidin-3-ol (280 mg, 2.77 mmol) and DIPEA (482 μl, 2.77 mmol), and the mixture was stirred at 120° C. for two days. After cooling to RT, the mixture was concentrated and the residue was dissolved in acetonitrile and purified by means of preparative HPLC (Method 6). The combined target fractions were concentrated, and the residue was dried under reduced pressure. 154 mg (98% purity, 69% of theory) of the title compound were obtained.

LC-MS (Method 1): R$_t$=2.39 min; MS (ESIpos): m/z=630/632 [M+H]$^+$ $^1$H-NMR (400 MHz, DMSO-d6) δ [ppm]: −0.008 (0.24), 0.008 (0.23), 1.209 (0.06), 1.313 (0.17), 1.369 (16.00), 1.526 (0.07), 1.603 (0.13), 1.783 (0.25), 1.813 (0.28), 1.922 (0.18), 1.943 (0.17), 2.052 (0.18), 2.074 (1.10), 2.087 (0.64), 2.110 (0.30), 2.132 (1.38), 2.327 (0.05), 2.366 (0.06), 2.635

(0.16), 2.665 (0.13), 2.710 (0.07), 2.778 (0.17), 3.356 (0.21), 3.387 (0.19), 3.512 (0.22), 3.543 (0.22), 3.589 (0.19), 3.677 (0.47), 4.852 (0.66), 4.864 (0.65), 7.254 (0.16), 7.272 (0.37), 7.291 (0.27), 7.353 (0.22), 7.372 (0.41), 7.391 (0.21), 7.439 (0.62), 7.442 (0.63), 7.458 (0.53), 7.462 (0.52), 7.482 (0.55), 7.501 (0.44), 7.621 (0.36), 7.643 (1.27), 7.656 (0.83), 7.661 (0.76), 7.678 (0.23), 7.684 (0.24), 8.713 (0.19), 8.727 (0.39), 8.741 (0.19).

Example 96A tert-Butyl 5-{[(6-bromo-2-{3-[(tert-butoxycarbonyl)amino]piperidin-1-yl}-3-methylquinolin-4-yl)carbonyl]amino}-4-(2-chlorophenyl)pentanoate (Diastereomer Mixture)

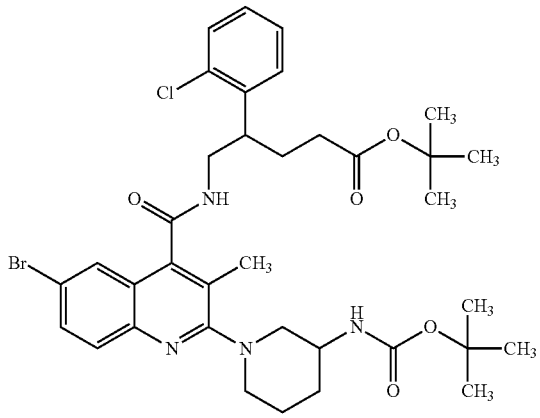 [SMILES: Cc1c(N2CCCC(NC(=O)OC(C)(C)C)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (200 mg, 98% purity, 346 µmol, Example 37A) in NMP (3 ml) were added (+/−)-tert-butyl piperidin-3-ylcarbamate (555 mg, 2.77 mmol) and DIPEA (482 µl, 2.77 mmol), and the mixture was stirred at 120° C. for two days. After cooling to RT, the mixture was concentrated and the residue was dissolved in acetonitrile and purified by means of preparative HPLC (Method 6). The combined target fractions were concentrated, and the residue was dried under reduced pressure. 162 mg (98% purity, 63% of theory) of the title compound were obtained.

LC-MS (Method 1): $R_t$=2.78 min; MS (ESIpos): m/z=729/731 [M+H]$^+$ $^1$H-NMR (400 MHz, DMSO-d6) δ [ppm]: 1.209 (0.07), 1.235 (0.09), 1.369 (16.00), 1.395 (10.53), 1.525 (0.08), 1.551 (0.07), 1.643 (0.13), 1.797 (0.32), 1.831 (0.36), 2.073 (1.14), 2.086 (0.69), 2.103 (0.26), 2.155 (0.93), 2.328 (0.06), 2.615 (0.10), 2.670 (0.10), 2.752 (0.19), 3.369 (0.20), 3.401 (0.18), 3.473 (0.18), 3.501 (0.18), 3.581 (0.33), 3.679 (0.35), 6.961 (0.19), 7.251 (0.16), 7.269 (0.39), 7.289 (0.27), 7.352 (0.22), 7.371 (0.41), 7.389 (0.22), 7.436 (0.57), 7.455 (0.49), 7.482 (0.55), 7.499 (0.46), 7.631 (0.31), 7.653 (1.19), 7.665 (0.76), 7.670 (0.69), 7.687 (0.20), 7.692 (0.21), 8.730 (0.34).

Example 97A tert-Butyl 5-[({6-bromo-2-[3-ethylpiperidin-1-yl]-3-methylquinolin-4-yl}carbonyl)amino]-4-(2-chlorophenyl)pentanoate (Diastereomer Mixture)

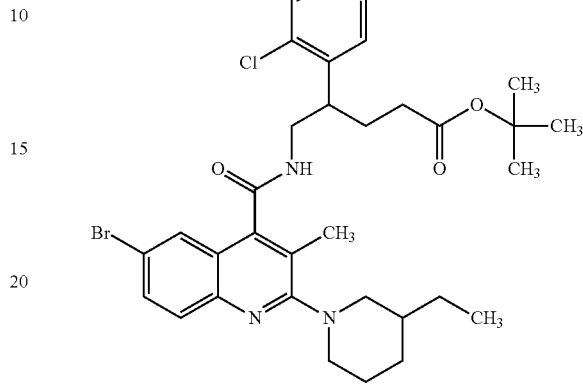

To a suspension of (+/−)-tert-butyl 5-{[(6-bromo-2-chloro-3-methylquinolin-4-yl)carbonyl]amino}-4-(2-chlorophenyl)pentanoate (2.50 g, 98% purity, 4.33 mmol, Example 37A) in NMP (37 ml) were added (+/−)-3-ethylpiperidine (3.92 g, 34.6 mmol) and DIPEA (6.0 ml, 34.6 mmol), and the mixture was stirred at 120° C. for 4 h. After cooling to RT, the mixture was concentrated, and the residue was taken up in dichloromethane and washed with water and saturated aqueous sodium chloride solution. Subsequently, the combined aqueous phases were extracted twice with dichloromethane. The combined organic phases were dried over sodium sulfate, filtered and concentrated, and the residue was dried under reduced pressure. 2.40 g (98% purity, 85% of theory) of the title compound were obtained.

LC-MS (Method 1): $R_t$=3.04 min; MS (ESIpos): m/z=642/644 [M+H]$^+$ $^1$H-NMR (400 MHz, DMSO-d6) δ [ppm]: −0.078 (0.08), 0.218 (0.08), 0.962 (0.85), 0.980 (2.01), 0.999 (1.05), 1.135 (0.19), 1.158 (0.20), 1.187 (0.09), 1.228 (0.15), 1.246 (0.30), 1.264 (0.15), 1.281 (0.08), 1.329 (0.39), 1.347 (0.51), 1.364 (0.36), 1.403 (0.11), 1.440 (16.00), 1.636 (0.22), 1.817 (0.28), 1.849 (0.27), 1.889 (0.24), 1.917 (0.27), 1.948 (0.22), 2.059 (0.56), 2.118 (0.24), 2.146 (1.40), 2.157 (0.81), 2.201 (1.34), 2.816 (0.18), 3.566 (0.40), 3.591 (0.36), 3.658 (0.24), 3.744 (0.46), 4.092 (0.14), 4.110 (0.13), 5.825 (0.10), 7.322 (0.20), 7.341 (0.49), 7.359 (0.36), 7.423 (0.27), 7.442 (0.51), 7.460 (0.26), 7.506 (0.65), 7.526 (0.55), 7.554 (0.67), 7.571 (0.54), 7.697 (0.19), 7.720 (1.78), 7.749 (0.15), 8.772 (0.24), 8.787 (0.50), 8.801 (0.24).

Separation of the Diastereomers/Enantiomers:

The title compound (2.4 g) was dissolved in methanol (60 ml) and separated into the diastereomers by means of preparative SFC on chiral phase [column: Daicel Chiralcel OX-H, 5 µm, 250 mm×30 mm; flow rate: 80 ml/min; detection: 210 nm; temperature: 40° C., injection: 0.40 ml; eluent: 22% methanol/78% carbon dioxide, isocratic]. One mixed fraction (peak 1 and peak 2) and two fractions that were each sufficiently pure (peak 3, see Example 100A, and peak 4, see Example 101A) were obtained. The mixed fraction was separated into the diastereomers once more by means of preparative SFC on chiral phase [column: Daicel Chiralcel OX-H, 5 µm, 250 mm×20 mm; flow rate: 80 ml/min; detection: 210 nm; temperature: 40° C., injection: 2.20 ml; eluent: 15% isopropanol/85% carbon dioxide, isocratic]. Two fractions that were each sufficiently pure (peak 1, see Example 98A, and peak 2, see Example 99A) were obtained. The combined target fractions were each concentrated, and the respective residue was lyophilized.

Example 98A (+)-tert-Butyl 5-[({6-bromo-2-[3-ethylpiperidin-1-yl]-3-methylquinolin-4-yl}carbonyl)amino]-4-(2-chlorophenyl)pentanoate (Diastereomer 1)

In the diastereomer separation described in Example 97A, 200 mg (100% purity, ee>99%) of the title compound were obtained as the diastereomer (peak 1) that eluted first.

$[\alpha]_D^{20}$=+7.7°, 589 nm, c=0.39 g/100 ml, methanol
LC-MS (Method 1): $R_t$=3.03 min; MS (ESIpos): m/z=642/644 [M+H]$^+$
$^1$H-NMR (400 MHz, DMSO-d6) δ [ppm]: 0.976 (0.88), 0.995 (2.21), 1.014 (1.10), 1.121 (0.06), 1.149 (0.17), 1.179 (0.17), 1.200 (0.08), 1.294 (0.07), 1.325 (0.13), 1.342 (0.35), 1.360 (0.47), 1.377 (0.32), 1.397 (0.17), 1.415 (0.11), 1.454 (16.00), 1.611 (0.12), 1.649 (0.22), 1.682 (0.20), 1.713 (0.17), 1.831 (0.24), 1.872 (0.23), 1.902 (0.21), 1.930 (0.23), 1.961 (0.19), 2.131 (0.24), 2.140 (0.20), 2.158 (1.28), 2.169 (0.75), 2.203 (1.17), 2.413 (0.04), 2.755 (0.04), 2.804 (0.13), 2.832 (0.23), 2.861 (0.13), 3.584 (0.38), 3.607 (0.28), 3.671 (0.21), 3.757 (0.39), 7.336 (0.18), 7.354 (0.42), 7.371 (0.30), 7.436 (0.25), 7.455 (0.46), 7.473 (0.23), 7.519 (0.57), 7.537 (0.47), 7.568 (0.57), 7.584 (0.48), 7.711 (0.19), 7.733 (1.47), 7.741 (0.89), 7.759 (0.12), 7.764 (0.14), 8.786 (0.21), 8.801 (0.43), 8.815 (0.21).

Example 99A (−)-tert-Butyl 5-[({6-bromo-2-[3-ethylpiperidin-1-yl]-3-methylquinolin-4-yl}carbonyl)amino]-4-(2-chlorophenyl)pentanoate (Diastereomer 2)

In the diastereomer separation described in Example 97A, 219 mg (100% purity, ee 95%) of the title compound were obtained as the diastereomer (peak 2) that eluted second.

$[\alpha]_D^{20}$=−23.1°, 589 nm, c=0.42 g/100 ml, methanol
LC-MS (Method 1): $R_t$=3.02 min; MS (ESIpos): m/z=642/644 [M+H]$^+$
$^1$H-NMR (400 MHz, DMSO-d6) δ [ppm]: 0.961 (0.87), 0.979 (2.07), 0.998 (1.02), 1.107 (0.07), 1.135 (0.17), 1.157 (0.17), 1.187 (0.08), 1.280 (0.08), 1.311 (0.15), 1.329 (0.34), 1.346 (0.45), 1.364 (0.31), 1.385 (0.18), 1.440 (16.00), 1.597 (0.15), 1.629 (0.19), 1.675 (0.18), 1.706 (0.16), 1.816 (0.25), 1.849 (0.24), 1.888 (0.21), 1.917 (0.23), 1.948 (0.19), 2.118 (0.22), 2.128 (0.23), 2.147 (1.23), 2.158 (0.74), 2.180 (0.37), 2.201 (1.75), 2.239 (0.09), 2.399 (0.04), 2.473 (0.12), 2.776 (0.11), 2.803 (0.20), 2.831 (0.11), 3.559 (0.38), 3.588 (0.35), 3.658 (0.21), 3.744 (0.41), 3.791 (0.10), 3.896 (0.07), 4.109 (0.04), 7.324 (0.19), 7.342 (0.41), 7.362 (0.30), 7.425 (0.25), 7.443 (0.44), 7.461 (0.23), 7.507 (0.62), 7.509 (0.57), 7.526 (0.53), 7.529 (0.49), 7.554 (0.60), 7.570 (0.47), 7.697 (0.19), 7.720 (1.51), 7.727 (0.87), 7.744 (0.12), 7.749 (0.14), 7.960 (0.11), 8.773 (0.23), 8.787 (0.45), 8.801 (0.21).

Example 100A (−)-tert-Butyl 5-[({6-bromo-2-[3-ethylpiperidin-1-yl]-3-methylquinolin-4-yl}carbonyl)amino]-4-(2-chlorophenyl)pentanoate (Diastereomer 3)

In the diastereomer separation described in Example 97A, 462 mg (100% purity, ee>99%) of the title compound were obtained as the diastereomer (peak 3) that eluted third.

$[\alpha]_D^{20}$=−6.9°, 589 nm, c=0.36 g/100 ml, methanol
LC-MS (Method 1): $R_t$=3.03 min; MS (ESIpos): m/z=642/644 [M+H]$^+$
$^1$H-NMR (400 MHz, DMSO-d6) δ [ppm]: 0.077 (0.11), 0.093 (0.12), 0.976 (0.84), 0.995 (2.12), 1.014 (1.04), 1.121 (0.06), 1.150 (0.16), 1.179 (0.16), 1.201 (0.08), 1.294 (0.07), 1.325 (0.13), 1.342 (0.33), 1.359 (0.45), 1.377 (0.31), 1.397 (0.16), 1.416 (0.11), 1.454 (16.00), 1.611 (0.12), 1.649 (0.20), 1.682 (0.19), 1.713 (0.15), 1.831 (0.23), 1.863 (0.22), 1.901 (0.20), 1.930 (0.22), 1.961 (0.18), 2.131 (0.22), 2.140 (0.19), 2.158 (1.19), 2.169 (0.70), 2.203 (1.05), 2.413 (0.04), 2.755 (0.04), 2.805 (0.12), 2.832 (0.21), 2.861 (0.11), 3.584 (0.35), 3.605 (0.26), 3.671 (0.19), 3.757 (0.36), 7.336 (0.17), 7.354 (0.39), 7.371 (0.29), 7.437 (0.24), 7.455 (0.43), 7.474 (0.22), 7.517 (0.53), 7.520 (0.55), 7.537 (0.44), 7.539 (0.45), 7.565 (0.52), 7.568 (0.53), 7.584 (0.45), 7.711 (0.18), 7.734 (1.41), 7.736 (1.18), 7.741 (0.85), 7.759 (0.12), 7.764 (0.14), 8.786 (0.20), 8.801 (0.40), 8.815 (0.20).

Example 101A (+)-tert-Butyl 5-[({6-bromo-2-[3-ethylpiperidin-1-yl]-3-methylquinolin-4-yl}carbonyl)amino]-4-(2-chlorophenyl)pentanoate (Diastereomer 4)

In the diastereomer separation described in Example 97A, 483 mg (100% purity, ee 93%) of the title compound were obtained as the diastereomer (peak 4) that eluted last.

$[\alpha]_D^{20}$=+23.3°, 589 nm, c=0.39 g/100 ml, methanol
LC-MS (Method 1): $R_t$=3.02 min; MS (ESIpos): m/z=642/644 [M+H]$^+$
$^1$H-NMR (400 MHz, DMSO-d6) δ [ppm]: 0.931 (0.89), 0.950 (2.16), 0.968 (1.10), 1.077 (0.07), 1.106 (0.18), 1.136 (0.19), 1.156 (0.08), 1.251 (0.08), 1.282 (0.15), 1.299 (0.35), 1.317 (0.48), 1.334 (0.34), 1.356 (0.18), 1.374 (0.13), 1.411 (16.00), 1.599 (0.20), 1.646 (0.19), 1.677 (0.19), 1.787 (0.27), 1.819 (0.26), 1.858 (0.23), 1.886 (0.26), 1.919 (0.21), 2.089 (0.21), 2.099 (0.21), 2.117 (1.38), 2.129 (0.83), 2.151 (0.35), 2.172 (2.06), 2.370 (0.04), 2.445 (0.13), 2.472 (0.21), 2.746 (0.12), 2.775 (0.23), 2.804 (0.13), 3.530 (0.42), 3.559 (0.40), 3.628 (0.24), 3.715 (0.46), 7.294 (0.20), 7.312 (0.47), 7.330 (0.33), 7.395 (0.28), 7.414 (0.51), 7.432 (0.27), 7.478 (0.68), 7.498 (0.58), 7.524 (0.68), 7.541 (0.54), 7.668 (0.17), 7.691 (1.78), 7.697 (0.99), 7.719 (0.14), 8.743 (0.25), 8.758 (0.50), 8.772 (0.24).

Example 102A tert-Butyl 5-[({6-bromo-2-[3-hydroxy-3-methylpiperidin-1-yl]-3-methylquinolin-4-yl}carbonyl)amino]-4-(2-chlorophenyl)pentanoate (Diastereomer Mixture)

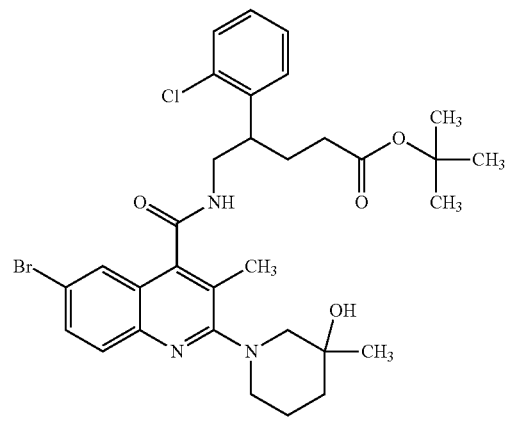 [SMILES: Cc1c(N2CCCC(C)(O)C2)nc2ccc(Br)cc2c1C(=O)NCC(CCC(=O)OC(C)(C)C)c1ccccc1Cl]

To a suspension of (+/−)-tert-butyl 5-{[(6-bromo-2-chloro-3-methylquinolin-4-yl)carbonyl]amino}-4-(2-chlorophenyl)pentanoate (200 mg, 98% purity, 346 µmol, Example 37A) in NMP (3.0 ml) were added (+/−)-3-methylpiperidin-3-ol hydrochloride (420 mg, 2.77 mmol) and DIPEA (482 µl, 2.77 mmol), and the mixture was stirred at 120° C. for two days. After cooling to RT, the mixture was concentrated, and the residue was purified by means of preparative HPLC (Method 6). The combined target fractions were concentrated, and the residue was dried under reduced pressure. 148 mg (98% purity, 65% of theory) of the title compound were obtained.

LC-MS (Method 1): $R_t$=2.52 min; MS (ESIpos): m/z=644/646 [M+H]$^+$ $^1$H-NMR (400 MHz, DMSO-d6) δ [ppm]: 1.024 (0.28), 1.190 (2.69), 1.333 (0.13), 1.356 (0.61), 1.370 (16.00), 1.558 (0.67), 1.571 (0.73), 1.612 (0.18), 1.819 (0.32), 2.047 (0.21), 2.075 (1.34), 2.087 (0.74), 2.103 (0.26), 2.167 (1.65), 2.327 (0.05), 2.393 (0.05), 2.411 (0.05), 3.022 (1.29), 3.076 (0.57), 3.587 (0.22), 3.672 (0.40), 4.100 (0.08), 4.603 (0.40), 4.617 (0.43), 7.254 (0.20), 7.273 (0.46), 7.290 (0.32), 7.354 (0.28), 7.372 (0.50), 7.391 (0.26), 7.439 (0.70), 7.459 (0.60), 7.483 (0.66), 7.500 (0.53), 7.616 (0.38), 7.638 (1.32), 7.651 (0.85), 7.656 (0.75), 7.674 (0.23), 7.678 (0.23), 8.709 (0.24), 8.723 (0.48), 8.737 (0.23).

Example 103A tert-Butyl 5-[({6-bromo-2-[3,5-dimethylpiperidin-1-yl]-3-methylquinolin-4-yl}carbonyl)amino]-4-(2-chlorophenyl)pentanoate (Diastereomer Mixture)

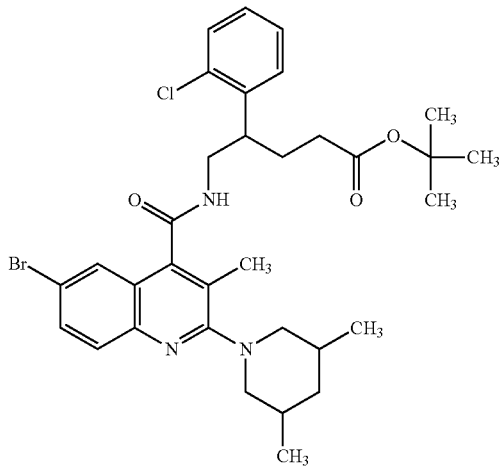 [SMILES: Cc1c(N2CC(C)CC(C)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (+/−)(cis-trans)-3,5-dimethylpiperidine (80 mg, 706 µmol, diastereomer mixture, CAS-RN 35794-11-7) and DIPEA (140 µl, 780 µmol), and the mixture was stirred at 100° C. for 18 h. Subsequently, (+/−)(cis-trans)-3,5-dimethylpiperidine (40 mg, 353 µmol, diastereomer mixture, CAS-RN 35794-11-7) and DIPEA (76 µl, 425 µmol) were again added, and stirring of the mixture continued at 100° C.

After a total of 42 h, the mixture was cooled to RT and filtered. The filtrate was purified by means of preparative HPLC (Method 6). The combined target fractions were concentrated, and the residue was dried under reduced pressure. 91 mg (100% purity, 40% of theory) of the title compound were obtained.

LC-MS (Method 2): $R_t$=1.59 min; MS (ESIpos): m/z=642/644 [M+H]$^+$ $^1$H-NMR (400 MHz, DMSO-d6) δ [ppm]: 0.008 (0.63), 0.719 (0.19), 0.749 (0.22), 0.897 (2.28), 0.913 (2.32), 1.007 (0.49), 1.020 (0.49), 1.234 (0.32), 1.369 (16.00), 1.438 (0.18), 1.807 (0.53), 1.988 (0.18), 2.074 (1.32), 2.085 (0.78), 2.137 (1.33), 2.170 (0.39), 2.327 (0.25), 3.490 (0.35), 3.518 (0.33), 3.583 (0.21), 3.669 (0.33), 5.754 (1.78), 7.255 (0.17), 7.272 (0.41), 7.290 (0.29), 7.354 (0.24), 7.373 (0.45), 7.391 (0.25), 7.440 (0.61), 7.458 (0.53), 7.481 (0.59), 7.498 (0.47), 7.649 (2.04), 8.708 (0.37).

Example 104A tert-Butyl 5-[({6-bromo-2-[3-(difluoromethyl)piperidin-1-yl]-3-methylquinolin-4-yl}carbonyl)amino]-4-(2-chlorophenyl)pentanoate (Diastereomer Mixture)

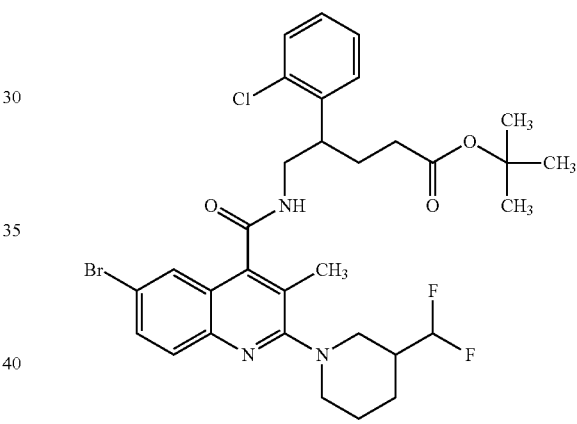

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (+/−)-3-(difluoromethyl)piperidine hydrochloride (121 mg, 706 µmol) and DIPEA (140 µl, 780 µmol), and the mixture was stirred at 100° C. for 18 h. Subsequently, (+/−)-3-(difluoromethyl)piperidine hydrochloride (60 mg, 353 µmol) and DIPEA (70 µl, 390 µmol) were added again, and the mixture was stirred at 100° C. for a further 24 h. Thereafter, the mixture was stirred in a closed glass vessel in a microwave apparatus (Biotage) at 100° C. for 15 min. After cooling to RT, the mixture was admixed with saturated aqueous sodium hydrogencarbonate solution and extracted repeatedly with dichloromethane. The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 95:5→20:80, Isolera One). The two combined target fractions were concentrated, and the respective

Example 105A tert-Butyl 5-[({6-bromo-2-[(3S)-3-fluoropyrrolidin-1-yl]-3-methylquinolin-4-yl}carbonyl)amino]-4-(2-chlorophenyl)pentanoate (Epimer Mixture)

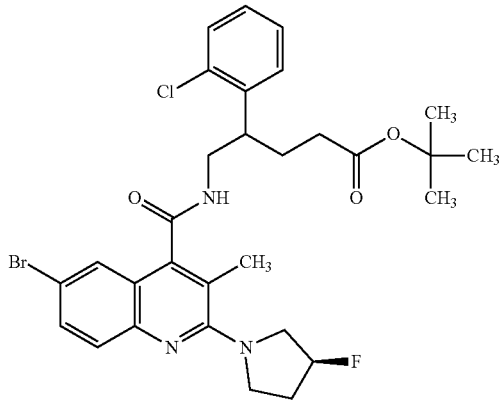 [SMILES: Cc1c(N2CC[C@H](F)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (3S)-3-fluoropyrrolidine hydrochloride (89 mg, 706 µmol) and DIPEA (140 µl, 780 µmol), and the mixture was stirred at 100° C. for 18 h. Subsequently, (3S)-3-fluoropyrrolidine hydrochloride (45 mg, 353 µmol) and DIPEA (76 µl, 425 µmol) were added again, and the mixture was stirred at 100° C. for a further 24 h. After cooling to RT, the mixture was filtered. The filtrate was purified by means of preparative HPLC (Method 6). The combined target fractions were concentrated, and the residue was dried under reduced pressure. 141 mg (89% purity, 57% of theory) of the title compound were obtained.

LC-MS (Method 2): $R_t$=1.26 min; MS (ESIpos): m/z=618/620 [M+H]$^+$ $^1$H-NMR (400 MHz, DMSO-d6) δ [ppm]: −0.150 (0.32), −0.008 (3.09), 0.007 (3.00), 0.146 (0.31), 1.156 (0.38), 1.175 (0.78), 1.192 (0.41), 1.366 (15.46), 1.370 (16.00), 1.818 (0.30), 1.988 (1.44), 2.074 (1.85), 2.175 (1.40), 2.327 (0.23), 2.366 (0.27), 2.523 (0.66), 2.669 (0.21), 2.709 (0.24), 3.598 (0.58), 3.867 (0.24), 4.020 (0.45), 4.038 (0.40), 5.330 (0.35), 5.464 (0.34), 7.260 (0.44), 7.277 (0.49), 7.362 (0.56), 7.380 (0.52), 7.435 (0.94), 7.454 (0.79), 7.476 (0.57), 7.504 (0.83), 7.526 (1.00), 7.531 (1.04), 7.575 (0.54), 7.581 (0.97), 7.587 (0.53), 7.603 (0.55), 7.895 (0.27), 8.688 (0.52).

Example 106A tert-Butyl 5-[({6-bromo-2-[(3R)-3-fluoropyrrolidin-1-yl]-3-methylquinolin-4-yl}carbonyl)amino]-4-(2-chlorophenyl)pentanoate (Epimer Mixture)

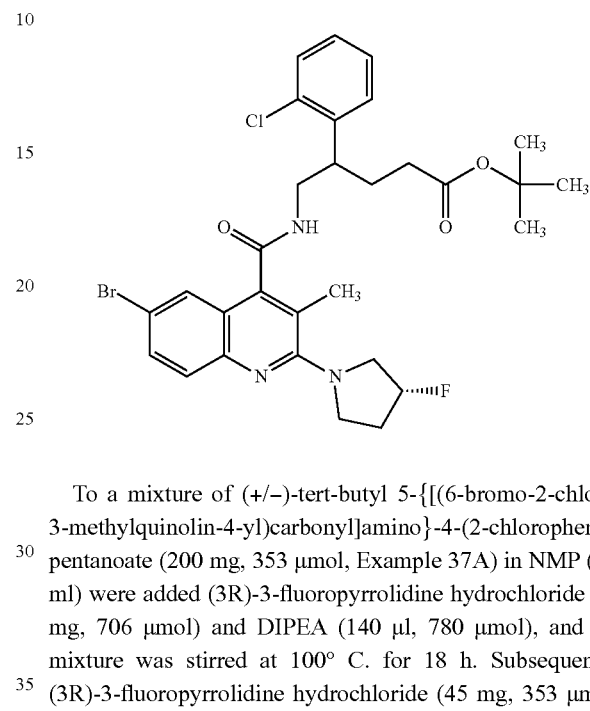

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.6 ml) were added (3R)-3-fluoropyrrolidine hydrochloride (89 mg, 706 µmol) and DIPEA (140 µl, 780 µmol), and the mixture was stirred at 100° C. for 18 h. Subsequently, (3R)-3-fluoropyrrolidine hydrochloride (45 mg, 353 µmol) and DIPEA (76 µl, 425 µmol) were added again, and the mixture was stirred at 100° C. for a further 24 h. After cooling to RT, the mixture was admixed with saturated aqueous sodium hydrogencarbonate solution and extracted repeatedly with dichloromethane. The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→4:6, Isolera One). The combined target fractions were concentrated, and the residue was dried under reduced pressure. 98 mg (41% purity, 17% of theory) of the title compound were obtained.

LC-MS (Method 1): $R_t$=2.50 min; MS (ESIpos): m/z=618/620 [M+H]$^+$ $^1$H-NMR (400 MHz, DMSO-d6) δ [ppm]: −0.008 (1.50), 0.008 (0.91), 1.157 (0.46), 1.175 (0.91), 1.192 (0.46), 1.366 (16.00), 1.370 (14.31), 1.817 (0.28), 1.988 (1.65), 2.074 (1.82), 2.085 (1.02), 2.174 (1.43), 2.327 (0.20), 2.366 (0.24), 2.669 (0.21), 2.709 (0.24), 3.595 (0.63), 3.867 (0.27), 4.020 (0.51), 4.038 (0.47), 5.330 (0.36), 5.465 (0.36), 7.261 (0.44), 7.278 (0.48), 7.344 (0.31), 7.363 (0.56), 7.379 (0.49), 7.435 (0.95), 7.455 (0.80), 7.476 (0.59), 7.504 (0.86), 7.508 (0.77), 7.526 (1.06), 7.530 (1.06), 7.575 (0.58), 7.581 (1.00), 7.587 (0.55), 7.598 (0.33), 7.603 (0.57), 7.609 (0.32), 8.689 (0.55).

--- residue was dried under reduced pressure. 98 mg (41% purity, 17% of theory) of a first batch of the title compound and 18 g (54% purity, 4% of theory, see analysis) of a second batch of the title compound were obtained, which were subsequently combined.

LC-MS (Method 1): $R_t$=2.75 min; MS (ESIpos): m/z=664/666 [M+H]$^+$

Example 107A tert-Butyl 5-[({6-bromo-2-[trans-3,4-difluoropyrrolidin-1-yl]-3-methylquinolin-4-yl}carbonyl)amino]-4-(2-chlorophenyl)pentanoate (Diastereomer Mixture)

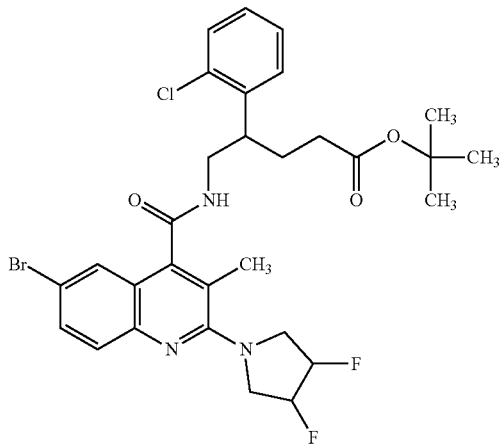 [SMILES: Cc1c(N2CC(F)C(F)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (+/−)trans-3,4-difluoropyrrolidine hydrochloride (101 mg, 706 µmol) and DIPEA (140 µl, 780 µmol), and the mixture was stirred at 100° C. for 18 h. Subsequently, (+/−)-trans-3,4-difluoropyrrolidine hydrochloride (50 mg, 353 µmol) and DIPEA (70 µl, 390 µmol) were added again, and the mixture was stirred at 100° C. for a further 24 h. Thereafter, the mixture was stirred in a closed glass vessel in a microwave apparatus (Biotage) at 100° C. for 15 min. After cooling to RT, the mixture was filtered and purified by preparative HPLC (Method 6). The combined target fractions were concentrated, and the residue was dried under reduced pressure. 169 mg (77% purity, 58% of theory) of the title compound were obtained.

LC-MS (Method 2): $R_t$=1.33 min; MS (ESIpos): m/z=636/638 [M+H]$^+$ $^1$H-NMR (400 MHz, DMSO-d6) δ [ppm]: 0.008 (0.49), 1.157 (2.03), 1.175 (4.09), 1.193 (2.07), 1.333 (0.19), 1.367 (13.18), 1.371 (16.00), 1.820 (0.30), 1.988 (7.63), 2.076 (1.81), 2.089 (1.06), 2.106 (0.39), 2.192 (1.13), 2.327 (0.11), 2.366 (0.09), 3.596 (0.32), 3.714 (0.37), 4.003 (0.63), 4.021 (1.85), 4.039 (1.84), 4.056 (0.69), 4.185 (0.19), 5.360 (0.41), 5.494 (0.41), 7.261 (0.39), 7.280 (0.47), 7.345 (0.22), 7.364 (0.49), 7.382 (0.47), 7.437 (0.79), 7.457 (0.66), 7.480 (0.48), 7.490 (0.55), 7.508 (0.39), 7.549 (0.48), 7.568 (0.84), 7.571 (0.84), 7.617 (0.73), 7.639 (0.40), 7.895 (0.86), 8.696 (0.43), 8.859 (0.16).

Example 108A (+/−)-tert-Butyl 5-[({6-bromo-2-[cis-3,4-difluoropyrrolidin-1-yl]-3-methylquinolin-4-yl}carbonyl)amino]-4-(2-chlorophenyl)pentanoate (Racemate)

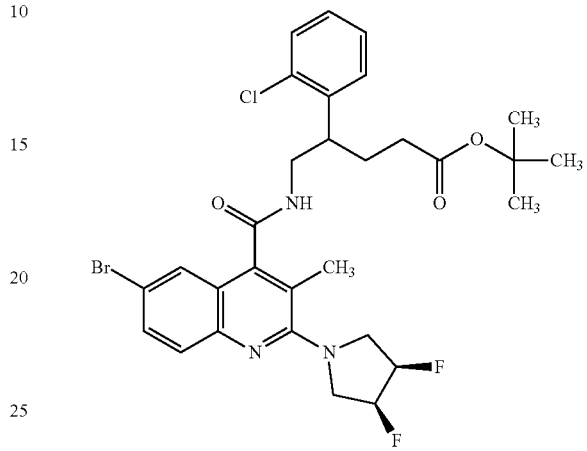

To a mixture of (+/−)-tert-butyl 5-{[(6-bromo-2-chloro-3-methylquinolin-4-yl)carbonyl]amino}-4-(2-chlorophenyl) pentanoate (200 mg, 353 µmol, Example 37A) in NMP (2.5 ml) were added cis-3,4-difluoropyrrolidine hydrochloride (101 mg, 706 µmol) and DIPEA (140 µl, 780 µmol), and the mixture was stirred at 100° C. for 18 h. Subsequently, cis-3,4-difluoropyrrolidine hydrochloride (50 mg, 353 µmol) and DIPEA (70 µl, 390 µmol) were added again, and the mixture was stirred at 100° C. for a further 24 h. After cooling to RT, the mixture was filtered and purified by preparative HPLC (Method 6). The combined target fractions were each concentrated, and the respective residue was dried under reduced pressure. 60 mg (97% purity, 26% of theory) of a first batch of the title compound and 100 mg (88% purity, 39% of theory) of a second batch of the title compound were obtained, which were combined for the subsequent reaction.

Analysis of the First Batch:

LC-MS (Method 2): $R_t$=1.31 min; MS (ESIpos): m/z=636/638 [M+H]$^+$ $^1$H-NMR (400 MHz, DMSO-d6) δ [ppm]: 1.157 (1.14), 1.175 (2.31), 1.192 (1.17), 1.308 (0.09), 1.335 (0.15), 1.368 (16.00), 1.818 (0.20), 1.988 (4.34), 2.074 (1.23), 2.086 (0.67), 2.103 (0.28), 2.159 (0.85), 3.581 (0.22), 3.670 (0.24), 3.782 (0.23), 4.002 (0.52), 4.020 (1.17), 4.038 (1.12), 4.056 (0.38), 5.298 (0.23), 5.426 (0.20), 5.435 (0.20), 5.461 (0.22), 7.251 (0.17), 7.269 (0.39), 7.289 (0.28), 7.353 (0.25), 7.371 (0.44), 7.389 (0.25), 7.435 (0.70), 7.455 (0.58), 7.481 (0.56), 7.498 (0.41), 7.542 (0.67), 7.564 (1.21), 7.610 (0.68), 7.616 (0.62), 7.633 (0.36), 7.638 (0.35), 8.690 (0.40).

Analysis of the Second Batch:

LC-MS (Method 2): $R_t$=1.31 min; MS (ESIpos): m/z=636/638 [M+H]$^+$

¹H-NMR (400 MHz, DMSO-d6) δ [ppm]: -0.009 (0.47), 0.007 (0.35), 1.156 (1.58), 1.174 (3.21), 1.192 (1.61), 1.208 (0.07), 1.308 (0.10), 1.335 (0.15), 1.368 (16.00), 1.524 (0.06), 1.817 (0.19), 1.988 (5.93), 2.046 (0.19), 2.074 (1.20), 2.086 (0.64), 2.103 (0.26), 2.158 (0.75), 2.327 (0.06), 2.365 (0.06), 3.582 (0.21), 3.670 (0.22), 3.779 (0.20), 4.002 (0.61), 4.020 (1.51), 4.038 (1.48), 4.056 (0.49), 5.298 (0.20), 5.324 (0.16), 5.426 (0.17), 5.435 (0.18), 5.460 (0.20), 7.251 (0.15), 7.269 (0.34), 7.288 (0.25), 7.353 (0.22), 7.371 (0.40), 7.390 (0.23), 7.434 (0.64), 7.437 (0.62), 7.454 (0.55), 7.481 (0.51), 7.497 (0.39), 7.542 (0.63), 7.564 (1.13), 7.610 (0.63), 7.616 (0.57), 7.632 (0.34), 7.638 (0.33), 7.894 (0.26), 8.690 (0.36).

dried under reduced pressure. 98 mg (41% purity, 17% of theory) of the title compound were obtained.

LC-MS (Method 1): $R_t$=2.58 min; MS (ESIpos): m/z=632/634 [M+H]$^+$

¹H-NMR (400 MHz, DMSO-d6) δ [ppm]: -0.009 (0.89), 0.007 (0.80), 1.366 (11.66), 1.370 (10.65), 1.398 (16.00), 1.539 (2.15), 1.591 (2.13), 1.815 (0.21), 2.073 (1.38), 2.084 (0.84), 2.100 (0.38), 2.169 (1.12), 2.327 (0.17), 2.365 (0.21), 2.669 (0.18), 2.709 (0.21), 3.608 (0.44), 3.798 (0.16), 3.920 (0.28), 7.259 (0.33), 7.278 (0.37), 7.343 (0.23), 7.362 (0.42), 7.378 (0.36), 7.434 (0.71), 7.454 (0.59), 7.473 (0.40), 7.494 (0.66), 7.499 (0.63), 7.517 (0.80), 7.521 (0.79), 7.567 (0.41), 7.573 (0.72), 7.579 (0.39), 7.595 (0.43), 8.688 (0.37).

Example 109A tert-Butyl 5-[({6-bromo-2-[3-fluoro-3-methylpyrrolidin-1-yl]-3-methylquinolin-4-yl}carbonyl)amino]-4-(2-chlorophenyl)pentanoate (Diastereomer Mixture)

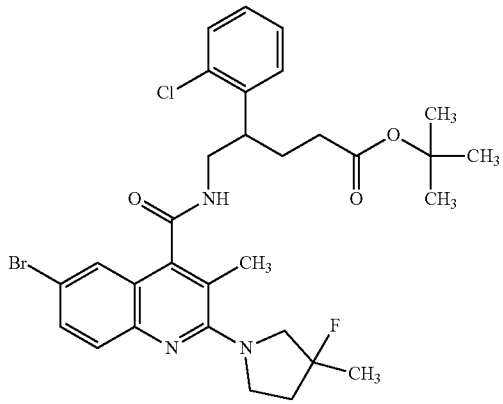 [SMILES: Cc1c(N2CCC(C)(F)C2)nc2ccc(Br)cc2c1C(=O)NCC(CCC(=O)OC(C)(C)C)c1ccccc1Cl]

Example 110A (+/-)-tert-Butyl 5-({[6-bromo-3-methyl-2-(3,3,4,4-tetrafluoropyrrolidin-1-yl)quinolin-4-yl]carbonyl}amino)-4-(2-chlorophenyl)pentanoate (Racemate)

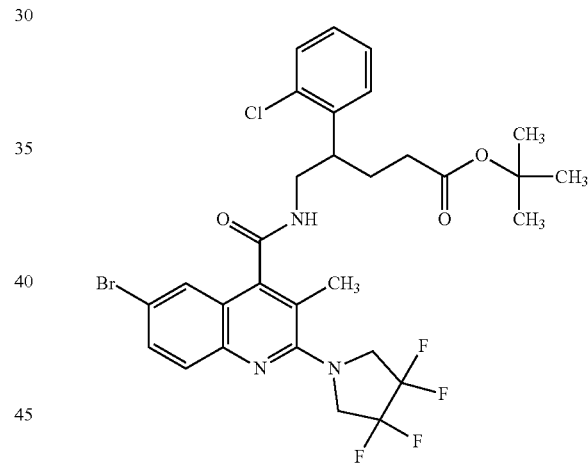

To a mixture of (+/-)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (+/-)-3-fluoro-3-methylpyrrolidine hydrochloride (99 mg, 706 µmol) and DIPEA (140 µl, 780 µmol), and the mixture was stirred at 100° C. for 18 h. Subsequently, (+/-)-3-fluoro-3-methylpyrrolidine hydrochloride (50 mg, 353 µmol) and DIPEA (76 µl, 425 µmol) were added again, and the mixture was stirred at 100° C. for a further 24 h. After cooling to RT, the mixture was admixed with saturated aqueous sodium hydrogencarbonate solution and extracted repeatedly with dichloromethane. The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→4:6, Isolera One). The combined target fractions were concentrated, and the residue was To a mixture of (+/-)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added (+/-)-3,3,4,4-tetrafluoropyrrolidine hydrochloride (127 mg, 706 µmol) and DIPEA (140 µl, 780 µmol), and the mixture was stirred at 100° C. for 18 h. Subsequently, (+/-)-3,3,4,4-tetrafluoropyrrolidine hydrochloride (64 mg, 353 µmol) and DIPEA (76 µl, 425 µmol) were added again, and the mixture was stirred at 100° C. for a further 24 h. Thereafter, the mixture was stirred in a closed glass vessel in a microwave apparatus (Biotage) at 100° C. for 15 min. Subsequently, the mixture was stirred in a closed glass vessel in a microwave apparatus (Biotage) at 120° C. for 1 h. After cooling to RT, the mixture was admixed with saturated aqueous sodium hydrogencarbonate solution and extracted repeatedly with dichloromethane. The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 71 mg (9% purity, 3% of theory) of the title compound were obtained.

LC-MS (Method 2): $R_t$=1.43 min; MS (ESIpos): m/z=672/674 [M+H]$^+$

Example 111A (+/−)-tert-Butyl 5-[({2-[3-azabicyclo[3.1.1]hept-3-yl]-6-bromo-3-methylquinolin-4-yl}carbonyl)amino]-4-(2-chlorophenyl)pentanoate (Racemate)

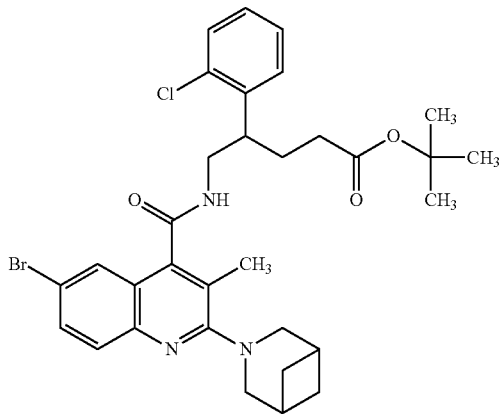 [SMILES: Cc1c(N2CC3CC(C3)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (200 mg, 353 μmol, Example 37A) in NMP (1.9 ml) were added 3-azabicyclo[3.1.1]heptane hydrochloride (92 mg, 689 μmol) and DIPEA (150 μl, 860 μmol), and the mixture was stirred at 100° C. for four days. After cooling to RT, the mixture was filtered and purified by preparative HPLC (Method 8). The combined target fractions were concentrated, and the residue was dried under reduced pressure. 66 mg (100% purity, 31% of theory) of the title compound were obtained.

LC-MS (Method 1): $R_t$=2.81 min; MS (ESIpos): m/z=626/628 [M+H]$^+$ $^1$H-NMR (400 MHz, DMSO-d6) δ [ppm]: 1.234 (0.16), 1.330 (0.12), 1.367 (16.00), 1.438 (0.73), 1.444 (0.67), 1.454 (0.69), 1.460 (0.77), 1.816 (0.21), 2.045 (0.25), 2.074 (1.55), 2.086 (1.09), 2.102 (0.76), 2.192 (1.21), 3.584 (0.24), 3.663 (0.33), 3.868 (0.34), 7.249 (0.19), 7.269 (0.44), 7.287 (0.32), 7.351 (0.28), 7.370 (0.51), 7.388 (0.29), 7.436 (0.77), 7.456 (0.61), 7.480 (0.59), 7.497 (0.43), 7.524 (0.63), 7.546 (1.26), 7.583 (0.68), 7.588 (0.63), 7.605 (0.33), 7.610 (0.32), 8.713 (0.45).

Example 112A (+/−)-tert-Butyl 5-[({2-[3-azabicyclo[3.2.1]oct-3-yl]-6-bromo-3-methylquinolin-4-yl}carbonyl)amino]-4-(2-chlorophenyl)pentanoate (Racemate)

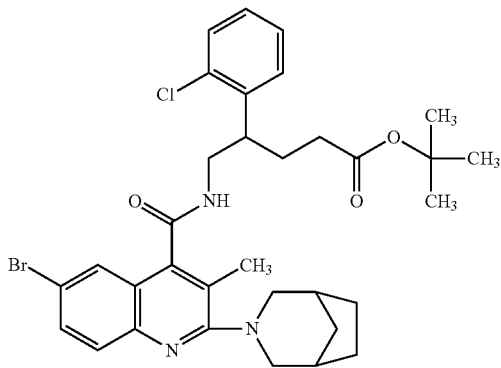 [SMILES: Cc1c(N2CC3CCC(C3)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (108 mg, 98% purity, 185 μmol, Example 37A) in NMP (1.0 ml) were added 3-azabicyclo[3.2.1]octane hydrochloride (219 mg, 1.48 mmol) and DIPEA (390 μl, 2.2 mmol), and the mixture was stirred at 100° C. for 48 h. After cooling to RT, water and ethyl acetate (50 ml of each) were added to the mixture, which was agitated. After phase separation, the aqueous phase was extracted twice with ethyl acetate. The combined organic phases were dried over sodium sulfate, filtered and concentrated, and the residue was purified by preparative HPLC (Method 8). The combined target fractions were concentrated, and the residue was lyophilized. 80 mg (100% purity, 67% of theory) of the title compound were obtained.

LC-MS (Method 1): $R_t$=3.01 min; MS (ESIpos): m/z=640/642 [M+H]$^+$ $^1$H-NMR (400 MHz, DMSO-d6) δ [ppm]: −0.028 (0.90), −0.013 (0.70), 0.848 (0.17), 1.229 (2.08), 1.254 (0.24), 1.364 (16.00), 1.547 (0.92), 1.659 (0.41), 1.742 (0.48), 1.761 (0.50), 1.810 (0.21), 2.040 (0.21), 2.068 (1.18), 2.079 (0.59), 2.095 (0.22), 2.178 (1.29), 2.292 (0.63), 2.361 (0.15), 2.664 (0.12), 2.705 (0.16), 2.906 (0.35), 2.932 (0.29), 3.577 (0.20), 3.662 (0.35), 7.251 (0.17), 7.270 (0.38), 7.286 (0.28), 7.349 (0.24), 7.368 (0.43), 7.386 (0.22), 7.440 (0.60), 7.460 (0.54), 7.475 (0.59), 7.491 (0.44), 7.602 (0.41), 7.624 (1.25), 7.642 (0.77), 7.647 (0.69), 7.664 (0.25), 7.669 (0.25), 8.728 (0.42).

Example 113A (+/−)-tert-Butyl 5-({[6-bromo-2-(3,3-difluoroazetidin-1-yl)-3-methylquinolin-4-yl]carbonyl}amino)-4-(2-chlorophenyl)pentanoate (Racemate)

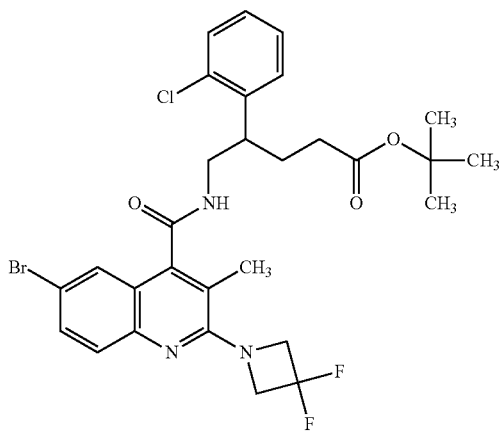 [SMILES: Cc1c(N2CC(F)(F)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (200 mg, 353 µmol, Example 37A) in NMP (2.5 ml) were added 3,3-difluoroazetidine hydrochloride (92 mg, 706 µmol) and DIPEA (140 µl, 780 µmol), and the mixture was stirred at 100° C. for 18 h. Subsequently, 3,3-difluoroazetidine hydrochloride (46 mg, 353 µmol) and DIPEA (76 µl, 425 µmol) were added again, and the mixture was stirred at 100° C. for a further 24 h. Thereafter, the mixture was stirred in a closed glass vessel in a microwave apparatus (Biotage) at 100° C. for 15 min. After cooling to RT, the mixture was admixed with saturated aqueous sodium hydrogencarbonate solution and extracted repeatedly with dichloromethane. The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 95:5→5:5, Isolera One). The combined target fractions were concentrated, and the residue was lyophilized. 32 mg (96% purity, 14% of theory) of the title compound were obtained.

LC-MS (Method 2): $R_t$=1.35 min; MS (ESIpos): m/z=622/624 [M+H]$^+$ $^1$H-NMR (400 MHz, DMSO-d6) δ [ppm]: −0.149 (0.48), −0.008 (4.16), 0.008 (4.20), 0.146 (0.48), 1.367 (16.00), 1.398 (1.97), 2.070 (1.48), 2.084 (0.81), 2.327 (0.52), 2.366 (0.69), 2.523 (1.89), 2.670 (0.58), 2.710 (0.67), 4.581 (0.48), 4.613 (0.89), 4.645 (0.44), 7.435 (0.60), 7.455 (0.50), 7.475 (0.50), 7.492 (0.40), 7.589 (0.60), 7.611 (1.20), 7.648 (0.64), 7.654 (0.60).

Example 114A tert-Butyl 5-[({6-bromo-2-[3-cyanopiperidin-1-yl]-3-methylquinolin-4-yl}carbonyl)amino]-4-(2-chlorophenyl)pentanoate (Diastereomer Mixture)

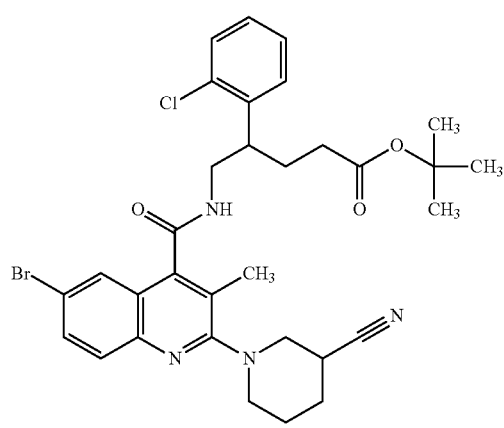 [SMILES: Cc1c(N2CCCC(C#N)C2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (250 mg, 441 µmol, Example 37A) in NMP (2.0 ml) were added (+/−)piperidine-3-carbonitrile (389 mg, 3.53 mmol) and DIPEA (620 µl, 3.5 mmol), and the mixture was stirred at 110° C. for 42 h. After cooling to RT, the mixture was filtered and purified by preparative HPLC (Method 8). The combined target fractions were concentrated, and the residue was lyophilized. 197 mg (91% purity, 63% of theory) of the title compound were obtained.

LC-MS (Method 1): $R_t$=2.58 min; MS (ESIpos): m/z=639/641 [M+H]$^+$ $^1$H-NMR (400 MHz, DMSO-d6) δ [ppm]: 1.209 (0.07), 1.309 (0.05), 1.333 (0.10), 1.369 (16.00), 1.526 (0.08), 1.714 (0.17), 1.819 (0.35), 1.876 (0.37), 1.889 (0.55), 1.902 (0.46), 2.046 (0.19), 2.075 (1.26), 2.088 (0.72), 2.104 (0.25), 2.183 (1.43), 2.327 (0.05), 2.365 (0.05), 2.669 (0.05), 2.709 (0.05), 3.020 (0.16), 3.268 (0.30), 3.293 (0.34), 3.444 (0.22), 3.458 (0.22), 3.475 (0.18), 3.490 (0.14), 3.588 (0.21), 3.683 (0.36), 7.254 (0.18), 7.272 (0.41), 7.292 (0.29), 7.354 (0.25), 7.373 (0.45), 7.391 (0.23), 7.441 (0.59), 7.461 (0.49), 7.486 (0.54), 7.505 (0.42), 7.671 (0.21), 7.693 (1.42), 7.697 (1.08), 7.702 (0.83), 7.724 (0.14), 7.894 (0.21), 8.723 (0.21), 8.737 (0.42), 8.751 (0.20).

Example 115A (+/−)-tert-Butyl 5-({[6-bromo-2-(3,6-dihydro-2H-1,2-oxazin-2-yl)-3-methylquinolin-4-yl]carbonyl}amino)-4-(2-chlorophenyl)pentanoate (Racemate)

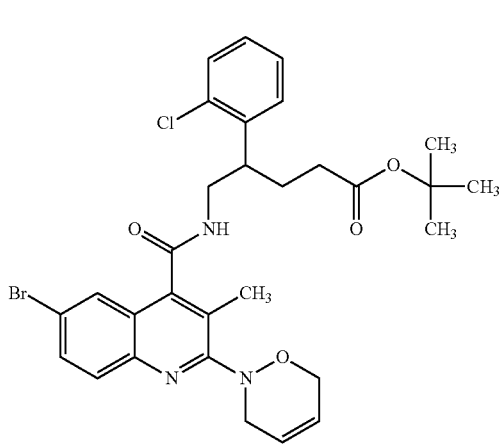 [SMILES: Cc1c(N2CC=CCO2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (300 mg, 530 µmol, Example 37A) in NMP (3.0 ml) were added 3,6-dihydro-2H-1,2-oxazine hydrochloride (515 mg, 4.24 mmol) and DIPEA (920 µl, 5.3 mmol), and the mixture was stirred at 120° C. for 44 h. After cooling to RT, the mixture was filtered and the filtrate was concentrated. The residue was taken up in DMSO and purified by means of preparative HPLC (method 6). The combined target fractions were concentrated, and the residue was dried under reduced pressure. 70 mg (100% purity, 21% of theory) of the title compound were obtained.

LC-MS (Method 1): $R_t$=2.70 min; MS (ESIpos): m/z=614/616 [M+H]$^+$ $^1$H-NMR (400 MHz, DMSO-d6) δ [ppm]: −0.150 (0.08), −0.023 (0.15), 0.007 (0.69), 0.146 (0.08), 1.233 (0.28), 1.312 (0.08), 1.330 (0.11), 1.370 (16.00), 1.826 (0.20), 2.051 (0.24), 2.079 (1.25), 2.090 (0.67), 2.106 (0.25), 2.188 (0.96), 2.327 (0.08), 2.669 (0.08), 3.596 (0.21), 3.691 (0.36), 4.069 (0.88), 4.503 (0.49), 5.991 (0.19), 6.017 (0.46), 6.050 (0.40), 6.075 (0.17), 7.259 (0.21), 7.275 (0.39), 7.294 (0.27), 7.356 (0.23), 7.375 (0.42), 7.393 (0.22), 7.445 (0.61), 7.465 (0.51), 7.486 (0.48), 7.502 (0.37), 7.749 (2.16), 7.752 (2.17), 8.830 (0.21), 8.844 (0.42).

Example 116A tert-Butyl 5-[({6-bromo-2-[3-fluoropiperidin-1-yl]-3-methylquinolin-4-yl}carbonyl)amino]-4-(2-chlorophenyl)pentanoate (Diastereomer Mixture)

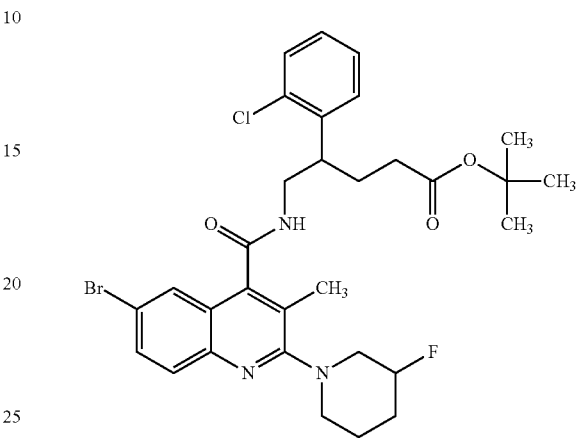

To a mixture of (+/−)-tert-butyl 5-{[(6-bromo-2-chloro-3-methylquinolin-4-yl)carbonyl]amino}-4-(2-chlorophenyl)pentanoate (3.00 g, 98% purity, 5.19 mmol, Example 37A) in NMP (48 ml) were added (+/−)-3-fluoropiperidine hydrochloride (3.99 g, 28.6 mmol) and DIPEA (5.0 ml, 29 mmol), and the mixture was stirred at 120° C. for two days. After cooling to RT, water (200 ml) and ethyl acetate (100 ml) were added to the mixture, which was agitated. After phase separation, the aqueous phase was extracted repeatedly with ethyl acetate (100 ml each time). The combined organic phases were dried over sodium sulfate, filtered and concentrated, and the residue was purified by means of flash column chromatography (100 g silica gel Biotage Snap-Cartridge Ultra, cyclohexane/ethyl acetate gradient 95:5→7:3, Isolera One). The combined target fractions were concentrated, and the residue was dried under reduced pressure. 2.61 g (98% purity, 78% of theory) of the title compound were obtained.

LC-MS (Method 1): $R_t$=2.69 min; MS (ESIpos): m/z=632/634 [M+H]$^+$ $^1$H-NMR (400 MHz, DMSO-d6) δ [ppm]: 1.209 (0.07), 1.333 (0.09), 1.369 (16.00), 1.398 (5.31), 1.526 (0.07), 1.644 (0.17), 1.813 (0.31), 1.898 (0.28), 2.054 (0.19), 2.074 (1.20), 2.087 (0.67), 2.103 (0.27), 2.144 (1.42), 2.327 (0.06), 2.670 (0.06), 3.093 (0.19), 3.160 (0.20), 3.376 (0.18), 3.406 (0.10), 3.433 (0.17), 3.466 (0.11), 3.586 (0.20), 3.677 (0.36), 4.815 (0.13), 4.938 (0.13), 7.254 (0.17), 7.272 (0.41), 7.290 (0.30), 7.354 (0.24), 7.373 (0.45), 7.391 (0.23), 7.439 (0.61), 7.458 (0.52), 7.484 (0.54), 7.500 (0.45), 7.647 (0.26), 7.669 (1.41), 7.676 (0.96), 7.681 (0.83), 7.699 (0.17), 7.704 (0.18), 8.712 (0.21), 8.726 (0.43), 8.740 (0.20).

Example 117A tert-Butyl 5-[({6-bromo-3-methyl-2-[(2S)-2-methylpyrrolidin-1-yl]quinolin-4-yl}carbonyl)amino]-4-(2-chlorophenyl)pentanoate (Epimer Mixture)

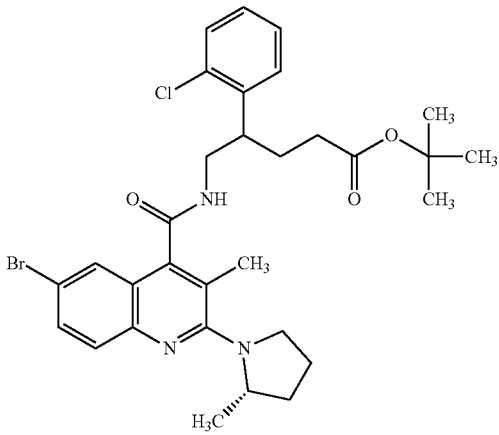 [SMILES: Cc1c(N2CCC[C@@H]2C)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (450 mg, 795 µmol, Example 37A) in NMP (4.0 ml) were added (2S)-2-methylpyrrolidine (650 µl, 6.4 mmol) and DIPEA (1.4 ml, 7.9 mmol), and the mixture was stirred at 100° C. for 3 h. After cooling to RT, the mixture was filtered and purified by preparative HPLC (Method 6). The combined target fractions were concentrated, and the residue was dried under reduced pressure. 391 mg (100% purity, 80% of theory) of the title compound were obtained.

LC-MS (Method 1): $R_t$=2.70 min; MS (ESIpos): m/z=614/616 [M+H]$^+$ $^1$H-NMR (400 MHz, DMSO-d6) δ [ppm]: −0.008 (0.42), 0.008 (0.37), 1.142 (2.75), 1.157 (2.75), 1.208 (0.09), 1.234 (0.15), 1.301 (0.11), 1.330 (0.16), 1.366 (16.00), 1.369 (14.87), 1.541 (0.23), 1.557 (0.27), 1.579 (0.27), 1.607 (0.18), 1.687 (0.22), 1.812 (0.28), 1.897 (0.31), 2.045 (0.38), 2.072 (1.98), 2.084 (1.41), 2.103 (1.71), 2.327 (0.10), 2.366 (0.10), 2.669 (0.09), 2.710 (0.09), 3.610 (0.34), 3.694 (0.29), 3.716 (0.45), 3.736 (0.45), 4.361 (0.23), 4.376 (0.38), 4.398 (0.35), 4.414 (0.21), 7.241 (0.17), 7.259 (0.47), 7.278 (0.52), 7.296 (0.22), 7.341 (0.28), 7.360 (0.62), 7.379 (0.55), 7.398 (0.22), 7.434 (0.98), 7.454 (0.83), 7.474 (0.62), 7.499 (0.87), 7.503 (0.82), 7.521 (1.03), 7.526 (1.04), 7.569 (0.53), 7.575 (0.94), 7.580 (0.52), 7.591 (0.30), 7.597 (0.51), 7.603 (0.30), 8.698 (0.57).

Separation of the Epimer Mixture:

The title compound (376 mg) was dissolved in methanol (30 ml) and separated into the enantiomers/epimers by means of preparative SFC on chiral phase (see Examples 118A and 119A) [column: Daicel Chiralcel OX-H, 5 µm, 250 mm×20 mm; flow rate: 80 ml/min; injection: 1.0 ml; eluent: 17% ethanol/83% carbon dioxide; run time 11 min, isocratic, UV detection 210 nm, temperature 40° C.]. The combined target fractions were concentrated, and the respective residue was lyophilized.

Example 118A tert-Butyl 5-[({6-bromo-3-methyl-2-[(2S)-2-methylpyrrolidin-1-yl]quinolin-4-yl}carbonyl)amino]-4-(2-chlorophenyl)pentanoate (epimer 1)

In the epimer separation described in Example 117A, 150 mg (100% purity, ee>99%) of the title compound were obtained as the epimer/enantiomer that eluted earlier.

$[α]_D^{20}$=−29.3°, 589 nm, c=0.37 g/100 ml, methanol

LC-MS (Method 1): $R_t$=2.67 min; MS (ESIpos): m/z=614/616 [M+H]$^+$ $^1$H-NMR (400 MHz, DMSO-d6) δ [ppm]: 1.140 (1.67), 1.155 (1.68), 1.205 (0.07), 1.300 (0.10), 1.333 (0.09), 1.365 (16.00), 1.540 (0.14), 1.556 (0.16), 1.562 (0.16), 1.578 (0.16), 1.606 (0.10), 1.662 (0.14), 1.688 (0.14), 1.708 (0.09), 1.794 (0.13), 1.812 (0.18), 1.895 (0.18), 2.050 (0.22), 2.072 (1.24), 2.085 (1.14), 2.124 (0.28), 2.327 (0.03), 2.669 (0.03), 3.285 (0.15), 3.580 (0.24), 3.625 (0.16), 3.691 (0.14), 3.715 (0.33), 3.732 (0.36), 3.755 (0.21), 4.360 (0.14), 4.375 (0.23), 4.390 (0.19), 4.397 (0.22), 4.413 (0.14), 7.259 (0.15), 7.277 (0.35), 7.295 (0.25), 7.360 (0.26), 7.379 (0.43), 7.397 (0.25), 7.434 (0.62), 7.436 (0.60), 7.454 (0.50), 7.456 (0.48), 7.481 (0.42), 7.499 (0.90), 7.521 (1.12), 7.568 (0.59), 7.573 (0.55), 7.590 (0.32), 7.596 (0.32), 8.683 (0.19), 8.697 (0.32).

Example 119A tert-Butyl 5-[({6-bromo-3-methyl-2-[(2S)-2-methylpyrrolidin-1-yl]quinolin-4-yl}carbonyl)amino]-4-(2-chlorophenyl)pentanoate (epimer 2)

In the epimer separation described in Example 117A, 147 mg (100% purity, ee 97%) of the title compound were obtained as the epimer/enantiomer that eluted later.

$[α]_D^{20}$=−10.3°, 589 nm, c=0.46 g/100 ml, methanol

LC-MS (Method 1): $R_t$=2.64 min; MS (ESIpos): m/z=614/616 [M+H]$^+$ $^1$H-NMR (400 MHz, DMSO-d6) δ [ppm]: 1.142 (2.01), 1.157 (2.03), 1.209 (0.07), 1.318 (0.08), 1.329 (0.15), 1.369 (16.00), 1.512 (0.06), 1.527 (0.12), 1.540 (0.15), 1.556 (0.18), 1.563 (0.17), 1.579 (0.17), 1.591 (0.13), 1.607 (0.12), 1.659 (0.14), 1.684 (0.14), 1.793 (0.15), 1.813 (0.19), 1.896 (0.20), 1.910 (0.19), 2.045 (0.28), 2.073 (1.27), 2.105 (1.49), 2.156 (0.20), 2.202 (0.04), 2.327 (0.03), 2.669 (0.03), 3.605 (0.29), 3.695 (0.27), 3.712 (0.27), 3.720 (0.35), 3.736 (0.31), 3.744 (0.19), 3.760 (0.13), 4.362 (0.15), 4.377 (0.24), 4.392 (0.20), 4.399 (0.23), 4.414 (0.14), 7.240 (0.20), 7.259 (0.44), 7.275 (0.32), 7.278 (0.32), 7.340 (0.29), 7.359 (0.53), 7.376 (0.28), 7.432 (0.65), 7.435 (0.65), 7.452 (0.59), 7.470 (0.64), 7.474 (0.65), 7.490 (0.49), 7.504 (0.76), 7.526 (1.26), 7.575 (0.72), 7.580 (0.63), 7.597 (0.39), 7.602 (0.36), 8.685 (0.22), 8.699 (0.41).

Example 120A tert-Butyl 5-[({6-bromo-3-methyl-2-[(2R)-2-methylpyrrolidin-1-yl]quinolin-4-yl}carbonyl)amino]-4-(2-chlorophenyl)pentanoate (Epimer Mixture)

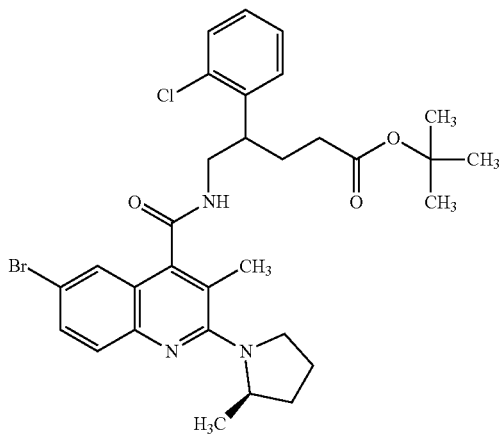 [SMILES: Cc1c(N2CCC[C@H]2C)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (450 mg, 795 µmol, Example 37A) in NMP (4.0 ml) were added (2R)-2-methylpyrrolidine (650 µl, 6.4 mmol) and DIPEA (1.4 ml, 7.9 mmol), and the mixture was stirred at 100° C. for 3 h. After cooling to RT, the mixture was filtered and purified by preparative HPLC (Method 6). The combined target fractions were concentrated, and the residue was dried under reduced pressure. 391 mg (100% purity, 80% of theory) of the title compound were obtained.

LC-MS (Method 1): $R_t$=2.69 min; MS (ESIpos): m/z=614/616 [M+H]$^+$ $^1$H-NMR (400 MHz, DMSO-d6) δ [ppm]: 1.141 (2.84), 1.156 (2.86), 1.207 (0.09), 1.234 (0.15), 1.300 (0.09), 1.329 (0.14), 1.365 (16.00), 1.369 (15.64), 1.540 (0.25), 1.557 (0.29), 1.579 (0.29), 1.607 (0.20), 1.662 (0.25), 1.812 (0.31), 1.896 (0.33), 2.044 (0.39), 2.072 (2.12), 2.084 (1.52), 2.103 (1.85), 2.327 (0.07), 2.365 (0.06), 2.669 (0.08), 2.709 (0.06), 3.610 (0.37), 3.694 (0.31), 3.718 (0.49), 3.735 (0.50), 4.361 (0.23), 4.376 (0.39), 4.398 (0.37), 4.413 (0.23), 7.240 (0.18), 7.259 (0.50), 7.278 (0.56), 7.295 (0.24), 7.340 (0.30), 7.359 (0.66), 7.378 (0.59), 7.397 (0.23), 7.434 (1.03), 7.454 (0.88), 7.474 (0.66), 7.499 (0.93), 7.503 (0.87), 7.521 (1.07), 7.525 (1.10), 7.568 (0.54), 7.574 (0.96), 7.580 (0.54), 7.591 (0.31), 7.596 (0.54), 7.602 (0.31), 8.698 (0.61).

Separation of the Epimer Mixture:

The title compound (376 mg) was dissolved in a mixture of methanol and acetonitrile (5 ml) and separated into the enantiomers/epimers by means of preparative SFC on chiral phase (see Examples 121A and 122A) [column: Daicel Chiralcel OX-H, 5 µm, 250 mm×20 mm; flow rate: 80 ml/min; injection: 0.3 ml; eluent: 17% isopropanol/83% carbon dioxide; run time 15 min, isocratic, UV detection 210 nm, temperature 40° C.]. The combined target fractions were concentrated, and the respective residue was lyophilized.

Example 121A (+)-tert-Butyl 5-[({6-bromo-3-methyl-2-[(2R)-2-methylpyrrolidin-1-yl]quinolin-4-yl}carbonyl)amino]-4-(2-chlorophenyl)pentanoate (epimer 1)

In the epimer separation described in Example 120A, 144 mg (95% purity, ee>99%) of the title compound were obtained as the epimer/enantiomer that eluted earlier.

$[α]_D^{20}$=+7.9°, 589 nm, c=0.49 g/100 ml, methanol

LC-MS (Method 2): $R_t$=1.37 min; MS (ESIpos): m/z=614/616 [M+H]$^+$ $^1$H-NMR (400 MHz, DMSO-d6) δ [ppm]: 1.142 (2.00), 1.157 (2.00), 1.209 (0.08), 1.231 (0.05), 1.317 (0.09), 1.329 (0.16), 1.369 (16.00), 1.511 (0.06), 1.526 (0.13), 1.540 (0.16), 1.556 (0.19), 1.562 (0.19), 1.578 (0.18), 1.606 (0.12), 1.658 (0.15), 1.684 (0.16), 1.702 (0.10), 1.794 (0.17), 1.812 (0.21), 1.895 (0.22), 1.909 (0.21), 2.033 (0.19), 2.045 (0.32), 2.073 (1.39), 2.105 (1.59), 2.156 (0.22), 2.202 (0.04), 2.327 (0.03), 2.365 (0.03), 2.669 (0.02), 2.709 (0.02), 3.605 (0.32), 3.694 (0.29), 3.711 (0.29), 3.719 (0.36), 3.735 (0.32), 3.760 (0.13), 4.361 (0.15), 4.377 (0.25), 4.392 (0.21), 4.399 (0.24), 4.414 (0.14), 7.240 (0.21), 7.258 (0.47), 7.275 (0.35), 7.340 (0.31), 7.357 (0.55), 7.376 (0.30), 7.432 (0.68), 7.452 (0.62), 7.470 (0.69), 7.490 (0.53), 7.504 (0.73), 7.526 (1.19), 7.575 (0.69), 7.580 (0.61), 7.597 (0.38), 7.602 (0.35), 7.845 (0.02), 8.685 (0.23), 8.699 (0.42).

Example 122A (+)-tert-Butyl 5-[({6-bromo-3-methyl-2-[(2R)-2-methylpyrrolidin-1-yl]quinolin-4-yl}carbonyl)amino]-4-(2-chlorophenyl)pentanoate (epimer 2)

In the epimer separation described in Example 120A, 142 mg (100% purity, ee 96%) of the title compound were obtained as the epimer/enantiomer that eluted later.

$[α]_D^{20}$=+25.9°, 589 nm, c=0.36 g/100 ml, methanol

LC-MS (Method 2): $R_t$=1.36 min; MS (ESIpos): m/z=614/616 [M+H]$^+$ $^1$H-NMR (400 MHz, DMSO-d6) δ [ppm]: 1.141 (1.99), 1.155 (1.99), 1.205 (0.10), 1.232 (0.06), 1.301 (0.11), 1.334 (0.13), 1.365 (16.00), 1.540 (0.17), 1.556 (0.22), 1.579 (0.21), 1.606 (0.13), 1.663 (0.20), 1.687 (0.20), 1.794 (0.20), 1.812 (0.27), 1.896 (0.26), 2.072 (1.75), 2.085 (1.56), 2.327 (0.04), 3.285 (0.22), 3.581 (0.34), 3.625 (0.25), 3.690 (0.20), 3.715 (0.43), 3.732 (0.47), 3.755 (0.28), 4.360 (0.18), 4.376 (0.31), 4.397 (0.29), 4.413 (0.17), 7.258 (0.24), 7.277 (0.49), 7.295 (0.35), 7.360 (0.39), 7.378 (0.60), 7.397 (0.35), 7.435 (0.82), 7.454 (0.66), 7.481 (0.59), 7.499 (1.04), 7.521 (1.19), 7.569 (0.66), 7.591 (0.36), 8.697 (0.45).

Example 123A (+/−)-tert-Butyl 5-({[2-(azepan-1-yl)-6-bromo-3-methylquinolin-4-yl]carbonyl}amino)-4-(2-chlorophenyl)pentanoate (Racemate)

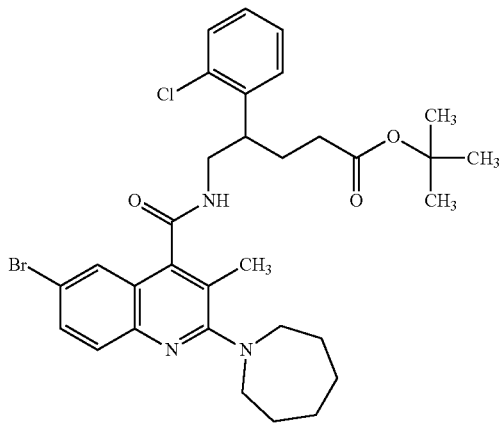 [SMILES: Cc1c(N2CCCCCC2)nc2ccc(Br)cc2c1C(=O)NCC(CCC(=O)OC(C)(C)C)c1ccccc1Cl]

To a mixture of (+/−)-tert-butyl 5-{[(6-bromo-2-chloro-3-methylquinolin-4-yl)carbonyl]amino}-4-(2-chlorophenyl)pentanoate (1.50 g, 2.65 mmol, Example 37A) in NMP (15 ml) were added azepane (2.4 ml, 21 mmol) and DIPEA (4.6 ml, 26 mmol), and the mixture was stirred at 100° C. for 3 h. After cooling to RT, the mixture was concentrated and the residue was taken up in DMSO and purified by means of preparative HPLC (Method 6). The combined target fractions were concentrated, and the residue was dried under reduced pressure. 1.40 g (97% purity, 84% of theory) of the title compound were obtained.

LC-MS (Method 1): $R_t$=2.89 min; MS (ESIpos): m/z=628/630 [M+H]$^+$ $^1$H-NMR (400 MHz, DMSO-d6) δ [ppm]: 1.234 (0.16), 1.368 (16.00), 1.602 (1.61), 1.779 (1.14), 2.046 (0.30), 2.073 (1.46), 2.085 (0.83), 2.126 (1.55), 2.731 (2.95), 2.890 (3.44), 3.489 (1.34), 3.503 (1.82), 3.518 (1.20), 3.582 (0.26), 3.662 (0.35), 7.251 (0.21), 7.270 (0.46), 7.289 (0.33), 7.352 (0.30), 7.371 (0.51), 7.389 (0.29), 7.436 (0.80), 7.456 (0.65), 7.479 (0.61), 7.498 (0.44), 7.526 (0.69), 7.548 (1.23), 7.593 (0.70), 7.598 (0.62), 7.615 (0.37), 7.621 (0.34), 7.952 (0.45), 8.696 (0.47).

Separation of the Enantiomers:

The title compound (1.4 g) was dissolved in a methanol/acetonitrile mixture (70 ml) and separated into the enantiomers by means of preparative SFC on chiral phase (see Examples 124A and 125A) [column: Daicel Chiralcel OX-H, 5 μm, 250 mm×20 mm; flow rate: 80 ml/min; injection: 1.50 ml; UV detection: 210 nm, temperature: 40° C.; eluent: 17% ethanol/83% carbon dioxide; run time 14 min, isocratic]. The combined target fractions were concentrated, and the residue was lyophilized.

Example 124A (−)-tert-Butyl 5-({[2-(azepan-1-yl)-6-bromo-3-methylquinolin-4-yl]carbonyl}amino)-4-(2-chlorophenyl)pentanoate (Enantiomer 1)

In the enantiomer separation described in Example 123A, 496 mg (100% purity, ee>99%) of the title compound were obtained as the enantiomer that eluted earlier.

$[α]_D^{20}$=−7.2°, 589 nm, c=0.36 g/100 ml, methanol

LC-MS (Method 1): $R_t$=2.90 min; MS (ESIpos): m/z=628/630 [M+H]$^+$ $^1$H-NMR (400 MHz, DMSO-d6) δ [ppm]: 1.208 (0.07), 1.309 (0.09), 1.330 (0.12), 1.368 (16.00), 1.524 (0.07), 1.602 (1.44), 1.779 (0.99), 1.838 (0.14), 2.046 (0.23), 2.055 (0.20), 2.074 (1.33), 2.085 (0.74), 2.107 (0.35), 2.127 (1.42), 3.489 (1.18), 3.503 (1.67), 3.517 (1.15), 3.583 (0.22), 3.661 (0.30), 7.252 (0.18), 7.270 (0.42), 7.288 (0.31), 7.352 (0.26), 7.371 (0.47), 7.389 (0.26), 7.437 (0.73), 7.455 (0.58), 7.480 (0.56), 7.497 (0.40), 7.526 (0.66), 7.548 (1.22), 7.592 (0.66), 7.598 (0.62), 7.615 (0.35), 7.620 (0.34), 8.682 (0.22), 8.696 (0.43), 8.710 (0.21).

Example 125A (+)-tert-Butyl 5-({[2-(azepan-1-yl)-6-bromo-3-methylquinolin-4-yl]carbonyl}amino)-4-(2-chlorophenyl)pentanoate (Enantiomer 2)

In the enantiomer separation described in Example 123A, 490 mg (100% purity, ee 97%) of the title compound were obtained as the enantiomer that eluted later.

$[α]_D^{20}$=+8.6°, 589 nm, c=0.35 g/100 ml, methanol

LC-MS (Method 1): $R_t$=2.90 min; MS (ESIpos): m/z=628/630 [M+H]$^+$ $^1$H-NMR (400 MHz, DMSO-d6) δ [ppm]: 1.208 (0.07), 1.309 (0.09), 1.331 (0.14), 1.368 (16.00), 1.524 (0.08), 1.601 (1.71), 1.779 (1.22), 1.838 (0.16), 2.046 (0.29), 2.074 (1.56), 2.085 (0.86), 2.108 (0.48), 2.127 (1.68), 2.327 (0.03), 2.669 (0.03), 3.488 (1.38), 3.503 (1.93), 3.517 (1.26), 3.584 (0.28), 3.661 (0.37), 7.251 (0.22), 7.270 (0.48), 7.288 (0.33), 7.351 (0.31), 7.370 (0.54), 7.388 (0.30), 7.436 (0.82), 7.456 (0.67), 7.479 (0.65), 7.498 (0.47), 7.526 (0.69), 7.548 (1.24), 7.593 (0.69), 7.597 (0.62), 7.615 (0.36), 7.620 (0.34), 8.682 (0.28), 8.696 (0.50), 8.710 (0.25).

Example 126A (+/−)-tert-Butyl 5-({[6-bromo-3-methyl-2-(piperidin-1-yl)quinolin-4-yl]carbonyl}amino)-4-[2-(trifluoromethyl)phenyl]pentanoate (Racemate)

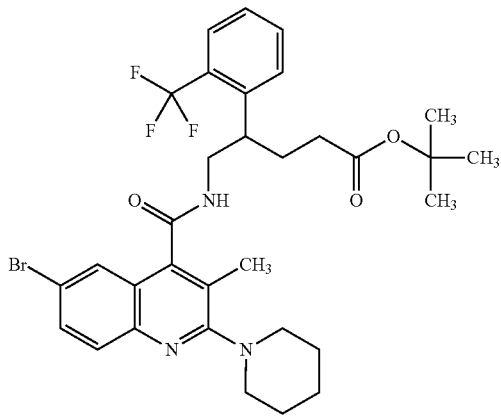 [SMILES: Cc1c(N2CCCCC2)nc2ccc(Br)cc2c1C(=O)NCC(CCC(=O)OC(C)(C)C)c1ccccc1C(F)(F)F]

To a mixture of (+/−)-tert-butyl 5-{[(6-bromo-2-chloro-3-methylquinolin-4-yl)carbonyl]amino}-4-[2-(trifluoromethyl)phenyl]pentanoate (1.00 g, 1.67 mmol, Example 38A) in NMP (6 ml) were added piperidine (1.3 ml, 13 mmol) and DIPEA (2.3 ml, 13 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 648 mg (100% purity, 60% of theory) of the title compound were obtained.

LC-MS (Method 1): $R_t$=2.84 min; MS (ESIpos): m/z=648/650 [M+H]$^+$ $^1$H-NMR (400 MHz, DMSO-d6) δ [ppm]: −0.008 (0.31), 0.008 (0.32), 0.924 (0.26), 0.939 (1.95), 0.955 (1.87), 1.186 (0.07), 1.346 (16.00), 1.398 (0.63), 1.503 (0.09), 1.613 (0.43), 1.679 (0.81), 1.919 (0.14), 1.949 (0.10), 1.971 (0.09), 1.989 (0.24), 2.012 (0.34), 2.024 (0.27), 2.033 (0.32), 2.054 (0.25), 2.074 (0.09), 2.094 (0.21), 2.166 (1.19), 2.328 (0.07), 2.366 (0.07), 2.417 (0.11), 2.435 (0.11), 2.670 (0.07), 2.968 (0.10), 3.151 (1.04), 3.225 (0.08), 3.680 (0.18), 7.462 (0.25), 7.481 (0.41), 7.500 (0.24), 7.636 (0.22), 7.658 (1.37), 7.663 (1.06), 7.668 (0.86), 7.685 (0.27), 7.706 (0.42), 7.722 (0.85), 7.733 (0.64), 8.761 (0.20), 8.776 (0.41), 8.791 (0.19).

Separation of the Enantiomers:

The title compound (560 mg) was dissolved in a mixture of isopropanol and heptane (4 ml of each) and separated into the enantiomers by means of preparative HPLC on chiral phase (see Examples 127A and 128A) [column: Daicel Chiralpak IA, 5 μm, 250 mm×20 mm; flow rate: 15 ml/min; injection: 0.14 ml; UV detection: 220 nm, temperature: 40° C.; eluent: 15% isopropanol/85% heptane; run time 11 min, isocratic]. The combined target fractions were each concentrated, and the respective residue was lyophilized from acetonitrile/water.

Example 127A (−)-tert-Butyl 5-({[6-bromo-3-methyl-2-(piperidin-1-yl)quinolin-4-yl]carbonyl}amino)-4-[2-(trifluoromethyl)phenyl]pentanoate (Enantiomer 1)

In the enantiomer separation described in Example 126A, 241 mg (100% purity, ee 99%) of the title compound were obtained as the enantiomer that eluted earlier.

$[α]_D^{20}$=−14.5°, 589 nm, c=0.38 g/100 ml, methanol

LC-MS (Method 2): $R_t$=1.50 min; MS (ESIpos): m/z=648/650 [M+H]$^+$ $^1$H-NMR (400 MHz, DMSO-d6) δ [ppm]: 1.187 (0.07), 1.243 (0.06), 1.258 (0.07), 1.273 (0.05), 1.312 (0.11), 1.324 (0.17), 1.347 (16.00), 1.503 (0.08), 1.613 (0.49), 1.679 (0.96), 1.888 (0.16), 1.897 (0.16), 1.909 (0.16), 1.920 (0.16), 1.949 (0.12), 1.972 (0.10), 1.990 (0.27), 2.003 (0.20), 2.013 (0.39), 2.025 (0.32), 2.034 (0.36), 2.056 (0.28), 2.075 (0.11), 2.096 (0.24), 2.110 (0.18), 2.128 (0.24), 2.167 (1.40), 2.328 (0.03), 2.671 (0.02), 3.151 (1.24), 3.640 (0.20), 3.662 (0.18), 3.680 (0.22), 3.696 (0.17), 7.462 (0.30), 7.481 (0.47), 7.499 (0.29), 7.636 (0.21), 7.658 (1.49), 7.663 (1.15), 7.668 (0.90), 7.686 (0.29), 7.706 (0.48), 7.721 (0.97), 7.734 (0.78), 7.751 (0.24), 8.763 (0.23), 8.778 (0.46), 8.792 (0.22).

Example 128A (+)-tert-Butyl 5-({[6-bromo-3-methyl-2-(piperidin-1-yl)quinolin-4-yl]carbonyl}amino)-4-[2-(trifluoromethyl)phenyl]pentanoate (Enantiomer 2)

In the enantiomer separation described in Example 126A, 249 mg (100% purity, ee 99%) of the title compound were obtained as the enantiomer that eluted later.

$[α]_D^{20}$=+14.3°, 589 nm, c=0.38 g/100 ml, methanol

LC-MS (Method 2): $R_t$=1.50 min; MS (ESIpos): m/z=648/650 [M+H]$^+$ $^1$H-NMR (400 MHz, DMSO-d6) δ [ppm]: 1.187 (0.07), 1.243 (0.08), 1.258 (0.09), 1.273 (0.06), 1.312 (0.09), 1.324 (0.16), 1.347 (16.00), 1.503 (0.08), 1.612 (0.48), 1.679 (0.94), 1.897 (0.15), 1.908 (0.16), 1.920 (0.16), 1.949 (0.12), 1.971 (0.09), 1.990 (0.26), 2.012 (0.38), 2.025 (0.31), 2.034 (0.36), 2.055 (0.28), 2.074 (0.10), 2.095 (0.24), 2.109 (0.17), 2.128 (0.23), 2.167 (1.39), 2.328 (0.04), 2.670 (0.03), 3.151 (1.22), 3.639 (0.20), 3.662 (0.18), 3.680 (0.21), 3.696 (0.17), 7.462 (0.30), 7.481 (0.47), 7.499 (0.29), 7.636 (0.21), 7.658 (1.47), 7.663 (1.14), 7.667 (0.91), 7.685 (0.29), 7.706 (0.48), 7.721 (0.97), 7.734 (0.76), 7.750 (0.24), 8.762 (0.23), 8.777 (0.46), 8.792 (0.22).

Example 129A (+/−)-tert-Butyl 5-({[6-bromo-3-methyl-2-(pyrrolidin-1-yl)quinolin-4-yl]carbonyl}amino)-4-[2-(trifluoromethyl)phenyl]pentanoate (Racemate)

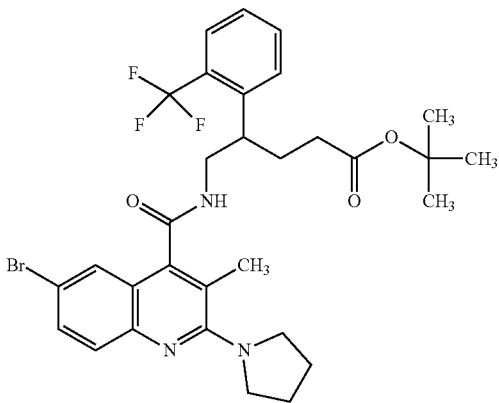 [SMILES: Cc1c(N2CCCC2)nc2ccc(Br)cc2c1C(=O)NCC(CCC(=O)OC(C)(C)C)c1ccccc1C(F)(F)F]

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4 ml) were added pyrrolidine (670 µl, 8.0 mmol) and DIPEA (1.4 ml, 8.0 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 551 mg (100% purity, 87% of theory) of the title compound were obtained.

LC-MS (Method 1): $R_t$=2.27 min; MS (ESIpos): m/z=634/636 $[M+H]^+$ $^1$H-NMR (400 MHz, DMSO-d6) δ [ppm]: −0.008 (0.58), 0.008 (0.56), 0.923 (0.30), 0.938 (2.40), 0.955 (2.28), 1.344 (16.00), 1.398 (1.68), 1.879 (1.44), 1.942 (0.15), 1.965 (0.11), 1.983 (0.24), 2.006 (0.30), 2.018 (0.37), 2.034 (0.32), 2.056 (0.27), 2.074 (0.12), 2.093 (0.27), 2.182 (0.53), 2.327 (0.08), 2.416 (0.14), 2.434 (0.14), 2.967 (0.12), 3.584 (1.09), 3.689 (0.17), 7.457 (0.19), 7.478 (0.97), 7.501 (1.24), 7.553 (0.65), 7.558 (0.60), 7.575 (0.36), 7.580 (0.35), 7.684 (0.16), 7.703 (0.47), 7.713 (0.66), 7.731 (1.08), 7.747 (0.20), 8.719 (0.37).

Separation of the Enantiomers:

The title compound (463 mg) was dissolved in methanol (30 ml) and separated into the enantiomers by means of preparative SFC on chiral phase (see Examples 130A and 131A) [column: Daicel Chiralcel OD-H, 5 µm, 250 mm×20 mm; flow rate: 80 ml/min; injection: 1.0 ml; UV detection: 210 nm, temperature: 40° C.; eluent: 15% ethanol/85% carbon dioxide; run time 10 min, isocratic]. The combined target fractions were each concentrated, and the respective residue was lyophilized from acetonitrile/water.

Example 130A (+)-tert-Butyl 5-({[6-bromo-3-methyl-2-(pyrrolidin-1-yl)quinolin-4-yl]carbonyl}amino)-4-[2-(trifluoromethyl)phenyl]pentanoate (Enantiomer 1)

In the enantiomer separation described in Example 129A, 177 mg (100% purity, ee>99%) of the title compound were obtained as the enantiomer that eluted earlier.

$[α]_D^{20}$=+13.9°, 589 nm, c=0.43 g/100 ml, methanol

LC-MS (Method 1): $R_t$=2.26 min; MS (ESIpos): m/z=634/636 $[M+H]^+$ $^1$H-NMR (400 MHz, DMSO-d6) δ [ppm]: 1.184 (0.07), 1.312 (0.12), 1.323 (0.19), 1.344 (16.00), 1.501 (0.07), 1.880 (1.62), 1.944 (0.17), 1.967 (0.12), 1.985 (0.28), 1.998 (0.19), 2.007 (0.35), 2.019 (0.42), 2.035 (0.37), 2.057 (0.31), 2.076 (0.14), 2.094 (0.31), 2.122 (0.25), 2.138 (0.26), 2.183 (0.61), 2.281 (0.04), 2.327 (0.04), 2.670 (0.03), 3.585 (1.24), 3.689 (0.20), 7.344 (0.07), 7.457 (0.21), 7.480 (0.76), 7.503 (0.95), 7.554 (0.56), 7.559 (0.55), 7.577 (0.32), 7.582 (0.32), 7.684 (0.18), 7.704 (0.52), 7.714 (0.75), 7.731 (1.21), 7.748 (0.24), 8.707 (0.21), 8.721 (0.41), 8.736 (0.21).

Example 131A (−)-tert-Butyl 5-({[6-bromo-3-methyl-2-(pyrrolidin-1-yl)quinolin-4-yl]carbonyl}amino)-4-[2-(trifluoromethyl)phenyl]pentanoate (Enantiomer 2)

In the enantiomer separation described in Example 129A, 183 mg (100% purity, ee 96%) of the title compound were obtained as the enantiomer that eluted later.

$[α]_D^{20}$=−11.9°, 589 nm, c=0.41 g/100 ml, methanol

LC-MS (Method 1): $R_t$=2.27 min; MS (ESIpos): m/z=634/636 $[M+H]^+$ $^1$H-NMR (400 MHz, DMSO-d6) δ [ppm]: 1.183 (0.07), 1.311 (0.28), 1.343 (16.00), 1.499 (0.07), 1.878 (1.68), 1.942 (0.18), 1.966 (0.13), 1.984 (0.29), 2.006 (0.37), 2.018 (0.44), 2.034 (0.38), 2.056 (0.32), 2.075 (0.15), 2.093 (0.32), 2.121 (0.27), 2.137 (0.30), 2.180 (0.64), 2.279 (0.05), 2.327 (0.04), 2.669 (0.03), 3.583 (1.31), 3.688 (0.21), 7.347 (0.07), 7.456 (0.24), 7.479 (0.86), 7.502 (1.07), 7.553 (0.64), 7.558 (0.57), 7.575 (0.36), 7.580 (0.33), 7.683 (0.21), 7.703 (0.58), 7.712 (0.81), 7.730 (1.20), 7.746 (0.24), 8.705 (0.24), 8.720 (0.43), 8.734 (0.21).

Example 132A (+/−)-tert-Butyl 5-({[6-bromo-2-(3,3-difluoropiperidin-1-yl)-3-methylquinolin-4-yl]carbonyl}amino)-4-[2-(trifluoromethyl)phenyl]pentanoate (Racemate)

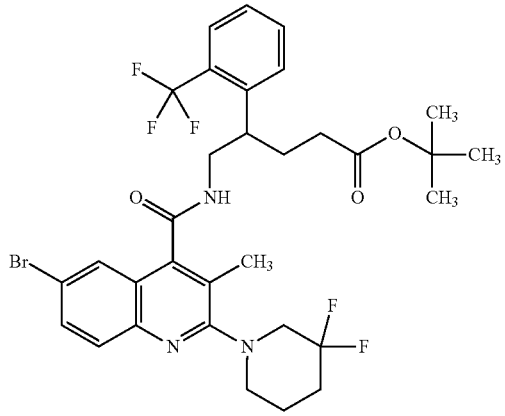 [SMILES: Cc1c(N2CCCC(F)(F)C2)nc2ccc(Br)cc2c1C(=O)NCC(CCC(=O)OC(C)(C)C)c1ccccc1C(F)(F)F]

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4 ml) were added 3,3-difluoropiperidine hydrochloride (1.26 g, 8.00 mmol) and DIPEA (1.7 ml, 10 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 415 mg (98% purity, 59% of theory) of the title compound were obtained.

LC-MS (Method 1): $R_t$=2.72 min; MS (ESIpos): m/z=684/686 [M+H]$^+$ $^1$H-NMR (400 MHz, DMSO-d6) δ [ppm]: −0.009 (0.79), 0.919 (0.53), 0.934 (4.45), 0.950 (4.42), 1.345 (16.00), 1.397 (0.88), 1.889 (0.53), 1.992 (0.25), 2.014 (0.44), 2.033 (0.37), 2.054 (0.35), 2.093 (0.42), 2.187 (1.12), 2.327 (0.16), 2.391 (0.18), 2.408 (0.52), 2.426 (0.52), 2.444 (0.19), 2.944 (0.28), 2.960 (0.37), 2.976 (0.28), 3.183 (0.51), 3.462 (0.31), 3.491 (0.60), 3.519 (0.29), 3.689 (0.17), 5.753 (1.38), 7.483 (0.46), 7.502 (0.29), 7.686 (0.32), 7.708 (1.77), 7.716 (1.09), 7.738 (1.04), 8.785 (0.41).

Separation of the Enantiomers:

The title compound (327 mg) was dissolved in methanol (30 ml) and separated into the enantiomers by means of preparative SFC on chiral phase (see Examples 133A and 134A) [column: Daicel Chiralcel OX-H, 5 μm, 250 mm×30 mm; flow rate: 100 ml/min; injection: 3.0 ml; UV detection: 210 nm, temperature: 40° C.; eluent: 15% methanol/85% carbon dioxide; run time 15 min, isocratic]. The combined target fractions were each concentrated, and the respective residue was lyophilized.

Example 133A (−)-tert-Butyl 5-({[6-bromo-2-(3,3-difluoropiperidin-1-yl)-3-methylquinolin-4-yl]carbonyl}amino)-4-[2-(trifluoromethyl)phenyl]pentanoate (Enantiomer 1)

In the enantiomer separation described in Example 132A, 104 mg (100% purity, ee>99%) of the title compound were obtained as the enantiomer that eluted earlier.

$[α]_D^{20}$=−12.1°, 589 nm, c=0.39 g/100 ml, methanol

LC-MS (Method 1): $R_t$=2.71 min; MS (ESIpos): m/z=684/686 [M+H]$^+$ $^1$H-NMR (400 MHz, DMSO-d6) δ [ppm]: 1.185 (0.06), 1.305 (0.17), 1.311 (0.11), 1.322 (0.16), 1.345 (16.00), 1.502 (0.06), 1.889 (0.64), 1.946 (0.12), 1.974 (0.09), 1.993 (0.27), 2.016 (0.49), 2.034 (0.42), 2.055 (0.40), 2.095 (0.51), 2.119 (0.41), 2.141 (0.36), 2.188 (1.32), 2.327 (0.03), 2.669 (0.03), 3.183 (0.62), 3.463 (0.37), 3.492 (0.71), 3.520 (0.36), 3.648 (0.19), 3.689 (0.20), 7.463 (0.27), 7.482 (0.52), 7.500 (0.33), 7.686 (0.34), 7.708 (2.09), 7.715 (1.26), 7.721 (0.97), 7.738 (1.17), 7.755 (0.24), 8.772 (0.24), 8.787 (0.48), 8.801 (0.23).

Example 134A (+)-tert-Butyl 5-({[6-bromo-2-(3,3-difluoropiperidin-1-yl)-3-methylquinolin-4-yl]carbonyl}amino)-4-[2-(trifluoromethyl)phenyl]pentanoate (Enantiomer 2)

In the enantiomer separation described in Example 132A, 75 mg (100% purity, ee 97%) of the title compound were obtained as the enantiomer that eluted later.

$[α]_D^{20}$=+13.5°, 589 nm, c=0.45 g/100 ml, methanol

LC-MS (Method 1): $R_t$=2.70 min; MS (ESIpos): m/z=684/686 [M+H]$^+$ $^1$H-NMR (400 MHz, DMSO-d6) δ [ppm]: −0.009 (0.18), 1.185 (0.06), 1.311 (0.08), 1.322 (0.14), 1.345 (16.00), 1.502 (0.06), 1.889 (0.54), 1.945 (0.10), 1.974 (0.08), 1.993 (0.24), 2.016 (0.43), 2.034 (0.37), 2.055 (0.35), 2.095 (0.44), 2.119 (0.35), 2.188 (1.15), 2.327 (0.04), 3.184 (0.52), 3.463 (0.33), 3.492 (0.63), 3.520 (0.31), 3.648 (0.16), 3.689 (0.17), 7.463 (0.24), 7.482 (0.47), 7.501 (0.30), 7.686 (0.32), 7.708 (1.90), 7.715 (1.12), 7.721 (0.84), 7.738 (1.08), 7.755 (0.22), 8.772 (0.21), 8.787 (0.43), 8.802 (0.20).

Example 135A (+/−)-tert-Butyl 5-({[2-(azepan-1-yl)-6-bromo-3-methylquinolin-4-yl]carbonyl}amino)-4-[2-(trifluoromethyl)phenyl]pentanoate (Racemate)

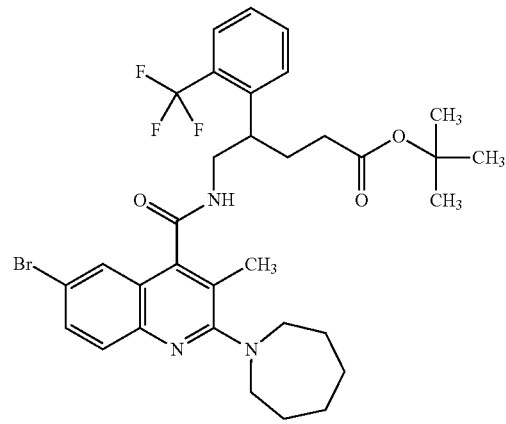 [SMILES: Cc1c(N2CCCCCC2)nc2ccc(Br)cc2c1C(=O)NCC(CCC(=O)OC(C)(C)C)c1ccccc1C(F)(F)F]

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4 ml) were added azepane (900 μl, 8.0 mmol) and DIPEA (1.4 ml, 8.0 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3 8:2, Isolera One). The combined target fractions were concentrated, and the residue was dried under reduced pressure. 303 mg (100% purity, 46% of theory) of the title compound were obtained.

LC-MS (Method 1): $R_t$=2.91 min; MS (ESIpos): m/z=662/664 [M+H]$^+$ $^1$H-NMR (400 MHz, DMSO-d6) δ [ppm]: −0.150 (0.09), −0.009 (0.77), 0.007 (0.77), 0.146 (0.09), 0.926 (0.28), 0.941 (2.02), 0.957 (1.89), 1.184 (0.07), 1.345 (16.00), 1.501 (0.07), 1.609 (1.32), 1.789 (0.86), 1.905 (0.16), 1.946 (0.13), 1.987 (0.25), 2.009 (0.38), 2.029 (0.34), 2.051 (0.26), 2.070 (0.10), 2.092 (0.19), 2.153 (0.93), 2.327 (0.10), 2.366 (0.11), 2.440 (0.12), 2.669 (0.08), 2.709 (0.10), 2.973 (0.08), 3.505 (1.11), 3.519 (1.48), 3.534 (1.07), 3.623 (0.14), 3.680 (0.16), 7.389 (0.08), 7.461 (0.19), 7.479 (0.39), 7.498 (0.24), 7.538 (0.60), 7.560 (1.16), 7.601 (0.65), 7.607 (0.60), 7.624 (0.33), 7.629 (0.33), 7.686 (0.16), 7.705 (0.45), 7.717 (0.69), 7.735 (1.02), 7.751 (0.20), 8.734 (0.20), 8.749 (0.41), 8.764 (0.19).

Separation of the Enantiomers:

The title compound (215 mg) was dissolved in methanol (30 ml) and separated into the enantiomers by means of preparative SFC on chiral phase (see Examples 136A and 137A) [column: Daicel Chiralcel OX-H, 5 μm, 250 mm×20 mm; flow rate: 80 ml/min; injection: 1.0 ml; UV detection: 210 nm, temperature: 40° C.; eluent: 17% methanol/83% carbon dioxide; run time 9 min, isocratic]. The combined target fractions were each concentrated, and the respective residue was lyophilized.

Example 136A (−)-tert-Butyl 5-({[2-(azepan-1-yl)-6-bromo-3-methylquinolin-4-yl]carbonyl}amino)-4-[2-(trifluoromethyl)phenyl]pentanoate (Enantiomer 1)

In the enantiomer separation described in Example 135A, 86 mg (99% purity, ee>99%) of the title compound were obtained as the enantiomer that eluted earlier.

$[\alpha]_D^{20}$=−12.1°, 589 nm, c=0.36 g/100 ml, methanol
LC-MS (Method 2): $R_t$=1.53 min; MS (ESIpos): m/z=662/664 [M+H]$^+$ $^1$H-NMR (400 MHz, DMSO-d6) δ [ppm]: 1.185 (0.07), 1.311 (0.12), 1.346 (16.00), 1.502 (0.08), 1.610 (1.59), 1.790 (1.05), 1.908 (0.19), 1.947 (0.16), 1.970 (0.11), 1.988 (0.30), 2.011 (0.46), 2.023 (0.36), 2.031 (0.42), 2.052 (0.32), 2.072 (0.13), 2.094 (0.24), 2.109 (0.24), 2.154 (1.14), 2.327 (0.05), 2.670 (0.05), 3.505 (1.26), 3.520 (1.78), 3.534 (1.23), 3.625 (0.18), 3.682 (0.20), 7.393 (0.10), 7.461 (0.23), 7.480 (0.47), 7.498 (0.30), 7.539 (0.64), 7.561 (1.22), 7.602 (0.67), 7.607 (0.62), 7.625 (0.34), 7.630 (0.33), 7.686 (0.19), 7.706 (0.54), 7.718 (0.85), 7.736 (1.20), 7.751 (0.26), 8.735 (0.24), 8.751 (0.48), 8.765 (0.24).

Example 137A (+)-tert-Butyl 5-({[2-(azepan-1-yl)-6-bromo-3-methylquinolin-4-yl]carbonyl}amino)-4-[2-(trifluoromethyl)phenyl]pentanoate (Enantiomer 2)

In the enantiomer separation described in Example 135A, 83 mg (100% purity, ee 97%) of the title compound were obtained as the enantiomer that eluted later.

$[\alpha]_D^{20}$=+12.6°, 589 nm, c=0.37 g/100 ml, methanol
LC-MS (Method 2): $R_t$=1.53 min; MS (ESIpos): m/z=662/664 [M+H]$^+$ $^1$H-NMR (400 MHz, DMSO-d6) δ [ppm]: 1.185 (0.06), 1.310 (0.09), 1.322 (0.15), 1.344 (16.00), 1.501 (0.07), 1.609 (1.35), 1.789 (0.88), 1.907 (0.16), 1.946 (0.14), 1.969 (0.09), 1.987 (0.26), 2.010 (0.38), 2.023 (0.30), 2.030 (0.36), 2.052 (0.28), 2.071 (0.11), 2.094 (0.20), 2.154 (0.96), 3.504 (1.11), 3.519 (1.52), 3.533 (1.10), 3.623 (0.15), 3.681 (0.17), 7.390 (0.09), 7.460 (0.20), 7.479 (0.41), 7.497 (0.26), 7.538 (0.62), 7.560 (1.18), 7.601 (0.65), 7.606 (0.63), 7.623 (0.33), 7.629 (0.33), 7.686 (0.17), 7.705 (0.47), 7.717 (0.73), 7.734 (1.07), 7.751 (0.22), 8.735 (0.20), 8.750 (0.41), 8.765 (0.20).

Example 138A tert-Butyl 5-[({6-bromo-2-[3-fluoropiperidin-1-yl]-3-methylquinolin-4-yl}carbonyl)amino]-4-[2-(trifluoromethyl)phenyl]pentanoate (Diastereomer Mixture)

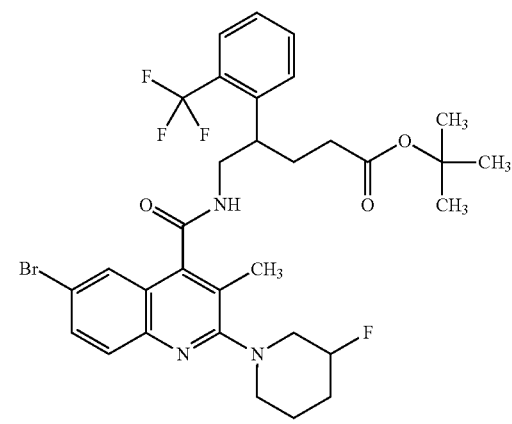 [SMILES: Cc1c(N2CCCC(F)C2)nc2ccc(Br)cc2c1C(=O)NCC(CCC(=O)OC(C)(C)C)c1ccccc1C(F)(F)F]

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4.0 ml) were added (+/−)-3-fluoropiperidine hydrochloride (1.12 g, 8.00 mmol) and DIPEA (1.7 ml, 10 mmol), and the mixture was stirred at 110° C. for two days. After cooling to RT, the mixture was filtered and purified by means of flash column chromatography (100 g silica gel Biotage Snap-Cartridge Ultra, cyclohexane/ethyl acetate gradient 97:3→8:2, Isolera One). The combined target fractions were concentrated and the residue was dried under reduced pressure. 452 mg (100% purity, 68% of theory) of the title compound were obtained.

LC-MS (Method 1): $R_t$=2.69 min; MS (ESIpos): m/z=666/668 [M+H]$^+$ $^1$H-NMR (400 MHz, DMSO-d6) δ [ppm]: 0.007 (0.52), 0.923 (0.29), 0.939 (2.28), 0.955 (2.16), 1.345 (16.00), 1.397 (1.13), 1.652 (0.17), 1.906 (0.40), 1.990 (0.32), 2.013 (0.41), 2.033 (0.34), 2.054 (0.26), 2.093 (0.24), 2.178 (1.15), 2.435 (0.12), 2.669 (0.12), 3.115 (0.19), 3.173 (0.19), 3.393 (0.19), 3.451 (0.17), 3.684 (0.18), 4.823 (0.14), 4.942 (0.14), 7.463 (0.27), 7.482 (0.45), 7.500 (0.27), 7.659 (0.19), 7.681 (1.39), 7.685 (1.19), 7.690 (0.93), 7.707 (0.53), 7.721 (0.80), 7.738 (0.86), 8.780 (0.39).

Example 139A (+/−)-tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer Mixture)

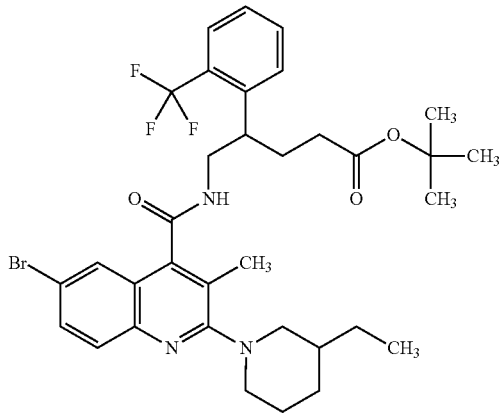 [SMILES: CCC1CCCN(c2nc3ccc(Br)cc3c(C(=O)NCC(CCC(=O)OC(C)(C)C)c3ccccc3C(F)(F)F)c2C)C1]

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4.0 ml) were added (+/−)-3-ethylpiperidine (906 mg, 8.00 mmol) and DIPEA (1.4 ml, 8.0 mmol), and the mixture was stirred at 110° C. for two days. After cooling to RT, the mixture was filtered and purified by means of flash column chromatography (100 g silica gel Biotage Snap-Cartridge Ultra, cyclohexane/ethyl acetate gradient 97:3→8:2, Isolera One). The combined target fractions were concentrated and the residue was dried under reduced pressure. 546 mg (100% purity, 81% of theory) of the title compound were obtained.

LC-MS (Method 1): $R_t$=3.04 min; MS (ESIpos): m/z=676/678 [M+H]$^+$ $^1$H-NMR (400 MHz, DMSO-d6) δ [ppm]: 0.895 (0.88), 0.913 (2.18), 0.934 (3.62), 0.950 (2.84), 1.072 (0.17), 1.102 (0.18), 1.185 (0.09), 1.263 (0.33), 1.281 (0.44), 1.346 (16.00), 1.397 (2.53), 1.569 (0.21), 1.641 (0.17), 1.753 (0.24), 1.884 (0.32), 1.990 (0.26), 2.012 (0.49), 2.027 (0.45), 2.051 (0.24), 2.140 (0.56), 2.166 (0.81), 2.327 (0.08), 2.390 (0.14), 2.408 (0.42), 2.426 (0.43), 2.443 (0.27), 2.669 (0.08), 2.727 (0.13), 2.755 (0.23), 2.784 (0.13), 2.927 (0.08), 2.943 (0.19), 2.960 (0.24), 2.976 (0.18), 2.993 (0.07), 3.514 (0.34), 3.536 (0.31), 3.635 (0.20), 3.696 (0.21), 5.753 (0.93), 7.461 (0.28), 7.479 (0.46), 7.497 (0.27), 7.637 (0.13), 7.659 (1.99), 7.686 (0.26), 7.706 (0.49), 7.720 (0.60), 7.735 (1.01), 7.753 (0.22), 8.753 (0.22), 8.768 (0.44), 8.782 (0.21).

Example 140A tert-Butyl 5-[({6-bromo-3-methyl-2-[3-methylpiperidin-1-yl]quinolin-4-yl}carbonyl)amino]-4-[2-(trifluoromethyl)phenyl]pentanoate (Diastereomer Mixture)

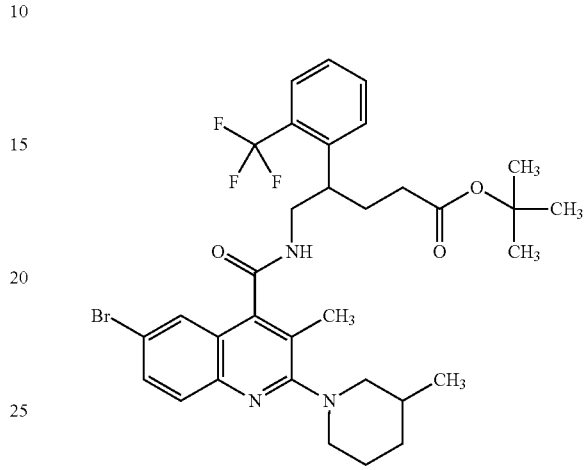

To a mixture of (+/−)-tert-butyl 5-{[(6-bromo-2-chloro-3-methylquinolin-4-yl)carbonyl]amino}-4-[2-(trifluoromethyl)phenyl]pentanoate (600 mg, 1.00 mmol, Example 38A) in NMP (4.0 ml) were added (+/−)-3-methylpiperidine (940 µl, 8.0 mmol) and DIPEA (1.4 ml, 8.0 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated and the residue was dried under reduced pressure. 543 mg (100% purity, 82% of theory) of the title compound were obtained.

LC-MS (Method 1): $R_t$=2.93 min; MS (ESIpos): m/z=662/664 [M+H]$^+$ $^1$H-NMR (400 MHz, DMSO-d6) δ [ppm]: 0.007 (0.26), 0.927 (1.58), 0.936 (2.24), 0.942 (1.80), 0.953 (1.81), 1.086 (0.16), 1.109 (0.17), 1.186 (0.07), 1.305 (0.09), 1.322 (0.14), 1.346 (16.00), 1.397 (0.61), 1.502 (0.07), 1.633 (0.14), 1.662 (0.17), 1.737 (0.28), 1.797 (0.34), 1.828 (0.22), 1.908 (0.15), 1.948 (0.11), 1.970 (0.08), 1.989 (0.25), 2.011 (0.46), 2.029 (0.38), 2.051 (0.26), 2.070 (0.09), 2.096 (0.14), 2.110 (0.17), 2.169 (1.03), 2.327 (0.06), 2.365 (0.05), 2.413 (0.12), 2.431 (0.18), 2.466 (0.24), 2.694 (0.12), 2.722 (0.23), 2.750 (0.12), 2.948 (0.07), 2.964 (0.08), 2.980 (0.06), 3.453 (0.24), 3.480 (0.44), 3.510 (0.21), 3.679 (0.18), 7.461 (0.26), 7.481 (0.42), 7.500 (0.25), 7.638 (0.13), 7.660 (2.06), 7.665 (1.00), 7.687 (0.26), 7.706 (0.45), 7.721 (0.82), 7.737 (0.80), 7.751 (0.21), 8.757 (0.21), 8.771 (0.42), 8.786 (0.20).

Example 141A (+/−)-tert-Butyl 5-({[6-bromo-3-methyl-2-(piperidin-1-yl)quinolin-4-yl]carbonyl}amino)-4-[2-(trifluoromethoxy)phenyl]pentanoate (Racemate)

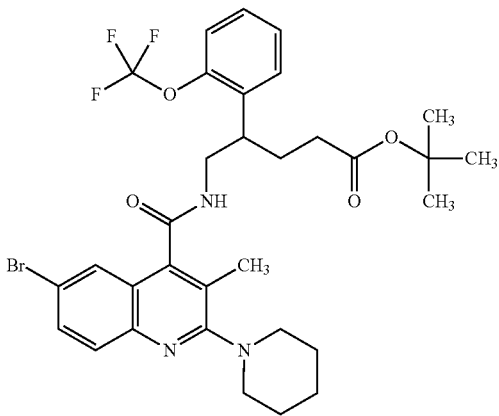 [SMILES: Cc1c(N2CCCCC2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (1.00 g, 1.62 mmol, Example 41A) in NMP (6 ml) were added piperidine (1.3 ml, 13 mmol) and DIPEA (2.3 ml, 13 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 351 mg (92% purity, 30% of theory) of the title compound were obtained.

LC-MS (Method 1): $R_f$=2.86 min; MS (ESIpos): m/z=664/666 [M+H]$^+$ $^1$H-NMR (400 MHz, DMSO-d6) δ [ppm]: −0.009 (0.40), 0.007 (0.37), 0.922 (0.14), 0.937 (1.10), 0.953 (1.05), 1.200 (0.07), 1.301 (0.27), 1.325 (0.11), 1.360 (16.00), 1.373 (0.47), 1.381 (0.28), 1.397 (0.20), 1.516 (0.08), 1.610 (0.44), 1.674 (0.84), 1.805 (0.19), 1.829 (0.19), 1.855 (0.11), 2.033 (0.24), 2.066 (1.13), 2.088 (0.27), 2.142 (0.91), 2.208 (0.15), 2.327 (0.08), 2.366 (0.07), 2.430 (0.08), 2.669 (0.08), 2.709 (0.07), 2.965 (0.07), 3.143 (1.07), 3.386 (0.18), 3.612 (0.21), 3.628 (0.40), 3.643 (0.37), 3.661 (0.20), 7.362 (0.35), 7.386 (0.19), 7.398 (0.69), 7.403 (0.52), 7.410 (0.51), 7.416 (0.48), 7.422 (0.61), 7.472 (0.12), 7.544 (0.44), 7.557 (0.35), 7.568 (0.30), 7.631 (0.24), 7.653 (1.28), 7.661 (0.88), 7.665 (0.76), 7.683 (0.18), 7.688 (0.17), 8.729 (0.19), 8.744 (0.39), 8.758 (0.19).

Separation of the Enantiomers:

The title compound (262 mg) was dissolved in a mixture of ethanol (3 ml) and acetonitrile (2 ml) and separated into the enantiomers by means of preparative HPLC on chiral phase (see Examples 142A and 143A) [column: Daicel Chiralcel OZ-H, 5 μm, 250 mm×20 mm; flow rate: 20 ml/min; injection: 0.04 ml; UV detection: 220 nm, temperature: 40° C.; eluent: 20% ethanol/80% heptane; run time 7 min, isocratic]. The combined target fractions were each concentrated, and the respective residue was lyophilized.

Example 142A (−)-tert-Butyl 5-({[6-bromo-3-methyl-2-(piperidin-1-yl)quinolin-4-yl]carbonyl}amino)-4-[2-(trifluoromethoxy)phenyl]pentanoate (Enantiomer 1)

In the enantiomer separation described in Example 141A, 104 mg (89% purity, ee 100%) of the title compound were obtained as the enantiomer that eluted earlier.

$[α]_D^{20}$=−11.9°, 589 nm, c=0.36 g/100 ml, methanol

LC-MS (Method 1): $R_f$=2.86 min; MS (ESIpos): m/z=664/666 [M+H]$^+$ $^1$H-NMR (400 MHz, DMSO-d6) δ [ppm]: −0.150 (0.03), 0.857 (0.03), 1.038 (0.14), 1.055 (0.28), 1.073 (0.15), 1.199 (0.09), 1.210 (0.06), 1.242 (0.24), 1.257 (0.25), 1.272 (0.18), 1.301 (0.54), 1.316 (0.11), 1.325 (0.13), 1.360 (16.00), 1.381 (0.51), 1.516 (0.09), 1.609 (0.55), 1.673 (1.07), 1.787 (0.10), 1.805 (0.23), 1.830 (0.22), 1.855 (0.13), 2.015 (0.07), 2.034 (0.27), 2.045 (0.33), 2.066 (1.36), 2.089 (0.32), 2.142 (1.11), 2.208 (0.29), 2.327 (0.04), 2.669 (0.04), 2.974 (0.07), 3.143 (1.36), 3.369 (0.25), 3.386 (0.24), 3.431 (0.10), 3.449 (0.09), 3.466 (0.04), 3.612 (0.26), 3.628 (0.49), 3.644 (0.46), 3.661 (0.25), 7.362 (0.41), 7.378 (0.22), 7.385 (0.25), 7.398 (0.84), 7.410 (0.60), 7.416 (0.56), 7.421 (0.67), 7.434 (0.15), 7.474 (0.15), 7.544 (0.52), 7.557 (0.40), 7.568 (0.33), 7.631 (0.26), 7.653 (1.42), 7.661 (0.97), 7.665 (0.83), 7.683 (0.20), 7.687 (0.17), 8.730 (0.23), 8.744 (0.46), 8.758 (0.23).

Example 143A (+)-tert-Butyl 5-({[6-bromo-3-methyl-2-(piperidin-1-yl)quinolin-4-yl]carbonyl}amino)-4-[2-(trifluoromethoxy)phenyl]pentanoate (Enantiomer 2)

In the enantiomer separation described in Example 141A, 95 mg (97% purity, ee 97%) of the title compound were obtained as the enantiomer that eluted later.

$[α]_D^{20}$=+13.8°, 589 nm, c=0.37 g/100 ml, methanol

LC-MS (Method 1): $R_f$=2.86 min; MS (ESIpos): m/z=664/666 [M+H]$^+$ $^1$H-NMR (400 MHz, DMSO-d6) δ [ppm]: 0.857 (0.06), 1.101 (0.05), 1.119 (0.05), 1.199 (0.08), 1.242 (0.43), 1.257 (0.43), 1.272 (0.28), 1.325 (0.11), 1.359 (16.00), 1.373 (0.55), 1.516 (0.08), 1.609 (0.49), 1.673 (0.95), 1.805 (0.22), 1.830 (0.22), 1.856 (0.12), 2.034 (0.28), 2.066 (1.32), 2.089 (0.30), 2.143 (1.07), 3.144 (1.24), 3.369 (0.27), 3.613 (0.26), 3.628 (0.48), 3.644 (0.43), 3.662 (0.21), 7.362 (0.40), 7.385 (0.18), 7.398 (0.76), 7.410 (0.57), 7.416 (0.55), 7.421 (0.67), 7.474 (0.16), 7.544 (0.45), 7.557 (0.38), 7.568 (0.32), 7.631 (0.26), 7.653 (1.39), 7.660 (0.96), 7.665 (0.82), 7.683 (0.16), 7.687 (0.17), 8.730 (0.22), 8.744 (0.44), 8.759 (0.21).

Example 144A (+/−)-tert-Butyl 5-({[6-bromo-3-methyl-2-(pyrrolidin-1-yl)quinolin-4-yl]carbonyl}amino)-4-[2-(trifluoromethoxy)phenyl]pentanoate (Racemate)

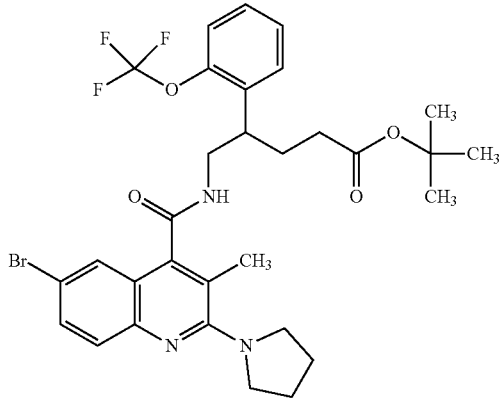 [SMILES: Cc1c(N2CCCC2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 μmol, Example 41A) in NMP (4 ml) were added pyrrolidine (650 μl, 7.8 mmol) and DIPEA (1.4 ml, 7.8 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3 8:2, Isolera One). The combined target fractions were concentrated, and the residue was dried under reduced pressure. 564 mg (95% purity, 85% of theory) of the title compound were obtained.

LC-MS (Method 1): $R_t$=2.41 min; MS (ESIpos): m/z=650/652 [M+H]$^+$ $^1$H-NMR (400 MHz, DMSO-d6) δ [ppm]: 0.920 (0.21), 0.935 (1.75), 0.951 (1.69), 1.198 (0.08), 1.301 (0.37), 1.314 (0.09), 1.326 (0.12), 1.358 (16.00), 1.380 (0.40), 1.397 (0.73), 1.514 (0.07), 1.805 (0.23), 1.827 (0.26), 1.875 (1.57), 2.033 (0.27), 2.043 (0.32), 2.064 (1.48), 2.085 (0.30), 2.160 (0.54), 2.239 (0.17), 2.327 (0.06), 2.365 (0.05), 2.391 (0.06), 2.409 (0.17), 2.427 (0.17), 2.444 (0.07), 2.669 (0.05), 2.944 (0.10), 2.961 (0.13), 2.977 (0.10), 3.367 (0.22), 3.384 (0.23), 3.575 (1.25), 3.627 (0.32), 3.645 (0.31), 3.663 (0.24), 7.355 (0.49), 7.379 (0.30), 7.394 (0.81), 7.405 (0.62), 7.417 (0.64), 7.475 (0.67), 7.497 (1.15), 7.541 (0.49), 7.552 (0.93), 7.557 (0.88), 7.564 (0.41), 7.574 (0.40), 7.579 (0.37), 8.679 (0.21), 8.693 (0.40), 8.707 (0.21).

Separation of the Enantiomers:

The title compound (475 mg) was dissolved in methanol (30 ml) and separated into the enantiomers by means of preparative SFC on chiral phase (see Examples 145A and 146A) [column: Daicel Chiralcel OH-X, 5 μm, 250 mm×30 mm; flow rate: 100 ml/min; injection: 1.00 ml; UV detection: 210 nm, temperature: 40° C.; eluent: 20% methanol/80% carbon dioxide; run time 9 min, isocratic]. The combined target fractions were each concentrated, and the respective residue was lyophilized.

Example 145A (−)-tert-Butyl 5-({[6-bromo-3-methyl-2-(pyrrolidin-1-yl)quinolin-4-yl]carbonyl}amino)-4-[2-(trifluoromethoxy)phenyl]pentanoate (Enantiomer 1)

In the enantiomer separation described in Example 144A, 159 mg (100% purity, ee>99%) of the title compound were obtained as the enantiomer that eluted earlier.

$[α]_D^{20}$=−13.2°, 589 nm, c=0.33 g/100 ml, methanol

LC-MS (Method 1): $R_t$=2.34 min; MS (ESIpos): m/z=650/652 [M+H]$^+$ $^1$H-NMR (400 MHz, DMSO-d6) δ [ppm]: 0.145 (0.03), 1.198 (0.07), 1.301 (0.28), 1.314 (0.08), 1.327 (0.12), 1.358 (16.00), 1.380 (0.29), 1.514 (0.07), 1.786 (0.10), 1.805 (0.22), 1.828 (0.25), 1.875 (1.49), 2.034 (0.25), 2.043 (0.31), 2.065 (1.44), 2.085 (0.29), 2.161 (0.52), 2.240 (0.07), 2.327 (0.04), 2.669 (0.03), 3.311 (6.84), 3.367 (0.22), 3.384 (0.23), 3.627 (0.31), 3.646 (0.28), 3.663 (0.22), 7.355 (0.47), 7.379 (0.27), 7.394 (0.78), 7.405 (0.61), 7.417 (0.63), 7.429 (0.15), 7.475 (0.66), 7.497 (1.12), 7.541 (0.48), 7.552 (0.91), 7.557 (0.87), 7.564 (0.39), 7.574 (0.38), 7.579 (0.36), 8.680 (0.20), 8.694 (0.39), 8.708 (0.20).

Example 146A (+)-tert-Butyl 5-({[6-bromo-3-methyl-2-(pyrrolidin-1-yl)quinolin-4-yl]carbonyl}amino)-4-[2-(trifluoromethoxy)phenyl]pentanoate (Enantiomer 2)

In the enantiomer separation described in Example 144A, 146 mg (100% purity, ee 98%) of the title compound were obtained as the enantiomer that eluted later.

$[α]_D^{20}$=+14.4°, 589 nm, c=0.35 g/100 ml, methanol

LC-MS (Method 1): $R_t$=2.33 min; MS (ESIpos): m/z=650/652 [M+H]$^+$ $^1$H-NMR (400 MHz, DMSO-d6) δ [ppm]: 1.198 (0.07), 1.315 (0.08), 1.327 (0.12), 1.358 (16.00), 1.515 (0.07), 1.806 (0.24), 1.828 (0.28), 1.876 (1.60), 2.034 (0.28), 2.044 (0.34), 2.065 (1.61), 2.086 (0.32), 2.161 (0.57), 2.327 (0.04), 3.311 (7.94), 3.367 (0.24), 3.385 (0.25), 3.628 (0.33), 3.646 (0.31), 3.663 (0.23), 7.356 (0.52), 7.380 (0.27), 7.394 (0.84), 7.405 (0.66), 7.417 (0.71), 7.430 (0.17), 7.475 (0.70), 7.498 (1.19), 7.541 (0.51), 7.553 (1.00), 7.557 (0.92), 7.564 (0.44), 7.574 (0.41), 7.579 (0.38), 8.680 (0.23), 8.694 (0.43), 8.708 (0.23).

Example 147A (+/−)-tert-Butyl 5-({[6-bromo-2-(3,3-difluoropiperidin-1-yl)-3-methylquinolin-4-yl]carbonyl}amino)-4-[2-(trifluoromethoxy)phenyl]pentanoate (Racemate)

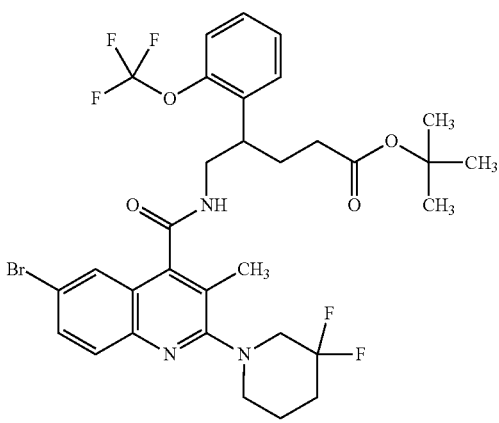 [SMILES: Cc1c(N2CCCC(F)(F)C2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 µmol, Example 41A) in NMP (4 ml) were added 3,3-difluoropiperidine hydrochloride (1.23 g, 7.79 mmol) and DIPEA (1.4 ml, 7.8 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 493 mg (92% purity, 66% of theory) of the title compound were obtained.

LC-MS (Method 1): $R_t$=2.73 min; MS (ESIpos): m/z=700/702 [M+H]$^+$ $^1$H-NMR (400 MHz, DMSO-d6) δ [ppm]: 0.937 (0.80), 0.953 (0.74), 1.301 (0.37), 1.360 (16.00), 1.398 (0.44), 1.808 (0.24), 1.831 (0.25), 1.884 (0.57), 2.067 (1.68), 2.098 (0.61), 2.161 (1.10), 2.227 (0.16), 2.327 (0.12), 2.366 (0.11), 3.176 (0.67), 3.370 (0.24), 3.455 (0.39), 3.484 (0.73), 3.512 (0.38), 3.638 (0.46), 3.654 (0.43), 7.363 (0.43), 7.401 (0.82), 7.413 (0.62), 7.424 (0.67), 7.549 (0.49), 7.561 (0.43), 7.572 (0.35), 7.683 (0.24), 7.704 (1.40), 7.710 (1.04), 7.732 (0.18), 8.755 (0.46).

Separation of the Enantiomers:

The title compound (405 mg) was dissolved in methanol (30 ml) and separated into the enantiomers by means of preparative SFC on chiral phase (see Examples 148A and 149A) [column: Daicel Chiralcel OX-H, 5 µm, 250 mm×30 mm; flow rate: 100 ml/min; injection: 0.7 ml; UV detection: 210 nm, temperature: 40° C.; eluent: 12% methanol/88% carbon dioxide; run time 11 min, isocratic]. The combined target fractions were each concentrated, and the respective residue was lyophilized.

Example 148A (−)-tert-Butyl 5-({[6-bromo-2-(3,3-difluoropiperidin-1-yl)-3-methylquinolin-4-yl]carbonyl}amino)-4-[2-(trifluoromethoxy)phenyl]pentanoate (Enantiomer 1)

In the enantiomer separation described in Example 147A, 134 mg (98% purity, ee>99%) of the title compound were obtained as the enantiomer that eluted earlier.

$[α]_D^{20}$=−12.4°, 589 nm, c=0.41 g/100 ml, methanol

LC-MS (Method 1): $R_t$=2.73 min; MS (ESIpos): m/z=700/702 [M+H]$^+$ $^1$H-NMR (400 MHz, DMSO-d6) δ [ppm]: 1.199 (0.07), 1.269 (0.03), 1.301 (0.37), 1.314 (0.07), 1.325 (0.09), 1.360 (16.00), 1.380 (0.42), 1.516 (0.07), 1.789 (0.09), 1.808 (0.23), 1.832 (0.24), 1.885 (0.53), 2.017 (0.08), 2.036 (0.30), 2.067 (1.63), 2.098 (0.58), 2.162 (1.09), 2.327 (0.04), 2.669 (0.03), 3.177 (0.64), 3.371 (0.23), 3.388 (0.23), 3.455 (0.39), 3.484 (0.74), 3.513 (0.37), 3.623 (0.25), 3.639 (0.46), 3.654 (0.42), 3.673 (0.21), 7.363 (0.41), 7.387 (0.19), 7.400 (0.78), 7.412 (0.60), 7.418 (0.56), 7.424 (0.67), 7.436 (0.13), 7.511 (0.14), 7.549 (0.50), 7.561 (0.43), 7.572 (0.36), 7.682 (0.23), 7.704 (1.46), 7.709 (1.06), 7.714 (0.88), 7.732 (0.14), 7.736 (0.16), 8.740 (0.24), 8.755 (0.48), 8.769 (0.24).

Example 149A (+)-tert-Butyl 5-({[6-bromo-2-(3,3-difluoropiperidin-1-yl)-3-methylquinolin-4-yl]carbonyl}amino)-4-[2-(trifluoromethoxy)phenyl]pentanoate (Enantiomer 2)

In the enantiomer separation described in Example 147A, 122 mg (100% purity, ee 98%) of the title compound were obtained as the enantiomer that eluted later.

$[α]_D^{20}$=+13.3°, 589 nm, c=0.36 g/100 ml, methanol

LC-MS (Method 1): $R_t$=2.73 min; MS (ESIpos): m/z=700/702 [M+H]$^+$ $^1$H-NMR (400 MHz, DMSO-d6) δ [ppm]: 1.200 (0.07), 1.315 (0.08), 1.325 (0.11), 1.360 (16.00), 1.516 (0.07), 1.790 (0.09), 1.809 (0.23), 1.833 (0.24), 1.885 (0.51), 2.018 (0.08), 2.037 (0.30), 2.068 (1.61), 2.099 (0.56), 2.162 (1.07), 2.326 (0.04), 3.177 (0.62), 3.371 (0.22), 3.388 (0.22), 3.456 (0.38), 3.485 (0.72), 3.513 (0.36), 3.624 (0.24), 3.639 (0.45), 3.655 (0.41), 3.673 (0.20), 7.363 (0.42), 7.387 (0.18), 7.400 (0.78), 7.412 (0.59), 7.418 (0.56), 7.424 (0.67), 7.436 (0.13), 7.509 (0.14), 7.549 (0.49), 7.561 (0.42), 7.572 (0.35), 7.682 (0.24), 7.704 (1.48), 7.709 (1.07), 7.714 (0.88), 7.736 (0.16), 8.741 (0.24), 8.755 (0.48), 8.770 (0.24).

Example 150A (+/−)-tert-Butyl 5-({[2-(azepan-1-yl)-6-bromo-3-methylquinolin-4-yl]carbonyl}amino)-4-[2-(trifluoromethoxy)phenyl]pentanoate (Racemate)

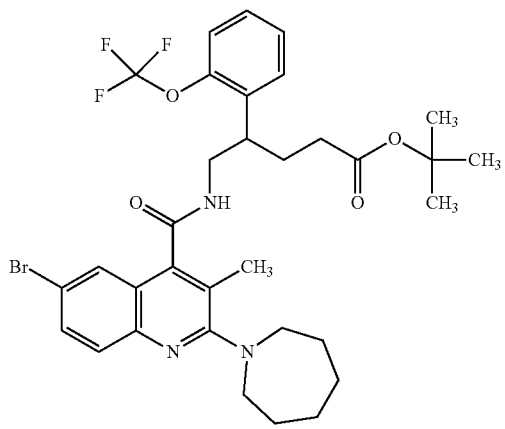 [SMILES: Cc1c(N2CCCCCC2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 μmol, Example 41A) in NMP (4 ml) were added azepane (880 μl, 7.8 mmol) and DIPEA (1.4 ml, 7.8 mmol), and the mixture was stirred at 110° C. for 30 h. After cooling to RT, dichloromethane (150 ml) was added to the mixture, and it was washed once with water (120 ml) and once with a mixture of 1 M hydrochloric acid (20 ml) in water (100 ml).

The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 557 mg (100% purity, 84% of theory) of the title compound were obtained.

LC-MS (Method 1): $R_t$=2.94 min; MS (ESIpos): m/z=678/680 [M+H]$^+$ $^1$H-NMR (400 MHz, DMSO-d6) δ [ppm]: −0.009 (0.15), 0.007 (0.15), 1.199 (0.06), 1.234 (0.05), 1.301 (0.35), 1.313 (0.08), 1.324 (0.10), 1.359 (16.00), 1.373 (0.45), 1.382 (0.35), 1.397 (1.92), 1.515 (0.07), 1.606 (1.33), 1.786 (0.91), 1.829 (0.22), 1.856 (0.12), 2.014 (0.06), 2.033 (0.25), 2.044 (0.27), 2.065 (1.16), 2.089 (0.32), 2.097 (0.28), 2.128 (0.68), 2.201 (0.10), 2.327 (0.04), 2.669 (0.03), 3.369 (0.18), 3.387 (0.19), 3.496 (1.06), 3.511 (1.44), 3.525 (1.04), 3.602 (0.18), 3.618 (0.24), 3.631 (0.24), 3.646 (0.24), 3.663 (0.18), 7.358 (0.37), 7.362 (0.34), 7.384 (0.23), 7.397 (0.75), 7.401 (0.60), 7.408 (0.60), 7.414 (0.57), 7.420 (0.68), 7.432 (0.18), 7.534 (0.65), 7.545 (0.46), 7.557 (1.42), 7.569 (0.32), 7.600 (0.64), 7.606 (0.60), 7.623 (0.34), 7.628 (0.33), 8.704 (0.19), 8.718 (0.37), 8.733 (0.19).

Separation of the Enantiomers:

The title compound (450 mg) was dissolved in methanol (30 ml) and separated into the enantiomers by means of preparative SFC on chiral phase (see Examples 151A and 152A) [column: Daicel Chiralcel OH-X, 5 μm, 250 mm×20 mm; flow rate: 80 ml/min; injection: 0.40 ml; UV detection: 210 nm, temperature: 40° C.; eluent: 20% methanol/80% carbon dioxide; run time 5 min, isocratic]. The combined target fractions were each concentrated, and the respective residue was lyophilized.

Example 151A (−)-tert-Butyl 5-({[2-(azepan-1-yl)-6-bromo-3-methylquinolin-4-yl]carbonyl}amino)-4-[2-(trifluoromethoxy)phenyl]pentanoate (Enantiomer 1)

In the enantiomer separation described in Example 150A, 154 mg (100% purity, ee>99%) of the title compound were obtained as the enantiomer that eluted earlier.

$[α]_D^{20}$=−12.0°, 589 nm, c=0.47 g/100 ml, methanol
LC-MS (Method 1): $R_t$=2.95 min; MS (ESIpos): m/z=678/680 [M+H]$^+$ $^1$H-NMR (400 MHz, DMSO-d6) δ [ppm]: 1.200 (0.08), 1.301 (0.35), 1.313 (0.09), 1.324 (0.11), 1.359 (16.00), 1.381 (0.38), 1.515 (0.08), 1.606 (1.70), 1.786 (1.21), 1.856 (0.15), 2.033 (0.31), 2.066 (1.56), 2.089 (0.40), 2.129 (0.92), 2.201 (0.09), 3.369 (0.24), 3.387 (0.25), 3.496 (1.27), 3.511 (1.87), 3.525 (1.28), 3.602 (0.24), 3.618 (0.33), 3.631 (0.32), 3.646 (0.31), 3.663 (0.23), 7.358 (0.47), 7.397 (0.94), 7.408 (0.75), 7.420 (0.83), 7.534 (0.71), 7.546 (0.53), 7.557 (1.60), 7.569 (0.39), 7.601 (0.64), 7.605 (0.67), 7.623 (0.35), 7.627 (0.36), 8.704 (0.25), 8.718 (0.49), 8.733 (0.25).

Example 152A (+)-tert-Butyl 5-({[2-(azepan-1-yl)-6-bromo-3-methylquinolin-4-yl]carbonyl}amino)-4-[2-(trifluoromethoxy)phenyl]pentanoate (Enantiomer 2)

In the enantiomer separation described in Example 150A, 149 mg (100% purity, ee 97%) of the title compound were obtained as the enantiomer that eluted later.

$[α]_D^{20}$=+13.3°, 589 nm, c=0.40 g/100 ml, methanol
LC-MS (Method 1): $R_t$=2.95 min; MS (ESIpos): m/z=678/680 [M+H]$^+$ $^1$H-NMR (400 MHz, DMSO-d6) δ [ppm]: −0.150 (0.03), 0.145 (0.03), 1.199 (0.06), 1.313 (0.08), 1.324 (0.10), 1.359 (16.00), 1.515 (0.07), 1.606 (1.36), 1.786 (0.95), 1.829 (0.23), 1.856 (0.12), 2.014 (0.07), 2.033 (0.27), 2.044 (0.29), 2.065 (1.27), 2.089 (0.32), 2.096 (0.28), 2.128 (0.72), 2.327 (0.04), 2.669 (0.04), 3.369 (0.20), 3.386 (0.20), 3.496 (1.10), 3.511 (1.53), 3.525 (1.08), 3.602 (0.20), 3.618 (0.27), 3.630 (0.26), 3.645 (0.24), 3.663 (0.18), 7.358 (0.39), 7.384 (0.20), 7.397 (0.78), 7.408 (0.64), 7.414 (0.61), 7.420 (0.72), 7.432 (0.19), 7.534 (0.65), 7.546 (0.46), 7.556 (1.45), 7.569 (0.34), 7.600 (0.62), 7.606 (0.59), 7.623 (0.33), 7.628 (0.32), 8.703 (0.21), 8.718 (0.40), 8.732 (0.20).

Example 153A tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer Mixture)

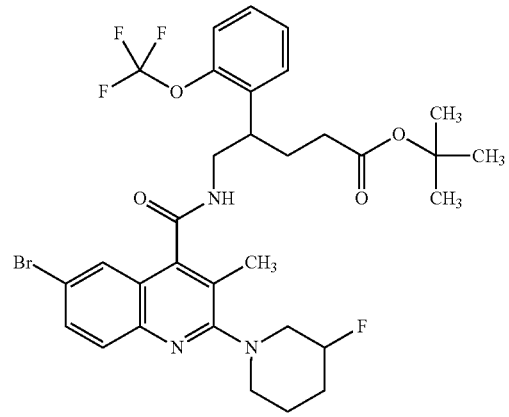 [SMILES: Cc1c(N2CCCC(F)C2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 μmol, Example 41A) in NMP (3.9 ml) were added (+/−)-3-fluoropiperidine hydrochloride (1.09 g, 7.79 mmol) and DIPEA (1.7 ml, 9.7 mmol), and the mixture was stirred at 110° C. for 30 h. After cooling to RT, dichloromethane (150 ml) was added to the mixture, and it was washed once with water (120 ml) and once with a mixture of 1 M hydrochloric acid (25 ml) in water (100 ml). The organic phase was dried over sodium sulfate, filtered and concentrated, and the residue was taken up in dichloromethane and purified by means of flash column chromatography (50 g silica gel Biotage Snap- Cartridge Ultra, cyclohexane/ethyl acetate gradient 97:3→7:3, Isolera One). The combined target fractions were concentrated, and the residue was dried under reduced pressure. 463 mg (92% purity, 64% of theory) of the title compound were obtained.

LC-MS (Method 1): R$_t$=2.74 min; MS (ESIpos): m/z=682/684 [M+H]$^+$ $^1$H-NMR (400 MHz, DMSO-d6) δ [ppm]: 1.199 (0.07), 1.233 (0.05), 1.301 (0.32), 1.314 (0.07), 1.325 (0.09), 1.360 (16.00), 1.381 (0.37), 1.397 (3.74), 1.516 (0.07), 1.646 (0.18), 1.807 (0.33), 1.831 (0.31), 1.855 (0.18), 1.902 (0.27), 1.952 (0.17), 2.036 (0.24), 2.067 (1.20), 2.089 (0.27), 2.156 (0.93), 2.222 (0.14), 2.327 (0.04), 3.104 (0.18), 3.181 (0.18), 3.333 (0.26), 3.353 (0.21), 3.387 (0.36), 3.412 (0.15), 3.444 (0.16), 3.472 (0.10), 3.618 (0.21), 3.634 (0.38), 3.650 (0.35), 4.818 (0.14), 4.938 (0.14), 7.362 (0.37), 7.386 (0.19), 7.399 (0.69), 7.410 (0.52), 7.417 (0.49), 7.422 (0.59), 7.434 (0.12), 7.491 (0.13), 7.546 (0.43), 7.559 (0.38), 7.570 (0.30), 7.656 (0.23), 7.677 (1.30), 7.683 (0.96), 7.688 (0.80), 7.706 (0.17), 7.711 (0.16), 7.901 (0.04), 8.735 (0.20), 8.750 (0.39), 8.765 (0.19).

Example 154A tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer Mixture)

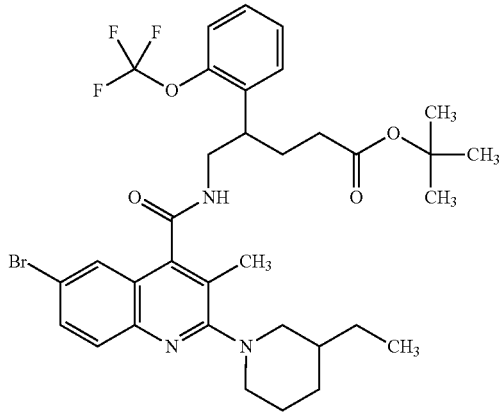 [SMILES: CCC1CCCN(c2nc3ccc(Br)cc3c(C(=O)NCC(CCC(=O)OC(C)(C)C)c3ccccc3OC(F)(F)F)c2C)C1]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 μmol, Example 41A) in NMP (4.0 ml) were added (+/−)-3-ethylpiperidine (882 mg, 7.79 mmol) and DIPEA (1.4 ml, 7.8 mmol), and the mixture was stirred at 110° C. for two days. After cooling to RT, the mixture was purified by means of flash column chromatography (100 g silica gel Biotage Snap-Cartridge Ultra, cyclohexane/ethyl acetate gradient 97:3→8:2, Isolera One). The combined target fractions were concentrated, and the residue was dried under reduced pressure. 501 mg (98% purity, 73% of theory) of the title compound were obtained.

LC-MS (Method 1): R$_t$=3.07 min; MS (ESIpos): m/z=692/694 [M+H]$^+$ $^1$H-NMR (400 MHz, DMSO-d6) δ [ppm]: 0.964 (0.91), 0.983 (2.24), 1.002 (1.37), 1.023 (0.48), 1.141 (0.18), 1.170 (0.19), 1.271 (0.09), 1.333 (0.37), 1.350 (0.49), 1.372 (0.61), 1.432 (16.00), 1.452 (0.35), 1.469 (0.15), 1.636 (0.22), 1.822 (0.26), 1.855 (0.25), 1.873 (0.25), 1.898 (0.22), 1.924 (0.31), 1.952 (0.22), 2.103 (0.27), 2.137 (1.26), 2.188 (0.46), 2.215 (0.65), 2.272 (0.11), 2.398 (0.08), 2.437 (0.09), 2.741 (0.08), 2.823 (0.23), 2.852 (0.13), 3.458 (0.21), 3.569 (0.37), 3.598 (0.35), 3.701 (0.31), 3.716 (0.34), 3.733 (0.27), 3.750 (0.17), 7.430 (0.34), 7.468 (0.71), 7.480 (0.54), 7.492 (0.61), 7.549 (0.12), 7.620 (0.40), 7.632 (0.34), 7.643 (0.28), 7.705 (0.17), 7.727 (1.51), 7.757 (0.11), 8.795 (0.22), 8.810 (0.42), 8.825 (0.21).

Example 155A tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer Mixture)

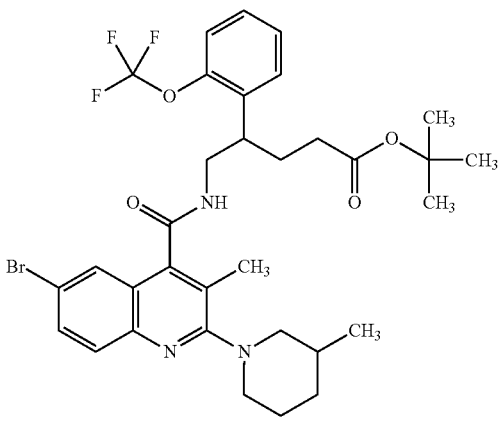 [SMILES: Cc1c(N2CCCC(C)C2)nc2ccc(Br)cc2c1C(=O)NCC(CCC(=O)OC(C)(C)C)c1ccccc1OC(F)(F)F]

To a mixture of (+/−)-tert-butyl 5-{[(6-bromo-2-chloro-3-methylquinolin-4-yl)carbonyl]amino}-4-[2-(trifluoromethoxy)phenyl]pentanoate (600 mg, 974 μmol, Example 41A) in NMP (3.9 ml) were added (+/−)-3-methylpiperidine (910 μl, 7.8 mmol) and DIPEA (1.4 ml, 7.8 mmol), and the mixture was stirred at 110° C. for 30 h. After cooling to RT, dichloromethane (150 ml) was added to the mixture, and it was washed once with water (120 ml) and once with a mixture of 1 M hydrochloric acid (20 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 646 mg (100% purity, 98% of theory) of the title compound were obtained.

LC-MS (Method 1): R$_t$=2.97 min; MS (ESIpos): m/z=678/680 [M+H]$^+$ $^1$H-NMR (400 MHz, DMSO-d6) δ [ppm]: 0.833 (0.04), 0.849 (0.05), 0.922 (1.43), 0.938 (1.46), 1.082 (0.16), 1.111 (0.18), 1.200 (0.08), 1.233 (0.08), 1.301 (0.35), 1.324 (0.10), 1.360 (16.00), 1.381 (0.36), 1.397 (3.29), 1.516 (0.07), 1.628 (0.15), 1.657 (0.17), 1.733 (0.30), 1.765 (0.31), 1.804 (0.43), 1.830 (0.37), 2.014 (0.07), 2.033 (0.25), 2.066 (1.17), 2.092 (0.29), 2.146 (0.69), 2.210 (0.14), 2.327 (0.03), 2.435 (0.12), 2.461 (0.19), 2.687 (0.12), 2.717 (0.21), 2.747 (0.12), 3.369 (0.19), 3.386 (0.20), 3.442 (0.24), 3.471 (0.44), 3.502 (0.21), 3.611 (0.21), 3.629 (0.35), 3.647 (0.31), 3.666 (0.20), 7.361 (0.38), 7.378 (0.15), 7.385 (0.20), 7.398 (0.74), 7.403 (0.56), 7.410 (0.55), 7.416 (0.51), 7.421 (0.63), 7.434 (0.15), 7.472 (0.14), 7.546 (0.43), 7.558 (0.35), 7.570 (0.29), 7.634 (0.17), 7.657 (1.59), 7.663 (0.95), 7.681 (0.13), 7.685 (0.12), 8.725 (0.20), 8.739 (0.40), 8.754 (0.20).

Example 156A (+/−)-tert-Butyl 5-({[6-bromo-3-methyl-2-(piperidin-1-yl)quinolin-4-yl]carbonyl}amino)-4-(2-chloro-3-fluorophenyl)pentanoate (Racemate)

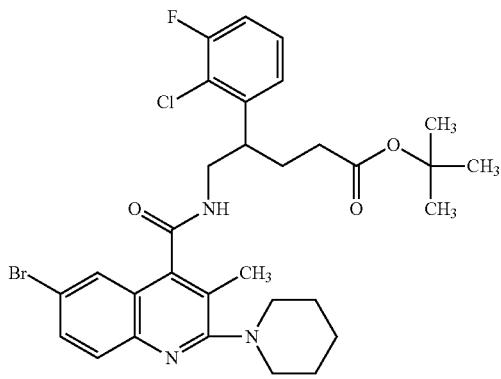 [SMILES: Cc1c(N2CCCCC2)nc2ccc(Br)cc2c1C(=O)NCC(CCC(=O)OC(C)(C)C)c1cccc(F)c1Cl]

To a mixture of (+/−)-tert-butyl 5-{[(6-bromo-2-chloro-3-methylquinolin-4-yl)carbonyl]amino}-4-(2-chloro-3-fluorophenyl)pentanoate (204 mg, 349 µmol, Example 44A) in NMP (3.4 ml) were added piperidine (280 µl, 2.8 mmol) and DIPEA (490 µl, 2.8 mmol), and the mixture was stirred at 100° C. overnight. After cooling to RT, the mixture was filtered and purified by preparative HPLC (Method 6). The combined target fractions were concentrated, and the residue was dried under reduced pressure. 175 mg (100% purity, 79% of theory) of the title compound were obtained.

LC-MS (Method 1): $R_t$=2.81 min; MS (ESIpos): m/z=632/634 [M+H]$^+$ $^1$H-NMR (400 MHz, DMSO-d6) δ [ppm]: −0.150 (0.06), −0.023 (0.27), 0.007 (0.41), 0.145 (0.05), 1.208 (0.07), 1.233 (0.57), 1.303 (0.08), 1.327 (0.10), 1.368 (16.00), 1.525 (0.07), 1.606 (0.45), 1.670 (0.88), 1.808 (0.14), 1.826 (0.19), 2.048 (0.17), 2.061 (0.18), 2.086 (1.12), 2.100 (0.81), 2.130 (1.45), 2.327 (0.06), 2.365 (0.06), 2.669 (0.06), 2.709 (0.06), 3.134 (1.16), 3.604 (0.21), 3.692 (0.32), 7.286 (0.18), 7.306 (0.40), 7.329 (0.27), 7.345 (0.30), 7.363 (0.54), 7.394 (0.26), 7.413 (0.35), 7.427 (0.36), 7.447 (0.19), 7.624 (0.26), 7.646 (1.35), 7.653 (0.89), 7.658 (0.80), 7.675 (0.17), 7.680 (0.19), 8.716 (0.21), 8.730 (0.45), 8.744 (0.22).

Example 157A (+/−)-tert-Butyl 5-({[6-bromo-3-methyl-2-(piperidin-1-yl)quinolin-4-yl]carbonyl}amino)-4-(6-chloro-2,3-difluorophenyl)pentanoate (Racemate)

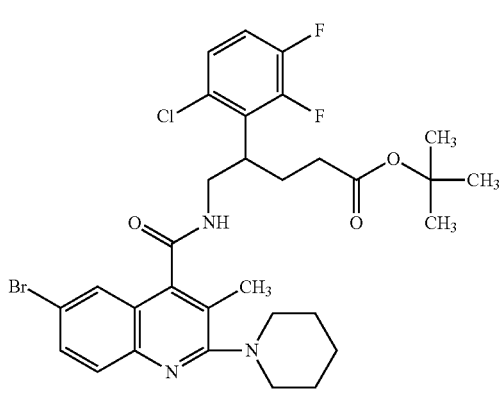 [SMILES: Cc1c(N2CCCCC2)nc2ccc(Br)cc2c1C(=O)NCC(CCC(=O)OC(C)(C)C)c1c(Cl)ccc(F)c1F]

To a mixture of (+/−)-tert-butyl 5-{[(6-bromo-2-chloro-3-methylquinolin-4-yl)carbonyl]amino}-4-(6-chloro-2,3-difluorophenyl)pentanoate (154 mg, 87% purity, 222 µmol, Example 45A) in NMP (2 ml) were added piperidine (180 µl, 1.8 mmol) and DIPEA (310 µl, 1.8 mmol), and the mixture was stirred at 100° C. overnight. After cooling to RT, the mixture was filtered and purified by preparative HPLC (Method 6). The combined target fractions were concentrated, and the residue was dried under reduced pressure. 126 mg (100% purity, 87% of theory) of the title compound were obtained.

LC-MS (Method 1): $R_t$=2.82 min; MS (ESIpos): m/z=650/652 [M+H]$^+$ $^1$H-NMR (400 MHz, DMSO-d6) δ [ppm]: −0.150 (0.07), −0.023 (0.47), 1.202 (0.10), 1.233 (0.72), 1.362 (16.00), 1.518 (0.09), 1.606 (0.59), 1.670 (1.09), 1.981 (0.14), 2.064 (0.26), 2.143 (3.28), 2.169 (0.73), 2.327 (0.09), 2.365 (0.09), 2.670 (0.08), 2.709 (0.07), 3.134 (1.42), 3.689 (0.24), 3.766 (0.34), 7.377 (0.42), 7.389 (0.49), 7.412 (0.33), 7.433 (0.29), 7.627 (0.40), 7.649 (1.50), 7.659 (0.92), 7.664 (0.81), 7.681 (0.21), 7.686 (0.21), 8.811 (0.45).

Example 158A (+/−)-tert-Butyl 5-({[6-bromo-3-methyl-2-(piperidin-1-yl)quinolin-4-yl]carbonyl}amino)-4-(5-fluoro-2-methylphenyl)pentanoate (Racemate)

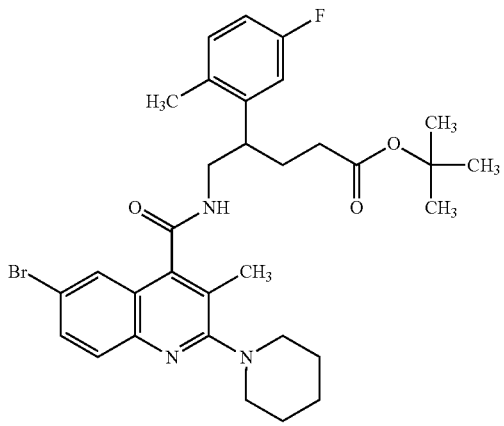 [SMILES: Cc1ccc(F)cc1C(CCC(=O)OC(C)(C)C)CNC(=O)c1c(C)c(N2CCCCC2)nc2ccc(Br)cc12]

To a mixture of (+/−)-tert-butyl 5-{[(6-bromo-2-chloro-3-methylquinolin-4-yl)carbonyl]amino}-4-(5-fluoro-2-methylphenyl)pentanoate (200 mg, 355 µmol, Example 46A) in NMP (2 ml) were added piperidine (280 µl, 2.8 mmol) and DIPEA (620 µl, 3.5 mmol), and the mixture was stirred at 100° C. overnight. After cooling to RT, the mixture was filtered and purified by preparative HPLC (Method 6). The combined target fractions were concentrated, and the residue was dried under reduced pressure. 190 mg (100% purity, 87% of theory) of the title compound were obtained.

LC-MS (Method 1): $R_t$=2.83 min; MS (ESIpos): m/z=612/614 [M+H]$^+$ $^1$H-NMR (400 MHz, DMSO-d6) δ [ppm]: −0.023 (0.35), 0.852 (0.06), 1.211 (0.08), 1.233 (0.83), 1.317 (0.07), 1.337 (0.10), 1.371 (16.00), 1.528 (0.08), 1.606 (0.47), 1.669

(0.92), 1.754 (0.13), 1.787 (0.20), 1.811 (0.16), 2.000 (0.19), 2.016 (0.18), 2.036 (0.20), 2.061 (0.78), 2.077 (0.97), 2.099 (1.51), 2.291 (2.74), 2.365 (0.06), 2.669 (0.07), 2.709 (0.06), 3.135 (1.22), 3.478 (0.17), 3.497 (0.20), 3.512 (0.23), 3.635 (0.15), 3.653 (0.23), 3.671 (0.21), 3.686 (0.17), 3.706 (0.10), 6.928 (0.17), 6.943 (0.33), 6.949 (0.37), 6.971 (0.20), 7.136 (0.36), 7.142 (0.37), 7.163 (0.37), 7.169 (0.36), 7.198 (0.35), 7.213 (0.40), 7.234 (0.31), 7.455 (0.20), 7.628 (0.26), 7.650 (1.44), 7.657 (0.95), 7.662 (0.83), 7.679 (0.16), 7.684 (0.18), 8.702 (0.23), 8.717 (0.39), 8.730 (0.23).

Example 159A (+/−)-tert-Butyl 5-({[6-bromo-2-(3,3-difluoropiperidin-1-yl)-3-methylquinolin-4-yl]carbonyl}amino)-4-(5-fluoro-2-methylphenyl)pentanoate (Racemate)

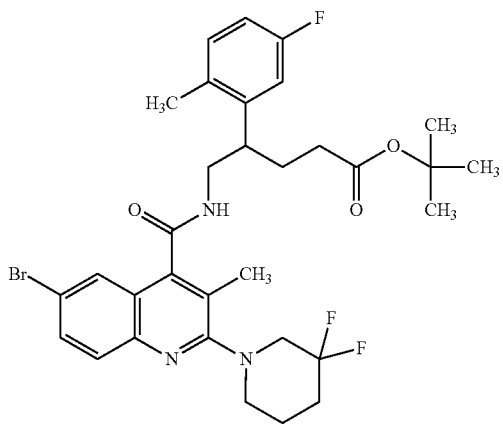 [SMILES: Cc1ccc(F)cc1C(CCC(=O)OC(C)(C)C)CNC(=O)c1c(C)c(N2CCCC(F)(F)C2)nc2ccc(Br)cc12]

To a mixture of (+/−)-tert-butyl 5-{[(6-bromo-2-chloro-3-methylquinolin-4-yl)carbonyl]amino}-4-(5-fluoro-2-methylphenyl)pentanoate (336 mg, 596 μmol, Example 46A) in NMP (4.0 ml) were added 3,3-difluoropiperidine hydrochloride (751 mg, 4.77 mmol) and DIPEA (1.0 ml, 6.0 mmol), and the mixture was stirred at 100° C. for 44 h. Subsequently, the temperature was increased to 120° C., and the mixture was stirred for a further 24 h. After cooling to RT, the mixture was filtered and purified by preparative HPLC (Method 6). The combined target fractions were concentrated, and the residue was dried under reduced pressure. 265 mg (100% purity, 69% of theory) of the title compound were obtained.

LC-MS (Method 1): $R_t$=2.70 min; MS (ESIpos): m/z=648/650 [M+H]⁺

¹H-NMR (400 MHz, DMSO-d6) δ [ppm]: 1.212 (0.07), 1.316 (0.06), 1.337 (0.10), 1.372 (16.00), 1.528 (0.07), 1.757 (0.13), 1.790 (0.21), 1.814 (0.18), 1.829 (0.12), 1.878 (0.50), 1.988 (0.16), 2.002 (0.21), 2.018 (0.21), 2.064 (0.98), 2.080 (1.25), 2.099 (0.84), 2.119 (1.49), 2.291 (2.79), 3.166 (0.61), 3.449 (0.39), 3.478 (0.84), 3.507 (0.56), 3.523 (0.27), 3.646 (0.16), 3.664 (0.25), 3.681 (0.22), 3.698 (0.18), 3.717 (0.10), 6.930 (0.19), 6.945 (0.35), 6.951 (0.38), 6.972 (0.20), 7.142 (0.38), 7.148 (0.38), 7.169 (0.39), 7.175 (0.37), 7.199 (0.37), 7.215 (0.43), 7.236 (0.33), 7.492 (0.19), 7.679 (0.24), 7.701 (1.55), 7.706 (1.07), 7.711 (0.88), 7.734 (0.16), 8.716 (0.25), 8.730 (0.42), 8.744 (0.25).

Example 160A (+/−)-tert-Butyl 5-({[6-bromo-3-methyl-2-(piperidin-1-yl)quinolin-4-yl]carbonyl}amino)-4-(2-chloro-3,6-difluorophenyl)pentanoate (Racemate)

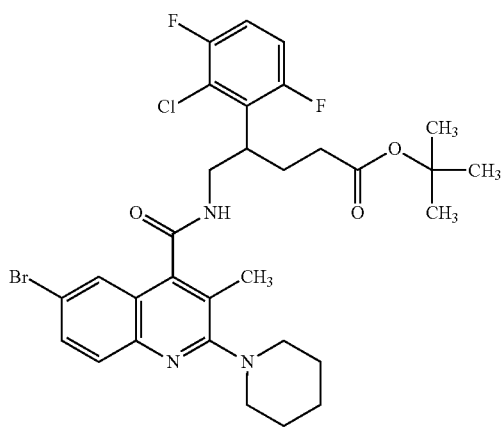 [SMILES: Cc1c(N2CCCCC2)nc2ccc(Br)cc2c1C(=O)NCC(CCC(=O)OC(C)(C)C)c1c(F)ccc(F)c1Cl]

To a mixture of (+/−)-tert-butyl 5-{[(6-bromo-2-chloro-3-methylquinolin-4-yl)carbonyl]amino}-4-(2-chloro-3,6-difluorophenyl)pentanoate (314 mg, 521 μmol, Example 47A) in NMP (3.1 ml) were added piperidine (410 μl, 4.2 mmol) and DIPEA (730 μl, 4.2 mmol), and the mixture was stirred at 100° C. overnight. After cooling to RT, the mixture was filtered and purified by preparative HPLC (Method 6). The combined target fractions were concentrated, and the residue was dried under reduced pressure. 272 mg (100% purity, 80% of theory) of the title compound were obtained.

LC-MS (Method 1): $R_t$=2.80 min; MS (ESIpos): m/z=650/652 [M+H]⁺

¹H-NMR (400 MHz, DMSO-d6) δ [ppm]: −0.022 (0.18), −0.008 (0.77), 0.008 (0.66), 1.234 (0.33), 1.361 (16.00), 1.608 (0.43), 1.673 (0.83), 2.142 (2.24), 2.366 (0.22), 2.710 (0.22), 3.138 (1.09), 3.759 (0.22), 7.303 (0.24), 7.317 (0.19), 7.421 (0.24), 7.630 (0.32), 7.652 (1.33), 7.662 (0.94), 7.667 (0.81), 7.684 (0.21), 7.690 (0.22), 8.814 (0.34).

Example 161A (+/−)-tert-Butyl 5-({[6-bromo-3-methyl-2-(pyrrolidin-1-yl)quinolin-4-yl]carbonyl}amino)-4-(2-chloro-3,6-difluorophenyl)pentanoate (Racemate)

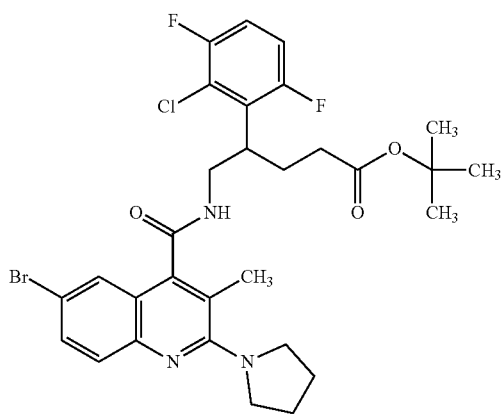 [SMILES: Cc1c(N2CCCC2)nc2ccc(Br)cc2c1C(=O)NCC(CCC(=O)OC(C)(C)C)c1c(F)ccc(F)c1Cl]

To a mixture of (+/−)-tert-butyl 5-{[(6-bromo-2-chloro-3-methylquinolin-4-yl)carbonyl]amino}-4-(2-chloro-3,6-difluorophenyl)pentanoate (600 mg, 996 μmol, Example 47A) in NMP (4.0 ml) were added pyrrolidine (670 μl, 8.0 mmol) and DIPEA (1.4 ml, 8.0 mmol), and the mixture was stirred at 110° C. for 5 h. After cooling to RT, dichloromethane (150 ml) was added to the mixture, and it was successively washed with water and 1 M hydrochloric acid (100 ml of each). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 90 mg (100% purity, 14% of theory) of the title compound were obtained.

LC-MS (Method 1): $R_t$=2.25 min; MS (ESIpos): m/z=636/638 [M+H]$^+$ $^1$H-NMR (400 MHz, DMSO-d6) δ [ppm]: 0.007 (0.21), 1.211 (0.07), 1.300 (0.11), 1.332 (0.11), 1.372 (16.00), 1.397 (2.79), 1.755 (0.12), 1.789 (0.19), 1.812 (0.17), 1.969 (0.16), 1.982 (0.20), 1.999 (0.20), 2.019 (0.15), 2.032 (0.13), 2.067 (0.69), 2.084 (0.98), 2.103 (0.46), 2.283 (1.44), 3.504 (0.12), 3.517 (0.18), 3.537 (0.20), 3.551 (0.24), 3.565 (0.15), 3.706 (0.13), 3.724 (0.19), 3.744 (0.16), 3.758 (0.14), 6.957 (0.24), 7.156 (0.31), 7.162 (0.31), 7.183 (0.32), 7.206 (0.36), 7.221 (0.40), 7.242 (0.31), 7.876 (0.11), 7.898 (2.22), 7.925 (0.09), 8.851 (0.31).

Example 162A (+/−)-tert-Butyl 5-({[6-bromo-2-(3,3-difluoropiperidin-1-yl)-3-methylquinolin-4-yl]carbonyl}amino)-4-(2-chloro-3,6-difluorophenyl)pentanoate (Racemate)

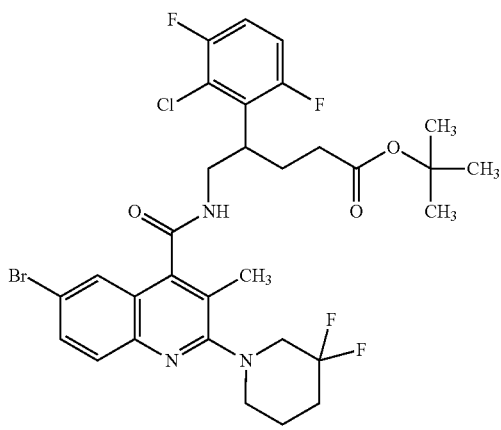 [SMILES: Cc1c(N2CCCC(F)(F)C2)nc2ccc(Br)cc2c1C(=O)NCC(CCC(=O)OC(C)(C)C)c1c(F)ccc(F)c1Cl]

To a mixture of (+/−)-tert-butyl 5-{[(6-bromo-2-chloro-3-methylquinolin-4-yl)carbonyl]amino}-4-(2-chloro-3,6-difluorophenyl)pentanoate (536 mg, 890 μmol, Example 47A) in NMP (3.6 ml) were added 3,3-difluoropiperidine hydrochloride (1.12 g, 7.12 mmol) and DIPEA (1.6 ml, 8.9 mmol), and the mixture was stirred at 110° C. for three days. After cooling to RT, dichloromethane (150 ml) was added to the mixture, and it was washed once with water (120 ml) and once with a mixture of 1 M hydrochloric acid (25 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 204 mg (100% purity, 33% of theory) of the title compound were obtained.

LC-MS (Method 1): $R_t$=2.67 min; MS (ESIpos): m/z=686/688 [M+H]$^+$ $^1$H-NMR (400 MHz, DMSO-d6) δ [ppm]: 1.156 (0.07), 1.174 (0.12), 1.200 (0.08), 1.233 (0.12), 1.269 (0.09), 1.315 (0.44), 1.360 (16.00), 1.377 (0.68), 1.406 (0.22), 1.517 (0.07), 1.883 (0.55), 1.987 (0.32), 2.082 (0.53), 2.097 (0.54), 2.136 (0.81), 2.163 (2.62), 2.327 (0.07), 2.669 (0.05), 3.171 (0.66), 3.450 (0.40), 3.479 (0.77), 3.508 (0.39), 3.696 (0.24), 3.771 (0.26), 4.020 (0.06), 4.038 (0.05), 7.270 (0.14), 7.281 (0.16), 7.294 (0.28), 7.305 (0.29), 7.319 (0.22), 7.330 (0.20), 7.410 (0.28), 7.421 (0.27), 7.681 (0.32), 7.703 (1.51), 7.711 (1.02), 7.716 (0.87), 7.734 (0.20), 7.738 (0.21), 8.828 (0.41).

Example 163A tert-Butyl 5-[({6-bromo-2-[3-fluoropiperidin-1-yl]-3-methylquinolin-4-yl}carbonyl)amino]-4-(2-chloro-3,6-difluorophenyl)pentanoate (Diastereomer Mixture)

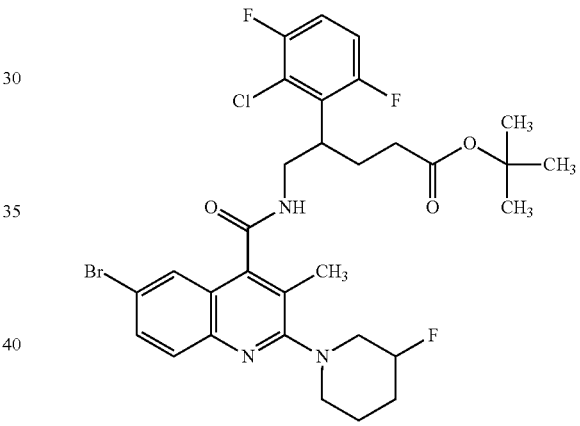

To a mixture of (+/−)-tert-butyl 5-{[(6-bromo-2-chloro-3-methylquinolin-4-yl)carbonyl]amino}-4-(2-chloro-3,6-difluorophenyl)pentanoate (600 mg, 996 μmol, Example 47A) in NMP (4.0 ml) were added (+/−)-3-fluoropiperidine hydrochloride (1.11 g, 7.97 mmol) and DIPEA (1.7 ml, 10 mmol), and the mixture was stirred at 110° C. for 30 h. After cooling to RT, dichloromethane (150 ml) was added to the mixture, and it was washed once with water (120 ml) and once with a mixture of 1 M hydrochloric acid (25 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 463 mg (100% purity, 69% of theory) of the title compound were obtained.

LC-MS (Method 1): $R_t$=2.68 min; MS (ESIpos): m/z=668/670 [M+H]$^+$ $^1$H-NMR (400 MHz, DMSO-d6) δ [ppm]: −0.008 (0.17), 1.157 (0.10), 1.175 (0.20), 1.193 (0.11), 1.201 (0.08), 1.235 (0.07), 1.268 (0.07), 1.316 (0.43), 1.361 (16.00), 1.378 (0.68), 1.398 (2.22), 1.518 (0.07), 1.646 (0.20), 1.808 (0.18), 1.901 (0.32), 1.920 (0.30), 1.952 (0.27), 1.989 (0.53), 2.067 (0.21), 2.084 (0.21), 2.103 (0.18), 2.137 (0.65), 2.157 (2.66), 2.260 (0.06), 2.670 (0.04), 3.099 (0.21), 3.168 (0.22), 3.349 (0.16), 3.380 (0.21), 3.410 (0.11), 3.437 (0.19), 3.468 (0.12), 3.698 (0.22), 3.767 (0.25), 4.003 (0.04), 4.021 (0.09), 4.039 (0.09), 4.057 (0.04), 4.820 (0.15), 4.940 (0.15), 7.269 (0.13), 7.280 (0.15), 7.293 (0.26), 7.304 (0.28), 7.318 (0.21), 7.329 (0.19), 7.410 (0.26), 7.421 (0.26), 7.499 (0.08), 7.655 (0.32), 7.677 (1.46), 7.686 (0.97), 7.691 (0.89), 7.709 (0.21), 7.713 (0.23), 7.906 (0.04), 8.823 (0.37).

Example 164A tert-Butyl 5-[({6-bromo-3-methyl-2-[3-methylpiperidin-1-yl]quinolin-4-yl}carbonyl)amino]-4-(2-chloro-3,6-difluorophenyl)pentanoate (Diastereomer Mixture)

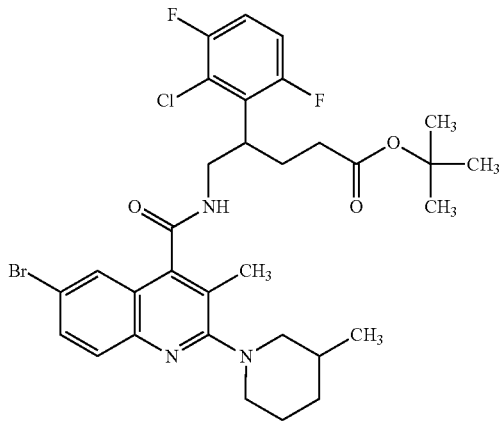 [SMILES: Cc1c(N2CCCC(C)C2)nc2ccc(Br)cc2c1C(=O)NCC(CCC(=O)OC(C)(C)C)c1c(F)ccc(F)c1Cl]

To a mixture of (+/−)-tert-butyl 5-{[(6-bromo-2-chloro-3-methylquinolin-4-yl)carbonyl]amino}-4-(2-chloro-3,6-difluorophenyl)pentanoate (600 mg, 996 μmol, Example 47A) in NMP (4.0 ml) were added (+/−)-3-methylpiperidine (940 μl, 8.0 mmol) and DIPEA (1.4 ml, 8.0 mmol), and the mixture was stirred at 110° C. for 30 h. After cooling to RT, dichloromethane (150 ml) was added to the mixture, and it was washed once with water (120 ml) and once with a mixture of 1 M hydrochloric acid (20 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 550 mg (100% purity, 83% of theory) of the title compound were obtained.

LC-MS (Method 1): $R_t$=2.90 min; MS (ESIpos): m/z=664/666 [M+H]+

1H-NMR (400 MHz, DMSO-d6) δ [ppm]: 0.867 (0.06), 0.884 (0.06), 0.954 (1.62), 0.970 (1.65), 1.114 (0.19), 1.142 (0.20), 1.165 (0.08), 1.235 (0.08), 1.267 (0.11), 1.303 (0.07), 1.348 (0.51), 1.395 (16.00), 1.411 (0.72), 1.431 (5.54), 1.551 (0.07), 1.663 (0.17), 1.686 (0.19), 1.765 (0.35), 1.796 (0.33), 1.826 (0.41), 1.857 (0.26), 2.017 (0.12), 2.102 (0.22), 2.118 (0.22), 2.138 (0.22), 2.181 (2.31), 2.280 (0.06), 2.361 (0.04), 2.478 (0.17), 2.752 (0.17), 3.470 (0.28), 3.498 (0.51), 3.528 (0.24), 3.730 (0.23), 3.795 (0.26), 7.301 (0.14), 7.312 (0.16), 7.325 (0.27), 7.336 (0.28), 7.351 (0.22), 7.362 (0.20), 7.421 (0.18), 7.432 (0.21), 7.443 (0.28), 7.454 (0.28), 7.465 (0.18), 7.476 (0.15), 7.667 (0.24), 7.689 (1.52), 7.694 (1.18), 7.698 (0.95), 7.716 (0.16), 7.721 (0.18), 8.828 (0.22), 8.842 (0.38), 11.235 (0.02).

Example 165A tert-Butyl 5-[({6-bromo-2-[3-ethylpiperidin-1-yl]-3-methylquinolin-4-yl}carbonyl)amino]-4-(2-chloro-3,6-difluorophenyl)pentanoate (Diastereomer Mixture)

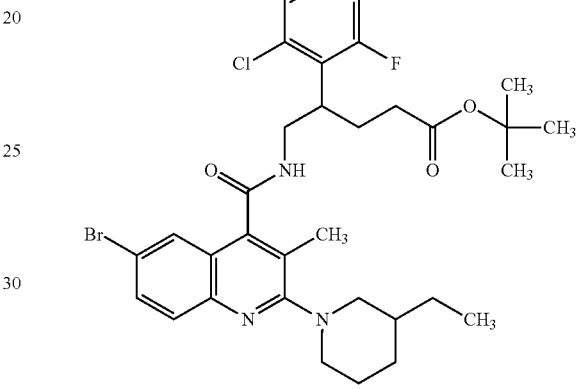

To a mixture of (+/−)-tert-butyl 5-{[(6-bromo-2-chloro-3-methylquinolin-4-yl)carbonyl]amino}-4-(2-chloro-3,6-difluorophenyl)pentanoate (600 mg, 996 μmol, Example 47A) in NMP (4.0 ml) were added (+/−)-3-ethylpiperidine (1.1 ml, 8.0 mmol) and DIPEA (1.4 ml, 8.0 mmol), and the mixture was stirred at 110° C. for 30 h. After cooling to RT, dichloromethane (150 ml) was added to the mixture, and it was washed once with water (150 ml) and once with a mixture of 1 M hydrochloric acid (20 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 558 mg (100% purity, 83% of theory) of the title compound were obtained.

LC-MS (Method 1): $R_t$=3.00 min; MS (ESIpos): m/z=678/680 [M+H]+

1H-NMR (400 MHz, DMSO-d6) δ [ppm]: 0.890 (0.96), 0.909 (2.20), 0.927 (1.16), 1.065 (0.24), 1.095 (0.25), 1.200 (0.09), 1.259 (0.54), 1.276 (0.70), 1.294 (0.48), 1.313 (0.75), 1.360 (16.00), 1.377 (0.79), 1.396 (1.93), 1.566 (0.29), 1.747 (0.34), 1.779 (0.23), 1.847 (0.29), 1.877 (0.29), 1.973 (0.15), 2.066 (0.28), 2.082 (0.29), 2.139 (2.33), 2.241 (0.08), 2.424 (0.20), 2.695 (0.12), 2.752 (0.22), 3.490 (0.54), 3.519 (0.51), 3.694 (0.28), 3.763 (0.32), 7.276 (0.19), 7.290 (0.33), 7.300 (0.34), 7.314 (0.25), 7.325 (0.22), 7.404 (0.35), 7.415 (0.35), 7.632 (0.27), 7.654 (1.72), 7.686 (0.19), 8.809 (0.48).

Example 166A (+/−)-tert-Butyl 5-({[2-(azepan-1-yl)-6-bromo-3-methylquinolin-4-yl]carbonyl}amino)-4-(2-chloro-3,6-difluorophenyl)pentanoate (Racemate)

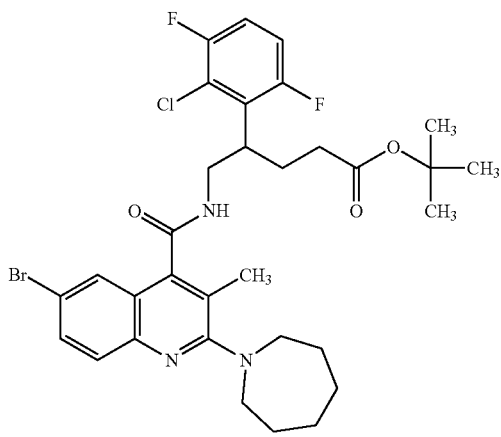 [SMILES: Cc1c(N2CCCCCC2)nc2ccc(Br)cc2c1C(=O)NCC(CCC(=O)OC(C)(C)C)c1c(F)ccc(F)c1Cl]

To a mixture of (+/−)-tert-butyl 5-{[(6-bromo-2-chloro-3-methylquinolin-4-yl)carbonyl]amino}-4-(2-chloro-3,6-difluorophenyl)pentanoate (600 mg, 996 μmol, Example 47A) in NMP (4.0 ml) were added azepane (900 μl, 8.0 mmol) and DIPEA (1.4 ml, 8.0 mmol), and the mixture was stirred at 110° C. for 5 h. After cooling to RT, dichloromethane (150 ml) was added to the mixture, and it was washed once with a mixture of 1 M hydrochloric acid (20 ml) in water (100 ml) and once with water (150 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 599 mg (100% purity, 90% of theory) of the title compound were obtained.

LC-MS (Method 1): $R_t$=2.85 min; MS (ESIpos): m/z=664/666 [M+H]$^+$ $^1$H-NMR (400 MHz, DMSO-d6) δ [ppm]: 0.851 (0.05), 1.200 (0.08), 1.234 (0.20), 1.267 (0.10), 1.312 (0.62), 1.360 (16.00), 1.377 (0.75), 1.397 (4.30), 1.517 (0.09), 1.602 (1.91), 1.780 (1.21), 1.882 (0.08), 1.901 (0.11), 1.920 (0.13), 1.972 (0.15), 2.065 (0.25), 2.082 (0.27), 2.133 (2.63), 2.150 (1.06), 2.195 (0.12), 2.236 (0.07), 2.328 (0.05), 2.670 (0.04), 2.695 (0.40), 3.285 (0.13), 3.492 (1.43), 3.506 (2.16), 3.520 (1.38), 3.708 (0.30), 7.266 (0.15), 7.277 (0.18), 7.290 (0.31), 7.301 (0.33), 7.315 (0.24), 7.326 (0.22), 7.407 (0.35), 7.418 (0.34), 7.532 (0.71), 7.554 (1.27), 7.602 (0.76), 7.607 (0.67), 7.624 (0.42), 7.629 (0.39), 8.789 (0.43).

Example 167A (+/−)-tert-Butyl 5-({[6-bromo-3-methyl-2-(piperidin-1-yl)quinolin-4-yl]carbonyl}amino)-4-[2-fluoro-6-(trifluoromethyl)phenyl]pentanoate (Racemate)

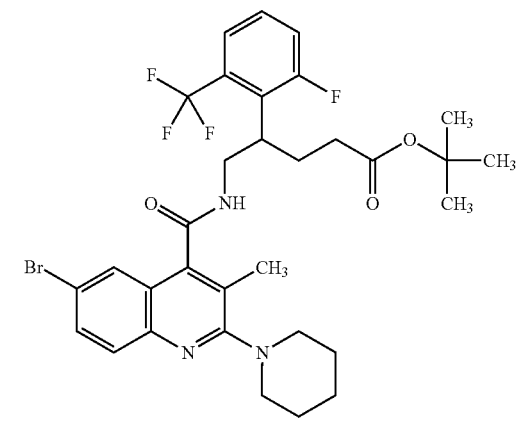 [SMILES: Cc1c(N2CCCCC2)nc2ccc(Br)cc2c1C(=O)NCC(CCC(=O)OC(C)(C)C)c1c(F)cccc1C(F)(F)F]

To a mixture of (+/−)-tert-butyl 5-{[(6-bromo-2-chloro-3-methylquinolin-4-yl)carbonyl]amino}-4-[2-fluoro-6-(trifluoromethyl)phenyl]pentanoate (300 mg, 97% purity, 471 μmol, Example 50A) in NMP (4.0 ml) were added, in a thick-walled glass vessel (microwave vessel), piperidine (230 μl, 2.4 mmol) and DIPEA (410 μl, 2.4 mmol). The vessel was purged with argon, closed and agitated at 100° C. by means of a heated agitator overnight. This was followed by agitation at 130° C. for a further 24 h. After cooling to RT, the mixture was purified directly (without further workup) by preparative HPLC (Method 14). The combined target fractions were concentrated, and the residue was taken up in dichloromethane, concentrated again and dried under reduced pressure. 258 mg (100% purity, 82% of theory) of the title compound were obtained.

LC-MS (Method 4): $R_t$=1.80 min; ionization without detection of the target mass $^1$H-NMR (400 MHz, DMSO-d6) δ [ppm]: −0.149 (0.10), −0.008 (0.85), 0.008 (0.95), 0.146 (0.10), 1.307 (0.15), 1.340 (16.00), 1.613 (0.43), 1.678 (0.85), 2.042 (0.25), 2.073 (0.48), 2.093 (0.35), 2.114 (0.48), 2.141 (0.39), 2.168 (1.23), 2.328 (0.11), 2.670 (0.11), 3.151 (1.11), 3.700 (0.12), 3.849 (0.11), 5.754 (0.33), 7.561 (0.48), 7.571 (0.44), 7.594 (0.69), 7.622 (0.44), 7.634 (0.51), 7.656 (1.32), 7.661 (0.97), 7.666 (0.84), 7.688 (0.17), 8.803 (0.21), 8.818 (0.42), 8.833 (0.21).

Separation of the Enantiomers:

The title compound (188 mg) was separated into the enantiomers by means of preparative SFC on chiral phase (see Examples 168A and 169A) [column: Daicel Chiralcel OX-H, 5 μm, 250 mm×20 mm; flow rate: 60 ml/min; UV detection: 260 nm, temperature: 25° C.; eluent: 10% methanol/90% carbon dioxide; outlet pressure 150 bar, isocratic]. The combined target fractions were each concentrated, and the respective residue was dried under reduced pressure.

Example 168A tert-Butyl 5-({[6-bromo-3-methyl-2-(piperidin-1-yl)quinolin-4-yl]carbonyl}amino)-4-[2-fluoro-6-(trifluoromethyl)phenyl]pentanoate (Enantiomer 1)

In the enantiomer separation described in Example 167A, 85 mg (100% purity, ee 99%) of the title compound were obtained as the enantiomer that eluted earlier.

R*t*=11.5 min (chiral analytical HPLC; column: Chiralpak IE, 5 μm, 250 mm×4.6 mm, eluent: heptane/isopropanol/diethylamine 80:20:0.1; flow rate 1 ml/min; temperature 25° C.; detection 225 nm)

LC-MS (Method 2): R*t*=1.48 min; MS (ESIpos): m/z=666/668 [M+H]+

1H-NMR (400 MHz, DMSO-d6) δ [ppm]: 1.348 (16.00), 1.621 (0.41), 1.687 (0.81), 2.080 (0.44), 2.122 (0.46), 2.177 (1.18), 3.158 (1.06), 7.569 (0.47), 7.579 (0.44), 7.603 (0.69), 7.631 (0.44), 7.642 (0.51), 7.664 (1.33), 7.669 (1.00), 7.674 (0.86), 8.826 (0.40).

Example 169A tert-Butyl 5-({[6-bromo-3-methyl-2-(piperidin-1-yl)quinolin-4-yl]carbonyl}amino)-4-[2-fluoro-6-(trifluoromethyl)phenyl]pentanoate (Enantiomer 2)

In the enantiomer separation described in Example 167A, 93 mg (100% purity, ee 97%) of the title compound were obtained as the enantiomer that eluted later.

R*t*=10.3 min (chiral analytical HPLC; column: Chiralpak IE, 5 am, 250 mm×4.6 mm, eluent: heptane/isopropanol/diethylamine 80:20:0.1; flow rate 1 ml/min; temperature 25° C.; detection 225 nm)

LC-MS (Method 2): R*t*=1.48 min; MS (ESIpos): m/z=666/668 [M+H]+

1H-NMR (400 MHz, DMSO-d6) δ [ppm]: −0.009 (0.46), 0.007 (0.43), 1.029 (0.54), 1.044 (0.55), 1.235 (0.26), 1.307 (0.15), 1.340 (16.00), 1.613 (0.42), 1.678 (0.83), 2.041 (0.24), 2.072 (0.47), 2.092 (0.34), 2.114 (0.47), 2.140 (0.39), 2.167 (1.21), 2.327 (0.11), 2.669 (0.11), 3.154 (1.12), 3.714 (0.12), 3.847 (0.11), 7.561 (0.47), 7.570 (0.43), 7.594 (0.69), 7.622 (0.44), 7.633 (0.49), 7.655 (1.31), 7.661 (0.93), 7.666 (0.80), 7.688 (0.16), 8.802 (0.20), 8.817 (0.41), 8.832 (0.20).

Example 170A (+/−)-tert-Butyl 5-({[6-bromo-3-methyl-2-(pyrrolidin-1-yl)quinolin-4-yl]carbonyl}amino)-4-[2-fluoro-6-(trifluoromethyl)phenyl]pentanoate (Racemate)

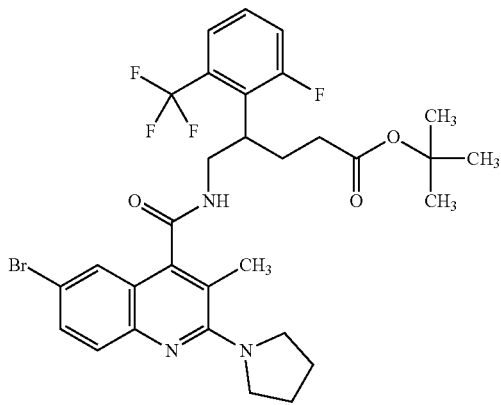 [SMILES: Cc1c(N2CCCC2)nc2ccc(Br)cc2c1C(=O)NCC(CCC(=O)OC(C)(C)C)c1c(F)cccc1C(F)(F)F]

To a mixture of (+/−)-tert-butyl 5-{[(6-bromo-2-chloro-3-methylquinolin-4-yl)carbonyl]amino}-4-[2-fluoro-6-(trifluoromethyl)phenyl]pentanoate (300 mg, 97% purity, 471 μmol, Example 50A) in NMP (4.0 ml) were added, in a thick-walled glass vessel (microwave vessel), pyrrolidine (200 μl, 2.4 mmol) and DIPEA (410 μl, 2.4 mmol). The vessel was purged with argon, closed and agitated at 100° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 239 mg (100% purity, 78% of theory) of the title compound were obtained.

LC-MS (Method 4): R*t*=1.46 min; MS (ESIpos): m/z=652/654 [M+H]+

1H-NMR (400 MHz, DMSO-d6) δ [ppm]: −0.149 (0.10), −0.008 (0.85), 0.008 (0.95), 0.146 (0.10), 1.290 (0.07), 1.308 (0.14), 1.337 (16.00), 1.879 (1.23), 2.038 (0.27), 2.067 (0.53), 2.093 (0.41), 2.115 (0.61), 2.144 (0.39), 2.178 (0.48), 2.328 (0.11), 2.669 (0.10), 3.581 (0.86), 3.867 (0.11), 5.754 (0.65), 7.476 (0.63), 7.499 (1.10), 7.552 (0.74), 7.557 (0.95), 7.574 (0.65), 7.580 (0.59), 7.590 (0.62), 7.613 (0.41), 8.745 (0.19), 8.760 (0.38), 8.775 (0.20).

Separation of the Enantiomers:

The title compound (163 mg) was separated into the enantiomers by means of preparative SFC on chiral phase (see Examples 171A and 172A) [column: Daicel Chiralpak IG, 5 μm, 250 mm×20 mm; flow rate: 60 ml/min; UV detection: 230 nm, temperature: 25° C.; eluent: 20% (methanol+1% diethylamine)/80% carbon dioxide; outlet pressure 150 bar, isocratic]. The combined target fractions were each concentrated, and the respective residue was dried under reduced pressure.

Example 171A tert-Butyl 5-({[6-bromo-3-methyl-2-(pyrrolidin-1-yl)quinolin-4-yl]carbonyl}amino)-4-[2-fluoro-6-(trifluoromethyl)phenyl]pentanoate (Enantiomer 1)

In the enantiomer separation described in Example 170A, 75 mg (98% purity, ee 98%) of the title compound were obtained as the enantiomer that eluted earlier.

R*t*=10.8 min (chiral analytical HPLC; column: Chiralpak IC, 5 μm, 250 mm×4.6 mm, eluent: heptane/isopropanol/diethylamine 70:30:0.1; flow rate 1 ml/min; temperature 25° C.; detection 260 nm)

LC-MS (Method 2): R*t*=1.11 min; MS (ESIpos): m/z=652/654 [M+H]+

1H-NMR (400 MHz, DMSO-d6) δ [ppm]: 1.029 (0.47), 1.045 (0.47), 1.337 (16.00), 1.879 (1.24), 2.038 (0.29), 2.067 (0.55), 2.092 (0.43), 2.115 (0.62), 2.144 (0.40), 2.179 (0.49), 2.327 (0.16), 2.669 (0.15), 3.581 (0.87), 7.476 (0.64), 7.498 (1.12), 7.552 (0.76), 7.557 (0.98), 7.574 (0.67), 7.580 (0.60), 7.590 (0.64), 7.613 (0.42), 8.760 (0.38).

Example 172A tert-Butyl 5-({[6-bromo-3-methyl-2-(pyrrolidin-1-yl)quinolin-4-yl]carbonyl}amino)-4-[2-fluoro-6-(trifluoromethyl)phenyl]pentanoate (Enantiomer 2)

In the enantiomer separation described in Example 170A, 79 mg (97% purity, ee 98%) of the title compound were obtained as the enantiomer that eluted later.

R*t*=13.4 min (chiral analytical HPLC; column: Chiralpak IC, 5 μm, 250 mm×4.6 mm, eluent: heptane/isopropanol/diethylamine 70:30:0.1; flow rate 1 ml/min; temperature 25° C.; detection 260 nm)

LC-MS (Method 2): R*t*=1.11 min; MS (ESIpos): m/z=652/654 [M+H]+

¹H-NMR (400 MHz, DMSO-d6) δ [ppm]: 1.030 (1.27), 1.045 (1.26), 1.235 (0.11), 1.308 (0.16), 1.337 (16.00), 1.879 (1.30), 1.960 (0.11), 2.037 (0.29), 2.067 (0.56), 2.093 (0.44), 2.115 (0.64), 2.144 (0.41), 2.178 (0.52), 2.327 (0.12), 3.580 (0.92), 3.864 (0.12), 7.476 (0.67), 7.498 (1.16), 7.552 (0.83), 7.557 (1.01), 7.574 (0.69), 7.580 (0.63), 7.589 (0.66), 7.613 (0.43), 8.760 (0.40).

Example 173A (+/−)-tert-Butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (Racemate)

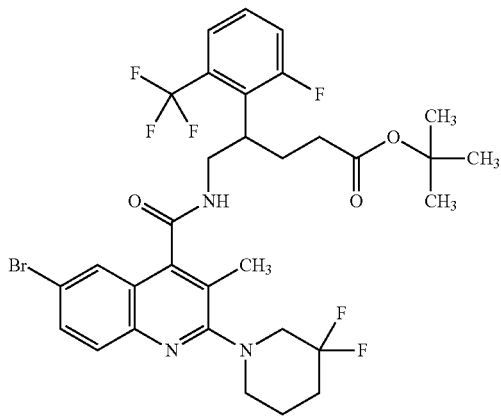 [SMILES: Cc1c(N2CCCC(F)(F)C2)nc2ccc(Br)cc2c1C(=O)NCC(CCC(=O)OC(C)(C)C)c1c(F)cccc1C(F)(F)F]

To a mixture of (+/−)-tert-butyl 5-{[(6-bromo-2-chloro-3-methylquinolin-4-yl)carbonyl]amino}-4-[2-fluoro-6-(trifluoromethyl)phenyl]pentanoate (300 mg, 98% purity, 476 μmol, Example 50A) in NMP (4.0 ml) were added, in a thick-walled glass vessel (microwave vessel), 3,3-difluoropiperidine hydrochloride (387 mg, 97% purity, 2.38 mmol) and DIPEA (410 μl, 2.4 mmol). The vessel was purged with argon, closed and agitated at 100° C. by means of a heated agitator overnight. This was followed by agitation at 130° C. for a further 24 h. After cooling to RT, the mixture was purified directly (without further workup) by preparative HPLC (Method 14). The combined target fractions were concentrated, and the residue was taken up in dichloromethane, concentrated again and dried under reduced pressure. 248 mg (100% purity, 74% of theory) of the title compound were obtained.

LC-MS (Method 1): $R_t$=2.72 min; MS (ESIpos): m/z=702/704 [M+H]⁺

¹H-NMR (400 MHz, DMSO-d6) δ [ppm]: −0.149 (0.05), −0.008 (0.42), 0.008 (0.38), 0.146 (0.05), 1.180 (0.06), 1.290 (0.07), 1.307 (0.14), 1.340 (16.00), 1.497 (0.06), 1.889 (0.41), 2.049 (0.30), 2.078 (0.59), 2.100 (0.65), 2.117 (0.70), 2.141 (0.44), 2.189 (1.10), 2.328 (0.07), 2.670 (0.07), 3.181 (0.46), 3.462 (0.32), 3.491 (0.63), 3.520 (0.31), 3.717 (0.11), 3.864 (0.10), 5.754 (0.18), 7.565 (0.44), 7.574 (0.43), 7.598 (0.65), 7.625 (0.43), 7.634 (0.28), 7.648 (0.20), 7.684 (0.20), 7.706 (1.32), 7.710 (1.02), 7.715 (0.83), 7.733 (0.12), 7.737 (0.15), 8.815 (0.20), 8.831 (0.42), 8.846 (0.20).

Separation of the Enantiomers:

The title compound (179 mg) was separated into the enantiomers by means of preparative SFC on chiral phase (see Examples 174A and 175A) [column: Daicel Chiralpak AD-H, 5 μm, 250 mm×30 mm; flow rate: 120 ml/min; UV detection: 260 nm, temperature: 25° C.; eluent: 10% isopropanol/90% carbon dioxide; outlet pressure 150 bar, isocratic]. The combined target fractions were each concentrated, and the respective residue was dried under reduced pressure.

Example 174A tert-Butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (Enantiomer 1)

In the enantiomer separation described in Example 173A, 91 mg (100% purity, ee>99%) of the title compound were obtained as the enantiomer that eluted earlier.

$R_t$=18.1 min (chiral analytical HPLC; column: Chiralpak IC, 5 μm, 250 mm×4.6 mm, eluent: heptane/isopropanol/diethylamine 90:10:0.1; flow rate 1 ml/min; temperature 25° C.; detection 225 nm)

LC-MS (Method 2): $R_t$=1.43 min; MS (ESIpos): m/z=702/704 [M+H]⁺

¹H-NMR (400 MHz, DMSO-d6) δ [ppm]: −0.008 (0.91), 0.008 (0.87), 1.030 (1.67), 1.045 (1.69), 1.237 (0.39), 1.340 (16.00), 1.888 (0.40), 2.100 (0.64), 2.117 (0.68), 2.141 (0.43), 2.189 (1.08), 2.328 (0.16), 2.670 (0.17), 3.187 (0.45), 3.462 (0.32), 3.491 (0.62), 3.520 (0.31), 4.323 (0.21), 4.334 (0.21), 7.565 (0.44), 7.575 (0.42), 7.598 (0.64), 7.625 (0.42), 7.684 (0.20), 7.706 (1.29), 7.710 (1.00), 7.715 (0.82), 7.737 (0.15), 8.830 (0.40).

Example 175A tert-Butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (Enantiomer 2)

In the enantiomer separation described in Example 173A, 93 mg (100% purity, ee>99%) of the title compound were obtained as the enantiomer that eluted later.

$R_t$=21.4 min (chiral analytical HPLC; column: Chiralpak IC, 5 μm, 250 mm×4.6 mm, eluent: heptane/isopropanol/diethylamine 90:10:0.1; flow rate 1 ml/min; temperature 25° C.; detection 225 nm)

LC-MS (Method 2): $R_t$=1.43 min; MS (ESIpos): m/z=702/704 [M+H]⁺

¹H-NMR (400 MHz, DMSO-d6) δ [ppm]: 0.007 (0.93), 1.029 (1.51), 1.044 (1.53), 1.236 (0.47), 1.340 (16.00), 1.889 (0.45), 2.100 (0.71), 2.115 (0.76), 2.140 (0.47), 2.188 (1.18), 2.327 (0.16), 2.669 (0.17), 3.183 (0.50), 3.462 (0.34), 3.490 (0.67), 3.519 (0.33), 4.322 (0.21), 4.333 (0.20), 7.564 (0.46), 7.574 (0.46), 7.597 (0.67), 7.624 (0.45), 7.683 (0.20), 7.705 (1.37), 7.709 (1.07), 7.714 (0.86), 7.737 (0.15), 8.830 (0.43).

Example 176A tert-Butyl 5-[({6-bromo-2-[3-fluoropiperidin-1-yl]-3-methylquinolin-4-yl}carbonyl)amino]-4-[2-fluoro-6-(trifluoromethyl)phenyl]pentanoate (Diastereomer Mixture)

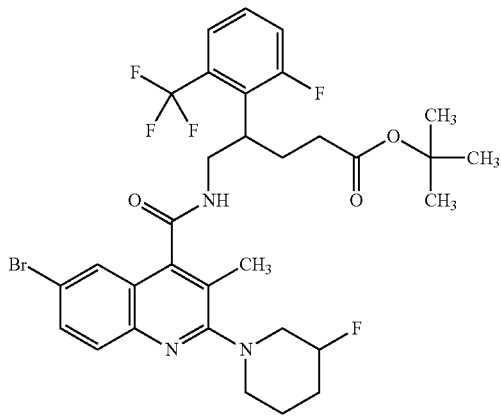 [SMILES: Cc1c(N2CCCC(F)C2)nc2ccc(Br)cc2c1C(=O)NCC(CCC(=O)OC(C)(C)C)c1c(F)cccc1C(F)(F)F]

To a mixture of (+/−)-tert-butyl 5-{[(6-bromo-2-chloro-3-methylquinolin-4-yl)carbonyl]amino}-4-[2-fluoro-6-(trifluoromethyl)phenyl]pentanoate (400 mg, 98% purity, 634 μmol, Example 50A) in NMP (4.0 ml) were added, in a thick-walled glass vessel (microwave vessel), (+/−)-3-fluoropiperidine hydrochloride (457 mg, 97% purity, 3.17 mmol) and DIPEA (550 μl, 3.2 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 351 mg (100% purity, 81% of theory) of the title compound were obtained.

LC-MS (Method 1): $R_t$=2.71 min; MS (ESIpos): m/z=684/686 [M+H]$^+$ $^1$H-NMR (400 MHz, DMSO-d6) δ [ppm]: −0.008 (0.42), 0.008 (0.45), 1.307 (0.13), 1.340 (16.00), 1.654 (0.14), 1.813 (0.14), 1.906 (0.24), 2.075 (0.45), 2.097 (0.36), 2.116 (0.48), 2.142 (0.31), 2.181 (1.06), 2.328 (0.11), 2.670 (0.12), 3.113 (0.17), 3.179 (0.17), 3.391 (0.18), 3.449 (0.16), 3.482 (0.10), 3.705 (0.11), 3.861 (0.11), 4.825 (0.12), 4.945 (0.12), 5.754 (0.82), 7.562 (0.45), 7.573 (0.42), 7.595 (0.65), 7.623 (0.43), 7.636 (0.28), 7.657 (0.21), 7.679 (1.15), 7.712 (0.12), 8.824 (0.35).

Example 177A tert-Butyl 5-[({6-bromo-2-[3-ethylpiperidin-1-yl]-3-methylquinolin-4-yl}carbonyl)amino]-4-[2-fluoro-6-(trifluoromethyl)phenyl]pentanoate (Diastereomer Mixture)

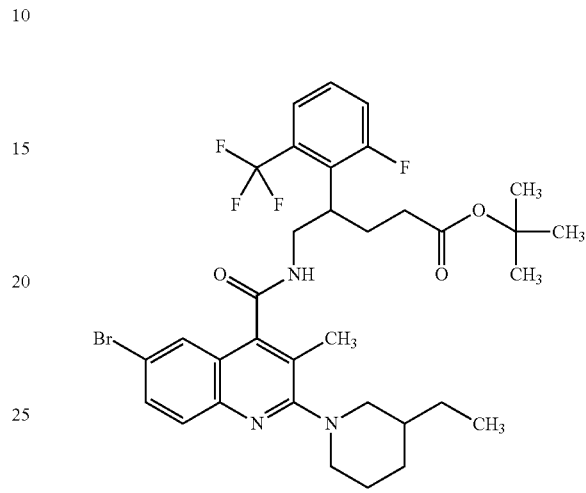

To a mixture of (+/−)-tert-butyl 5-{[(6-bromo-2-chloro-3-methylquinolin-4-yl)carbonyl]amino}-4-[2-fluoro-6-(trifluoromethyl)phenyl]pentanoate (400 mg, 98% purity, 634 μmol, Example 50A) in NMP (4.0 ml) were added, in a thick-walled glass vessel (microwave vessel), (+/−)-3-ethylpiperidine (378 mg, 95% purity, 3.17 mmol) and DIPEA (550 μl, 3.2 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 383 mg (100% purity, 87% of theory) of the title compound were obtained.

LC-MS (Method 1): $R_t$=3.01 min; MS (ESIpos): m/z=684/686 [M+H]$^+$ $^1$H-NMR (400 MHz, DMSO-d6) δ [ppm]: −0.009 (0.42), 0.007 (0.45), 1.306 (0.13), 1.339 (16.00), 1.653 (0.14), 1.812 (0.14), 1.905 (0.24), 2.075 (0.45), 2.096 (0.36), 2.116 (0.48), 2.141 (0.31), 2.180 (1.06), 2.327 (0.11), 2.669 (0.12), 3.112 (0.17), 3.178 (0.17), 3.390 (0.18), 3.448 (0.16), 3.482 (0.10), 3.704 (0.11), 3.860 (0.11), 4.825 (0.12), 4.944 (0.12), 5.753 (0.82), 7.562 (0.45), 7.572 (0.42), 7.595 (0.65), 7.622 (0.43), 7.635 (0.28), 7.656 (0.21), 7.679 (1.15), 7.711 (0.12), 8.823 (0.35).

Example 178A (+/−)-tert-Butyl 5-({[6-bromo-3-methyl-2-(piperi-din-1-yl)quinolin-4-yl]carbonyl}amino)-4-(2,3,6-trichlorophenyl)pentanoate (Racemate)

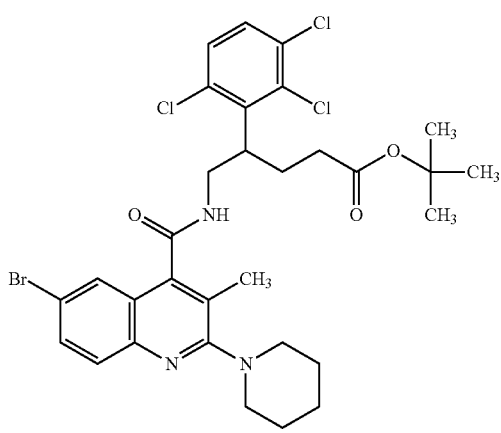 [SMILES: Cc1c(N2CCCCC2)nc2ccc(Br)cc2c1C(=O)NCC(CCC(=O)OC(C)(C)C)c1c(Cl)ccc(Cl)c1Cl]

To a mixture of (+/−)-tert-butyl 5-{[(6-bromo-2-chloro-3-methylquinolin-4-yl)carbonyl]amino}-4-(2,3,6-trichlorophenyl)pentanoate (300 mg, 472 μmol, Example 51A) in NMP (4.0 ml) were added, in a thick-walled glass vessel (microwave vessel), piperidine (230 μl, 2.4 mmol) and DIPEA (410 μl, 2.4 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 242 mg (100% purity, 75% of theory) of the title compound were obtained.

LC-MS (Method 4): $R_t$=1.87 min; ionization without detection of the target mass $^1$H-NMR (400 MHz, DMSO-d6) δ [ppm]: −0.008 (1.20), 0.008 (1.31), 1.351 (14.79), 1.355 (16.00), 1.610 (0.78), 1.674 (1.51), 2.073 (3.11), 2.138 (2.16), 2.156 (0.92), 2.169 (3.50), 2.327 (0.31), 2.670 (0.18), 3.141 (1.94), 3.819 (0.29), 4.033 (0.51), 7.473 (0.58), 7.495 (0.81), 7.532 (0.71), 7.554 (1.23), 7.593 (0.84), 7.614 (0.57), 7.631 (0.37), 7.637 (0.35), 7.653 (1.38), 7.659 (1.35), 7.669 (1.22), 7.674 (0.69), 7.691 (0.30), 8.806 (0.51).

Separation of the Enantiomers:

The title compound (194 mg) was separated into the enantiomers by means of preparative SFC on chiral phase (see Examples 179A and 180A) [column: Chiralpak IG, 5 μm, 250 mm×20 mm; flow rate: 60 ml/min; UV detection: 260 nm, temperature: 25° C.; eluent: 35% (isopropanol+1% diethylamine)/65% carbon dioxide; outlet pressure 150 bar, isocratic]. The combined target fractions were each concentrated, and the respective residue was dried under reduced pressure. Peak 2 was reseparated by means of chiral HPLC [column: Daicel Chiralpak IG, 5 μm, 250 mm×20 mm; flow rate: 20 ml/min; UV detection: 260 nm, temperature: 25° C.; eluent: 20% ethyl acetate/80% heptane, isocratic]

Example 179A tert-Butyl 5-({[6-bromo-3-methyl-2-(piperidin-1-yl)quinolin-4-yl]carbonyl}amino)-4-(2,3,6-trichlorophenyl)pentanoate (Enantiomer 1)

In the enantiomer separation described in Example 178A, 92 mg (100% purity, ee 98%) of the title compound were obtained as the enantiomer that eluted earlier.

$R_t$=8.3 min (chiral analytical HPLC; column: Chiralpak IG, 5 am, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.58 min; MS (ESIpos): m/z=682/684/686 [M+H]$^+$ $^1$H-NMR (400 MHz, DMSO-d6) δ [ppm]: −0.008 (0.84), 0.008 (0.66), 1.029 (4.38), 1.045 (4.40), 1.236 (0.62), 1.351 (15.34), 1.355 (16.00), 1.609 (0.80), 1.673 (1.53), 2.083 (0.46), 2.098 (0.48), 2.112 (0.60), 2.137 (2.18), 2.156 (0.97), 2.169 (3.55), 2.523 (0.44), 3.141 (1.98), 4.032 (0.52), 4.323 (0.54), 4.334 (0.53), 7.473 (0.56), 7.495 (0.78), 7.532 (0.67), 7.554 (1.18), 7.593 (0.80), 7.599 (0.70), 7.615 (0.56), 7.653 (1.35), 7.659 (1.31), 7.662 (1.07), 7.669 (1.19), 7.674 (0.67), 8.792 (0.44), 8.806 (0.51).

Example 180A tert-Butyl 5-({[6-bromo-3-methyl-2-(piperidin-1-yl)quinolin-4-yl]carbonyl}amino)-4-(2,3,6-trichlorophenyl)pentanoate (Enantiomer 2)

In the enantiomer separation described in Example 178A, 96 mg (100% purity, ee>99%) of the title compound were obtained as the enantiomer that eluted later.

$R_t$=11.0 min (chiral analytical HPLC; column: Chiralpak IG, 5 am, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.58 min; MS (ESIpos): m/z=682/684/686 [M+H]$^+$ $^1$H-NMR (400 MHz, DMSO-d6) δ [ppm]: −0.008 (0.62), 0.008 (0.63), 0.854 (0.49), 0.858 (0.46), 1.237 (2.83), 1.249 (1.11), 1.258 (0.60), 1.336 (0.75), 1.351 (15.06), 1.355 (16.00), 1.610 (0.78), 1.673 (1.51), 2.083 (0.45), 2.098 (0.47), 2.111 (0.58), 2.137 (2.17), 2.156 (0.95), 2.169 (3.50), 3.141 (1.96), 4.032 (0.52), 7.473 (0.54), 7.495 (0.77), 7.532 (0.67), 7.554 (1.15), 7.593 (0.79), 7.599 (0.69), 7.615 (0.55), 7.653 (1.32), 7.658 (1.27), 7.662 (1.06), 7.668 (1.15), 7.674 (0.65), 8.791 (0.43), 8.806 (0.50).

Example 181A (+/−)-tert-Butyl 5-({[6-bromo-3-methyl-2-(pyrrolidin-1-yl)quinolin-4-yl]carbonyl}amino)-4-(2,3,6-trichlorophenyl)pentanoate (Racemate)

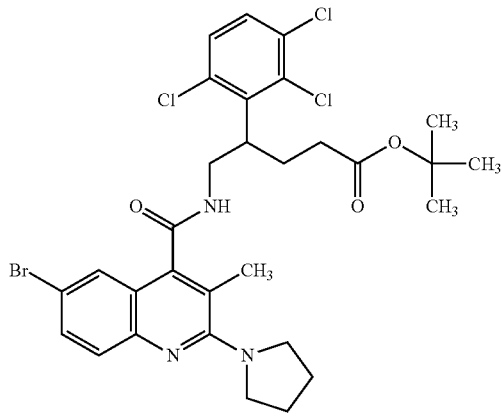 [SMILES: Cc1c(N2CCCC2)nc2ccc(Br)cc2c1C(=O)NCC(CCC(=O)OC(C)(C)C)c1c(Cl)ccc(Cl)c1Cl]

To a mixture of (+/−)-tert-butyl 5-{[(6-bromo-2-chloro-3-methylquinolin-4-yl)carbonyl]amino}-4-(2,3,6-trichlorophenyl)pentanoate (300 mg, 472 μmol, Example 51A) in NMP (4.0 ml) were added, in a thick-walled glass vessel (microwave vessel), pyrrolidine (200 µl, 2.4 mmol) and DIPEA (410 µl, 2.4 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 261 mg (100% purity, 82% of theory) of the title compound were obtained.

LC-MS (Method 1): $R_t$=2.45 min; MS (ESIpos): m/z=668/670/672 [M+H]$^+$ $^1$H-NMR (400 MHz, DMSO-d6) δ [ppm]: −0.149 (0.69), −0.008 (5.80), 0.008 (5.56), 0.146 (0.67), 1.349 (16.00), 1.353 (15.98), 1.875 (2.13), 2.073 (0.92), 2.095 (0.52), 2.121 (0.82), 2.134 (1.09), 2.158 (1.22), 2.174 (0.95), 2.193 (2.16), 2.327 (0.75), 2.669 (0.62), 3.575 (1.49), 4.035 (0.47), 7.473 (1.07), 7.480 (0.77), 7.495 (1.59), 7.502 (1.19), 7.522 (0.70), 7.544 (1.21), 7.553 (0.77), 7.560 (0.99), 7.566 (0.60), 7.576 (0.52), 7.587 (0.94), 7.608 (0.50), 8.754 (0.54).

Separation of the Enantiomers:

The title compound (199 mg) was separated into the enantiomers by means of preparative SFC on chiral phase (see Examples 182A and 183A) [column: Daicel Chiralpak IG, 5 µm, 250 mm×20 mm; flow rate: 60 ml/min; UV detection: 230 nm, temperature: 25° C.; eluent: 40% (isopropanol+1% diethylamine)/60% carbon dioxide; outlet pressure 150 bar, isocratic]. The combined target fractions were each concentrated, and the respective residue was dried under reduced pressure.

Example 182A tert-Butyl 5-({[6-bromo-3-methyl-2-(pyrrolidin-1-yl)quinolin-4-yl]carbonyl}amino)-4-(2,3,6-trichlorophenyl)pentanoate (Enantiomer 1)

In the enantiomer separation described in Example 181A, 92 mg (100% purity, ee>99%) of the title compound were obtained as the enantiomer that eluted earlier.

$R_t$=12.0 min (chiral analytical HPLC; column: Chiralpak IG, 5 µm, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.21 min; MS (ESIpos): m/z=668/670/672 [M+H]$^+$ $^1$H-NMR (400 MHz, DMSO-d6) δ [ppm]: −0.008 (0.88), 0.008 (0.72), 1.030 (1.55), 1.045 (1.56), 1.236 (1.18), 1.349 (15.95), 1.353 (16.00), 1.875 (2.18), 2.080 (0.50), 2.095 (0.55), 2.108 (0.59), 2.121 (0.86), 2.135 (1.11), 2.158 (1.23), 2.174 (0.99), 2.193 (2.17), 2.327 (0.41), 3.574 (1.54), 4.037 (0.49), 7.473 (1.01), 7.480 (0.76), 7.495 (1.53), 7.502 (1.18), 7.522 (0.66), 7.544 (1.14), 7.554 (0.74), 7.560 (0.96), 7.566 (0.59), 7.576 (0.51), 7.588 (0.95), 7.609 (0.51), 8.755 (0.50).

Example 183A tert-Butyl 5-({[6-bromo-3-methyl-2-(pyrrolidin-1-yl)quinolin-4-yl]carbonyl}amino)-4-(2,3,6-trichlorophenyl)pentanoate (Enantiomer 2)

In the enantiomer separation described in Example 181A, 98 mg (100% purity, ee 99%) of the title compound were obtained as the enantiomer that eluted later.

$R_t$=16.7 min (chiral analytical HPLC; column: Chiralpak IG, 5 am, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.21 min; MS (ESIpos): m/z=668/670/672 [M+H]$^+$ $^1$H-NMR (400 MHz, DMSO-d6) δ [ppm]: −0.008 (0.95), 0.008 (0.59), 0.854 (0.51), 1.030 (1.60), 1.045 (1.59), 1.092 (0.52), 1.236 (2.83), 1.259 (0.57), 1.331 (0.85), 1.349 (16.00), 1.353 (15.73), 1.875 (2.07), 1.961 (0.65), 2.081 (0.48), 2.095 (0.54), 2.108 (0.58), 2.120 (0.84), 2.134 (1.06), 2.158 (1.19), 2.174 (0.97), 2.193 (2.12), 2.327 (0.40), 3.574 (1.44), 4.037 (0.47), 7.473 (1.00), 7.480 (0.76), 7.495 (1.52), 7.502 (1.18), 7.522 (0.67), 7.544 (1.15), 7.554 (0.74), 7.560 (0.97), 7.567 (0.59), 7.576 (0.49), 7.588 (0.93), 7.609 (0.51), 8.756 (0.50).

Example 184A (+/−)-tert-Butyl 5-({[6-bromo-2-(3,3-difluoropiperidin-1-yl)-3-methylquinolin-4-yl]carbonyl}amino)-4-(2,3,6-trichlorophenyl)pentanoate (Racemate)

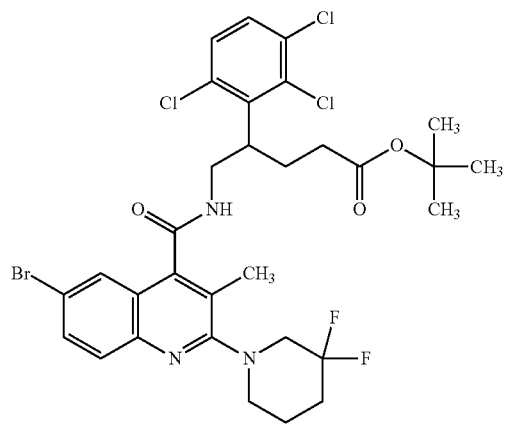 [SMILES: Cc1c(N2CCCC(F)(F)C2)nc2ccc(Br)cc2c1C(=O)NCC(CCC(=O)OC(C)(C)C)c1c(Cl)ccc(Cl)c1Cl]

To a mixture of (+/−)-tert-butyl 5-{[(6-bromo-2-chloro-3-methylquinolin-4-yl)carbonyl]amino}-4-(2,3,6-trichlorophenyl)pentanoate (300 mg, 472 µmol, Example 51A) in NMP (4.0 ml) were added, in a thick-walled glass vessel (microwave vessel), 3,3-difluoropiperidine hydrochloride (372 mg, 2.36 mmol) and DIPEA (410 µl, 2.4 mmol). The vessel was purged with argon, closed and agitated at 130° C. by means of a heated agitator overnight. This was followed by agitation at 140° C. for 24 h. After cooling to RT, the mixture was purified directly (without further workup) by preparative HPLC (Method 14). The combined target fractions were concentrated, and the residue was taken up in dichloromethane, concentrated again and dried under reduced pressure. 241 mg (100% purity, 71% of theory) of the title compound were obtained.

LC-MS (Method 1): $R_t$=2.83 min; MS (ESIpos): m/z=718/720/722 [M+H]$^+$ $^1$H-NMR (400 MHz, DMSO-d6) δ [ppm]: −0.008 (2.55), 0.008 (2.50), 1.331 (0.53), 1.351 (14.99), 1.355 (16.00), 1.883 (0.79), 2.100 (0.98), 2.115 (0.97), 2.128 (1.23), 2.159 (1.91), 2.189 (3.51), 2.328 (0.53), 3.177 (0.91), 3.453 (0.61), 3.483 (1.16), 3.511 (0.61), 4.035 (0.51), 7.476 (0.52), 7.498 (0.75), 7.534 (0.65), 7.556 (1.20), 7.595 (0.89), 7.617 (0.61), 7.704 (1.44), 7.711 (1.65), 7.718 (1.30), 7.724 (0.76), 8.819 (0.53).

Separation of the Enantiomers:

The title compound (172 mg) was separated into the enantiomers by means of preparative SFC on chiral phase (see Examples 185A and 186A) [column: Daicel Chiralpak IG, 5 µm, 250 mm×20 mm; flow rate: 60 ml/min; UV detection: 260 nm, temperature: 25° C.; eluent: 25% isopropanol/75% carbon dioxide; outlet pressure 150 bar, isocratic]. The combined target fractions were each concentrated, and the respective residue was dried under reduced pressure. Peak 2 was reseparated by means of chiral HPLC [column: Daicel Chiralpak IG, 5 µm, 250 mm×20 mm; flow rate: 20 ml/min; UV detection: 260 nm, temperature: 25° C.; eluent: 20% ethyl acetate/80% heptane, isocratic]

Example 185A tert-Butyl 5-({[6-bromo-2-(3,3-difluoropiperidin-1-yl)-3-methylquinolin-4-yl]carbonyl}amino)-4-(2,3,6-trichlorophenyl)pentanoate (Enantiomer 1)

In the enantiomer separation described in Example 184A, 79 mg (100% purity, ee 97%) of the title compound were obtained as the enantiomer that eluted earlier.

$R_t$=7.9 min (chiral analytical HPLC; column: Chiralpak IG, 5 µm, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.49 min; MS (ESIpos): m/z=718/720/722 [M+H]$^+$ $^1$H-NMR (400 MHz, DMSO-d6) δ [ppm]: −0.008 (1.18), 0.008 (1.05), 1.029 (2.87), 1.045 (2.90), 1.236 (1.65), 1.330 (0.53), 1.351 (15.41), 1.355 (16.00), 1.884 (0.77), 2.085 (0.83), 2.100 (0.95), 2.115 (0.96), 2.128 (1.21), 2.159 (1.89), 2.173 (0.76), 2.189 (3.45), 3.176 (0.89), 3.453 (0.59), 3.482 (1.14), 3.511 (0.60), 4.036 (0.49), 7.476 (0.50), 7.498 (0.72), 7.534 (0.62), 7.556 (1.17), 7.595 (0.80), 7.617 (0.56), 7.704 (1.34), 7.711 (1.51), 7.718 (1.22), 7.724 (0.71), 8.805 (0.43), 8.819 (0.52).

Example 186A tert-Butyl 5-({[6-bromo-2-(3,3-difluoropiperidin-1-yl)-3-methylquinolin-4-yl]carbonyl}amino)-4-(2,3,6-trichlorophenyl)pentanoate (Enantiomer 2)

In the enantiomer separation described in Example 184A, 100 mg (100% purity, ee>99%) of the title compound were obtained as the enantiomer that eluted later.

$R_t$=10.1 min (chiral analytical HPLC; column: Chiralpak IG, 5 am, 250 mm×4.6 mm, eluent: heptane/isopropanol/diethylamine 70:30:0.1; flow rate 1 ml/min; temperature 25° C.; detection 225 nm)

LC-MS (Method 2): $R_t$=1.49 min; MS (ESIpos): m/z=718/720/722 [M+H]$^+$ $^1$H-NMR (400 MHz, DMSO-d6) δ [ppm]: −0.008 (1.56), 0.008 (1.36), 0.836 (0.55), 0.854 (1.20), 0.858 (0.83), 0.870 (0.53), 1.237 (6.54), 1.249 (2.69), 1.259 (1.82), 1.298 (1.07), 1.335 (1.81), 1.351 (15.42), 1.355 (16.00), 1.883 (0.75), 2.085 (0.81), 2.100 (0.95), 2.115 (0.92), 2.128 (1.16), 2.159 (1.85), 2.189 (3.47), 2.322 (0.42), 2.327 (0.45), 3.176 (0.87), 3.453 (0.60), 3.482 (1.12), 3.511 (0.57), 4.036 (0.49), 7.476 (0.51), 7.498 (0.72), 7.534 (0.62), 7.556 (1.16), 7.595 (0.80), 7.617 (0.57), 7.704 (1.36), 7.711 (1.52), 7.718 (1.22), 7.724 (0.72), 8.806 (0.41), 8.819 (0.51).

Example 187A tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer Mixture)

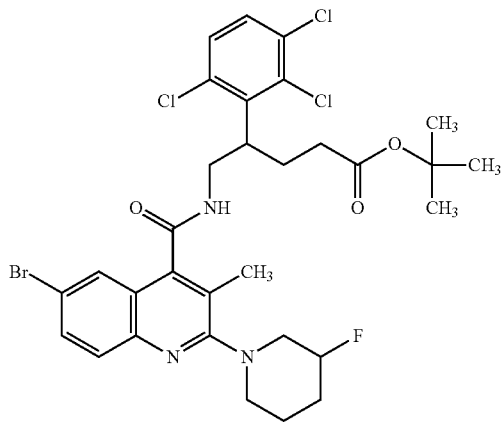 [SMILES: Cc1c(N2CCCC(F)C2)nc2ccc(Br)cc2c1C(=O)NCC(CCC(=O)OC(C)(C)C)c1c(Cl)ccc(Cl)c1Cl]

To a mixture of (+/−)-tert-butyl 5-{[(6-bromo-2-chloro-3-methylquinolin-4-yl)carbonyl]amino}-4-(2,3,6-trichlorophenyl)pentanoate (400 mg, 630 µmol, Example 51A) in NMP (4.0 ml) were added, in a thick-walled glass vessel (microwave vessel), (+/−)-3-fluoropiperidine hydrochloride (440 mg, 3.15 mmol) and DIPEA (550 µl, 3.1 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 355 mg (100% purity, 80% of theory) of the title compound were obtained.

LC-MS (Method 4): $R_t$=1.80 min; ionization without detection of the target mass $^1$H-NMR (400 MHz, DMSO-d6) δ [ppm]: 1.330 (0.83), 1.351 (14.93), 1.354 (16.00), 1.899 (0.53), 2.085 (0.47), 2.099 (0.52), 2.126 (0.99), 2.139 (1.04), 2.155 (2.15), 2.182 (3.06), 2.327 (0.43), 4.036 (0.55), 5.754 (0.98), 7.475 (0.50), 7.496 (0.70), 7.533 (0.63), 7.554 (1.12), 7.593 (0.76), 7.615 (0.53), 7.677 (1.36), 7.683 (1.42), 7.692 (1.25), 8.800 (0.49), 8.814 (0.55).

Example 188A tert-Butyl 5-[({6-bromo-2-[3-ethylpiperidin-1-yl]-3-methylquinolin-4-yl}carbonyl)amino]-4-(2,3,6-trichlorophenyl)pentanoate (Diastereomer Mixture)

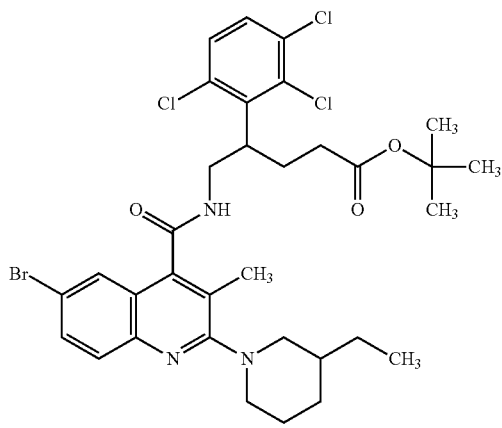 [SMILES: CCC1CCCN(c2nc3ccc(Br)cc3c(C(=O)NCC(CCC(=O)OC(C)(C)C)c3c(Cl)ccc(Cl)c3Cl)c2C)C1]

To a mixture of (+/−)-tert-butyl 5-{[(6-bromo-2-chloro-3-methylquinolin-4-yl)carbonyl]amino}-4-(2,3,6-trichlorophenyl)pentanoate (400 mg, 630 μmol, Example 51A) in NMP (4.0 ml) were added, in a thick-walled glass vessel (microwave vessel), (+/−)-3-ethylpiperidine (356 mg, 3.15 mmol) and DIPEA (550 μl, 3.1 mmol). The vessel was purged with argon, closed and agitated at 130° C. by means of a heated agitator overnight. After cooling to RT, the mixture was purified directly (without further workup) by preparative HPLC (Method 14). The combined target fractions were concentrated, and the residue was taken up in dichloromethane, concentrated again and dried under reduced pressure. 383 mg (100% purity, 85% of theory) of the title compound were obtained.

LC-MS (Method 4): $R_t$=1.80 min; ionization without detection of the target mass $^1$H-NMR (400 MHz, DMSO-d6) δ [ppm]: −0.008 (1.66), 0.008 (1.50), 0.893 (1.23), 0.912 (2.91), 0.930 (1.51), 1.263 (0.60), 1.281 (0.76), 1.303 (0.62), 1.352 (15.56), 1.356 (16.00), 2.086 (0.46), 2.099 (0.52), 2.133 (1.62), 2.158 (2.77), 2.163 (1.99), 3.494 (0.64), 3.525 (0.59), 4.025 (0.41), 4.037 (0.41), 5.754 (1.33), 7.473 (0.59), 7.495 (0.85), 7.527 (0.71), 7.549 (1.21), 7.588 (0.74), 7.596 (0.78), 7.610 (0.51), 7.617 (0.44), 7.656 (1.49), 7.660 (2.02), 7.665 (1.35), 8.790 (0.44).

Example 189A (+/−)-tert-Butyl 5-({[6-bromo-3-methyl-2-(piperidin-1-yl)quinolin-4-yl]carbonyl}amino)-4-[2-(difluoromethoxy)-6-fluorophenyl]pentanoate (Racemate)

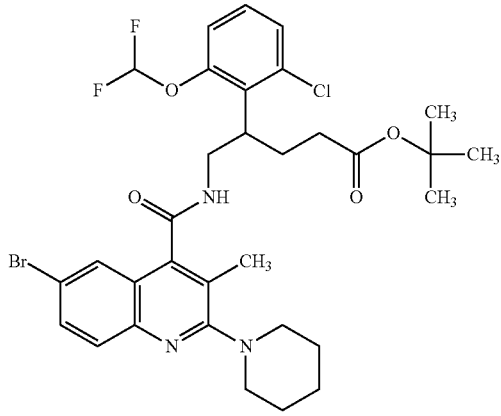 [SMILES: Cc1c(N2CCCCC2)nc2ccc(Br)cc2c1C(=O)NCC(CCC(=O)OC(C)(C)C)c1c(Cl)cccc1OC(F)F]

To a mixture of (+/−)-tert-butyl 5-{[(6-bromo-2-chloro-3-methylquinolin-4-yl)carbonyl]amino}-4-[2-(difluoromethoxy)-6-fluorophenyl]pentanoate (1.00 g, 1.62 mmol, Example 52A) in NMP (5.8 ml) were added piperidine (1.3 ml, 13 mmol) and DIPEA (2.3 ml, 13 mmol), and the mixture was stirred at 110° C. for 5 h. After cooling to RT, dichloromethane (150 ml) was added to the mixture, and it was washed once with water (150 ml) and once with a mixture of 1 M hydrochloric acid (40 ml) in water (100 ml). The organic phase was dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. 933 mg (96% purity, 83% of theory) of the title compound were obtained.

LC-MS (Method 1): $R_t$=2.73 min; MS (ESIpos): m/z=664/666 [M+H]$^+$ $^1$H-NMR (400 MHz, DMSO-d6) δ [ppm]: 0.833 (0.05), 0.850 (0.06), 1.196 (0.08), 1.234 (0.17), 1.289 (0.08), 1.307 (0.33), 1.311 (0.43), 1.356 (16.00), 1.369 (0.64), 1.397 (5.74), 1.512 (0.08), 1.607 (0.50), 1.672 (0.95), 1.881 (0.06), 1.901 (0.09), 1.920 (0.12), 1.937 (0.14), 1.954 (0.18), 2.027 (0.16), 2.042 (0.21), 2.056 (0.20), 2.079 (1.01), 2.093 (0.71), 2.114 (0.39), 2.133 (1.36), 2.175 (0.13), 2.195 (0.07), 2.240 (0.10), 2.294 (0.03), 2.327 (0.03), 2.669 (0.03), 2.694 (0.32), 3.137 (1.23), 3.284 (0.10), 3.516 (0.18), 3.661 (0.08), 3.676 (0.13), 3.693 (0.24), 3.709 (0.30), 3.727 (0.24), 3.746 (0.21), 3.765 (0.17), 3.799 (0.06), 7.019 (0.42), 7.039 (0.45), 7.060 (0.33), 7.089 (0.29), 7.111 (0.42), 7.135 (0.31), 7.244 (0.63), 7.357 (0.17), 7.378 (0.33), 7.395 (0.31), 7.415 (0.15), 7.428 (0.34), 7.485 (0.11), 7.627 (0.32), 7.650 (1.43), 7.659 (0.90), 7.664 (0.80), 7.682 (0.20), 7.686 (0.21), 8.772 (0.23), 8.787 (0.45), 8.801 (0.22).

Separation of the Enantiomers:

The title compound (810 mg) was dissolved in methanol (30 ml) and separated into the enantiomers by means of preparative SFC on chiral phase (see Examples 190A and 191A) [column: Daicel Chiralcel OX-H, 5 μm, 250 mm×30 mm; flow rate: 90 ml/min; injection: 0.3 ml; UV detection: 210 nm, temperature: 40° C.; eluent: 15% methanol/85% carbon dioxide; run time 6 min, isocratic]. The combined target fractions were each concentrated, and the respective residue was lyophilized.

Example 190A (−)-tert-Butyl 5-({[6-bromo-3-methyl-2-(piperidin-1-yl)quinolin-4-yl]carbonyl}amino)-4-[2-(difluoromethoxy)-6-fluorophenyl]pentanoate (Enantiomer 1)

In the enantiomer separation described in Example 189A, 810 mg (96% purity, ee>99%) of the title compound were obtained as the enantiomer that eluted earlier.

$[α]_D^{20}$=−23.0°, 589 nm, c=0.36 g/100 ml, methanol

LC-MS (Method 2): $R_t$=1.47 min; MS (ESIpos): m/z=664/666 [M+H]$^+$ $^1$H-NMR (400 MHz, DMSO-d6) δ [ppm]: 0.889 (5.96), 0.908 (13.53), 0.926 (6.80), 1.034 (0.52), 1.062 (1.29), 1.085 (1.31), 1.114 (0.57), 1.240 (1.11), 1.256 (2.40), 1.274 (3.14), 1.283 (2.64), 1.291 (2.25), 1.301 (1.76), 1.558 (1.43), 1.604 (1.33), 1.635 (1.24), 1.665 (0.54), 1.745 (1.84), 1.779 (1.51), 1.813 (1.49), 1.835 (2.39), 1.854 (2.18), 1.877 (1.62), 2.033 (1.16), 2.048 (3.43), 2.077 (3.31), 2.085 (3.74), 2.093 (4.43), 2.124 (16.00), 2.138 (2.92), 2.162 (0.92), 2.402 (0.93), 2.429 (1.47), 2.701 (0.89), 2.730 (1.56), 2.757 (0.85), 3.484 (2.87), 3.515 (2.61), 3.596 (1.53), 3.661 (1.81), 3.675 (2.56), 7.254 (1.40), 7.271 (3.10), 7.289 (2.16), 7.355 (1.92), 7.374 (3.34), 7.392 (1.74), 7.438 (4.62), 7.458 (4.18), 7.481 (4.49), 7.500 (3.11), 7.624 (1.31), 7.647 (11.41), 7.671 (0.73), 7.675 (0.82), 8.697 (1.73), 8.712 (3.17), 8.726 (1.55), 12.043 (3.31).

Example 191A (+)-tert-Butyl 5-({[6-bromo-3-methyl-2-(piperidin-1-yl)quinolin-4-yl]carbonyl}amino)-4-[2-(difluoromethoxy)-6-fluorophenyl]pentanoate (Enantiomer 2)

In the enantiomer separation described in Example 189A, 159 mg (100% purity, ee 94%) of the title compound were obtained as the enantiomer that eluted later.

[α]$_D^{20}$=+24.9°, 589 nm, c=0.38 g/100 ml, methanol
LC-MS (Method 2): R$_t$=1.47 min; MS (ESIneg): m/z=664/666 [M+H]

$^1$H-NMR (400 MHz, DMSO-d6) δ [ppm]: 1.197 (0.07), 1.290 (0.06), 1.311 (0.12), 1.356 (16.00), 1.513 (0.08), 1.608 (0.51), 1.672 (0.99), 1.955 (0.20), 2.043 (0.23), 2.056 (0.21), 2.079 (1.09), 2.093 (0.76), 2.134 (1.45), 3.138 (1.29), 3.518 (0.20), 3.676 (0.14), 3.694 (0.25), 3.709 (0.31), 3.727 (0.26), 3.747 (0.24), 3.765 (0.19), 7.019 (0.44), 7.040 (0.49), 7.061 (0.33), 7.089 (0.29), 7.112 (0.45), 7.136 (0.33), 7.245 (0.65), 7.358 (0.17), 7.378 (0.34), 7.395 (0.32), 7.416 (0.16), 7.429 (0.36), 7.489 (0.12), 7.628 (0.33), 7.650 (1.42), 7.659 (0.88), 7.664 (0.86), 7.682 (0.19), 7.686 (0.22), 8.772 (0.24), 8.787 (0.47), 8.802 (0.24).

Example 192A (−)-tert-Butyl 5-[({6-bromo-2-[3-fluoropiperidin-1-yl]-3-methylquinolin-4-yl}carbonyl)amino]-4-(2-chlorophenyl)pentanoate (Diastereomer 1)

[For structural formula see Example 116A (diastereomer mixture)]
Separation of the diastereomers/enantiomers from Example 116A:
tert-Butyl 5-[({6-bromo-2-[3-fluoropiperidin-1-yl]-3-methylquinolin-4-yl}carbonyl)amino]-4-(2-chlorophenyl)pentanoate (diastereomer mixture, 2.53 g, Example 116A) was taken up in ethanol (60 ml), filtered, and first subjected to preliminary separation by means of preparative SFC on chiral phase [column: Daicel Chiralpak OX-H, 5 μm, 250 mm×30 mm; flow rate: 125 ml/min; injection: 0.6 ml; temperature 38° C., UV detection 210 nm, eluent: 80% carbon dioxide/20% ethanol; run time 19 min, isocratic]. One mixed fraction (peak 1) and two sufficiently clean fractions (peak 2 and peak 3, see Examples 194A and 195A) were obtained. The mixed fraction (peak 1) was purified by means of preparative SFC [column: Daicel Chiralpak IC, 5 am, 250 mm×20 mm; flow rate: 80 ml/min; injection: 0.35 ml; temperature 40° C., UV detection 210 nm, eluent: 76% carbon dioxide/24% ethanol; run time 10.5 min, isocratic] (see Examples 192A and 193A). The combined target fractions were each concentrated, and each residue was lyophilized.

(−)-tert-Butyl 5-[({6-bromo-2-[3-fluoropiperidin-1-yl]-3-methylquinolin-4-yl}carbonyl)amino]-4-(2-chlorophenyl)pentanoate (Diastereomer 1)

In the diastereomer separation of the mixed fraction described (peak 1, see above), 485 mg (100% purity, ee>99%) of the title compound were obtained as the diastereomer (peak 1-1) that eluted first.

[α]$_D^{20}$=−6.3°, 589 nm, c=0.40 g/100 ml, methanol
LC-MS (Method 1): R$_t$=2.66 min; MS (ESIpos): m/z=632/634 [M+H]$^+$ $^1$H-NMR (400 MHz, DMSO-d6) δ [ppm]: 1.370 (16.00), 1.639 (0.22), 1.795 (0.34), 1.815 (0.41), 1.837 (0.27), 1.898 (0.35), 1.917 (0.31), 1.948 (0.22), 2.027 (0.17), 2.047 (0.24), 2.055 (0.24), 2.075 (1.54), 2.087 (0.82), 2.104 (0.33), 2.110 (0.30), 2.145 (1.93), 3.092 (0.24), 3.160 (0.26), 3.177 (0.25), 3.292 (0.20), 3.341 (0.17), 3.380 (0.23), 3.437 (0.22), 3.589 (0.26), 3.678 (0.51), 4.817 (0.18), 4.937 (0.18), 7.252 (0.21), 7.271 (0.50), 7.289 (0.36), 7.352 (0.30), 7.371 (0.55), 7.389 (0.29), 7.439 (0.71), 7.459 (0.59), 7.482 (0.67), 7.501 (0.56), 7.648 (0.27), 7.670 (1.50), 7.677 (1.05), 7.681 (0.86), 7.699 (0.17), 7.704 (0.18), 8.712 (0.27), 8.727 (0.54), 8.741 (0.26).

Example 193A (−)-tert-Butyl 5-[({6-bromo-2-[3-fluoropiperidin-1-yl]-3-methylquinolin-4-yl}carbonyl)amino]-4-(2-chlorophenyl)pentanoate (Diastereomer 2)

In the diastereomer separation of the mixed fraction described in Example 192A (peak 1, see above), 437 mg (100% purity, ee>99%) of the title compound were obtained as the diastereomer (peak 1-2) that eluted second.

[α]$_D^{20}$=−11.5°, 589 nm, c=0.44 g/100 ml, methanol
LC-MS (Method 1): R$_t$=2.66 min; MS (ESIpos): m/z=632/634 [M+H]$^+$ $^1$H-NMR (400 MHz, DMSO-d6) δ [ppm]: 1.369 (16.00), 1.644 (0.19), 1.802 (0.30), 1.814 (0.35), 1.837 (0.23), 1.900 (0.32), 1.921 (0.26), 1.947 (0.16), 2.046 (0.20), 2.055 (0.21), 2.075 (1.37), 2.087 (0.76), 2.104 (0.30), 2.110 (0.28), 2.144 (1.53), 3.102 (0.22), 3.148 (0.23), 3.164 (0.22), 3.295 (0.18), 3.324 (0.30), 3.377 (0.21), 3.434 (0.19), 3.586 (0.23), 3.676 (0.39), 7.254 (0.19), 7.273 (0.44), 7.292 (0.31), 7.354 (0.27), 7.373 (0.49), 7.391 (0.25), 7.439 (0.64), 7.441 (0.64), 7.459 (0.54), 7.484 (0.60), 7.503 (0.51), 7.648 (0.25), 7.670 (1.41), 7.676 (0.97), 7.681 (0.83), 7.703 (0.17), 8.712 (0.24), 8.726 (0.46), 8.740 (0.23).

Example 194A (+)-tert-Butyl 5-[({6-bromo-2-[3-fluoropiperidin-1-yl]-3-methylquinolin-4-yl}carbonyl)amino]-4-(2-chlorophenyl)pentanoate (Diastereomer 3)

In the diastereomer separation described in Example 192A, 593 mg (100% purity) of the title compound were obtained as the diastereomer (peak 3) that eluted third.

[α]$_D^{20}$=+7.2°, 436 nm, c=0.36 g/100 ml, methanol
LC-MS (Method 1): R$_t$=2.69 min; MS (ESIpos): m/z=632/634 [M+H]$^+$ $^1$H-NMR (400 MHz, DMSO-d6) δ [ppm]: −0.008 (0.40), 0.008 (0.38), 1.369 (16.00), 1.640 (0.16), 1.795 (0.24), 1.813 (0.29), 1.836 (0.19), 1.897 (0.25), 1.918 (0.22), 2.047 (0.17), 2.053 (0.17), 2.074 (1.13), 2.086 (0.61), 2.103 (0.24), 2.109 (0.23), 2.144 (1.45), 2.523 (0.16), 3.092 (0.17), 3.161 (0.19), 3.178 (0.18), 3.380 (0.18), 3.438 (0.16), 3.589 (0.19), 3.677 (0.36), 7.254 (0.17), 7.272 (0.38), 7.289 (0.27), 7.292 (0.27), 7.354 (0.24), 7.372 (0.43), 7.391 (0.22), 7.439 (0.59), 7.441 (0.58), 7.458 (0.50), 7.462 (0.48), 7.480 (0.51), 7.484 (0.52), 7.500 (0.43), 7.503 (0.42), 7.648 (0.26), 7.670 (1.32), 7.677 (0.92), 7.682 (0.81), 7.704 (0.18), 8.712 (0.21), 8.726 (0.42), 8.741 (0.20).

Example 195A (+)-tert-Butyl 5-[({6-bromo-2-[3-fluoropiperidin-1-yl]-3-methylquinolin-4-yl}carbonyl)amino]-4-(2-chlorophenyl)pentanoate (Diastereomer 4)

In the diastereomer separation described in Example 192A, 621 mg (100% purity) of the title compound were obtained as the diastereomer (peak 4) that eluted fourth.

[α]$_D^{20}$=+20.8°, 589 nm, c=0.49 g/100 ml, DMSO
LC-MS (Method 1): R$_t$=2.69 min; MS (ESIpos): m/z=632/634 [M+H]$^+$ $^1$H-NMR (400 MHz, DMSO-d6) δ [ppm]: 1.038 (0.20), 1.056 (0.41), 1.073 (0.21), 1.369 (16.00), 1.644 (0.19), 1.795 (0.28), 1.814 (0.34), 1.837 (0.22), 1.900 (0.32), 1.921 (0.26), 1.948 (0.16), 2.045 (0.19), 2.054 (0.21), 2.075 (1.31), 2.087 (0.75), 2.103 (0.29), 2.109 (0.28), 2.143 (1.52), 3.101 (0.22), 3.147 (0.23), 3.162 (0.33), 3.175 (0.25), 3.376 (0.21), 3.426 (0.26), 3.438 (0.22), 3.456 (0.17), 3.585 (0.22), 3.675 (0.39), 7.255 (0.19), 7.273 (0.43), 7.291 (0.30), 7.354 (0.26), 7.373 (0.48), 7.392 (0.25), 7.441 (0.63), 7.459 (0.52), 7.484 (0.59), 7.501 (0.50), 7.648 (0.26), 7.670 (1.41), 7.676 (0.95), 7.681 (0.82), 7.699 (0.16), 7.703 (0.17), 8.711 (0.24), 8.726 (0.47), 8.740 (0.23).

Example 196A (+)-tert-Butyl 5-[({6-bromo-2-[3-fluoropiperidin-1-yl]-3-methylquinolin-4-yl}carbonyl)amino]-4-[2-(trifluoromethyl)phenyl]pentanoate (Diastereomer 1)

[For structural formula see Example 138A (diastereomer mixture)]
Separation of the diastereomers/enantiomers from Example 138A:
tert-Butyl 5-[({6-bromo-2-[3-fluoropiperidin-1-yl]-3-methylquinolin-4-yl}carbonyl)amino]-4-[2-(trifluoromethyl)phenyl]pentanoate (diastereomer mixture, 364 mg, Example 138A) was taken up in a mixture of methanol and acetonitrile (5 ml) and purified by means of preparative SFC on chiral phase [column: Daicel Chiralpak OX-H, 5 µm, 250 mm×20 mm; flow rate: 80 ml/min; injection: 0.35 ml; temperature 40° C., UV detection 210 nm, eluent: 86% carbon dioxide/14% ethanol; run time 15 min, isocratic]. One mixed fraction (peak 1) and two sufficiently clean fractions (peak 2 and peak 3, see Examples 196A and 197A) were obtained. The combined target fractions were each concentrated, and each residue was lyophilized. The mixed fraction (peak 1) was used directly in the reaction described in Example 191.

(+)-tert-Butyl 5-[({6-bromo-2-[3-fluoropiperidin-1-yl]-3-methylquinolin-4-yl}carbonyl)amino]-4-[2-(trifluoromethyl)phenyl]pentanoate (Diastereomer 1)

In the diastereomer separation described, 72 mg (100% purity, ee>99%) of the title compound were obtained as peak 2.
$[\alpha]_D^{20}$=+10.9°, 589 nm, c=0.34 g/100 ml, methanol
LC-MS (Method 2): $R_t$=1.45 min; MS (ESIpos): m/z=666/668 [M+H]$^+$
$^1$H-NMR (400 MHz, DMSO-d6) δ [ppm]: 1.323 (0.17), 1.347 (16.00), 1.650 (0.21), 1.813 (0.20), 1.875 (0.22), 1.907 (0.50), 1.921 (0.44), 1.953 (0.29), 1.973 (0.18), 1.992 (0.39), 2.005 (0.26), 2.015 (0.49), 2.027 (0.37), 2.035 (0.42), 2.057 (0.32), 2.095 (0.29), 2.108 (0.18), 2.126 (0.24), 2.143 (0.25), 2.180 (1.55), 3.114 (0.24), 3.174 (0.25), 3.190 (0.24), 3.340 (0.48), 3.359 (0.23), 3.395 (0.23), 3.452 (0.21), 3.631 (0.18), 3.646 (0.22), 3.667 (0.23), 3.684 (0.25), 3.700 (0.19), 4.824 (0.17), 4.943 (0.17), 7.462 (0.34), 7.481 (0.58), 7.500 (0.35), 7.661 (0.24), 7.683 (1.73), 7.707 (0.62), 7.722 (1.07), 7.738 (0.99), 7.753 (0.27), 8.768 (0.26), 8.783 (0.53), 8.797 (0.25).

Example 197A (+)-tert-Butyl 5-[({6-bromo-2-[3-fluoropiperidin-1-yl]-3-methylquinolin-4-yl}carbonyl)amino]-4-[2-(trifluoromethyl)phenyl]pentanoate (Diastereomer 2)

In the diastereomer separation described in Example 196A, 72 mg (100% purity, ee>99%) of the title compound were obtained as peak 3.
$[\alpha]_D^{20}$=+16.2°, 589 nm, c=0.37 g/100 ml, methanol
LC-MS (Method 2): $R_t$=1.45 min; MS (ESIpos): m/z=666/668 [M+H]$^+$
$^1$H-NMR (400 MHz, DMSO-d6) δ [ppm]: 1.324 (0.18), 1.347 (16.00), 1.652 (0.22), 1.812 (0.20), 1.830 (0.18), 1.907 (0.53), 1.920 (0.46), 1.944 (0.28), 1.953 (0.30), 1.974 (0.19), 1.992 (0.41), 2.016 (0.56), 2.027 (0.39), 2.034 (0.45), 2.056 (0.33), 2.095 (0.29), 2.108 (0.20), 2.126 (0.25), 2.143 (0.27), 2.179 (1.49), 3.117 (0.25), 3.172 (0.25), 3.187 (0.24), 3.341 (0.50), 3.359 (0.23), 3.394 (0.24), 3.452 (0.22), 3.628 (0.19), 3.644 (0.23), 3.671 (0.18), 3.688 (0.24), 3.704 (0.20), 4.823 (0.18), 4.942 (0.18), 7.463 (0.34), 7.482 (0.56), 7.500 (0.35), 7.660 (0.21), 7.682 (1.69), 7.708 (0.67), 7.722 (0.98), 7.738 (1.19), 7.754 (0.28), 8.766 (0.26), 8.780 (0.52), 8.795 (0.26).

Example 198A (+)-tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer 1)

[For structural formula see Example 139A (diastereomer mixture)]
Separation of the Diastereomers/Enantiomers from Example 139A:
tert-Butyl 5-[({6-bromo-2-[3-ethylpiperidin-1-yl]-3-methylquinolin-4-yl}carbonyl)amino]-4-[2-(trifluoromethyl)phenyl]pentanoate (diastereomer mixture, 548 mg, 677 µmol, Example 139A) was taken up in a mixture of methanol (20 ml) and acetonitrile (20 ml) and separated into the diastereomers by means of preparative SFC on chiral phase [column: Daicel Chiralcel OZ-H, 5 µm, 250 mm×30 mm; flow rate: 100 ml/min; injection: 0.3 ml; temperature 40° C., UV detection 210 nm, eluent: 80% carbon dioxide/20% methanol; run time 9.8 min, isocratic]. Four fractions (peak 1 to peak 4, see Examples 198A and 201A) were obtained. The combined target fractions were each concentrated, and each residue was lyophilized.

(+)-tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer 1)

In the diastereomer separation described, 63 mg (100% purity) of the title compound were obtained as the diastereomer (peak 1) that eluted first.
$[\alpha]_D^{20}$=+19.1°, 436 nm, c=0.32 g/100 ml, methanol
LC-MS (Method 1): $R_t$=3.02 min; MS (ESIpos): m/z=676/678 [M+H]$^+$
$^1$H-NMR (400 MHz, DMSO-d6) δ [ppm]: 0.895 (0.93), 0.914 (2.23), 0.932 (1.13), 1.070 (0.18), 1.101 (0.20), 1.264 (0.37), 1.281 (0.50), 1.299 (0.36), 1.321 (0.27), 1.347 (16.00), 1.570 (0.23), 1.608 (0.22), 1.639 (0.18), 1.754 (0.27), 1.786 (0.18), 1.884 (0.36), 1.991 (0.29), 2.014 (0.51), 2.031 (0.44), 2.053 (0.32), 2.094 (0.28), 2.140 (1.02), 2.431 (0.21), 2.758 (0.27), 3.514 (0.39), 3.536 (0.35), 3.619 (0.19), 3.637 (0.21), 3.680 (0.17), 3.697 (0.29), 3.713 (0.24), 7.461 (0.35), 7.480 (0.56), 7.498 (0.33), 7.661 (2.27), 7.687 (0.30), 7.706 (0.58), 7.714 (0.73), 7.724 (0.54), 7.735 (1.21), 7.755 (0.27), 8.755 (0.24), 8.770 (0.47), 8.785 (0.24).

Example 199A (−)-tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer 2)

In the diastereomer separation described in Example 198A, 57 mg (100% purity) of the title compound were obtained as the diastereomer (peak 2) that eluted second.

[α]$_D^{20}$=−25.0°, 589 nm, c=0.34 g/100 ml, methanol

LC-MS (Method 1): R$_t$=3.03 min; MS (ESIpos): m/z=676/678 [M+H]$^+$ $^1$H-NMR (400 MHz, DMSO-d6) δ [ppm]: 0.895 (0.88), 0.914 (2.18), 0.932 (1.09), 1.073 (0.17), 1.102 (0.18), 1.263 (0.32), 1.281 (0.45), 1.293 (0.39), 1.310 (0.31), 1.346 (16.00), 1.570 (0.20), 1.612 (0.19), 1.643 (0.17), 1.753 (0.24), 1.786 (0.16), 1.853 (0.24), 1.886 (0.33), 1.917 (0.16), 1.993 (0.27), 2.014 (0.51), 2.029 (0.56), 2.050 (0.27), 2.113 (0.18), 2.133 (0.26), 2.168 (1.42), 2.444 (0.23), 2.473 (0.16), 2.753 (0.22), 3.508 (0.36), 3.540 (0.33), 3.621 (0.18), 3.637 (0.21), 3.684 (0.21), 3.699 (0.18), 7.461 (0.27), 7.480 (0.46), 7.499 (0.28), 7.660 (2.23), 7.687 (0.27), 7.707 (0.49), 7.720 (0.80), 7.737 (1.06), 7.754 (0.23), 8.754 (0.23), 8.769 (0.47), 8.784 (0.22).

Example 200A tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer 3)

In the diastereomer separation described in Example 198A, 72 mg (100% purity) of the title compound were obtained as the diastereomer (peak 3) that eluted third.

LC-MS (Method 1): R$_t$=3.02 min; MS (ESIpos): m/z=676/678 [M+H]$^+$ $^1$H-NMR (400 MHz, DMSO-d6) δ [ppm]: 0.895 (0.90), 0.913 (2.13), 0.932 (1.03), 1.071 (0.16), 1.093 (0.17), 1.246 (0.17), 1.263 (0.36), 1.281 (0.46), 1.287 (0.39), 1.298 (0.36), 1.306 (0.38), 1.312 (0.35), 1.322 (0.43), 1.347 (16.00), 1.570 (0.21), 1.596 (0.19), 1.606 (0.19), 1.753 (0.23), 1.850 (0.24), 1.884 (0.32), 1.991 (0.27), 2.014 (0.46), 2.032 (0.37), 2.053 (0.27), 2.094 (0.27), 2.139 (0.86), 2.432 (0.18), 2.755 (0.23), 3.505 (0.34), 3.515 (0.35), 3.535 (0.30), 3.619 (0.18), 3.636 (0.19), 3.697 (0.25), 3.713 (0.21), 7.461 (0.32), 7.479 (0.48), 7.497 (0.28), 7.639 (0.19), 7.661 (2.09), 7.666 (1.01), 7.688 (0.28), 7.706 (0.54), 7.714 (0.66), 7.724 (0.49), 7.735 (1.00), 7.755 (0.22), 8.755 (0.22), 8.770 (0.40), 8.785 (0.19).

Example 201A (+)-tert-Butyl 5-[({6-bromo-2-[3-ethylpiperidin-1-yl]-3-methylquinolin-4-yl}carbonyl)amino]-4-[2-(trifluoromethyl)phenyl]pentanoate (Diastereomer 4)

In the diastereomer separation described in Example 198A, 62 mg (100% purity) of the title compound were obtained as the diastereomer (peak 4) that eluted fourth.

[α]$_D^{20}$=+27.0°, 589 nm, c=0.33 g/100 ml, methanol

LC-MS (Method 2): R$_t$=1.63 min; MS (ESIpos): m/z=676/678 [M+H]$^+$ $^1$H-NMR (400 MHz, DMSO-d6) δ [ppm]: 0.895 (0.96), 0.914 (2.24), 0.932 (1.16), 1.072 (0.21), 1.101 (0.22), 1.246 (0.17), 1.263 (0.37), 1.280 (0.53), 1.292 (0.48), 1.310 (0.38), 1.346 (16.00), 1.569 (0.24), 1.612 (0.23), 1.643 (0.21), 1.753 (0.29), 1.784 (0.20), 1.862 (0.29), 1.884 (0.41), 1.992 (0.32), 2.013 (0.61), 2.028 (0.66), 2.049 (0.32), 2.098 (0.17), 2.112 (0.22), 2.132 (0.29), 2.167 (1.77), 2.415 (0.18), 2.443 (0.29), 2.501 (6.18), 2.754 (0.27), 3.508 (0.44), 3.538 (0.40), 3.619 (0.22), 3.637 (0.25), 3.652 (0.17), 3.666 (0.18), 3.682 (0.27), 3.699 (0.21), 7.461 (0.32), 7.480 (0.54), 7.499 (0.33), 7.659 (2.38), 7.686 (0.30), 7.706 (0.57), 7.720 (0.97), 7.736 (1.22), 7.753 (0.27), 8.754 (0.27), 8.768 (0.55), 8.783 (0.27).

Example 202A (+)-tert-Butyl 5-[({6-bromo-3-methyl-2-[3-methylpiperidin-1-yl]quinolin-4-yl}carbonyl)amino]-4-[2-(trifluoromethyl)phenyl]pentanoate (Diastereomer 1)

[For structural formula see Example 140A (diastereomer mixture)]

Separation of the Diastereomers/Enantiomers from Example 140A:

tert-Butyl 5-[({6-bromo-3-methyl-2-[3-methylpiperidin-1-yl]quinolin-4-yl}carbonyl)amino]-4-[2-(trifluoromethyl)phenyl]pentanoate (diastereomer mixture, 455 mg, Example 140A) was taken up in a mixture (6 ml) of methanol and acetonitrile and purified by means of preparative SFC on chiral phase [column: Daicel Chiralpak OX-H, 5 μm, 250 mm×20 mm; flow rate: 80 ml/min; injection: 0.25 ml; temperature 40° C., UV detection 210 nm, eluent: 89% carbon dioxide/11% ethanol; run time 19 min, isocratic]. One mixed fraction (peak 1) and two sufficiently clean fractions (peak 2 and peak 3, see Examples 202A and 203A) were obtained. The combined target fractions were each concentrated, and each residue was lyophilized. The mixed fraction (peak 1) was used directly in the reaction described in Example 199.

(+)-tert-Butyl 5-[({6-bromo-3-methyl-2-[3-methylpiperidin-1-yl]quinolin-4-yl}carbonyl)amino]-4-[2-(trifluoromethyl)phenyl]pentanoate (Diastereomer 1)

In the diastereomer separation described, 80 mg (100% purity) of the title compound were obtained as peak 2.

[α]$_D^{20}$=+17.0°, 589 nm, c=0.35 g/100 ml, methanol

LC-MS (Method 2): R$_t$=1.59 min; MS (ESIpos): m/z=662/664 [M+H]$^+$ $^1$H-NMR (400 MHz, DMSO-d6) δ [ppm]: 0.927 (1.56), 0.943 (1.58), 1.085 (0.17), 1.116 (0.17), 1.324 (0.18), 1.347 (16.00), 1.662 (0.17), 1.737 (0.30), 1.772 (0.30), 1.798 (0.37), 1.828 (0.23), 1.908 (0.16), 1.990 (0.27), 2.013 (0.47), 2.031 (0.39), 2.052 (0.28), 2.097 (0.16), 2.111 (0.18), 2.130 (0.24), 2.166 (1.28), 2.465 (0.25), 2.723 (0.25), 3.454 (0.25), 3.480 (0.47), 3.510 (0.23), 3.640 (0.19), 3.659 (0.21), 3.677 (0.22), 3.694 (0.17), 7.462 (0.29), 7.481 (0.47), 7.500 (0.29), 7.661 (2.16), 7.688 (0.27), 7.707 (0.48), 7.721 (0.89), 7.737 (0.91), 7.752 (0.24), 8.757 (0.21), 8.772 (0.44), 8.787 (0.21).

Example 203A (+)-tert-Butyl 5-[({6-bromo-3-methyl-2-[3-methylpiperidin-1-yl]quinolin-4-yl}carbonyl)amino]-4-[2-(trifluoromethyl)phenyl]pentanoate (Diastereomer 2)

In the diastereomer separation described in Example 202A, 82 mg (100% purity) of the title compound were obtained as peak 3.

[α]$_D^{20}$=+7.3°, 589 nm, c=0.36 g/100 ml, methanol

LC-MS (Method 2): R$_t$=1.59 min; MS (ESIpos): m/z=662/664 [M+H]$^+$ $^1$H-NMR (400 MHz, DMSO-d6) δ [ppm]: 0.928 (1.80), 0.944 (1.86), 1.087 (0.22), 1.115 (0.23), 1.324 (0.21), 1.347 (16.00), 1.635 (0.20), 1.665 (0.23), 1.738 (0.39), 1.771 (0.38), 1.798 (0.48), 1.829 (0.30), 1.889 (0.20), 1.898 (0.20), 1.909 (0.22), 1.920 (0.21), 1.990 (0.33), 2.013 (0.63), 2.030 (0.55), 2.052 (0.35), 2.099 (0.18), 2.114 (0.23), 2.133 (0.28), 2.174 (1.76), 2.440 (0.22), 2.469 (0.35), 2.694 (0.17), 2.722 (0.30), 2.751 (0.16), 3.455 (0.35), 3.482 (0.62), 3.513 (0.29), 3.619 (0.21), 3.634 (0.24), 3.683 (0.26), 3.698 (0.21), 7.463 (0.34), 7.482 (0.56), 7.501 (0.34), 7.661 (2.34), 7.688 (0.31), 7.707 (0.59), 7.722 (1.10), 7.737 (1.07), 7.752 (0.29), 8.759 (0.29), 8.774 (0.57), 8.788 (0.28).

Example 204A (−)-tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer 1)

[For structural formula see Example 153A (diastereomer mixture)]
Separation of the Diastereomers/Enantiomers from Example 153A:
tert-Butyl 5-[({6-bromo-2-[3-fluoropiperidin-1-yl]-3-methylquinolin-4-yl}carbonyl)amino]-4-[2-(trifluoromethoxy)phenyl]pentanoate (diastereomer mixture, 359 mg, 486 µmol, Example 153A) was separated into the diastereomers by means of preparative HPLC [Method 1: column: Daicel Chiralcel OZ-H, 5 µm, 250 mm×20 mm; flow rate: 20 ml/min; temperature 25° C., eluent: 90% heptane/10% ethanol; UV detection 255 nm, isocratic; Method 2: column: Daicel Chiralcel OZ-H, 5 am, 250 mm×20 mm; flow rate: 20 ml/min; temperature 25° C., eluent: 90% heptane/10% isopropanol, UV detection 255 nm, isocratic]. Four fractions (peak 1 to peak 4, see Examples 204A and 207A) were obtained. The combined target fractions were concentrated in each case (conditions: 25° C., 40 mbar).

(−)-tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer 1)

In the diastereomer separation described, 85 mg (90% purity, ee>98%) of the title compound were obtained as the diastereomer (peak 1) that eluted first.
$[\alpha]_D^{20}=-9.4°$, 436 nm, c=0.38 g/100 ml, methanol
LC-MS (Method 2): $R_t=1.43$ min; MS (ESIpos): m/z=682/684 [M+H]$^+$
$^1$H-NMR (400 MHz, DMSO-d6) δ [ppm]: 1.234 (0.80), 1.258 (0.70), 1.301 (0.94), 1.336 (0.21), 1.360 (16.00), 1.381 (0.64), 1.646 (0.25), 1.808 (0.42), 1.831 (0.39), 1.855 (0.23), 1.903 (0.37), 1.922 (0.32), 1.954 (0.23), 2.036 (0.29), 2.068 (1.52), 2.089 (0.32), 2.156 (1.22), 2.222 (0.27), 3.106 (0.24), 3.168 (0.25), 3.186 (0.25), 3.333 (0.33), 3.352 (0.27), 3.388 (0.45), 3.413 (0.20), 3.445 (0.21), 3.619 (0.28), 3.634 (0.50), 3.650 (0.49), 3.666 (0.27), 4.820 (0.18), 4.940 (0.19), 7.363 (0.48), 7.379 (0.23), 7.386 (0.26), 7.399 (0.90), 7.411 (0.64), 7.417 (0.60), 7.422 (0.70), 7.495 (0.17), 7.547 (0.52), 7.559 (0.48), 7.570 (0.36), 7.656 (0.27), 7.678 (1.54), 7.685 (1.05), 7.689 (0.93), 7.707 (0.21), 8.736 (0.25), 8.751 (0.50), 8.765 (0.25).

Example 205A (−)-tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer 2)

In the diastereomer separation described in Example 204A, 85 mg (100% purity, ee 97%) of the title compound were obtained as the diastereomer (peak 2) that eluted second.
$[\alpha]_D^{20}=-14.3°$, 589 nm, c=0.39 g/100 ml, methanol
LC-MS (Method 2): $R_t=1.42$ min; MS (ESIpos): m/z=682/684 [M+H]$^+$
$^1$H-NMR (400 MHz, DMSO-d6) δ [ppm]: 0.853 (0.18), 1.234 (1.31), 1.249 (0.44), 1.259 (1.44), 1.299 (1.16), 1.326 (0.17), 1.336 (0.40), 1.360 (16.00), 1.381 (0.22), 1.646 (0.21), 1.808 (0.39), 1.831 (0.36), 1.856 (0.20), 1.903 (0.32), 1.924 (0.27), 1.951 (0.18), 2.036 (0.27), 2.067 (1.41), 2.090 (0.29), 2.156 (1.05), 3.109 (0.21), 3.164 (0.22), 3.179 (0.21), 3.337 (0.29), 3.356 (0.26), 3.387 (0.42), 3.412 (0.16), 3.444 (0.19), 3.618 (0.24), 3.635 (0.44), 3.651 (0.38), 3.671 (0.21), 4.938 (0.16), 7.363 (0.45), 7.388 (0.19), 7.400 (0.79), 7.412 (0.61), 7.418 (0.58), 7.424 (0.68), 7.548 (0.45), 7.560 (0.40), 7.571 (0.33), 7.656 (0.24), 7.678 (1.42), 7.684 (1.00), 7.689 (0.87), 7.707 (0.18), 7.711 (0.19), 8.736 (0.22), 8.751 (0.44), 8.765 (0.23).

Example 206A (+)-tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer 3)

In the diastereomer separation described in Example 204A, 79 mg (98% purity, ee>98%) of the title compound were obtained as the diastereomer (peak 3) that eluted third.
$[\alpha]_D^{20}=+14.1°$, 589 nm, c=0.37 g/100 ml, methanol
LC-MS (Method 2): $R_t=1.43$ min; MS (ESIpos): m/z=682/684 [M+H]$^+$
$^1$H-NMR (400 MHz, DMSO-d6) δ [ppm]: 1.360 (16.00), 1.644 (0.23), 1.808 (0.45), 1.830 (0.42), 1.854 (0.24), 1.901 (0.38), 1.922 (0.32), 1.953 (0.23), 2.036 (0.38), 2.067 (1.64), 2.089 (0.34), 2.156 (1.32), 3.100 (0.25), 3.168 (0.28), 3.185 (0.26), 3.332 (0.40), 3.353 (0.30), 3.388 (0.49), 3.413 (0.21), 3.445 (0.23), 3.620 (0.33), 3.634 (0.56), 3.649 (0.52), 3.666 (0.26), 4.820 (0.18), 4.939 (0.19), 7.363 (0.47), 7.386 (0.25), 7.399 (0.89), 7.410 (0.66), 7.417 (0.62), 7.422 (0.72), 7.495 (0.17), 7.547 (0.53), 7.559 (0.45), 7.570 (0.37), 7.656 (0.31), 7.678 (1.54), 7.684 (0.98), 7.688 (0.86), 7.711 (0.16), 8.737 (0.29), 8.751 (0.53), 8.765 (0.25).

Example 207A (+)-tert-Butyl 5-[({6-bromo-2-[3-fluoropiperidin-1-yl]-3-methylquinolin-4-yl}carbonyl)amino]-4-[2-(trifluoromethoxy)phenyl]pentanoate (Diastereomer 4)

In the diastereomer separation described in Example 204A, 79 mg (100% purity, ee>99%) of the title compound were obtained as the diastereomer (peak 4) that eluted fourth.
$[\alpha]_D^{20}=+55.1°$, 436 nm, c=0,081 g/100 ml, methanol
LC-MS (Method 2): $R_t=1.42$ min; MS (ESIpos): m/z=682/684 [M+H]$^+$
$^1$H-NMR (400 MHz, DMSO-d6) δ [ppm]: 1.234 (0.20), 1.258 (0.18), 1.360 (16.00), 1.646 (0.22), 1.789 (0.23), 1.808 (0.43), 1.831 (0.41), 1.855 (0.23), 1.903 (0.36), 1.923 (0.30), 1.953 (0.20), 2.036 (0.30), 2.068 (1.63), 2.090 (0.33), 2.156 (1.21), 3.110 (0.24), 3.169 (0.27), 3.335 (0.42), 3.356 (0.32), 3.387 (0.49), 3.412 (0.20), 3.443 (0.22), 3.618 (0.28), 3.635 (0.50), 3.652 (0.43), 3.670 (0.24), 4.819 (0.17), 4.938 (0.17), 7.363 (0.46), 7.388 (0.20), 7.400 (0.86), 7.412 (0.65), 7.418 (0.63), 7.423 (0.73), 7.435 (0.16), 7.486 (0.17), 7.548

(0.49), 7.560 (0.44), 7.571 (0.36), 7.656 (0.26), 7.678 (1.51), 7.684 (1.05), 7.688 (0.92), 7.711 (0.17), 8.737 (0.26), 8.752 (0.50), 8.766 (0.25).

Example 208A (+)-tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer 1)

[For structural formula see Example 154A (diastereomer mixture)]
Separation of the Diastereomers/Enantiomers from Example 154A:
tert-Butyl 5-[({6-bromo-2-[3-ethylpiperidin-1-yl]-3-methylquinolin-4-yl}carbonyl)amino]-4-[2-(trifluoromethoxy)phenyl]pentanoate (diastereomer mixture, 458 mg, 648 μmol, Example 154A) was taken up in a mixture of methanol (12 ml) and acetonitrile (5 ml) and separated into the diastereomers by means of preparative SFC on chiral phase [column: Daicel Chiralcel OZ-H, 5 μm, 250 mm×20 mm; flow rate: 80 ml/min; injection: 0.3 ml; temperature 40° C., UV detection 210 nm, eluent: 88% carbon dioxide/12% methanol; run time 9.5 min, isocratic]. Four fractions (peak 1 to peak 4, see Examples 208A and 211A) were obtained. The combined target fractions were each concentrated, and each residue was lyophilized.

(+)-tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer 1)

In the diastereomer separation described, 64 mg (99% purity, ee>95%) of the title compound were obtained as the diastereomer (peak 1) that eluted first.
$[\alpha]_D^{20}$=+17.0°, 436 nm, c=0.35 g/100 ml, methanol
LC-MS (Method 1): $R_t$=3.05 min; MS (ESIpos): m/z=692/694 $[M+H]^+$
$^1$H-NMR (400 MHz, DMSO-d6) δ [ppm]: 0.893 (0.87), 0.912 (2.16), 0.930 (1.06), 1.069 (0.16), 1.098 (0.17), 1.260 (0.35), 1.278 (0.46), 1.301 (0.60), 1.315 (0.18), 1.360 (16.00), 1.382 (0.29), 1.565 (0.20), 1.600 (0.18), 1.751 (0.23), 1.784 (0.23), 1.802 (0.23), 1.827 (0.20), 1.854 (0.28), 1.881 (0.19), 2.033 (0.24), 2.065 (1.20), 2.089 (0.38), 2.118 (0.69), 2.422 (0.17), 2.755 (0.23), 3.370 (0.19), 3.388 (0.19), 3.497 (0.33), 3.525 (0.32), 3.609 (0.23), 3.625 (0.27), 3.644 (0.26), 3.661 (0.28), 3.679 (0.23), 7.356 (0.37), 7.383 (0.18), 7.396 (0.70), 7.408 (0.57), 7.414 (0.51), 7.420 (0.62), 7.549 (0.44), 7.555 (0.28), 7.562 (0.37), 7.573 (0.32), 7.635 (0.19), 7.657 (1.45), 7.664 (0.92), 8.725 (0.20), 8.740 (0.38), 8.754 (0.20).

Example 209A (−)-tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer 2)

In the diastereomer separation described in Example 208A, 48 mg (100% purity, ee>95%) of the title compound were obtained as the diastereomer (peak 2) that eluted second.

$[\alpha]_D^{20}$=−25.7°, 589 nm, c=0.34 g/100 ml, methanol
LC-MS (Method 1): $R_t$=3.05 min; MS (ESIpos): m/z=692/694 $[M+H]^+$
$^1$H-NMR (400 MHz, DMSO-d6) δ [ppm]: 0.893 (0.84), 0.912 (2.08), 0.930 (1.04), 1.070 (0.16), 1.101 (0.17), 1.261 (0.31), 1.270 (0.28), 1.279 (0.42), 1.287 (0.37), 1.297 (0.32), 1.325 (0.18), 1.361 (16.00), 1.564 (0.19), 1.607 (0.18), 1.640 (0.17), 1.749 (0.23), 1.784 (0.22), 1.803 (0.23), 1.828 (0.21), 1.854 (0.28), 1.883 (0.20), 2.033 (0.26), 2.047 (0.31), 2.067 (1.23), 2.092 (0.29), 2.144 (1.08), 2.437 (0.20), 2.749 (0.20), 3.370 (0.20), 3.388 (0.20), 3.499 (0.35), 3.530 (0.33), 3.617 (0.27), 3.632 (0.46), 3.647 (0.43), 3.663 (0.22), 7.359 (0.37), 7.385 (0.17), 7.398 (0.72), 7.410 (0.57), 7.416 (0.53), 7.421 (0.65), 7.547 (0.42), 7.560 (0.36), 7.571 (0.30), 7.634 (0.16), 7.657 (1.61), 7.663 (0.91), 8.725 (0.22), 8.739 (0.44), 8.754 (0.22).

Example 210A (−)-tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer 3)

In the diastereomer separation described in Example 208A, 59 mg (98% purity, ee>93%) of the title compound were obtained as the diastereomer (peak 3) that eluted third.
$[\alpha]_D^{20}$=−17.5°, 436 nm, c=0.32 g/100 ml, methanol
LC-MS (Method 1): $R_t$=3.05 min; MS (ESIpos): m/z=692/694 $[M+H]^+$
$^1$H-NMR (400 MHz, DMSO-d6) δ [ppm]: 0.893 (0.89), 0.912 (2.18), 0.930 (1.08), 1.069 (0.17), 1.091 (0.17), 1.261 (0.36), 1.278 (0.48), 1.296 (0.34), 1.315 (0.18), 1.361 (16.00), 1.565 (0.21), 1.601 (0.20), 1.633 (0.16), 1.750 (0.23), 1.784 (0.23), 1.802 (0.24), 1.828 (0.22), 1.853 (0.30), 1.880 (0.20), 2.033 (0.26), 2.065 (1.28), 2.090 (0.38), 2.119 (0.72), 2.422 (0.18), 2.754 (0.24), 3.371 (0.20), 3.388 (0.20), 3.495 (0.35), 3.526 (0.33), 3.610 (0.24), 3.625 (0.29), 3.643 (0.28), 3.662 (0.28), 3.679 (0.24), 7.356 (0.38), 7.396 (0.72), 7.408 (0.57), 7.414 (0.52), 7.420 (0.65), 7.550 (0.45), 7.555 (0.29), 7.562 (0.38), 7.573 (0.33), 7.635 (0.19), 7.657 (1.52), 7.665 (0.91), 8.726 (0.20), 8.740 (0.41), 8.754 (0.20).

Example 211A (+)-tert-Butyl 5-[({6-bromo-2-[3-ethylpiperidin-1-yl]-3-methylquinolin-4-yl}carbonyl)amino]-4-[2-(trifluoromethoxy)phenyl]pentanoate (Diastereomer 4)

In the diastereomer separation described in Example 208A, 65 mg (100% purity, ee>95%) of the title compound were obtained as the diastereomer (peak 4) that eluted fourth.
$[\alpha]_D^{20}$=+26.9°, 589 nm, c=0.34 g/100 ml, methanol
LC-MS (Method 1): $R_t$=3.05 min; MS (ESIpos): m/z=692/694 $[M+H]^+$
$^1$H-NMR (400 MHz, DMSO-d6) δ [ppm]: 0.893 (0.99), 0.912 (2.18), 0.930 (1.09), 1.071 (0.20), 1.092 (0.21), 1.261 (0.41), 1.269 (0.39), 1.279 (0.52), 1.287 (0.46), 1.297 (0.39), 1.305 (0.36), 1.325 (0.40), 1.361 (16.00), 1.565 (0.24), 1.607 (0.22), 1.639 (0.20), 1.749 (0.29), 1.784 (0.27), 1.803 (0.29), 1.828 (0.28), 1.854 (0.36), 1.884 (0.23), 2.033 (0.35), 2.048 (0.45), 2.066 (1.46), 2.092 (0.36), 2.144 (1.32), 2.408 (0.17), 2.436 (0.27), 2.747 (0.25), 3.369 (0.25), 3.387 (0.25), 3.498 (0.46), 3.529 (0.40), 3.618 (0.36), 3.632 (0.57), 3.648 (0.52), 3.663 (0.26), 7.359 (0.46), 7.385 (0.25), 7.398 (0.86), 7.410 (0.67), 7.416 (0.62), 7.421 (0.72), 7.434 (0.20), 7.466

(0.19), 7.547 (0.50), 7.560 (0.42), 7.571 (0.34), 7.633 (0.22), 7.656 (1.87), 8.725 (0.29), 8.740 (0.51), 8.754 (0.24).

Example 212A tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer 1)

[For structural formula see Example 155A (diastereomer mixture)]
Separation of the diastereomers/enantiomers from Example 155A:
tert-Butyl 5-[({6-bromo-2-[3-ethylpiperidin-1-yl]-3-methylquinolin-4-yl}carbonyl)amino]-4-[2-(trifluoromethoxy)phenyl]pentanoate (diastereomer mixture, 539 mg, 781 µmol, Example 155A) was separated into the diastereomers by means of preparative HPLC on chiral phase [column: Daicel Chiralcel AD-H, 5 µm, 250 mm×20 mm; flow rate: 7 ml/min; temperature 25° C., UV detection 240 nm, eluent: 95% heptane/5% isopropanol; isocratic]. Four fractions (peak 1 to peak 4, see Examples 212A and 215A) were obtained. The combined target fractions were each concentrated, and each was repurified one to three times by the same method, then concentrated (rotary evaporator at 40° C.) and dried under reduced pressure.

tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer 1)

In the diastereomer separation described, 55 mg (100% purity) of the title compound were obtained as the diastereomer (peak 1) that eluted first.
LC-MS (Method 1): $R_t$=2.99 min; MS (ESIpos): m/z=678/680 $[M+H]^+$ Example 213A tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer 2)

In the diastereomer separation described in Example 212A, 54 mg (100% purity) of the title compound were obtained as the diastereomer (peak 2) that eluted second.
LC-MS (Method 1): $R_t$=2.99 min; MS (ESIpos): m/z=678/680 $[M+H]^+$ Example 214A tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer 3)

In the diastereomer separation described in Example 212A, 43 mg (100% purity) of the title compound were obtained as the diastereomer (peak 3) that eluted third.
LC-MS (Method 1): $R_t$=2.99 min; MS (ESIpos): m/z=678/680 $[M+H]^+$ Example 215A tert-Butyl 5-[({6-bromo-3-methyl-2-[3-methylpiperidin-1-yl]quinolin-4-yl}carbonyl)amino]-4-[2-(trifluoromethoxy)phenyl]pentanoate (Diastereomer 4)

In the diastereomer separation described in Example 212A, 53 mg (100% purity) of the title compound were obtained as the diastereomer (peak 4) that eluted fourth.
LC-MS (Method 1): $R_t$=2.99 min; MS (ESIpos): m/z=678/680 $[M+H]^+$ Example 216A (+)-tert-Butyl 5-({[6-bromo-2-(3,3-difluoropiperidin-1-yl)-3-methylquinolin-4-yl]carbonyl}amino)-4-(2-chloro-3,6-difluorophenyl)pentanoate (Enantiomer 1)

[For structural formula see Example 162A (racemate)]
Separation of the Enantiomers from Example 162A:
(+/−)-tert-Butyl 5-({[6-bromo-2-(3,3-difluoropiperidin-1-yl)-3-methylquinolin-4-yl]carbonyl}amino)-4-(2-chloro-3,6-difluorophenyl)pentanoate (racemate, 185 mg, 269 µmol, Example 162A) was separated into the enantiomers by means of preparative SFC on chiral phase [column: Daicel Chiralpak AD-H, 5 µm, 250 mm×30 mm; flow rate: 120 ml/min; temperature 25° C., UV detection 230 nm, eluent: 85% heptane/15% isopropanol; isocratic]. The combined target fractions were each concentrated at 30° C./30 mbar.

(+)-tert-Butyl 5-({[6-bromo-2-(3,3-difluoropiperidin-1-yl)-3-methylquinolin-4-yl]carbonyl}amino)-4-(2-chloro-3,6-difluorophenyl)pentanoate (Enantiomer 1)

In the enantiomer separation described, 85 mg (98% purity, ee>99%) of the title compound were obtained as the enantiomer that eluted earlier.
$[\alpha]_D^{20}$=+32.2°, 589 nm, c=0.32 g/100 ml, methanol
LC-MS (Method 2): $R_t$=1.40 min; MS (ESIpos): m/z=686/688 $[M+H]^+$
$^1$H-NMR (400 MHz, DMSO-d6) δ [ppm]: 1.235 (0.22), 1.311 (0.16), 1.362 (16.00), 1.884 (0.53), 2.066 (0.38), 2.083 (0.51), 2.099 (0.52), 2.115 (0.43), 2.137 (0.79), 2.165 (2.62), 3.172 (0.64), 3.451 (0.40), 3.480 (0.76), 3.509 (0.38), 3.699 (0.23), 3.774 (0.26), 7.295 (0.27), 7.306 (0.28), 7.321 (0.21), 7.332 (0.19), 7.390 (0.16), 7.402 (0.20), 7.412 (0.27), 7.423 (0.26), 7.682 (0.31), 7.704 (1.50), 7.712 (0.98), 7.717 (0.88), 7.735 (0.19), 7.739 (0.20), 8.815 (0.22), 8.830 (0.41), 8.844 (0.21).

Example 217A (−)-tert-Butyl 5-({[6-bromo-2-(3,3-difluoropiperidin-1-yl)-3-methylquinolin-4-yl]carbonyl}amino)-4-(2-chloro-3,6-difluorophenyl)pentanoate (Enantiomer 2)

In the enantiomer separation described in Example 216A, 85 mg (100% purity, ee>98%) of the title compound were obtained as the enantiomer that eluted later.

[α]$_D^{20}$=−28.0°, 589 nm, c=0.38 g/100 ml, methanol
LC-MS (Method 2): R$_t$=1.40 min; MS (ESIpos): m/z=686/688 [M+H]$^+$
$^1$H-NMR (400 MHz, DMSO-d6) δ [ppm]: 1.235 (0.31), 1.361 (16.00), 1.884 (0.70), 1.975 (0.18), 2.082 (0.68), 2.098 (0.69), 2.115 (0.58), 2.137 (1.03), 2.164 (3.20), 3.172 (0.85), 3.451 (0.49), 3.480 (0.92), 3.508 (0.47), 3.699 (0.31), 3.773 (0.36), 7.271 (0.16), 7.282 (0.19), 7.295 (0.34), 7.305 (0.35), 7.320 (0.26), 7.331 (0.23), 7.391 (0.21), 7.412 (0.34), 7.422 (0.33), 7.444 (0.17), 7.681 (0.34), 7.704 (1.55), 7.712 (1.11), 7.716 (0.97), 7.735 (0.21), 7.739 (0.22), 8.829 (0.52).

Example 218A tert-Butyl 5-({[2-(azepan-1-yl)-6-bromo-3-methylquinolin-4-yl]carbonyl}amino)-4-(2-chloro-3,6-difluorophenyl)pentanoate (Enantiomer 1)

[For structural formula see Example 166A (racemate)]
Separation of the Enantiomers from Example 166A:
(+/−)-tert-Butyl 5-({[2-(azepan-1-yl)-6-bromo-3-methylquinolin-4-yl]carbonyl}amino)-4-(2-chloro-3,6-difluorophenyl)pentanoate (racemate, 489 mg, 735 μmol, Example 166A) was separated into the enantiomers by means of preparative SFC on chiral phase [column: Daicel Chiralpak AD-H, 5 μm, 250 mm×20 mm; flow rate: 80 ml/min; injection: 0.3 ml; temperature 40° C., UV detection 210 nm, eluent: 85% heptane/15% isopropanol; run time 13 min, isocratic]. The combined target fractions were each concentrated, and the respective residue was lyophilized from acetonitrile/water.

tert-Butyl 5-({[2-(azepan-1-yl)-6-bromo-3-methylquinolin-4-yl]carbonyl}amino)-4-(2-chloro-3,6-difluorophenyl)pentanoate (Enantiomer 1)

In the enantiomer separation described, 39 mg (93% purity, ee>99%) of the title compound were obtained as the enantiomer that eluted earlier.
LC-MS (Method 2): R$_t$=1.50 min; MS (ESIpos): m/z=664/666 [M+H]$^+$
$^1$H-NMR (400 MHz, DMSO-d6) δ [ppm]: 1.360 (16.00), 1.371 (1.06), 1.603 (1.40), 1.780 (0.84), 2.080 (0.23), 2.133 (1.95), 2.150 (0.79), 3.492 (1.08), 3.506 (1.58), 3.521 (1.04), 3.706 (0.25), 7.278 (0.16), 7.290 (0.27), 7.302 (0.27), 7.316 (0.21), 7.327 (0.19), 7.408 (0.31), 7.420 (0.29), 7.532 (0.64), 7.554 (1.12), 7.602 (0.66), 7.607 (0.60), 7.624 (0.35), 7.629 (0.34), 8.788 (0.31).

Example 219A tert-Butyl 5-({[2-(azepan-1-yl)-6-bromo-3-methylquinolin-4-yl]carbonyl}amino)-4-(2-chloro-3,6-difluorophenyl)pentanoate (Enantiomer 2)

In the enantiomer separation described in Example 218A, 32 mg (93% purity, ee 89%) of the title compound were obtained as the enantiomer that eluted later.
LC-MS (Method 2): R$_t$=1.50 min; MS (ESIpos): m/z=664/666 [M+H]$^+$
$^1$H-NMR (400 MHz, DMSO-d6) δ [ppm]: 1.309 (0.17), 1.361 (16.00), 1.603 (1.35), 1.780 (0.81), 2.066 (0.24), 2.082 (0.22), 2.103 (0.22), 2.134 (1.94), 2.151 (0.80), 3.492 (1.06), 3.507 (1.53), 3.521 (1.01), 3.711 (0.25), 7.278 (0.16), 7.290 (0.27), 7.301 (0.27), 7.316 (0.22), 7.327 (0.19), 7.386 (0.20), 7.398 (0.24), 7.408 (0.31), 7.419 (0.29), 7.532 (0.60), 7.555 (1.06), 7.602 (0.61), 7.607 (0.55), 7.624 (0.34), 7.630 (0.32), 8.775 (0.18), 8.789 (0.32).

Example 220A tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer 1)

[For structural formula see Example 187A (diastereomer mixture)]
Separation of the Diastereomers/Enantiomers from Example 187A:
tert-Butyl 5-[({6-bromo-2-[3-fluoropiperidin-1-yl]-3-methylquinolin-4-yl}carbonyl)amino]-4-(2,3,6-trichlorophenyl)pentanoate (diastereomer mixture, 294 mg, 419 μmol, Example 187A) was separated into the diastereomers by means of preparative HPLC using three different separation methods on chiral phase [Method 1: column: Daicel Chiralpak AD-H, 5 μm, 250 mm×20 mm; flow rate: 14 ml/min; temperature 25° C., UV detection 240 nm, eluent: 90% heptane/10% isopropanol; isocratic; Method 2: column: Daicel Chiralpak AD-H, 5 μm, 250 mm×20 mm; flow rate: 9 ml/min; temperature 25° C., UV detection 240 nm, eluent: 100% ethanol; Method 3: column: Daicel Chiralcel OD-H, 5 μm, 250 mm×20 mm; flow rate: 9 ml/min; temperature 25° C., UV detection 240 nm, eluent: 90% heptane/10% isopropanol; isocratic]. Four fractions (see Examples 219A and 222A) were obtained, and the sequence of the peaks was in some cases dependent on the preparative separation method used. The sequence of Examples 219A-222A correlates with the elution sequence of peaks 1-4 in the following analytical HPLC method: column: Daicel Chiralpak OD-H, 5 μm, 250 mm×4.6 mm; flow rate: 0.3 ml/min; temperature 25° C., UV detection 240 nm, eluent: 90% heptane/10% isopropanol; isocratic. The combined target fractions were each concentrated (rotary evaporator at 40° C.) and then dried under reduced pressure.

tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer 1)

In the diastereomer separation described, 14 mg (100% purity) of the title compound were obtained (peak 1 in the analytical HPLC, see above).
LC-MS (Method 1): R$_t$=2.83 min; MS (ESIpos): m/z=700/702/704 [M+H]$^+$ Example 221A tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer 2)

In the diastereomer separation described in Example 220A, 17 mg (100% purity) of the title compound were obtained (peak 2 in the analytical HPLC, see Example 220A).
LC-MS (Method 1): R$_t$=2.84 min; MS (ESIpos): m/z=700/702/704 [M+H]$^+$ Example 222A tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer 3)

In the diastereomer separation described in Example 220A, 32 mg (100% purity) of the title compound were obtained (peak 3 in the analytical HPLC, see Example 220A).

LC-MS (Method 1): $R_t$=2.83 min; MS (ESIpos): m/z=700/702/704 [M+H]$^+$

Example 223A tert-Butyl 5-[({6-bromo-2-[3-fluoropiperidin-1-yl]-3-methylquinolin-4-yl}carbonyl)amino]-4-(2,3,6-trichlorophenyl)pentanoate (Diastereomer 4)

In the diastereomer separation described in Example 220A, 27 mg (94% purity) of the title compound were obtained (peak 4 in the analytical HPLC, see Example 220A).

LC-MS (Method 1): $R_t$=2.83 min; MS (ESIpos): m/z=700/702/704 [M+H]$^+$

Example 224A (+/−)-tert-Butyl 4-cyano-4-(2,5-difluorophenyl)butanoate (Racemate)

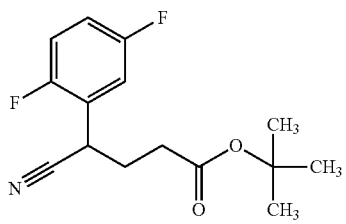 [SMILES: CC(C)(C)OC(=O)CCC(C#N)c1cc(F)ccc1F]

Under an argon atmosphere, an LDA solution was prepared by gradually adding an n-butyllithium solution (1.6 M in hexane, 44 ml, 70 mmol) to an initial charge of diisopropylamine (10 ml, 74 mmol) in THF (44 ml) at −78° C. After the addition had ended, the solution was stirred at 0° C. for a further 10 min. This LDA solution was slowly added dropwise to a solution, cooled to −78° C., of (2,5-difluorophenyl)acetonitrile (8.1 ml, 98% purity, 64 mmol) in THF (120 ml). On completion of addition, the cooling bath was removed, the reaction mixture was allowed to come to 0° C. and, after 15 min, was cooled again to −78° C. Then a solution of tert-butyl 3-bromopropanoate (13 ml, 97% purity, 77 mmol) in 44 ml of THF was added dropwise and the mixture was stirred at −78° C. for a further 1 h, then allowed to warm up to RT and stirred at RT overnight. For workup, ammonium chloride solution (300 ml, 10% in water) was added. The mixture was stirred vigorously for 5 minutes and then extracted twice with ethyl acetate. The combined organic phases were successively washed twice each with 1 M hydrochloric acid, a saturated sodium bicarbonate solution and a saturated sodium chloride solution. The organic phase was then dried over sodium sulfate and concentrated on a rotary evaporator. The residue was dissolved in a little DMSO and purified in 4 portions by means of preparative HPLC (Method 29). The product-containing fractions were combined and concentrated on a rotary evaporator. 8.05 g (100% purity, 45% of theory) of the title compound were obtained.

LC-MS (Method 1): $R_t$=2.11 min; MS (ESIpos): m/z=282 [M+H]$^+$ $^1$H-NMR (400 MHz, DMSO-d6) δ [ppm]: 1.381 (16.00), 2.313 (0.86), 2.332 (1.28), 2.350 (0.44), 4.414 (0.63), 7.353 (0.40), 7.366 (0.62), 7.374 (0.51), 7.377 (0.49).

Example 225A (+/−)-tert-Butyl 5-amino-4-(2,5-difluorophenyl)pentanoate (Racemate)

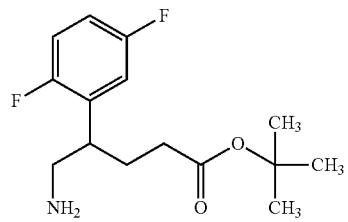 [SMILES: CC(C)(C)OC(=O)CCC(CN)c1cc(F)ccc1F]

To an initial charge of the (+/−)-tert-butyl 4-cyano-4-(2,5-difluorophenyl)butanoate (racemate, 8.05 g, 100% purity, 28.6 mmol) obtained in Example 224A in tert-butanol (210 ml, 2.2 mol) and methanol (9.3 ml) was added Raney nickel (1.68 g, 28.6 mmol). The reaction mixture was stirred under standard hydrogen pressure for 9 days. In spite of incomplete conversion, the reaction was stopped. The catalyst was filtered off through kieselguhr and washed three times with methanol (30 ml each time). The filtrate was concentrated by rotary evaporation and the residue was taken up in ethyl acetate (200 ml). The organic phase was extracted twice with 1 M hydrochloric acid (200 ml each time). The combined aqueous phases were brought to pH 8 by gradual addition of sodium bicarbonate and then extracted twice with dichloromethane (200 ml each time). The combined organic phases were dried over sodium sulfate, filtered and concentrated. 3.84 g (100% purity, 47% of theory) of the title compound were obtained.

LC-MS (Method 1): $R_t$=1.12 min; MS (ESIpos): m/z=286 [M+H]$^+$ $^1$H-NMR (400 MHz, DMSO-d$_6$): δ [ppm]=7.29-7.04 (m, 3H), 2.92-2.84 (m, 1H), 2.79-2.67 (m, 2H), 2.05-1.91 (m, 3H), 1.74-1.61 (m, 1H), 1.35 (s, 9H).

$^1$H-NMR (400 MHz, DMSO-d6) δ [ppm]: 1.111 (0.42), 1.354 (16.00), 2.012 (1.26), 2.025 (0.85), 2.728 (0.47), 2.736 (0.51), 2.747 (0.69), 2.751 (0.69).

Example 226A (+/−)-tert-Butyl 5-{[(6-bromo-2-chloro-3-methylquinolin-4-yl)carbonyl]amino}-4-(2,5-difluorophenyl)pentanoate (Racemate)

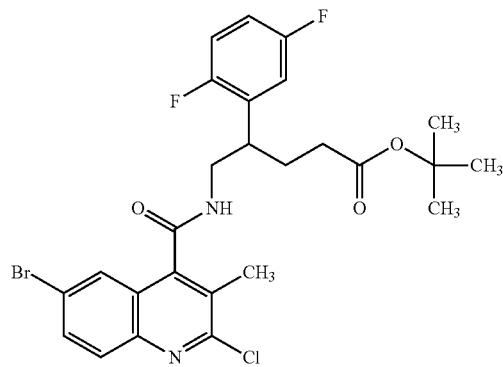 [SMILES: Cc1c(Cl)nc2ccc(Br)cc2c1C(=O)NCC(CCC(=O)OC(C)(C)C)c1cc(F)ccc1F]

To an initial charge of the (+/−)-tert-butyl 5-amino-4-(2,5-difluorophenyl)pentanoate (racemate, 3.00 g, 10.5 mmol) in dichloromethane (80 ml) obtained in Example 225A were added, at RT, DIPEA (4.6 ml, 26 mmol), then a solution of 6-bromo-2-chloro-3-methylquinoline-4-carbonyl chloride (2.79 g, 8.76 mmol, Example 3A) in dichloromethane (20 ml). The reaction mixture was stirred for two hours, then diluted with dichloromethane (100 ml), and washed twice with 1 M hydrochloric acid, then twice with a saturated sodium bicarbonate solution. The organic phase was dried over sodium sulfate, filtered and concentrated. The residue was dried under reduced pressure. 4.92 g (99% purity, 98% of theory) of the title compound were obtained.

LC-MS (Method 1): $R_t$=2.48 min; MS (ESIneg): m/z=565/567 [M−H]⁻

$^1$H-NMR (400 MHz, DMSO-d$_6$): δ [ppm]=8.89 (t, 1H), 7.94-7.86 (m, 2H), 7.82-7.40 (br. m, 1H), 7.34-7.29 (m, 1H), 7.24 (td, 1H), 7.19-7.07 (m, 1H), 3.81-3.62 (m, 2H), 3.41-3.34 (m, 1H), 2.30-2.15 (m, 3H), 2.14-2.06 (m, 2H), 2.05-1.98 (m, 1H), 1.88-1.73 (m, 1H), 1.37 (s, 9H).

Example 227A tert-Butyl 5-[({6-bromo-2-[3-ethylpiperidin-1-yl]-3-methylquinolin-4-yl}carbonyl)amino]-4-(2,5-difluorophenyl)pentanoate (Diastereomer Mixture)

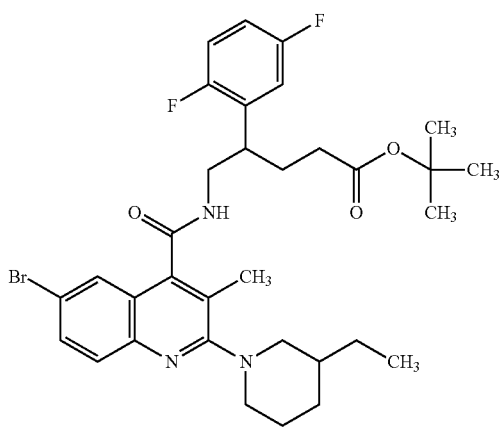 [SMILES: CCC1CCCN(c2nc3ccc(Br)cc3c(C(=O)NCC(CCC(=O)OC(C)(C)C)c3cc(F)ccc3F)c2C)C1]

To an initial charge of tert-butyl 5-{[(6-bromo-2-chloro-3-methylquinolin-4-yl)carbonyl]amino}-4-(2,5-difluorophenyl)pentanoate (400 mg, 704 µmol, Example 226A) in NMP (4.5 ml) in a thick-walled microwave vessel were successively added 3-ethylpiperidine (399 mg, 3.52 mmol) and DIPEA (610 µl, 3.5 mmol). The vessel was closed and agitated at 130° C. overnight. The reaction solution was allowed to cool to RT and purified directly (without further workup) by means of preparative HPLC (Method 14). The product-containing fractions were concentrated and dried under reduced pressure. The residue obtained was dissolved in a little dichloromethane and foamed under reduced pressure. 375 mg (100% purity, 83% of theory) of the title compound were obtained.

LC-MS (Method 1): $R_t$=2.90 min; MS (ESIpos): m/z=644/646 [M+H]⁺

$^1$H-NMR (400 MHz, DMSO-d$_6$): δ [ppm]=8.73 (br t, 1H), 7.70-7.60 (m, 2H), 7.44 (br s, 1H), 7.33-7.27 (m, 1H), 7.26-7.19 (m, 1H), 7.16-7.09 (m, 1H), 3.74-3.59 (m, 2H), 3.55-3.42 (m, 2H), 3.40-3.34 (m, 1H), 2.80-2.69 (m, 1H), 2.48-2.37 (m, 1H), 2.16-1.98 (m, 6H), 1.91-1.72 (m, 3H), 1.68-1.51 (m, 2H), 1.37 (s, 9H), 1.34-1.21 (m, 2H), 1.13-1.02 (m, 1H), 0.91 (t, 3H).

Separation of the Diastereomers/Enantiomers:

The title compound (316 mg, 490 µmol) was dissolved in methanol (12 ml) and an attempt was made to separate it into the diastereomers by means of preparative SFC on chiral phase [column: Daicel Chiralcel OX-H, 5 µm, 250 mm×20 mm; injection: 0.30 ml; eluent: 82% carbon dioxide/18% methanol; flow rate: 80 ml/min; temperature 40° C., UV detection 210 nm, run time 6.1 min, isocratic]. Three fractions were obtained (peaks 1-3), of which peak 1 was obtained as a mixture of two diastereomer/enantiomers (see Example 228A) and peak 2 and peak 3 were each obtained as a separate diastereomers (see Examples 229A and 230A). The combined target fractions were each concentrated, and each residue was lyophilized.

Example 228A tert-Butyl 5-[({6-bromo-2-[3-ethylpiperidin-1-yl]-3-methylquinolin-4-yl}carbonyl)amino]-4-(2,5-difluorophenyl)pentanoate (Mixture of Two Diastereomers)

In the diastereomer separation described in Example 227A, 125 mg (100% purity) of the title compound were obtained as fraction 1 (mixture of two diastereomers).

LC-MS (Method 1): $R_t$=2.92 min; MS (ESIpos): m/z=644/646 [M+H]⁺

$^1$H-NMR (500 MHz, DMSO-d6) δ [ppm]: 0.893 (0.86), 0.908 (1.93), 0.923 (0.96), 1.084 (0.16), 1.090 (0.16), 1.244 (0.19), 1.258 (0.30), 1.272 (0.40), 1.281 (0.30), 1.286 (0.31), 1.294 (0.24), 1.372 (16.00), 1.560 (0.17), 1.748 (0.23), 1.754 (0.20), 1.774 (0.26), 1.799 (0.17), 1.848 (0.19), 1.873 (0.18), 2.010 (0.19), 2.025 (0.20), 2.085 (0.63), 2.099 (1.07), 2.104 (0.83), 2.113 (1.02), 2.741 (0.18), 3.340 (1.17), 3.358 (0.24), 3.360 (0.22), 3.494 (0.35), 3.512 (0.29), 3.642 (0.21), 3.651 (0.22), 7.122 (0.24), 7.203 (0.20), 7.212 (0.21), 7.222 (0.33), 7.231 (0.32), 7.240 (0.17), 7.289 (0.20), 7.296 (0.27), 7.304 (0.20), 7.632 (0.23), 7.649 (1.27), 7.655 (0.79), 7.658 (0.68), 8.725 (0.21), 8.736 (0.36), 8.747 (0.20).

Example 229A tert-Butyl 5-[({6-bromo-2-[3-ethylpiperidin-1-yl]-3-methylquinolin-4-yl}carbonyl)amino]-4-(2,5-difluorophenyl)pentanoate (Diastereomer 1)

In the diastereomer separation described in Example 227A, 43 mg (100% purity) of the title compound were obtained as peak 2.

LC-MS (Method 1): $R_t$=2.92 min; MS (ESIpos): m/z=644/646 [M+H]⁺

$^1$H-NMR (500 MHz, DMSO-d6) δ [ppm]: 0.894 (0.95), 0.909 (2.24), 0.924 (1.09), 1.084 (0.16), 1.090 (0.16), 1.244 (0.20), 1.258 (0.30), 1.272 (0.42), 1.286 (0.35), 1.294 (0.23), 1.372 (16.00), 1.560 (0.18), 1.567 (0.16), 1.748 (0.23), 1.754 (0.20), 1.773 (0.27), 1.786 (0.20), 1.792 (0.16), 1.800 (0.18), 1.806 (0.16), 1.849 (0.19), 1.873 (0.18), 2.010 (0.20), 2.024 (0.21), 2.051 (0.17), 2.085 (0.68), 2.098 (1.17), 2.111 (0.81), 2.743 (0.21), 3.494 (0.35), 3.511 (0.26), 3.631 (0.20), 3.642 (0.27), 3.689 (0.16), 7.122 (0.23), 7.203 (0.19), 7.212 (0.21), 7.221 (0.32), 7.231 (0.31), 7.240 (0.16), 7.277 (0.17), 7.283 (0.21), 7.288 (0.21), 7.295 (0.29), 7.302 (0.21), 7.306

(0.20), 7.313 (0.16), 7.632 (0.26), 7.650 (1.35), 7.655 (0.95), 7.659 (0.81), 7.673 (0.16), 7.677 (0.17), 8.723 (0.23), 8.734 (0.39), 8.746 (0.22).

Example 230A tert-Butyl 5-[({6-bromo-2-[3-ethylpiperidin-1-yl]-3-methylquinolin-4-yl}carbonyl)amino]-4-(2,5-difluorophenyl)pentanoate (Diastereomer 2)

In the diastereomer separation described in Example 227A, 48 mg (100% purity) of the title compound were obtained as peak 3.

LC-MS (Method 1): $R_t$=2.92 min; MS (ESIpos): m/z=644/646 [M+H]$^+$ $^1$H-NMR (500 MHz, DMSO-d6) δ [ppm]: 0.892 (1.06), 0.907 (2.36), 0.922 (1.19), 1.066 (0.21), 1.084 (0.22), 1.245 (0.24), 1.260 (0.41), 1.274 (0.54), 1.287 (0.40), 1.372 (16.00), 1.558 (0.23), 1.580 (0.20), 1.606 (0.21), 1.631 (0.22), 1.748 (0.31), 1.773 (0.34), 1.783 (0.30), 1.797 (0.25), 1.804 (0.22), 1.817 (0.20), 1.848 (0.26), 1.872 (0.25), 1.999 (0.20), 2.010 (0.25), 2.024 (0.25), 2.041 (0.18), 2.050 (0.19), 2.085 (0.75), 2.099 (1.24), 2.114 (1.70), 2.421 (0.19), 2.737 (0.25), 3.490 (0.48), 3.512 (0.43), 3.624 (0.19), 3.639 (0.29), 3.651 (0.40), 3.662 (0.30), 3.682 (0.23), 7.105 (0.16), 7.122 (0.32), 7.138 (0.21), 7.203 (0.24), 7.213 (0.27), 7.222 (0.40), 7.231 (0.39), 7.241 (0.20), 7.250 (0.18), 7.279 (0.22), 7.285 (0.27), 7.290 (0.28), 7.297 (0.37), 7.304 (0.28), 7.315 (0.20), 7.631 (0.27), 7.649 (1.49), 7.653 (1.13), 7.657 (0.93), 7.671 (0.18), 7.675 (0.18), 8.725 (0.30), 8.737 (0.53), 8.748 (0.28).

Example 231A (+/−)-tert-Butyl 4-cyano-4-(2-methylphenyl)butanoate (Racemate)

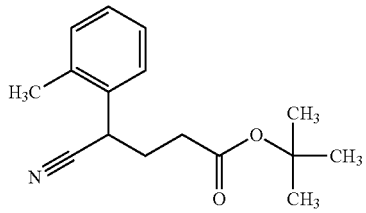

(2-Methylphenyl)acetonitrile (7.08 g, 54.0 mmol) was dissolved in DMF, sodium hydride was added gradually, and the mixture was stirred at RT for a further 10 min. Subsequently, tert-butyl 3-bromopropanoate (9.0 ml, 54 mmol) was slowly added dropwise, in the course of which gentle foaming and heating to about 35° C. occurred. The reaction vessel was cooled in a water bath during the further addition. Then the water bath was removed and stirring was continued at RT for 2.5 h. The reaction mixture was added to water, extracted with dichloromethane, dried (sodium sulfate) and concentrated on a rotary evaporator. The crude product was purified by means of flash column chromatography (Isolera, KP-Sil, eluent: hexane/ethyl acetate, gradient: 1-30%). 8.32 g (74% purity, 44% of theory) of the title compound were obtained.

LC-MS (Method 25): $R_t$=1.39 min; MS (ESIpos): m/z=260 [M+H]$^+$ $^1$H-NMR (400 MHz, CHLOROFORM-d) δ [ppm]: 1.494 (16.00), 2.146 (0.44), 2.148 (0.40), 2.382 (0.77), 2.411 (3.67), 2.491 (0.43), 2.522 (0.58), 3.702 (0.51), 7.241 (0.45), 7.279 (0.68), 7.288 (0.62).

Example 232A (+/−)-tert-Butyl 5-amino-4-(2-methylphenyl)pentanoate (Racemate)

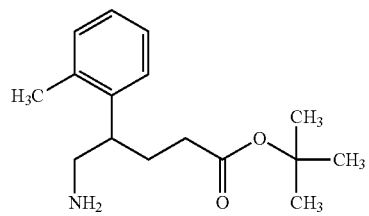 [SMILES: Cc1ccccc1C(CN)CCC(=O)OC(C)(C)C]

To an initial charge of (+/−)-tert-butyl 4-cyano-4-(2-methylphenyl)butanoate (racemate, 8.32 g, 74% purity, 23.8 mmol, Example 231A) in tert-butanol (200 ml) was added Raney nickel (1.88 g, 32.1 mmol). Hydrogenation was effected with hydrogen at standard pressure for 6 h. Subsequently, Raney nickel (1.88 g, 32.1 mmol) was added again, and hydrogenation was effected for a further 8 h. Thereafter, the same amount of catalyst was added again and hydrogenation was effected for a further 5 h. The reaction mixture was filtered through kieselguhr, the filtrate was concentrated on a rotary evaporator and the residue was purified by column chromatography (Isolera, RP18, eluent: water+0.1% by volume of formic acid/acetonitrile, gradient: 5-95% acetonitrile). 5.74 g (98% purity, 90% of theory) of the title compound were obtained.

LC-MS (Method 25): $R_t$=0.71 min; MS (ESIpos): m/z=264 [M+H]$^+$ $^1$H-NMR (400 MHz, CHLOROFORM-d) δ [ppm]: 1.517 (16.00), 2.171 (1.18), 2.178 (0.59), 2.432 (3.54), 3.574 (2.02), 7.250 (0.67), 7.254 (0.75), 7.256 (0.51), 7.400 (1.05), 8.286 (0.70).

Example 233A (+/−)-tert-Butyl 5-{[(6-bromo-2-chloro-3-methylquinolin-4-yl)carbonyl]amino}-4-(2-methylphenyl)pentanoate (Racemate)

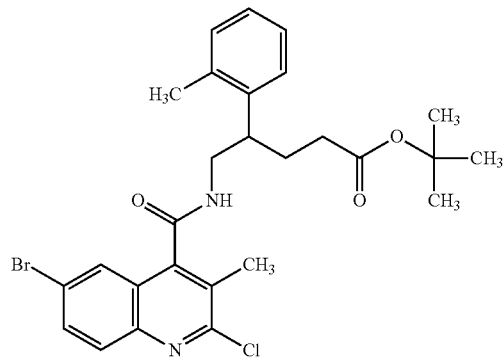 [SMILES: Cc1ccccc1C(CCC(=O)OC(C)(C)C)CNC(=O)c1c(C)c(Cl)nc2ccc(Br)cc12]

(+/−)-tert-Butyl 5-amino-4-(2-methylphenyl)pentanoate (5.74 g, 98% purity, 21.4 mmol, Example 232A) and 6-bromo-2-chloro-3-methylquinoline-4-carbonyl chloride (6.32 g, 19.8 mmol, Example 3A) were dissolved in dichloromethane, aqueous sodium hydrogencarbonate solution (240 ml, 1.0 M, 240 mmol) was added, and the reaction mixture was stirred vigorously at RT for 1.5 h. The reaction mixture was added to water and extracted with dichloromethane, and the organic phase was washed with 1 M hydrochloric acid and saturated aqueous sodium chloride solution, dried over sodium sulfate, filtered and concentrated on a rotary evaporator. The crude product was purified by column chromatography (Isolera, KP-Sil, eluent: hexane/ethyl acetate, gradient: 0-100%). 7.72 g (84% purity, 61% of theory) of the title compound were obtained.

LC-MS (Method 26): $R_t$=1.59 min; MS (ESIpos): m/z=545/547 [M+H]$^+$

Example 234A (+/−)-5-{[(6-Bromo-2-chloro-3-methylquinolin-4-yl)carbonyl]amino}-4-(2-methylphenyl)pentanoic acid (Racemate)

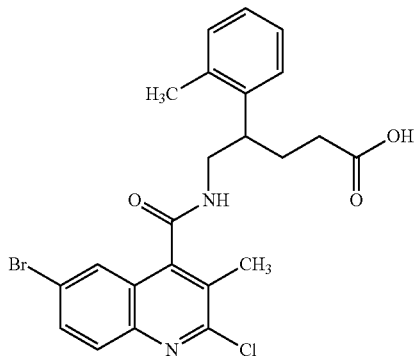 [SMILES: Cc1ccccc1C(CCC(=O)O)CNC(=O)c1c(C)c(Cl)nc2ccc(Br)cc12]

(+/−)-tert-Butyl 5-{[(6-bromo-2-chloro-3-methylquinolin-4-yl)carbonyl]amino}-4-(2-methylphenyl)pentanoate (racemate, 7.72 g, 84% purity, 11.9 mmol, Example 233A) was dissolved in dichloromethane (25 ml). Subsequently, TFA (22 ml, 280 mmol) was added and the mixture was stirred at RT overnight. The reaction mixture was concentrated and the residue was purified by column chromatography (Isolera, LiChroprep RP-18 (40-63 µm), eluent: water+0.1% by volume of ammonia/acetonitrile, gradient: 10-90% acetonitrile). 6.71 g (86% purity, 99% of theory) of the title compound were obtained.

LC-MS (Method 26): $R_t$=0.76 min; MS (ESIneg): m/z=487/489 [M−H]$^-$

Example 235A (+/−)-tert-Butyl 4-cyano-4-(2-methoxyphenyl)butanoate (Racemate)

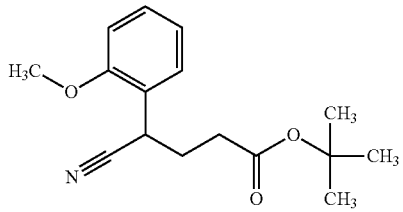 [SMILES: COc1ccccc1C(C#N)CCC(=O)OC(C)(C)C]

Method A:

To a solution of (2-methoxyphenyl)acetonitrile (2.00 g, 13.6 mmol) in THF (17 ml) under argon were added gradually while stirring, at −78° C., a 2 M solution of LDA in THF (10 ml, 20 mmol). The mixture was allowed to come to 0° C. and, after 15 min, cooled back down again to −78° C. Subsequently, tert-butyl 3-bromopropanoate (2.6 ml, 16 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated sodium chloride solution, dried over sodium sulfate, filtered and concentrated, and the residue was prepurified by means of flash column chromatography (100 g silica gel Biotage Snap-Cartridge KP-Sil, cyclohexane/ethyl acetate gradient 93:7→6:4, Isolera One). This was followed by repurification by means of preparative HPLC (Method 12). The combined target fractions were concentrated and the residue was dried under reduced pressure. 495 mg (98% purity, 13% of theory) of the title compound were obtained.

LC-MS (Method 1): $R_t$=2.13 min; MS (ESIpos): m/z=276 [M+H]$^+$

Method B:

(2-Methoxyphenyl)acetonitrile (7.98 g, 54.2 mmol) was dissolved in DMF (200 ml), sodium hydride was added gradually, and the mixture was stirred at RT for 10 min. Subsequently, while cooling (water bath), tert-butyl 3-bromopropanoate (11.3 g, 54.2 mmol) was slowly added dropwise, in the course of which the reaction solution heated up to about 35° C. After stirring at RT for 3 h, the reaction mixture was added to water and extracted with dichloromethane. The organic phase was dried over sodium sulfate, filtered and concentrated, and the residue was purified by means of flash column chromatography (silica gel, gradient: 1-30% ethyl acetate in hexane). 9.79 g (62% purity, 40% of theory) of the title compound were obtained.

LC-MS (Method 25): $R_t$=1.32-1.35 min; MS (ESIpos): m/z=276 [M+H]$^+$

Example 236A (+/−)-tert-Butyl 5-amino-4-(2-methoxyphenyl)pentanoate (Racemate)

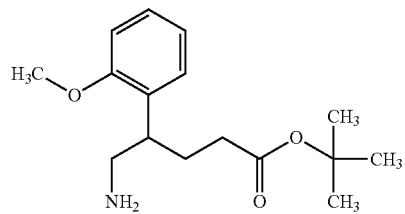 [SMILES: COc1ccccc1C(CN)CCC(=O)OC(C)(C)C]

Method A:

To a solution of (+/−)-tert-butyl 4-cyano-4-(2-methoxyphenyl)butanoate (495 mg, 1.80 mmol, Example 235A, Method A) in tert-butanol (11 ml) was added Raney nickel (106 mg, 1.80 mmol), and hydrogenation was effected at standard pressure overnight. Subsequently, the catalyst was filtered off through kieselguhr and the mother liquor was concentrated. 269 mg (85% purity, 46% of theory) of the title compound were obtained.

LC-MS (Method 2): $R_t$=0.68 min; MS (ESIpos): m/z=280 [M+H]$^+$

Method B: To a solution of (+/−)-tert-butyl 4-cyano-4-(2-methoxyphenyl)butanoate (9.79 g, 62% purity, 22.4 mmol, Example 235A, Method B) in tert-butanol (350 ml) was added Raney nickel (2.09 g, 35.6 mmol), and hydrogenation was effected at standard pressure for 6 h. Subsequently, Raney nickel (2.09 g, 35.6 mmol) was again added to the mixture and hydrogenation was effected for a further 8 h. Addition of Raney nickel (2.09 g, 35.6 mmol) was followed by hydrogenation once again for 5 h. The solids were filtered off through kieselguhr and washed through with ethyl acetate, and the filtrate was concentrated. The crude product was purified by means of flash chromatography (LiChroprep RP-18 40-63 µm; gradient: 5-95% acetonitrile in 0.1% aqueous formic acid). 2.69 g (99% purity, 42% of theory) of the title compound were obtained.

LC-MS (Method 25): $R_t$=0.74 min; MS (ESIpos): m/z=280 $[M+H]^+$

Separation of the Enantiomers:

The title compound (2.69 g, 99% purity, from Method B) was separated into the enantiomers by means of preparative HPLC on chiral phase [column: Cellulose SC 10p 250×50 mm; flow rate: 120 ml/min; eluent: 20% isopropanol/(80% hexane+0.1% diethylamine), isocratic]. The combined target fractions were each concentrated, and the residues were dried under reduced pressure.

Example 237A tert-Butyl 5-amino-4-(2-methoxyphenyl)pentanoate (Enantiomer 1)

In the enantiomer separation described in Example 236A, 1.16 g (45% purity, ee 99%) of the title compound were obtained as the enantiomer that eluted earlier (impurity was obtained in the separation).

LC-MS (Method 25): $R_t$=0.74 min; MS (ESIpos): m/z=280 $[M+H]^+$

Example 238A tert-Butyl 5-amino-4-(2-methoxyphenyl)pentanoate (Enantiomer 2)

In the enantiomer separation described in Example 236A, 1.19 g (33% purity, ee 99%) of the title compound were obtained as the enantiomer that eluted later (impurity was obtained in the separation).

LC-MS (Method 25): $R_t$=0.75 min; MS (ESIpos): m/z=280 $[M+H]^+$

Example 239A tert-Butyl 5-{[(6-bromo-2-chloro-3-methylquinolin-4-yl)carbonyl]amino}-4-(2-methoxyphenyl)pentanoate (Enantiomer 1)

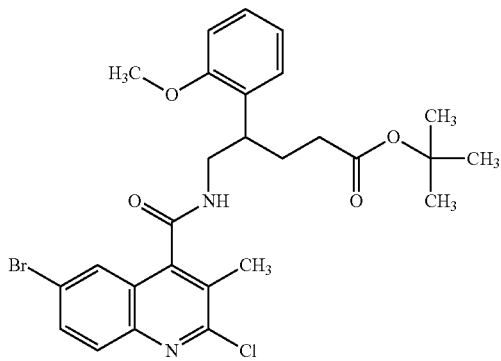 [SMILES: COc1ccccc1C(CCC(=O)OC(C)(C)C)CNC(=O)c1c(C)c(Cl)nc2ccc(Br)cc12]

To a mixture of 6-bromo-2-chloro-3-methylquinoline-4-carbonyl chloride (1.21 g, 3.78 mmol, Example 3A) and tert-butyl 5-amino-4-(2-methoxyphenyl)pentanoate (1.16 g, 45% purity, 1.87 mmol, enantiomer 1, Example 237A) in dichloromethane (25 ml) was added 1 M aqueous sodium hydrogencarbonate solution (25 ml), and the reaction mixture was agitated vigorously at RT for 2 h. The organic phase was removed, dried over sodium sulfate, filtered and concentrated and the residue was purified by means of flash column chromatography (LiChroprep RP-18 40-63 µm; gradient: 50-100% acetonitrile in water). 1.27 g (73% purity, 88% of theory) of the title compound were obtained.

LC-MS (Method 25): $R_t$=1.54 min; MS (ESIpos): m/z=561/563 $[M+H]^+$

Example 240A tert-Butyl 5-{[(6-bromo-2-chloro-3-methylquinolin-4-yl)carbonyl]amino}-4-(2-methoxyphenyl)pentanoate (Enantiomer 2)

To a mixture of 6-bromo-2-chloro-3-methylquinoline-4-carbonyl chloride (1.24 g, 3.90 mmol, Example 3A) and tert-butyl 5-amino-4-(2-methoxyphenyl)pentanoate (1.19 g, 33% purity, 1.41 mmol, enantiomer 2, Example 238A) in dichloromethane (25 ml) was added 1 M aqueous sodium hydrogencarbonate solution (25 ml), and the reaction mixture was agitated vigorously at RT for 2 h. The organic phase was removed, dried over sodium sulfate, filtered and concentrated, and the residue was purified by means of flash column chromatography (LiChroprep RP-18 40-63 am; gradient: 50-100% acetonitrile in water). 693 mg (97% purity, 85% of theory) of the title compound were obtained.

LC-MS (Method 25): $R_t$=1.54 min; MS (ESIpos): m/z=561/563 $[M+H]^+$ $^1$H-NMR (400 MHz, CHLOROFORM-d) δ [ppm]: 1.390 (0.43), 1.428 (16.00), 2.160 (0.41), 2.190 (0.50), 2.280 (1.48), 3.751 (5.16), 6.858 (0.50), 6.878 (0.54), 6.994 (0.51), 7.218 (0.55), 7.237 (0.47), 7.243 (0.46), 7.720 (0.49), 7.725 (0.70), 7.761 (1.42), 7.783 (0.51).

Example 241A

5-{[(6-Bromo-2-chloro-3-methylquinolin-4-yl)carbonyl]amino}-4-(2-methoxyphenyl)pentanoic acid (Enantiomer 1)

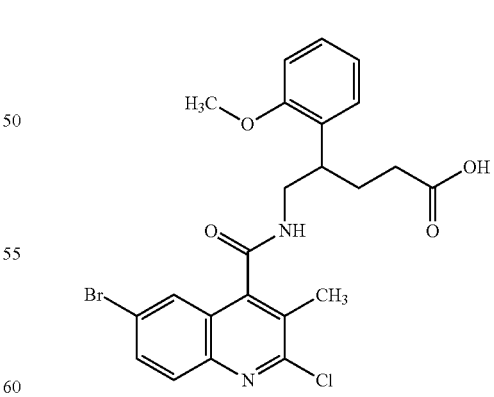

To a solution of tert-butyl 5-{[(6-bromo-2-chloro-3-methylquinolin-4-yl)carbonyl]amino}-4-(2-methoxyphenyl)pentanoate (1.27 g, 73% purity, 1.65 mmol, enantiomer 1, Example 239A) in dichloromethane (15 ml) was added TFA (3.5 ml), and the mixture was stirred at RT overnight. Subsequently, the reaction mixture was concentrated, and the residue was purified by means of flash column chromatography (LiChroprep RP-18 40-63 μm; gradient: 20-90% acetonitrile in water). 800 mg (85% purity, 81% of theory) of the title compound were obtained.

LC-MS (Method 25): $R_t$=1.19 min; MS (ESIpos): m/z=505/507 [M+H]$^+$

Example 242A

5-{[(6-Bromo-2-chloro-3-methylquinolin-4-yl)carbonyl]amino}-4-(2-methoxyphenyl)pentanoic acid (Enantiomer 2)

To a solution of tert-butyl 5-{[(6-bromo-2-chloro-3-methylquinolin-4-yl)carbonyl]amino}-4-(2-methoxyphenyl)pentanoate (690 mg, 97% purity, 1.19 mmol, enantiomer 2, Example 240A) in dichloromethane (7 ml) was added TFA (1.9 ml), and the mixture was stirred at RT overnight. Subsequently, the reaction mixture was concentrated, and the residue was purified by means of flash column chromatography (LiChroprep RP-18 40-63 μm; gradient: 20-80% acetonitrile in water). 482 mg (87% purity, 70% of theory) of the title compound were obtained.

LC-MS (Method 25): $R_t$=1.19 min; MS (ESIpos): m/z=505/507 [M+H]$^+$ $^1$H-NMR (400 MHz, CHLOROFORM-d) δ [ppm]: 1.262 (0.78), 2.044 (0.43), 2.049 (0.43), 2.132 (0.59), 2.144 (0.71), 2.152 (0.41), 2.165 (0.59), 2.279 (4.28), 2.291 (1.50), 2.301 (1.46), 2.306 (1.22), 2.311 (1.15), 2.320 (1.60), 2.340 (0.70), 2.472 (0.42), 3.480 (0.50), 3.492 (0.62), 3.504 (0.52), 3.713 (0.42), 3.760 (16.00), 3.861 (0.44), 3.875 (0.40), 3.943 (0.42), 3.957 (0.72), 3.972 (0.45), 3.991 (0.41), 5.945 (0.48), 5.959 (0.94), 5.972 (0.47), 6.867 (1.49), 6.887 (1.60), 6.977 (0.69), 6.980 (0.68), 6.996 (1.56), 6.998 (1.55), 7.015 (0.94), 7.017 (0.87), 7.218 (1.09), 7.221 (1.57), 7.233 (1.33), 7.237 (1.62), 7.240 (1.40), 7.254 (1.31), 7.693 (0.80), 7.698 (0.88), 7.715 (1.75), 7.720 (2.24), 7.750 (3.37), 7.761 (1.28), 7.772 (1.63).

Example 243A (+/−)-tert-Butyl 4-cyano-4-(2,6-dichlorophenyl)butanoate (Racemate)

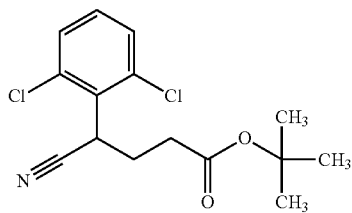 [SMILES: CC(C)(C)OC(=O)CCC(C#N)c1c(Cl)cccc1Cl]

(2,6-Dichlorophenyl)acetonitrile (10.0 g, 54.0 mmol) was dissolved in DMF (200 ml, 2.6 mol), NaH (2.59 g, 60% purity, 64.8 mmol) was added gradually, and the mixture was stirred at RT for a further 10 min. Subsequently, tert-butyl 3-bromopropanoate (9.0 ml, 54 mmol) was slowly added dropwise, in the course of which gentle foaming and heating to about 35° C. was observed. The reaction vessel was cooled in a water bath during the further addition, then the water bath was removed and the mixture was stirred at RT for 2.5 h. The reaction mixture was added to water and extracted with dichloromethane. The organic phase was dried and concentrated on a rotary evaporator. The crude product was purified by column chromatography (Isolera, KP-Sil, eluent: hexane/ethyl acetate, gradient: 1-30%). 13.2 g (75% purity, 59% of theory) of the title compound were obtained.

LC-MS (Method 25): $R_t$=1.43 min; MS (ESIpos): m/z=314 [M+H]$^+$ $^1$H-NMR (400 MHz, CHLOROFORM-d) δ [ppm]: 1.170 (0.43), 1.369 (16.00), 1.957 (0.77), 2.323 (0.44), 2.343 (0.91), 2.354 (0.40), 4.770 (0.57), 7.128 (0.41), 7.147 (0.55), 7.150 (0.58), 7.169 (0.69).

Example 244A (+/−)-tert-Butyl 5-amino-4-(2,6-dichlorophenyl)pentanoate (Racemate)

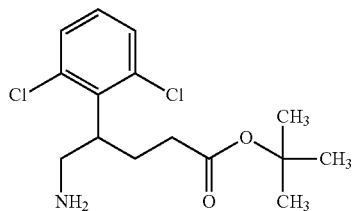

To an initial charge of (+/−)-tert-butyl 4-cyano-4-(2,6-dichlorophenyl)butanoate (racemate, 2.00 g, 75% purity, 4.78 mmol, Example 243A) in tert-butanol (3.9 ml, 67 mmol) was added Raney nickel. The reaction mixture was hydrogenated with hydrogen at standard pressure for 6 h. Subsequently, catalyst was added again and hydrogenation was effected for a further 8 h. The catalyst was filtered through kieselguhr and the filtrate was concentrated on a rotary evaporator. The residue was purified by column chromatography (Isolera, LiChroprep RP-18, eluent: water+ 0.1% by volume of formic acid/acetonitrile, gradient: 5-95% acetonitrile). 660 mg (99% purity, 44% of theory) of the title compound were obtained.

LC-MS (Method 25): $R_t$=0.76 min; MS (ESIpos): m/z=318 [M+H]$^+$ $^1$H-NMR (400 MHz, CHLOROFORM-d) δ [ppm]: 1.403 (16.00), 7.115 (0.42), 7.135 (1.08), 7.155 (0.65), 7.287 (0.47), 7.290 (0.46), 7.321 (0.70), 7.324 (0.62), 7.341 (0.67), 7.344 (0.61).

Example 245A (+/−)-tert-Butyl 5-{[(6-bromo-2-chloro-3-methylquinolin-4-yl)carbonyl]amino}-4-(2,6-dichlorophenyl)pentanoate (Racemate)

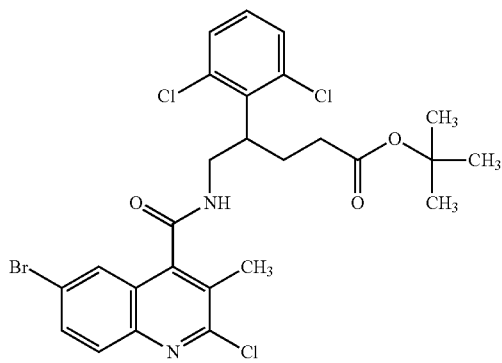 [SMILES: Cc1c(Cl)nc2ccc(Br)cc2c1C(=O)NCC(CCC(=O)OC(C)(C)C)c1c(Cl)cccc1Cl]

6-Bromo-2-chloro-3-methylquinoline-4-carbonyl chloride (4.31 g, 13.5 mmol, Example 3A) and (+/−)-tert-butyl 5-amino-4-(2,6-dichlorophenyl)pentanoate (racemate, 4.74 g, 14.9 mmol, Example 244A) were dissolved in dichloromethane (25 ml, 390 mmol), and aqueous sodium hydrogencarbonate solution (25 ml, 1.0 M, 25 mmol) was added to the solution. The reaction mixture was agitated vigorously at RT for 1.5 h. Subsequently, the reaction mixture was added to water and extracted with dichloromethane, and the organic phase was washed with 1 M hydrochloric acid and saturated aqueous sodium chloride solution, dried over sodium sulfate and concentrated on a rotary evaporator. The crude product was purified by column chromatography (Isolera, LiChroprep RP-18, eluent: water/acetonitrile, gradient: 40-100% acetonitrile). 2.33 g of title compound (contaminated) were obtained, which were used in the subsequent stage without further purification.

LC-MS (Method 25): $R_t$=1.60 min; MS (ESIneg): m/z=597/599 [M−H]⁻

Example 246A (+/−)-5-{[(6-Bromo-2-chloro-3-methylquinolin-4-yl)carbonyl]amino}-4-(2,6-dichlorophenyl)pentanoic acid (Racemate)

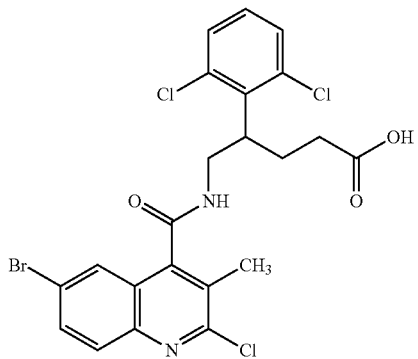 [SMILES: Cc1c(Cl)nc2ccc(Br)cc2c1C(=O)NCC(CCC(=O)O)c1c(Cl)cccc1Cl]

(+/−)-tert-Butyl 5-{[(6-bromo-2-chloro-3-methylquinolin-4-yl)carbonyl]amino}-4-(2,6-dichlorophenyl)pentanoate (racemate, 2.33 g, Example 245A) was dissolved in dichloromethane (29 ml, 460 mmol). At RT, TFA (6.0 ml, 77 mmol) was added and the mixture was stirred at RT for 16 h. Subsequently, the reaction mixture was concentrated on a rotary evaporator and repeatedly taken up again in dichloromethane and concentrated again. The crude product was purified by column chromatography (Isolera, LiChroprep RP-18, eluent: water+0.1% by volume of ammonia/acetonitrile, gradient: 5-40% acetonitrile, followed by flushing through with methanol in order to flush the product completely to the bottom). The combined target fractions were concentrated and the residue was dried under reduced pressure. 950 mg (72% purity, 26% of theory over two stages) of the title compound were obtained.

LC-MS (Method 26): $R_t$=0.74 min; MS (ESIpos): m/z=543/545 [M+H]⁺

Example 247A (+/−)-tert-Butyl 4-cyano-4-(2,6-difluorophenyl)butanoate (Racemate)

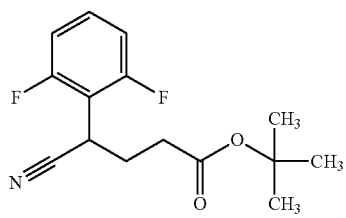 [SMILES: CC(C)(C)OC(=O)CCC(C#N)c1c(F)cccc1F]

Method A:
To a solution of (2,6-difluorophenyl)acetonitrile (5.00 g, 32.7 mmol) in THF (30 ml) under argon were added gradually while stirring, at −78° C., a 2 M solution of LDA in THF (20 ml, 39 mmol). The mixture was allowed to come to 0° C. and, after 15 min, cooled back down again to −78° C. Subsequently, a solution of tert-butyl 3-bromopropanoate (6.2 ml, 39 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated sodium chloride solution (150 ml), dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. 4.87 g (76% purity, 40% of theory) of the title compound were obtained.

LC-MS (Method 1): $R_t$=2.06 min; MS (ESIpos): m/z=282 [M+H]⁺

Method B:
Under argon, an LDA solution was prepared by gradually adding an n-butyllithium solution (1.6 M in hexane, 43 ml, 68 mmol) to an initial charge of diisopropylamine (10 ml, 71 mmol) in THF (43 ml) at −15° C. After the addition had ended, the solution was stirred at 0° C. for a further 10 min. This LDA solution was slowly added dropwise to a solution, cooled to −78° C., of (2,6-difluorophenyl)acetonitrile (9.90 g, 96% purity, 62.1 mmol) in THF (119 ml). On completion of addition, the reaction mixture was allowed to come to 0° C. and, after 15 min, was cooled again to −78° C. Then a solution of tert-butyl 3-bromopropanoate (13 ml, 97% purity, 74 mmol) in 45 ml of THF was slowly added dropwise. The mixture was stirred at −78° C. for 1 h and then stirred at RT overnight. For workup, ammonium chloride solution (400 ml, 10% in water) was added. The mixture was stirred vigorously for 5 minutes and then extracted twice with ethyl acetate. The combined organic phases were successively washed twice each with 1 M hydrochloric acid, a saturated sodium bicarbonate solution and a saturated sodium chloride solution. The organic phase was then dried over sodium sulfate and concentrated on a rotary evaporator. The oily residue was dissolved in dichloromethane, kieselguhr was added, and the mixture was concentrated on a rotary evaporator. The adsorbed residue was purified in multiple passes by means of flash column chromatography (silica gel, Isolera, 100 g Ultra Snap cartridges; gradient: cyclohexane/ethyl acetate 100:0 to 70:30). The product-containing fractions were concentrated together. 12.9 g (100% purity, 74% of theory) of the title compound were obtained.

LC-MS (Method 1): $R_t$=2.08 min; MS (ESIpos): m/z=282 [M+H]$^+$ $^1$H-NMR (400 MHz, DMSO-d6) δ [ppm]: 1.374 (16.00), 2.313 (0.89), 2.331 (1.31), 2.349 (0.45), 4.499 (0.52), 7.197 (0.60), 7.219 (1.24), 7.240 (0.68), 7.519 (0.45).

Example 248A (+/−)-tert-Butyl 5-amino-4-(2,6-difluorophenyl)pentanoate (Racemate)

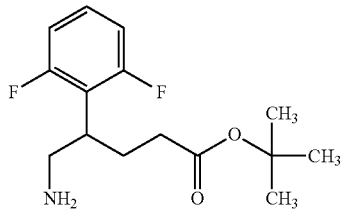

Method A:

To a solution of (+/−)-tert-butyl 4-cyano-4-(2,6-difluorophenyl)butanoate (4.80 g, 17.1 mmol, Example 247A, Method A) in tert-butanol (100 ml) was added Raney nickel (1.00 g, 17.1 mmol), and hydrogenation was effected at standard pressure overnight. Subsequently, the catalyst was filtered off through kieselguhr and the mother liquor was concentrated. 4.06 g (81% purity, 67% of theory) of the title compound were obtained.

LC-MS (Method 2): $R_t$=0.64 min; MS (ESIpos): m/z=286 [M+H]$^+$

Method B:

To an initial charge of (+/−)-tert-butyl 4-cyano-4-(2,6-difluorophenyl)butanoate (12.9 g, 100% purity, 46.0 mmol, Example 247A, Method B) in a mixture of tert-butanol (340 ml) and methanol (15 ml) was added Raney nickel (2.00 g, 34.1 mmol). The reaction mixture was stirred under standard hydrogen pressure overnight. Thereafter, a further 2 g of Raney nickel were added to the reaction mixture, and the reaction was stirred under standard hydrogen pressure for a further two nights. The catalyst was filtered off through kieselguhr and washed three times with methanol (50 ml each time). The filtrate was concentrated and the residue was dissolved in 400 ml of ethyl acetate. The solution was extracted twice with 1 M hydrochloric acid (400 ml each time). The combined aqueous phases were divided between three Erlenmeyer flasks. One of the three portions was brought to pH 8-9 with sodium bicarbonate (powder) and extracted twice with 200 ml of ethyl acetate. Owing to the large amount of sodium bicarbonate required, the next two aqueous portions were brought to pH 8-10 with lithium hydroxide and each was extracted twice with 200 ml of ethyl acetate. The combined organic phases were dried over sodium sulfate, filtered and concentrated. The residue was treated with ethyl acetate and water. After phase separation, the aqueous phase was extracted twice with ethyl acetate. The combined organic phases were concentrated and the residue was dried under reduced pressure. 7.76 g (76% purity, 45% of theory) of the title compound were obtained.

LC-MS (Method 1): $R_t$=1.05 min; MS (ESIpos): m/z=286 [M+H]$^+$ $^1$H-NMR (400 MHz, DMSO-d$_6$): δ [ppm]=7.35-7.24 (m, 1H), 7.08-6.98 (m, 2H), 3.10-2.95 (m, 1H), 2.91-2.73 (m, 2H), 2.09-1.99 (m, 3H), 1.85-1.70 (m, 1H), 1.60-1.40 (m, 2H), 1.34 (s, 9H).

Example 249A (+/−)-tert-Butyl 5-{[(6-bromo-2-chloro-3-methylquinolin-4-yl)carbonyl]amino}-4-(2,6-difluorophenyl) pentanoate (Racemate)

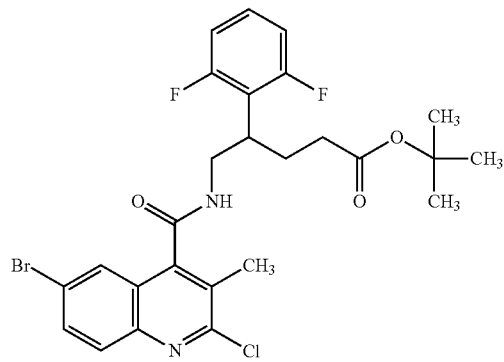 [SMILES: Cc1c(Cl)nc2ccc(Br)cc2c1C(=O)NCC(CCC(=O)OC(C)(C)C)c1c(F)cccc1F]

(+/−)-tert-Butyl 5-amino-4-(2,6-difluorophenyl)pentanoate (racemate, 3.12 g, 76% purity, 8.31 mmol, Example 248A, Method B) was initially charged in dichloromethane (65 ml) at RT. DIPEA (3.6 ml, 21 mmol) was added, followed by a solution of 6-bromo-2-chloro-3-methylquinoline-4-carbonyl chloride (2.21 g, 6.93 mmol, Example 3A) in dichloromethane (15 ml). The reaction mixture was stirred overnight, and then water and dichloromethane (200 ml of each) were added. The phases were separated and the aqueous phase was extracted with dichloromethane (200 ml). The combined organic phases were washed with saturated sodium chloride solution (200 ml), dried over sodium sulfate, filtered and concentrated. The residue was dissolved in a little DMSO and purified in two portions by means of preparative HPLC (Method 30). The combined target fractions were concentrated and the residue was dried under reduced pressure. 3.77 g (98% purity, 94% of theory) of the title compound were obtained.

LC-MS (Method 2): $R_t$=1.30 min; MS (ESIneg): m/z=565/567 [M−H]$^-$ $^1$H-NMR (400 MHz, DMSO-d$_6$): δ [ppm]=8.97 (t, 1H), 7.94-7.86 (m, 2H), 7.84-7.46 (very broad m, 1H), 7.43-7.29 (m, 1H), 7.09 (t, 2H), 3.83-3.68 (m, 2H), 3.57-3.41 (m, 1H), 2.35-1.99 (m, 6H), 1.96-1.83 (m, 1H), 1.37 (s, 9H).

Example 250A (+/−)-tert-Butyl 5-({[6-bromo-3-methyl-2-(piperidin-1-yl)quinolin-4-yl]carbonyl}amino)-4-(2,6-difluorophenyl)pentanoate (Racemate)

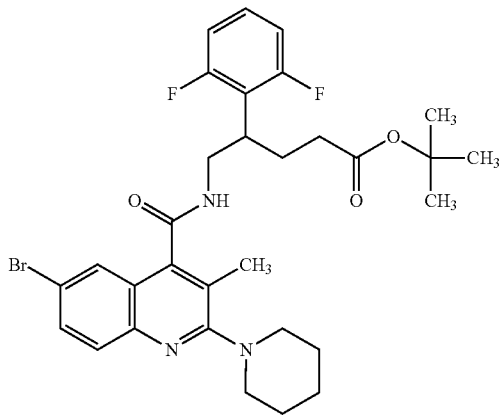 [SMILES: Cc1c(N2CCCCC2)nc2ccc(Br)cc2c1C(=O)NCC(CCC(=O)OC(C)(C)C)c1c(F)cccc1F]

To an initial charge of (+/−)-tert-butyl 5-{[(6-bromo-2-chloro-3-methylquinolin-4-yl)carbonyl]amino}-4-(2,6-difluorophenyl)pentanoate (300 mg, 98% purity, 518 μmol, Example 249A) in NMP (4.4 ml) in a thick-walled microwave vessel were successively added piperidine (260 μl, 2.6 mmol) and DIPEA (450 μl, 2.6 mmol). The vessel was closed and filled with argon via a cannula. The reaction solution was agitated at 100° C. overnight and then at 130° C. for a further 20 h. After cooling to RT, the reaction solution was purified by means of preparative HPLC (Method 14). The product-containing fractions were concentrated and dried under reduced pressure. The residue was dissolved in dichloromethane and foamed under reduced pressure. 252 mg (100% purity, 79% of theory) of the title compound were obtained.

LC-MS (Method 1): $R_t$=2.76 min; MS (ESIpos): m/z=616/618 [M+H]$^+$ $^1$H-NMR (400 MHz, DMSO-d$_6$): δ [ppm]=8.81 (t, 1H), 7.71-7.61 (m, 2H), 7.57-7.42 (m, 1H), 7.42-7.30 (m, 1H), 7.08 (t, 2H), 3.83-3.63 (m, 2H), 3.56-3.42 (m, 1H), 3.13 (br. d, 4H), 2.22-2.00 (m, 6H), 1.97-1.84 (m, 1H), 1.73-1.54 (m, 6H), 1.36 (s, 9H)

Separation of the Enantiomers:

The title compound (169 mg) was separated into the enantiomers by means of preparative HPLC on chiral phase (see Examples 251A and 252A) [column: Daicel Chiralpak IG, 5 μm, 250 mm×20 mm; eluent: n-heptane/isopropanol 90:10; flow rate: 25 ml/min; UV detection: 225 nm, temperature: 25° C.]. The combined target fractions were concentrated in each case (22° C., 40 mbar).

Example 251A tert-Butyl 5-({[6-bromo-3-methyl-2-(piperidin-1-yl)quinolin-4-yl]carbonyl}amino)-4-(2,6-difluorophenyl)pentanoate (Enantiomer 1)

In the enantiomer separation described in Example 250A, 88 mg (99% purity, ee>95%) of the title compound were obtained as the enantiomer that eluted earlier.

Chiral analytical HPLC [column: Daicel Chiralpak IG, 5 μm, 250 mm×4.6 mm; eluent: n-heptane/isopropanol 90:10; flow rate: 1 ml/min; UV detection: 225 nm, temperature: 25° C.]: $R_t$=28.9 min.

LC-MS (Method 1): $R_t$=2.73 min; MS (ESIpos): m/z=616/618 [M+H]$^+$ $^1$H-NMR (400 MHz, DMSO-d6) δ [ppm]: 1.236 (0.76), 1.259 (0.48), 1.364 (16.00), 1.607 (0.49), 1.671 (0.94), 2.096 (0.45), 2.113 (0.86), 2.135 (1.82), 3.134 (1.22), 3.707 (0.42), 7.057 (0.50), 7.079 (0.89), 7.102 (0.58), 7.647 (1.36), 7.658 (0.88), 7.663 (0.81), 8.811 (0.46).

Example 252A tert-Butyl 5-({[6-bromo-3-methyl-2-(piperidin-1-yl)quinolin-4-yl]carbonyl}amino)-4-(2,6-difluorophenyl)pentanoate (Enantiomer 2)

In the enantiomer separation described in Example 250A, 66 mg (95% purity, ee 98%) of the title compound were obtained as the enantiomer that eluted later.

Chiral analytical HPLC [column: Daicel Chiralpak IG, 5 μm, 250 mm×4.6 mm; eluent: n-heptane/isopropanol 90:10; flow rate: 1 ml/min; UV detection: 225 nm, temperature: 25° C.]: $R_t$=34.9 min.

LC-MS (Method 1): $R_t$=2.73 min; MS (ESIpos): m/z=616/618 [M+H]$^+$ $^1$H-NMR (400 MHz, DMSO-d6) δ [ppm]: 1.236 (0.63), 1.259 (0.47), 1.364 (16.00), 1.606 (0.44), 1.670 (0.85), 2.095 (0.41), 2.112 (0.81), 2.135 (1.69), 3.133 (1.12), 7.057 (0.47), 7.079 (0.84), 7.101 (0.55), 7.647 (1.32), 7.658 (0.86), 7.663 (0.75), 8.811 (0.44).

Example 253A (+/−)-tert-Butyl (5-({[6-bromo-3-methyl-2-(pyrrolidin-1-yl)quinolin-4-yl]carbonyl}amino)-4-(2,6-difluorophenyl)pentanoate (Racemate)

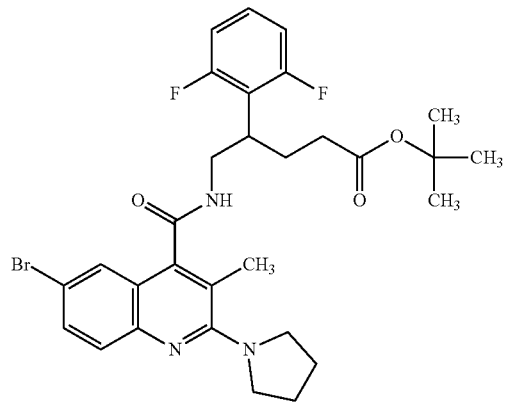 [SMILES: Cc1c(N2CCCC2)nc2ccc(Br)cc2c1C(=O)NCC(CCC(=O)OC(C)(C)C)c1c(F)cccc1F]

To an initial charge of (+/−)-tert-butyl 5-{[(6-bromo-2-chloro-3-methylquinolin-4-yl)carbonyl]amino}-4-(2,6-difluorophenyl)pentanoate (300 mg, 98% purity, 518 μmol, Example 249A) in NMP (4.4 ml) in a microwave vessel were successively added pyrrolidine (220 μl, 2.6 mmol) and DIPEA (450 μl, 2.6 mmol). The vessel was closed and filled with argon via a cannula. The reaction solution was agitated at 100° C. overnight. After cooling to RT, the reaction solution was purified by means of preparative HPLC (Method 14). The product-containing fractions were concentrated and dried under reduced pressure. The residue was dissolved in a little dichloromethane and foamed under reduced pressure. 193 mg (100% purity, 62% of theory) of the title compound were obtained.

LC-MS (Method 4): $R_t$=1.37 min; MS (ESIpos): m/z=602/604 [M+H]$^+$ $^1$H-NMR (400 MHz, DMSO-d$_6$): δ [ppm]=8.76 (t, 1H), 7.56 (dd, 1H), 7.48 (d, 1H), 7.42-7.27 (m, 2H), 7.07 (t, 2H), 3.73-3.66 (m, 2H), 3.57 (br s, 4H), 3.52-3.40 (m, 1H), 2.22-2.01 (m, 6H), 1.95-1.82 (m, 5H), 1.36 (s, 9H).

Separation of the Enantiomers:

119 mg of the title compound were separated into the enantiomers by means of preparative HPLC on chiral phase (see Examples 254A and 255A) [column: Daicel Chiralpak IC, 5 μm, 250 mm×30 mm; eluent: n-heptane/isopropanol 80:20; flow rate: 42.5 ml/min; UV detection: 225 nm, temperature: 25° C.]. The combined target fractions were concentrated in each case (22° C., 40 mbar).

Example 254A tert-Butyl (5-({[6-bromo-3-methyl-2-(pyrrolidin-1-yl)quinolin-4-yl]carbonyl}amino)-4-(2,6-difluorophenyl)pentanoate (Enantiomer 1)

In the enantiomer separation described in Example 253A, 57 mg (95% purity, ee 96%) of the title compound were obtained as the enantiomer that eluted earlier.

Chiral analytical HPLC [column: Daicel Chiralpak IC, 5 μm, 250 mm×4.6 mm; eluent: n-heptane/isopropanol 80:20; flow rate: 1 ml/min; UV detection: 260 nm, temperature: 25° C.]: $R_t$=23.1 min.

LC-MS (Method 1): $R_t$=2.14 min; MS (ESIpos): m/z=602/604 [M+H]$^+$ $^1$H-NMR (400 MHz, DMSO-d6) δ [ppm]: 1.235 (0.87), 1.258 (0.56), 1.298 (0.40), 1.362 (16.00), 1.871 (1.37), 2.095 (0.48), 2.111 (0.81), 2.129 (0.63), 2.160 (0.80), 3.566 (0.86), 7.050 (0.50), 7.072 (0.90), 7.094 (0.57), 7.467 (0.69), 7.489 (1.13), 7.549 (0.60), 7.554 (0.55), 8.763 (0.47).

Example 255A tert-Butyl (5-({[6-bromo-3-methyl-2-(pyrrolidin-1-yl)quinolin-4-yl]carbonyl}amino)-4-(2,6-difluorophenyl)pentanoate (Enantiomer 2)

In the enantiomer separation described in Example 253A, 50 mg (95% purity, ee 99%) of the title compound were obtained as the enantiomer that eluted later.

Chiral analytical HPLC [column: Daicel Chiralpak IC, 5 μm, 250 mm×4.6 mm; eluent: n-heptane/isopropanol 80:20; flow rate: 1 ml/min; UV detection: 260 nm, temperature: 25° C.]: $R_t$=28.2 min.

LC-MS (Method 1): $R_t$=2.14 min; MS (ESIpos): m/z=602/604 [M+H]$^+$ $^1$H-NMR (400 MHz, DMSO-d6) δ [ppm]: −0.008 (1.15), 0.008 (0.74), 0.859 (0.62), 1.245 (0.48), 1.362 (16.00), 1.872 (1.21), 2.096 (0.42), 2.111 (0.72), 2.129 (0.57), 2.160 (0.70), 2.523 (0.69), 3.566 (0.77), 7.050 (0.45), 7.072 (0.79), 7.095 (0.51), 7.468 (0.69), 7.490 (1.11), 7.549 (0.62), 7.555 (0.57), 8.763 (0.41).

Example 256A (+/−)-tert-Butyl 5-({[6-bromo-2-(3,3-difluoropiperidin-1-yl)-3-methylquinolin-4-yl]carbonyl}amino)-4-(2,6-difluorophenyl)pentanoate (Racemate)

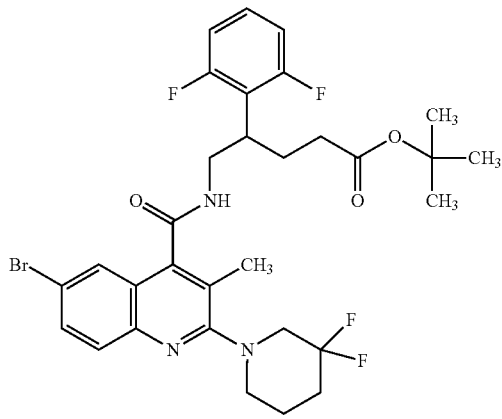 [SMILES: Cc1c(N2CCCC(F)(F)C2)nc2ccc(Br)cc2c1C(=O)NCC(CCC(=O)OC(C)(C)C)c1c(F)cccc1F]

To an initial charge of (+/−)-tert-butyl 5-{[(6-bromo-2-chloro-3-methylquinolin-4-yl)carbonyl]amino}-4-(2,6-difluorophenyl)pentanoate (racemate, 300 mg, 98% purity, 518 μmol, Example 249A) in NMP (4.4 ml) in a thick-walled microwave vessel were successively added 3,3-difluoropiperidine hydrochloride (421 mg, 97% purity, 2.59 mmol) and DIPEA (450 μl, 2.6 mmol). The vessel was closed and filled with argon via a cannula. The reaction solution was agitated at 100° C. overnight, and then at 130° C. for a further 20 h. After cooling to RT, the reaction solution was purified by means of preparative HPLC (Method 14). The product-containing fractions were concentrated and dried under reduced pressure. The residue was dissolved in dichloromethane and foamed under reduced pressure. 234 mg (100% purity, 69% of theory) of the title compound were obtained.

LC-MS (Method 1): $R_t$=2.64 min; MS (ESIpos): m/z=652/654 [M+H]$^+$ $^1$H-NMR (400 MHz, DMSO-d$_6$): δ [ppm]=8.83 (t, 1H), 7.76-7.65 (m, 2H), 7.61-7.43 (m, 1H), 7.42-7.30 (m, 1H), 7.08 (t, 2H), 3.83-3.64 (m, 2H), 3.53-3.42 (m, 3H), 3.22-3.11 (m, 2H), 2.22-1.99 (m, 8H), 1.97-1.82 (m, 3H), 1.36 (s, 9H).

Separation of the Enantiomers:

170 mg of the title compound were separated into the enantiomers by means of preparative HPLC on chiral phase (see Examples 257A and 258A) [column: Daicel Chiralpak OX-H, 5 μm, 250 mm×20 mm; eluent: n-heptane/isopropanol 82:18; flow rate: 30 ml/min; UV detection: 220 nm, temperature: RT]. The combined target fractions were each concentrated on a rotary evaporator.

Example 257A tert-Butyl 5-({[6-bromo-2-(3,3-difluoropiperidin-1-yl)-3-methylquinolin-4-yl]carbonyl}amino)-4-(2,6-difluorophenyl)pentanoate (Enantiomer 1)

In the enantiomer separation described in Example 256A, 82 mg (98% purity, ee 98%) of the title compound were obtained as the enantiomer that eluted earlier.

Chiral analytical HPLC [column: Daicel Chiralpak OX-H, 5 μm, 250 mm×4.6 mm; eluent: n-heptane/isopropanol 80:20; flow rate: 1 ml/min; UV detection: 220 nm, temperature: 30° C.]: $R_t$=2.13 min.

LC-MS (Method 1): $R_t$=2.65 min; MS (ESIpos): m/z=652/654 [M+H]$^+$ $^1$H-NMR (400 MHz, DMSO-d6) δ [ppm]: −0.008 (0.49), 0.008 (0.47), 1.105 (0.66), 1.120 (0.67), 1.364 (16.00), 1.887 (0.54), 2.071 (0.51), 2.097 (0.69), 2.114 (0.87), 2.135 (0.66), 2.154 (1.54), 3.166 (0.53), 3.448 (0.62), 3.478 (1.91), 7.059 (0.45), 7.081 (0.83), 7.104 (0.53), 7.698 (1.28), 7.707 (0.88), 7.712 (0.77), 8.825 (0.44).

Example 258A tert-Butyl 5-({[6-bromo-2-(3,3-difluoropiperidin-1-yl)-3-methylquinolin-4-yl]carbonyl}amino)-4-(2,6-difluorophenyl)pentanoate (Enantiomer 2)

In the enantiomer separation described in Example 256A, 73 mg (98% purity, ee 95%) of the title compound were obtained as the enantiomer that eluted later.

Chiral analytical HPLC [column: Daicel Chiralpak OX-H, 5 μm, 250 mm×4.6 mm; eluent: n-heptane/isopropanol 80:20; flow rate: 1 ml/min; UV detection: 220 nm, temperature: 30° C.]: $R_t$=3.23 min.

LC-MS (Method 1): $R_t$=2.65 min; MS (ESIpos): m/z=652/654 [M+H]$^+$ $^1$H-NMR (400 MHz, DMSO-d6) δ [ppm]: −0.008 (0.50), 0.008 (0.51), 1.105 (0.61), 1.120 (0.60), 1.364 (16.00), 1.888 (0.54), 2.072 (0.50), 2.097 (0.68), 2.114 (0.86), 2.136 (0.64), 2.154 (1.50), 3.166 (0.52), 3.475 (1.28), 3.504 (0.56), 7.059 (0.46), 7.081 (0.80), 7.104 (0.52), 7.698 (1.25), 7.707 (0.84), 7.712 (0.75), 8.825 (0.43).

Example 259A tert-Butyl 5-[({6-bromo-2-(3-fluoropiperidin-1-yl)-3-methylquinolin-4-yl}carbonyl)amino]-4-(2,6-difluorophenyl)pentanoate (Diastereomer Mixture)

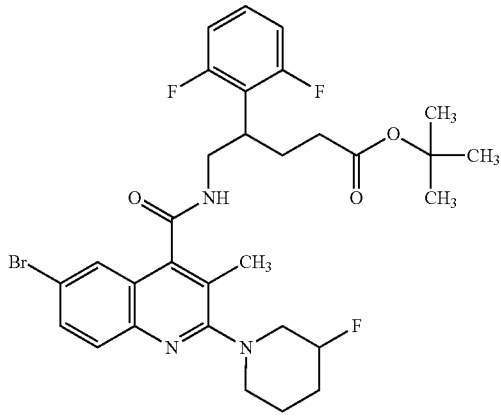 [SMILES: Cc1c(N2CCCC(F)C2)nc2ccc(Br)cc2c1C(=O)NCC(CCC(=O)OC(C)(C)C)c1c(F)cccc1F]

To an initial charge of (+/−)-tert-butyl 5-{[(6-bromo-2-chloro-3-methylquinolin-4-yl)carbonyl]amino}-4-(2,6-difluorophenyl)pentanoate (racemate, 400 mg, 98% purity, 690 μmol, Example 249A) in NMP (4.0 ml) in a thick-walled microwave vessel were successively added 3-fluoropiperidine hydrochloride (497 mg, 97% purity, 3.45 mmol) and DIPEA (600 μl, 3.5 mmol). The vessel was closed and agitated at 130° C. overnight. After cooling to RT, the reaction solution was purified by means of preparative HPLC (Method 14). The product-containing fractions were concentrated and dried under reduced pressure. The residue was dissolved in a little dichloromethane and foamed under reduced pressure. 343 mg (100% purity, 78% of theory) of the title compound were obtained.

LC-MS (Method 1): $R_t$=2.60 min; MS (ESIpos): m/z=634/636 [M+H]$^+$ $^1$H-NMR (400 MHz, DMSO-d$_6$): δ [ppm]=8.82 (t, 1H), 7.72-7.64 (m, 2H), 7.61-7.43 (m, 1H), 7.41-7.30 (m, 1H), 7.08 (d, 2H), 4.98-4.76 (m, 1H), 3.82-3.63 (m, 2H), 3.56-3.30 (m, 3H), 3.24-3.02 (m, 2H), 2.23-1.72 (m, 1 OH), 1.70-1.57 (m, 1H), 1.36 (s, 9H).

Example 260A tert-Butyl 5-[({6-bromo-2-(3-ethylpiperidin-1-yl)-3-methylquinolin-4-yl}carbonyl)amino]-4-(2,6-difluorophenyl)pentanoate (Diastereomer Mixture)

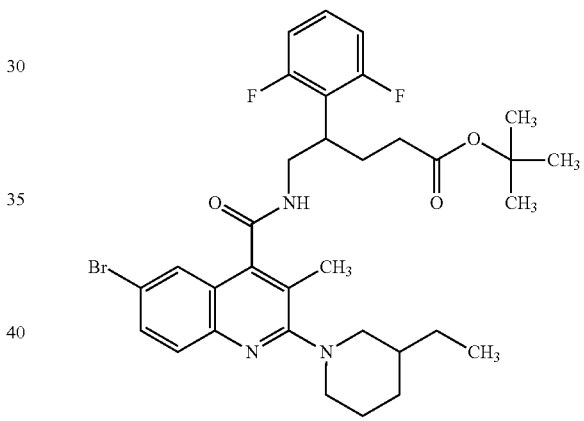

To an initial charge of (+/−)-tert-butyl 5-{[(6-bromo-2-chloro-3-methylquinolin-4-yl)carbonyl]amino}-4-(2,6-difluorophenyl)pentanoate (racemate, 400 mg, 98% purity, 690 μmol, Example 249A) in NMP (4.0 ml) in a thick-walled microwave vessel were successively added 3-ethylpiperidine (411 mg, 95% purity, 3.45 mmol) and DIPEA (600 μl, 3.5 mmol). The vessel was closed and agitated at 130° C. overnight. After cooling to RT, the reaction solution was purified by means of preparative HPLC (Method 14). The product-containing fractions were concentrated and dried under reduced pressure. The residue was dissolved in a little dichloromethane and foamed under reduced pressure. 365 mg (100% purity, 82% of theory) of the title compound were obtained.

$^1$H-NMR (400 MHz, DMSO-d$_6$): δ [ppm]=8.81 (t, 1H), 7.71-7.59 (m, 2H), 7.56-7.42 (m, 1H), 7.42-7.29 (m, 1H), 7.08 (t, 2H), 3.80-3.64 (m, 2H), 3.57-3.42 (m, 3H), 2.83-2.69 (m, 1H), 2.48-2.36 (m, 1H), 2.24-1.99 (m, 6H), 1.98-1.81 (m, 2H), 1.81-1.70 (m, 1H), 1.68-1.48 (m, 2H), 1.36 (s, 9H), 1.32-1.20 (m, 2H), 1.16-1.00 (m, 1H), 0.97-0.83 (m, 3H).

Example 261A (+/−)-tert-Butyl 5-({[6-bromo-3-methyl-2-(piperidin-1-yl)quinolin-4-yl]carbonyl}amino)-4-(2,5-difluorophenyl)pentanoate (Racemate)

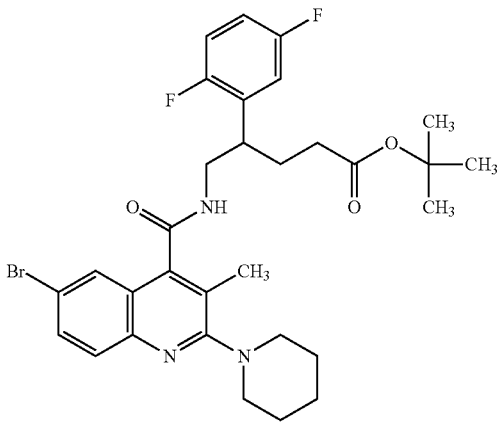 [SMILES: Cc1c(N2CCCCC2)nc2ccc(Br)cc2c1C(=O)NCC(CCC(=O)OC(C)(C)C)c1cc(F)ccc1F]

To an initial charge of (+/−)-tert-butyl 5-{[(6-bromo-2-chloro-3-methylquinolin-4-yl)carbonyl]amino}-4-(2,5-difluorophenyl)pentanoate (racemate, 300 mg, 528 μmol, Example 226A) in NMP (4.0 ml) in a thick-walled microwave vessel were successively added piperidine (260 μl, 2.6 mmol) and DIPEA (460 ml, 2.6 mmol). The vessel was closed and agitated at 130° C. overnight. After cooling to RT, the reaction solution was separated by preparative HPLC (Method 14). The product-containing fractions were concentrated and dried under reduced pressure. The residue was dissolved in a little dichloromethane and foamed under reduced pressure. 265 mg (100% purity, 81% of theory) of the title compound were obtained.

LC-MS (Method 1): $R_t$=2.72 min; MS (ESIpos): m/z=616/618 [M+H]$^+$ $^1$H-NMR (400 MHz, DMSO-d$_6$): δ [ppm]=8.81-8.67 (m, 1H), 7.73-7.58 (m, 2H), 7.55-7.36 (m, 1H), 7.33-7.27 (m, 1H), 7.27-7.19 (m, 1H), 7.18-7.06 (m, 1H), 3.76-3.56 (m, 2H), 3.40-3.33 (m, 1H), 3.19-3.07 (m, 4H), 2.16-2.07 (m, 5H), 2.06-1.96 (m, 1H), 1.86-1.73 (m, 1H), 1.73-1.55 (m, 6H), 1.37 (s, 9H).

Separation of the Enantiomers:

The title compound (268 mg) was separated into the enantiomers by means of preparative HPLC on chiral phase (see Intermediates 262 and 263) [column: Daicel Chiralpak OX-H, 5 μm, 250 mm×20 mm; eluent: n-heptane/ethanol 80:20; flow rate: 20 ml/min; UV detection: 210 nm, temperature: 23° C.]. The combined target fractions were each concentrated on a rotary evaporator. The respective residues were admixed with 2 ml of acetonitrile and 15 ml of water, and lyophilized.

Example 262A tert-Butyl 5-({[6-bromo-3-methyl-2-(piperidin-1-yl)quinolin-4-yl]carbonyl}amino)-4-(2,5-difluorophenyl)pentanoate (Enantiomer 1)

In the enantiomer separation described in Example 261A, 82 mg (99% purity, ee 100%) of the title compound were obtained as the enantiomer that eluted earlier.

Chiral analytical HPLC [column: Daicel Chiralpak OX-3, 3 μm, 50 mm×4.6 mm; eluent: isohexane/ethanol 80:20; flow rate: 1 ml/min; UV detection: 220 nm, temperature: 25° C.]: $R_t$=2.24 min.

LC-MS (Method 1): $R_t$=2.74 min; MS (ESIpos): m/z=616/618 [M+H]$^+$ $^1$H-NMR (400 MHz, DMSO-d6) δ [ppm]: −0.008 (0.46), 0.008 (0.40), 1.371 (16.00), 1.607 (0.40), 1.670 (0.79), 2.079 (0.65), 2.096 (0.94), 2.115 (1.18), 3.132 (1.05), 7.646 (1.28), 7.655 (0.84), 7.660 (0.76).

Example 263A tert-Butyl 5-({[6-bromo-3-methyl-2-(piperidin-1-yl)quinolin-4-yl]carbonyl}amino)-4-(2,5-difluorophenyl)pentanoate (Enantiomer 2)

In the enantiomer separation described in Example 261A, 90 mg (98% purity, ee 97%) of the title compound were obtained as the enantiomer that eluted later.

Chiral analytical HPLC [column: Daicel Chiralpak OX-3, 3 μm, 50 mm×4.6 mm; eluent: isohexane/ethanol 80:20; flow rate: 1 ml/min; UV detection: 220 nm, temperature: 25° C.]: $R_t$=2.60 min.

LC-MS (Method 1): $R_t$=2.74 min; MS (ESIpos): m/z=616/618 [M+H]$^+$ $^1$H-NMR (400 MHz, DMSO-d6) δ [ppm]: −0.008 (0.44), 1.372 (16.00), 1.605 (0.43), 1.670 (0.83), 2.080 (0.67), 2.096 (0.97), 2.115 (1.24), 3.133 (1.10), 7.646 (1.31), 7.655 (0.88), 7.660 (0.81), 8.740 (0.40).

Example 264A (+/−)-tert-Butyl 5-({[6-bromo-3-methyl-2-(pyrrolidin-1-yl)quinolin-4-yl]carbonyl}amino)-4-(2,5-difluorophenyl)pentanoate (Racemate)

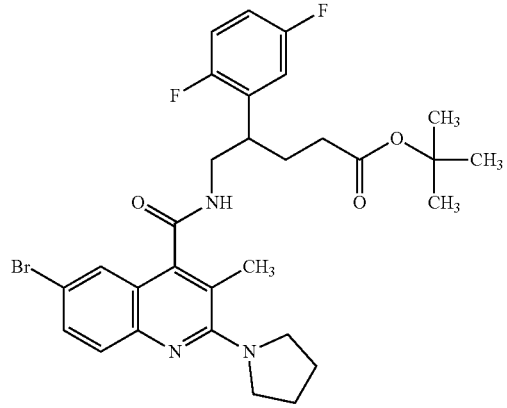 [SMILES: Cc1c(N2CCCC2)nc2ccc(Br)cc2c1C(=O)NCC(CCC(=O)OC(C)(C)C)c1cc(F)ccc1F]

To an initial charge of (+/−)-tert-butyl 5-{[(6-bromo-2-chloro-3-methylquinolin-4-yl)carbonyl]amino}-4-(2,5-difluorophenyl)pentanoate (racemate, 300 mg, 528 μmol, Example 226A) in NMP (4.0 ml) in a thick-walled microwave vessel were successively added pyrrolidine (220 μl, 2.6 mmol) and DIPEA (460 μl, 2.6 mmol). The vessel was closed and agitated at 130° C. overnight. After cooling to RT, the reaction solution was purified by means of preparative HPLC (Method 14). The product-containing fractions were concentrated and dried under reduced pressure. 245 mg (100% purity, 77% of theory) of the title compound were obtained.

LC-MS (Method 1): $R_t$=2.13 min; MS (ESIpos): m/z=602/604 [M+H]$^+$ $^1$H-NMR (400 MHz, DMSO-d$_6$): δ [ppm]=8.69 (t, 1H), 7.56 (dd, 1H), 7.48 (d, 1H), 7.44-7.18 (m, 3H), 7.17-7.08 (m, 1H), 3.73-3.50 (m, 6H), 3.39-3.33 (m, 1H), 2.20-1.97 (m, 6H), 1.91-1.84 (m, 4H), 1.85-1.73 (m, 1H), 1.37 (s, 9H).

Separation of the Enantiomers:

The title compound (173 mg) was separated into the enantiomers by means of preparative HPLC on chiral phase (see Examples 265A and 266A) [column: Daicel Chiralpak IC, 5 μm, 250 mm×30 mm; eluent: n-heptane/isopropanol 80:20; flow rate: 42.5 ml/min; UV detection: 260 nm, temperature: 25° C.]. The combined target fractions were concentrated in each case (25° C., 40 mbar).

Example 265A tert-Butyl 5-({[6-bromo-3-methyl-2-(pyrrolidin-1-yl)quinolin-4-yl]carbonyl}amino)-4-(2,5-difluoro-phenyl)pentanoate (Enantiomer 1)

In the enantiomer separation described in Example 264A, 83 mg (90% purity, solvent-containing, ee 96%) of the title compound were obtained as the enantiomer that eluted earlier.

Chiral analytical HPLC [column: Daicel Chiralpak IC, 5 μm, 250 mm×4.6 mm; eluent: n-heptane/isopropanol 80:20; flow rate: 1 ml/min; UV detection: 260 nm, temperature: 25° C.]: $R_t$=19.2 min.

LC-MS (Method 1): $R_t$=2.13 min; MS (ESIpos): m/z=602/604 [M+H]$^+$ $^1$H-NMR (400 MHz, DMSO-d6) δ [ppm]: −0.008 (0.81), 0.008 (0.79), 1.236 (0.96), 1.259 (0.72), 1.298 (0.54), 1.370 (16.00), 1.871 (1.18), 2.078 (0.65), 2.095 (0.85), 2.115 (0.44), 2.142 (0.50), 2.523 (0.56), 3.565 (0.80), 7.466 (0.63), 7.488 (1.07), 7.545 (0.55), 7.551 (0.50).

Example 266A tert-Butyl 5-({[6-bromo-3-methyl-2-(pyrrolidin-1-yl)quinolin-4-yl]carbonyl}amino)-4-(2,5-difluoro-phenyl)pentanoate (Enantiomer 2)

In the enantiomer separation described in Example 264A, 86 mg (90% purity, solvent-containing, ee 96%) of the title compound were obtained as the enantiomer that eluted later.

Chiral analytical HPLC [column: Daicel Chiralpak IC, 5 μm, 250 mm×4.6 mm; eluent: n-heptane/isopropanol 80:20; flow rate: 1 ml/min; UV detection: 260 nm, temperature: 25° C.]: $R_t$=23.1 min.

LC-MS (Method 1): $R_t$=2.13 min; MS (ESIpos): m/z=602/604 [M+H]$^+$ $^1$H-NMR (400 MHz, DMSO-d6) δ [ppm]: −0.008 (0.66), 0.008 (0.62), 0.839 (0.47), 1.235 (1.44), 1.259 (1.15), 1.298 (0.84), 1.352 (0.50), 1.370 (16.00), 1.871 (1.21), 2.078 (0.67), 2.095 (0.87), 2.115 (0.46), 2.141 (0.51), 2.523 (0.47), 3.567 (0.83), 7.466 (0.64), 7.488 (1.07), 7.545 (0.55), 7.551 (0.51).

Example 267A (+/−)-tert-Butyl 5-({[6-bromo-2-(3,3-difluoropiperi-din-1-yl)-3-methylquinolin-4-yl]carbonyl}amino)-4-(2,5-difluorophenyl)pentanoate (Racemate)

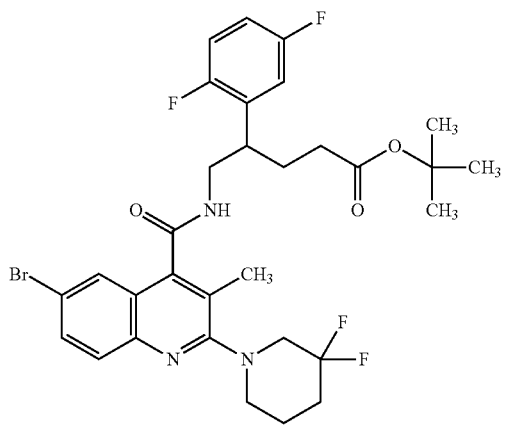 [SMILES: Cc1c(N2CCCC(F)(F)C2)nc2ccc(Br)cc2c1C(=O)NCC(CCC(=O)OC(C)(C)C)c1cc(F)ccc1F]

To an initial charge of (+/−)-tert-butyl 5-{[(6-bromo-2-chloro-3-methylquinolin-4-yl)carbonyl]amino}-4-(2,5-difluorophenyl)pentanoate (racemate, 300 mg, 528 μmol, Example 226A) in NMP (4.0 ml) in a thick-walled microwave vessel were successively added 3,3-difluoropiperidine hydrochloride (416 mg, 2.64 mmol) and DIPEA (460 μl, 2.6 mmol). The vessel was closed and agitated at 130° C. overnight and at 140° C. for a further 20 h. After cooling to RT, the reaction solution was separated by preparative HPLC (Method 14). The product-containing fractions were concentrated and dried under reduced pressure. The residue was dissolved in a little dichloromethane and foamed under reduced pressure. 253 mg (100% purity, 73% of theory) of the title compound were obtained.

LC-MS (Method 1): $R_t$=2.60 min; MS (ESIpos): m/z=652/654 [M+H]$^+$ $^1$H-NMR (400 MHz, DMSO-d$_6$): δ [ppm]=8.75 (t, 1H), 7.74-7.67 (m, 2H), 7.48 (br s, 1H), 7.39-7.20 (m, 2H), 7.17-7.09 (m, 1H), 3.78-3.56 (m, 2H), 3.48 (t, 2H), 3.40-3.29 (m, 1H), 3.17 (br s, 2H), 2.20-1.97 (m, 8H), 1.92-1.75 (m, 3H), 1.39-1.29 (m, 9H).

Separation of the Enantiomers:

The title compound (202 mg) was separated into the enantiomers by means of preparative HPLC on chiral phase (see Intermediates 268A and 269A) [column: Daicel Chiralpak OX-H, 5 μm, 250 mm×30 mm; eluent: n-heptane/ethanol 85:15; flow rate: 42.5 ml/min; UV detection: 220 nm, temperature: 20° C.]. The combined target compounds were each concentrated, and each residue was dried under reduced pressure.

Example 268A tert-Butyl 5-({[6-bromo-2-(3,3-difluoropiperidin-1-yl)-3-methylquinolin-4-yl]carbonyl}amino)-4-(2,5-difluorophenyl)pentanoate (Enantiomer 1)

In the enantiomer separation described in Example 267A, 71 mg (99% purity, ee 99%) of the title compound were obtained as the enantiomer that eluted earlier.

Example 269A tert-Butyl 5-({[6-bromo-2-(3,3-difluoropiperidin-1-yl)-3-methylquinolin-4-yl]carbonyl}amino)-4-(2,5-difluorophenyl)pentanoate (Enantiomer 2)

In the enantiomer separation described in Example 267A, 71 mg (95% purity, ee 93%) of the title compound were obtained as the enantiomer that eluted later.

Chiral analytical HPLC [column: Daicel Chiralpak OX-3, 3 μm, 50 mm×4.6 mm; eluent: i-hexane/ethanol 80:20; flow rate: 1 ml/min; UV detection: 220 nm, temperature: 25° C.]: $R_t$=1.10 min.

LC-MS (Method 1): $R_t$=2.60 min; MS (ESIpos): m/z=652/654 $[M+H]^+$ $^1$H-NMR (400 MHz, DMSO-d6) δ [ppm]: −0.008 (1.68), 0.008 (1.48), 1.372 (16.00), 1.879 (0.41), 2.081 (0.84), 2.098 (1.10), 2.119 (0.69), 2.134 (1.02), 3.165 (0.52), 3.475 (0.62), 7.697 (1.27), 7.704 (0.89), 7.709 (0.79), 8.752 (0.41).

Example 270A tert-Butyl 5-[({6-bromo-2-(3-fluoropiperidin-1-yl)-3-methylquinolin-4-yl}carbonyl)amino]-4-(2,5-difluorophenyl)pentanoate (Diastereomer Mixture)

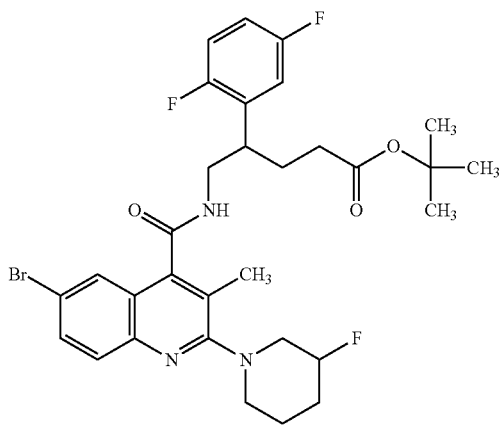 [SMILES: Cc1c(N2CCCC(F)C2)nc2ccc(Br)cc2c1C(=O)NCC(CCC(=O)OC(C)(C)C)c1cc(F)ccc1F]

To an initial charge of (+/−)-tert-butyl 5-{[(6-bromo-2-chloro-3-methylquinolin-4-yl)carbonyl]amino}-4-(2,5-difluorophenyl)pentanoate (racemate, 400 mg, 704 μmol, Example 226A) in NMP (4.5 ml) in a thick-walled microwave vessel were successively added 3-fluoropiperidine hydrochloride (492 mg, 3.52 mmol) and DIPEA (610 μl, 3.5 mmol). The vessel was closed and agitated at 130° C. overnight. After cooling to RT, the reaction solution was purified by means of preparative HPLC (Method 14). The product-containing fractions were concentrated and dried under reduced pressure. 293 mg (100% purity, 66% of theory) of the title compound were obtained.

LC-MS (Method 1): $R_t$=2.59 min; MS (ESIpos): m/z=634/636 $[M+H]^+$ $^1$H-NMR (400 MHz, DMSO-d$_6$): 5 [ppm]=8.75 (t, 1H), 7.71-7.64 (m, 2H), 7.60-7.36 (m, 1H), 7.33-7.20 (m, 2H), 7.17-7.08 (m, 1H), 4.98-4.76 (m, 1H), 3.77-3.57 (m, 2H), 3.50-3.35 (m, 2H), 3.23-3.14 (m, 1H), 3.13-3.03 (m, 1H), 2.16-1.87 (m, 8H), 1.86-1.73 (m, 2H), 1.71-1.57 (m, 1H), 1.37 (s, 9H), 1H concealed.

Example 271A (+/−)-tert-Butyl 5-[(tert-butoxycarbonyl)amino]-4-(2-chlorophenyl)pentanoate (Racemate)

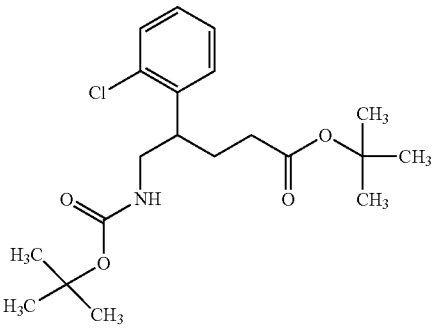 [SMILES: CC(C)(C)OC(=O)CCC(CNC(=O)OC(C)(C)C)c1ccccc1Cl]

To a mixture of (+/−)-tert-butyl 5-amino-4-(2-chlorophenyl)pentanoate (6.57 g, 83% purity, 19.2 mmol, Example 25A) in dichloromethane (40 ml) were added, at RT, triethylamine (3.0 ml, 21.5 mmol) and di-tert-butyl dicarbonate (4.70 g, 21.5 mmol) (evolution of gas), and the mixture was first stirred at RT and then left to stand for five days. Subsequently, the mixture was admixed with dichloromethane (60 ml) and washed once with sodium hydrogencarbonate solution and once with saturated sodium chloride solution. The organic phase was dried over sodium sulfate, filtered and concentrated. The residue was purified by means of flash column chromatography (100 g silica gel Biotage Snap-Cartridge Ultra, cyclohexane/ethyl acetate gradient 97:3→7:3, Isolera One). The combined target fractions were concentrated on a rotary evaporator at 20° C., and the residue was dried under reduced pressure. Two fractions of the title compound with slightly different purity were obtained: Fraction 1: 4.33 g (100% purity, 59% of theory, see analysis) and fraction 2: 1.66 g (94% purity, 21% of theory).

LC-MS (Method 2): $R_t$=1.26 min; MS (ESIpos): m/z=384 $[M+H]^+$ $^1$H-NMR (400 MHz, DMSO-d6) δ [ppm]: 1.333 (9.46), 1.353 (16.00), 1.398 (0.17), 1.692 (0.21), 1.708 (0.24), 1.716 (0.21), 1.731 (0.18), 1.933 (0.16), 1.947 (0.27), 1.957 (0.23), 1.976 (0.92), 1.999 (0.31), 2.012 (0.23), 3.038 (0.18), 3.055 (0.25), 3.072 (0.28), 3.087 (0.19), 3.183 (0.25), 3.200 (0.23), 3.335 (0.25), 3.352 (0.23), 3.363 (0.16), 6.843 (0.18), 6.857 (0.33), 6.871 (0.17), 7.220 (0.26), 7.227 (0.32), 7.238 (0.32), 7.248 (0.27), 7.311 (0.94), 7.320 (1.08), 7.395 (0.60), 7.415 (0.50).

Separation of the Enantiomers:

The two combined fractions of the title compound (5.9 g) were dissolved in ethanol (100 ml), filtered and separated into the enantiomers by means of preparative SFC on chiral phase (see Examples 272A and 273A) [column: Daicel Chiral analytical HPLC [column: Daicel Chiralpak OX-3, 3 μm, 50 mm×4.6 mm; eluent: i-hexane/ethanol 80:20; flow rate: 1 ml/min; UV detection: 220 nm, temperature: 25° C.]: $R_t$=1.10 min.

LC-MS (Method 1): $R_t$=2.60 min; MS (ESIpos): m/z=652/654 $[M+H]^+$ $^1$H-NMR (400 MHz, DMSO-d6) δ [ppm]: −0.008 (0.84), 0.008 (0.94), 1.358 (0.70), 1.371 (16.00), 1.880 (0.44), 2.081 (0.90), 2.098 (1.18), 2.120 (0.74), 2.134 (1.11), 3.164 (0.56), 3.475 (0.68), 7.697 (1.31), 7.704 (0.89), 7.709 (0.81), 8.752 (0.43).

Chiralcel OX, 20 µm, 380 mm×50 mm; flow rate: 300 ml/min; injection: 1.2 ml; UV detection: 210 nm, temperature: 40° C.; eluent: 90% carbon dioxide/10% ethanol; run time 10 min, isocratic]. The combined target fractions were each concentrated and dried under reduced pressure.

Example 272A (+)-tert-Butyl 5-[(tert-butoxycarbonyl)amino]-4-(2-chlorophenyl)pentanoate (Enantiomer 1)

In the enantiomer separation described in Example 271A, 2.59 g (99% purity, ee>99%) of the title compound were obtained as the enantiomer that eluted earlier.
[α]$_D^{20}$=+8.5°, 589 nm, c=0.41 g/100 ml, methanol
LC-MS (Method 1): R$_t$=2.42 min; MS (ESIpos): m/z=384 [M+H]$^+$
$^1$H-NMR (400 MHz, DMSO-d6) δ [ppm]: 1.332 (9.45), 1.352 (16.00), 1.691 (0.22), 1.706 (0.24), 1.715 (0.21), 1.730 (0.18), 1.946 (0.27), 1.955 (0.24), 1.975 (0.91), 2.011 (0.23), 3.037 (0.17), 3.054 (0.24), 3.071 (0.28), 3.086 (0.19), 3.182 (0.25), 3.198 (0.23), 3.334 (0.28), 3.351 (0.24), 6.843 (0.19), 6.857 (0.33), 6.871 (0.18), 7.219 (0.26), 7.227 (0.33), 7.238 (0.32), 7.247 (0.27), 7.311 (0.98), 7.320 (1.08), 7.395 (0.60), 7.415 (0.51).

Example 273A (−)-tert-Butyl 5-[(tert-butoxycarbonyl)amino]-4-(2-chlorophenyl)pentanoate (Enantiomer 2)

In the enantiomer separation described in Example 271A, 2.47 g (100% purity, ee>99%) of the title compound were obtained as the enantiomer that eluted later.
[α]$_D^{20}$=−8.2°, 589 nm, c=0.65 g/100 ml, methanol
LC-MS (Method 1): R$_t$=2.42 min; MS (ESIpos): m/z=384 [M+H]$^+$
$^1$H-NMR (400 MHz, DMSO-d6) δ [ppm]: −0.008 (0.33), 0.008 (0.34), 1.332 (8.75), 1.352 (16.00), 1.691 (0.19), 1.706 (0.22), 1.715 (0.19), 1.730 (0.16), 1.946 (0.22), 1.955 (0.20), 1.975 (0.81), 2.012 (0.21), 3.053 (0.22), 3.071 (0.25), 3.086 (0.17), 3.162 (0.18), 3.175 (0.18), 3.181 (0.23), 3.198 (0.20), 3.333 (0.28), 3.351 (0.22), 6.858 (0.30), 7.219 (0.23), 7.227 (0.30), 7.238 (0.30), 7.248 (0.25), 7.311 (0.89), 7.320 (0.99), 7.396 (0.57), 7.415 (0.48).

Example 274A (−)-tert-Butyl 5-amino-4-(2-chlorophenyl)pentanoate hydrochloride (Enantiomer 1)

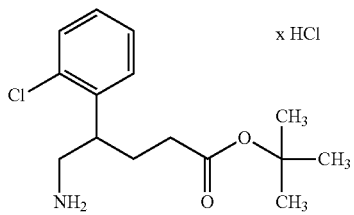

To a mixture of (+)-tert-butyl 5-[(tert-butoxycarbonyl)amino]-4-(2-chlorophenyl)pentanoate (2.55 g, 6.64 mmol, Example 272A) in dioxane (13 ml) was slowly added dropwise, at RT, a 4 M solution of hydrogen chloride in dioxane (3.3 ml, 13.28 mmol), and the mixture was stirred at RT for 22 h. Subsequently, a 4 M solution of hydrogen chloride in dioxane (830 al, 3.32 mmol) was again added dropwise, and the mixture was stirred at RT for a further hour. Subsequently, a 4 M solution of hydrogen chloride in dioxane (830 µl, 3.32 mmol) was again added dropwise, and the mixture was stirred at RT for a further two hours. This was followed by concentration of the mixture, and repeated additions of dichloromethane followed by concentration again. The residue was dried under reduced pressure. 2.29 g (67% purity, 72% of theory) of the title compound were obtained.
[α]$_D^{20}$=−4.4°, 589 nm, c=0.72 g/100 ml, methanol
LC-MS (Method 1): R$_t$=1.14 min; MS (ESIpos): m/z=284 [M+H]$^+$ Example 275A (+)-tert-Butyl 5-amino-4-(2-chlorophenyl)pentanoate hydrochloride (Enantiomer 2)

To a mixture of (−)-tert-butyl 5-[(tert-butoxycarbonyl)amino]-4-(2-chlorophenyl)pentanoate (2.42 g, 6.30 mmol, Example 273A) in dioxane (12 ml) was slowly added dropwise, at RT, a 4 M solution of hydrogen chloride in dioxane (3.2 ml, 12.61 mmol), and the mixture was stirred at RT for 22 h. Subsequently, a 4 M solution of hydrogen chloride in dioxane (790 µl, 3.16 mmol) was again added dropwise, and the mixture was stirred at RT for a further hour. Subsequently, a 4 M solution of hydrogen chloride in dioxane (790 µl, 3.16 mmol) was again added dropwise, and the mixture was stirred at RT for a further two hours. This was followed by concentration of the mixture, and repeated additions of dichloromethane followed by concentration again. The residue was dried under reduced pressure. 2.15 g (68% purity, 73% of theory) of the title compound were obtained.
[α]$_D^{20}$=+5.9°, 589 nm, c=0.66 g/100 ml, methanol
LC-MS (Method 1): R$_t$=1.12 min; MS (ESIpos): m/z=284 [M+H]$^+$ Example 276A (+)-tert-Butyl 5-{[(6-bromo-2-chloro-3-methylquinolin-4-yl)carbonyl]amino}-4-(2-chlorophenyl)pentanoate (Enantiomer 1)

[For structural formula see Example 37A (racemate)]
To a suspension of (−)-tert-butyl 5-amino-4-(2-chlorophenyl)pentanoate hydrochloride (2.25 g, 67% purity, 5.29 mmol, Example 274A) in dichloromethane (50 ml) at RT was added DIPEA (2.3 ml, 13.22 mmol). Subsequently, 6-bromo-2-chloro-3-methylquinoline-4-carbonyl chloride (1.41 g, 4.41 mmol, Example 3A) was added, and the mixture was stirred at RT for 16 h. Subsequently, water (100 ml) was added to the mixture, which was agitated. After phase separation, the aqueous phase was extracted once with dichloromethane (100 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 2.26 g (100% purity, 91% of theory) of the title compound were obtained.
[α]$_D^{20}$=+12.8°, 589 nm, c=0.59 g/100 ml, methanol
LC-MS (Method 2): R$_t$=1.33 min; MS (ESIpos): m/z=565/567/569 [M+H]$^+$
$^1$H-NMR (400 MHz, DMSO-d6) δ [ppm]: 1.157 (0.24), 1.175 (0.47), 1.193 (0.24), 1.371 (16.00), 1.816 (0.18), 1.820 (0.18), 1.989 (0.88), 2.028 (0.18), 2.033 (0.17), 2.045 (0.19), 2.051 (0.17), 2.065 (0.28), 2.077 (0.96), 2.093 (0.81), 2.110 (0.29), 2.114 (0.28), 2.213 (0.28), 3.569 (0.16), 3.589 (0.19), 3.713 (0.29), 4.021 (0.20), 4.039 (0.20), 7.279 (0.27), 7.297 (0.20), 7.360 (0.17), 7.378 (0.29), 7.396 (0.16), 7.448 (0.58), 7.451 (0.58), 7.468 (0.48), 7.471 (0.48), 7.491 (0.44), 7.509 (0.33), 7.894 (2.14), 7.899 (1.08), 8.847 (0.21), 8.861 (0.40), 8.874 (0.20).

Example 277A (−)-tert-Butyl 5-{[(6-bromo-2-chloro-3-methylquinolin-4-yl)carbonyl]amino}-4-(2-chlorophenyl)pentanoate (Enantiomer 2)

To a suspension of (+)-tert-butyl 5-amino-4-(2-chlorophenyl)pentanoate hydrochloride (2.12 g, 68% purity, 5.08 mmol, Example 275A) in dichloromethane (50 ml) at RT was added DIPEA (2.2 ml, 12.70 mmol). Subsequently, 6-bromo-2-chloro-3-methylquinoline-4-carbonyl chloride (1.35 g, 4.23 mmol, Example 3A) was added, and the mixture was stirred at RT for 16 h. Subsequently, water (100 ml) was added to the mixture, which was agitated. After phase separation, the aqueous phase was extracted once with dichloromethane (100 ml). The combined organic phases were dried over sodium sulfate, filtered and concentrated, and the residue was taken up in dichloromethane and purified by means of flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. 2.21 g (99% purity, 91% of theory) of the title compound were obtained.

$[\alpha]_D^{20}$=−12.2°, 589 nm, c=0.43 g/100 ml, methanol
LC-MS (Method 2): $R_t$=1.33 min; MS (ESIpos): m/z=565/567/569 [M+H]$^+$
$^1$H-NMR (400 MHz, DMSO-d6) δ [ppm]: −0.008 (0.24), 0.008 (0.21), 1.157 (0.30), 1.175 (0.59), 1.193 (0.30), 1.371 (16.00), 1.815 (0.17), 1.989 (1.13), 2.027 (0.17), 2.045 (0.18), 2.050 (0.16), 2.064 (0.27), 2.076 (0.96), 2.092 (0.80), 2.109 (0.28), 2.210 (0.28), 3.588 (0.19), 3.712 (0.28), 4.021 (0.26), 4.039 (0.26), 7.279 (0.27), 7.298 (0.19), 7.359 (0.17), 7.377 (0.29), 7.396 (0.16), 7.448 (0.59), 7.451 (0.63), 7.468 (0.50), 7.470 (0.52), 7.491 (0.44), 7.509 (0.33), 7.894 (2.22), 8.846 (0.20), 8.860 (0.39), 8.874 (0.20).

Example 278A (+)-tert-Butyl 5-[({6-bromo-3-methyl-2-[($^2$H$_{10}$)piperidin-1-yl]quinolin-4-yl}carbonyl)amino]-4-(2-chlorophenyl)pentanoate (Enantiomer 1)

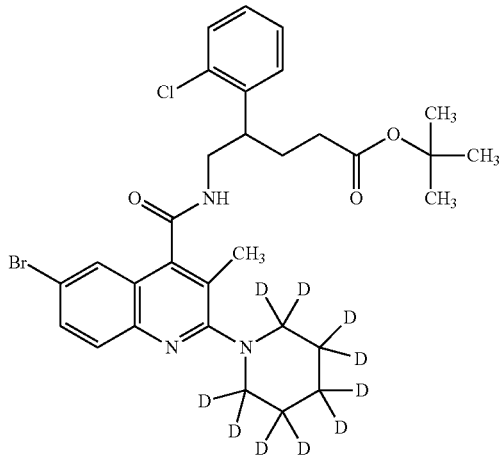 [SMILES: [2H]C1([2H])N(c2nc3ccc(Br)cc3c(C(=O)NCC(CCC(=O)OC(C)(C)C)c3ccccc3Cl)c2C)C([2H])([2H])C([2H])([2H])C([2H])([2H])C1([2H])[2H]]

To a solution of (+)-tert-butyl 5-{[(6-bromo-2-chloro-3-methylquinolin-4-yl)carbonyl]amino}-4-(2-chlorophenyl)pentanoate (283 mg, 0.5 mmol, Example 276A) in NMP (2 ml) was added piperidine-D11 (148 µl, 1.50 mmol), and the mixture was stirred at 110° C. for 2 h. After cooling to RT, water (75 ml) was added to the mixture, and the solids present were filtered off and washed twice with water (4 ml each time). Drying under reduced pressure gave 284 mg (92% purity, 83% of theory) of the title compound.

$[\alpha]_D^{20}$=+9.2°, 589 nm, c=0.39 g/100 ml, methanol
LC-MS (Method 1): $R_t$=2.79 min; MS (ESIpos): m/z=624/626 [M+H]$^+$
$^1$H-NMR (500 MHz, DMSO-d6) δ [ppm]: 1.087 (1.47), 1.369 (16.00), 1.814 (0.16), 2.055 (0.21), 2.075 (1.01), 2.085 (0.55), 2.099 (0.27), 2.104 (0.27), 2.129 (1.02), 2.695 (0.24), 3.585 (0.18), 3.671 (0.28), 7.255 (0.18), 7.271 (0.36), 7.285 (0.23), 7.356 (0.22), 7.371 (0.39), 7.385 (0.20), 7.440 (0.61), 7.442 (0.58), 7.456 (0.53), 7.458 (0.48), 7.479 (0.49), 7.482 (0.50), 7.495 (0.41), 7.624 (0.34), 7.641 (1.25), 7.651 (0.85), 7.655 (0.79), 7.669 (0.21), 7.673 (0.23), 8.709 (0.23), 8.720 (0.41), 8.732 (0.19).

Example 279A (−)-tert-Butyl 5-[({6-bromo-3-methyl-2-[($^2$H$_{10}$)piperidin-1-yl]quinolin-4-yl}carbonyl)amino]-4-(2-chlorophenyl)pentanoate (Enantiomer 2)

To a solution of (−)-tert-butyl 5-{[(6-bromo-2-chloro-3-methylquinolin-4-yl)carbonyl]amino}-4-(2-chlorophenyl)pentanoate (283 mg, 0.5 mmol, Example 277A) in NMP (2 ml) was added piperidine-D11 (148 µl, 1.50 mmol), and the mixture was stirred at 1100° C. for 4 h. After cooling to RT, water (75 ml) was added to the mixture, and the solids present were filtered off and washed twice with water (4 ml each time). Drying under reduced pressure gave 276 mg (100% purity, 88% of theory) of the title compound.

$[\alpha]_D^{20}$=−9.3°, 589 nm, c=0.33 g/100 ml, methanol
LC-MS (Method 1): $R_t$=2.78 min; MS (ESIpos): m/z=624/626 [M+H]$^+$
$^1$H-NMR (600 MHz, DMSO-d6) δ [ppm]: 1.087 (0.22), 1.369 (16.00), 1.807 (0.17), 2.041 (0.18), 2.045 (0.16), 2.053 (0.21), 2.056 (0.23), 2.073 (1.08), 2.083 (0.72), 2.095 (0.33), 2.098 (0.34), 2.126 (0.65), 2.695 (0.20), 3.585 (0.20), 3.670 (0.22), 7.262 (0.16), 7.274 (0.33), 7.286 (0.21), 7.361 (0.21), 7.373 (0.37), 7.385 (0.20), 7.444 (0.62), 7.446 (0.64), 7.458 (0.55), 7.459 (0.55), 7.487 (0.49), 7.499 (0.40), 7.628 (0.47), 7.643 (1.32), 7.656 (0.76), 7.660 (0.72), 7.671 (0.26), 7.674 (0.27), 8.734 (0.24), 8.744 (0.45), 8.753 (0.23).

Example 280A (−)-tert-Butyl 5-[({6-bromo-3-methyl-2-[($^2$H$_{10}$)piperidin-1-yl]quinolin-4-yl}carbonyl)amino]-4-[2-(trifluoromethyl)phenyl]pentanoate (Enantiomer 1)

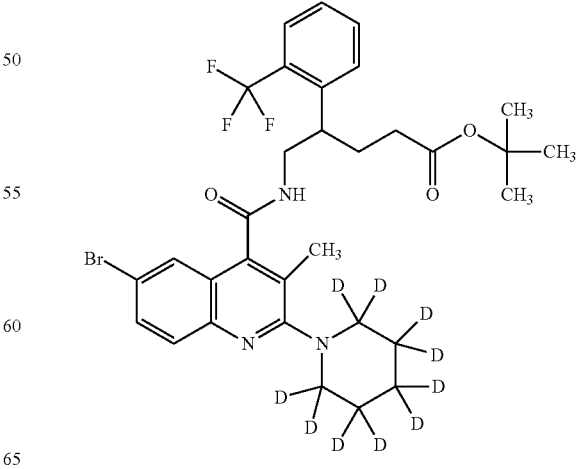

To a solution of (−)-tert-butyl 5-{[(6-bromo-2-chloro-3-methylquinolin-4-yl)carbonyl]amino}-4-[2-(trifluoromethyl)phenyl]pentanoate (234 mg, 391 µmol, Example 39A) in NMP (1.6 ml) was added piperidine-D11 (116 µl, 1.17 mmol), and the mixture was stirred at 1100° C. for 4 h. After cooling to RT, water (75 ml) was added to the mixture, and the solids present were filtered off and washed twice with water (4 ml each time). Drying under reduced pressure gave 228 mg (86% purity, 97% of theory) of the title compound.

$[\alpha]_D^{20}$=−14.0°, 589 nm, c=0.48 g/100 ml, methanol
LC-MS (Method 1): $R_t$=2.80 min; MS (ESIpos): m/z=658/660 [M+H]$^+$ $^1$H-NMR (600 MHz, DMSO-d6) δ [ppm]: 1.346 (16.00), 1.889 (0.17), 1.903 (0.18), 1.913 (0.17), 1.991 (0.23), 2.001 (0.18), 2.006 (0.26), 2.015 (0.21), 2.022 (0.23), 2.034 (0.30), 2.049 (0.29), 2.116 (0.17), 2.128 (0.26), 2.140 (0.30), 2.163 (0.54), 2.696 (0.21), 3.303 (0.21), 3.315 (0.26), 7.470 (0.21), 7.483 (0.41), 7.495 (0.24), 7.640 (0.39), 7.655 (1.29), 7.665 (0.77), 7.669 (0.70), 7.680 (0.22), 7.684 (0.24), 7.697 (0.18), 7.709 (0.43), 7.726 (0.60), 7.739 (0.99), 7.752 (0.27), 8.790 (0.23), 8.800 (0.46), 8.809 (0.23).

Example 281A (+)-tert-Butyl 5-[({6-bromo-3-methyl-2-[($^2$H$_{10}$)piperidin-1-yl]quinolin-4-yl}carbonyl)amino]-4-[2-(trifluoromethyl)phenyl]pentanoate (Enantiomer 2)

To a solution of (+)-tert-butyl 5-{[(6-bromo-2-chloro-3-methylquinolin-4-yl)carbonyl]amino}-4-[2-(trifluoromethyl)phenyl]pentanoate (234 mg, 391 µmol, Example 40A) in NMP (1.6 ml) was added piperidine-D11 (116 µl, 1.17 mmol), and the mixture was stirred at 1100° C. for 4 h. After cooling to RT, water (75 ml) was added to the mixture, and the solids present were filtered off and washed twice with water (4 ml each time). Drying under reduced pressure gave 221 mg (100% purity, 86% of theory) of the title compound.

$[\alpha]_D^{20}$=+13.9°, 589 nm, c=0.49 g/100 ml, methanol
LC-MS (Method 1): $R_t$=2.80 min; MS (ESIpos): m/z=658/660 [M+H]$^+$ $^1$H-NMR (600 MHz, DMSO-d6) δ [ppm]: 1.346 (16.00), 1.890 (0.18), 1.898 (0.18), 1.905 (0.19), 1.913 (0.18), 1.991 (0.24), 2.001 (0.19), 2.006 (0.28), 2.016 (0.22), 2.023 (0.25), 2.034 (0.32), 2.049 (0.31), 2.116 (0.19), 2.129 (0.28), 2.140 (0.33), 2.163 (0.58), 3.303 (0.19), 3.314 (0.26), 3.322 (0.25), 7.470 (0.23), 7.482 (0.45), 7.495 (0.27), 7.641 (0.40), 7.655 (1.33), 7.665 (0.80), 7.669 (0.72), 7.680 (0.23), 7.683 (0.24), 7.696 (0.20), 7.709 (0.47), 7.726 (0.64), 7.739 (1.05), 7.752 (0.29), 8.790 (0.25), 8.800 (0.49), 8.810 (0.24).

Example 282A (+)-tert-Butyl 5-[({6-bromo-3-methyl-2-[($^2$H$_{10}$)piperidin-1-yl]quinolin-4-yl}carbonyl)amino]-4-[2-(trifluoromethoxy)phenyl]pentanoate (Enantiomer 1)

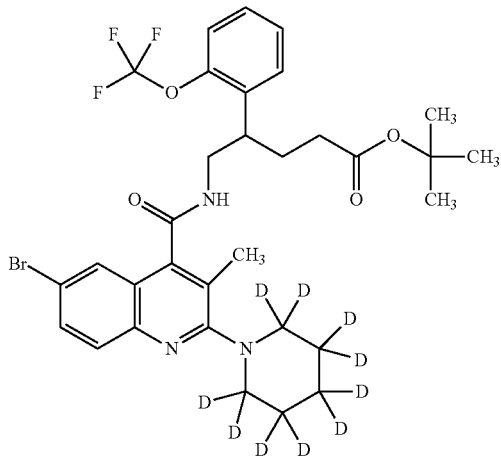 [SMILES: [2H]C1([2H])N(c2nc3ccc(Br)cc3c(C(=O)NCC(CCC(=O)OC(C)(C)C)c3ccccc3OC(F)(F)F)c2C)C([2H])([2H])C([2H])([2H])C([2H])([2H])C1([2H])[2H]]

To a solution of (+)-tert-butyl 5-{[(6-bromo-2-chloro-3-methylquinolin-4-yl)carbonyl]amino}-4-[2-(trifluoromethoxy)phenyl]pentanoate (241 mg, 391 µmol, Example 42A) in NMP (1.6 ml) was added piperidine-D11 (116 µl, 1.17 mmol), and the mixture was stirred at 1100° C. for 4 h. After cooling to RT, water (75 ml) was added to the mixture, and the solids present were filtered off and washed twice with water (4 ml each time). Drying under reduced pressure gave 211 mg (100% purity, 80% of theory) of the title compound.

$[\alpha]_D^{20}$=+12.4°, 589 nm, c=0.45 g/100 ml, DMSO
LC-MS (Method 1): $R_t$=2.82 min; MS (ESIpos): m/z=674/676 [M+H]$^+$ $^1$H-NMR (600 MHz, DMSO-d6) δ [ppm]: 1.360 (16.00), 1.374 (0.22), 1.809 (0.20), 1.824 (0.21), 2.038 (0.29), 2.052 (0.31), 2.055 (0.30), 2.065 (1.21), 2.085 (0.35), 2.089 (0.32), 2.097 (0.18), 2.138 (0.38), 3.383 (0.27), 3.615 (0.18), 3.626 (0.22), 3.636 (0.22), 3.648 (0.20), 3.659 (0.16), 7.352 (0.25), 7.364 (0.40), 7.394 (0.18), 7.407 (0.67), 7.413 (0.58), 7.419 (0.65), 7.554 (0.41), 7.564 (0.31), 7.569 (0.31), 7.637 (0.43), 7.652 (1.21), 7.665 (0.69), 7.668 (0.64), 7.679 (0.23), 7.683 (0.23), 8.758 (0.21), 8.767 (0.40), 8.777 (0.21).

Example 283A (−)-tert-Butyl 5-[({6-bromo-3-methyl-2-[($^2$H$_{10}$)piperidin-1-yl]quinolin-4-yl}carbonyl)amino]-4-[2-(trifluoromethoxy)phenyl]pentanoate (Enantiomer 2)

To a solution of (−)-tert-butyl 5-{[(6-bromo-2-chloro-3-methylquinolin-4-yl)carbonyl]amino}-4-[2-(trifluoromethoxy)phenyl]pentanoate (241 mg, 391 µmol, Example 43A) in NMP (1.6 ml) was added piperidine-D11 (116 µl, 1.17 mmol), and the mixture was stirred at 1100° C. for 4 h. After cooling to RT, water (75 ml) was added to the mixture, and the solids present were filtered off and washed twice with water (4 ml each time). Drying under reduced pressure gave 196 mg (94% purity, 69% of theory) of the title compound.

$[\alpha]_D^{20}$=−11.9°, 589 nm, c=0.49 g/l 00 ml, DMSO
LC-MS (Method 1): $R_t$=2.83 min; MS (ESIpos): m/z=674/676 [M+H]$^+$ $^1$H-NMR (600 MHz, DMSO-d6) δ [ppm]: 1.360 (16.00), 1.817 (1.14), 2.064 (3.81), 2.137 (2.64), 2.694 (0.27), 3.635 (1.64), 7.362 (1.83), 7.410 (3.01), 7.562 (1.69), 7.657 (2.27), 8.767 (1.34).

Example 284A (+)-tert-Butyl 5-[({6-bromo-3-methyl-2-[($^2$H8)pyrrolidin-1-yl]quinolin-4-yl}carbonyl)amino]-4-(2-chlorophenyl)pentanoate (Enantiomer 1)

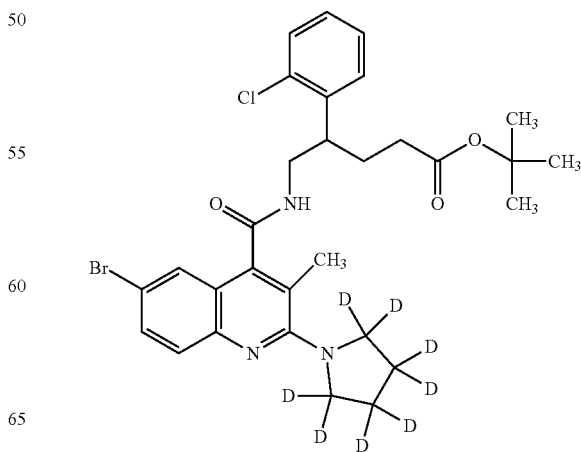

To a solution of (+)-tert-butyl 5-{[(6-bromo-2-chloro-3-methylquinolin-4-yl)carbonyl]amino}-4-(2-chlorophenyl)pentanoate (283 mg, 0.5 mmol, Example 276A) in NMP (2 ml) was added pyrrolidine-2,2,3,3,4,4,5,5-D8 (150 μl, 1.50 mmol), and the mixture was stirred at 1100° C. for 2 h. After cooling to RT, water (75 ml) was added to the mixture, and the solids present were filtered off and washed twice with water (4 ml each time). Drying under reduced pressure gave 254 mg (93% purity, 77% of theory) of the title compound.

$[\alpha]_D^{20}$=+9.0°, 589 nm, c=0.47 g/100 ml, methanol

LC-MS (Method 1): $R_t$=2.13 min; MS (ESIpos): m/z=608/610 [M+H]$^+$ $^1$H-NMR (500 MHz, DMSO-d6) δ [ppm]: 1.085 (1.40), 1.334 (0.21), 1.367 (16.00), 1.798 (0.21), 1.815 (0.28), 2.028 (0.20), 2.038 (0.23), 2.044 (0.23), 2.052 (0.34), 2.073 (1.32), 2.083 (0.78), 2.097 (0.37), 2.103 (0.32), 2.156 (0.92), 2.694 (0.20), 3.578 (0.30), 3.655 (0.31), 7.250 (0.26), 7.266 (0.49), 7.281 (0.32), 7.352 (0.34), 7.367 (0.56), 7.381 (0.34), 7.434 (0.82), 7.449 (0.69), 7.468 (0.97), 7.474 (0.78), 7.486 (1.43), 7.545 (0.71), 7.549 (0.68), 7.562 (0.47), 7.567 (0.44), 8.658 (0.31), 8.669 (0.50), 8.680 (0.26).

Example 285A (−)-tert-Butyl 5-[({6-bromo-3-methyl-2-[($^2$H8)pyrrolidin-1-yl]quinolin-4-yl}carbonyl)amino]-4-(2-chlorophenyl)pentanoate (Enantiomer 2)

To a solution of (−)-tert-butyl 5-{[(6-bromo-2-chloro-3-methylquinolin-4-yl)carbonyl]amino}-4-(2-chlorophenyl)pentanoate (283 mg, 0.5 mmol, Example 277A) in NMP (2 ml) was added pyrrolidine-2,2,3,3,4,4,5,5-D8 (150 μl, 1.50 mmol), and the mixture was stirred at 1100° C. for 2 h. After cooling to RT, water (75 ml) was added to the mixture, and the solids present were filtered off and washed twice with water (4 ml each time). Drying under reduced pressure gave 274 mg (100% purity, 90% of theory) of the title compound.

$[\alpha]_D^{20}$=−9.2°, 589 nm, c=0.37 g/100 ml, methanol

LC-MS (Method 1): $R_t$=2.11 min; MS (ESIpos): m/z=608/610 [M+H]$^+$ $^1$H-NMR (600 MHz, DMSO-d6) δ [ppm]: 1.085 (0.23), 1.367 (16.00), 1.809 (0.17), 2.039 (0.17), 2.051 (0.20), 2.055 (0.24), 2.072 (0.92), 2.081 (0.59), 2.093 (0.27), 2.098 (0.25), 2.152 (0.30), 2.162 (0.29), 2.175 (0.22), 2.694 (0.25), 3.580 (0.19), 7.268 (0.25), 7.280 (0.18), 7.357 (0.18), 7.369 (0.29), 7.381 (0.17), 7.437 (0.60), 7.439 (0.60), 7.451 (0.53), 7.452 (0.51), 7.471 (0.89), 7.482 (0.51), 7.486 (1.32), 7.493 (0.39), 7.550 (0.57), 7.553 (0.53), 7.564 (0.40), 7.568 (0.38), 8.686 (0.18), 8.695 (0.32), 8.703 (0.18).

Example 286A (−)-tert-Butyl 5-[({6-bromo-3-methyl-2-[($^2$H8)pyrrolidin-1-yl]quinolin-4-yl}carbonyl)amino]-4-[2-(trifluoromethyl)phenyl]pentanoate (Enantiomer 1)

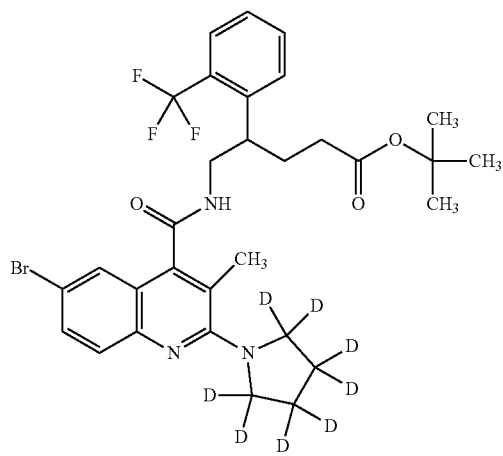 [SMILES: [2H]C1([2H])N(c2nc3ccc(Br)cc3c(C(=O)NCC(CCC(=O)OC(C)(C)C)c3ccccc3C(F)(F)F)c2C)C([2H])([2H])C([2H])([2H])C1([2H])[2H]]

To a solution of (−)-tert-butyl 5-{[(6-bromo-2-chloro-3-methylquinolin-4-yl)carbonyl]amino}-4-[2-(trifluoromethyl)phenyl]pentanoate (234 mg, 391 μmol, Example 39A) in NMP (1.6 ml) was added pyrrolidine-2,2,3,3,4,4,5,5-D8 (98 μl, 1.17 mmol), and the mixture was stirred at 110° C. for 3 h. After cooling to RT, water (75 ml) was added to the mixture, and the solids present were filtered off and washed twice with water (4 ml each time). Drying under reduced pressure gave 218 mg (100% purity, 87% of theory) of the title compound.

$[\alpha]_D^{20}$=−13.1°, 589 nm, c=0.44 g/100 ml, methanol

LC-MS (Method 1): $R_t$=2.16 min; MS (ESIpos): m/z=642/644 [M+H]$^+$ $^1$H-NMR (600 MHz, DMSO-d6) δ [ppm]: 1.324 (0.18), 1.345 (16.00), 1.890 (0.20), 1.898 (0.21), 1.904 (0.21), 1.913 (0.21), 1.987 (0.25), 1.997 (0.20), 2.002 (0.28), 2.012 (0.21), 2.027 (0.24), 2.038 (0.33), 2.053 (0.33), 2.065 (0.17), 2.103 (0.18), 2.113 (0.24), 2.125 (0.32), 2.136 (0.33), 2.148 (0.28), 2.163 (0.25), 2.177 (0.27), 2.190 (0.23), 2.696 (0.25), 3.302 (0.24), 3.313 (0.29), 7.465 (0.22), 7.478 (0.42), 7.484 (0.92), 7.499 (1.13), 7.559 (0.59), 7.562 (0.58), 7.574 (0.41), 7.577 (0.41), 7.694 (0.20), 7.706 (0.48), 7.719 (0.84), 7.736 (0.81), 7.750 (0.34), 8.746 (0.35).

Example 287A (+)-tert-Butyl 5-[({6-bromo-3-methyl-2-[($^2$H8)pyrrolidin-1-yl]quinolin-4-yl}carbonyl)amino]-4-[2-(trifluoromethyl)phenyl]pentanoate (Enantiomer 2)

To a solution of (+)-tert-butyl 5-{[(6-bromo-2-chloro-3-methylquinolin-4-yl)carbonyl]amino}-4-[2-(trifluoromethyl)phenyl]pentanoate (234 mg, 391 μmol, Example 40A) in NMP (1.6 ml) was added pyrrolidine-2,2,3,3,4,4,5,5-D8 (98 μl, 1.17 mmol), and the mixture was stirred at 110° C. for 3 h. After cooling to RT, water (75 ml) was added to the mixture, and the solids present were filtered off and washed twice with water (4 ml each time). Drying under reduced pressure gave 239 mg (100% purity, 95% of theory) of the title compound.

$[\alpha]_D^{20}$=+14.1°, 589 nm, c=0.44 g/100 ml, methanol

LC-MS (Method 1): $R_t$=2.16 min; MS (ESIpos): m/z=642/644 [M+H]$^+$ $^1$H-NMR (600 MHz, DMSO-d6) δ [ppm]: 1.345 (16.00), 1.890 (0.16), 1.897 (0.17), 1.904 (0.17), 1.913 (0.17), 1.987 (0.22), 1.997 (0.17), 2.002 (0.24), 2.012 (0.18), 2.027 (0.21), 2.038 (0.30), 2.053 (0.30), 2.112 (0.19), 2.125 (0.27), 2.136 (0.27), 2.144 (0.22), 2.148 (0.22), 2.159 (0.20), 2.176 (0.21), 2.186 (0.18), 2.696 (0.17), 3.302 (0.19), 3.313 (0.23), 7.465 (0.18), 7.477 (0.35), 7.484 (0.89), 7.499 (1.12), 7.559 (0.56), 7.562 (0.52), 7.573 (0.39), 7.577 (0.37), 7.694 (0.17), 7.706 (0.41), 7.719 (0.73), 7.736 (0.68), 7.750 (0.28), 8.736 (0.17), 8.745 (0.30).

Example 288A (+)-tert-Butyl 5-[({6-bromo-3-methyl-2-[($^2$H8)pyrrolidin-1-yl]quinolin-4-yl}carbonyl)amino]-4-[2-(trifluoromethoxy)phenyl]pentanoate (Enantiomer 1)

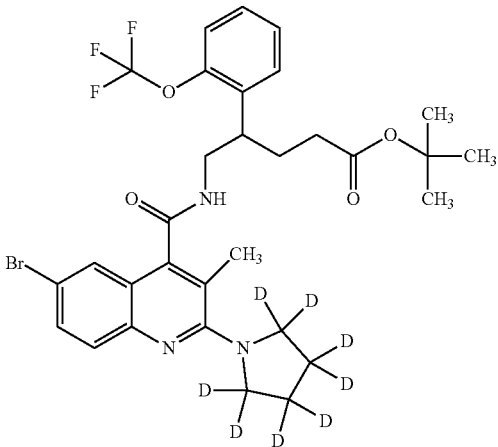 [SMILES: [2H]C1([2H])N(c2nc3ccc(Br)cc3c(C(=O)NCC(CCC(=O)OC(C)(C)C)c3ccccc3OC(F)(F)F)c2C)C([2H])([2H])C([2H])([2H])C1([2H])[2H]]

To a solution of (+)-tert-butyl 5-{[(6-bromo-2-chloro-3-methylquinolin-4-yl)carbonyl]amino}-4-[2-(trifluoromethoxy)phenyl]pentanoate (241 mg, 391 μmol, Example 42A) in NMP (1.6 ml) was added pyrrolidine-2,2,3,3,4,4,5,5-D8 (98 μl, 1.17 mmol), and the mixture was stirred at 1100° C. for 2 h. After cooling to RT, water (75 ml) was added to the mixture, and the solids present were filtered off and washed twice with water (4 ml each time). Drying under reduced pressure gave 241 mg (98% purity, 91% of theory) of the title compound.

[α]$_D^{20}$=+13.9°, 589 nm, c=0.46 g/100 ml, methanol

LC-MS (Method 1): R$_t$=2.22 min; MS (ESIpos): m/z=658/660 [M+H]$^+$ $^1$H-NMR (600 MHz, DMSO-d6) δ [ppm]: 1.358 (16.00), 1.372 (0.17), 1.806 (0.22), 1.823 (0.20), 2.039 (0.27), 2.049 (0.34), 2.062 (1.24), 2.080 (0.32), 2.084 (0.26), 2.16 (0.14), 3.369 (0.20), 3.381 (0.20), 3.61 (0.14), 3.65 (0.15), 7.345 (0.26), 7.357 (0.41), 7.402 (0.47), 7.407 (0.47), 7.414 (0.50), 7.478 (0.71), 7.493 (0.98), 7.550 (0.42), 7.557 (0.64), 7.561 (0.73), 7.565 (0.37), 7.572 (0.36), 7.575 (0.33), 8.715 (0.25).

Example 289A (−)-tert-Butyl 5-[({6-bromo-3-methyl-2-[($^2$H8)pyrrolidin-1-yl]quinolin-4-yl}carbonyl)amino]-4-[2-(trifluoromethoxy)phenyl]pentanoate (Enantiomer 2)

To a solution of (−)-tert-butyl 5-{[(6-bromo-2-chloro-3-methylquinolin-4-yl)carbonyl]amino}-4-[2-(trifluoromethoxy)phenyl]pentanoate (241 mg, 391 μmol, Example 43A) in NMP (1.6 ml) was added pyrrolidine-2,2,3,3,4,4,5,5-D8 (98 μl, 1.17 mmol), and the mixture was stirred at 110° C. for 3 h. After cooling to RT, water (75 ml) was added to the mixture, and the solids present were filtered off and washed twice with water (4 ml each time). Drying under reduced pressure gave 225 mg (100% purity, 88% of theory) of the title compound.

[α]$_D^{20}$=−13.7°, 589 nm, c=0.43 g/100 ml, methanol

LC-MS (Method 1): R$_t$=2.24 min; MS (ESIpos): m/z=658/660 [M+H]$^+$ $^1$H-NMR (600 MHz, DMSO-d6) δ [ppm]: 1.359 (16.00), 1.807 (0.21), 1.824 (0.20), 2.040 (0.26), 2.050 (0.33), 2.064 (1.21), 2.081 (0.31), 2.086 (0.25), 2.16 (0.14), 3.383 (0.24), 3.61 (0.13), 3.65 (0.13), 7.345 (0.25), 7.355 (0.33), 7.358 (0.41), 7.402 (0.47), 7.408 (0.47), 7.414 (0.49), 7.480 (0.71), 7.495 (0.99), 7.550 (0.40), 7.553 (0.33), 7.558 (0.60), 7.562 (0.71), 7.565 (0.38), 7.573 (0.35), 7.576 (0.33), 8.718 (0.24).

Example 290A tert-Butyl 5-[({6-bromo-3-methyl-2-[($^2$H8)pyrrolidin-1-yl]quinolin-4-yl}carbonyl)amino]-4-(2-chloro-3,6-difluorophenyl)pentanoate (Enantiomer 1)

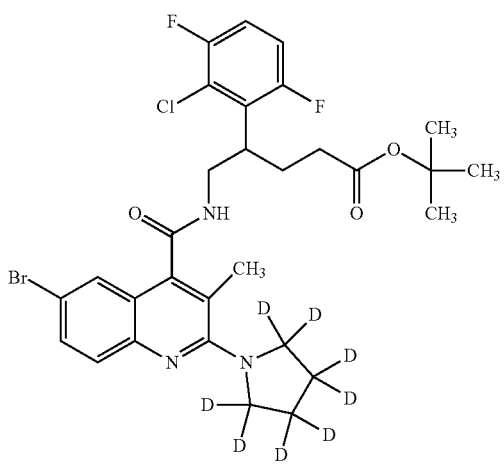 [SMILES: [2H]C1([2H])N(c2nc3ccc(Br)cc3c(C(=O)NCC(CCC(=O)OC(C)(C)C)c3c(F)ccc(F)c3Cl)c2C)C([2H])([2H])C([2H])([2H])C1([2H])[2H]]

To a solution of (+)-tert-butyl 5-{[(6-bromo-2-chloro-3-methylquinolin-4-yl)carbonyl]amino}-4-(2-chloro-3,6-difluorophenyl)pentanoate (241 mg, 400 μmol, Example 48A) in NMP (1.6 ml) was added pyrrolidine-2,2,3,3,4,4,5,5-D8 (100 μl, 1.20 mmol), and the mixture was stirred at 110° C. for 20 h. After cooling to RT, water (100 ml) was added to the mixture, which was extracted twice with ethyl acetate (80 ml each time). The combined organic phases were dried over sodium sulfate, filtered and concentrated, and the residue was purified by preparative HPLC (Method 32). The combined target fractions were concentrated, and the residue was lyophilized from acetonitrile/water. Two fractions were obtained: Obtained as fraction 1 were 34 mg (100% purity) of (+)-5-[({6-bromo-3-methyl-2-[($^2$H$_8$)pyrrolidin-1-yl]quinolin-4-yl}carbonyl)amino]-4-(2-chloro-3,6-difluorophenyl)pentanoic acid (see Example 281, Method B). Obtained as fraction 2 were 42 mg (93% purity, 15% of theory, see analysis) of the title compound.

LC-MS (Method 1): R$_t$=2.14 min; MS (ESIpos): m/z=644/646 [M+H]$^+$ $^1$H-NMR (600 MHz, DMSO-d6) δ [ppm]: 1.231 (0.25), 1.359 (16.00), 2.053 (0.22), 2.061 (0.26), 2.074 (0.26), 2.084 (0.19), 2.139 (0.80), 2.151 (1.21), 2.162 (0.89), 3.689 (0.28), 7.302 (0.28), 7.413 (0.24), 7.475 (1.03), 7.490 (1.40), 7.558 (0.72), 7.562 (0.66), 7.573 (0.51), 7.576 (0.48), 8.786 (0.36).

Example 291A tert-Butyl 5-[({6-bromo-3-methyl-2-[($^2$H$_8$)pyrrolidin-1-yl]quinolin-4-yl}carbonyl)amino]-4-(2-chloro-3,6-difluorophenyl)pentanoate (Enantiomer 2)

To a solution of (−)-tert-butyl 5-{[(6-bromo-2-chloro-3-methylquinolin-4-yl)carbonyl]amino}-4-(2-chloro-3,6-difluorophenyl)pentanoate (241 mg, 400 μmol, Example 49A)

in NMP (1.6 ml) was added pyrrolidine-2,2,3,3,4,4,5,5-D8 (100 µl, 1.20 mmol), and the mixture was stirred at 110° C. for 20 h. After cooling to RT, water (100 ml) was added to the mixture, which was extracted twice with ethyl acetate (80 ml each time). The combined organic phases were dried over sodium sulfate, filtered and concentrated, and the residue was purified by preparative HPLC (Method 32). The combined target fractions were concentrated, and the residue was lyophilized from acetonitrile/water. Two fractions were obtained: Obtained as fraction 1 were 55 mg (100% purity) of the (−)-5-[({6-bromo-3-methyl-2-[($^2$H$_8$)pyrrolidin-1-yl]quinolin-4-yl}carbonyl)amino]-4-(2-chloro-3,6-difluorophenyl)pentanoic acid described in Example 282. Obtained as fraction 2 were 24 mg (100% purity, 9% of theory, see analysis) of the title compound.

LC-MS (Method 1): $R_t$=2.09 min; MS (ESIpos): m/z=644/646 [M+H]$^+$ $^1$H-NMR (600 MHz, DMSO-d6) δ [ppm]: 1.231 (0.36), 1.359 (16.00), 1.962 (0.21), 2.054 (0.30), 2.063 (0.36), 2.075 (0.36), 2.086 (0.28), 2.097 (0.23), 2.141 (1.07), 2.152 (1.57), 3.692 (0.39), 3.751 (0.22), 7.301 (0.37), 7.412 (0.33), 7.476 (0.97), 7.491 (1.32), 7.558 (0.76), 7.573 (0.56), 8.786 (0.47).

Example 292A tert-Butyl (4R)-5-({[6-bromo-3-methyl-2-(pyrrolidin-1-yl)quinolin-4-yl]carbonyl}amino)-4-(2-chlorophenyl)pentanoate (Enantiomer 1)

[For structural formula see Example 79A (racemate)]

To a solution of (+)-tert-butyl 5-{[(6-bromo-2-chloro-3-methylquinolin-4-yl)carbonyl]amino}-4-(2-chlorophenyl)pentanoate (2.30 g, 4.06 mmol, Example 276A) in NMP (34 ml) was added pyrrolidine (1.0 ml, 12.18 mmol), and the mixture was stirred at 100° C. for 17 h. After cooling to RT, the mixture was concentrated, and water (100 ml) and ethyl acetate (100 ml) were added to the residue, which was agitated. After phase separation, the aqueous phase was extracted once with ethyl acetate (75 ml). The combined organic phases were washed once with saturated sodium chloride solution (150 ml), dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 93:7→6:4, Isolera One). The combined target fractions were concentrated, and the residue was dried under reduced pressure. 2.19 g (100% purity, 90% of theory) of the title compound were obtained.

$[α]_D^{20}$=+6.3°, 589 nm, c=0.45 g/100 ml, methanol

LC-MS (Method 2): $R_t$=1.08 min; MS (ESIpos): m/z=600/602 [M+H]$^+$ $^1$H-NMR (400 MHz, DMSO-d6) δ [ppm]: 1.175 (0.27), 1.367 (16.00), 1.794 (0.16), 1.814 (0.23), 1.870 (1.42), 1.988 (0.49), 2.034 (0.17), 2.044 (0.23), 2.051 (0.21), 2.072 (1.29), 2.083 (0.65), 2.100 (0.28), 2.107 (0.25), 2.158 (0.97), 3.567 (1.19), 3.657 (0.32), 7.248 (0.18), 7.266 (0.42), 7.285 (0.31), 7.349 (0.28), 7.368 (0.50), 7.386 (0.30), 7.432 (0.66), 7.434 (0.67), 7.452 (0.54), 7.454 (0.54), 7.467 (0.78), 7.473 (0.61), 7.490 (1.36), 7.544 (0.64), 7.550 (0.60), 7.567 (0.38), 7.572 (0.37), 8.657 (0.22), 8.671 (0.42), 8.685 (0.22).

The absolute configuration of the compound was determined by means of VCD spectroscopy (cf. Kuppens et al., "Determination of absolute configuration via vibrational circular dichroism", Drug Discovery Today: Technologies 2004, 1, 269-275 (2004); Stephens, P. J., "Vibrational circular dichroism spectroscopy: A new tool for the stereochemical characterization of chiral molecules", Computational Medicinal Chemistry for Drug Discovery 2004, 699-725).

The title compound therefore has R configuration.

Example 293A (−)-tert-Butyl 5-({[6-bromo-3-methyl-2-(pyrrolidin-1-yl)quinolin-4-yl]carbonyl}amino)-4-(2-chlorophenyl)pentanoate (Enantiomer 2)

To a solution of (−)-tert-butyl 5-{[(6-bromo-2-chloro-3-methylquinolin-4-yl)carbonyl]amino}-4-(2-chlorophenyl)pentanoate (2.25 g, 3.97 mmol, Example 277A) in NMP (34 ml) was added pyrrolidine (1.0 ml, 11.92 mmol), and the mixture was stirred at 100° C. for 17 h. After cooling to RT, the mixture was concentrated, and water (100 ml) and ethyl acetate (100 ml) were added to the residue, which was agitated. After phase separation, the aqueous phase was extracted once with ethyl acetate (75 ml). The combined organic phases were washed once with saturated sodium chloride solution (150 ml), dried over sodium sulfate, filtered and concentrated, and the residue was taken up in dichloromethane and purified by means of flash column chromatography (50 g silica gel Biotage Snap-Cartridge Ultra, cyclohexane/ethyl acetate gradient 93:7→6:4, Isolera One). The combined target fractions were concentrated, and the residue was dried under reduced pressure. 2.14 g (98% purity, 88% of theory) of the title compound were obtained.

$[α]_D^{20}$=−10.4°, 589 nm, c=0.46 g/100 ml, methanol

LC-MS (Method 2): $R_t$=1.08 min; MS (ESIpos): m/z=600/602 [M+H]$^+$ $^1$H-NMR (400 MHz, DMSO-d6) δ [ppm]: 1.157 (0.18), 1.175 (0.36), 1.192 (0.18), 1.367 (16.00), 1.814 (0.20), 1.870 (1.24), 1.988 (0.67), 2.044 (0.20), 2.051 (0.18), 2.072 (1.15), 2.083 (0.57), 2.100 (0.24), 2.108 (0.22), 2.158 (0.85), 3.311 (8.02), 3.657 (0.27), 7.248 (0.16), 7.266 (0.37), 7.286 (0.27), 7.349 (0.25), 7.368 (0.45), 7.386 (0.27), 7.432 (0.64), 7.434 (0.64), 7.451 (0.53), 7.454 (0.52), 7.467 (0.78), 7.473 (0.55), 7.476 (0.54), 7.490 (1.36), 7.544 (0.64), 7.550 (0.59), 7.567 (0.37), 7.572 (0.36), 8.657 (0.20), 8.671 (0.38), 8.686 (0.19).

WORKING EXAMPLES

Example 1

(+/−)-4-({[6-Bromo-3-methyl-2-(piperidin-1-yl)quinolin-4-yl]carbonyl}amino)-3-(2-chloro-6-fluorophenyl)butanoic acid (Racemate)

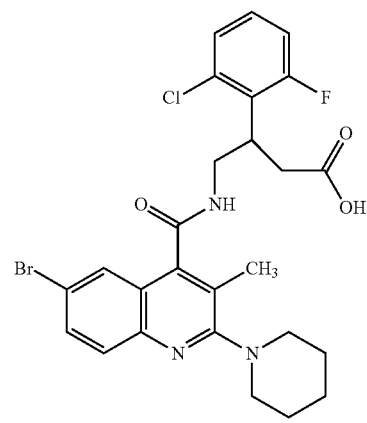 [SMILES: Cc1c(N2CCCCC2)nc2ccc(Br)cc2c1C(=O)NCC(CC(=O)O)c1c(F)cccc1Cl]

To a solution of (+/−)-tert-butyl 4-({[6-bromo-3-methyl-2-(piperidin-1-yl)quinolin-4-yl]carbonyl}amino)-3-(2-chloro-6-fluorophenyl)butanoate (150 mg, 242 μmol, racemate, Example 53A) in dichloromethane (2.3 ml) was added TFA (370 μl, 4.8 mmol), and the mixture was stirred at RT for 16 h. The mixture was then concentrated and repeatedly dichloromethane was added and the mixture was concentrated again. The residue was dissolved in acetonitrile and purified by means of preparative HPLC (Method 11). The combined target fractions were concentrated, and the residue was lyophilized. 125 mg (98% purity, 90% of theory) of the title compound were obtained.

LC-MS (Method 1): $R_t$=2.13 min; MS (ESIpos): m/z=562/564 [M+H]$^+$ $^1$H-NMR (400 MHz, DMSO-d6) δ [ppm]: −0.008 (3.57), 0.008 (2.96), 0.146 (0.41), 1.611 (4.57), 1.676 (8.94), 2.072 (0.69), 2.150 (16.00), 2.327 (0.68), 2.366 (0.48), 2.670 (0.79), 2.709 (0.98), 2.774 (1.22), 2.796 (3.04), 2.812 (3.09), 2.835 (1.38), 2.851 (1.09), 3.153 (11.54), 3.711 (1.62), 3.816 (1.22), 4.070 (2.46), 4.089 (3.00), 4.106 (2.39), 7.176 (1.51), 7.186 (1.95), 7.200 (2.59), 7.208 (2.12), 7.227 (2.29), 7.303 (2.07), 7.315 (8.43), 7.323 (9.04), 7.341 (2.19), 7.362 (0.73), 7.481 (0.59), 7.637 (3.03), 7.659 (13.06), 7.669 (8.47), 7.673 (7.54), 7.691 (1.75), 7.695 (1.86), 8.799 (2.25), 8.815 (4.44), 8.829 (2.18).

$^1$H-NMR (400 MHz, DMSO-d6) δ [ppm]: 12.21 (s, 1H), 8.81 (t, 1H), 7.68 (dd, 1H), 7.66 (d, 1H), 7.48 (br. s, 1H), 7.37-7.29 (m, 2H), 7.24-7.16 (m, 1H), 4.14-4.06 (m, 1H), 3.82 (br. s, 1H), 3.71 (br. s, 1H), 3.19-3.12 (m, 4H), 2.89-2.62 (m, 2H), 2.15 (s, 3H), 1.74-1.52 (m, 6H).

Separation of the Enantiomers:

The title compound (100 mg) was dissolved in isopropanol (2.5 ml) and separated into the enantiomers by means of preparative HPLC on chiral phase (see Examples 2 and 3) [column: Daicel Chiralpak ID, 5 μm, 250 mm×20 mm; flow rate: 20 ml/min; injection: 0.06 ml; eluent: 30% isopropanol/70% heptane; run time 15 min, isocratic]. The combined target fractions were concentrated and the residue was lyophilized. This was followed by repurification by means of preparative HPLC on achiral phase (acetonitrile/water gradient). The residue was lyophilized again.

Example 2

(−)-4-({[6-Bromo-3-methyl-2-(piperidin-1-yl)quinolin-4-yl]carbonyl}amino)-3-(2-chloro-6-fluorophenyl)butanoic acid (Enantiomer 1)

In the enantiomer separation described in Example 1, 29 mg (ee 99%) of the prepurified title compound were obtained as the enantiomer that eluted earlier. This was followed by repurification by means of preparative HPLC (Method 9). The combined target fractions were concentrated and the residue was taken up in dichloromethane and washed with saturated aqueous sodium hydrogencarbonate solution. The organic phase was dried over sodium sulfate, filtered and concentrated, and the residue was lyophilized. 13 mg (98% purity, 13% of theory) of the repurified title compound were obtained.

$[α]_D^{20}$=−16.9°, 589 nm, c=0.25 g/100 ml, methanol

LC-MS (Method 1): $R_t$=2.13 min; MS (ESIpos): m/z=562/564 [M+H]$^+$ $^1$H-NMR (400 MHz, DMSO-d6) δ [ppm]: −0.149 (1.61), −0.008 (16.00), 0.008 (13.21), 0.146 (1.69), 0.959 (0.44), 1.040 (0.73), 1.235 (2.64), 1.374 (0.95), 1.607 (3.23), 1.673 (6.17), 2.150 (9.39), 2.327 (2.50), 2.366 (2.57), 2.518 (10.06), 2.523 (8.00), 2.670 (3.23), 2.674 (2.50), 2.710 (3.38), 2.777 (1.25), 3.140 (7.93), 3.510 (1.54), 3.689 (1.03), 3.819 (0.81), 4.076 (1.39), 7.193 (1.47), 7.216 (1.17), 7.317 (5.06), 7.624 (1.91), 7.646 (8.22), 7.657 (5.28), 7.661 (4.70), 7.684 (1.25), 8.900 (0.73).

Example 3

(+)-4-({[6-Bromo-3-methyl-2-(piperidin-1-yl)quinolin-4-yl]carbonyl}amino)-3-(2-chloro-6-fluorophenyl)butanoic acid (Enantiomer 2)

In the enantiomer separation described in Example 1, 26 mg (ee 96%) of the prepurified title compound were obtained as the enantiomer that eluted later. This was followed by repurification by means of preparative HPLC (Method 9). The combined target fractions were concentrated and the residue was taken up in dichloromethane and washed with saturated aqueous sodium hydrogencarbonate solution. The organic phase was dried over sodium sulfate, filtered and concentrated, and the residue was lyophilized. 12 mg (98% purity, 12% of theory) of the repurified title compound were obtained.

$[α]_D^{20}$=+15.6°, 589 nm, c=0.25 g/100 ml, methanol

LC-MS (Method 1): $R_t$=2.13 min; MS (ESIpos): m/z=562/564 [M+H]$^+$ $^1$H-NMR (400 MHz, DMSO-d6) δ [ppm]: −0.150 (1.51), −0.008 (16.00), 0.008 (12.20), 0.146 (1.58), 1.234 (2.73), 1.372 (1.87), 1.610 (1.72), 1.669 (3.23), 2.149 (5.60), 2.327 (3.01), 2.366 (2.65), 2.523 (10.48), 2.669 (3.23), 2.709 (3.30), 2.799 (1.00), 3.139 (4.23), 3.509 (0.93), 3.707 (0.86), 4.084 (0.86), 7.198 (1.08), 7.321 (3.01), 7.625 (1.22), 7.647 (4.74), 7.658 (3.09), 7.663 (2.58), 7.680 (1.00), 8.842 (0.57).

Example 4

(+/−)-4-[({6-Bromo-3-methyl-2-[(2-phenylethyl)amino]quinolin-4-yl}carbonyl)amino]-3-(2-chloro-6-fluorophenyl)butanoic acid (Racemate)

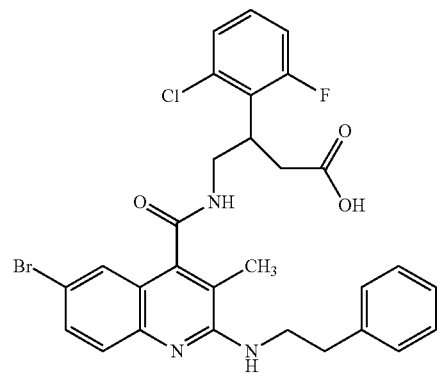 [SMILES: Cc1c(NCCc2ccccc2)nc2ccc(Br)cc2c1C(=O)NCC(CC(=O)O)c1c(F)cccc1Cl]

To a solution of (+/−)-tert-butyl 4-[({6-bromo-3-methyl-2-[(2-phenylethyl)amino]quinolin-4-yl}carbonyl)amino]-3-(2-chloro-6-fluorophenyl)butanoate (150 mg, 229 μmol, racemate, Example 54A) in dichloromethane (2.2 ml) was added TFA (350 μl, 4.6 mmol), and the mixture was stirred at RT for 16 h. The mixture was then concentrated and repeatedly dichloromethane was added and the mixture was concentrated again. The residue was dissolved in acetonitrile and purified by means of preparative HPLC (Method 9). The combined target fractions were concentrated, and the residue was dried under reduced pressure. 55 mg (98% purity, 39% of theory) of the title compound were obtained.

LC-MS (Method 2): $R_t$=0.92 min; MS (ESIpos): m/z=598/600 [M+H]$^+$ $^1$H-NMR (400 MHz, DMSO-d6) δ [ppm]: 12.23 (br. s, 1H), 8.88 (br. s, 1H), 8.02-7.06 (m, 11H), 4.07 (br. s, partially hidden, 1H), 3.93-3.63 (m, partly concealed, 4H), 3.04-2.90 (m, 2H), 2.88-2.68 (m, 2H), 2.11-1.83 (m, 3H).

Example 5

(+/−)-5-({[6-Bromo-3-methyl-2-(piperidin-1-yl)quinolin-4-yl]carbonyl}amino)-4-(2-chloro-5-fluorophenyl)pentanoic acid (Racemate)

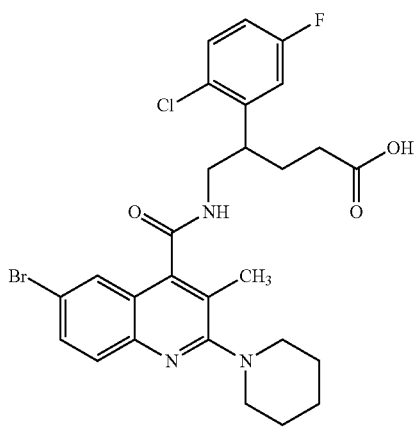 [SMILES: Cc1c(N2CCCCC2)nc2ccc(Br)cc2c1C(=O)NCC(CCC(=O)O)c1cc(F)ccc1Cl]

To a solution of (+/−)-tert-butyl 5-({[6-bromo-3-methyl-2-(piperidin-1-yl)quinolin-4-yl]carbonyl}-amino)-4-(2-chloro-5-fluorophenyl)pentanoate (90 mg, 98% purity, 139 µmol, racemate, Example 55A) in dichloromethane (990 µl) was added TFA (210 µl, 2.8 mmol), and the mixture was stirred at RT overnight. The mixture was then concentrated and repeatedly dichloromethane was added and the mixture was concentrated again. The residue was purified by preparative HPLC (Method 9). The combined target fractions were concentrated and the residue was admixed with ethyl acetate and saturated aqueous sodium hydrogencarbonate solution (20 ml of each) and agitated. After phase separation, the aqueous phase was extracted twice with ethyl acetate (20 ml each time). The combined organic phases were dried over sodium sulfate, filtered and concentrated, and the residue was dried under reduced pressure. 45 mg (98% purity, 55% of theory) of the title compound were obtained.

LC-MS (Method 1): $R_t$=2.22 min; MS (ESIpos): m/z=576/578 [M+H]$^+$ $^1$H-NMR (400 MHz, DMSO-d6) δ [ppm]: 1.235 (2.02), 1.605 (3.36), 1.670 (6.76), 1.768 (0.41), 1.782 (0.67), 1.804 (1.37), 1.824 (1.54), 1.835 (1.07), 1.865 (0.45), 1.899 (0.47), 2.020 (1.25), 2.041 (2.87), 2.068 (2.26), 2.080 (2.13), 2.090 (2.63), 2.101 (1.69), 2.128 (16.00), 2.160 (1.18), 2.176 (0.61), 2.689 (0.94), 2.731 (0.90), 2.890 (1.03), 3.132 (8.80), 3.585 (1.45), 3.689 (3.38), 7.124 (1.14), 7.144 (2.04), 7.159 (1.20), 7.165 (1.14), 7.385 (2.26), 7.392 (2.36), 7.410 (2.44), 7.417 (2.40), 7.484 (2.83), 7.497 (2.85), 7.506 (2.61), 7.519 (2.32), 7.622 (1.58), 7.644 (8.32), 7.651 (5.86), 7.655 (5.07), 7.674 (1.01), 7.678 (1.08), 8.719 (1.55), 8.734 (2.96), 8.747 (1.48).

$^1$H-NMR (400 MHz, DMSO-d6) δ [ppm]: 8.73 (t, 1H), 7.70-7.60 (m, 2H), 7.50 (dd, 1H), 7.46 (br. s, 1H, partly concealed), 7.40 (dd, 1H), 7.14 (td, 1H), 3.78-3.51 (m, 3H), 3.13 (br. s, 4H), 2.20-1.96 (m, 6H), 1.91-1.75 (m, 1H), 1.72-1.52 (m, 6H).

Example 6

(−)-5-({[6-Bromo-3-methyl-2-(piperidin-1-yl)quinolin-4-yl]carbonyl}amino)-4-(2-chloro-5-fluorophenyl)pentanoic acid (Enantiomer 1)

To a solution of (−)-tert-butyl 5-({[6-bromo-3-methyl-2-(piperidin-1-yl)quinolin-4-yl]carbonyl}amino)-4-(2-chloro-5-fluorophenyl)pentanoate (230 mg, 98% purity, 356 µmol, enantiomer 1, Example 56A) in dichloromethane (2.5 ml) was added TFA (550 µl, 7.1 mmol), and the mixture was stirred at RT overnight. Subsequently, TFA (270 µl, 3.6 mmol) was added again, and the mixture was stirred at RT for a further night. This was followed by concentration of the mixture, and repeated additions of dichloromethane followed by concentration again. The residue was purified by preparative HPLC (Method 8). The combined target fractions were concentrated and the residue was dried under reduced pressure. 165 mg (98% purity, ee 99%, 79% of theory) of the title compound were obtained.

$[α]_D^{20}$=−18.7°, 589 nm, c=0.38 g/100 ml, methanol

LC-MS (Method 1): $R_t$=2.18 min; MS (ESIpos): m/z=576/578 [M+H]$^+$ $^1$H-NMR (400 MHz, DMSO-d6) δ [ppm]: −0.008 (1.97), 0.008 (1.54), 1.604 (2.79), 1.670 (5.48), 1.786 (0.53), 1.808 (1.09), 1.829 (1.31), 1.850 (0.77), 2.012 (0.76), 2.023 (1.05), 2.041 (1.18), 2.055 (2.69), 2.082 (2.31), 2.095 (2.27), 2.102 (2.81), 2.128 (16.00), 2.149 (2.04), 2.172 (0.75), 3.132 (7.19), 3.590 (1.09), 3.692 (2.69), 7.119 (0.93), 7.126 (1.05), 7.140 (1.72), 7.147 (1.83), 7.160 (1.06), 7.168 (1.05), 7.390 (2.22), 7.397 (2.22), 7.415 (2.32), 7.422 (2.27), 7.457 (0.69), 7.485 (3.00), 7.499 (2.98), 7.508 (2.75), 7.521 (2.53), 7.622 (1.66), 7.644 (8.81), 7.652 (5.93), 7.657 (5.03), 7.674 (1.03), 7.679 (1.13), 8.711 (1.34), 8.726 (2.72), 8.740 (1.29), 12.066 (0.66).

$^1$H-NMR (400 MHz, DMSO-d6) δ [ppm]: 12.07 (br. s, 1H), 8.73 (t, 1H), 7.70-7.60 (m, 2H), 7.50 (dd, 1H), 7.46 (br. s, 1H, partly concealed), 7.41 (dd, 1H), 7.14 (td, 1H), 3.74-3.64 (m, 2H), 3.63-3.54 (m, 1H), 3.17-3.09 (m, 4H), 2.20-1.98 (m, 6H), 1.89-1.76 (m, 1H), 1.72-1.55 (m, 6H).

Example 7

(+)-5-({[6-Bromo-3-methyl-2-(piperidin-1-yl)quinolin-4-yl]carbonyl}amino)-4-(2-chloro-5-fluorophenyl)pentanoic acid (Enantiomer 2)

To a solution of (+)-tert-butyl 5-({[6-bromo-3-methyl-2-(piperidin-1-yl)quinolin-4-yl]carbonyl}-amino)-4-(2-chloro-5-fluorophenyl)pentanoate (200 mg, 98% purity, 310 µmol, enantiomer 2, Example 57A) in dichloromethane (2.2 ml) was added TFA (480 µl, 6.2 mmol), and the mixture was stirred at RT overnight. Subsequently, TFA (240 µl, 3.1 mmol) was added again, and the mixture was stirred at RT for a further night. This was followed by concentration of the mixture, and repeated additions of dichloromethane followed by concentration again. The residue was purified by preparative HPLC (Method 8). The combined target fractions were concentrated and the residue was dried under reduced pressure. 150 mg (98% purity, ee 99%, 82% of theory) of the title compound were obtained.

$[α]_D^{20}$=+17.4°, 589 nm, c=0.35 g/100 ml, methanol

LC-MS (Method 1): $R_t$=2.18 min; MS (ESIpos): m/z=576/578 [M+H]$^+$ $^1$H-NMR (400 MHz, DMSO-d6) δ [ppm]: −0.008 (1.88), 0.008 (1.49), 1.605 (2.71), 1.670 (5.29), 1.786 (0.50), 1.809 (1.07), 1.830 (1.30), 1.850 (0.76), 2.011 (0.75), 2.024 (0.98), 2.042 (1.13), 2.056 (2.63), 2.083 (2.20), 2.097 (2.19), 2.103 (2.78), 2.128 (16.00), 2.150 (2.00), 2.173 (0.74), 3.134 (6.98), 3.591 (1.11), 3.692 (2.69), 7.119 (0.86), 7.127 (1.00), 7.141 (1.66), 7.147 (1.80), 7.161 (1.03), 7.168 (1.04), 7.390 (2.13), 7.398 (2.20), 7.416 (2.28), 7.423 (2.26), 7.486 (2.99), 7.499 (2.96), 7.508 (2.77), 7.521 (2.58), 7.624 (1.61), 7.646 (8.66), 7.654 (5.91), 7.658 (5.11), 7.676 (1.01), 7.681 (1.11), 8.712 (1.32), 8.727 (2.75), 8.741 (1.30).

$^1$H-NMR (400 MHz, DMSO-d6) δ [ppm]: 12.06 (br. s, 1H), 8.73 (t, 1H), 7.70-7.61 (m, 2H), 7.50 (dd, 1H), 7.46 (br. s, 1H, partly concealed), 7.41 (dd, 1H), 7.14 (td, 1H), 3.75-3.64 (m, 2H), 3.63-3.53 (m, 1H), 3.19-3.08 (m, 4H), 2.21-1.98 (m, 6H), 1.88-1.75 (m, 1H), 1.72-1.52 (m, 6H).

Example 8

(+/−)-5-({[6-Bromo-2-(4,4-difluoropiperidin-1-yl)-3-methylquinolin-4-yl]carbonyl}amino)-4-(2-chloro-5-fluorophenyl)pentanoic acid (Racemate)

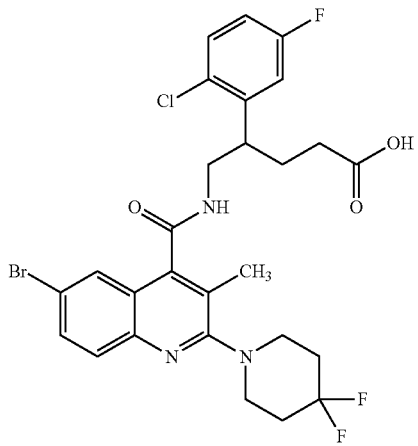 [SMILES: Cc1c(N2CCC(F)(F)CC2)nc2ccc(Br)cc2c1C(=O)NCC(CCC(=O)O)c1cc(F)ccc1Cl]

To a solution of (+/−)-tert-butyl 5-({[6-bromo-2-(4,4-difluoropiperidin-1-yl)-3-methylquinolin-4-yl]carbonyl}amino)-4-(2-chloro-5-fluorophenyl)pentanoate (19 mg, 72% purity, 20.4 µmol, racemate, Example 58A) in dichloromethane (140 µl) was added TFA (32 µl, 410 µmol), and the mixture was stirred at RT overnight. Subsequently, TFA (32 µl, 410 µmol) was added again, and the mixture was stirred at RT for a further night. This was followed by concentration of the mixture, and repeated additions of dichloromethane followed by concentration again. The residue was purified by preparative HPLC (Method 10). The combined target fractions were concentrated and the residue was dried under reduced pressure. 8 mg (98% purity, 61% of theory) of the title compound were obtained.

LC-MS (Method 2): $R_t$=1.14 min; MS (ESIpos): m/z=612/614 [M+H]$^+$ $^1$H-NMR (400 MHz, DMSO-d6) δ [ppm]: 1.242 (0.50), 1.789 (0.50), 1.811 (1.11), 1.832 (1.34), 1.854 (0.80), 2.012 (0.86), 2.025 (1.09), 2.044 (1.23), 2.058 (2.67), 2.085 (2.29), 2.105 (3.75), 2.119 (3.73), 2.134 (4.47), 2.167 (16.00), 3.302 (5.23), 3.315 (7.55), 3.598 (1.20), 3.702 (2.68), 4.410 (1.45), 6.962 (0.45), 7.090 (0.51), 7.121 (0.84), 7.128 (0.99), 7.148 (1.77), 7.163 (1.04), 7.169 (1.00), 7.218 (0.48), 7.398 (2.06), 7.405 (2.18), 7.423 (2.18), 7.430 (2.11), 7.486 (2.77), 7.499 (2.87), 7.508 (2.68), 7.521 (2.39), 7.661 (1.50), 7.684 (7.74), 7.691 (5.10), 7.696 (4.49), 7.714 (0.99), 7.718 (1.05), 8.736 (1.40), 8.750 (2.79), 8.764 (1.38).

$^1$H-NMR (400 MHz, DMSO-d6) δ [ppm]: 8.75 (t, 1H), 7.73-7.63 (m, 2H), 7.50 (dd, 1H), 7.46 (br. s, 1H, concealed), 7.41 (dd, 1H), 7.15 (td, 1H), 3.70 (br. s, 2H), 3.60 (br. s, 1H), 3.38-3.24 (m, 4H), 2.24-1.97 (m, 10H), 1.89-1.74 (m, 1H).

Example 9

(+/−)-5-({[6-Bromo-3-methyl-2-(morpholin-4-yl)quinolin-4-yl]carbonyl}amino)-4-(2-chloro-5-fluorophenyl)pentanoic acid (Racemate)

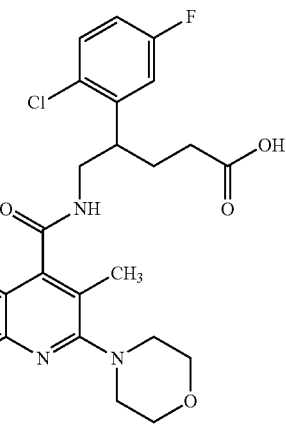

To a solution of (+/−)-tert-butyl 5-({[6-bromo-3-methyl-2-(morpholin-4-yl)quinolin-4-yl]carbonyl}amino)-4-(2-chloro-5-fluorophenyl)pentanoate (55 mg, 98% purity, 84.9 µmol, racemate, Example 59A) in dichloromethane (600 µl) was added TFA (130 µl, 1.7 mmol), and the mixture was stirred at RT overnight. The mixture was then concentrated and repeatedly dichloromethane was added and the mixture was concentrated again. The residue was purified by preparative HPLC (Method 9). The combined target fractions were concentrated and the residue was admixed with ethyl acetate and saturated aqueous sodium hydrogencarbonate solution (20 ml of each) and agitated. After phase separation, the aqueous phase was extracted twice with ethyl acetate (20 ml each time). The combined organic phases were dried over sodium sulfate, filtered and concentrated, and the residue was dried under reduced pressure. 37 mg (98% purity, 74% of theory) of the title compound were obtained.

LC-MS (Method 1): $R_t$=1.89 min; MS (ESIpos): m/z=578/580 [M+H]$^+$ $^1$H-NMR (400 MHz, DMSO-d6) δ [ppm]: −0.061 (0.65), 0.854 (0.64), 1.175 (0.42), 1.235 (4.42), 1.769 (0.44), 1.783 (0.75), 1.805 (1.56), 1.826 (1.77), 1.837 (1.11), 1.847 (0.98), 1.866 (0.49), 1.988 (0.93), 2.005 (1.13), 2.019 (1.47), 2.045 (3.35), 2.072 (2.85), 2.084 (2.55), 2.093 (3.17), 2.105 (1.88), 2.123 (3.22), 2.151 (16.00), 2.690 (0.60), 2.890 (0.46), 3.175 (11.00), 3.184 (8.56), 3.510 (0.50), 3.586 (1.72), 3.696 (3.93), 3.755 (9.55), 3.766 (12.93), 3.777 (8.58), 7.119 (1.16), 7.125 (1.35), 7.140 (2.19), 7.146 (2.28), 7.160 (1.31), 7.167 (1.25), 7.390 (2.73), 7.397 (2.79), 7.415 (2.82), 7.423 (2.73), 7.485 (3.89), 7.499 (3.92), 7.507 (3.56), 7.521 (3.08), 7.659 (1.54), 7.682 (12.34), 7.688 (7.12), 7.706 (0.79), 7.711 (0.94), 8.743 (1.86), 8.757 (3.48), 8.771 (1.67).

¹H-NMR (400 MHz, DMSO-d6) δ [ppm]: 12.03 (br. s, 1H), 8.76 (t, 1H), 7.73-7.63 (m, 2H), 7.50 (dd, 1H), 7.46 (br. s, 1H, concealed), 7.41 (dd, 1H), 7.14 (td, 1H), 3.82-3.64 (m, 6H), 3.59 (br. s, 1H), 3.20-3.12 (m, 4H), 2.21-1.95 (m, 6H), 1.88-1.75 (m, 1H).

Example 10

(+/−)-5-({[6-Bromo-2-(3,6-dihydropyridin-1(2H)-yl)-3-methylquinolin-4-yl]carbonyl}amino)-4-(2-chloro-5-fluorophenyl)pentanoic acid (Racemate)

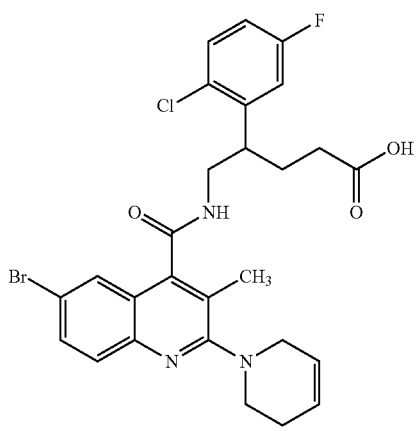 [SMILES: Cc1c(N2CC=CCC2)nc2ccc(Br)cc2c1C(=O)NCC(CCC(=O)O)c1cc(F)ccc1Cl]

To a solution of (+/−)-tert-butyl 5-({[6-bromo-2-(3,6-dihydropyridin-1(2H)-yl)-3-methylquinolin-4-yl]carbonyl}amino)-4-(2-chloro-5-fluorophenyl)pentanoate (50 mg, 79.2 µmol, racemate, Example 60A) in dichloromethane (580 µl) was added TFA (61 µl, 790 µmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated and the residue was lyophilized. 25 mg (98% purity, 53% of theory) of the title compound were obtained.

LC-MS (Method 2): $R_t$=1.12 min; MS (ESIpos): m/z=574/576 [M+H]$^+$

¹H-NMR (400 MHz, DMSO-d6) δ [ppm]: 1.369 (0.42), 1.787 (0.60), 1.809 (1.26), 1.829 (1.41), 1.841 (0.94), 1.870 (0.43), 1.989 (0.41), 2.010 (0.86), 2.027 (1.19), 2.046 (2.98), 2.073 (2.55), 2.085 (2.25), 2.093 (2.89), 2.106 (1.49), 2.124 (2.93), 2.141 (16.00), 2.163 (1.30), 2.180 (0.59), 2.304 (2.87), 3.275 (3.32), 3.309 (3.34), 3.590 (1.31), 3.795 (5.16), 5.817 (0.94), 5.843 (3.17), 5.863 (2.80), 5.889 (0.85), 7.117 (0.97), 7.124 (1.11), 7.139 (1.80), 7.145 (1.90), 7.159 (1.09), 7.166 (1.06), 7.390 (2.34), 7.398 (2.37), 7.416 (2.44), 7.423 (2.38), 7.484 (3.06), 7.497 (3.07), 7.506 (2.86), 7.519 (2.63), 7.617 (2.21), 7.639 (8.00), 7.653 (5.10), 7.658 (4.43), 7.675 (1.38), 7.680 (1.36), 8.731 (1.43), 8.745 (2.71), 8.759 (1.30).

¹H-NMR (400 MHz, DMSO-d6) δ [ppm]: 12.15 (br. s, 1H), 8.75 (t, 1H), 7.69-7.61 (m, 2H), 7.50 (dd, 1H), 7.46 (br. s, 1H, partly concealed), 7.41 (dd, 1H), 7.14 (td, 1H), 5.92-5.79 (m, 2H), 3.80 (br. s, 2H), 3.75-3.65 (m, 2H), 3.59 (br. s, 1H), 3.35-3.22 (concealed, 2H), 2.30 (br. s, 2H), 2.22-1.96 (m, 6H), 1.90-1.73 (m, 1H).

Example 11

(+/−)-5-({[6-Bromo-3-methyl-2-(thiomorpholin-4-yl)quinolin-4-yl]carbonyl}amino)-4-(2-chloro-5-fluorophenyl)pentanoic acid (Racemate)

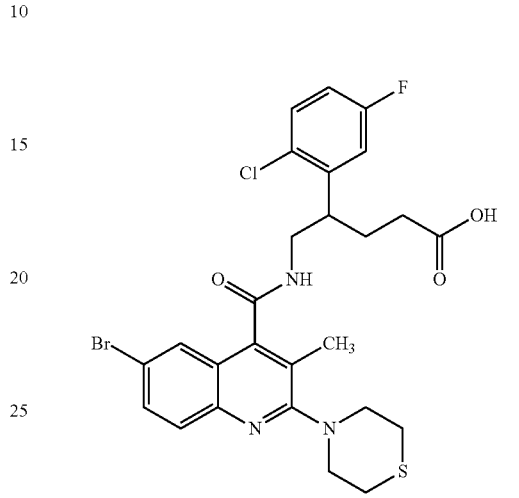

To a solution of (+/−)-tert-butyl 5-({[6-bromo-3-methyl-2-(thiomorpholin-4-yl)quinolin-4-yl]carbonyl}-amino)-4-(2-chloro-5-fluorophenyl)pentanoate (55 mg, 84.5 µmol, racemate, Example 61A) in dichloromethane (620 µl) was added TFA (65 µl, 840 µmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated and the residue was lyophilized. 41 mg (98% purity, 80% of theory) of the title compound were obtained.

LC-MS (Method 2): $R_t$=1.10 min; MS (ESIpos): m/z=594/596 [M+H]$^+$

¹H-NMR (400 MHz, DMSO-d6) δ [ppm]: −0.008 (1.05), 0.008 (0.98), 1.788 (0.49), 1.810 (1.08), 1.820 (0.71), 1.831 (1.32), 1.852 (0.79), 2.011 (0.78), 2.024 (1.04), 2.042 (1.18), 2.056 (2.70), 2.074 (0.77), 2.083 (2.28), 2.097 (2.36), 2.103 (2.82), 2.131 (16.00), 2.149 (2.40), 2.172 (0.86), 2.189 (0.44), 2.523 (0.52), 2.775 (6.19), 2.787 (7.27), 2.798 (6.78), 3.413 (6.57), 3.419 (6.69), 3.426 (7.12), 3.436 (6.16), 3.590 (1.20), 3.695 (2.52), 7.120 (0.86), 7.127 (1.01), 7.141 (1.67), 7.147 (1.76), 7.161 (1.04), 7.169 (1.00), 7.393 (2.19), 7.401 (2.24), 7.418 (2.29), 7.426 (2.20), 7.485 (3.17), 7.499 (3.20), 7.507 (2.93), 7.521 (2.65), 7.656 (1.27), 7.678 (9.12), 7.683 (6.85), 7.687 (5.30), 7.705 (0.85), 7.709 (0.91), 8.720 (1.43), 8.734 (2.85), 8.748 (1.36), 12.055 (0.73).

¹H-NMR (400 MHz, DMSO-d6) δ [ppm]: 12.06 (br. s, 1H), 8.73 (t, 1H), 7.73-7.63 (m, 2H), 7.50 (dd, 1H), 7.46 (br. s, 1H, partly concealed), 7.41 (dd, 1H), 7.14 (td, 1H), 3.69 (br. s, 2H), 3.59 (br. s, 1H), 3.46-3.39 (m, 4H), 2.83-2.75 (m, 4H), 2.21-1.97 (m, 6H), 1.89-1.75 (m, 1H).

Example 12

(+/−)-5-[({6-Bromo-2-[cis-2,6-dimethylmorpholin-4-yl]-3-methylquinolin-4-yl}carbonyl)amino]-4-(2-chloro-5-fluorophenyl)pentanoic acid (Racemate)

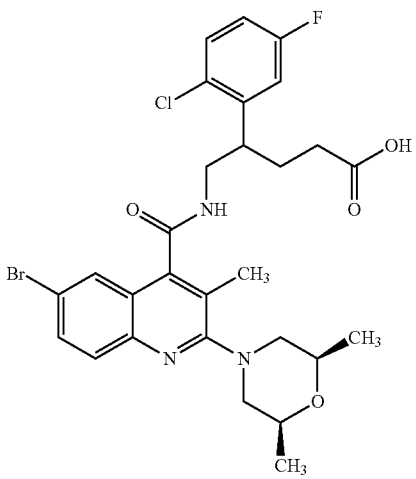 [SMILES: Cc1c(N2C[C@@H](C)O[C@@H](C)C2)nc2ccc(Br)cc2c1C(=O)NCC(CCC(=O)O)c1cc(F)ccc1Cl]

To a solution of (+/−)-tert-butyl 5-[({6-bromo-2-[cis-2,6-dimethylmorpholin-4-yl]-3-methylquinolin-4-yl}carbonyl)amino]-4-(2-chloro-5-fluorophenyl)pentanoate (70 mg, 106 µmol, racemate, Example 62A) in dichloromethane (780 µl) was added TFA (81 µl, 1.1 mmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated and the residue was lyophilized. 47 mg (98% purity, 71% of theory) of the title compound were obtained.

LC-MS (Method 2): $R_t$=1.10 min; MS (ESIpos): m/z=606/608 [M+H]$^+$ $^1$H-NMR (400 MHz, DMSO-d6) δ [ppm]: 1.134 (16.00), 1.149 (15.70), 1.793 (0.43), 1.814 (0.86), 1.835 (1.00), 1.856 (0.57), 2.013 (0.68), 2.026 (0.87), 2.045 (1.01), 2.057 (2.01), 2.084 (1.82), 2.098 (1.82), 2.104 (2.14), 2.119 (1.55), 2.132 (2.14), 2.157 (11.42), 2.190 (0.41), 2.469 (1.68), 3.431 (2.87), 3.462 (2.59), 3.589 (0.93), 3.693 (1.77), 3.756 (1.66), 3.776 (2.04), 7.120 (0.71), 7.127 (0.80), 7.142 (1.27), 7.148 (1.30), 7.162 (0.75), 7.169 (0.70), 7.391 (1.65), 7.398 (1.65), 7.416 (1.69), 7.423 (1.58), 7.486 (2.10), 7.499 (2.07), 7.508 (1.83), 7.521 (1.63), 7.655 (0.55), 7.676 (9.58), 8.710 (1.15), 8.725 (2.08), 8.739 (0.98), 12.063 (4.18).

$^1$H-NMR (400 MHz, DMSO-d6) δ [ppm]: 12.06 (s, 1H), 8.72 (t, 1H), 7.72-7.63 (m, 2H), 7.50 (dd, 1H), 7.47 (br. s, 1H, partly concealed), 7.41 (dd, 1H), 7.14 (td, 1H), 3.84-3.53 (m, 5H), 3.45 (br. d, 2H), 2.53-2.45 (concealed, 2H), 2.21-1.97 (m, 6H), 1.91-1.75 (m, 1H), 1.15 (s, 3H), 1.13 (s, 3H).

Example 13

(+/−)-5-({[6-Bromo-3-methyl-2-(pyrrolidin-1-yl)quinolin-4-yl]carbonyl}amino)-4-(2-chloro-5-fluorophenyl)pentanoic acid (Racemate)

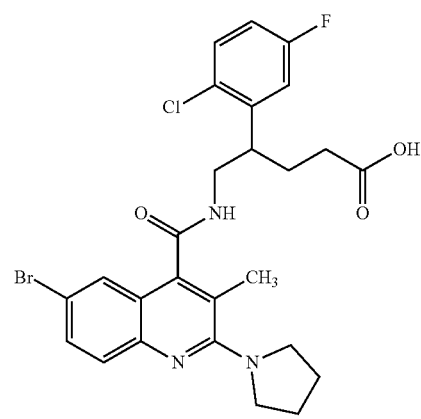 [SMILES: Cc1c(N2CCCC2)nc2ccc(Br)cc2c1C(=O)NCC(CCC(=O)O)c1cc(F)ccc1Cl]

To a solution of (+/−)-tert-butyl 5-({[6-bromo-3-methyl-2-(pyrrolidin-1-yl)quinolin-4-yl]carbonyl}-amino)-4-(2-chloro-5-fluorophenyl)pentanoate (63 mg, 102 µmol, racemate, Example 63A) in dichloromethane (750 µl) was added TFA (78 µl, 1.0 mmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 36 mg (98% purity, 62% of theory) of the title compound were obtained.

LC-MS (Method 2): $R_t$=0.77 min; MS (ESIpos): m/z=562/564 [M+H]$^+$ $^1$H-NMR (400 MHz, DMSO-d6) δ [ppm]: 12.06 (br. s, 1H), 8.68 (t, 1H), 7.59-7.53 (m, 1H), 7.50 (dd, 2H), 7.40 (dd, 1H), 7.35 (br. s, partly concealed), 7.14 (td, 1H), 3.68 (br. s, 2H), 3.57 (br. s, 5H), 2.26-1.97 (m, 6H), 1.94-1.74 (m, 5H).

Example 14

(+/−)-5-({[6-Bromo-3-methyl-2-(1,2-oxazolidin-2-yl)quinolin-4-yl]carbonyl}amino)-4-(2-chloro-5-fluorophenyl)pentanoic acid (Racemate)

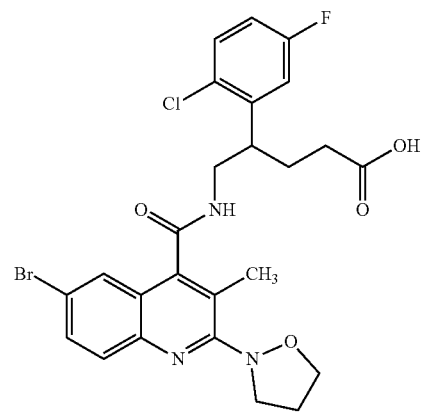 [SMILES: Cc1c(N2CCCO2)nc2ccc(Br)cc2c1C(=O)NCC(CCC(=O)O)c1cc(F)ccc1Cl]

To a solution of (+/−)-tert-butyl 5-({[6-bromo-3-methyl-2-(1,2-oxazolidin-2-yl)quinolin-4-yl]carbonyl}-amino)-4-(2-chloro-5-fluorophenyl)pentanoate (35 mg, 56.4 µmol, racemate, Example 64A) in dichloromethane (410 µl) was added TFA (43 µl, 560 µmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 24 mg (95% purity, 72% of theory) of the title compound were obtained.

LC-MS (Method 2): $R_t$=0.96 min; MS (ESIpos): m/z=564/566 [M+H]$^+$ $^1$H-NMR (400 MHz, DMSO-d6) δ [ppm]: −0.008 (1.04), 0.008 (0.83), 1.134 (1.33), 1.150 (1.34), 1.788 (0.58), 1.810 (1.36), 1.820 (0.87), 1.831 (1.64), 1.853 (1.06), 1.873 (0.44), 1.989 (0.45), 2.010 (0.97), 2.023 (1.32), 2.041 (1.43), 2.057 (3.36), 2.073 (2.58), 2.085 (2.55), 2.098 (2.36), 2.106 (2.63), 2.120 (1.78), 2.134 (2.29), 2.138 (2.23), 2.156 (2.79), 2.179 (1.33), 2.209 (10.75), 2.242 (4.23), 2.260 (5.79), 2.278 (4.24), 2.296 (1.31), 2.523 (0.63), 3.432 (0.53), 3.463 (0.64), 3.658 (0.84), 3.693 (2.87), 3.706 (3.75), 3.777 (2.81), 3.825 (4.26), 3.844 (7.14), 3.862 (3.86), 7.121 (0.95), 7.128 (1.11), 7.142 (1.89), 7.149 (1.96), 7.163 (1.16), 7.170 (1.12), 7.394 (2.57), 7.401 (2.60), 7.419 (2.65), 7.426 (2.51), 7.489 (3.30), 7.502 (3.52), 7.511 (3.35), 7.525 (3.11), 7.677 (0.86), 7.712 (0.64), 7.733 (16.00), 7.759 (0.50), 8.775 (1.61), 8.790 (3.19), 8.804 (1.53).

$^1$H-NMR (400 MHz, DMSO-d6) δ [ppm]: 8.79 (t, 1H), 7.78-7.70 (m, 2H), 7.51 (dd, 1H), 7.46 (br. s, 1H, concealed), 7.41 (dd, 1H), 7.15 (td, 1H), 3.84 (t, 2H), 3.78 (br. s, 2H), 3.74-3.67 (m, 2H), 3.65-3.55 (m, 1H), 2.32-1.95 (m, 8H), 1.90-1.74 (m, 1H).

Example 15

(+/−)-5-({[6-Bromo-2-(2,5-dihydro-1H-pyrrol-1-yl)-3-methylquinolin-4-yl]carbonyl}amino)-4-(2-chloro-5-fluorophenyl)pentanoic acid (Racemate)

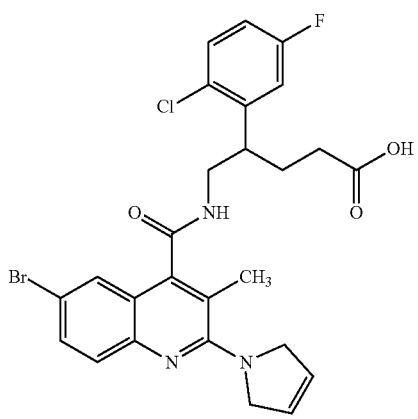 [SMILES: Cc1c(N2CC=CC2)nc2ccc(Br)cc2c1C(=O)NCC(CCC(=O)O)c1cc(F)ccc1Cl]

To a solution of (+/−)-tert-butyl 5-({[6-bromo-2-(2,5-dihydro-1H-pyrrol-1-yl)-3-methylquinolin-4-yl]carbonyl}amino)-4-(2-chloro-5-fluorophenyl)pentanoate (32 mg, 51.9 µmol, racemate, Example 65A) in dichloromethane (380 µl) was added TFA (40 µl, 520 µmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 20 mg (90% purity, 61% of theory) of the title compound were obtained.

LC-MS (Method 2): $R_t$=0.87 min; MS (ESIpos): m/z=560/562 [M+H]$^+$ $^1$H-NMR (400 MHz, DMSO-d6) δ [ppm]: 1.773 (0.50), 1.787 (0.88), 1.808 (1.83), 1.819 (1.42), 1.829 (2.14), 1.840 (1.55), 1.851 (1.30), 1.870 (0.65), 2.026 (1.76), 2.048 (4.09), 2.075 (3.34), 2.087 (3.15), 2.097 (3.64), 2.108 (2.21), 2.128 (2.86), 2.145 (2.35), 2.169 (1.45), 2.188 (2.40), 2.247 (7.74), 2.324 (0.57), 3.586 (1.76), 3.677 (2.88), 4.527 (3.34), 5.964 (16.00), 6.305 (1.64), 6.311 (2.40), 6.316 (1.56), 7.141 (2.44), 7.256 (1.95), 7.262 (2.79), 7.267 (1.88), 7.384 (3.11), 7.391 (3.20), 7.409 (3.34), 7.416 (3.32), 7.439 (0.90), 7.446 (0.82), 7.474 (5.90), 7.479 (3.94), 7.496 (10.52), 7.501 (4.70), 7.515 (3.18), 7.525 (0.90), 7.553 (4.95), 7.558 (4.50), 7.575 (2.94), 7.580 (2.80), 7.880 (3.13), 8.688 (1.91), 8.702 (3.51), 8.716 (1.74), 8.886 (0.68).

$^1$H-NMR (400 MHz, DMSO-d6) δ [ppm]: 12.09 (br. s, 1H), 8.70 (t, 1H), 7.56 (dd, 1H), 7.53-7.46 (m, 2H), 7.46 (broad, concealed, 1H), 7.40 (dd, 1H), 7.18-7.10 (m, 1H), 5.96 (s, 2H), 4.53 (br. s, 4H), 3.78-3.53 (m, 3H), 2.29-1.97 (m, 6H), 1.88-1.72 (m, 1H).

Example 16

5-[({6-Bromo-2-[3-hydroxypyrrolidin-1-yl]-3-methylquinolin-4-yl}carbonyl)amino]-4-(2-chloro-5-fluorophenyl)pentanoic acid (Diastereomer Mixture)

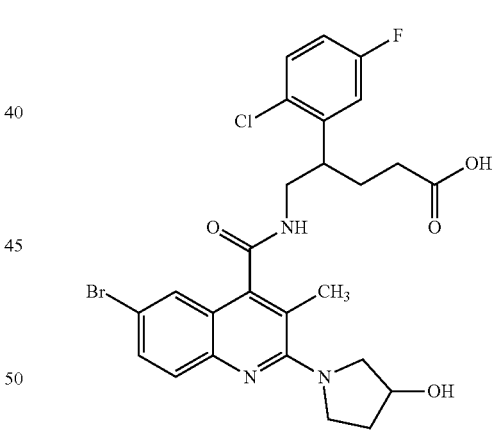

To a solution of tert-butyl 5-[({6-bromo-2-[3-hydroxypyrrolidin-1-yl]-3-methylquinolin-4-yl}carbonyl)amino]-4-(2-chloro-5-fluorophenyl)pentanoate (60 mg, 94.5 µmol, diastereomer mixture, Example 66A) in dichloromethane (690 µl) was added TFA (73 µl, 940 µmol), and the mixture was stirred at RT for two days. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 50 mg (98% purity, 90% of theory) of the title compound were obtained.

LC-MS (Method 2): $R_t$=0.69 min; MS (ESIpos): m/z=578/580 [M+H]$^+$

¹H-NMR (400 MHz, DMSO-d6) δ [ppm]: −0.008 (1.27), 0.008 (1.10), 1.772 (0.54), 1.786 (0.97), 1.808 (2.80), 1.830 (3.88), 1.850 (3.12), 1.920 (1.78), 1.938 (1.54), 1.988 (0.75), 2.023 (1.72), 2.040 (1.99), 2.053 (4.47), 2.081 (3.66), 2.094 (3.39), 2.102 (4.12), 2.115 (3.02), 2.147 (16.00), 2.171 (1.97), 2.189 (1.08), 2.327 (0.57), 2.523 (1.83), 2.669 (0.59), 2.710 (0.40), 3.356 (2.29), 3.569 (2.21), 3.667 (3.45), 3.678 (3.50), 3.782 (2.75), 4.331 (3.12), 4.898 (3.56), 4.905 (5.60), 4.912 (3.39), 7.130 (2.10), 7.138 (2.24), 7.149 (2.13), 7.262 (0.51), 7.381 (2.88), 7.388 (3.99), 7.406 (2.94), 7.414 (3.80), 7.466 (5.93), 7.480 (3.91), 7.488 (11.07), 7.500 (3.34), 7.514 (3.02), 7.544 (5.14), 7.566 (2.99), 8.699 (3.26), 12.057 (4.53).

¹H-NMR (400 MHz, DMSO-d6) δ [ppm]: 12.06 (br. s, 1H), 8.70 (br. t, 1H), 7.58-7.53 (m, 1H), 7.52-7.45 (m, 2H), 7.40 (br. dt, 1H), 7.34 (br. s, partly concealed, 1H), 7.19-7.09 (m, 1H), 4.91 (t, 1H), 4.33 (br. s, 1H), 3.88-3.47 (m, 7H), 2.19-1.78 (m, 9H).

Example 17

5-[({6-Bromo-3-methyl-2-[3-methylpiperidin-1-yl]quinolin-4-yl}carbonyl)amino]-4-(2-chloro-5-fluorophenyl)pentanoic acid (Diastereomer Mixture)

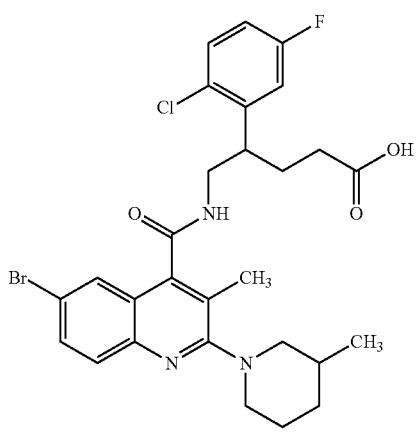 [SMILES: Cc1c(N2CCCC(C)C2)nc2ccc(Br)cc2c1C(=O)NCC(CCC(=O)O)c1cc(F)ccc1Cl]

To a solution of tert-butyl 5-[({6-bromo-3-methyl-2-[3-methylpiperidin-1-yl]quinolin-4-yl}carbonyl)amino]-4-(2-chloro-5-fluorophenyl)pentanoate (75 mg, 116 μmol, diastereomer mixture, Example 67A) in dichloromethane (850 μl) was added TFA (89 μl, 1.2 mmol), and the mixture was stirred at RT for two days. The mixture was then concentrated and repeatedly dichloromethane was added and the mixture was concentrated again. The residue was dissolved in acetonitrile and purified by means of preparative HPLC (Method 12). The combined target fractions were concentrated and the residue was admixed with ethyl acetate and saturated aqueous sodium hydrogencarbonate solution (10 ml of each) and agitated. After phase separation, the aqueous phase was extracted twice with ethyl acetate (10 ml each time). The combined organic phases were dried over sodium sulfate, filtered and concentrated, and the residue was lyophilized. 57 mg (98% purity, 82% of theory) of the title compound were obtained.

LC-MS (Method 1): $R_t$=2.34 min; MS (ESIpos): m/z=590/592 [M+H]⁺

¹H-NMR (400 MHz, DMSO-d6) δ [ppm]: −0.022 (0.66), −0.008 (1.50), 0.008 (1.14), 0.920 (8.53), 0.936 (8.61), 0.963 (0.41), 1.077 (0.96), 1.099 (1.00), 1.127 (0.40), 1.233 (1.61), 1.627 (0.77), 1.650 (0.89), 1.729 (1.77), 1.767 (1.86), 1.783 (2.28), 1.791 (2.42), 1.801 (2.33), 1.823 (2.39), 2.001 (0.74), 2.015 (1.13), 2.034 (2.73), 2.048 (0.97), 2.060 (2.13), 2.072 (1.97), 2.083 (2.19), 2.093 (1.23), 2.115 (2.53), 2.131 (16.00), 2.153 (1.13), 2.169 (0.45), 2.417 (0.53), 2.458 (0.99), 2.523 (0.79), 2.670 (0.67), 2.696 (0.88), 2.710 (1.15), 3.432 (1.94), 3.459 (2.87), 3.487 (1.47), 3.579 (1.20), 3.686 (2.45), 7.116 (0.84), 7.123 (0.97), 7.137 (1.62), 7.144 (1.72), 7.158 (0.99), 7.165 (0.98), 7.381 (2.07), 7.389 (2.10), 7.407 (2.19), 7.414 (2.11), 7.456 (0.62), 7.482 (2.69), 7.495 (2.67), 7.504 (2.47), 7.517 (2.35), 7.624 (0.93), 7.647 (9.27), 7.654 (5.14), 7.672 (0.63), 7.676 (0.73), 8.719 (1.20), 8.733 (2.27), 8.746 (1.13).

¹H-NMR (400 MHz, DMSO-d6) δ [ppm]: 12.26 (br. s, 1H), 8.73 (t, 1H), 7.69-7.61 (m, 2H), 7.50 (dd, 1H), 7.46 (br. s, partly concealed, 1H), 7.40 (dd, 1H), 7.14 (td, 1H), 3.76-3.40 (m, 5H), 2.80-2.61 (m, 1H), 2.48-2.34 (m, 1H), 2.20-1.95 (m, 6H), 1.88-1.55 (m, 5H), 1.17-1.01 (m, 1H), 0.93 (d, 3H).

Example 18

(+/−)-5-({[6-Bromo-3-methyl-2-(4-methylpiperidin-1-yl)quinolin-4-yl]carbonyl}amino)-4-(2-chloro-5-fluorophenyl)pentanoic acid (Racemate)

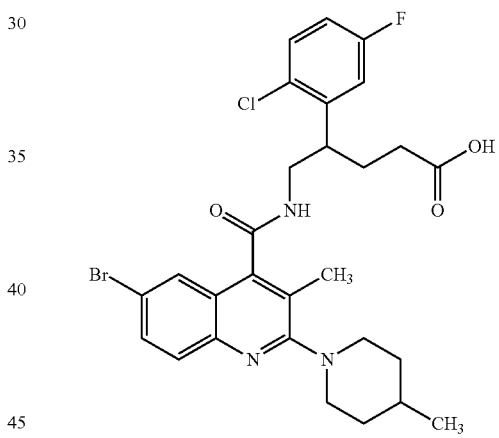

To a solution of (+/−)-tert-butyl 5-({[6-bromo-3-methyl-2-(4-methylpiperidin-1-yl)quinolin-4-yl]carbonyl}amino)-4-(2-chloro-5-fluorophenyl)pentanoate (70 mg, 108 μmol, racemate, Example 68A) in dichloromethane (790 μl) was added TFA (83 μl, 1.1 μmol), and the mixture was stirred at RT for two days. The mixture was then concentrated and repeatedly dichloromethane was added and the mixture was concentrated again. The residue was dissolved in acetonitrile and purified by means of preparative HPLC (Method 12). The combined target fractions were concentrated and the residue was admixed with ethyl acetate and saturated aqueous sodium hydrogencarbonate solution (10 ml of each) and agitated. After phase separation, the aqueous phase was extracted twice with ethyl acetate (10 ml each time). The combined organic phases were dried over sodium sulfate, filtered and concentrated, and the residue was lyophilized. 35 mg (98% purity, 53% of theory) of the title compound were obtained.

LC-MS (Method 1): $R_t$=2.33 min; MS (ESIpos): m/z=590/592 [M+H]⁺

¹H-NMR (400 MHz, DMSO-d6) δ [ppm]: 0.964 (10.37), 0.980 (10.93), 1.233 (0.56), 1.256 (0.68), 1.286 (1.96), 1.315 (2.22), 1.345 (0.95), 1.552 (0.89), 1.562 (1.05), 1.578 (0.95), 1.588 (0.80), 1.718 (2.85), 1.746 (2.59), 1.780 (0.95), 1.802 (1.29), 1.821 (1.41), 1.833 (0.90), 1.844 (0.79), 1.863 (0.41), 2.001 (0.79), 2.017 (1.16), 2.036 (3.01), 2.063 (2.22), 2.075 (2.05), 2.086 (2.34), 2.097 (1.62), 2.119 (16.00), 2.156 (0.97), 2.173 (0.46), 2.730 (1.03), 2.759 (2.00), 2.774 (2.10), 2.802 (1.10), 3.302 (2.59), 3.314 (2.67), 3.508 (3.25), 3.540 (3.16), 3.580 (1.37), 3.688 (2.97), 7.116 (0.92), 7.123 (1.05), 7.137 (1.77), 7.144 (1.90), 7.157 (1.08), 7.165 (1.08), 7.383 (2.21), 7.390 (2.26), 7.408 (2.34), 7.415 (2.30), 7.457 (0.72), 7.482 (2.87), 7.495 (2.84), 7.504 (2.61), 7.517 (2.39), 7.617 (1.88), 7.639 (8.36), 7.648 (5.27), 7.653 (4.59), 7.671 (1.10), 7.676 (1.17), 8.719 (1.41), 8.734 (2.79), 8.748 (1.35).

¹H-NMR (400 MHz, DMSO-d6) δ [ppm]: 12.16 (br. s, 1H), 8.73 (t, 1H), 7.69-7.61 (m, 2H), 7.50 (dd, 1H), 7.46 (br. s, partly concealed, 1H), 7.40 (dd, 1H), 7.14 (td, 1H), 3.74-3.48 (m, 5H), 2.82-2.69 (m, 2H), 2.19-1.96 (m, 6H), 1.88-1.67 (m, 3H), 1.63-1.50 (m, 1H), 1.38-1.19 (m, 2H), 0.97 (d, 3H).

Example 19

5-[({6-Bromo-2-[3-methoxypiperidin-1-yl]-3-methylquinolin-4-yl}carbonyl)amino]-4-(2-chloro-5-fluorophenyl)pentanoic acid (Diastereomer Mixture)

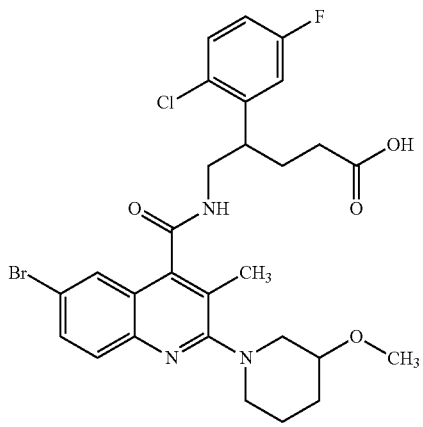 [SMILES: COC1CCCN(c2nc3ccc(Br)cc3c(C(=O)NCC(CCC(=O)O)c3cc(F)ccc3Cl)c2C)C1]

To a solution of tert-butyl 5-[({6-bromo-2-[3-methoxypiperidin-1-yl]-3-methylquinolin-4-yl}carbonyl)amino]-4-(2-chloro-5-fluorophenyl)pentanoate (65 mg, 98.0 µmol, diastereomer mixture, Example 69A) in dichloromethane (720 µl) was added TFA (76 µl, 980 µmol), and the mixture was stirred at RT for two days. The mixture was then concentrated and repeatedly dichloromethane was added and the mixture was concentrated again. The residue was dissolved in acetonitrile and purified by means of preparative HPLC (Method 12). The combined target fractions were concentrated and the residue was admixed with ethyl acetate and saturated aqueous sodium hydrogencarbonate solution (10 ml of each) and agitated. After phase separation, the aqueous phase was extracted twice with ethyl acetate (10 ml each time). The combined organic phases were dried over sodium sulfate, filtered and concentrated, and the residue was lyophilized. 35 mg (98% purity, 57% of theory) of the title compound were obtained.

LC-MS (Method 1): R$_t$=2.04 min; MS (ESIpos): m/z=606/608 [M+H]$^+$

¹H-NMR (400 MHz, DMSO-d6) δ [ppm]: 1.400 (0.45), 1.806 (0.89), 1.817 (0.65), 1.828 (0.90), 2.020 (0.80), 2.048 (1.24), 2.076 (0.89), 2.089 (0.77), 2.097 (1.04), 2.131 (6.49), 2.732 (0.44), 2.845 (0.41), 2.861 (0.42), 3.301 (16.00), 3.313 (7.33), 3.425 (0.66), 3.434 (0.65), 3.588 (1.07), 3.616 (0.82), 3.694 (1.18), 7.123 (0.42), 7.138 (0.70), 7.144 (0.75), 7.158 (0.43), 7.165 (0.42), 7.390 (0.84), 7.398 (0.87), 7.416 (0.89), 7.423 (0.87), 7.481 (1.16), 7.495 (1.15), 7.503 (1.03), 7.517 (0.93), 7.633 (0.58), 7.656 (3.28), 7.662 (2.19), 7.667 (1.89), 8.714 (0.52), 8.727 (1.00), 8.741 (0.50).

¹H-NMR (400 MHz, DMSO-d6) δ [ppm]: 12.09 (br. s, 1H), 8.73 (t, 1H), 7.70-7.62 (m, 2H), 7.50 (dd, 1H), 7.46 (br. s, partly concealed, 1H), 7.41 (dd, 1H), 7.14 (td, 1H), 3.75-3.66 (m, 2H), 3.65-3.54 (m, 2H), 3.47-3.39 (m, 1H), 3.30 (s, partly concealed, 3H), 2.93-2.80 (m, 1H), 2.78-2.65 (m, 1H), 2.18-1.96 (m, 7H), 1.89-1.75 (m, 2H), 1.66-1.51 (m, 1H), 1.46-1.32 (m, 1H).

Example 20

5-[({6-Bromo-2-[2-(hydroxymethyl)morpholin-4-yl]-3-methylquinolin-4-yl}carbonyl)amino]-4-(2-chloro-5-fluorophenyl)pentanoic acid (Diastereomer Mixture)

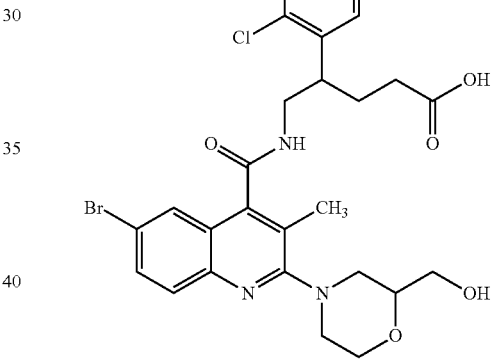

To a solution of tert-butyl 5-[({6-bromo-2-[2-(hydroxymethyl)morpholin-4-yl]-3-methylquinolin-4-yl}-carbonyl)amino]-4-(2-chloro-5-fluorophenyl)pentanoate (35 mg, 52.6 µmol, diastereomer mixture, Example 70A) in dichloromethane (390 µl) was added TFA (41 µl, 530 µmol), and the mixture was stirred at RT for two days. The mixture was then concentrated and repeatedly dichloromethane was added and the mixture was concentrated again. The residue was dissolved in acetonitrile and purified by means of preparative HPLC (Method 12). The combined target fractions were concentrated and the residue was admixed with ethyl acetate and saturated aqueous sodium hydrogencarbonate solution (10 ml of each) and agitated. After phase separation, the aqueous phase was extracted twice with ethyl acetate (10 ml each time). The combined organic phases were dried over sodium sulfate, filtered and concentrated, and the residue was lyophilized. 26 mg (98% purity, 78% of theory) of the title compound were obtained.

LC-MS (Method 1): R$_t$=1.67 min; MS (ESIpos): m/z=608/610 [M+H]$^+$

¹H-NMR (400 MHz, DMSO-d6) δ [ppm]: 1.788 (0.65), 1.810 (1.36), 1.831 (1.64), 1.852 (0.96), 1.871 (0.44), 1.991 (0.46), 2.011 (0.97), 2.024 (1.28), 2.042 (1.48), 2.055 (3.21), 2.082 (2.67), 2.095 (2.49), 2.102 (3.16), 2.116 (1.97), 2.131 (3.02), 2.157 (16.00), 2.189 (0.75), 2.643 (0.63), 2.670 (1.36), 2.691 (1.24), 2.710 (0.74), 2.717 (0.78), 2.891 (1.17), 2.921 (0.67), 3.385 (3.18), 3.415 (3.71), 3.428 (2.50), 3.490 (2.32), 3.502 (3.16), 3.517 (3.57), 3.529 (2.32), 3.551 (2.26), 3.605 (2.21), 3.619 (2.39), 3.644 (1.89), 3.659 (1.32), 3.688 (3.34), 3.710 (4.45), 3.739 (1.84), 3.909 (2.58), 3.936 (2.02), 4.762 (0.56), 7.120 (1.03), 7.126 (1.19), 7.141 (2.03), 7.147 (2.14), 7.161 (1.24), 7.168 (1.20), 7.394 (2.43), 7.401 (2.44), 7.419 (2.54), 7.426 (2.41), 7.486 (3.59), 7.499 (3.61), 7.508 (3.33), 7.521 (2.98), 7.661 (0.94), 7.683 (14.87), 7.706 (0.58), 7.710 (0.70), 8.743 (1.59), 8.756 (2.91), 8.770 (1.45).

$^1$H-NMR (400 MHz, DMSO-d6) δ [ppm]: 12.07 (br. s, 1H), 8.76 (t, 1H), 7.72-7.64 (m, 2H), 7.50 (dd, 1H), 7.47 (br. s, partly concealed, 1H), 7.41 (dd, 1H), 7.14 (td, 1H), 4.76 (br. s, 1H), 3.92 (br. d, 1H), 3.78-3.36 (m, 9H), 2.97-2.80 (m, 1H), 2.77-2.60 (m, 1H), 2.21-1.95 (m, 6H), 1.90-1.71 (m, 1H).

Example 21

5-[({6-Bromo-2-[3-(hydroxymethyl)piperidin-1-yl]-3-methylquinolin-4-yl}carbonyl)amino]-4-(2-chloro-5-fluorophenyl)pentanoic acid (Diastereomer Mixture)

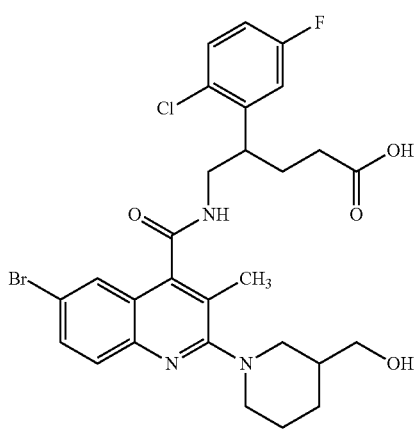 [SMILES: Cc1c(N2CCCC(CO)C2)nc2ccc(Br)cc2c1C(=O)NCC(CCC(=O)O)c1cc(F)ccc1Cl]

To a solution of tert-butyl 5-[({6-bromo-2-[3-(hydroxymethyl)piperidin-1-yl]-3-methylquinolin-4-yl}carbonyl)amino]-4-(2-chloro-5-fluorophenyl)pentanoate (63 mg, 95.0 μmol, diastereomer mixture, Example 71A) in dichloromethane (700 μl) was added TFA (73 μl, 950 μmol), and the mixture was stirred at RT for two days. The mixture was then concentrated and repeatedly dichloromethane was added and the mixture was concentrated again. The residue was dissolved in acetonitrile and purified by means of preparative HPLC (Method 12). The combined target fractions were concentrated, and the residue was lyophilized. 20 mg (98% purity, 34% of theory) of the title compound were obtained.

LC-MS (Method 1): $R_t$=1.80 min; MS (ESIpos): m/z=606/608 [M+H]$^+$ $^1$H-NMR (400 MHz, DMSO-d6) δ [ppm]: 1.089 (0.50), 1.117 (1.29), 1.140 (1.38), 1.622 (1.10), 1.648 (1.20), 1.676 (0.84), 1.746 (5.89), 1.773 (5.29), 1.812 (1.66), 1.833 (1.70), 1.857 (2.04), 1.871 (1.27), 1.885 (1.70), 1.904 (1.40), 1.917 (1.31), 1.924 (1.32), 1.959 (0.47), 2.151 (16.00), 2.566 (0.62), 2.723 (1.19), 2.747 (1.22), 2.776 (0.57), 3.336 (11.62), 3.450 (2.50), 3.481 (3.01), 7.083 (1.12), 7.090 (1.27), 7.105 (2.10), 7.111 (2.23), 7.125 (1.26), 7.132 (1.23), 7.298 (2.44), 7.305 (2.40), 7.323 (2.44), 7.330 (2.25), 7.458 (3.55), 7.471 (3.44), 7.479 (3.00), 7.493 (2.57), 7.621 (1.06), 7.643 (11.76), 7.672 (0.74), 8.997 (1.74).

$^1$H-NMR (400 MHz, DMSO-d6) δ [ppm]: 9.00 (br. s, 1H), 7.69-7.60 (m, 1H), 7.48 (dd, 1H), 7.43 (br. s, partly concealed, 1H), 7.31 (dd, 1H), 7.11 (td, 1H), 4.63 (br. s, 1H), 3.74-3.18 (m, partly concealed, 8H), 2.82-2.62 (m, 1H), 2.15 (s, 3H), 1.99-1.55 (m, 8H), 1.21-1.04 (m, 1H).

Example 22

(+/−)-5-({[6-Bromo-3-methyl-2-(piperidin-1-yl)quinolin-4-yl]carbonyl}amino)-4-(2-chlorophenyl)pentanoic acid (Racemate)

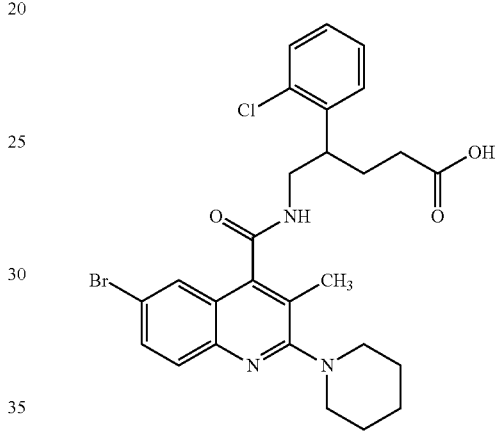

To a solution of (+/−)-tert-butyl 5-({[6-bromo-3-methyl-2-(piperidin-1-yl)quinolin-4-yl]carbonyl}amino)-4-(2-chlorophenyl)pentanoate (100 mg, 163 μmol, racemate, Example 72A) in dichloromethane (2.9 ml) was added TFA (130 μl, 1.6 mmol), and the mixture was stirred at RT for 66 h. The mixture was then concentrated and repeatedly dichloromethane was added and the mixture was concentrated again. The residue was dissolved in acetonitrile and purified by means of preparative HPLC (Method 6). The combined target fractions were concentrated. The residue was repeatedly taken up in dichloromethane and concentrated again, and then dried under reduced pressure. 62 mg (100% purity, 68% of theory) of the title compound were obtained.

LC-MS (Method 1): $R_t$=2.18 min; MS (ESIpos): m/z=558/560 [M+H]$^+$ $^1$H-NMR (400 MHz, DMSO-d6) δ [ppm]: −0.149 (0.58), −0.008 (7.08), 0.008 (4.63), 0.146 (0.60), 1.235 (0.47), 1.370 (2.53), 1.605 (4.27), 1.670 (8.18), 1.793 (0.89), 1.811 (1.74), 1.834 (2.19), 1.857 (1.16), 2.045 (4.22), 2.081 (5.18), 2.089 (5.36), 2.103 (3.13), 2.130 (16.00), 2.159 (1.61), 2.327 (0.92), 2.366 (0.92), 2.518 (4.78), 2.523 (4.22), 2.669 (1.05), 2.710 (0.87), 3.119 (8.34), 3.132 (10.53), 3.591 (1.94), 3.674 (3.53), 5.754 (4.60), 7.257 (1.83), 7.275 (3.80), 7.291 (2.79), 7.295 (2.66), 7.356 (2.55), 7.373 (4.60), 7.391 (2.66), 7.441 (6.50), 7.444 (6.06), 7.461 (5.90), 7.464 (5.52), 7.479 (5.92), 7.482 (5.83), 7.498 (4.36), 7.622 (2.73), 7.643 (12.72), 7.651 (9.12), 7.656 (7.69), 7.673 (1.72), 7.678 (1.77), 8.707 (2.17), 8.722 (4.09), 8.736 (1.92), 12.039 (6.06).

Example 23

(−)-5-({[6-Bromo-3-methyl-2-(piperidin-1-yl)quinolin-4-yl]carbonyl}amino)-4-(2-chlorophenyl)pentanoic acid (Enantiomer 1)

To a solution of (−)-tert-butyl 5-({[6-bromo-3-methyl-2-(piperidin-1-yl)quinolin-4-yl]carbonyl}amino)-4-(2-chlorophenyl)pentanoate (70 mg, 114 µmol, enantiomer 1, Example 73A) in dichloromethane (2.0 ml) was added TFA (88 µl, 1.1 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 48 mg (98% purity, ee 99%, 73% of theory) of the title compound were obtained.

$[\alpha]_D^{20}$=−17.0°, 589 nm, c=0.27 g/100 ml, methanol

LC-MS (Method 1): $R_t$=2.19 min; MS (ESIpos): m/z=558/560 [M+H]$^+$ $^1$H-NMR (400 MHz, DMSO-d6) δ [ppm]: −0.060 (0.99), −0.008 (2.24), 0.008 (1.64), 0.084 (0.74), 1.607 (4.12), 1.672 (7.98), 1.782 (0.53), 1.793 (0.79), 1.812 (1.62), 1.835 (2.14), 1.858 (1.17), 2.014 (0.51), 2.035 (1.18), 2.046 (4.07), 2.073 (4.15), 2.082 (4.75), 2.089 (5.01), 2.103 (2.60), 2.132 (16.00), 2.159 (1.48), 2.327 (0.44), 2.366 (0.43), 2.523 (1.22), 2.670 (0.41), 3.143 (10.38), 3.595 (3.12), 3.620 (2.84), 3.676 (7.44), 3.690 (7.13), 7.257 (1.62), 7.275 (3.74), 7.292 (2.72), 7.295 (2.61), 7.356 (2.25), 7.374 (4.12), 7.392 (2.14), 7.441 (5.77), 7.444 (5.50), 7.461 (5.08), 7.464 (4.86), 7.480 (5.49), 7.482 (5.54), 7.499 (4.21), 7.630 (2.09), 7.652 (11.83), 7.658 (8.30), 7.663 (7.08), 7.680 (1.37), 7.685 (1.52), 8.712 (2.04), 8.726 (4.16), 8.740 (2.01).

$^1$H-NMR (400 MHz, DMSO-d6) δ [ppm]: 12.02 (br. s, 1H), 8.73 (t, 1H), 7.71-7.62 (m, 2H), 7.54-7.42 (m, 3H), 7.37 (t, 1H), 7.31-7.24 (m, 1H), 3.95-3.45 (m, 3H, partly concealed), 3.19-3.08 (m, 4H), 2.20-2.01 (m, 6H), 1.95-1.73 (m, 1H), 1.72-1.49 (m, 6H).

Example 24

(+)-5-({[6-Bromo-3-methyl-2-(piperidin-1-yl)quinolin-4-yl]carbonyl}amino)-4-(2-chlorophenyl)pentanoic acid (Enantiomer 2)

To a solution of (+)-tert-butyl 5-({[6-bromo-3-methyl-2-(piperidin-1-yl)quinolin-4-yl]carbonyl}amino)-4-(2-chlorophenyl)pentanoate (70 mg, 114 µmol, enantiomer 2, Example 74A) in dichloromethane (2.0 ml) was added TFA (88 µl, 1.1 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 43 mg (98% purity, ee 96%, 66% of theory) of the title compound were obtained.

$[\alpha]_D^{20}$=+8.1°, 589 nm, c=0.26 g/100 ml, methanol

LC-MS (Method 1): $R_t$=2.19 min; MS (ESIpos): m/z=558/560 [M+H]$^+$ $^1$H-NMR (400 MHz, DMSO-d6) δ [ppm]: −0.149 (0.47), −0.008 (3.94), 0.008 (4.07), 0.146 (0.50), 1.606 (3.77), 1.671 (7.49), 1.793 (0.66), 1.810 (1.47), 1.834 (2.05), 1.857 (1.10), 2.024 (0.78), 2.044 (3.30), 2.077 (4.23), 2.086 (4.55), 2.094 (2.58), 2.131 (16.00), 2.155 (1.53), 2.327 (0.52), 2.366 (0.40), 2.523 (1.73), 2.670 (0.61), 2.710 (0.46), 3.133 (9.79), 3.591 (1.72), 3.674 (3.17), 3.687 (2.47), 7.256 (1.53), 7.274 (3.55), 7.291 (2.47), 7.294 (2.51), 7.355 (2.17), 7.374 (3.95), 7.392 (2.04), 7.441 (5.56), 7.444 (5.59), 7.461 (4.94), 7.464 (4.94), 7.481 (5.29), 7.497 (3.95), 7.622 (2.32), 7.644 (12.05), 7.651 (8.27), 7.656 (7.28), 7.673 (1.50), 7.678 (1.62), 8.712 (1.84), 8.726 (3.79), 8.740 (1.84).

$^1$H-NMR (400 MHz, DMSO-d6) δ [ppm]: 12.05 (br. s, 1H), 8.73 (t, 1H), 7.69-7.61 (m, 2H), 7.53-7.42 (m, 3H), 7.37 (t, 1H), 7.31-7.23 (m, 1H), 3.76-3.62 (m, 2H), 3.62-3.53 (m, 1H), 3.20-3.06 (m, 4H), 2.20-1.98 (m, 6H), 1.90-1.75 (m, 1H), 1.72-1.50 (m, 6H).

Example 25

(+/−)-5-({[6-Bromo-3-methyl-2-(thiomorpholin-4-yl)quinolin-4-yl]carbonyl}amino)-4-(2-chlorophenyl)pentanoic acid (Racemate)

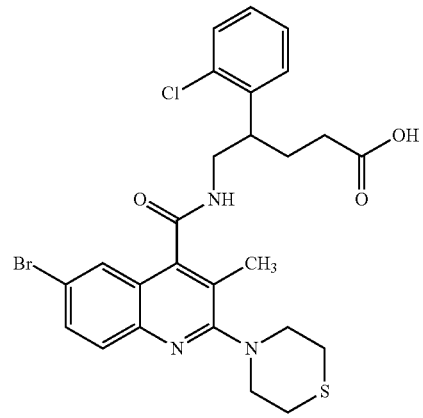 [SMILES: Cc1c(N2CCSCC2)nc2ccc(Br)cc2c1C(=O)NCC(CCC(=O)O)c1ccccc1Cl]

To a solution of (+)-tert-butyl 5-({[6-bromo-3-methyl-2-(thiomorpholin-4-yl)quinolin-4-yl]carbonyl}amino)-4-(2-chlorophenyl)pentanoate (70 mg, 111 µmol, racemate, Example 75A) in dichloromethane (810 µl) was added TFA (85 µl, 1.1 mmol), and the mixture was stirred at RT overnight.

The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 58 mg (98% purity, 89% of theory) of the title compound were obtained.

LC-MS (Method 1): $R_t$=2.11 min; MS (ESIpos): m/z=576/578 [M+H]$^+$ $^1$H-NMR (400 MHz, DMSO-d6) δ [ppm]: −0.022 (0.68), 1.004 (2.17), 1.234 (1.54), 1.394 (0.86), 1.809 (1.65), 1.831 (2.44), 1.854 (1.44), 2.037 (3.90), 2.064 (5.65), 2.072 (5.19), 2.085 (3.39), 2.095 (2.40), 2.134 (16.00), 2.196 (0.47), 2.327 (0.57), 2.670 (0.65), 2.710 (0.50), 2.787 (11.08), 2.798 (10.38), 2.864 (0.71), 3.045 (0.42), 3.414 (11.05), 3.425 (11.71), 3.584 (2.28), 3.676 (3.53), 7.255 (1.81), 7.273 (4.16), 7.293 (2.93), 7.353 (2.45), 7.372 (4.50), 7.391 (2.36), 7.442 (6.27), 7.462 (5.42), 7.478 (5.58), 7.495 (4.58), 7.655 (2.31), 7.677 (13.29), 7.681 (10.73), 7.686 (8.04), 7.704 (1.13), 7.708 (1.41), 8.732 (2.04), 8.745 (3.71), 8.759 (1.92).

$^1$H-NMR (400 MHz, DMSO-d6) δ [ppm]: 12.01 (br. s, 1H), 8.75 (t, 1H), 7.73-7.64 (m, 2H), 7.58-7.42 (m, 3H), 7.37

(t, 1H), 7.28 (t, 1H), 3.78-3.63 (m, 2H), 3.62-3.53 (m, 1H), 3.46-3.39 (m, 4H), 2.85-2.74 (m, 4H), 2.22-1.98 (m, 6H), 1.92-1.74 (m, 1H).

Separation of the Enantiomers:

The title compound (50 mg) was dissolved in methanol (50 ml) and separated into the enantiomers by means of preparative SFC on chiral phase (see Examples 26 and 27) [column: Daicel Chiralpak ID, 5 m, 250 mm×20 mm; flow rate: 70 ml/min; injection: 0.40 ml; eluent: 30% methanol/ 70% carbon dioxide; run time 7 min, isocratic]. The combined target fractions were concentrated and the residue was lyophilized.

Example 26

(+)-5-({[6-Bromo-3-methyl-2-(thiomorpholin-4-yl) quinolin-4-yl]carbonyl}amino)-4-(2-chlorophenyl) pentanoic acid (Enantiomer 1)

In the enantiomer separation described in Example 25, 8 mg (98% purity, ee 99%) of the title compound were obtained as the enantiomer that eluted earlier.

$[\alpha]_D^{20}$=+8.9°, 589 nm, c=0.30 g/100 ml, methanol

LC-MS (Method 1): $R_t$=2.08 min; MS (ESIpos): m/z=576/578 [M+H]$^+$ $^1$H-NMR (400 MHz, DMSO-d6) δ [ppm]: −0.149 (1.02), 0.068 (1.62), 0.146 (1.00), 0.940 (0.50), 0.955 (0.52), 1.139 (0.50), 1.157 (0.52), 1.811 (1.54), 1.835 (2.04), 1.857 (1.14), 2.042 (3.63), 2.076 (4.73), 2.083 (5.00), 2.133 (16.00), 2.327 (1.22), 2.366 (1.12), 2.402 (0.95), 2.669 (1.42), 2.710 (1.29), 2.788 (10.55), 3.425 (10.48), 3.587 (1.94), 3.677 (3.31), 7.256 (1.72), 7.275 (3.73), 7.294 (2.66), 7.355 (2.26), 7.374 (4.08), 7.391 (2.24), 7.443 (5.60), 7.463 (4.80), 7.481 (5.08), 7.499 (4.23), 7.655 (1.74), 7.677 (11.84), 7.686 (7.42), 7.709 (1.39), 8.720 (1.84), 8.735 (3.66), 8.749 (1.97), 12.054 (0.80).

$^1$H-NMR (400 MHz, DMSO-d6) δ [ppm]: 12.05 (br. s, 1H), 8.74 (t, 1H), 7.74-7.62 (m, 2H), 7.58-7.42 (m, 3H), 7.37 (t, 1H), 7.31-7.23 (m, 1H), 3.76-3.63 (m, 2H), 3.62-3.54 (m, 1H), 3.47-3.38 (m, 4H), 2.83-2.74 (m, 4H), 2.19-1.99 (m, 6H), 1.89-1.76 (m, 1H).

Example 27

(−)-5-({[6-Bromo-3-methyl-2-(thiomorpholin-4-yl) quinolin-4-yl]carbonyl}amino)-4-(2-chlorophenyl) pentanoic acid (Enantiomer 2)

In the enantiomer separation described in Example 25, 8 mg (98% purity, ee 93%) of the title compound were obtained as the enantiomer that eluted later.

$[\alpha]_D^{20}$=−6.4°, 589 nm, c=0.25 g/100 ml, methanol

LC-MS (Method 1): $R_t$=2.08 min; MS (ESIpos): m/z=576/578 [M+H]$^+$ $^1$H-NMR (400 MHz, DMSO-d6) δ [ppm]: −0.149 (1.15), 0.008 (8.73), 0.069 (2.56), 0.146 (1.10), 1.812 (1.58), 1.834 (2.06), 1.859 (1.15), 2.043 (3.66), 2.083 (5.02), 2.133 (16.00), 2.328 (1.39), 2.366 (0.98), 2.523 (6.60), 2.670 (1.39), 2.709 (1.15), 2.786 (10.64), 3.425 (10.43), 3.588 (2.08), 3.677 (3.35), 7.256 (1.77), 7.274 (3.85), 7.292 (2.63), 7.354 (2.37), 7.374 (4.14), 7.391 (2.20), 7.441 (6.07), 7.461 (5.33), 7.481 (5.14), 7.498 (4.21), 7.655 (2.20), 7.677 (13.30), 7.686 (7.49), 7.709 (1.43), 8.734 (3.56), 12.050 (0.84).

$^1$H-NMR (400 MHz, DMSO-d6) δ [ppm]: 12.05 (br. s, 1H), 8.73 (t, 1H), 7.73-7.63 (m, 2H), 7.59-7.41 (m, 3H), 7.37 (t, 1H), 7.31-7.22 (m, 1H), 3.76-3.63 (m, 2H), 3.62-3.53 (m, 1H), 3.47-3.38 (m, 4H), 2.83-2.73 (m, 4H), 2.18-1.98 (m, 6H), 1.89-1.74 (m, 1H).

Example 28

(+/−)-5-({[6-Bromo-2-(4,4-difluoropiperidin-1-yl)-3-methylquinolin-4-yl]carbonyl}amino)-4-(2-chlorophenyl)pentanoic acid (Racemate)

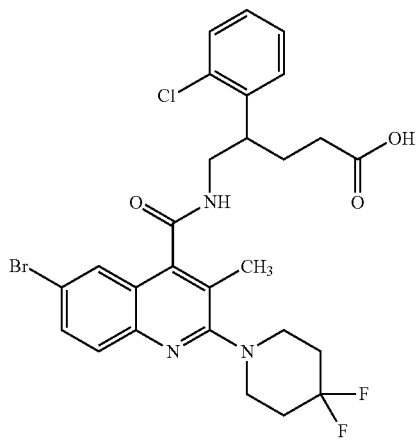 [SMILES: Cc1c(N2CCC(F)(F)CC2)nc2ccc(Br)cc2c1C(=O)NCC(CCC(=O)O)c1ccccc1Cl]

To a solution of (+/−)-tert-butyl 5-({[6-bromo-2-(4,4-difluoropiperidin-1-yl)-3-methylquinolin-4-yl] carbonyl}amino)-4-(2-chlorophenyl)pentanoate (28 mg, 43.0 μmol, racemate, Example 76A) in dichloromethane (320 μl) was added TFA (33 μl, 430 μmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 6 mg (98% purity, 23% of theory) of the title compound were obtained.

LC-MS (Method 2): $R_t$=1.13 min; MS (ESIpos): m/z=594/596 [M+H]$^+$ $^1$H-NMR (400 MHz, DMSO-d6) δ [ppm]: −0.149 (0.57), −0.008 (8.43), 0.008 (4.79), 0.146 (0.52), 1.234 (0.75), 1.810 (1.45), 1.831 (1.86), 1.854 (1.14), 2.034 (3.35), 2.062 (5.16), 2.093 (2.83), 2.118 (5.33), 2.170 (16.00), 2.327 (1.03), 2.366 (0.89), 2.523 (6.12), 2.669 (0.98), 2.710 (0.58), 3.586 (1.93), 3.681 (3.12), 7.255 (1.54), 7.272 (3.22), 7.290 (2.24), 7.355 (2.13), 7.373 (3.61), 7.391 (1.95), 7.440 (5.04), 7.459 (4.37), 7.481 (4.37), 7.499 (3.62), 7.658 (2.37), 7.680 (10.19), 7.688 (6.97), 7.693 (5.96), 7.710 (1.28), 7.715 (1.33), 8.771 (2.79).

$^1$H-NMR (400 MHz, DMSO-d6) δ [ppm]: 12.14 (br. s, 1H), 8.77 (t, 1H), 7.74-7.62 (m, 2H), 7.59-7.41 (m, 3H), 7.37 (t, 1H), 7.31-7.23 (m, 1H), 3.76-3.62 (m, 2H), 3.62-3.53 (m, 1H), 2.24-1.97 (m, 11H), 1.89-1.75 (m, 1H).

Example 29

(+/−)-5-({[6-Bromo-2-(3,6-dihydropyridin-1(2H)-yl)-3-methylquinolin-4-yl]carbonyl}amino)-4-(2-chlorophenyl)pentanoic acid (Racemate)

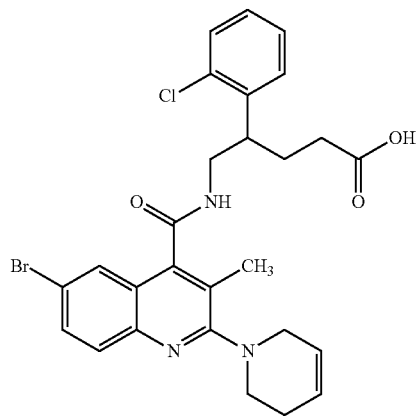 [SMILES: Cc1c(N2CC=CCC2)nc2ccc(Br)cc2c1C(=O)NCC(CCC(=O)O)c1ccccc1Cl]

To a solution of (+/−)-tert-butyl 5-({[6-bromo-2-(3,6-dihydropyridin-1(2H)-yl)-3-methylquinolin-4-yl]carbonyl}amino)-4-(2-chlorophenyl)pentanoate (80 mg, 131 μmol, racemate, Example 77A) in dichloromethane (960 μl) was added TFA (100 μl, 1.3 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 65 mg (98% purity, 88% of theory) of the title compound were obtained.

LC-MS (Method 1): $R_t$=2.15 min; MS (ESIpos): m/z=556/558 [M+H]$^+$ $^1$H-NMR (400 MHz, DMSO-d6) δ [ppm]: 1.195 (1.62), 1.211 (1.64), 1.233 (0.51), 1.242 (0.74), 1.257 (0.81), 1.272 (0.44), 1.800 (0.79), 1.819 (1.67), 1.842 (2.17), 1.865 (1.23), 2.052 (3.96), 2.086 (5.33), 2.093 (5.55), 2.143 (16.00), 2.303 (4.60), 3.271 (3.84), 3.596 (2.12), 3.680 (3.38), 3.796 (7.68), 5.818 (1.47), 5.844 (4.74), 5.863 (4.13), 5.889 (1.26), 7.256 (1.75), 7.274 (3.79), 7.293 (2.71), 7.357 (2.33), 7.376 (4.04), 7.394 (2.21), 7.442 (5.66), 7.462 (5.13), 7.484 (5.68), 7.502 (4.18), 7.618 (2.71), 7.640 (9.36), 7.653 (6.42), 7.657 (5.51), 7.675 (1.77), 7.680 (1.64), 8.721 (2.17), 8.735 (3.91), 8.748 (1.96), 12.047 (4.68).

$^1$H-NMR (400 MHz, DMSO-d6) δ [ppm]: 12.05 (s, 1H), 8.73 (t, 1H), 7.70-7.60 (m, 2H), 7.57-7.41 (m, 3H), 7.37 (t, 1H), 7.28 (t, 1H), 5.93-5.79 (m, 2H), 3.80 (br. s, 2H), 3.73-3.63 (m, 2H), 3.63-3.54 (m, 1H), 3.27 (br. s, 2H, partly concealed), 2.30 (br. s, 2H), 2.19-1.99 (m, 6H), 1.91-1.72 (m, 1H).

Separation of the Enantiomers:

The title compound (60 mg) was dissolved in a mixture of isopropanol (3 ml), heptane (2 ml) and acetonitrile (1 ml) in an ultrasound bath, filtered and separated into the enantiomers by means of preparative HPLC on chiral phase (see Examples 30 and 31) [column: Daicel Chiralcel OX-H, 5 μm, 250 mm×20 mm; flow rate: 15 ml/min; detection: 220 nm; temperature: 35° C.; injection: 0.40 ml; eluent: 80% heptane/20% isopropanol; run time 16 min, isocratic]. The combined target fractions were concentrated, and the respective residue was lyophilized in acetonitrile/water.

Example 30

5-({[6-Bromo-2-(3,6-dihydropyridin-1(2H)-yl)-3-methylquinolin-4-yl]carbonyl}amino)-4-(2-chlorophenyl)pentanoic acid (Enantiomer 1)

In the enantiomer separation described in Example 29, the prepurified title compound was obtained as the enantiomer that eluted earlier (ee 99%). This was followed by repurification by means of preparative HPLC (Method 7). The combined target fractions were concentrated, and the residue was lyophilized in acetonitrile/water. 22 mg (98% purity, 37% of theory) of the repurified title compound were obtained.

LC-MS (Method 1): $R_t$=2.15 min; MS (ESIpos): m/z=556/558 [M+H]$^+$ $^1$H-NMR (400 MHz, DMSO-d6) δ [ppm]: −0.150 (1.15), 0.145 (1.01), 1.234 (0.91), 1.836 (2.69), 1.859 (1.58), 2.044 (4.28), 2.072 (6.37), 2.143 (16.00), 2.302 (4.72), 2.366 (1.79), 2.669 (1.95), 2.709 (1.62), 3.589 (2.46), 3.677 (3.54), 3.796 (7.65), 5.844 (4.82), 5.863 (4.28), 7.253 (2.12), 7.273 (4.35), 7.291 (3.03), 7.356 (2.86), 7.374 (4.65), 7.392 (2.49), 7.441 (6.91), 7.461 (6.23), 7.481 (6.16), 7.498 (4.58), 7.617 (3.40), 7.639 (11.59), 7.652 (7.07), 7.657 (6.27), 7.674 (2.19), 8.750 (3.57).

Example 31

5-({[6-Bromo-2-(3,6-dihydropyridin-1(2H)-yl)-3-methylquinolin-4-yl]carbonyl}amino)-4-(2-chlorophenyl)pentanoic acid (Enantiomer 2)

In the enantiomer separation described in Example 29, the prepurified title compound was obtained as the enantiomer that eluted later (ee 99%). This was followed by repurification by means of preparative HPLC (Method 7). The combined target fractions were concentrated, and the residue was lyophilized in acetonitrile/water. 11 mg (98% purity, 18% of theory) of the repurified title compound were obtained.

LC-MS (Method 1): $R_t$=2.15 min; MS (ESIpos): m/z=556/558 [M+H]$^+$ $^1$H-NMR (400 MHz, DMSO-d6) δ [ppm]: −0.150 (2.35), 0.146 (2.13), 0.936 (2.03), 0.952 (2.03), 1.234 (6.29), 1.795 (2.13), 1.996 (4.48), 2.154 (16.00), 2.327 (8.96), 2.366 (4.59), 2.670 (6.72), 2.709 (5.01), 3.545 (3.09), 3.661 (4.16), 3.801 (10.77), 5.844 (6.61), 7.260 (4.05), 7.362 (4.27), 7.429 (6.08), 7.450 (6.93), 7.615 (3.84), 7.637 (14.83), 7.650 (10.03), 8.925 (1.71).

Example 32

(+/−)-5-({[6-Bromo-3-methyl-2-(1,2-oxazinan-2-yl)quinolin-4-yl]carbonyl}amino)-4-(2-chlorophenyl)pentanoic acid (Racemate)

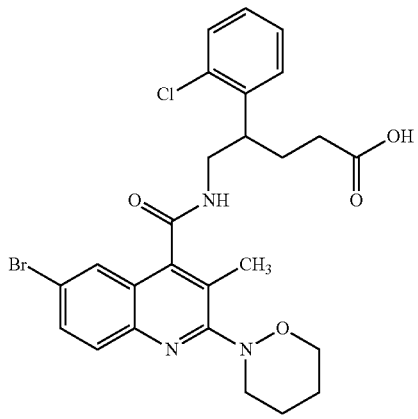 [SMILES: Cc1c(N2CCCCO2)nc2ccc(Br)cc2c1C(=O)NCC(CCC(=O)O)c1ccccc1Cl]

To a solution of (+)-tert-butyl 5-({[6-bromo-3-methyl-2-(1,2-oxazinan-2-yl)quinolin-4-yl]carbonyl}amino)-4-(2-chlorophenyl)pentanoate (24 mg, 38.9 µmol, racemate, Example 78A) in dichloromethane (1.0 ml) was added TFA (30 µl, 390 µmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 12 mg (98% purity, 56% of theory) of the title compound were obtained.

LC-MS (Method 2): $R_t$=1.11 min; MS (ESIpos): m/z=560/562 [M+H]$^+$ $^1$H-NMR (400 MHz, DMSO-d6) δ [ppm]: 0.008 (1.62), 1.172 (0.42), 1.189 (0.42), 1.696 (3.60), 1.708 (2.94), 1.784 (0.42), 1.795 (0.61), 1.813 (1.31), 1.836 (1.81), 1.868 (3.31), 1.883 (3.96), 1.897 (2.58), 2.046 (3.08), 2.081 (3.58), 2.089 (3.69), 2.141 (10.12), 3.575 (3.73), 3.647 (0.92), 3.667 (1.81), 3.681 (2.72), 3.695 (1.97), 3.723 (1.12), 4.041 (3.52), 4.054 (5.58), 4.066 (3.45), 7.255 (1.27), 7.274 (2.96), 7.293 (2.11), 7.354 (1.73), 7.373 (3.18), 7.391 (1.68), 7.445 (4.44), 7.465 (3.92), 7.478 (3.64), 7.497 (2.80), 7.533 (0.87), 7.727 (16.00), 8.789 (1.61), 8.804 (3.12), 8.818 (1.54), 12.028 (0.59).

$^1$H-NMR (400 MHz, DMSO-d6) δ [ppm]: 12.03 (br. s, 1H), 8.80 (t, 1H), 7.73 (s, 2H), 7.53 (br. s, 1H), 7.47 (dd, 2H), 7.37 (t, 1H), 7.31-7.24 (m, 1H), 4.05 (t, 2H), 3.80-3.47 (m, 5H), 2.21-1.98 (m, 6H), 1.94-1.77 (m, 3H), 1.75-1.64 (m, 2H).

Example 33

(+/−)-5-({[6-Bromo-3-methyl-2-(pyrrolidin-1-yl)quinolin-4-yl]carbonyl}amino)-4-(2-chlorophenyl)pentanoic acid (Racemate)

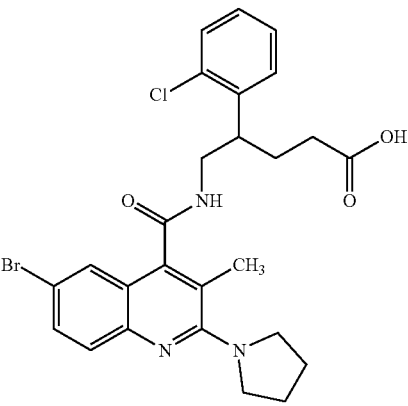 [SMILES: Cc1c(N2CCCC2)nc2ccc(Br)cc2c1C(=O)NCC(CCC(=O)O)c1ccccc1Cl]

To a solution of (+)-tert-butyl 5-({[6-bromo-3-methyl-2-(pyrrolidin-1-yl)quinolin-4-yl]carbonyl}amino)-4-(2-chlorophenyl)pentanoate (380 mg, 632 µmol, racemate, Example 79A) in dichloromethane (4.6 ml) was added TFA (490 µl, 6.3 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 256 mg (98% purity, 73% of theory) of the title compound were obtained.

LC-MS (Method 1): $R_t$=1.43 min; MS (ESIpos): m/z=544/546 [M+H]$^+$ $^1$H-NMR (400 MHz, DMSO-d6) δ [ppm]: −0.008 (1.19), 0.008 (1.14), 1.241 (0.73), 1.256 (0.78), 1.271 (0.46), 1.785 (0.59), 1.796 (0.85), 1.814 (1.80), 1.838 (3.17), 1.871 (12.01), 2.026 (1.00), 2.047 (3.97), 2.080 (4.63), 2.090 (4.73), 2.111 (1.81), 2.119 (1.82), 2.138 (3.86), 2.161 (9.89), 3.322 (16.00), 3.659 (2.60), 7.251 (1.67), 7.268 (3.84), 7.286 (2.77), 7.352 (2.63), 7.370 (4.65), 7.389 (2.83), 7.435 (6.55), 7.437 (6.28), 7.455 (5.45), 7.457 (5.19), 7.474 (6.87), 7.494 (8.62), 7.547 (4.32), 7.551 (4.10), 7.569 (2.55), 7.573 (2.43), 8.662 (1.99), 8.677 (3.85), 8.690 (1.92), 12.041 (3.75).

$^1$H-NMR (400 MHz, DMSO-d6) δ [ppm]: 8.68 (t, 1H), 7.56 (dd, 1H), 7.52-7.40 (m, 4H), 7.37 (t, 1H), 7.31-7.23 (m, 1H), 3.78-3.48 (m, 7H), 2.22-1.98 (m, 6H), 1.93-1.75 (m, 5H).

Separation of the Enantiomers:

The title compound (220 mg) was taken up in methanol (15 ml), filtered and separated into the enantiomers by means of preparative SFC on chiral phase (see Examples 34 and 35) [column: Daicel Chiralcel OX-H, 5 µm, 250 mm×20 mm; flow rate: 80 ml/min; detection: 210 nm; temperature: 40° C.; injection: 0.15 ml; eluent: 35% methanol/65% carbon dioxide; run time 5 min, isocratic]. The combined target fractions were concentrated and the residue was lyophilized.

Example 34

(−)-5-({[6-Bromo-3-methyl-2-(pyrrolidin-1-yl)quinolin-4-yl]carbonyl}amino)-4-(2-chlorophenyl)pentanoic acid (Enantiomer 1)

In the enantiomer separation described in Example 33, the prepurified title compound was obtained as the enantiomer that eluted earlier (ee 99%). This was followed by repurification by means of preparative HPLC (Method 6). The combined target fractions were concentrated, and the residue was dried under reduced pressure. 35 mg (98% purity) of the repurified title compound were obtained.

$[\alpha]_D^{20}$=−11.4°, 589 nm, c=0.30 g/100 ml, methanol
LC-MS (Method 1): $R_t$=1.49 min; MS (ESIpos): m/z=544/546 [M+H]$^+$ $^1$H-NMR (400 MHz, DMSO-d6) δ [ppm]: 1.811 (2.39), 1.835 (4.10), 1.871 (16.00), 2.043 (5.13), 2.076 (6.19), 2.086 (6.23), 2.134 (4.98), 2.158 (13.15), 2.286 (0.46), 2.328 (1.03), 2.366 (0.61), 2.670 (1.10), 2.710 (0.68), 3.567 (13.61), 3.656 (3.65), 7.251 (2.39), 7.268 (5.05), 7.287 (3.69), 7.352 (3.53), 7.370 (6.08), 7.388 (3.80), 7.435 (8.06), 7.455 (6.95), 7.466 (9.27), 7.474 (6.88), 7.488 (14.78), 7.543 (7.22), 7.548 (6.31), 7.565 (4.14), 7.570 (3.76), 8.661 (2.89), 8.676 (5.21), 8.690 (2.58), 12.038 (0.57).

$^1$H-NMR (400 MHz, DMSO-d6) δ [ppm]: 12.04 (br. s, 1H), 8.68 (t, 1H), 7.55 (dd, 1H), 7.52-7.40 (m, 4H), 7.37 (t, 1H), 7.31-7.23 (m, 1H), 3.77-3.48 (m, 7H), 2.24-1.97 (m, 6H), 1.95-1.75 (m, 5H).

Method B:

To a solution of (−)-tert-butyl 5-({[6-bromo-3-methyl-2-(pyrrolidin-1-yl)quinolin-4-yl]carbonyl}amino)-4-(2-chlorophenyl)pentanoate (2.11 g, 3.51 mmol, enantiomer 2, Example 293A) in dichloromethane (27 ml) was added TFA (6.0 ml, 77.24 mmol), and the mixture was left to stand at RT for 24 h. The mixture was then concentrated and repeatedly dichloromethane was added and the mixture was concentrated again. The residue was purified by preparative HPLC (Method 6). The combined target fractions were concentrated, and the residue was lyophilized. 1.44 g (100% purity, 75% of theory) of the title compound were obtained.

$[\alpha]_D^{20}$=−13.1°, 589 nm, c=0.32 g/100 ml, methanol
LC-MS (Method 1): $R_t$=1.44 min; MS (ESIpos): m/z=544/546 [M+H]$^+$ $^1$H-NMR (400 MHz, DMSO-d6) δ [ppm]: 1.795 (0.23), 1.814 (0.53), 1.837 (0.93), 1.871 (3.68), 2.026 (0.28), 2.046 (1.18), 2.079 (1.39), 2.089 (1.41), 2.110 (0.55), 2.118 (0.54), 2.137 (1.15), 2.160 (3.09), 3.316 (16.00), 3.658 (0.81), 7.251 (0.50), 7.269 (1.13), 7.289 (0.82), 7.352 (0.77), 7.371 (1.38), 7.389 (0.85), 7.437 (1.84), 7.457 (1.53), 7.469 (1.47), 7.477 (1.68), 7.491 (2.55), 7.545 (1.30), 7.549 (1.32), 7.567 (0.78), 7.571 (0.80), 8.661 (0.60), 8.675 (1.17), 8.689 (0.60), 12.039 (1.84).

Example 35

(+)-5-({[6-Bromo-3-methyl-2-(pyrrolidin-1-yl)quinolin-4-yl]carbonyl}amino)-4-(2-chlorophenyl)pentanoic acid (Enantiomer 2)

Method A:

In the enantiomer separation described in Example 33, the prepurified title compound was obtained as the enantiomer that eluted later (ee 93%). This was followed by repurification by means of preparative HPLC (Method 6). The combined target fractions were concentrated, and the residue was dried under reduced pressure. 37 mg (98% purity) of the repurified title compound were obtained.

$[\alpha]_D^{20}$=+11.4°, 589 nm, c=0.29 g/100 ml, methanol
LC-MS (Method 1): $R_t$=1.49 min; MS (ESIpos): m/z=544/546 [M+H]$^+$ $^1$H-NMR (400 MHz, DMSO-d6) δ [ppm]: 1.794 (1.17), 1.811 (2.44), 1.836 (4.11), 1.872 (16.00), 2.045 (5.39), 2.078 (6.39), 2.088 (6.44), 2.117 (2.50), 2.136 (5.11), 2.159 (13.11), 2.241 (0.50), 2.288 (0.50), 2.327 (0.83), 2.366 (0.67), 2.670 (0.83), 2.710 (0.67), 3.570 (13.00), 3.656 (3.56), 7.251 (2.33), 7.269 (5.06), 7.287 (3.61), 7.352 (3.56), 7.371 (6.17), 7.389 (3.78), 7.435 (8.33), 7.437 (8.00), 7.455 (6.94), 7.457 (6.67), 7.473 (8.39), 7.493 (11.33), 7.546 (5.61), 7.551 (5.22), 7.568 (3.33), 7.573 (3.17), 8.661 (2.72), 8.676 (5.11), 8.689 (2.56), 12.040 (3.78).

$^1$H-NMR (400 MHz, DMSO-d6) δ [ppm]: 12.04 (br. s, 1H), 8.68 (t, 1H), 7.59-7.53 (m, 1H), 7.53-7.40 (m, 4H), 7.37 (t, 1H), 7.30-7.23 (m, 1H), 3.79-3.48 (m, 7H), 2.21-2.00 (m, 6H), 1.92-1.77 (m, 5H).

Method B:

To a solution of tert-butyl (4R)-5-({[6-bromo-3-methyl-2-(pyrrolidin-1-yl)quinolin-4-yl]carbonyl}-amino)-4-(2-chlorophenyl)pentanoate (2.16 g, 3.59 mmol, enantiomer 1, Example 292A) in dichloromethane (28 ml) was added TFA (6.1 ml, 79.07 mmol), and the mixture was left to stand at RT for 24 h. The mixture was then concentrated and repeatedly dichloromethane was added and the mixture was concentrated again. The residue was purified by preparative HPLC (Method 6).

The combined target fractions were concentrated, and the residue was lyophilized. 1.37 g (100% purity, 70% of theory) of the title compound were obtained. For the starting compound, the R configuration was determined via VCD spectroscopy (see Example 292A), and for that reason the title compound likewise has R configuration.

$[\alpha]_D^{20}$=+11.3°, 589 nm, c=0.30 g/100 ml, methanol
LC-MS (Method 1): $R_t$=1.44 min; MS (ESIpos): m/z=544/546 [M+H]$^+$ $^1$H-NMR (400 MHz, DMSO-d6) δ [ppm]: 1.784 (0.16), 1.795 (0.23), 1.813 (0.53), 1.837 (0.95), 1.870 (3.74), 2.026 (0.28), 2.046 (1.18), 2.079 (1.40), 2.089 (1.42), 2.110 (0.56), 2.118 (0.55), 2.137 (1.18), 2.159 (3.13), 3.315 (16.00), 3.658 (0.81), 7.249 (0.49), 7.268 (1.13), 7.287 (0.82), 7.352 (0.77), 7.370 (1.38), 7.388 (0.85), 7.435 (1.80), 7.455 (1.49), 7.467 (1.84), 7.475 (1.60), 7.489 (3.11), 7.543 (1.54), 7.548 (1.45), 7.565 (0.91), 7.570 (0.88), 8.660 (0.62), 8.674 (1.23), 8.688 (0.62), 12.038 (2.54).

Example 36

5-[({6-Bromo-3-methyl-2-[3-methylpyrrolidin-1-yl]quinolin-4-yl}carbonyl)amino]-4-(2-chlorophenyl)pentanoic acid (Diastereomer Mixture)

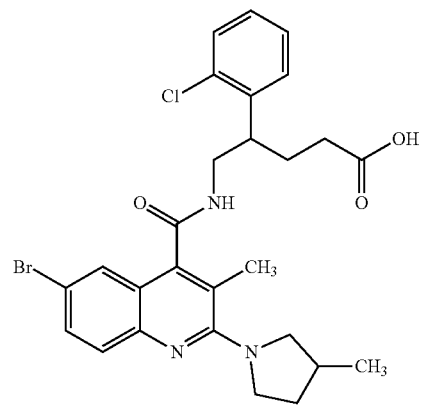 [SMILES: Cc1c(N2CCC(C)C2)nc2ccc(Br)cc2c1C(=O)NCC(CCC(=O)O)c1ccccc1Cl]

To a solution of tert-butyl 5-[({6-bromo-3-methyl-2-[3-methylpyrrolidin-1-yl]quinolin-4-yl}carbonyl)amino]-4-(2- chlorophenyl)pentanoate (25 mg, 40.6 µmol, diastereomer mixture, Example 80A) in dichloromethane (1.0 ml) was added TFA (31 µl, 410 µmol), and the mixture was stirred at RT overnight. Subsequently, TFA (31 µl, 410 µmol) was added again, and the mixture was stirred at RT for a further 24 h. Subsequently, TFA (31 µl, 410 µmol) was added again, and the mixture was stirred at 60° C. for a further 6 h. Subsequently, TFA (31 µl, 410 µmol) was added again, and the mixture was stirred at 60° C. for a further 8 h. This was followed by concentration of the mixture, and repeated additions of dichloromethane followed by concentration again. The residue was dissolved in acetonitrile and purified by means of preparative HPLC (Method 6). The combined target fractions were concentrated, and the residue was lyophilized. 7 mg (98% purity, 31% of theory) of the title compound were obtained.

LC-MS (Method 1): $R_t$=1.59 min; MS (ESIpos): m/z=560 [M+H]$^+$ $^1$H-NMR (400 MHz, DMSO-d6) δ [ppm]: −0.150 (0.99), −0.008 (14.17), 0.008 (8.09), 0.062 (1.26), 0.146 (1.04), 1.059 (16.00), 1.075 (15.93), 1.235 (1.80), 1.367 (2.66), 1.472 (1.69), 1.494 (2.37), 1.522 (1.83), 1.806 (2.03), 1.827 (2.59), 1.851 (1.76), 2.029 (6.85), 2.057 (7.53), 2.114 (3.25), 2.159 (12.03), 2.237 (2.23), 2.327 (1.40), 2.366 (0.95), 2.670 (1.78), 2.689 (10.39), 2.709 (1.31), 2.731 (5.54), 2.890 (6.63), 3.209 (2.70), 3.230 (4.30), 3.592 (4.55), 3.653 (6.72), 7.264 (3.47), 7.283 (2.64), 7.363 (4.26), 7.372 (3.74), 7.433 (8.11), 7.460 (8.29), 7.482 (12.53), 7.539 (6.04), 7.561 (3.58), 7.951 (0.86), 8.699 (3.61).

$^1$H-NMR (400 MHz, DMSO-d6) δ [ppm]: 8.74-8.65 (m, 1H), 7.59-7.51 (m, 1H), 7.51-7.40 (m, 4H), 7.40-7.33 (m, 1H), 7.31-7.22 (m, 1H), 3.76-3.52 (m, 6H), 3.28-3.17 (m, 1H, partly concealed), 2.29-1.97 (m, 8H), 1.90-1.76 (m, 1H), 1.58-1.42 (m, 1H), 1.07 (d, 3H).

Example 37

(+/−)-5-({[6-Bromo-2-(3,3-difluoropyrrolidin-1-yl)-3-methylquinolin-4-yl]carbonyl}amino)-4-(2-chlorophenyl)pentanoic acid (Racemate)

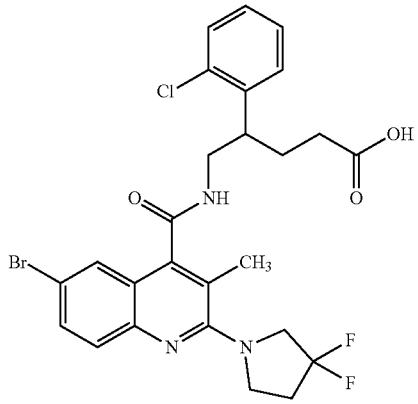 [SMILES: Cc1c(N2CCC(F)(F)C2)nc2ccc(Br)cc2c1C(=O)NCC(CCC(=O)O)c1ccccc1Cl]

To a solution of (+/−)-tert-butyl 5-({[6-bromo-2-(3,3-difluoropyrrolidin-1-yl)-3-methylquinolin-4-yl]carbonyl}amino)-4-(2-chlorophenyl)pentanoate (30 mg, 47.1 µmol, racemate, Example 81A) in dichloromethane (1.0 ml) was added TFA (36 µl, 470 µmol), and the mixture was stirred at RT overnight. Subsequently, TFA (31 µl, 410 µmol) was added again, and the mixture was stirred at RT for a further 24 h. Subsequently, TFA (31 µl, 410 µmol) was added again, and the mixture was stirred at 60° C. for a further 6 h. Subsequently, TFA (31 µl, 410 µmol) was added again, and the mixture was stirred at 60° C. for a further 8 h. This was followed by concentration of the mixture, and repeated additions of dichloromethane followed by concentration again. The residue was dissolved in acetonitrile and purified by means of preparative HPLC (Method 6). The combined target fractions were concentrated, and the residue was lyophilized. 12 mg (98% purity, 44% of theory) of the title compound were obtained.

LC-MS (Method 1): $R_t$=2.11 min; MS (ESIpos): m/z=580/582 [M+H]$^+$ $^1$H-NMR (400 MHz, DMSO-d6) δ [ppm]: −0.149 (1.00), −0.008 (8.49), 0.008 (8.89), 0.049 (0.70), 0.063 (1.25), 0.146 (1.05), 0.943 (1.12), 0.960 (1.05), 1.235 (0.75), 1.813 (2.12), 1.836 (3.07), 1.860 (1.72), 2.041 (5.02), 2.071 (6.34), 2.082 (6.27), 2.104 (2.65), 2.130 (4.19), 2.165 (12.61), 2.327 (1.40), 2.366 (0.92), 2.421 (1.70), 2.440 (3.49), 2.457 (4.82), 2.475 (7.21), 2.523 (5.14), 2.669 (1.50), 2.689 (10.68), 2.709 (1.05), 2.731 (5.17), 2.890 (6.34), 3.584 (2.77), 3.671 (3.42), 3.781 (5.62), 3.965 (3.17), 7.253 (2.12), 7.271 (4.89), 7.290 (3.59), 7.354 (3.10), 7.372 (5.57), 7.391 (3.17), 7.437 (8.89), 7.440 (8.96), 7.457 (7.54), 7.460 (7.51), 7.480 (6.99), 7.497 (5.12), 7.568 (8.01), 7.590 (16.00), 7.628 (8.79), 7.633 (8.11), 7.650 (4.27), 7.655 (4.19), 7.952 (0.85), 8.699 (2.67), 8.712 (5.19), 8.726 (2.70).

$^1$H-NMR (400 MHz, DMSO-d6) δ [ppm]: 12.04 (br. s, 1H), 8.71 (t, 1H), 7.64 (dd, 1H), 7.58 (d, 1H), 7.52-7.42 (m, 3H), 7.37 (t, 1H), 7.31-7.23 (m, 1H), 4.11-3.87 (m, 2H), 3.85-3.50 (m, 5H), 2.51-2.40 (m, 2H, concealed), 2.23-1.96 (m, 6H), 1.90-1.74 (m, 1H).

Example 38

(+/−)-5-({[6-Bromo-3-methyl-2-(1,2-oxazolidin-2-yl)quinolin-4-yl]carbonyl}amino)-4-(2-chlorophenyl)pentanoic acid (Racemate)

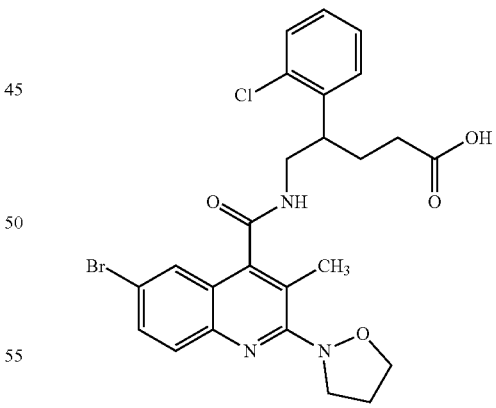

To a solution of (+)-tert-butyl 5-({[6-bromo-3-methyl-2-(1,2-oxazolidin-2-yl)quinolin-4-yl]carbonyl}-amino)-4-(2-chlorophenyl)pentanoate (110 mg, 182 µmol, racemate, Example 82A) in dichloromethane (1.3 ml) was added TFA (140 µl, 1.8 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 80 mg (98% purity, 79% of theory) of the title compound were obtained.

LC-MS (Method 1): $R_t$=1.83 min; MS (ESIpos): m/z=546/548 [M+H]$^+$ $^1$H-NMR (400 MHz, DMSO-d6) δ [ppm]: −0.008 (1.94), 0.008 (1.90), 1.782 (0.41), 1.793 (0.66), 1.814 (1.34), 1.835 (1.71), 1.858 (0.99), 2.033 (0.92), 2.045 (3.57), 2.073 (2.81), 2.081 (3.16), 2.093 (3.30), 2.121 (1.33), 2.129 (1.23), 2.141 (2.11), 2.164 (1.10), 2.210 (7.16), 2.240 (4.55), 2.257 (5.85), 2.276 (4.31), 2.294 (1.35), 3.604 (1.49), 3.651 (0.90), 3.670 (1.66), 3.684 (2.28), 3.698 (2.02), 3.714 (1.56), 3.771 (3.06), 3.822 (4.25), 3.840 (7.28), 3.859 (3.97), 7.257 (1.29), 7.275 (2.94), 7.293 (2.07), 7.356 (1.72), 7.375 (3.14), 7.393 (1.64), 7.445 (4.53), 7.447 (4.50), 7.465 (3.83), 7.467 (3.73), 7.486 (3.85), 7.502 (3.01), 7.707 (0.71), 7.729 (16.00), 7.756 (0.60), 8.767 (1.66), 8.782 (3.27), 8.796 (1.64), 12.043 (3.12).

$^1$H-NMR (400 MHz, DMSO-d6) δ [ppm]: 12.04 (s, 1H), 8.78 (t, 1H), 7.78-7.69 (m, 2H), 7.53 (br. s, 1H), 7.51-7.43 (m, 2H), 7.37 (t, 1H), 7.31-7.24 (m, 1H), 3.84 (t, 2H), 3.81-3.52 (m, 5H), 2.31-1.99 (m, 8H), 1.90-1.74 (m, 1H).

Separation of the Enantiomers:

The title compound (70 mg) was dissolved in a mixture of isopropanol (2 ml) and heptane (2 ml), and separated into the enantiomers by means of preparative HPLC on chiral phase (see Examples 39 and 40) [column: Daicel Chiralpak ID, 5 μm, 250 mm×20 mm; flow rate: 15 ml/min; injection: 0.4 ml; eluent: 50% isopropanol/50% (heptane+0.2% TFA); run time 13 min, isocratic]. The combined target fractions were concentrated, and the residue was lyophilized.

Example 39

(−)-5-({[6-Bromo-3-methyl-2-(1,2-oxazolidin-2-yl)quinolin-4-yl]carbonyl}amino)-4-(2-chlorophenyl)pentanoic acid (Enantiomer 1)

In the enantiomer separation described in Example 38, the prepurified title compound was obtained as the enantiomer that eluted earlier (ee 99%). This was followed by repurification by means of preparative HPLC (Method 7). The combined target fractions were concentrated, and the residue was lyophilized in acetonitrile/water. 39 mg (98% purity) of the repurified title compound were obtained.

$[α]_D^{20}$=−8.0°, 589 nm, c=0.30 g/100 ml, methanol

LC-MS (Method 2): $R_t$=0.94 min; MS (ESIpos): m/z=546/548 [M+H]$^+$ $^1$H-NMR (400 MHz, DMSO-d6) δ [ppm]: −0.149 (0.87), −0.008 (7.75), 0.008 (6.54), 0.146 (0.84), 1.809 (1.24), 1.832 (1.61), 1.856 (0.90), 2.039 (2.88), 2.073 (3.07), 2.084 (2.79), 2.133 (1.83), 2.209 (6.54), 2.240 (4.16), 2.257 (5.49), 2.276 (4.09), 2.294 (1.27), 2.327 (1.27), 2.366 (1.27), 2.523 (3.57), 2.669 (1.36), 2.710 (1.27), 3.600 (1.43), 3.667 (1.55), 3.682 (2.14), 3.697 (1.86), 3.771 (2.82), 3.822 (4.09), 3.840 (6.98), 3.859 (3.88), 7.256 (1.27), 7.274 (2.79), 7.292 (1.98), 7.355 (1.58), 7.374 (2.95), 7.392 (1.55), 7.444 (4.43), 7.464 (3.78), 7.484 (3.53), 7.501 (2.79), 7.707 (0.68), 7.729 (16.00), 8.777 (1.33), 8.791 (2.73), 8.805 (1.43).

Example 40

(+)-5-({[6-Bromo-3-methyl-2-(1,2-oxazolidin-2-yl)quinolin-4-yl]carbonyl}amino)-4-(2-chlorophenyl)pentanoic acid (Enantiomer 2)

In the enantiomer separation described in Example 38, the prepurified title compound was obtained as the enantiomer that eluted later (ee 97%). This was followed by repurification by means of preparative HPLC (Method 7). The combined target fractions were concentrated, and the residue was lyophilized in acetonitrile/water. 30 mg (98% purity) of the repurified title compound were obtained.

$[α]_D^{20}$=+14.0°, 589 nm, c=0.25 g/100 ml, methanol

LC-MS (Method 2): $R_t$=0.94 min; MS (ESIpos): m/z=546/548 [M+H]$^+$ $^1$H-NMR (400 MHz, DMSO-d6) δ [ppm]: −0.149 (0.52), 0.146 (0.52), 1.790 (0.55), 1.808 (1.29), 1.831 (1.85), 1.854 (0.98), 2.014 (0.69), 2.036 (2.96), 2.067 (3.48), 2.078 (3.21), 2.088 (2.20), 2.102 (1.35), 2.128 (2.06), 2.152 (0.94), 2.211 (7.24), 2.240 (4.66), 2.258 (6.01), 2.276 (4.41), 2.294 (1.36), 2.327 (0.74), 2.366 (0.66), 2.670 (0.77), 2.710 (0.69), 3.595 (1.54), 3.648 (0.94), 3.667 (1.68), 3.681 (2.27), 3.695 (2.04), 3.712 (1.60), 3.732 (1.47), 3.772 (3.13), 3.822 (4.34), 3.841 (7.47), 3.859 (4.08), 7.256 (1.29), 7.274 (2.92), 7.294 (2.04), 7.355 (1.74), 7.373 (3.20), 7.392 (1.67), 7.446 (4.48), 7.466 (3.78), 7.483 (3.92), 7.502 (3.00), 7.707 (0.67), 7.729 (16.00), 7.756 (0.66), 8.784 (1.45), 8.799 (2.85), 8.812 (1.52).

Example 41

5-[({6-Bromo-2-[3-methoxypyrrolidin-1-yl]-3-methylquinolin-4-yl}carbonyl)amino]-4-(2-chlorophenyl)pentanoic acid (Diastereomer Mixture)

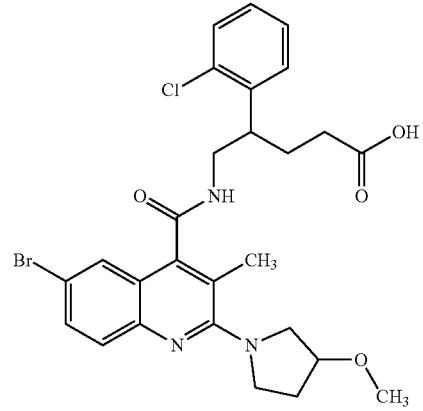 [SMILES: COC1CCN(c2nc3ccc(Br)cc3c(C(=O)NCC(CCC(=O)O)c3ccccc3Cl)c2C)C1]

To a solution of butyl 5-({[6-bromo-2-(3-methoxypyrrolidin-1-yl)-3-methylquinolin-4-yl]carbonyl}-amino)-4-(2-chlorophenyl)pentanoate (30 mg, 47.5 μmol, diastereomer mixture, Example 83A) in dichloromethane (1.0 ml) was added TFA (37 μl, 480 μmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 10 mg (98% purity, 37% of theory) of the title compound were obtained.

LC-MS (Method 2): $R_t$=0.80 min; MS (ESIpos): m/z=574/576 [M+H]$^+$ $^1$H-NMR (400 MHz, DMSO-d6) δ [ppm]: −0.008 (1.41), 0.008 (1.36), 1.812 (0.64), 1.834 (0.89), 1.858 (0.55), 1.954 (0.60), 2.018 (1.00), 2.040 (1.85), 2.068 (2.03), 2.079 (1.86), 2.103 (0.85), 2.129 (1.23), 2.158 (3.82), 2.523 (0.81), 3.199 (0.60), 3.245 (16.00), 3.417 (0.42), 3.511 (1.14), 3.551 (0.87), 3.572 (0.89), 3.591 (0.88), 3.659 (0.88), 3.714 (0.98), 3.778 (0.79), 3.807 (0.63), 4.017 (1.34), 7.245 (0.44), 7.263 (0.96), 7.275 (0.93), 7.293 (0.63), 7.346 (0.69), 7.364 (1.23), 7.378 (1.10), 7.395 (0.66), 7.435 (2.45), 7.437 (2.36), 7.455 (2.05), 7.457 (1.93), 7.478 (2.83), 7.500 (3.63), 7.556 (1.97), 7.561 (1.29), 7.579 (1.19), 8.694 (1.08).

$^1$H-NMR (400 MHz, DMSO-d6) δ [ppm]: 12.05 (br. s, 1H), 8.69 (br. s, 1H), 7.62-7.53 (m, 1H), 7.53-7.41 (m, 4H), 7.40-7.33 (m, 1H), 7.31-7.22 (m, 1H), 4.02 (br. s, 1H), 3.84-3.46 (m, 7H), 3.24 (s, 3H), 2.22-1.77 (m, 9H).

Example 42

(+/−)-5-({[6-Bromo-2-(3,3-dimethylpiperidin-1-yl)-3-methylquinolin-4-yl]carbonyl}amino)-4-(2-chlorophenyl)pentanoic acid (Racemate)

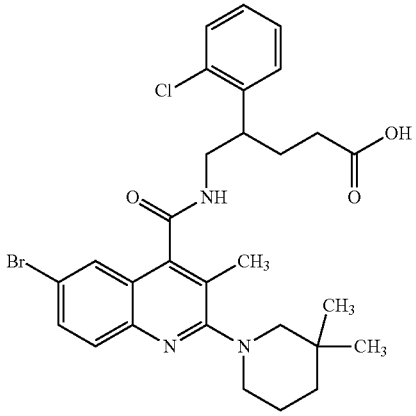

To a solution of (+/−)-tert-butyl 5-({[6-bromo-2-(3,3-dimethylpiperidin-1-yl)-3-methylquinolin-4-yl]carbonyl}amino)-4-(2-chlorophenyl)pentanoate (80 mg, 124 μmol, racemate, Example 84A) in dichloromethane (910 μl) was added TFA (96 μl, 1.2 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 65 mg (98% purity, 87% of theory) of the title compound were obtained.

LC-MS (Method 1): $R_t$=2.43 min; MS (ESIpos): m/z=586/588 [M+H]$^+$ $^1$H-NMR (600 MHz, DMSO-d6) δ [ppm]: 1.007 (16.00), 1.377 (1.50), 1.386 (2.45), 1.392 (2.05), 1.723 (2.48), 1.731 (2.30), 1.740 (1.95), 1.753 (1.20), 1.762 (0.78), 1.818 (0.64), 1.829 (0.83), 1.839 (0.50), 1.919 (0.68), 1.929 (0.67), 2.182 (3.52), 2.386 (0.52), 2.614 (0.58), 2.868 (3.61), 3.043 (1.14), 3.476 (0.92), 3.635 (0.64), 7.232 (0.61), 7.244 (1.47), 7.256 (1.05), 7.339 (0.71), 7.351 (1.38), 7.364 (0.79), 7.420 (2.16), 7.433 (2.83), 7.442 (1.31), 7.632 (0.62), 7.646 (4.36), 7.668 (0.51), 9.138 (0.94).

$^1$H-NMR (600 MHz, DMSO-d6) δ [ppm]: 9.14 (br. s, 1H), 7.69-7.60 (m, 2H), 7.48 (br. s, 1H), 7.45-7.40 (m, 2H), 7.35 (t, 1H), 7.27-7.21 (m, 1H), 3.64 (br. s, 2H), 3.52-3.44 (m, 1H), 3.04 (br. s, 2H), 2.87 (s, 2H), 2.18 (br. s, 3H), 1.98-1.88 (m, 1H), 1.87-1.78 (m, 1H), 1.78-1.68 (m, 4H), 1.41-1.34 (m, 2H), 1.01 (s, 6H).

Separation of the Enantiomers:

The title compound (50 mg) was dissolved in methanol (25 ml) and separated into the enantiomers by means of preparative SFC on chiral phase (see Examples 43 and 44) [column: Daicel Chiralpak AD, 5 μm, 250 mm×20 mm; flow rate: 80 ml/min; injection: 3 ml; eluent: 25% isopropanol/75% carbon dioxide; run time 9 min, isocratic]. The combined target fractions were concentrated, and the residue was lyophilized.

Example 43

(−)-5-({[6-Bromo-2-(3,3-dimethylpiperidin-1-yl)-3-methylquinolin-4-yl]carbonyl}amino)-4-(2-chlorophenyl)pentanoic acid (Enantiomer 1)

In the enantiomer separation described in Example 42, 10 mg (98% purity, ee 99%) of the title compound were obtained as the enantiomer that eluted earlier.

$[α]_D^{20}$=−12.0°, 589 nm, c=0.25 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: −0.008 (2.83), 0.008 (3.24), 1.004 (16.00), 1.373 (1.13), 1.387 (1.81), 1.402 (1.39), 1.721 (1.36), 1.805 (0.50), 1.827 (0.66), 1.850 (0.42), 2.024 (1.09), 2.054 (1.93), 2.070 (1.15), 2.106 (0.65), 2.165 (5.23), 2.710 (0.41), 2.864 (4.18), 3.044 (1.53), 3.576 (0.67), 3.669 (0.97), 7.253 (0.55), 7.272 (1.28), 7.289 (0.91), 7.353 (0.75), 7.371 (1.38), 7.389 (0.74), 7.438 (1.91), 7.440 (1.92), 7.458 (1.75), 7.461 (1.78), 7.475 (1.85), 7.491 (1.37), 7.628 (0.41), 7.650 (5.99), 7.655 (2.96), 8.762 (0.98).

$^1$H-NMR (400 MHz, DMSO-d6) δ [ppm]: 12.15 (br. s, 1H), 8.76 (t, 1H), 7.70-7.61 (m, 2H), 7.58-7.41 (m, 3H), 7.37 (t, 1H), 7.30-7.24 (m, 1H), 3.75-3.62 (m, 2H), 3.61-3.54 (m, 1H), 3.04 (br. s, 2H), 2.86 (s, 2H), 2.17 (s, 3H), 2.13-1.97 (m, 3H), 1.90-1.77 (m, 1H), 1.76-1.65 (m, 2H), 1.45-1.32 (m, 2H), 1.00 (s, 6H).

Example 44

(+)-5-({[6-Bromo-2-(3,3-dimethylpiperidin-1-yl)-3-methylquinolin-4-yl]carbonyl}amino)-4-(2-chlorophenyl)pentanoic acid (Enantiomer 2)

In the enantiomer separation described in Example 42, 10 mg (98% purity, ee 99%) of the title compound were obtained as the enantiomer that eluted later.

$[α]_D^{20}$=+9.3°, 589 nm, c=0.25 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: −0.008 (3.58), 0.008 (3.59), 0.146 (0.41), 1.004 (16.00), 1.372 (1.15), 1.386 (1.87), 1.401 (1.40), 1.720 (1.37), 1.810 (0.50), 1.833 (0.71), 1.857 (0.42), 2.039 (1.14), 2.067 (1.73), 2.122 (0.84), 2.163 (5.31), 2.327 (0.42), 2.669 (0.46), 2.863 (4.18), 3.044 (1.59), 3.583 (0.66), 3.673 (1.01), 7.256 (0.55), 7.274 (1.29), 7.291 (0.94), 7.355 (0.79), 7.373 (1.42), 7.393 (0.73), 7.440 (2.01), 7.442 (2.03), 7.460 (1.83), 7.478 (1.90), 7.495 (1.41), 7.628 (0.41), 7.650 (6.13), 7.655 (3.12), 7.678 (0.41), 8.737 (1.17).

$^1$H-NMR (400 MHz, DMSO-d6) δ [ppm]: 12.1 (br. s, 1H), 8.74 (t, 1H), 7.71-7.59 (m, 2H), 7.58-7.41 (m, 3H), 7.37 (t, 1H), 7.31-7.23 (m, 1H), 3.76-3.62 (m, 2H), 3.62-3.53 (m, 1H), 3.04 (br. s, 2H), 2.86 (s, 2H), 2.16 (s, 3H), 2.14-2.00 (m, 3H), 1.90-1.76 (m, 1H), 1.76-1.67 (m, 2H), 1.43-1.34 (m, 2H), 1.00 (s, 6H).

Example 45

5-[({6-Bromo-3-methyl-2-[3-methylpiperidin-1-yl]quinolin-4-yl}carbonyl)amino]-4-(2-chlorophenyl)pentanoic acid (Diastereomer Mixture)

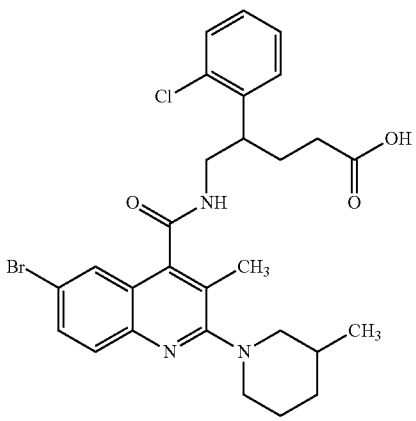 [SMILES: Cc1c(N2CCCC(C)C2)nc2ccc(Br)cc2c1C(=O)NCC(CCC(=O)O)c1ccccc1Cl]

To a solution of tert-butyl 5-[({6-bromo-3-methyl-2-[3-methylpiperidin-1-yl]quinolin-4-yl}carbonyl)amino]-4-(2-chlorophenyl)pentanoate (100 mg, 159 µmol, diastereomer mixture, Example 85A) in dichloromethane (1.2 ml) was added TFA (120 µl, 1.6 mmol), and the mixture was stirred at RT overnight. The mixture was then concentrated and repeatedly dichloromethane was added and the mixture was concentrated again. The residue was dissolved in acetonitrile and purified by means of preparative HPLC (Method 6). The combined target fractions were concentrated, and the residue was lyophilized. 82 mg (98% purity, 88% of theory) of the title compound were obtained.

LC-MS (Method 1): $R_t$=2.33 min; MS (ESIpos): m/z=572/574 [M+H]$^+$ $^1$H-NMR (400 MHz, DMSO-d6) δ [ppm]: 0.921 (4.93), 0.936 (4.95), 1.077 (0.56), 1.107 (0.57), 1.625 (0.46), 1.654 (0.54), 1.730 (1.03), 1.761 (1.00), 1.793 (1.35), 1.821 (1.21), 1.837 (1.07), 1.860 (0.44), 2.049 (1.51), 2.083 (1.79), 2.091 (1.94), 2.135 (6.39), 2.160 (0.58), 2.431 (0.42), 2.501 (16.00), 2.675 (0.41), 2.709 (0.64), 3.489 (3.11), 3.574 (1.10), 3.591 (1.05), 3.677 (1.20), 7.255 (0.62), 7.274 (1.47), 7.292 (1.12), 7.355 (0.86), 7.374 (1.53), 7.392 (0.80), 7.441 (2.18), 7.461 (1.95), 7.480 (2.10), 7.499 (1.51), 7.626 (0.50), 7.648 (5.52), 8.704 (0.73), 8.719 (1.40), 8.732 (0.68).

$^1$H-NMR (400 MHz, DMSO-d6) δ [ppm]: 12.05 (br. s, 1H), 8.72 (t, 1H), 7.70-7.61 (m, 2H), 7.58-7.41 (m, 3H), 7.37 (t, 1H), 7.32-7.23 (m, 1H), 3.82-3.26 (m, 5H, partly concealed), 2.78-2.62 (m, 1H), 2.48-2.38 (m, 1H, partly concealed), 2.20-1.98 (m, 6H), 1.90-1.54 (m, 5H), 1.17-1.01 (m, 1H), 0.93 (d, 3H).

Example 46

(−)-5-[({6-Bromo-3-methyl-2-[3-methylpiperidin-1-yl]quinolin-4-yl}carbonyl)amino]-4-(2-chlorophenyl)pentanoic acid (Diastereomer 1)

To a solution of (−)-tert-butyl 5-[({6-bromo-3-methyl-2-[3-methylpiperidin-1-yl]quinolin-4-yl}carbonyl)amino]-4-(2-chlorophenyl)pentanoate (185 mg, 294 µmol, diastereomer 1, Example 86A) in dichloromethane (2.2 ml) was added TFA (230 µl, 2.9 mmol), and the mixture was left to stand at RT for 24 h. The mixture was then concentrated and repeatedly dichloromethane was added and the mixture was concentrated again. The residue was dissolved in acetonitrile and purified by means of preparative HPLC (Method 7). The combined target fractions were concentrated, and the residue was lyophilized in acetonitrile/water. 117 mg (98% purity, ee>99%, 68% of theory) of the title compound were obtained.

$[α]_D^{20}$=−20.6°, 589 nm, c=0.35 g/100 ml, methanol

LC-MS (Method 2): $R_t$=1.20 min; MS (ESIpos): m/z=572/574 [M+H]$^+$ $^1$H-NMR (400 MHz, DMSO-d6) δ [ppm]: −0.008 (1.52), 0.920 (13.64), 0.936 (13.90), 1.048 (0.47), 1.077 (1.44), 1.106 (1.50), 1.128 (0.61), 1.234 (0.50), 1.589 (0.44), 1.621 (1.24), 1.651 (1.47), 1.679 (0.69), 1.729 (2.53), 1.765 (2.53), 1.791 (3.56), 1.821 (3.15), 1.837 (2.76), 1.861 (1.16), 2.016 (0.54), 2.029 (0.87), 2.049 (3.74), 2.082 (4.70), 2.090 (5.03), 2.134 (16.00), 2.160 (1.56), 2.186 (0.52), 2.419 (1.30), 2.447 (2.04), 2.476 (1.42), 2.523 (0.75), 2.682 (1.18), 2.710 (2.27), 2.738 (1.14), 3.439 (2.24), 3.460 (3.55), 3.486 (1.99), 3.577 (1.53), 3.593 (1.74), 3.680 (3.29), 7.256 (1.62), 7.274 (3.82), 7.291 (2.89), 7.355 (2.22), 7.374 (4.05), 7.392 (2.09), 7.441 (5.61), 7.443 (5.48), 7.461 (4.98), 7.463 (4.84), 7.482 (5.43), 7.498 (4.02), 7.624 (1.48), 7.647 (14.26), 7.654 (7.96), 7.672 (0.97), 7.676 (1.18), 8.700 (1.90), 8.715 (3.84), 8.729 (1.85), 12.043 (2.06).

$^1$H-NMR (400 MHz, DMSO-d6) δ [ppm]: 12.04 (br. s, 1H), 8.71 (t, 1H), 7.70-7.60 (m, 2H), 7.53-7.42 (m, 3H), 7.37 (t, 1H), 7.31-7.23 (m, 1H), 3.78-3.63 (m, 2H), 3.63-3.52 (m, 1H), 3.51-3.38 (m, 2H), 2.71 (t, 1H), 2.45 (t, 1H), 2.21-1.98 (m, 6H), 1.91-1.55 (m, 5H), 1.17-1.02 (m, 1H), 0.93 (d, 3H).

Example 47

(+)-5-[({6-Bromo-3-methyl-2-[3-methylpiperidin-1-yl]quinolin-4-yl}carbonyl)amino]-4-(2-chlorophenyl)pentanoic acid (Diastereomer 2)

To a solution of (+)-tert-butyl 5-[({6-bromo-3-methyl-2-[3-methylpiperidin-1-yl]quinolin-4-yl}carbonyl)amino]-4-(2-chlorophenyl)pentanoate (185 mg, 294 µmol, diastereomer 2, Example 87A) in dichloromethane (1.6 ml) was added TFA (170 µl, 2.2 mmol), and the mixture was left to stand at RT for 24 h. The mixture was then concentrated and repeatedly dichloromethane was added and the mixture was concentrated again. The residue was dissolved in acetonitrile and purified by means of preparative HPLC (Method 7). The combined target fractions were concentrated, and the residue was lyophilized in acetonitrile/water. 117 mg (98% purity, ee>99%, 68% of theory) of the title compound were obtained.

$[α]_D^{20}$=+24.9°, 589 nm, c=0.34 g/100 ml, methanol

LC-MS (Method 2): $R_t$=1.20 min; MS (ESIpos): m/z=572/574 [M+H]$^+$ $^1$H-NMR (400 MHz, DMSO-d6) δ [ppm]: −0.008 (2.59), 0.008 (2.07), 0.921 (13.42), 0.937 (13.48), 1.055 (0.46), 1.081 (1.40), 1.105 (1.43), 1.134 (0.56), 1.623 (1.22), 1.653 (1.43), 1.682 (0.67), 1.732 (2.48), 1.766 (2.50), 1.793 (3.54), 1.814 (2.99), 1.823 (3.07), 1.837 (2.80), 1.861 (1.12), 2.048 (3.60), 2.083 (4.54), 2.091 (4.85), 2.136 (16.00), 2.160 (1.50), 2.432 (1.28), 2.461 (2.09), 2.524 (0.99), 2.670 (0.41), 2.695 (1.08), 2.724 (1.92), 2.752 (1.03), 3.448 (2.22), 3.471 (3.55), 3.497 (1.95), 3.577 (1.64), 3.593 (1.85), 3.681 (3.38), 3.973 (1.31), 7.257 (1.61), 7.275 (3.65), 7.292 (2.61), 7.295 (2.61), 7.357 (2.19), 7.375 (4.01), 7.394 (2.04), 7.441 (5.78), 7.444 (5.83), 7.461 (5.09), 7.464 (5.09), 7.483 (5.41), 7.499

Example 48

(+)-5-[({6-Bromo-3-methyl-2-[3-methylpiperidin-1-yl]quinolin-4-yl}carbonyl)amino]-4-(2-chlorophenyl)pentanoic acid (Diastereomer 3)

To a solution of (+)-tert-butyl 5-[({6-bromo-3-methyl-2-[3-methylpiperidin-1-yl]quinolin-4-yl}carbonyl)amino]-4-(2-chlorophenyl)pentanoate (150 mg, 238 µmol, diastereomer 3, Example 88A) in dichloromethane (1.8 ml) was added TFA (180 µl, 2.4 mmol), and the mixture was left to stand at RT for 24 h. The mixture was then concentrated and repeatedly dichloromethane was added and the mixture was concentrated again. The residue was dissolved in acetonitrile and purified by means of preparative HPLC (Method 7). The combined target fractions were concentrated, and the residue was lyophilized in acetonitrile/water. 102 mg (100% purity, ee>99%, 74% of theory) of the title compound were obtained.

$[\alpha]_D^{20}$=+7.5°, 589 nm, c=0.38 g/100 ml, methanol
LC-MS (Method 2): $R_t$=1.20 min; MS (ESIpos): m/z=572/574 [M+H]$^+$
$^1$H-NMR (400 MHz, DMSO-d6) δ [ppm]: 0.921 (11.56), 0.937 (11.71), 1.050 (0.44), 1.077 (1.30), 1.106 (1.33), 1.128 (0.54), 1.234 (0.56), 1.626 (1.13), 1.657 (1.35), 1.686 (0.66), 1.729 (2.37), 1.760 (2.30), 1.794 (2.97), 1.821 (2.75), 1.836 (2.48), 1.860 (1.04), 2.048 (3.26), 2.083 (4.03), 2.090 (4.31), 2.104 (2.16), 2.135 (16.00), 2.159 (1.29), 2.429 (1.25), 2.458 (1.97), 2.669 (1.11), 2.697 (1.76), 2.726 (0.96), 3.434 (2.04), 3.461 (3.58), 3.492 (1.67), 3.592 (1.60), 3.670 (2.24), 7.256 (1.35), 7.274 (3.19), 7.292 (2.26), 7.356 (1.92), 7.374 (3.51), 7.392 (1.85), 7.441 (4.84), 7.461 (4.35), 7.480 (4.74), 7.499 (3.41), 7.625 (1.11), 7.648 (12.30), 7.654 (6.45), 7.672 (0.76), 7.676 (0.88), 8.703 (1.72), 8.717 (3.36), 8.731 (1.65), 12.052 (0.67).

Example 49

(−)-5-[({6-Bromo-3-methyl-2-[3-methylpiperidin-1-yl]quinolin-4-yl}carbonyl)amino]-4-(2-chlorophenyl)pentanoic acid (Diastereomer 4)

To a solution of (−)-tert-butyl 5-[({6-bromo-3-methyl-2-[3-methylpiperidin-1-yl]quinolin-4-yl}carbonyl)amino]-4-(2-chlorophenyl)pentanoate (140 mg, 223 µmol, diastereomer 4, Example 89A) in dichloromethane (1.6 ml) was added TFA (170 µl, 2.2 mmol), and the mixture was left to stand at RT for 30 h. The mixture was then concentrated and repeatedly dichloromethane was added and the mixture was concentrated again. The residue was dissolved in acetonitrile and purified by means of preparative HPLC (Method 7). The combined target fractions were concentrated, and the residue was lyophilized in acetonitrile/water. 78 mg (97% purity, ee>99%, 59% of theory) of the title compound were obtained.

$[\alpha]_D^{20}$=−17.3°, 436 nm, c=0.38 g/100 ml, methanol
LC-MS (Method 2): $R_t$=1.20 min; MS (ESIpos): m/z=572/574 [M+H]$^+$
$^1$H-NMR (400 MHz, DMSO-d6) δ [ppm]: 0.921 (6.01), 0.936 (6.18), 1.077 (0.69), 1.106 (0.70), 1.626 (0.59), 1.657 (0.70), 1.729 (1.24), 1.760 (1.21), 1.792 (1.61), 1.812 (1.34), 1.820 (1.42), 1.834 (1.41), 1.858 (0.57), 2.045 (1.68), 2.078 (2.14), 2.086 (2.32), 2.134 (8.43), 2.155 (0.82), 2.429 (0.64), 2.500 (16.00), 2.669 (0.63), 2.698 (0.92), 2.726 (0.50), 3.433 (1.14), 3.461 (1.93), 3.491 (0.91), 3.574 (0.74), 3.590 (0.85), 3.669 (1.16), 7.255 (0.73), 7.273 (1.75), 7.292 (1.28), 7.355 (1.03), 7.374 (1.87), 7.392 (0.98), 7.441 (2.63), 7.461 (2.35), 7.480 (2.52), 7.498 (1.77), 7.624 (0.61), 7.647 (6.71), 7.675 (0.51), 7.705 (0.85), 8.719 (1.68), 8.733 (0.85).

Example 50

(+/−)-5-({[6-Bromo-2-(3,3-difluoropiperidin-1-yl)-3-methylquinolin-4-yl]carbonyl}amino)-4-(2-chlorophenyl)pentanoic acid (Racemate)

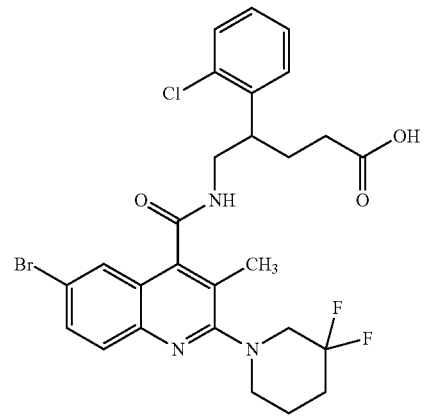 [SMILES: Cc1c(N2CCCC(F)(F)C2)nc2ccc(Br)cc2c1C(=O)NCC(CCC(=O)O)c1ccccc1Cl]

To a solution of (+/−)-tert-butyl 5-({[6-bromo-2-(3,3-difluoropiperidin-1-yl)-3-methylquinolin-4-yl]carbonyl}amino)-4-(2-chlorophenyl)pentanoate (100 mg, 154 µmol, racemate, Example 90A) in dichloromethane (1.1 ml) was added TFA (120 µl, 1.5 mmol), and the mixture was left to stand at RT for 16 h. The mixture was then concentrated and repeatedly dichloromethane was added and the mixture was concentrated again. The residue was dissolved in acetonitrile and purified by means of preparative HPLC (Method 7). The combined target fractions were concentrated, and the residue was lyophilized. 70 mg (98% purity, 75% of theory) of the title compound were obtained.

LC-MS (Method 2): $R_t$=1.13 min; MS (ESIpos): m/z=594/596 [M+H]$^+$
$^1$H-NMR (400 MHz, DMSO-d6) δ [ppm]: −0.008 (2.73), 0.008 (2.65), 1.795 (0.82), 1.814 (1.76), 1.838 (2.35), 1.881 (4.53), 2.047 (5.28), 2.082 (7.13), 2.091 (7.78), 2.150 (16.00), 2.225 (0.40), 2.327 (0.75), 2.366 (0.66), 2.670 (0.74), 2.709 (0.63), 3.164 (5.24), 3.447 (3.36), 3.476 (6.42), 3.505 (3.20), 3.593 (1.89), 3.686 (3.35), 7.256 (1.75), 7.275 (4.05), 7.293 (2.86), 7.358 (2.48), 7.375 (4.44), 7.394 (2.29), 7.443 (6.36), 7.462 (5.35), 7.486 (5.22), 7.502 (4.30), 7.673 (2.44), 7.695 (13.97), 7.700 (9.61), 7.705 (8.12), 7.723 (1.34), 7.728 (1.56), 8.720 (2.31), 8.734 (4.37), 8.748 (2.09), 12.047 (1.44).
$^1$H-NMR (400 MHz, DMSO-d6) δ [ppm]: 12.05 (br. s, 1H), 8.73 (t, 1H), 7.76-7.64 (m, 2H), 7.59-7.42 (m, 3H), 7.38 (t, 1H), 7.32-7.22 (m, 1H), 3.80-3.64 (m, 2H), 3.63-3.54 (m, 1H), 3.48 (t, 2H), 3.23-3.07 (m, 2H), 2.20-2.00 (m, 8H), 1.94-1.74 (m, 3H).

Example 51

(−)-5-({[6-Bromo-2-(3,3-difluoropiperidin-1-yl)-3-methylquinolin-4-yl]carbonyl}amino)-4-(2-chlorophenyl)pentanoic acid (Enantiomer 1)

To a solution of tert-butyl 5-({[6-bromo-2-(3,3-difluoropiperidin-1-yl)-3-methylquinolin-4-yl]carbonyl}-amino)-

4-(2-chlorophenyl)pentanoate (660 mg, 1.01 mmol, enantiomer 1, Example 91A) in dichloromethane (8.0 ml) was added TFA (1.6 ml, 20 mmol), and the mixture was left to stand at RT for 18 h. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 479 mg (100% purity, ee>99%, 79% of theory) of the title compound were obtained.

$[\alpha]_D^{20}$=−17.6°, 589 nm, c=0.39 g/100 ml, DMSO

LC-MS (Method 2): $R_t$=1.13 min; MS (ESIpos): m/z=594/596 $[M+H]^+$ $^1$H-NMR (400 MHz, DMSO-d6) δ [ppm]: −0.149 (0.52), −0.008 (6.12), 0.008 (4.60), 0.146 (0.48), 1.797 (0.95), 1.815 (1.92), 1.838 (2.60), 1.881 (4.78), 2.048 (5.58), 2.083 (7.57), 2.092 (8.27), 2.150 (16.00), 2.327 (0.76), 2.366 (0.59), 2.669 (0.62), 2.710 (0.52), 3.162 (5.51), 3.447 (3.52), 3.476 (6.45), 3.504 (3.21), 3.596 (2.04), 3.686 (3.52), 7.258 (1.92), 7.276 (4.03), 7.296 (2.81), 7.358 (2.54), 7.377 (4.41), 7.395 (2.25), 7.442 (6.36), 7.445 (6.48), 7.462 (5.42), 7.465 (5.37), 7.486 (5.36), 7.503 (4.30), 7.673 (2.60), 7.695 (13.64), 7.700 (10.23), 7.705 (8.55), 7.723 (1.42), 7.728 (1.67), 8.719 (2.31), 8.734 (4.43), 8.748 (2.10), 12.048 (3.00).

Example 52

(+)-5-({[6-Bromo-2-(3,3-difluoropiperidin-1-yl)-3-methylquinolin-4-yl]carbonyl}amino)-4-(2-chlorophenyl)pentanoic acid (Enantiomer 2)

To a solution of tert-butyl 5-({[6-bromo-2-(3,3-difluoropiperidin-1-yl)-3-methylquinolin-4-yl]carbonyl}-amino)-4-(2-chlorophenyl)pentanoate (620 mg, 952 µmol, enantiomer 2, Example 92A) in dichloromethane (8.0 ml) was added TFA (1.5 ml, 19 mmol), and the mixture was left to stand at RT for 18 h. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 397 mg (100% purity, ee 98%, 70% of theory) of the title compound were obtained.

$[\alpha]_D^{20}$=+12.1°, 589 nm, c=0.37 g/100 ml, DMSO

LC-MS (Method 2): $R_t$=1.13 min; MS (ESIpos): m/z=594/596 $[M+H]^+$ $^1$H-NMR (400 MHz, DMSO-d6) δ [ppm]: −0.008 (3.83), 0.008 (3.53), 0.146 (0.41), 1.784 (0.53), 1.795 (0.82), 1.814 (1.73), 1.837 (2.38), 1.881 (4.61), 2.013 (0.53), 2.047 (5.23), 2.082 (7.24), 2.090 (7.79), 2.110 (4.09), 2.150 (16.00), 2.327 (0.51), 2.366 (0.50), 2.670 (0.53), 2.709 (0.51), 3.163 (5.34), 3.447 (3.40), 3.476 (6.48), 3.504 (3.25), 3.594 (1.94), 3.685 (3.39), 7.258 (1.69), 7.275 (3.92), 7.293 (2.77), 7.358 (2.34), 7.376 (4.30), 7.393 (2.26), 7.442 (6.13), 7.445 (5.76), 7.462 (5.14), 7.465 (4.75), 7.486 (5.18), 7.503 (4.26), 7.673 (2.10), 7.695 (13.05), 7.700 (9.57), 7.705 (8.01), 7.723 (1.37), 7.728 (1.62), 8.720 (2.18), 8.734 (4.42), 8.748 (2.14), 12.051 (1.27).

Example 53

5-[({6-Bromo-3-methyl-2-[3-(trifluoromethyl)piperidin-1-yl]quinolin-4-yl}carbonyl)amino]-4-(2-chlorophenyl)pentanoic acid (Diastereomer Mixture)

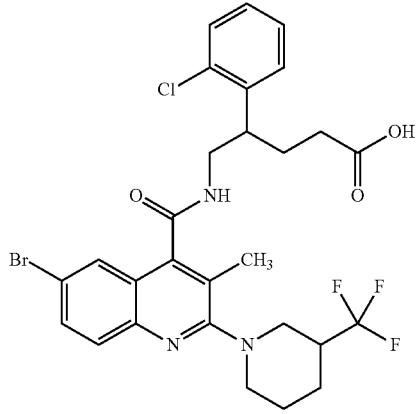 [SMILES: Cc1c(N2CCCC(C(F)(F)F)C2)nc2ccc(Br)cc2c1C(=O)NCC(CCC(=O)O)c1ccccc1Cl]

To a solution of tert-butyl 5-[({6-bromo-3-methyl-2-[3-(trifluoromethyl)piperidin-1-yl]quinolin-4-yl}carbonyl)amino]-4-(2-chlorophenyl)pentanoate (156 mg, 228 µmol, diastereomer mixture, Example 93A) in dichloromethane (1.7 ml) was added TFA (180 µl, 2.3 mmol), and the mixture was stirred at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 89 mg (98% purity, 61% of theory) of the title compound were obtained.

LC-MS (Method 1): $R_t$=2.33 min; MS (ESIpos): m/z=626/628 $[M+H]^+$ $^1$H-NMR (400 MHz, DMSO-d6) δ [ppm]: 1.367 (0.99), 1.466 (0.45), 1.487 (1.20), 1.496 (1.31), 1.517 (1.47), 1.525 (1.47), 1.547 (0.69), 1.555 (0.65), 1.656 (1.14), 1.680 (1.14), 1.815 (3.30), 1.838 (2.92), 2.004 (1.84), 2.034 (2.50), 2.048 (3.94), 2.083 (3.91), 2.092 (4.19), 2.140 (13.11), 2.753 (1.91), 2.871 (1.12), 2.900 (1.56), 2.926 (0.80), 3.482 (1.80), 3.513 (1.67), 3.599 (1.70), 3.686 (2.90), 3.713 (3.39), 3.742 (2.39), 7.255 (1.45), 7.274 (3.31), 7.292 (2.33), 7.356 (2.00), 7.375 (3.62), 7.393 (1.90), 7.440 (4.78), 7.459 (4.01), 7.487 (4.49), 7.506 (3.81), 7.668 (0.50), 7.689 (16.00), 8.714 (1.66), 8.727 (3.04), 8.741 (1.61), 12.057 (0.83).

Example 54

(+/−)-5-({[6-Bromo-3-methyl-2-(4-methylpiperazin-1-yl)quinolin-4-yl]carbonyl}amino)-4-(2-chlorophenyl)pentanoic acid (Racemate)

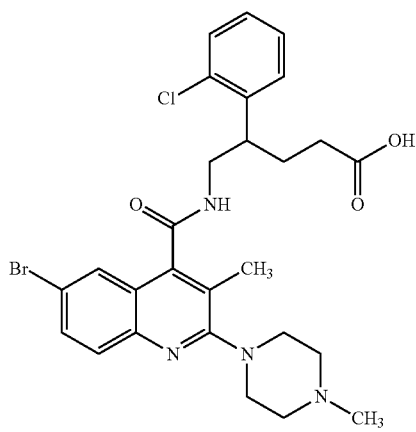 [SMILES: Cc1c(N2CCN(C)CC2)nc2ccc(Br)cc2c1C(=O)NCC(CCC(=O)O)c1ccccc1Cl]

To a solution of (+/−)-tert-butyl 5-({[6-bromo-3-methyl-2-(4-methylpiperazin-1-yl)quinolin-4-yl]carbonyl}amino)-4-(2-chlorophenyl)pentanoate (135 mg, 214 μmol, racemate, Example 94A) in dichloromethane (1.6 ml) was added TFA (170 μl, 2.1 mmol), and the mixture was stirred at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 115 mg (98% purity, 92% of theory) of the title compound were obtained.

LC-MS (Method 1): $R_t$=1.23 min; MS (ESIpos): m/z=573/575 [M+H]$^+$ $^1$H-NMR (400 MHz, DMSO-d6) δ [ppm]: −0.008 (2.30), 0.008 (2.32), 1.784 (0.56), 1.795 (0.95), 1.815 (1.86), 1.837 (2.38), 1.861 (1.34), 2.034 (1.33), 2.046 (5.04), 2.082 (4.92), 2.092 (5.43), 2.104 (2.68), 2.143 (16.00), 2.236 (0.40), 2.328 (0.48), 2.366 (0.50), 2.524 (3.16), 2.670 (0.68), 2.710 (0.66), 2.923 (3.22), 3.599 (2.22), 3.650 (1.13), 3.670 (2.61), 3.684 (4.10), 3.699 (3.14), 7.254 (1.94), 7.274 (4.49), 7.293 (3.29), 7.356 (2.73), 7.374 (4.99), 7.392 (2.56), 7.441 (7.40), 7.444 (6.82), 7.461 (6.18), 7.464 (5.59), 7.484 (5.88), 7.487 (5.82), 7.503 (4.97), 7.664 (2.93), 7.686 (13.99), 7.694 (9.19), 7.699 (7.80), 7.717 (1.75), 7.721 (1.89), 8.719 (2.52), 8.734 (5.03), 8.748 (2.36).

Example 55

5-[({6-Bromo-2-[3-hydroxypiperidin-1-yl]-3-methylquinolin-4-yl}carbonyl)amino]-4-(2-chlorophenyl)pentanoic acid (Diastereomer Mixture)

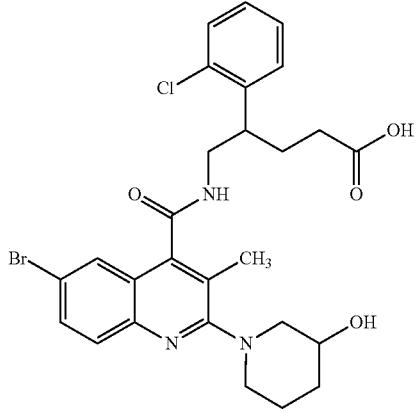

To a solution of tert-butyl 5-[({6-bromo-2-[3-hydroxypiperidin-1-yl]-3-methylquinolin-4-yl}carbonyl)amino]-4-(2-chlorophenyl)pentanoate (154 mg, 244 μmol, diastereomer mixture, Example 95A) in dichloromethane (1.8 ml) was added TFA (190 μl, 2.4 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 55 mg (98% purity, 38% of theory) of the title compound were obtained.

LC-MS (Method 1): $R_t$=1.71 min; MS (ESIpos): m/z=574/576 [M+H]$^+$ $^1$H-NMR (400 MHz, DMSO-d6) δ [ppm]: −0.008 (3.27), 0.008 (3.32), 0.146 (0.42), 1.284 (0.43), 1.295 (0.55), 1.315 (1.31), 1.347 (1.48), 1.368 (0.70), 1.378 (0.62), 1.576 (1.16), 1.604 (1.23), 1.775 (1.85), 1.783 (1.97), 1.795 (1.76), 1.810 (2.61), 1.835 (2.19), 1.857 (1.20), 1.882 (0.40), 1.913 (1.55), 1.922 (1.62), 1.944 (1.55), 2.044 (3.61), 2.078 (4.46), 2.086 (4.74), 2.133 (16.00), 2.156 (1.71), 2.327 (0.48), 2.366 (0.49), 2.523 (1.40), 2.631 (1.40), 2.664 (1.04), 2.710 (0.51), 2.745 (0.93), 2.775 (1.64), 2.804 (0.95), 3.357 (2.61), 3.388 (1.92), 3.512 (2.02), 3.543 (1.94), 3.593 (1.70), 3.682 (4.41), 4.864 (1.31), 7.256 (1.56), 7.274 (3.58), 7.294 (2.49), 7.355 (2.13), 7.374 (3.85), 7.393 (2.01), 7.441 (5.79), 7.444 (5.77), 7.461 (5.11), 7.464 (5.07), 7.481 (5.24), 7.501 (3.83), 7.619 (3.18), 7.642 (11.39), 7.654 (7.20), 7.659 (6.40), 7.676 (1.90), 7.682 (1.95), 8.721 (1.91), 8.735 (3.83), 8.749 (1.84).

Example 56

5-[({2-[3-Aminopiperidin-1-yl]-6-bromo-3-methylquinolin-4-yl}carbonyl)amino]-4-(2-chlorophenyl)pentanoic acid (Diastereomer Mixture)

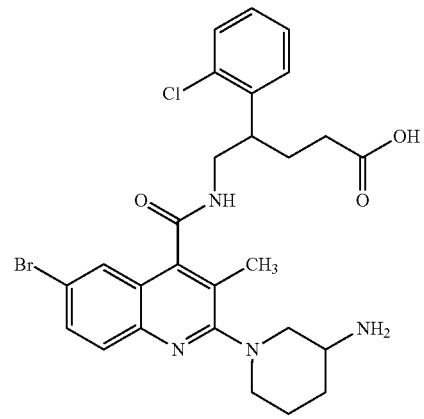

To a solution of tert-butyl 5-{[(6-bromo-2-{3-[(tert-butoxycarbonyl)amino]piperidin-1-yl}-3-methylquinolin-4-yl)carbonyl]amino}-4-(2-chlorophenyl)pentanoate (162 mg, 222 μmol, diastereomer mixture, Example 96A) in dichloromethane (1.6 ml) was added TFA (170 μl, 2.2 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 38 mg (98% purity, 29% of theory) of the title compound were obtained.

LC-MS (Method 1): $R_t$=1.27 min; MS (ESIpos): m/z=573/575 [M+H]$^+$ $^1$H-NMR (400 MHz, DMSO-d6) δ [ppm]: −0.149 (0.47), −0.008 (4.19), 0.008 (4.66), 0.146 (0.47), 1.442 (1.31), 1.469 (1.48), 1.676 (1.39), 1.836 (4.04), 1.859 (2.54), 1.961 (1.72), 1.985 (1.67), 2.043 (3.81), 2.074 (5.01), 2.081 (5.07), 2.129 (2.81), 2.164 (16.00), 2.327 (0.88), 2.366 (0.73), 2.670 (0.84), 2.710 (0.82), 2.875 (1.93), 3.228 (2.34), 3.303 (2.21), 3.578 (3.96), 3.671 (3.59), 3.685 (3.79), 7.257 (1.85), 7.276 (4.22), 7.295 (2.95), 7.356 (2.51), 7.375 (4.55), 7.393 (2.37), 7.444 (6.60), 7.463 (5.53), 7.484 (5.50), 7.504 (4.53), 7.647 (4.15), 7.669 (12.29), 7.686 (7.15), 7.691 (6.32), 7.709 (2.23), 7.713 (2.15), 8.751 (1.26), 8.765 (2.72), 8.782 (2.10).

Example 57

(+/−)-5-[({6-Bromo-2-[3-ethylpiperidin-1-yl]-3-methylquinolin-4-yl}carbonyl)amino]-4-(2-chlorophenyl)pentanoic acid (Diastereomer Mixture)

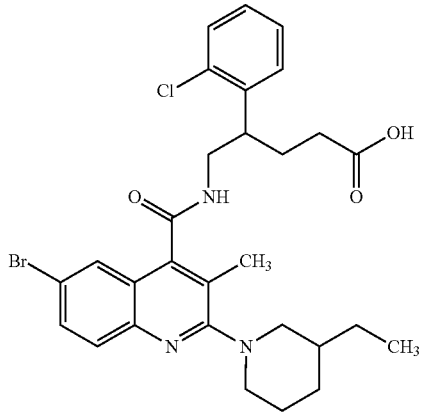 [SMILES: CCC1CCCN(c2nc3ccc(Br)cc3c(C(=O)NCC(CCC(=O)O)c3ccccc3Cl)c2C)C1]

To a solution of tert-butyl 5-[({6-bromo-2-[3-ethylpiperidin-1-yl]-3-methylquinolin-4-yl}carbonyl)amino]-4-(2-chlorophenyl)pentanoate (157 mg, 244 µmol, diastereomer mixture, Example 97A) in dichloromethane (1.8 ml) was added TFA (190 µl, 2.4 mmol), and the mixture was left to stand at RT for 16 h. The mixture was then concentrated and repeatedly dichloromethane was added and the mixture was concentrated again. The residue was purified by preparative HPLC (Method 7).

The combined target fractions were concentrated, and the residue was lyophilized. 93 mg (98% purity, 64% of theory) of the title compound were obtained.

LC-MS (Method 1): $R_t$=2.43 min; MS (ESIpos): m/z=586/588 [M+H]$^+$ $^1$H-NMR (400 MHz, DMSO-d6) δ [ppm]: 0.890 (7.22), 0.909 (15.43), 0.927 (7.98), 1.033 (0.70), 1.062 (1.77), 1.085 (1.79), 1.114 (0.79), 1.239 (1.58), 1.256 (3.34), 1.274 (4.29), 1.291 (3.01), 1.563 (2.10), 1.598 (1.87), 1.631 (1.58), 1.745 (2.50), 1.780 (2.02), 1.814 (2.13), 1.837 (3.69), 1.876 (2.18), 2.049 (4.75), 2.080 (5.39), 2.093 (6.18), 2.124 (14.79), 2.163 (1.56), 2.367 (0.47), 2.426 (1.73), 2.710 (1.27), 2.738 (1.77), 3.493 (3.77), 3.516 (3.09), 3.596 (2.29), 3.678 (3.79), 7.252 (1.99), 7.271 (4.31), 7.290 (2.97), 7.354 (2.63), 7.373 (4.57), 7.392 (2.44), 7.437 (6.02), 7.457 (5.32), 7.483 (6.32), 7.502 (4.67), 7.624 (1.86), 7.647 (16.00), 7.676 (1.20), 8.699 (2.34), 8.713 (4.23), 8.727 (2.09).

$^1$H-NMR (400 MHz, DMSO-d6) δ [ppm]: 11.86 (br. s, 1H), 8.71 (t, 1H), 7.71-7.59 (m, 2H), 7.56-7.42 (m, 3H), 7.37 (t, 1H), 7.27 (t, 1H), 3.78-3.43 (m, 5H), 2.82-2.61 (m, 1H), 2.48-2.34 (m, 1H), 2.21-1.97 (m, 6H), 1.94-1.69 (m, 3H), 1.68-1.46 (m, 2H), 1.37-1.18 (m, 2H), 1.16-0.98 (m, 1H), 0.91 (t, 3H).

Example 58

(+)-5-[({6-Bromo-2-[3-ethylpiperidin-1-yl]-3-methylquinolin-4-yl}carbonyl)amino]-4-(2-chlorophenyl) pentanoic acid (Diastereomer 1)

To a solution of (+)-tert-butyl 5-[({6-bromo-2-[3-ethylpiperidin-1-yl]-3-methylquinolin-4-yl}carbonyl)amino]-4-(2-chlorophenyl)pentanoate (180 mg, 280 µmol, diastereomer 1, Example 98A) in dichloromethane (2.4 ml) was added TFA (470 µl, 6.2 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 139 mg (100% purity, 85% of theory) of the title compound were obtained.

$[α]_D^{20}$=+4.8°, 589 nm, c=0.42 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: 0.892 (6.73), 0.910 (16.00), 0.929 (8.30), 1.034 (0.54), 1.064 (1.47), 1.093 (1.52), 1.115 (0.67), 1.240 (1.18), 1.257 (2.88), 1.275 (3.82), 1.292 (2.63), 1.563 (1.82), 1.598 (1.77), 1.629 (1.43), 1.658 (0.62), 1.746 (2.07), 1.780 (1.69), 1.812 (1.62), 1.837 (2.98), 1.855 (2.28), 1.876 (1.78), 2.025 (0.94), 2.046 (3.88), 2.080 (4.53), 2.091 (5.07), 2.114 (11.74), 2.138 (3.29), 2.162 (1.21), 2.390 (0.94), 2.418 (1.59), 2.445 (0.97), 2.713 (1.14), 2.742 (2.05), 2.772 (1.11), 3.475 (2.07), 3.498 (3.51), 3.520 (2.33), 3.596 (1.74), 3.678 (3.39), 3.693 (2.66), 7.252 (1.52), 7.271 (3.65), 7.289 (2.67), 7.353 (2.16), 7.372 (3.99), 7.390 (2.07), 7.436 (5.20), 7.456 (4.37), 7.484 (5.31), 7.502 (4.33), 7.624 (1.33), 7.647 (13.21), 7.676 (1.03), 8.697 (1.87), 8.711 (3.78), 8.725 (1.91), 12.043 (4.25).

Example 59

(−)-5-[({6-Bromo-2-[3-ethylpiperidin-1-yl]-3-methylquinolin-4-yl}carbonyl)amino]-4-(2-chlorophenyl) pentanoic acid (Diastereomer 2)

To a solution of (−)-tert-butyl 5-[({6-bromo-2-[3-ethylpiperidin-1-yl]-3-methylquinolin-4-yl}carbonyl)amino]-4-(2-chlorophenyl)pentanoate (200 mg, 311 µmol, diastereomer 2, Example 99A) in dichloromethane (2.6 ml) was added TFA (530 µl, 6.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 143 mg (100% purity, 78% of theory) of the title compound were obtained.

$[α]_D^{20}$=−26.0°, 589 nm, c=0.38 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: 0.889 (5.96), 0.908 (13.53), 0.926 (6.80), 1.034 (0.52), 1.062 (1.29), 1.085 (1.31), 1.114 (0.57), 1.240 (1.11), 1.256 (2.40), 1.274 (3.14), 1.283 (2.64), 1.291 (2.25), 1.301 (1.76), 1.558 (1.43), 1.604 (1.33), 1.635 (1.24), 1.665 (0.54), 1.745 (1.84), 1.779 (1.51), 1.813 (1.49), 1.835 (2.39), 1.854 (2.18), 1.877 (1.62), 2.033 (1.16), 2.048 (3.43), 2.077 (3.31), 2.085 (3.74), 2.093 (4.43), 2.124 (16.00), 2.138 (2.92), 2.162 (0.92), 2.402 (0.93), 2.429 (1.47), 2.701 (0.89), 2.730 (1.56), 2.757 (0.85), 3.484 (2.87), 3.515 (2.61), 3.596 (1.53), 3.661 (1.81), 3.675 (2.56), 7.254 (1.40), 7.271 (3.10), 7.289 (2.16), 7.355 (1.92), 7.374 (3.34), 7.392 (1.74), 7.438 (4.62), 7.458 (4.18), 7.481 (4.49), 7.500 (3.11), 7.624 (1.31), 7.647 (11.41), 7.671 (0.73), 7.675 (0.82), 8.697 (1.73), 8.712 (3.17), 8.726 (1.55), 12.043 (3.31).

Example 60

(−)-5-[({6-Bromo-2-[3-ethylpiperidin-1-yl]-3-methylquinolin-4-yl}carbonyl)amino]-4-(2-chlorophenyl)pentanoic acid (Diastereomer 3)

To a solution of (−)-tert-butyl 5-[({6-bromo-2-[3-ethylpiperidin-1-yl]-3-methylquinolin-4-yl}carbonyl)amino]-4-(2-chlorophenyl)pentanoate (420 mg, 650 µmol, diastereomer 3, Example 100A) in dichloromethane (5.5 ml) was added TFA (1.1 ml, 14 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 348 mg (100% purity, 91% of theory) of the title compound were obtained.

$[\alpha]_D^{20}$=−5.1°, 589 nm, c=0.48 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: 0.891 (6.76), 0.910 (16.00), 0.928 (8.20), 1.034 (0.55), 1.063 (1.49), 1.085 (1.52), 1.093 (1.51), 1.114 (0.67), 1.239 (1.17), 1.257 (2.87), 1.274 (3.81), 1.292 (2.60), 1.563 (1.83), 1.597 (1.73), 1.629 (1.44), 1.660 (0.62), 1.745 (2.09), 1.779 (1.67), 1.812 (1.63), 1.836 (3.03), 1.853 (2.24), 1.876 (1.77), 2.013 (0.54), 2.025 (0.97), 2.046 (3.88), 2.080 (4.59), 2.090 (5.07), 2.114 (11.27), 2.138 (3.27), 2.162 (1.16), 2.390 (0.94), 2.418 (1.57), 2.713 (1.09), 2.742 (1.95), 2.771 (1.06), 3.474 (2.09), 3.498 (3.43), 3.520 (2.33), 3.596 (1.71), 3.678 (3.31), 3.693 (2.57), 7.252 (1.56), 7.271 (3.74), 7.289 (2.72), 7.353 (2.19), 7.372 (4.02), 7.390 (2.08), 7.436 (5.26), 7.456 (4.43), 7.484 (5.27), 7.502 (4.30), 7.624 (1.39), 7.647 (13.75), 7.676 (1.02), 8.697 (1.88), 8.712 (3.76), 8.726 (1.87), 12.047 (1.45).

Example 61

(+)-5-[({6-Bromo-2-[3-ethylpiperidin-1-yl]-3-methylquinolin-4-yl}carbonyl)amino]-4-(2-chlorophenyl)pentanoic acid (Diastereomer 4)

To a solution of (+)-tert-butyl 5-[({6-bromo-2-[3-ethylpiperidin-1-yl]-3-methylquinolin-4-yl}carbonyl)amino]-4-(2-chlorophenyl)pentanoate (463 mg, 720 µmol, diastereomer 4, Example 101A) in dichloromethane (6.1 ml) was added TFA (1.2 ml, 16 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 360 mg (100% purity, 85% of theory) of the title compound were obtained.

$[\alpha]_D^{20}$=+27.7°, 589 nm, c=0.48 g/100 ml, methanol

LC-MS (Method 1): $R_t$=2.45 min; MS (ESIpos): m/z=586/588 [M+H]$^+$ $^1$H-NMR (400 MHz, DMSO-d6) δ [ppm]: 0.888 (5.59), 0.907 (13.71), 0.925 (6.95), 1.033 (0.43), 1.062 (1.18), 1.084 (1.19), 1.092 (1.20), 1.113 (0.54), 1.123 (0.48), 1.238 (0.87), 1.256 (2.08), 1.265 (1.91), 1.273 (2.87), 1.282 (2.43), 1.290 (2.12), 1.300 (1.70), 1.317 (0.67), 1.557 (1.25), 1.565 (1.23), 1.573 (1.20), 1.603 (1.20), 1.635 (1.16), 1.665 (0.50), 1.744 (1.64), 1.778 (1.28), 1.793 (0.94), 1.814 (1.27), 1.836 (2.25), 1.854 (1.87), 1.876 (1.47), 2.033 (0.90), 2.049 (3.07), 2.078 (2.80), 2.085 (3.19), 2.094 (3.73), 2.125 (16.00), 2.139 (2.89), 2.163 (0.88), 2.402 (0.81), 2.430 (1.33), 2.458 (0.81), 2.701 (0.82), 2.731 (1.48), 2.759 (0.82), 3.485 (2.59), 3.515 (2.44), 3.599 (1.42), 3.624 (0.88), 3.642 (0.73), 3.662 (1.56), 3.676 (2.32), 7.253 (1.31), 7.272 (3.02), 7.292 (2.12), 7.355 (1.80), 7.374 (3.28), 7.392 (1.70), 7.440 (4.50), 7.460 (3.99), 7.483 (4.32), 7.501 (2.96), 7.624 (1.00), 7.647 (12.31), 7.652 (6.71), 7.670 (0.66), 7.675 (0.81), 8.699 (1.53), 8.713 (3.02), 8.727 (1.49), 12.053 (0.70).

Example 62

5-[({6-Bromo-2-[3-hydroxy-3-methylpiperidin-1-yl]-3-methylquinolin-4-yl}carbonyl)amino]-4-(2-chlorophenyl)pentanoic acid (Diastereomer Mixture)

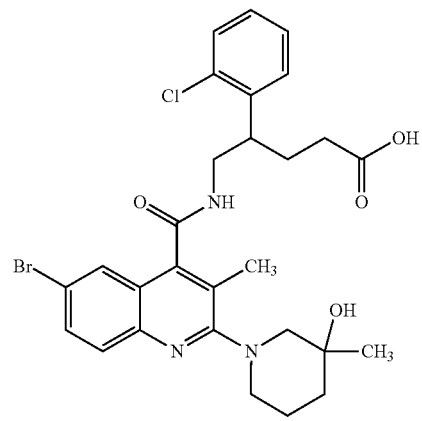 [SMILES: Cc1c(N2CCCC(C)(O)C2)nc2ccc(Br)cc2c1C(=O)NCC(CCC(=O)O)c1ccccc1Cl]

To a solution of tert-butyl 5-[({6-bromo-2-[3-hydroxy-3-methylpiperidin-1-yl]-3-methylquinolin-4-yl}carbonyl)amino]-4-(2-chlorophenyl)pentanoate (148 mg, 229 µmol, diastereomer mixture, Example 102A) in dichloromethane (1.7 ml) was added TFA (180 µl, 2.3 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 106 mg (98% purity, 77% of theory) of the title compound were obtained.

LC-MS (Method 1): $R_t$=1.83 min; MS (ESIpos): m/z=588/560 [M+H]$^+$ $^1$H-NMR (400 MHz, DMSO-d6) δ [ppm]: −0.008 (2.69), 1.190 (16.00), 1.557 (3.93), 1.570 (4.21), 1.613 (1.10), 1.627 (1.00), 1.796 (0.66), 1.814 (1.72), 1.836 (2.49), 1.859 (1.71), 2.045 (2.66), 2.061 (1.71), 2.079 (3.37), 2.086 (4.47), 2.134 (2.03), 2.165 (10.97), 2.855 (0.60), 3.021 (7.70), 3.075 (3.50), 3.592 (1.35), 3.676 (2.23), 4.614 (1.55), 7.254 (1.18), 7.274 (2.80), 7.292 (1.97), 7.356 (1.67), 7.374 (3.07), 7.392 (1.61), 7.441 (4.38), 7.461 (3.98), 7.481 (4.14), 7.499 (2.92), 7.614 (2.20), 7.636 (7.81), 7.649 (5.05), 7.654 (4.49), 7.671 (1.34), 7.676 (1.37), 8.712 (1.50), 8.727 (2.91), 8.741 (1.39).

Example 63

5-[({6-Bromo-2-[3,5-dimethylpiperidin-1-yl]-3-methylquinolin-4-yl}carbonyl)amino]-4-(2-chlorophenyl)pentanoic acid (Diastereomer Mixture)

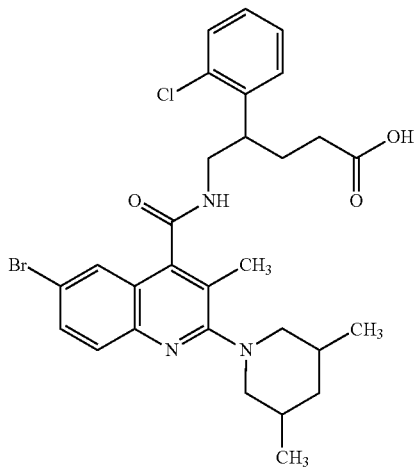 [SMILES: Cc1c(N2CC(C)CC(C)C2)nc2ccc(Br)cc2c1C(=O)NCC(CCC(=O)O)c1ccccc1Cl]

To a solution of tert-butyl 5-[({6-bromo-2-[3,5-dimethylpiperidin-1-yl]-3-methylquinolin-4-yl}carbonyl)amino]-4-(2-chlorophenyl)pentanoate (91 mg, 142 µmol, diastereomer mixture, Example 103A) in dichloromethane (4.8 ml) was added TFA (110 µl, 1.4 mmol), and the mixture was stirred at RT for 42 h. Subsequently, TFA (105 µl, 0.7 mmol) was added again, and the mixture was stirred at RT for a further 66 h. This was followed by concentration of the mixture, and repeated additions of dichloromethane followed by concentration again. The residue was first prepurified by means of preparative HPLC (Method 6) and then repurified by means of preparative HPLC (Method 7). The combined target fractions were concentrated, and the residue was lyophilized. 47 mg (100% purity, 57% of theory) of the title compound were obtained.

LC-MS (Method 1): $R_t$=2.42 & 2.44 min; MS (ESIpos): m/z=586/586 [M+H]$^+$ $^1$H-NMR (400 MHz, DMSO-d6) δ [ppm]: 0.718 (1.40), 0.748 (1.54), 0.778 (0.50), 0.898 (15.75), 0.913 (16.00), 1.005 (3.11), 1.021 (3.17), 1.234 (0.86), 1.424 (0.56), 1.437 (1.00), 1.451 (0.61), 1.808 (3.64), 1.839 (3.30), 1.861 (1.10), 2.049 (3.42), 2.083 (3.96), 2.090 (4.17), 2.134 (11.83), 2.164 (3.04), 2.266 (1.30), 2.294 (2.05), 2.323 (1.27), 2.848 (0.48), 3.116 (0.65), 3.146 (0.56), 3.488 (2.66), 3.517 (2.54), 3.592 (1.54), 3.674 (2.27), 7.256 (1.27), 7.274 (2.92), 7.292 (2.07), 7.356 (1.74), 7.375 (3.20), 7.393 (1.71), 7.440 (4.43), 7.460 (4.05), 7.480 (4.37), 7.499 (3.07), 7.625 (0.76), 7.647 (13.38), 7.673 (0.59), 8.692 (1.42), 8.705 (2.74), 12.049 (1.42).

Example 64

5-[({6-Bromo-2-[3-(difluoromethyl)piperidin-1-yl]-3-methylquinolin-4-yl}carbonyl)amino]-4-(2-chlorophenyl)pentanoic acid (Diastereomer Mixture)

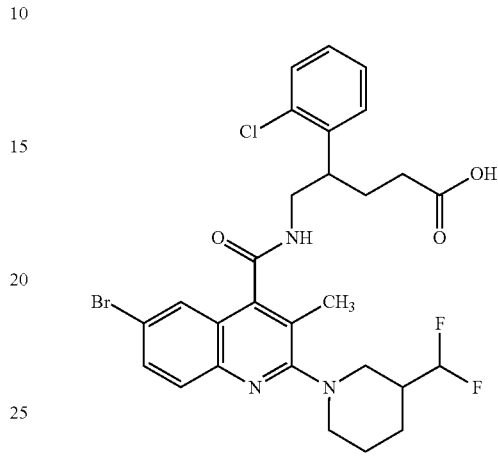

To a solution of tert-butyl 5-[({6-bromo-2-[3-(difluoromethyl)piperidin-1-yl]-3-methylquinolin-4-yl}carbonyl)amino]-4-(2-chlorophenyl)pentanoate (116 mg, 48% purity, 83.0 µmol, diastereomer mixture, Example 104A) in dichloromethane (2.9 ml) was added TFA (64 µl, 830 µmol), and the mixture was stirred at RT for 18 h. Subsequently, TFA (64 µl, 830 µmol) was added again, and the mixture was stirred at RT for a further 24 h. Subsequently, TFA (64 µl, 830 µmol) was added again, and the mixture was again stirred at RT for a further 24 h. This was followed by concentration of the mixture, and repeated additions of dichloromethane followed by concentration again. The residue was purified by preparative HPLC (Method 7). The combined target fractions were concentrated, and the residue was lyophilized. 34 mg (93% purity, 63% of theory) of the title compound were obtained.

LC-MS (Method 1): $R_t$=2.19 min; MS (ESIpos): m/z=608/610 [M+H]$^+$ $^1$H-NMR (400 MHz, DMSO-d6) δ [ppm]: −0.149 (1.13), −0.008 (16.00), 0.008 (9.90), 0.146 (1.18), 1.235 (0.65), 1.397 (0.96), 1.427 (1.09), 1.664 (0.92), 1.812 (2.31), 1.853 (2.49), 2.044 (2.96), 2.088 (3.57), 2.139 (9.68), 2.327 (1.57), 2.366 (1.57), 2.523 (9.59), 2.669 (1.96), 2.710 (2.40), 2.838 (1.48), 3.413 (1.57), 3.553 (2.18), 3.581 (2.75), 3.681 (2.44), 5.754 (0.70), 5.941 (0.70), 6.083 (1.40), 6.096 (1.31), 6.237 (0.74), 7.257 (1.26), 7.274 (2.57), 7.293 (1.87), 7.356 (1.61), 7.375 (2.92), 7.392 (1.66), 7.439 (4.40), 7.459 (3.75), 7.485 (3.79), 7.502 (3.10), 7.677 (13.34), 8.734 (2.31), 12.043 (1.13).

Example 65

5-[({6-Bromo-2-[(3S)-3-fluoropyrrolidin-1-yl]-3-methylquinolin-4-yl}carbonyl)amino]-4-(2-chlorophenyl)pentanoic acid (Epimer Mixture)

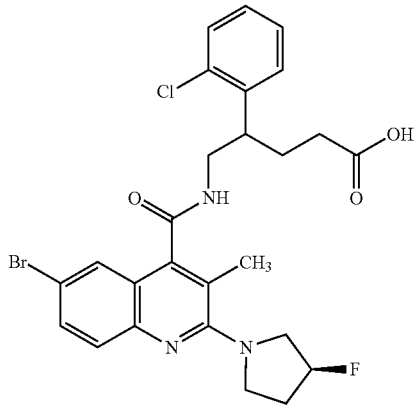 [SMILES: Cc1c(N2CC[C@H](F)C2)nc2ccc(Br)cc2c1C(=O)NCC(CCC(=O)O)c1ccccc1Cl]

To a solution of tert-butyl 5-[({6-bromo-2-[(3S)-3-fluoropyrrolidin-1-yl]-3-methylquinolin-4-yl}carbonyl)amino]-4-(2-chlorophenyl)pentanoate (141 mg, 89% purity, 203 µmol, epimer mixture, Example 105A) in dichloromethane (2.2 ml) was added TFA (160 µl, 2.0 mmol), and the mixture was stirred at RT for 42 h. Subsequently, TFA (80 µl, 1.0 mmol) was added again, and the mixture was stirred at RT for a further 24 h. This was followed by concentration of the mixture, and repeated additions of dichloromethane followed by concentration again. The residue was purified by preparative HPLC (Method 7). The combined target fractions were concentrated, and the residue was lyophilized. 44 mg (94% purity, 36% of theory) of the title compound were obtained.

LC-MS (Method 1): $R_t$=1.75 min; MS (ESIpos): m/z=562/564 [M+H]$^+$ $^1$H-NMR (400 MHz, DMSO-d6) δ [ppm]: −0.149 (0.50), −0.008 (4.85), 0.008 (4.45), 0.146 (0.45), 1.235 (0.77), 1.797 (1.23), 1.818 (2.56), 1.838 (3.44), 1.862 (1.98), 1.988 (0.79), 2.047 (7.30), 2.076 (7.77), 2.088 (7.95), 2.138 (4.97), 2.176 (16.00), 2.327 (0.92), 2.366 (0.79), 2.669 (0.79), 2.709 (0.74), 3.600 (6.02), 3.866 (2.36), 3.884 (2.32), 3.911 (2.23), 3.944 (1.37), 4.013 (1.48), 4.046 (1.24), 5.330 (3.51), 5.464 (3.44), 5.754 (5.44), 7.245 (1.57), 7.261 (4.38), 7.280 (5.05), 7.297 (2.40), 7.346 (2.58), 7.364 (5.51), 7.382 (5.14), 7.401 (2.31), 7.437 (10.14), 7.440 (9.69), 7.457 (8.61), 7.459 (8.00), 7.473 (5.24), 7.476 (5.21), 7.491 (5.14), 7.504 (8.41), 7.508 (7.91), 7.526 (10.05), 7.530 (9.68), 7.574 (5.17), 7.579 (8.88), 7.585 (4.72), 7.596 (2.97), 7.602 (5.05), 7.607 (2.72), 7.893 (1.57), 8.694 (4.86), 12.050 (1.46).

Example 66

5-[({6-Bromo-2-[(3R)-3-fluoropyrrolidin-1-yl]-3-methylquinolin-4-yl}carbonyl)amino]-4-(2-chlorophenyl)pentanoic acid (Epimer Mixture)

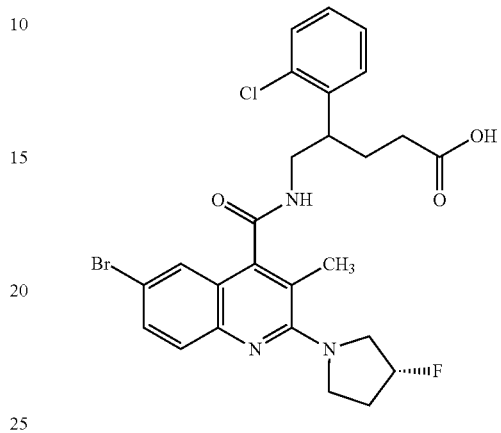

To a solution of tert-butyl 5-[({6-bromo-2-[(3R)-3-fluoropyrrolidin-1-yl]-3-methylquinolin-4-yl}carbonyl)amino]-4-(2-chlorophenyl)pentanoate (120 mg, 96% purity, 187 µmol, epimer mixture, Example 106A) in dichloromethane (2.4 ml) was added TFA (140 µl, 1.9 mmol), and the mixture was stirred at RT for 42 h. Subsequently, TFA (80 µl, 1.0 mmol) was added again, and the mixture was stirred at RT for a further 24 h. Subsequently, TFA (80 µl, 1.0 mmol) was added again, and the mixture was stirred at RT for a further 24 h. This was followed by concentration of the mixture, and repeated additions of dichloromethane followed by concentration again. The residue was purified by preparative HPLC (Method 11). The combined target fractions were concentrated, and the residue was lyophilized. 86 mg (97% purity, 79% of theory) of the title compound were obtained.

LC-MS (Method 1): $R_t$=1.76 min; MS (ESIpos): m/z=562/564 [M+H]$^+$ $^1$H-NMR (400 MHz, DMSO-d6) δ [ppm]: −0.149 (0.49), 0.146 (0.51), 1.798 (1.12), 1.817 (2.38), 1.839 (3.22), 1.862 (1.84), 2.049 (7.23), 2.078 (7.50), 2.089 (7.59), 2.121 (3.46), 2.139 (4.86), 2.176 (16.00), 2.327 (0.85), 2.366 (0.67), 2.670 (0.79), 2.710 (0.70), 3.600 (5.99), 3.626 (4.79), 3.657 (4.00), 3.867 (2.42), 3.883 (2.41), 3.912 (2.32), 3.945 (1.44), 4.012 (1.54), 4.046 (1.33), 5.331 (3.59), 5.465 (3.56), 5.754 (6.66), 7.245 (1.53), 7.263 (4.27), 7.280 (4.74), 7.297 (2.23), 7.326 (0.79), 7.346 (2.69), 7.364 (5.42), 7.383 (4.83), 7.400 (2.08), 7.437 (9.28), 7.440 (9.14), 7.457 (7.78), 7.477 (5.10), 7.492 (4.88), 7.504 (7.74), 7.508 (7.57), 7.526 (9.34), 7.530 (9.61), 7.574 (4.77), 7.580 (8.37), 7.585 (4.71), 7.596 (2.81), 7.602 (4.80), 7.607 (2.77), 8.693 (4.97), 12.045 (3.38).

Separation of the Epimer Mixture:

The title compound (72 mg) was dissolved in methanol (12 ml) and separated into the enantiomers/epimers by means of preparative SFC on chiral phase (see Examples 67 and 68) [column: Daicel Chiralcel OX-H, 5 µm, 250 mm×30 mm; flow rate: 100 ml/min; injection: 1.0 ml; eluent: 20% methanol/80% carbon dioxide; run time 21 min, isocratic, UV detection 210 nm, temperature 40° C.]. The combined target fractions were concentrated, and the respective residue was lyophilized.

Example 67

(+)-5-[({6-Bromo-2-[(3R)-3-fluoropyrrolidin-1-yl]-3-methylquinolin-4-yl}carbonyl)amino]-4-(2-chlorophenyl)pentanoic acid (epimer 1)

In the enantiomer separation described in Example 66, 16 mg (100% purity, ee>99%) of the title compound were obtained as the epimer/enantiomer that eluted earlier.

$[\alpha]_D^{20}$=+22.1°, 589 nm, c=0.29 g/100 ml, methanol

LC-MS (Method 1): $R_t$=1.79 min; MS (ESIpos): m/z=562/564 $[M+H]^+$ $^1$H-NMR (400 MHz, DMSO-d6) δ [ppm]: −0.149 (0.64), −0.008 (5.27), 0.008 (5.32), 0.070 (0.55), 0.146 (0.62), 1.236 (0.44), 1.359 (1.61), 1.754 (0.54), 1.819 (2.40), 1.840 (3.08), 1.865 (1.93), 2.025 (2.41), 2.051 (6.86), 2.078 (7.50), 2.092 (6.21), 2.100 (4.56), 2.115 (3.52), 2.141 (5.17), 2.177 (16.00), 2.295 (0.60), 2.327 (0.93), 2.670 (0.75), 2.994 (0.93), 3.207 (0.79), 3.601 (5.46), 3.672 (4.92), 3.840 (1.34), 3.867 (2.43), 3.884 (2.44), 3.913 (2.25), 3.946 (1.30), 4.023 (1.47), 4.047 (1.26), 5.331 (3.06), 5.466 (3.06), 6.311 (0.64), 7.246 (2.55), 7.264 (5.98), 7.283 (4.16), 7.347 (3.88), 7.366 (6.57), 7.384 (3.70), 7.437 (8.61), 7.440 (9.05), 7.457 (7.58), 7.460 (7.75), 7.477 (7.69), 7.493 (5.77), 7.496 (5.99), 7.508 (8.92), 7.530 (14.54), 7.580 (8.24), 7.585 (7.42), 7.602 (4.52), 7.608 (4.33), 7.879 (0.83), 8.680 (2.80), 8.695 (5.16), 8.708 (2.51), 12.041 (3.60).

Example 68

(+)-5-[({6-Bromo-2-[(3R)-3-fluoropyrrolidin-1-yl]-3-methylquinolin-4-yl}carbonyl)amino]-4-(2-chlorophenyl)pentanoic acid (epimer 2)

In the enantiomer separation described in Example 66, 14 mg (100% purity, ee>82%) of the title compound were obtained as the epimer/enantiomer that eluted later.

$[\alpha]_D^{20}$=+40.7°, 589 nm, c=0.30 g/100 ml, methanol

LC-MS (Method 1): $R_t$=1.79 min; MS (ESIpos): m/z=562/564 $[M+H]^+$ $^1$H-NMR (400 MHz, DMSO-d6) δ [ppm]: −0.149 (1.09), −0.008 (9.27), 0.008 (8.56), 0.069 (2.49), 0.146 (1.09), 1.235 (0.52), 1.359 (1.59), 1.754 (0.45), 1.798 (1.61), 1.819 (2.89), 1.839 (3.82), 1.861 (2.49), 2.048 (7.89), 2.089 (9.53), 2.136 (6.02), 2.174 (14.55), 2.327 (1.47), 2.366 (0.43), 2.670 (1.33), 2.994 (0.52), 3.207 (1.14), 3.462 (0.47), 3.578 (4.81), 3.602 (6.35), 3.627 (5.43), 3.640 (5.24), 3.703 (2.56), 3.857 (2.49), 3.876 (2.44), 3.903 (2.23), 3.944 (1.37), 4.011 (1.49), 4.044 (1.23), 5.330 (3.56), 5.464 (3.51), 6.305 (0.71), 6.310 (1.02), 6.316 (0.69), 7.260 (4.27), 7.280 (5.78), 7.298 (3.93), 7.365 (4.76), 7.383 (6.42), 7.400 (3.96), 7.421 (1.75), 7.437 (10.38), 7.440 (10.05), 7.457 (8.53), 7.460 (8.18), 7.486 (6.83), 7.504 (13.27), 7.525 (16.00), 7.574 (8.23), 7.579 (8.63), 7.596 (4.62), 7.601 (5.03), 7.879 (1.37), 8.675 (3.25), 8.689 (5.67), 8.703 (3.18), 9.688 (0.50), 12.040 (7.44).

Example 69

5-[({6-Bromo-2-[trans-3,4-difluoropyrrolidin-1-yl]-3-methylquinolin-4-yl}carbonyl)amino]-4-(2-chlorophenyl)pentanoic acid (Diastereomer Mixture)

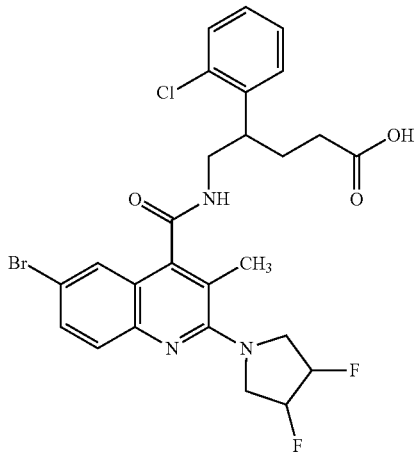 [SMILES: Cc1c(N2CC(F)C(F)C2)nc2ccc(Br)cc2c1C(=O)NCC(CCC(=O)O)c1ccccc1Cl]

To a solution of tert-butyl 5-[({6-bromo-2-[trans-3,4-difluoropyrrolidin-1-yl]-3-methylquinolin-4-yl}carbonyl) amino]-4-(2-chlorophenyl)pentanoate (169 mg, 77% purity, 204 µmol, diastereomer mixture, Example 107A) in dichloromethane (2.3 ml) was added TFA (160 µl, 2.0 mmol), and the mixture was stirred at RT for 42 h. The mixture was then concentrated and repeatedly dichloromethane was added and the mixture was concentrated again. The residue was purified by preparative HPLC (Method 6). The combined target fractions were each concentrated, and the respective residue was lyophilized. 8 mg (100% purity, 7% of theory) of a first batch of the title compound and 57 mg (98% purity, 47% of theory) of a second batch of the title compound were obtained.

Analysis of the First Batch:

LC-MS (Method 1): $R_t$=1.96 min; MS (ESIpos): m/z=580/582 $[M+H]^+$ $^1$H-NMR (600 MHz, DMSO-d6) δ [ppm]: 1.235 (1.28), 1.258 (0.52), 1.372 (6.58), 1.822 (1.87), 1.836 (3.94), 1.851 (4.34), 1.866 (2.51), 1.986 (0.72), 2.065 (8.57), 2.083 (9.10), 2.108 (4.07), 2.130 (4.83), 2.141 (4.69), 2.162 (3.43), 2.198 (16.00), 2.308 (0.51), 3.613 (3.36), 3.645 (3.02), 3.758 (4.47), 4.101 (3.01), 4.175 (3.15), 5.378 (6.46), 5.468 (6.57), 5.743 (0.97), 7.252 (2.23), 7.264 (4.72), 7.278 (4.83), 7.352 (2.93), 7.365 (5.53), 7.377 (4.90), 7.441 (9.98), 7.454 (9.21), 7.477 (6.06), 7.490 (8.21), 7.501 (4.48), 7.555 (5.84), 7.570 (8.53), 7.616 (6.75), 7.630 (4.65), 7.888 (1.25), 8.680 (7.05), 12.012 (1.02).

Analysis of the Second Batch:

LC-MS (Method 1): $R_t$=1.96 min; MS (ESIpos): m/z=580/582 $[M+H]^+$ $^1$H-NMR (400 MHz, DMSO-d6) δ [ppm]: −0.149 (0.66), −0.008 (6.04), 0.008 (5.65), 0.146 (0.64), 1.157 (0.68), 1.175 (1.34), 1.192 (0.75), 1.234 (0.57), 1.367 (1.36), 1.801 (1.23), 1.819 (2.68), 1.842 (3.65), 1.865 (2.07), 1.988 (2.50), 2.049 (6.83), 2.077 (7.97), 2.089 (8.19), 2.114 (3.09), 2.139 (3.90), 2.192 (16.00), 2.304 (0.43), 2.327 (1.16), 2.366 (0.91), 2.523 (3.13), 2.670 (1.02), 2.710 (1.00), 3.600 (3.25), 3.647 (2.77), 3.741 (3.54), 4.020 (0.79), 4.038 (0.93), 4.074 (2.36), 4.100 (2.22), 4.183 (2.45), 5.354 (5.11), 5.360 (5.45), 5.494 (5.49), 5.500 (5.36), 5.754 (2.75), 7.246 (1.66), 7.264 (4.63), 7.282 (5.06), 7.301 (2.25), 7.348 (2.63), 7.366 (5.81), 7.385 (5.15), 7.403 (2.16), 7.439 (10.44), 7.458 (8.76), 7.476 (5.56), 7.479 (5.83), 7.494 (6.33), 7.509 (3.43), 7.544 (5.83), 7.548 (6.45), 7.566 (10.80), 7.571 (11.57), 7.609 (5.56), 7.615 (9.74), 7.621 (5.65), 7.631 (3.13), 7.637 (5.38), 7.643 (3.27), 7.893 (0.68), 8.688 (3.29), 8.702 (6.42), 8.716 (3.43), 12.035 (0.98).

Example 70

(+/−)-5-[({6-Bromo-2-[cis-3,4-difluoropyrrolidin-1-yl]-3-methylquinolin-4-yl}carbonyl)amino]-4-(2-chlorophenyl)pentanoic acid (Racemate)

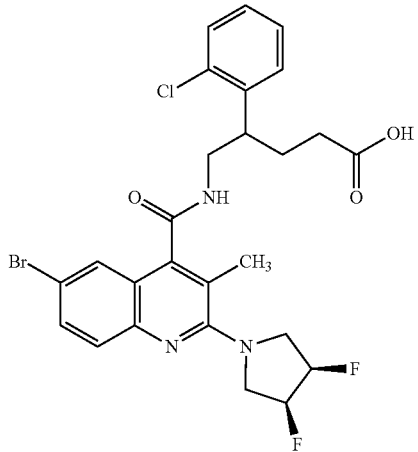 [SMILES: Cc1c(N2C[C@@H](F)[C@@H](F)C2)nc2ccc(Br)cc2c1C(=O)NCC(CCC(=O)O)c1ccccc1Cl]

To a solution of (+/−)-tert-butyl 5-[({6-bromo-2-[cis-3,4-difluoropyrrolidin-1-yl]-3-methylquinolin-4-yl}carbonyl)amino]-4-(2-chlorophenyl)pentanoate (160 mg, 93% purity, 233 µmol, racemate, Example 108A) in dichloromethane (2.3 ml) was added TFA (180 µl, 2.3 mmol), and the mixture was stirred at RT for 66 h. The mixture was then concentrated and repeatedly dichloromethane was added and the mixture was concentrated again. The residue was purified by preparative HPLC (Method 11). The combined target fractions were concentrated, and the residue was lyophilized. 68 mg (93% purity, 47% of theory) of the title compound were obtained.

LC-MS (Method 1): $R_t$=1.93 min; MS (ESIpos): m/z=580/582 [M+H]$^+$ $^1$H-NMR (400 MHz, DMSO-d6) δ [ppm]: −0.149 (1.26), −0.008 (12.03), 0.008 (11.85), 0.146 (1.32), 1.157 (0.60), 1.174 (1.32), 1.192 (0.60), 1.236 (0.54), 1.368 (0.42), 1.797 (1.08), 1.816 (2.41), 1.839 (3.25), 1.862 (1.80), 1.988 (2.47), 2.046 (5.95), 2.080 (7.04), 2.090 (7.22), 2.137 (6.02), 2.160 (14.20), 2.297 (0.42), 2.327 (1.80), 2.366 (1.86), 2.523 (6.44), 2.669 (2.11), 2.710 (2.05), 3.586 (2.89), 3.671 (3.55), 3.782 (3.19), 3.994 (2.53), 4.021 (2.47), 5.298 (3.07), 5.311 (2.29), 5.324 (2.41), 5.333 (2.47), 5.426 (2.65), 5.435 (2.77), 5.448 (2.41), 5.460 (3.07), 5.754 (7.10), 7.254 (2.35), 7.271 (5.17), 7.290 (3.73), 7.356 (3.25), 7.374 (5.95), 7.392 (3.43), 7.438 (9.32), 7.440 (9.44), 7.458 (7.70), 7.460 (7.58), 7.482 (7.46), 7.499 (5.53), 7.541 (8.78), 7.563 (16.00), 7.609 (8.54), 7.614 (8.18), 7.631 (4.63), 7.636 (4.69), 8.678 (3.13), 8.693 (6.38), 8.707 (3.13), 12.043 (7.52).

Example 71

5-[({6-Bromo-2-[3-fluoro-3-methylpyrrolidin-1-yl]-3-methylquinolin-4-yl}carbonyl)amino]-4-(2-chlorophenyl)pentanoic acid (Diastereomer Mixture)

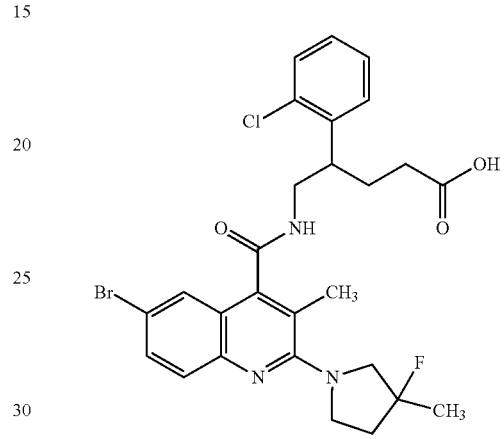

To a solution of tert-butyl 5-[({6-bromo-2-[3-fluoro-3-methylpyrrolidin-1-yl]-3-methylquinolin-4-yl}carbonyl)amino]-4-(2-chlorophenyl)pentanoate (120 mg, 96% purity, 181 µmol, diastereomer mixture, Example 109A) in dichloromethane (2.4 ml) was added TFA (140 µl, 1.8 mmol), and the mixture was stirred at RT for 42 h. Subsequently, TFA (70 µl, 0.9 mmol) was added again, and the mixture was stirred at RT for a further 24 h. This was followed by concentration of the mixture, and repeated additions of dichloromethane followed by concentration again. The residue was purified by preparative HPLC (Method 11). The combined target fractions were concentrated, and the residue was lyophilized. 83 mg (100% purity, 79% of theory) of the title compound were obtained.

LC-MS (Method 1): $R_t$=1.89 min; MS (ESIpos): m/z=576/578 [M+H]$^+$ $^1$H-NMR (400 MHz, DMSO-d6) δ [ppm]: 0.008 (2.03), 1.157 (4.22), 1.175 (8.34), 1.192 (4.18), 1.541 (8.21), 1.593 (8.22), 1.817 (0.84), 1.839 (1.06), 1.862 (0.58), 1.988 (16.00), 2.018 (0.92), 2.048 (2.34), 2.078 (2.77), 2.088 (2.72), 2.114 (1.68), 2.134 (2.41), 2.170 (5.51), 2.327 (0.45), 2.523 (1.92), 2.670 (0.43), 3.616 (1.97), 3.798 (0.72), 3.829 (0.51), 3.890 (0.85), 3.921 (1.25), 3.947 (0.84), 4.003 (1.38), 4.021 (3.82), 4.038 (3.71), 4.056 (1.22), 7.246 (0.61), 7.262 (1.49), 7.281 (1.62), 7.298 (0.74), 7.346 (1.01), 7.365 (1.86), 7.382 (1.59), 7.401 (0.70), 7.437 (3.28), 7.457 (2.76), 7.474 (1.73), 7.494 (3.00), 7.499 (2.45), 7.516 (3.28), 7.521 (3.10), 7.566 (1.68), 7.572 (2.81), 7.578 (1.55), 7.589 (0.99), 7.594 (1.61), 7.600 (0.88), 8.692 (1.46), 12.038 (3.86).

Example 72

(+/−)-5-({[6-Bromo-3-methyl-2-(3,3,4,4-tetrafluoro-pyrrolidin-1-yl)quinolin-4-yl]carbonyl}amino)-4-(2-chlorophenyl)pentanoic acid (Racemate)

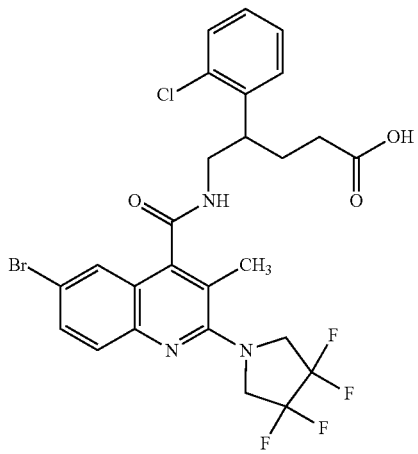 [SMILES: Cc1c(N2CC(F)(F)C(F)(F)C2)nc2ccc(Br)cc2c1C(=O)NCC(CCC(=O)O)c1ccccc1Cl]

To a solution of (+/−)-tert-butyl 5-({[6-bromo-3-methyl-2-(3,3,4,4-tetrafluoropyrrolidin-1-yl)quinolin-4-yl]carbonyl}amino)-4-(2-chlorophenyl)pentanoate (69 mg, 9% purity, 9.49 µmol, racemate, Example 110A) in dichloromethane (910 µl) was added TFA (7.3 µl, 95 µmol), and the mixture was stirred at RT for 18 h. Subsequently, TFA (7.3 µl, 95 µmol) was added again, and the mixture was stirred at RT for a further 48 h. This was followed by concentration of the mixture, and repeated additions of dichloromethane followed by concentration again. The residue was purified by preparative HPLC (Method 11). The combined target fractions were concentrated, and the residue was lyophilized. 4 mg (100% purity, 68% of theory) of the title compound were obtained.

LC-MS (Method 1): $R_t$=2.21 min; MS (ESIpos): m/z=616/618 [M+H]$^+$ $^1$H-NMR (600 MHz, DMSO-d6) δ [ppm]: −0.052 (0.83), 0.854 (0.54), 0.901 (1.54), 0.911 (1.52), 1.236 (2.63), 1.262 (1.41), 1.300 (0.66), 1.338 (0.74), 1.369 (1.41), 1.820 (1.99), 1.834 (4.21), 1.848 (4.54), 1.864 (2.58), 2.047 (3.16), 2.060 (9.95), 2.078 (9.12), 2.083 (7.22), 2.092 (4.10), 2.099 (3.52), 2.107 (3.71), 2.125 (4.63), 2.132 (5.17), 2.139 (6.68), 2.156 (4.33), 2.184 (16.00), 2.256 (0.78), 2.313 (0.61), 2.383 (0.51), 2.611 (0.63), 3.512 (0.66), 3.589 (4.04), 3.689 (4.56), 4.258 (10.47), 7.261 (3.41), 7.274 (6.97), 7.286 (4.66), 7.360 (4.30), 7.373 (7.46), 7.385 (4.17), 7.443 (11.50), 7.457 (10.28), 7.482 (9.64), 7.495 (8.17), 7.648 (9.39), 7.662 (15.42), 7.697 (9.84), 7.712 (5.70), 7.888 (0.93), 8.680 (4.82), 8.689 (8.49), 8.698 (4.46), 12.010 (4.14).

Example 73

(+/−)-5-[({2-[3-Azabicyclo[3.1.1]hept-3-yl]-6-bromo-3-methylquinolin-4-yl}carbonyl)amino]-4-(2-chlorophenyl)pentanoic acid (Racemate)

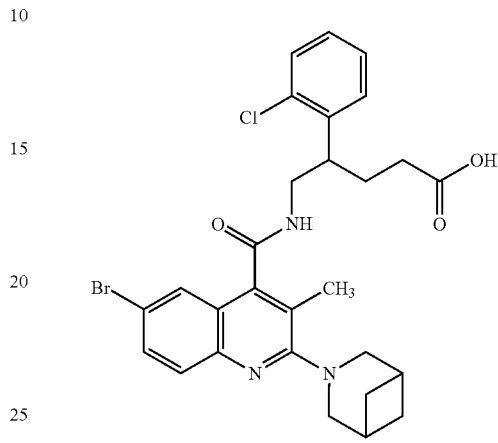

To a solution of (+/−)-tert-butyl 5-[({2-[3-azabicyclo [3.1.1]hept-3-yl]-6-bromo-3-methylquinolin-4-yl}carbonyl) amino]-4-(2-chlorophenyl)pentanoate (63 mg, 100 µmol, racemate, Example 111A) in dichloromethane (2.5 ml) was added TFA (120 µl, 1.5 mmol), and the mixture was stirred at RT for 24 h. Subsequently, TFA (7.3 µl, 95 µmol) was added again, and the mixture was stirred at RT for a further 48 h. This was followed by concentration of the mixture, and repeated additions of dichloromethane followed by concentration again. The residue was purified by preparative HPLC (Method 11). The combined target fractions were concentrated, and the residue was lyophilized. 38 mg (100% purity, 66% of theory) of the title compound were obtained.

LC-MS (Method 1): $R_t$=2.07 min; MS (ESIpos): m/z=570/572 [M+H]$^+$ $^1$H-NMR (400 MHz, DMSO-d6) δ [ppm]: −0.149 (1.04), −0.008 (9.81), 0.008 (9.81), 0.146 (1.07), 1.235 (0.70), 1.369 (1.83), 1.426 (1.48), 1.439 (9.09), 1.445 (8.32), 1.455 (8.53), 1.461 (9.55), 1.474 (1.76), 1.796 (1.00), 1.814 (2.18), 1.838 (3.04), 1.861 (1.76), 1.885 (0.56), 2.046 (5.15), 2.076 (9.00), 2.087 (12.29), 2.102 (8.74), 2.108 (8.81), 2.124 (4.50), 2.134 (4.24), 2.158 (2.02), 2.195 (16.00), 2.274 (0.46), 2.300 (0.56), 2.327 (0.86), 2.366 (0.93), 2.670 (0.83), 2.710 (0.93), 3.591 (2.83), 3.666 (3.99), 3.867 (3.83), 7.253 (2.32), 7.272 (5.24), 7.291 (3.69), 7.354 (3.39), 7.373 (6.14), 7.391 (3.73), 7.438 (8.74), 7.441 (8.70), 7.458 (7.05), 7.461 (6.91), 7.480 (6.61), 7.498 (4.78), 7.524 (7.63), 7.546 (15.61), 7.581 (8.77), 7.587 (8.16), 7.603 (4.20), 7.609 (4.20), 8.705 (2.81), 8.720 (5.43), 8.734 (2.81), 11.983 (0.42).

Example 74

(+/−)-5-[({2-[3-Azabicyclo[3.2.1]oct-3-yl]-6-bromo-3-methylquinolin-4-yl}carbonyl)amino]-4-(2-chlorophenyl)pentanoic acid (Racemate)

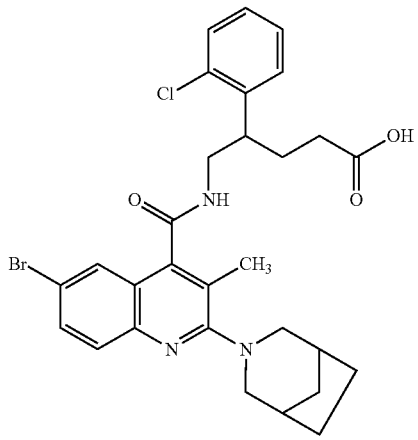 [SMILES: Cc1c(N2CC3CCC(C3)C2)nc2ccc(Br)cc2c1C(=O)NCC(CCC(=O)O)c1ccccc1Cl]

To a solution of (+/−)-tert-butyl 5-[({2-[3-azabicyclo[3.2.1]oct-3-yl]-6-bromo-3-methylquinolin-4-yl}carbonyl)amino]-4-(2-chlorophenyl)pentanoate (77 mg, 120 µmol, racemate, Example 112A) in dichloromethane (2.0 ml) was added TFA (140 µl, 1.8 mmol), and the mixture was stirred at RT for 48 h. Subsequently, TFA (140 µl, 1.8 mmol) was added again, and the mixture was stirred at RT for a further 18 h. This was followed by concentration of the mixture, and repeated additions of dichloromethane followed by concentration again. The residue was purified by preparative HPLC (Method 11). The combined target fractions were concentrated, and the residue was lyophilized. 38 mg (100% purity, 54% of theory) of the title compound were obtained.

LC-MS (Method 1): $R_t$=2.40 min; MS (ESIpos): m/z=584/586 [M+H]$^+$ $^1$H-NMR (400 MHz, DMSO-d6) δ [ppm]: −0.149 (0.42), −0.008 (3.49), 0.008 (3.22), 0.147 (0.42), 1.236 (0.97), 1.325 (1.08), 1.349 (4.20), 1.552 (10.36), 1.652 (4.29), 1.664 (4.68), 1.702 (1.24), 1.749 (5.47), 1.768 (5.29), 1.808 (2.02), 1.830 (2.75), 1.853 (1.69), 2.039 (4.17), 2.067 (6.22), 2.074 (5.47), 2.088 (3.49), 2.097 (2.29), 2.123 (3.05), 2.146 (1.53), 2.182 (16.00), 2.226 (0.73), 2.299 (7.19), 2.366 (0.81), 2.670 (0.80), 2.710 (0.78), 2.890 (2.64), 2.907 (3.61), 2.934 (3.27), 3.133 (0.41), 3.583 (2.22), 3.668 (3.76), 7.256 (2.02), 7.274 (4.53), 7.292 (3.24), 7.354 (2.83), 7.373 (5.00), 7.391 (2.71), 7.443 (7.29), 7.445 (7.37), 7.466 (7.25), 7.475 (6.63), 7.494 (4.54), 7.605 (4.66), 7.627 (14.17), 7.643 (8.36), 7.648 (7.56), 7.666 (2.56), 7.671 (2.59), 8.734 (2.17), 8.748 (4.20), 8.762 (2.05).

Example 75

(+/−)-5-({[6-Bromo-2-(3,3-difluoroazetidin-1-yl)-3-methylquinolin-4-yl]carbonyl}amino)-4-(2-chlorophenyl)pentanoic acid (Racemate)

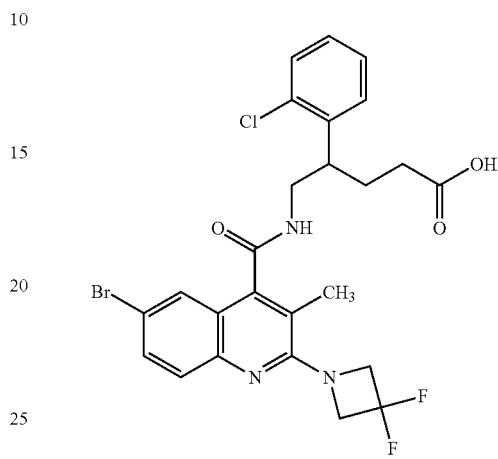

To a solution of (+/−)-tert-butyl 5-({[6-bromo-2-(3,3-difluoroazetidin-1-yl)-3-methylquinolin-4-yl]carbonyl}amino)-4-(2-chlorophenyl)pentanoate (30 mg, 96% purity, 46.2 µmol, racemate, Example 113A) in dichloromethane (1.9 ml) was added TFA (36 µl, 460 µmol), and the mixture was stirred at RT for 18 h. Subsequently, TFA (36 µl, 460 µmol) was added again, and the mixture was stirred at RT for a further 24 h. Subsequently, TFA (18 µl, 230 µmol) was added again, and the mixture was stirred at RT for a further 24 h. This was followed by concentration of the mixture, and repeated additions of dichloromethane followed by concentration again. The residue was purified by preparative HPLC (Method 11). The combined target fractions were concentrated, and the residue was lyophilized. 18 mg (100% purity, 69% of theory) of the title compound were obtained.

LC-MS (Method 1): $R_t$=2.00 min; MS (ESIpos): m/z=566/568 [M+H]$^+$ $^1$H-NMR (400 MHz, DMSO-d6) δ [ppm]: −0.149 (1.80), 0.008 (14.73), 0.146 (1.67), 1.236 (1.47), 1.367 (1.27), 1.793 (1.20), 1.813 (2.47), 1.835 (3.20), 1.858 (1.80), 2.041 (9.47), 2.066 (14.00), 2.085 (9.27), 2.113 (3.20), 2.133 (3.93), 2.156 (1.80), 2.327 (2.40), 2.366 (2.07), 2.523 (8.00), 2.669 (2.73), 2.710 (2.13), 3.585 (2.80), 3.673 (3.73), 4.581 (6.73), 4.613 (12.67), 4.644 (6.60), 5.754 (9.53), 7.254 (2.20), 7.271 (5.00), 7.290 (3.53), 7.352 (3.00), 7.371 (5.47), 7.389 (3.00), 7.438 (9.33), 7.458 (8.07), 7.476 (7.53), 7.493 (5.67), 7.588 (7.87), 7.610 (16.00), 7.647 (8.87), 7.652 (7.80), 7.669 (4.27), 7.674 (4.07), 8.693 (3.07), 8.707 (5.87), 8.722 (2.93), 12.045 (3.13).

Example 76

5-[({6-Bromo-2-[3-cyanopiperidin-1-yl]-3-methylquinolin-4-yl}carbonyl)amino]-4-(2-chlorophenyl)pentanoic acid (Diastereomer Mixture)

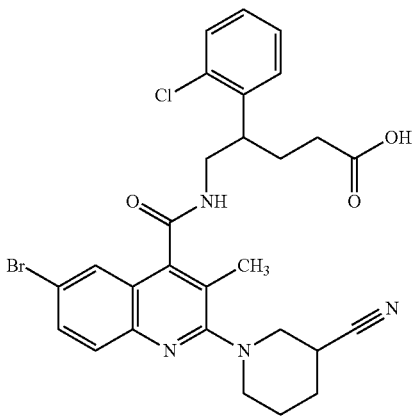 [SMILES: Cc1c(N2CCCC(C#N)C2)nc2ccc(Br)cc2c1C(=O)NCC(CCC(=O)O)c1ccccc1Cl]

To a solution of tert-butyl 5-[({6-bromo-2-[3-cyanopiperidin-1-yl]-3-methylquinolin-4-yl}carbonyl)amino]-4-(2-chlorophenyl)pentanoate (197 mg, 308 µmol, diastereomer mixture, Example 114A) in dichloromethane (4.0 ml) was added TFA (360 µl, 4.6 mmol), and the mixture was stirred at RT overnight. The mixture was then concentrated and repeatedly dichloromethane was added and the mixture was concentrated again. The residue was first prepurified by means of preparative HPLC (Method 8) and then repurified twice more by the same method. The combined target fractions were concentrated, and the residue was lyophilized. 55 mg (95% purity, 29% of theory) of the title compound were obtained.

LC-MS (Method 1): $R_t$=1.97 min; MS (ESIpos): m/z=583/585 [M+H]$^+$ $^1$H-NMR (400 MHz, DMSO-d6) δ [ppm]: −0.008 (3.11), 0.008 (3.20), 0.938 (0.76), 0.955 (0.75), 1.488 (9.73), 1.656 (0.56), 1.667 (0.80), 1.719 (1.80), 1.802 (2.69), 1.825 (3.97), 1.846 (2.65), 1.876 (4.02), 1.888 (5.87), 1.901 (4.88), 2.003 (1.54), 2.015 (3.69), 2.041 (6.06), 2.063 (3.89), 2.073 (3.24), 2.100 (2.40), 2.122 (1.26), 2.181 (16.00), 2.239 (0.56), 2.327 (0.59), 2.366 (0.58), 2.523 (1.43), 2.665 (0.46), 2.670 (0.55), 2.710 (0.66), 2.756 (4.54), 3.020 (2.08), 3.212 (2.91), 3.268 (4.82), 3.276 (4.72), 3.295 (4.84), 3.328 (5.24), 3.441 (3.75), 3.456 (3.51), 3.473 (2.89), 3.487 (2.47), 3.580 (2.53), 3.681 (3.48), 7.252 (1.84), 7.270 (4.21), 7.287 (2.95), 7.352 (2.53), 7.371 (4.60), 7.389 (2.37), 7.436 (6.16), 7.440 (5.96), 7.456 (5.23), 7.459 (4.98), 7.478 (5.40), 7.495 (4.41), 7.669 (1.98), 7.691 (14.43), 7.694 (12.09), 7.699 (8.72), 7.717 (1.14), 7.721 (1.37), 7.891 (0.91), 8.753 (2.20), 8.767 (4.21), 8.781 (2.02).

Example 77

(+/−)-5-({[6-Bromo-2-(3,6-dihydro-2H-1,2-oxazin-2-yl)-3-methylquinolin-4-yl]carbonyl}amino)-4-(2-chlorophenyl)pentanoic acid (Racemate)

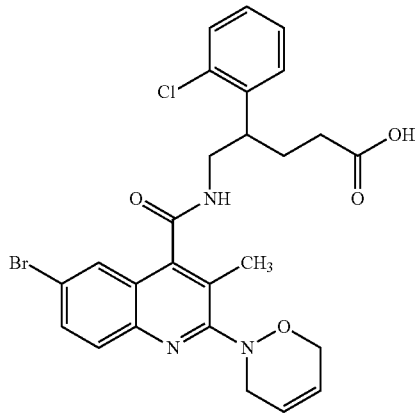 [SMILES: Cc1c(N2CC=CCO2)nc2ccc(Br)cc2c1C(=O)NCC(CCC(=O)O)c1ccccc1Cl]

To a solution of (+/−)-tert-butyl 5-({[6-bromo-2-(3,6-dihydro-2H-1,2-oxazin-2-yl)-3-methylquinolin-4-yl]carbonyl}amino)-4-(2-chlorophenyl)pentanoate (65 mg, 106 µmol, racemate, Example 115A) in dichloromethane (2.0 ml) was added TFA (160 µl, 2.1 mmol), and the mixture was stirred at RT for 18 h. The mixture was then concentrated and repeatedly dichloromethane was added and the mixture was concentrated again. The residue was purified by preparative HPLC (Method 6). The combined target fractions were concentrated, and the residue was lyophilized. 51 mg (97% purity, 83% of theory) of the title compound were obtained.

LC-MS (Method 1): $R_t$=2.09 min; MS (ESIpos): m/z=558/560 [M+H]$^+$ $^1$H-NMR (400 MHz, DMSO-d6) δ [ppm]: 0.935 (1.33), 0.952 (1.27), 1.066 (1.35), 1.082 (1.38), 1.531 (8.69), 1.809 (1.67), 1.830 (1.32), 1.945 (1.75), 1.972 (2.68), 1.992 (3.01), 2.006 (3.92), 2.033 (2.92), 2.187 (8.46), 2.327 (0.72), 2.365 (0.70), 2.669 (0.84), 2.730 (4.10), 3.334 (2.23), 3.556 (1.91), 3.673 (2.35), 4.069 (6.50), 4.505 (4.29), 5.990 (1.44), 6.015 (3.42), 6.049 (2.99), 6.074 (1.24), 7.246 (1.38), 7.264 (3.21), 7.282 (2.18), 7.346 (1.76), 7.365 (3.36), 7.384 (1.70), 7.436 (4.65), 7.459 (5.68), 7.481 (2.65), 7.548 (0.84), 7.743 (15.75), 7.745 (16.00), 8.955 (2.23).

Example 78

5-[({6-Bromo-2-[3-fluoropiperidin-1-yl]-3-methylquinolin-4-yl}carbonyl)amino]-4-(2-chlorophenyl)pentanoic acid (Diastereomer Mixture)

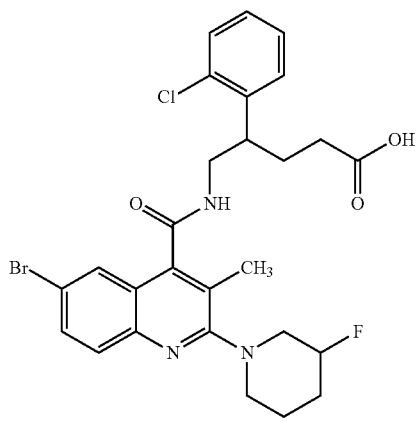 [SMILES: Cc1c(N2CCCC(F)C2)nc2ccc(Br)cc2c1C(=O)NCC(CCC(=O)O)c1ccccc1Cl]

To a solution of tert-butyl 5-[({6-bromo-2-[3-fluoropiperidin-1-yl]-3-methylquinolin-4-yl}carbonyl)amino]-4-(2-chlorophenyl)pentanoate (75 mg, 118 µmol, diastereomer mixture, Example 116A) in dichloromethane (870 µl) was added TFA (91 µl, 1.2 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized. 56 mg (98% purity, 80% of theory) of the title compound were obtained.

LC-MS (Method 2): $R_t$=1.09 min; MS (ESIpos): m/z=576/578 [M+H]$^+$ $^1$H-NMR (400 MHz, DMSO-d6) δ [ppm]: −0.008 (2.24), 0.008 (2.48), 1.642 (1.63), 1.765 (0.52), 1.793 (1.91), 1.810 (3.01), 1.819 (2.66), 1.834 (3.26), 1.858 (1.97), 1.900 (2.78), 1.920 (2.26), 1.950 (1.57), 1.982 (0.97), 2.011 (0.73), 2.034 (1.27), 2.045 (4.21), 2.079 (5.00), 2.088 (5.22), 2.143 (16.00), 2.217 (0.40), 2.327 (0.45), 2.366 (0.51), 2.523 (1.47), 2.669 (0.48), 2.710 (0.56), 3.094 (1.88), 3.159 (2.00), 3.377 (2.00), 3.410 (1.07), 3.434 (1.75), 3.465 (1.09), 3.593 (1.93), 3.679 (3.48), 4.816 (1.35), 4.936 (1.31), 7.256 (1.72), 7.274 (4.01), 7.294 (2.80), 7.356 (2.44), 7.374 (4.45), 7.393 (2.29), 7.441 (6.25), 7.444 (6.25), 7.461 (5.34), 7.464 (5.25), 7.484 (5.69), 7.500 (4.68), 7.647 (2.48), 7.669 (13.43), 7.675 (9.66), 7.680 (8.33), 7.697 (1.60), 7.702 (1.84), 8.715 (2.20), 8.730 (4.40), 8.744 (2.14), 12.062 (0.87).

Example 79

5-[({6-Bromo-3-methyl-2-[2-methylpyrrolidin-1-yl]quinolin-4-yl}carbonyl)amino]-4-(2-chlorophenyl)pentanoic acid (Diastereomer Mixture)

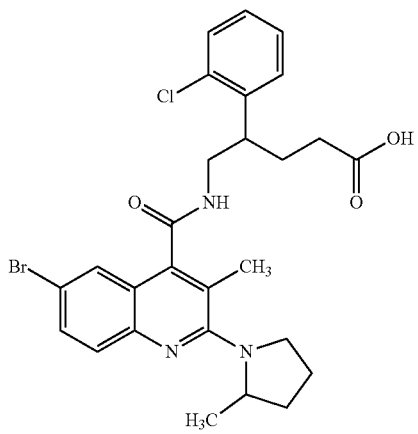 [SMILES: Cc1c(N2CCCC2C)nc2ccc(Br)cc2c1C(=O)NCC(CCC(=O)O)c1ccccc1Cl]

(+/−)-2-Methylpyrrolidine (9 mg, 100 µmol) was initially charged in a well of a 96-well MTP, and a solution of (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A) in NMP (800 µl) was added, followed by DIPEA (50 µl, 287 µmol). The MTP was sealed with an adhesive film and agitated at 120° C. overnight. Subsequently, the solvent was removed in a centrifugal dryer, and TFA (800 µl, 10.4 mmol) was added to the residue. The MTP was sealed again with an adhesive film and agitated at RT overnight. Subsequently, the TFA was removed in a centrifugal dryer, and the residue was dissolved in DMF (600 µl). The solution was filtered by means of a filter plate, and the filtrate was purified by means of preparative HPLC-MS (Method 17). Removal of the solvent and drying under reduced pressure gave 6 mg (100% purity, 11% of theory) of the title compound.

LC-MS (Method 16): $R_t$=0.95 min; MS (ESIpos): m/z=558/560 [M+H]$^+$

Example 80

(−)-5-[({6-Bromo-3-methyl-2-[(2S)-2-methylpyrrolidin-1-yl]quinolin-4-yl}carbonyl)amino]-4-(2-chlorophenyl)pentanoic acid (epimer 1)

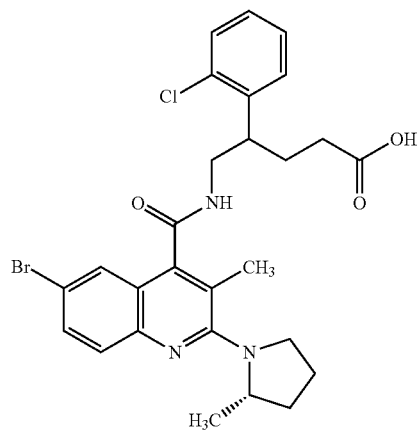 [SMILES: Cc1c(N2CCC[C@@H]2C)nc2ccc(Br)cc2c1C(=O)NCC(CCC(=O)O)c1ccccc1Cl]

To a solution of (−)-tert-butyl 5-[({6-bromo-3-methyl-2-[(2S)-2-methylpyrrolidin-1-yl]quinolin-4-yl}carbonyl)amino]-4-(2-chlorophenyl)pentanoate (135 mg, 220 µmol, epimer 1, Example 118A) in dichloromethane (1.7 ml) was added TFA (370 µl, 4.8 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 56 mg (100% purity, 46% of theory) of the title compound were obtained.

$[α]_D^{20}$=−33.3°, 589 nm, c=0.40 g/100 ml, methanol

LC-MS (Method 1): $R_t$=1.88 min; MS (ESIpos): m/z=558/560 [M+H]$^+$ $^1$H-NMR (400 MHz, DMSO-d6) δ [ppm]: 1.141 (15.77), 1.156 (16.00), 1.370 (0.82), 1.512 (0.44), 1.539 (1.29), 1.557 (1.57), 1.579 (1.54), 1.606 (0.94), 1.663 (1.38), 1.689 (1.45), 1.709 (0.94), 1.792 (0.79), 1.810 (1.53), 1.832 (1.99), 1.854 (1.21), 1.896 (1.94), 2.041 (4.08), 2.097 (10.55), 2.127 (4.78), 2.327 (0.46), 2.669 (0.44), 3.587 (2.86), 3.610 (1.84), 3.623 (2.08), 3.691 (1.33), 3.716 (2.88), 3.732 (3.30), 3.756 (2.27), 4.360 (1.38), 4.375 (2.28), 4.397 (2.15), 4.413 (1.32), 7.260 (1.69), 7.278 (3.73), 7.297 (2.73), 7.362 (2.89), 7.381 (4.34), 7.398 (2.39), 7.436 (6.24), 7.455 (5.02), 7.481 (4.21), 7.498 (8.03), 7.520 (9.92), 7.566 (5.37), 7.571 (4.99), 7.588 (2.85), 7.594 (2.78), 8.688 (2.06), 8.702 (3.28).

Example 81

(−)-5-[({6-Bromo-3-methyl-2-[(2S)-2-methylpyrrolidin-1-yl]quinolin-4-yl}carbonyl)amino]-4-(2-chlorophenyl)pentanoic acid (epimer 2)

To a solution of (−)-tert-butyl 5-[({6-bromo-3-methyl-2-[(2S)-2-methylpyrrolidin-1-yl]quinolin-4-yl}carbonyl)

amino]-4-(2-chlorophenyl)pentanoate (130 mg, 211 µmol, epimer-2, Example 119A) in dichloromethane (1.6 ml) was added TFA (360 µl, 4.7 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 71 mg (100% purity, 60% of theory) of the title compound were obtained.

$[\alpha]_D^{20}=-9.2°$, 589 nm, c=0.47 g/100 ml, methanol

LC-MS (Method 1): $R_t$=1.87 min; MS (ESIpos): m/z=558/560 $[M+H]^+$ $^1$H-NMR (400 MHz, DMSO-d6) δ [ppm]: 1.142 (15.85), 1.157 (16.00), 1.346 (0.61), 1.511 (0.44), 1.540 (1.31), 1.556 (1.56), 1.563 (1.55), 1.579 (1.52), 1.607 (0.99), 1.660 (1.32), 1.684 (1.35), 1.705 (0.86), 1.793 (0.68), 1.813 (1.62), 1.835 (2.04), 1.859 (1.20), 1.897 (1.92), 1.912 (1.82), 2.021 (0.92), 2.047 (4.11), 2.075 (5.50), 2.104 (14.49), 2.142 (4.74), 2.164 (2.34), 2.201 (0.49), 3.611 (2.35), 3.661 (2.85), 3.678 (2.70), 3.695 (2.70), 3.712 (2.42), 3.720 (2.96), 3.737 (2.63), 3.761 (1.12), 4.362 (1.27), 4.377 (2.15), 4.392 (1.83), 4.399 (2.04), 4.414 (1.23), 7.242 (1.76), 7.260 (4.06), 7.279 (2.87), 7.343 (2.51), 7.362 (4.68), 7.380 (2.49), 7.438 (6.32), 7.458 (5.90), 7.472 (5.71), 7.491 (4.08), 7.503 (5.93), 7.525 (9.65), 7.573 (5.51), 7.579 (5.04), 7.596 (2.97), 7.601 (2.83), 8.689 (2.01), 8.703 (3.73), 11.998 (0.66).

Example 82

(+)-5-[({6-Bromo-3-methyl-2-[(2R)-2-methylpyrrolidin-1-yl]quinolin-4-yl}carbonyl)amino]-4-(2-chlorophenyl)pentanoic acid (epimer 1)

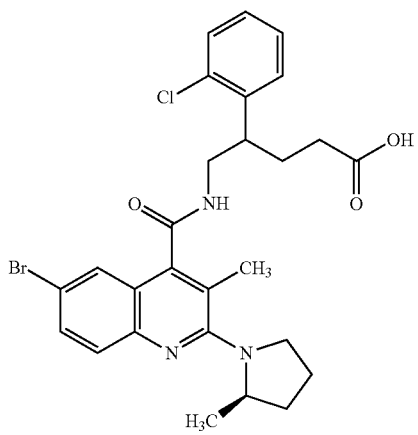 [SMILES: Cc1c(N2CCC[C@H]2C)nc2ccc(Br)cc2c1C(=O)NCC(CCC(=O)O)c1ccccc1Cl]

To a solution of (+)-tert-butyl 5-[({6-bromo-3-methyl-2-[(2R)-2-methylpyrrolidin-1-yl]quinolin-4-yl}carbonyl) amino]-4-(2-chlorophenyl)pentanoate (135 mg, 220 µmol, epimer 1, Example 121A) in dichloromethane (1.6 ml) was added TFA (360 µl, 4.7 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 66 mg (100% purity, 56% of theory) of the title compound were obtained.

$[\alpha]_D^{20}=+10.3°$, 589 nm, c=0.27 g/100 ml, methanol

LC-MS (Method 1): $R_t$=1.83 min; MS (ESIpos): m/z=558/560 $[M+H]^+$ $^1$H-NMR (400 MHz, DMSO-d6) δ [ppm]: −0.008 (1.99), 0.008 (1.83), 0.069 (0.74), 1.142 (15.94), 1.157 (16.00), 1.512 (0.42), 1.540 (1.20), 1.556 (1.41), 1.563 (1.38), 1.579 (1.40), 1.591 (1.01), 1.607 (0.94), 1.659 (1.18), 1.684 (1.19), 1.703 (0.76), 1.813 (1.41), 1.832 (1.75), 1.857 (1.04), 1.897 (1.67), 1.911 (1.60), 2.014 (0.79), 2.041 (3.65), 2.068 (4.96), 2.103 (12.77), 2.135 (4.21), 2.158 (2.42), 2.200 (0.41), 2.327 (0.42), 2.669 (0.40), 3.616 (1.97), 3.661 (2.55), 3.676 (2.39), 3.695 (2.33), 3.712 (2.11), 3.720 (2.73), 3.736 (2.47), 3.745 (1.54), 3.761 (1.03), 4.361 (1.20), 4.377 (2.01), 4.392 (1.64), 4.399 (1.83), 4.414 (1.14), 7.242 (1.70), 7.260 (3.70), 7.277 (2.72), 7.280 (2.68), 7.342 (2.47), 7.361 (4.37), 7.377 (2.29), 7.435 (5.99), 7.438 (5.94), 7.455 (5.61), 7.458 (5.42), 7.469 (5.23), 7.473 (5.18), 7.489 (3.79), 7.502 (6.11), 7.524 (10.25), 7.573 (6.05), 7.578 (5.39), 7.595 (3.25), 7.601 (3.05), 8.693 (1.77), 8.708 (3.30).

Example 83

(+)-5-[({6-Bromo-3-methyl-2-[(2R)-2-methylpyrrolidin-1-yl]quinolin-4-yl}carbonyl)amino]-4-(2-chlorophenyl)pentanoic acid (epimer 2)

To a solution of (+)-tert-butyl 5-[({6-bromo-3-methyl-2-[(2R)-2-methylpyrrolidin-1-yl]quinolin-4-yl}carbonyl) amino]-4-(2-chlorophenyl)pentanoate (130 mg, 211 µmol, epimer 2, Example 122A) in dichloromethane (1.6 ml) was added TFA (360 µl, 4.7 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 67 mg (100% purity, 57% of theory) of the title compound were obtained.

$[\alpha]_D^{20}=+32.3°$, 589 nm, c=0.29 g/100 ml, methanol

LC-MS (Method 1): $R_t$=1.82 min; MS (ESIpos): m/z=558/560 $[M+H]^+$ $^1$H-NMR (400 MHz, DMSO-d6) δ [ppm]: −0.008 (1.45), 0.008 (1.37), 0.070 (1.15), 1.141 (15.90), 1.156 (16.00), 1.234 (0.48), 1.511 (0.49), 1.540 (1.33), 1.556 (1.56), 1.563 (1.54), 1.578 (1.53), 1.591 (1.12), 1.607 (1.00), 1.618 (0.48), 1.646 (0.89), 1.663 (1.38), 1.688 (1.40), 1.708 (0.86), 1.792 (0.76), 1.810 (1.48), 1.832 (1.92), 1.854 (1.17), 1.879 (1.22), 1.895 (1.83), 1.910 (1.71), 1.924 (1.44), 2.040 (3.92), 2.082 (7.77), 2.097 (9.79), 2.127 (4.49), 2.149 (2.42), 3.551 (1.52), 3.586 (2.61), 3.609 (1.77), 3.623 (1.97), 3.636 (1.06), 3.691 (1.34), 3.708 (1.88), 3.715 (2.78), 3.732 (3.09), 3.740 (2.44), 3.756 (2.09), 4.360 (1.33), 4.375 (2.20), 4.382 (1.74), 4.391 (1.81), 4.397 (2.08), 4.413 (1.27), 7.260 (1.62), 7.278 (3.41), 7.297 (2.41), 7.362 (2.67), 7.381 (3.92), 7.399 (2.14), 7.435 (5.68), 7.438 (5.69), 7.455 (4.64), 7.458 (4.55), 7.481 (3.87), 7.498 (7.60), 7.520 (9.64), 7.566 (5.08), 7.572 (4.98), 7.588 (2.76), 7.594 (2.84), 8.688 (1.91), 8.703 (3.11), 8.715 (1.87).

Example 84

(+/−)-5-({[6-Bromo-2-(3,4-dihydroisoquinolin-2 (1H)-yl)-3-methylquinolin-4-yl]carbonyl}amino)-4-(2-chlorophenyl)pentanoic acid (Racemate)

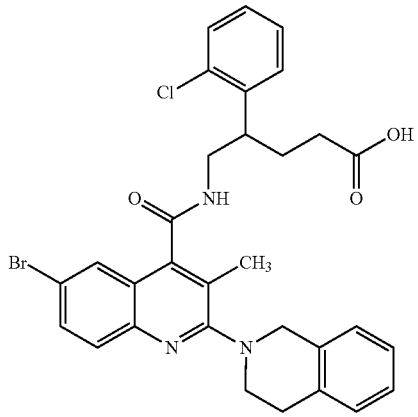 [SMILES: Cc1c(N2CCc3ccccc3C2)nc2ccc(Br)cc2c1C(=O)NCC(CCC(=O)O)c1ccccc1Cl]

1,2,3,4-Tetrahydroisoquinoline (13 mg, 100 µmol) was initially charged in a well of a 96-well MTP, and a solution of (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A) in NMP (800 µl) was added, followed by DIPEA (50 µl, 287 µmol). The MTP was sealed with an adhesive film and agitated at 120° C. overnight. Subsequently, the solvent was removed in a centrifugal dryer, and TFA (800 µl, 10.4 mmol) was added to the residue. The MTP was sealed again with an adhesive film and agitated at RT overnight. Subsequently, the TFA was removed in a centrifugal dryer, and the residue was dissolved in DMF (600 µl). The solution was filtered by means of a filter plate, and the filtrate was purified by means of preparative HPLC-MS (Method 17). Removal of the solvent and drying under reduced pressure gave 12 mg (96% purity, 19% of theory) of the title compound.

LC-MS (Method 16): $R_t$=1.26 min; MS (ESIpos): m/z=606/608 [M+H]$^+$

Example 85

5-[({6-Bromo-2-[3-carbamoylpiperidin-1-yl]-3-methylquinolin-4-yl}carbonyl)amino]-4-(2-chlorophenyl)pentanoic acid (Diastereomer Mixture)

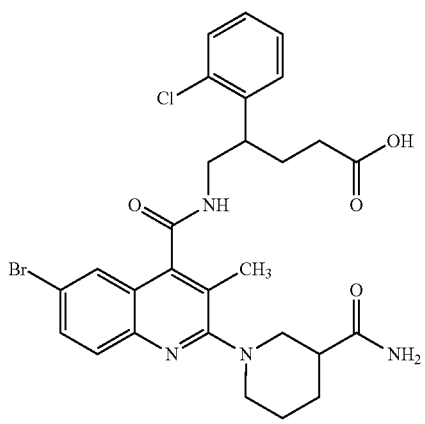 [SMILES: Cc1c(N2CCCC(C(N)=O)C2)nc2ccc(Br)cc2c1C(=O)NCC(CCC(=O)O)c1ccccc1Cl]

Proceeding from (+/−)-piperidine-3-carboxamide (13 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 11 mg (95% purity, 18% of theory) of the title compound were obtained.

LC-MS (Method 16): $R_t$=1.00 min; MS (ESIpos): m/z=601/603 [M+H]$^+$

Example 86

(+/−)-5-({[6-Bromo-3-methyl-2-(octahydro-2H-isoindol-2-yl)quinolin-4-yl]carbonyl}amino)-4-(2-chlorophenyl)pentanoic acid (racemate or diastereomer mixture)

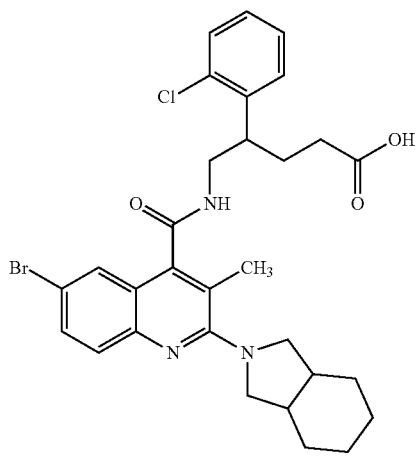 [SMILES: Cc1c(N2CC3CCCCC3C2)nc2ccc(Br)cc2c1C(=O)NCC(CCC(=O)O)c1ccccc1Cl]

Proceeding from octahydro-1H-isoindole hydrochloride (13 mg, 100 µmol, molar amount based on the free amine, stereochemistry unknown) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 8 mg (100% purity, 13% of theory) of the title compound were obtained.

LC-MS (Method 16): $R_t$=0.95 min; MS (ESIpos): m/z=598/600 [M+H]$^+$

Example 87

(+/−)-5-({[6-Bromo-2-(1,1-dioxidothiomorpholin-4-yl)-3-methylquinolin-4-yl]carbonyl}amino)-4-(2-chlorophenyl)pentanoic acid (Racemate)

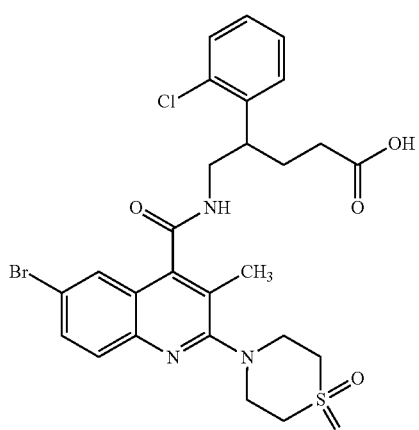

Proceeding from thiomorpholine 1,1-dioxide (14 mg, 100 μmol) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1 mg (100% purity, 2% of theory) of the title compound were obtained.

LC-MS (Method 16): $R_t$=1.08 min; MS (ESIpos): m/z=608/610 [M+H]$^+$

Example 88

(+/−)-5-({[6-Bromo-3-methyl-2-(4-oxoimidazolidin-1-yl)quinolin-4-yl]carbonyl}amino)-4-(2-chlorophenyl)pentanoic acid (Racemate)

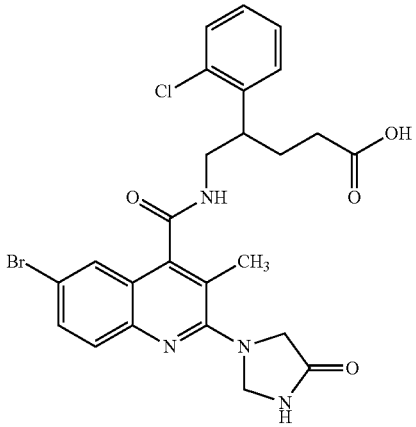 [SMILES: Cc1c(N2CNC(=O)C2)nc2ccc(Br)cc2c1C(=O)NCC(CCC(=O)O)c1ccccc1Cl]

Proceeding from imidazolidin-4-one hydrochloride (9 mg, 100 μmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}-amino)-4-(2-chlorophenyl)pentanoic acid (Example 84), 1.7 mg (100% purity, 3% of theory) of the title compound were obtained.

LC-MS (Method 16): $R_t$=1.00 min; MS (ESIpos): m/z=559/561 [M+H]$^+$

Example 89

5-[({6-Bromo-3-methyl-2-[2-methylmorpholin-4-yl]quinolin-4-yl}carbonyl)amino]-4-(2-chlorophenyl)pentanoic acid (Diastereomer Mixture)

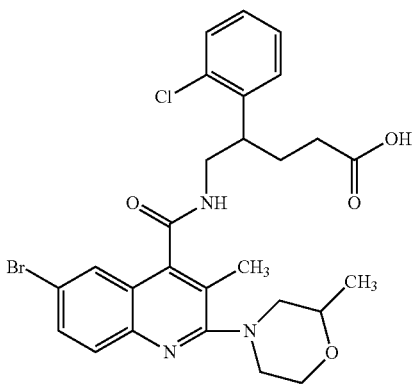 [SMILES: Cc1c(N2CCOC(C)C2)nc2ccc(Br)cc2c1C(=O)NCC(CCC(=O)O)c1ccccc1Cl]

Proceeding from (+/−)-2-methylmorpholine (10 mg, 100 μmol) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.7 mg (100% purity, 3% of theory) of the title compound were obtained.

LC-MS (Method 16): $R_t$=1.14 min; MS (ESIpos): m/z=574/576 [M+H]$^+$

Example 90

(+/−)-5-({[6-Bromo-3-methyl-2-(1,4-oxazepan-4-yl)quinolin-4-yl]carbonyl}amino)-4-(2-chlorophenyl)pentanoic acid (Racemate)

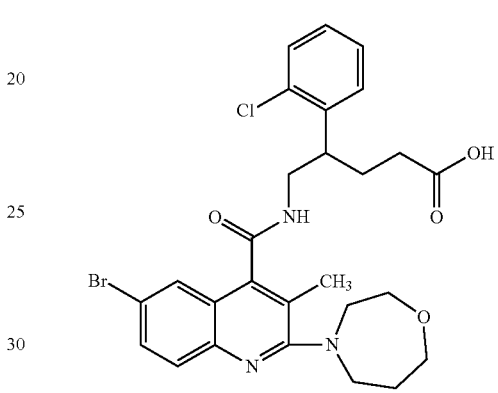

Proceeding from 1,4-oxazepane hydrochloride (10 mg, 100 μmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 3.4 mg (100% purity, 6% of theory) of the title compound were obtained.

LC-MS (Method 16): $R_t$=1.10 min; MS (ESIpos): m/z=574/576 [M+H]$^+$

Example 91

5-[({6-Bromo-2-[3-isopropylpiperidin-1-yl]-3-methylquinolin-4-yl}carbonyl)amino]-4-(2-chlorophenyl)pentanoic acid (Diastereomer Mixture)

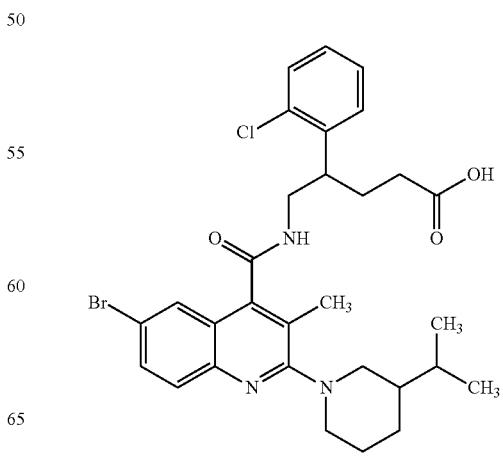

Proceeding from (+/−)-3-isopropylpiperidine (13 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 10 mg (99% purity, 16% of theory) of the title compound were obtained.

LC-MS (Method 16): R$_t$=1.28 min; MS (ESIpos): m/z=600/602 [M+H]$^+$

Example 92

(+/−)-5-({[6-Bromo-2-(3-methoxyazetidin-1-yl)-3-methylquinolin-4-yl]carbonyl}amino)-4-(2-chlorophenyl)pentanoic acid (Racemate)

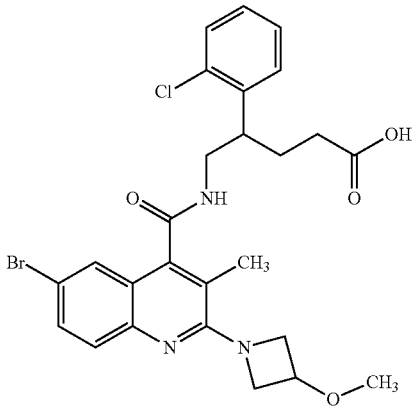 [SMILES: COC1CN(c2nc3ccc(Br)cc3c(C(=O)NCC(CCC(=O)O)c3ccccc3Cl)c2C)C1]

Proceeding from 3-methoxyazetidine hydrochloride (9 mg, 100 µmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 3.2 mg (100% purity, 7% of theory) of the title compound were obtained.

LC-MS (Method 16): R$_t$=0.88 min; MS (ESIpos): m/z=560/562 [M+H]$^+$

Example 93

5-[({6-Bromo-2-[3-(methoxymethyl)piperidin-1-yl]-3-methylquinolin-4-yl}carbonyl)amino]-4-(2-chlorophenyl)pentanoic acid (Diastereomer Mixture)

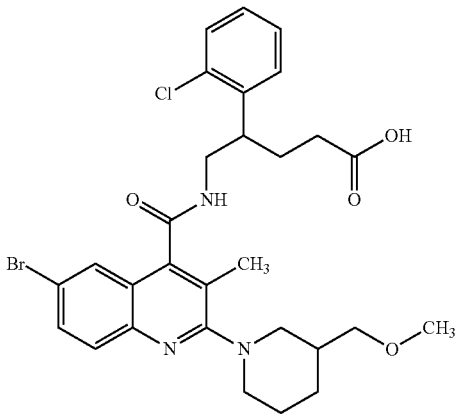 [SMILES: COCC1CCCN(c2nc3ccc(Br)cc3c(C(=O)NCC(CCC(=O)O)c3ccccc3Cl)c2C)C1]

Proceeding from (+/−)-3-(methoxymethyl)piperidine (13 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 10 mg (100% purity, 16% of theory) of the title compound were obtained.

LC-MS (Method 16): R$_t$=1.18 min; MS (ESIpos): m/z=602/604 [M+H]$^+$

Example 94

(+/−)-5-[({6-Bromo-3-methyl-2-[(2-phenylethyl)amino]quinolin-4-yl}carbonyl)amino]-4-(2-chlorophenyl)pentanoic acid (Racemate)

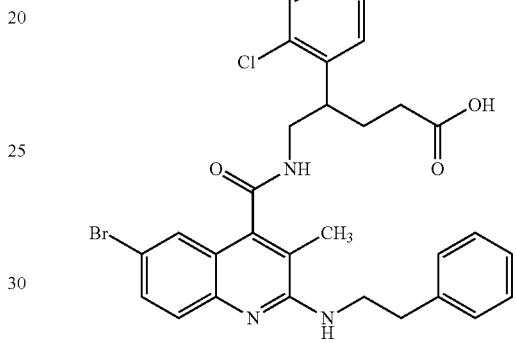

Proceeding from 2-phenylethanamine (12 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 8.5 mg (97% purity, 14% of theory) of the title compound were obtained.

LC-MS (Method 16): R$_t$=0.97 min; MS (ESIpos): m/z=594/596 [M+H]$^+$

Example 95

(+/−)-5-[({6-Bromo-3-methyl-2-[methyl(2-phenylethyl)amino]quinolin-4-yl}carbonyl)amino]-4-(2-chlorophenyl)pentanoic acid (Racemate)

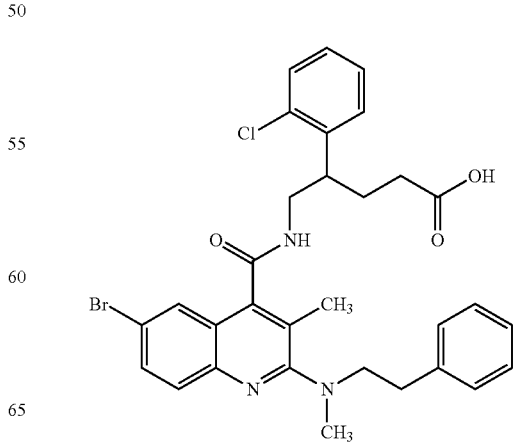

Proceeding from N-methyl-2-phenylethanamine (14 mg, 100 μmol) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 8 mg (98% purity, 12% of theory) of the title compound were obtained.

LC-MS (Method 16): $R_t$=1.23 min; MS (ESIpos): m/z=608/610 [M+H]$^+$

Example 96

(+/−)-5-({[2-(Benzylamino)-6-bromo-3-methylquinolin-4-yl]carbonyl}amino)-4-(2-chlorophenyl)pentanoic acid (Racemate)

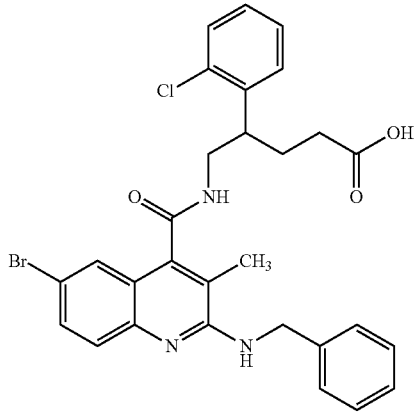 [SMILES: Cc1c(NCc2ccccc2)nc2ccc(Br)cc2c1C(=O)NCC(CCC(=O)O)c1ccccc1Cl]

Proceeding from 1-phenylmethanamine (11 mg, 100 μmol) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 4 mg (94% purity, 6% of theory) of the title compound were obtained.

LC-MS (Method 16): $R_t$=1.04 min; MS (ESIpos): m/z=580/582 [M+H]$^+$

Example 97

(+/−)-5-({[6-Bromo-2-(cyclobutylamino)-3-methylquinolin-4-yl]carbonyl}amino)-4-(2-chlorophenyl)pentanoic acid (Racemate)

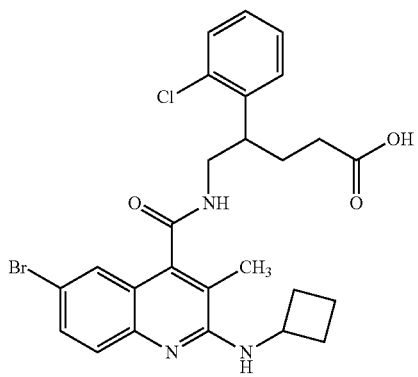 [SMILES: Cc1c(NC2CCC2)nc2ccc(Br)cc2c1C(=O)NCC(CCC(=O)O)c1ccccc1Cl]

Proceeding from cyclobutanamine hydrochloride (7 mg, 100 μmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 2 mg (100% purity, 4% of theory) of the title compound were obtained.

LC-MS (Method 16): $R_t$=0.87 min; MS (ESIpos): m/z=544/546 [M+H]$^+$

Example 98

(+/−)-5-[({6-Bromo-3-methyl-2-[(3,3,3-trifluoropropyl)amino]quinolin-4-yl}carbonyl)amino]-4-(2-chlorophenyl)pentanoic acid (Racemate)

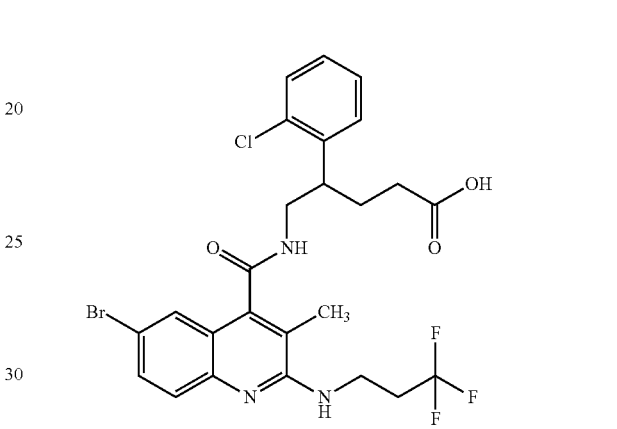

Proceeding from 3,3,3-trifluoropropan-1-amine (11 mg, 100 μmol) and (+/−)-tert-butyl 5-{[(6-bromo-2-chloro-3-methylquinolin-4-yl)carbonyl]amino}-4-(2-chlorophenyl)pentanoate (57 mg, 100 μmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.5 mg (98% purity, 2% of theory) of the title compound were obtained.

LC-MS (Method 16): $R_t$=1.09 min; MS (ESIpos): m/z=586/588 [M+H]$^+$

Example 99

(+/−)-5-[({6-Bromo-2-[(cyclohexylmethyl)amino]-3-methylquinolin-4-yl}carbonyl)amino]-4-(2-chlorophenyl)pentanoic acid (Racemate)

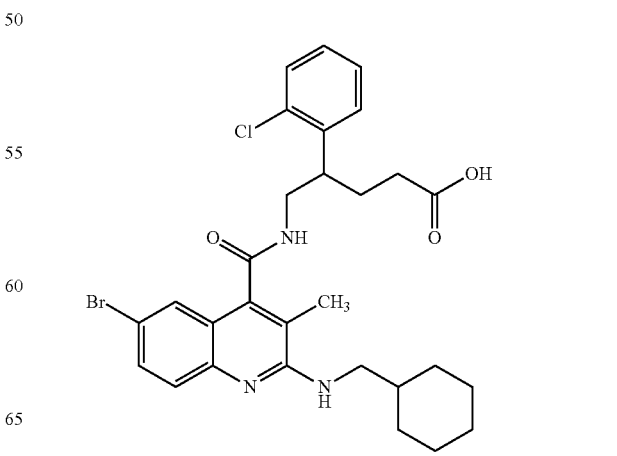

Proceeding from 1-cyclohexylmethanamine (11 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 5 mg (98% purity, 9% of theory) of the title compound were obtained.

LC-MS (Method 16): $R_t$=0.96 min; MS (ESIpos): m/z=586/588 [M+H]$^+$

Example 100

(+/−)-5-[({6-Bromo-2-[(cyclopropylmethyl)amino]-3-methylquinolin-4-yl}carbonyl)amino]-4-(2-chlorophenyl)pentanoic acid (Racemate)

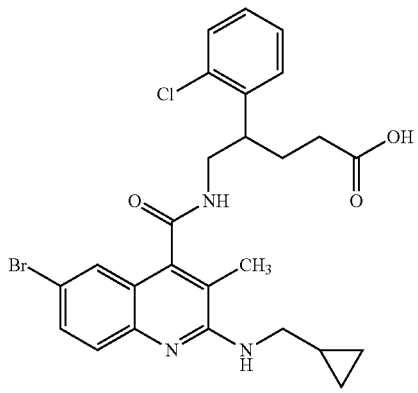 [SMILES: Cc1c(NCC2CC2)nc2ccc(Br)cc2c1C(=O)NCC(CCC(=O)O)c1ccccc1Cl]

Proceeding from 1-cyclopropylmethanamine hydrochloride (7 mg, 100 µmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.7 mg (100% purity, 3% of theory) of the title compound were obtained.

LC-MS (Method 16): $R_t$=0.86 min; MS (ESIpos): m/z=544/546 [M+H]$^+$

Example 101

(+/−)-5-({[6-Bromo-2-(butylamino)-3-methylquinolin-4-yl]carbonyl}amino)-4-(2-chlorophenyl)pentanoic acid (Racemate)

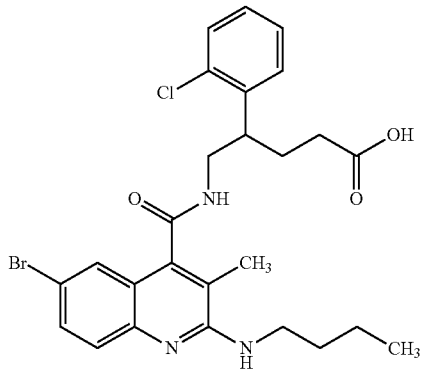 [SMILES: CCCCNc1nc2ccc(Br)cc2c(C(=O)NCC(CCC(=O)O)c2ccccc2Cl)c1C]

Proceeding from butan-1-amine (7.31 mg, 100 µmol) and (+/−)-tert-butyl 1.7-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.7 mg (100% purity, 3% of theory) of the title compound were obtained.

LC-MS (Method 16): $R_t$=0.88 min; MS (ESIpos): m/z=546/548 [M+H]$^+$

Example 102

(+/−)-5-({[6-Bromo-2-(isobutylamino)-3-methylquinolin-4-yl]carbonyl}amino)-4-(2-chlorophenyl)pentanoic acid (Racemate)

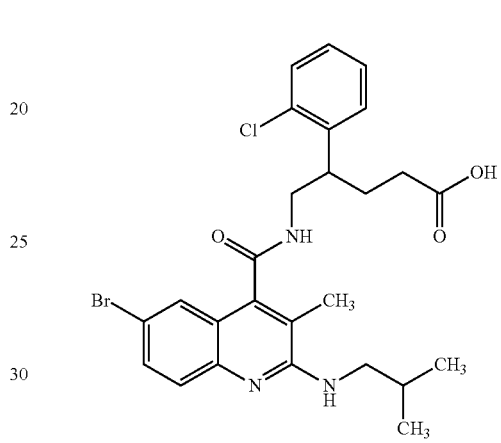

Proceeding from 2-methylpropan-1-amine (7 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.6 mg (100% purity, 3% of theory) of the title compound were obtained.

LC-MS (Method 16): $R_t$=0.88 min; MS (ESIpos): m/z=546/548 [M+H]$^+$

Example 103

(+/−)-5-({[6-Bromo-2-(cyclopentylamino)-3-methylquinolin-4-yl]carbonyl}amino)-4-(2-chlorophenyl)pentanoic acid (Racemate)

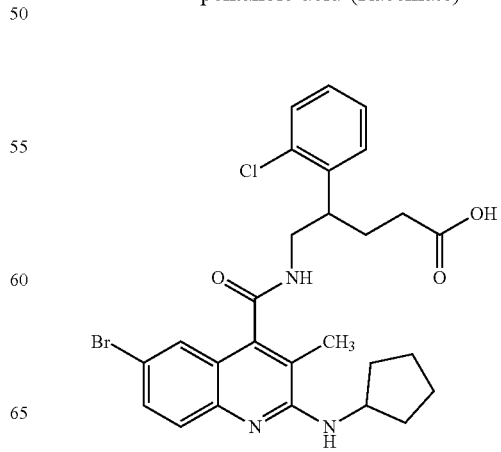

Proceeding from cyclopentanamine (8.5 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 6 mg (98% purity, 10% of theory) of the title compound were obtained.

LC-MS (Method 16): $R_t$=0.89 min; MS (ESIpos): m/z=558/560 [M+H]$^+$

Example 104

(+/−)-5-[({6-Bromo-2-[(2-methoxyethyl)amino]-3-methylquinolin-4-yl}carbonyl)amino]-4-(2-chlorophenyl)pentanoic acid (Racemate)

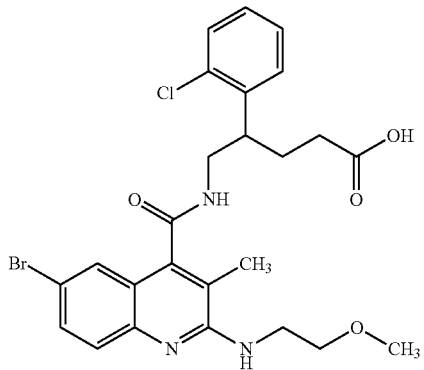 [SMILES: COCCNc1nc2ccc(Br)cc2c(C(=O)NCC(CCC(=O)O)c2ccccc2Cl)c1C]

Proceeding from 2-methoxyethanamine (7.5 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 5 mg (100% purity, 10% of theory) of the title compound were obtained.

LC-MS (Method 16): $R_t$=0.83 min; MS (ESIpos): m/z=548/550 [M+H]$^+$

Example 105

(+/−)-5-({[2-(Azepan-1-yl)-6-bromo-3-methylquinolin-4-yl]carbonyl}amino)-4-(2-chlorophenyl)pentanoic acid (Racemate)

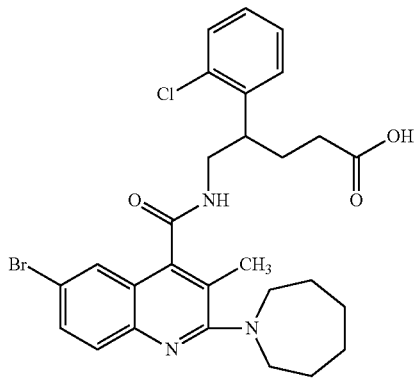 [SMILES: Cc1c(N2CCCCCC2)nc2ccc(Br)cc2c1C(=O)NCC(CCC(=O)O)c1ccccc1Cl]

Proceeding from azepane (10 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 9 mg (100% purity, 15% of theory) of the title compound were obtained.

LC-MS (Method 16): $R_t$=1.14 min; MS (ESIpos): m/z=572/574 [M+H]$^+$

Example 106

(−)-5-({[2-(Azepan-1-yl)-6-bromo-3-methylquinolin-4-yl]carbonyl}amino)-4-(2-chlorophenyl)pentanoic acid (Enantiomer 1)

To a solution of (−)-tert-butyl 5-({[2-(azepan-1-yl)-6-bromo-3-methylquinolin-4-yl]carbonyl}amino)-4-(2-chlorophenyl)pentanoate (460 mg, 731 µmol, enantiomer 1, Example 124A) in dichloromethane (5.6 ml) was added TFA (1.2 ml, 16 mmol), and the mixture was left to stand at RT for 22 h. The mixture was then concentrated and repeatedly dichloromethane was added and the mixture was concentrated again. The residue was purified by preparative HPLC (Method 6). The combined target fractions were concentrated, and the residue was lyophilized. 353 mg (100% purity, 84% of theory) of the title compound were obtained.

$[\alpha]_D^{20}$=−11.0°, 589 nm, c=0.45 g/100 ml, methanol

LC-MS (Method 1): $R_t$=2.24 min; MS (ESIpos): m/z=572/574 [M+H]$^+$ $^1$H-NMR (400 MHz, DMSO-d6) δ [ppm]: 1.234 (0.92), 1.602 (13.71), 1.781 (9.13), 1.838 (2.48), 1.861 (1.35), 1.885 (0.41), 2.015 (0.52), 2.027 (0.93), 2.047 (3.94), 2.080 (5.20), 2.088 (5.61), 2.097 (3.42), 2.126 (16.00), 2.158 (1.47), 2.188 (0.52), 3.488 (10.68), 3.503 (15.64), 3.517 (10.53), 3.575 (1.79), 3.591 (2.07), 3.666 (2.69), 7.254 (1.70), 7.273 (4.00), 7.292 (2.84), 7.355 (2.46), 7.374 (4.52), 7.392 (2.65), 7.440 (6.52), 7.460 (5.09), 7.481 (5.13), 7.500 (3.64), 7.525 (5.49), 7.547 (10.22), 7.591 (5.50), 7.596 (5.36), 7.613 (2.93), 7.618 (2.95), 8.684 (2.11), 8.698 (4.20), 8.712 (2.10), 12.061 (0.74).

Example 107

(+)-5-({[2-(Azepan-1-yl)-6-bromo-3-methylquinolin-4-yl]carbonyl}amino)-4-(2-chlorophenyl)pentanoic acid (Enantiomer 2)

To a solution of (+)-tert-butyl 5-({[2-(azepan-1-yl)-6-bromo-3-methylquinolin-4-yl]carbonyl}amino)-4-(2-chlorophenyl)pentanoate (460 mg, 731 µmol, enantiomer 2, Example 125A) in dichloromethane (5.6 ml) was added TFA (1.2 ml, 16 mmol), and the mixture was left to stand at RT for 22 h. The mixture was then concentrated and repeatedly dichloromethane was added and the mixture was concentrated again. The residue was purified by preparative HPLC (Method 6). The combined target fractions were concentrated, and the residue was lyophilized. 312 mg (100% purity, 74% of theory) of the title compound were obtained.

$[\alpha]_D^{20}$=+12.5°, 589 nm, c=0.50 g/100 ml, methanol

LC-MS (Method 1): $R_t$=2.25 min; MS (ESIpos): m/z=572/574 [M+H]$^+$ $^1$H-NMR (400 MHz, DMSO-d6) δ [ppm]: 1.602 (13.76), 1.780 (9.07), 1.839 (2.47), 1.861 (1.35), 1.884 (0.43), 2.048 (3.93), 2.082 (5.18), 2.089 (5.61), 2.126 (16.00), 2.159 (1.44), 2.188 (0.56), 3.488 (10.85), 3.503 (15.65), 3.517 (10.64), 3.592 (2.07), 3.666 (2.71), 7.255 (1.73), 7.273 (4.04), 7.293 (2.84), 7.355 (2.51), 7.374 (4.61), 7.392 (2.69), 7.438 (6.62), 7.441 (6.85), 7.458 (5.22), 7.461 (5.35), 7.482 (5.16), 7.499 (3.67), 7.525 (5.79), 7.547 (10.73), 7.591

(5.94), 7.596 (5.65), 7.613 (3.13), 7.618 (3.13), 8.684 (2.16), 8.698 (4.31), 8.712 (2.14), 12.058 (0.92).

Example 108

5-[({6-Bromo-3-methyl-2-[2-methylpiperidin-1-yl]quinolin-4-yl}carbonyl)amino]-4-(2-chlorophenyl)pentanoic acid (Diastereomer Mixture)

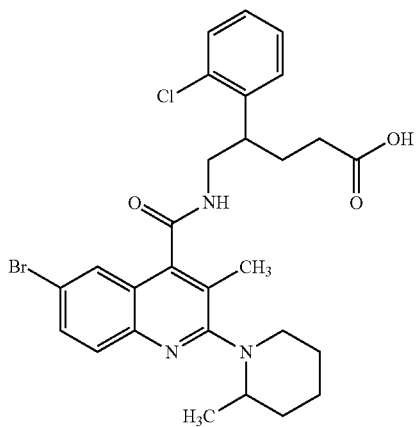 [SMILES: Cc1c(N2CCCCC2C)nc2ccc(Br)cc2c1C(=O)NCC(CCC(=O)O)c1ccccc1Cl]

Proceeding from (+/−)-2-methylpiperidine (10 mg, 100 µmol) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 2 mg (94% purity, 3% of theory) of the title compound were obtained.

LC-MS (Method 16): $R_t$=1.13 min; MS (ESIpos): m/z=572/574 [M+H]$^+$

Example 109

(+/−)-5-({[6-Bromo-2-(ethylamino)-3-methylquinolin-4-yl]carbonyl}amino)-4-(2-chlorophenyl)pentanoic acid (Racemate)

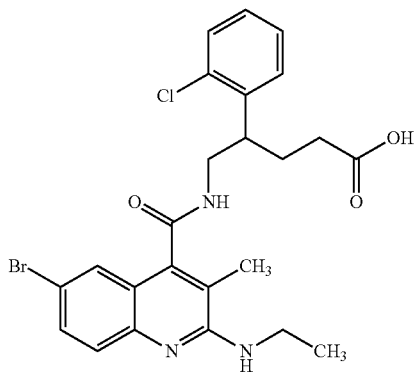 [SMILES: CCNc1nc2ccc(Br)cc2c(C(=O)NCC(CCC(=O)O)c2ccccc2Cl)c1C]

Proceeding from ethanamine hydrochloride (5 mg, 100 µmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 1.8 mg (100% purity, 3% of theory) of the title compound were obtained.

LC-MS (Method 16): $R_t$=0.8 min; MS (ESIpos): m/z=518/520 [M+H]$^+$

Example 110

(+/−)-5-({[2-(5-Azaspiro[2.5]oct-5-yl)-6-bromo-3-methylquinolin-4-yl]carbonyl}amino)-4-(2-chlorophenyl)pentanoic acid (Racemate)

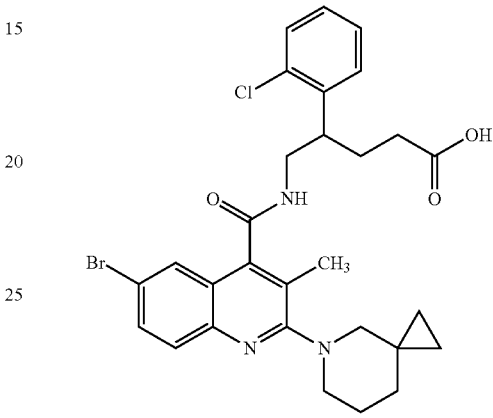

Proceeding from 5-azaspiro[2.5]octane hydrochloride (11 mg, 100 µmol, molar amount based on the free amine) and (+/−)-tert-butyl 5-{[(6-bromo-2-chloro-3-methylquinolin-4-yl)carbonyl]amino}-4-(2-chlorophenyl)pentanoate (57 mg, 100 µmol, racemate, Example 37A), analogously to the preparation of (+/−)-5-({[6-bromo-2-(3,4-dihydroisoquinolin-2(1H)-yl)-3-methylquinolin-4-yl]carbonyl}amino)-4-(2-chlorophenyl)pentanoic acid (Example 84), 2.6 mg (100% purity, 4% of theory) of the title compound were obtained.

LC-MS (Method 16): $R_t$=1.23 min; MS (ESIpos): m/z=584/586 [M+H]$^+$

Example 111

(+/−)-5-({[6-Bromo-3-methyl-2-(piperidin-1-yl)quinolin-4-yl]carbonyl}amino)-4-[2-(trifluoromethyl)phenyl]pentanoic acid (Racemate)

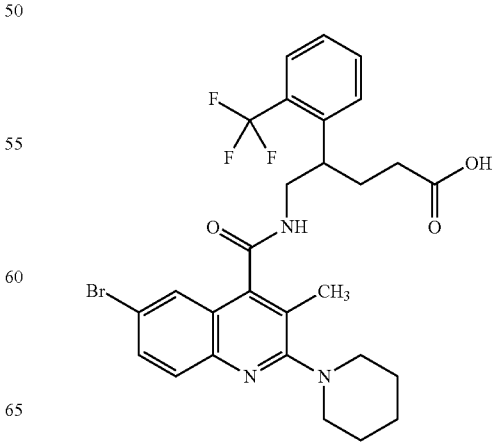

To a solution of (+/−)-tert-butyl 5-({[6-bromo-3-methyl-2-(piperidin-1-yl)quinolin-4-yl]carbonyl}-amino)-4-[2-(trifluoromethyl)phenyl]pentanoate (85 mg, 131 μmol, racemate, Example 126A) in dichloromethane (1.5 ml) was added TFA (200 μl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 52 mg (100% purity, 67% of theory) of the title compound were obtained.

LC-MS (Method 1): $R_t$=2.23 min; MS (ESIpos): m/z=592/594 $[M+H]^+$ $^1$H-NMR (400 MHz, DMSO-d6) δ [ppm]: 1.611 (5.32), 1.679 (10.54), 1.897 (1.82), 1.907 (1.73), 1.928 (2.08), 1.942 (1.97), 1.962 (1.64), 1.979 (2.69), 1.992 (1.70), 2.003 (3.05), 2.023 (0.92), 2.040 (1.68), 2.055 (3.02), 2.078 (3.08), 2.096 (1.81), 2.114 (3.33), 2.165 (16.00), 3.150 (13.69), 3.606 (1.32), 3.623 (2.06), 3.639 (2.27), 3.684 (1.45), 3.700 (2.32), 3.716 (1.96), 3.733 (1.31), 7.435 (1.23), 7.463 (2.79), 7.482 (4.90), 7.501 (3.01), 7.634 (2.00), 7.656 (15.77), 7.664 (9.55), 7.687 (3.06), 7.707 (5.08), 7.724 (11.45), 7.733 (8.28), 7.742 (6.88), 8.767 (2.49), 8.782 (4.97), 8.796 (2.45), 12.044 (0.78).

Example 112

(−)-5-({[6-Bromo-3-methyl-2-(piperidin-1-yl)quinolin-4-yl]carbonyl}amino)-4-[2-(trifluoromethyl)phenyl]pentanoic acid (Enantiomer 1)

To a solution of (−)-tert-butyl 5-({[6-bromo-3-methyl-2-(piperidin-1-yl)quinolin-4-yl]carbonyl}amino)-4-[2-(trifluoromethyl)phenyl]pentanoate (225 mg, 347 μmol, enantiomer 1, Example 127A) in dichloromethane (2.6 ml) was added TFA (590 μl, 7.6 mmol), and the mixture was left to stand at RT for 24 h. The mixture was then concentrated and repeatedly dichloromethane was added and the mixture was concentrated again. The residue was purified by preparative HPLC (Method 7).

The combined target fractions were concentrated, and the residue was lyophilized. 142 mg (100% purity, 69% of theory) of the title compound were obtained.

$[\alpha]_D^{20}$=−20.5°, 589 nm, c=0.37 g/100 ml, methanol

LC-MS (Method 1): $R_t$=2.25 min; MS (ESIpos): m/z=592/594 $[M+H]^+$ $^1$H-NMR (400 MHz, DMSO-d6) δ [ppm]: 1.163 (1.22), 1.181 (2.62), 1.199 (1.29), 1.614 (4.47), 1.681 (8.91), 1.897 (1.55), 1.907 (1.43), 1.928 (1.72), 1.942 (1.72), 1.964 (1.35), 1.981 (2.37), 1.993 (1.47), 2.005 (2.77), 2.024 (0.81), 2.041 (1.51), 2.055 (2.72), 2.078 (2.75), 2.096 (1.57), 2.114 (2.87), 2.166 (13.61), 2.328 (0.45), 3.077 (0.70), 3.089 (0.80), 3.095 (0.79), 3.107 (0.82), 3.160 (11.47), 3.324 (2.20), 3.345 (2.07), 3.589 (2.39), 3.605 (2.50), 3.622 (2.85), 3.638 (2.83), 3.685 (1.74), 3.700 (2.38), 3.716 (2.02), 3.733 (1.42), 7.432 (0.97), 7.464 (2.39), 7.483 (4.25), 7.501 (2.59), 7.643 (1.56), 7.665 (16.00), 7.672 (8.78), 7.689 (2.46), 7.708 (4.46), 7.724 (9.86), 7.734 (6.97), 7.742 (5.94), 8.769 (2.26), 8.784 (4.59), 8.799 (2.17).

Example 113

(+)-5-({[6-Bromo-3-methyl-2-(piperidin-1-yl)quinolin-4-yl]carbonyl}amino)-4-[2-(trifluoromethyl)phenyl]pentanoic acid (Enantiomer 2)

To a solution of (+)-tert-butyl 5-({[6-bromo-3-methyl-2-(piperidin-1-yl)quinolin-4-yl]carbonyl}-amino)-4-[2-(trifluoromethyl)phenyl]pentanoate (230 mg, 355 μmol, enantiomer 2, Example 128A) in dichloromethane (2.7 ml) was added TFA (600 μl, 7.8 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 158 mg (100% purity, 75% of theory) of the title compound were obtained.

$[\alpha]_D^{20}$=+22.7°, 589 nm, c=0.49 g/100 ml, methanol

LC-MS (Method 1): $R_t$=2.25 min; MS (ESIpos): m/z=592/594 $[M+H]^+$ $^1$H-NMR (400 MHz, DMSO-d6) δ [ppm]: 1.614 (4.61), 1.681 (9.03), 1.896 (1.62), 1.907 (1.52), 1.928 (1.80), 1.942 (1.79), 1.963 (1.45), 1.980 (2.43), 1.993 (1.57), 2.004 (2.84), 2.025 (0.92), 2.040 (1.60), 2.055 (2.81), 2.078 (2.82), 2.096 (1.75), 2.113 (3.02), 2.165 (13.52), 2.328 (0.42), 3.160 (11.56), 3.324 (2.39), 3.492 (2.62), 3.589 (1.71), 3.606 (1.97), 3.622 (2.44), 3.639 (2.48), 3.684 (1.64), 3.699 (2.30), 3.716 (1.91), 3.732 (1.31), 7.463 (2.54), 7.483 (4.26), 7.501 (2.53), 7.643 (1.92), 7.666 (16.00), 7.672 (8.62), 7.689 (2.69), 7.694 (2.06), 7.708 (4.85), 7.724 (10.06), 7.734 (7.01), 7.742 (5.89), 8.769 (2.40), 8.784 (4.53), 8.799 (2.10).

Example 114

(+/−)-5-({[6-Bromo-3-methyl-2-(pyrrolidin-1-yl)quinolin-4-yl]carbonyl}amino)-4-[2-(trifluoromethyl)phenyl]pentanoic acid (Racemate)

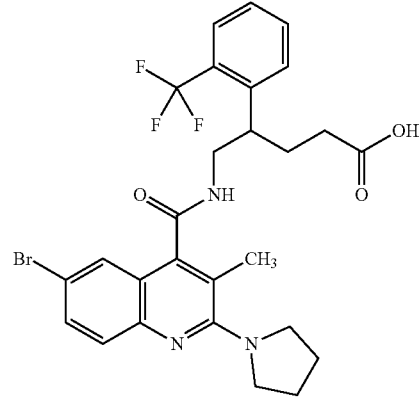 [SMILES: Cc1c(N2CCCC2)nc2ccc(Br)cc2c1C(=O)NCC(CCC(=O)O)c1ccccc1C(F)(F)F]

To a solution of (+/−)-tert-butyl 5-({[6-bromo-3-methyl-2-(pyrrolidin-1-yl)quinolin-4-yl]carbonyl}amino)-4-[2-(trifluoromethyl)phenyl]pentanoate (85 mg, 134 μmol, racemate, Example 129A) in dichloromethane (1.5 ml) was added TFA (210 μl, 2.7 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 40 mg (100% purity, 52% of theory) of the title compound were obtained.

LC-MS (Method 1): $R_t$=1.54 min; MS (ESIpos): m/z=578/580 $[M+H]^+$ $^1$H-NMR (400 MHz, DMSO-d6) δ [ppm]: 1.879 (16.00), 1.924 (3.02), 1.951 (2.34), 1.968 (2.79), 1.980 (1.68), 1.992 (2.98), 2.011 (1.08), 2.037 (1.55), 2.053 (3.01), 2.076 (3.20), 2.093 (2.11), 2.113 (3.51), 2.181 (6.81), 2.281 (0.57), 2.327

(0.41), 3.318 (6.26), 3.709 (2.16), 3.725 (1.96), 3.741 (1.48), 7.341 (0.65), 7.434 (0.44), 7.457 (2.26), 7.477 (11.20), 7.500 (13.68), 7.550 (6.77), 7.555 (6.41), 7.572 (3.79), 7.578 (3.74), 7.685 (1.86), 7.705 (5.30), 7.716 (8.48), 7.733 (10.38), 7.747 (2.43), 8.715 (2.47), 8.729 (4.76), 8.744 (2.37).

Example 115

(+)-5-({[6-Bromo-3-methyl-2-(pyrrolidin-1-yl)quinolin-4-yl]carbonyl}amino)-4-[2-(trifluoromethyl)phenyl]pentanoic acid (Enantiomer 1)

To a solution of (+)-tert-butyl 5-({[6-bromo-3-methyl-2-(pyrrolidin-1-yl)quinolin-4-yl]carbonyl}-amino)-4-[2-(trifluoromethyl)phenyl]pentanoate (160 mg, 252 µmol, enantiomer 1, Example 130A) in dichloromethane (1.9 ml) was added TFA (430 µl, 5.5 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 73 mg (100% purity, 50% of theory) of the title compound were obtained.

$[\alpha]_D^{20}$=+18.9°, 589 nm, c=0.47 g/100 ml, methanol

LC-MS (Method 1): $R_t$=1.52 min; MS (ESIpos): m/z=578/580 [M+H]$^+$ $^1$H-NMR (400 MHz, DMSO-d6) δ [ppm]: 1.879 (16.00), 1.925 (2.74), 1.954 (2.21), 1.971 (2.77), 1.984 (1.69), 1.996 (3.01), 2.014 (1.13), 2.041 (1.58), 2.055 (3.04), 2.079 (3.17), 2.096 (2.13), 2.115 (3.52), 2.138 (2.71), 2.181 (6.83), 2.281 (0.59), 2.328 (0.43), 3.583 (12.90), 3.693 (1.38), 3.709 (2.16), 3.725 (1.92), 3.742 (1.48), 7.335 (0.61), 7.459 (2.16), 7.477 (10.75), 7.500 (13.45), 7.551 (6.29), 7.556 (6.19), 7.573 (3.60), 7.578 (3.64), 7.686 (1.82), 7.706 (5.20), 7.717 (8.11), 7.734 (10.70), 7.749 (2.41), 8.711 (2.44), 8.726 (4.79), 8.741 (2.38), 12.044 (0.69).

Example 116

(−)-5-({[6-Bromo-3-methyl-2-(pyrrolidin-1-yl)quinolin-4-yl]carbonyl}amino)-4-[2-(trifluoromethyl)phenyl]pentanoic acid (Enantiomer 2)

To a solution of (−)-tert-butyl 5-({[6-bromo-3-methyl-2-(pyrrolidin-1-yl)quinolin-4-yl]carbonyl}-amino)-4-[2-(trifluoromethyl)phenyl]pentanoate (170 mg, 268 µmol, enantiomer 2, Example 131A) in dichloromethane (2.1 ml) was added TFA (450 µl, 5.9 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 81 mg (100% purity, 52% of theory) of the title compound were obtained.

$[\alpha]_D^{20}$=−17.5°, 589 nm, c=0.41 g/100 ml, methanol

LC-MS (Method 1): $R_t$=1.52 min; MS (ESIpos): m/z=578/580 [M+H]$^+$ $^1$H-NMR (400 MHz, DMSO-d6) δ [ppm]: 1.236 (0.42), 1.885 (16.00), 1.935 (2.55), 1.957 (2.22), 1.974 (2.98), 1.986 (1.84), 1.998 (3.37), 2.016 (1.29), 2.041 (1.73), 2.056 (3.35), 2.080 (3.42), 2.097 (2.31), 2.115 (3.73), 2.137 (2.74), 2.186 (6.71), 2.328 (0.54), 2.670 (0.46), 3.597 (11.63), 3.711 (2.35), 3.727 (2.10), 3.744 (1.60), 7.246 (0.44), 7.334 (0.66), 7.459 (2.46), 7.478 (5.04), 7.497 (4.57), 7.519 (2.99), 7.567 (3.96), 7.588 (2.35), 7.687 (1.96), 7.706 (5.62), 7.717 (8.55), 7.734 (12.13), 7.750 (2.51), 8.719 (2.21), 8.734 (4.05), 8.748 (2.14), 12.028 (1.34).

Example 117

(+/−)-5-({[6-Bromo-2-(3,3-difluoropiperidin-1-yl)-3-methylquinolin-4-yl]carbonyl}amino)-4-[2-(trifluoromethyl)phenyl]pentanoic acid (Racemate)

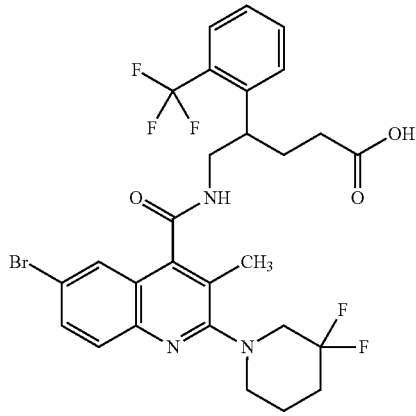 [SMILES: Cc1c(N2CCCC(F)(F)C2)nc2ccc(Br)cc2c1C(=O)NCC(CCC(=O)O)c1ccccc1C(F)(F)F]

To a solution of (+/−)-tert-butyl 5-({[6-bromo-2-(3,3-difluoropiperidin-1-yl)-3-methylquinolin-4-yl]carbonyl}amino)-4-[2-(trifluoromethyl)phenyl]pentanoate (85 mg, 124 µmol, racemate, Example 132A) in dichloromethane (1.5 ml) was added TFA (190 µl, 2.5 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 46 mg (100% purity, 59% of theory) of the title compound were obtained.

LC-MS (Method 1): $R_t$=2.17 min; MS (ESIpos): m/z=628/630 [M+H]$^+$ $^1$H-NMR (400 MHz, DMSO-d6) δ [ppm]: 1.896 (6.19), 1.980 (2.25), 2.004 (2.45), 2.055 (3.73), 2.078 (4.51), 2.114 (5.44), 2.136 (4.06), 2.185 (12.02), 2.670 (0.22), 3.180 (6.09), 3.463 (3.22), 3.492 (5.91), 3.520 (3.16), 3.648 (1.96), 3.710 (1.91), 7.465 (2.61), 7.483 (4.20), 7.501 (2.79), 7.707 (16.00), 7.725 (9.34), 7.738 (8.33), 8.793 (3.72), 12.049 (0.53).

Example 118

(−)-5-({[6-Bromo-2-(3,3-difluoropiperidin-1-yl)-3-methylquinolin-4-yl]carbonyl}amino)-4-[2-(trifluoromethyl)phenyl]pentanoic acid (Enantiomer 1)

To a solution of (−)-tert-butyl 5-({[6-bromo-2-(3,3-difluoropiperidin-1-yl)-3-methylquinolin-4-yl]carbonyl}amino)-4-[2-(trifluoromethyl)phenyl]pentanoate (85 mg, 124 µmol, enantiomer 1, Example 133A) in dichloromethane (960 µl) was added TFA (210 µl, 2.7 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 65 mg (100% purity, 83% of theory) of the title compound were obtained.

$[\alpha]_D^{20}$=−18.2°, 589 nm, c=0.49 g/100 ml, methanol

LC-MS (Method 1): $R_t$=2.19 min; MS (ESIpos): m/z=628/630 [M+H]$^+$ $^1$H-NMR (400 MHz, DMSO-d6) δ [ppm]: 1.899 (4.56), 1.946 (1.50), 1.953 (1.22), 1.967 (1.16), 1.984 (1.98), 1.997 (1.22), 2.008 (2.30), 2.028 (0.88), 2.043 (1.59), 2.057 (3.11), 2.065 (2.55), 2.081 (3.82), 2.099 (3.51), 2.118 (4.18), 2.137 (2.87), 2.152 (2.34), 2.186 (10.54), 2.227 (0.62), 3.182 (4.64), 3.464 (2.89), 3.493 (5.52), 3.522 (2.77), 3.617 (0.87), 3.634 (1.31), 3.649 (1.45), 3.712 (1.41), 3.727 (1.22), 7.467 (2.12), 7.486 (3.75), 7.504 (2.35), 7.685 (1.58), 7.692 (1.59), 7.708 (16.00), 7.713 (10.69), 7.727 (7.64), 7.743 (7.02), 7.758 (1.87), 8.777 (1.83), 8.792 (3.78), 8.807 (1.84), 12.035 (1.20).

Example 119

(+)-5-({[6-Bromo-2-(3,3-difluoropiperidin-1-yl)-3-methylquinolin-4-yl]carbonyl}amino)-4-[2-(trifluoromethyl)phenyl]pentanoic acid (Enantiomer 2)

To a solution of (+)-tert-butyl 5-({[6-bromo-2-(3,3-difluoropiperidin-1-yl)-3-methylquinolin-4-yl]carbonyl}amino)-4-[2-(trifluoromethyl)phenyl]pentanoate (60 mg, 87.6 µmol, enantiomer 2, Example 134A) in dichloromethane (670 µl) was added TFA (150 µl, 1.9 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 38 mg (100% purity, 69% of theory) of the title compound were obtained.

$[\alpha]_D^{20}$=+18.9°, 589 nm, c=0.39 g/100 ml, methanol
LC-MS (Method 1): $R_t$=2.19 min; MS (ESIpos): m/z=628/630 [M+H]$^+$
$^1$H-NMR (400 MHz, DMSO-d6) δ [ppm]: 1.898 (4.75), 1.944 (1.51), 1.965 (1.18), 1.982 (1.96), 1.995 (1.22), 2.006 (2.25), 2.026 (0.88), 2.041 (1.53), 2.055 (3.13), 2.063 (2.55), 2.079 (3.69), 2.097 (3.46), 2.116 (4.22), 2.136 (2.97), 2.150 (2.39), 2.185 (10.76), 2.225 (0.69), 3.180 (4.82), 3.463 (2.94), 3.492 (5.61), 3.520 (2.84), 3.632 (1.38), 3.648 (1.51), 3.710 (1.47), 3.726 (1.28), 7.466 (2.20), 7.485 (3.79), 7.503 (2.39), 7.684 (1.67), 7.691 (1.73), 7.707 (16.00), 7.726 (7.79), 7.742 (6.86), 7.757 (1.83), 8.777 (1.83), 8.791 (3.69), 8.806 (1.78), 12.037 (0.82).

Example 120

(+/−)-5-({[2-(Azepan-1-yl)-6-bromo-3-methylquinolin-4-yl]carbonyl}amino)-4-[2-(trifluoromethyl)phenyl]pentanoic acid (Racemate)

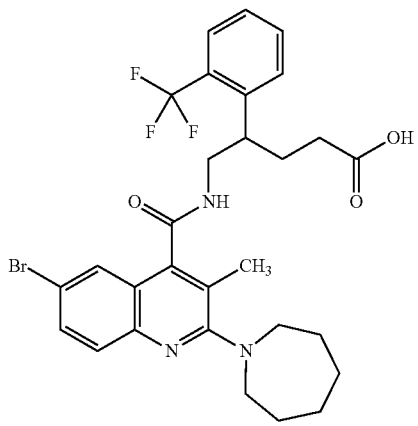 [SMILES: Cc1c(N2CCCCCC2)nc2ccc(Br)cc2c1C(=O)NCC(CCC(=O)O)c1ccccc1C(F)(F)F]

To a solution of (+/−)-tert-butyl 5-({[2-(azepan-1-yl)-6-bromo-3-methylquinolin-4-yl]carbonyl}-amino)-4-[2-(trifluoromethyl)phenyl]pentanoate (85 mg, 128 µmol, racemate, Example 135A) in dichloromethane (1.5 ml) was added TFA (200 µl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 60 mg (100% purity, 77% of theory) of the title compound were obtained.

LC-MS (Method 1): $R_t$=2.28 min; MS (ESIpos): m/z=606/608 [M+H]$^+$
$^1$H-NMR (400 MHz, DMSO-d6) δ [ppm]: 1.610 (14.32), 1.791 (9.69), 1.899 (1.71), 1.908 (1.60), 1.930 (2.04), 1.945 (1.85), 1.961 (1.78), 1.978 (2.56), 1.990 (1.59), 2.002 (2.80), 2.011 (1.67), 2.041 (1.48), 2.056 (2.80), 2.079 (3.00), 2.097 (1.87), 2.116 (3.51), 2.152 (11.34), 3.505 (10.82), 3.519 (16.00), 3.533 (10.80), 3.609 (1.63), 3.624 (1.73), 3.705 (1.75), 3.720 (1.56), 7.371 (0.83), 7.463 (2.07), 7.482 (4.24), 7.501 (2.63), 7.537 (5.32), 7.559 (10.25), 7.599 (5.62), 7.604 (5.69), 7.622 (2.80), 7.626 (2.98), 7.689 (1.75), 7.709 (4.73), 7.722 (8.25), 7.739 (9.99), 7.754 (2.31), 8.739 (2.25), 8.754 (4.52), 8.769 (2.24), 12.037 (1.01).

Example 121

(−)-5-({[2-(Azepan-1-yl)-6-bromo-3-methylquinolin-4-yl]carbonyl}amino)-4-[2-(trifluoromethyl)phenyl]pentanoic acid (Enantiomer 1)

To a solution of (−)-tert-butyl 5-({[2-(azepan-1-yl)-6-bromo-3-methylquinolin-4-yl]carbonyl}amino)-4-[2-(trifluoromethyl)phenyl]pentanoate (70 mg, 106 µmol, enantiomer 1, Example 136A) in dichloromethane (810 µl) was added TFA (180 µl, 2.3 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 44 mg (100% purity, 69% of theory) of the title compound were obtained.

$[\alpha]_D^{20}$=−17.2°, 589 nm, c=0.43 g/100 ml, methanol
LC-MS (Method 1): $R_t$=2.30 min; MS (ESIpos): m/z=606/608 [M+H]$^+$
$^1$H-NMR (400 MHz, DMSO-d6) δ [ppm]: 1.609 (14.30), 1.790 (9.46), 1.896 (1.66), 1.905 (1.58), 1.927 (2.05), 1.942 (1.89), 1.957 (1.86), 1.973 (2.51), 1.986 (1.54), 1.997 (2.79), 2.007 (1.65), 2.037 (1.43), 2.052 (2.75), 2.075 (2.90), 2.093 (1.79), 2.112 (3.33), 2.150 (11.02), 2.328 (0.44), 2.670 (0.42), 3.504 (11.33), 3.518 (16.00), 3.533 (11.13), 3.607 (1.63), 3.621 (1.70), 3.704 (1.72), 3.769 (0.84), 7.462 (2.12), 7.481 (4.20), 7.500 (2.62), 7.536 (5.72), 7.558 (10.90), 7.599 (6.17), 7.604 (5.82), 7.621 (3.10), 7.626 (3.06), 7.688 (1.73), 7.707 (4.75), 7.721 (8.19), 7.737 (9.36), 7.752 (2.20), 8.740 (2.23), 8.755 (4.40), 8.770 (2.18), 12.042 (0.47).

Example 122

(+)-5-({[2-(Azepan-1-yl)-6-bromo-3-methylquinolin-4-yl]carbonyl}amino)-4-[2-(trifluoromethyl)phenyl]pentanoic acid (Enantiomer 2)

To a solution of (+)-tert-butyl 5-({[2-(azepan-1-yl)-6-bromo-3-methylquinolin-4-yl]carbonyl}amino)-4-[2-(trifluoromethyl)phenyl]pentanoate (65 mg, 98.1 µmol, enantiomer 2, Example 137A) in dichloromethane (750 µl) was added TFA (170 µl, 2.2 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 44 mg (100% purity, 74% of theory) of the title compound were obtained.

[α]$_D^{20}$=+16.9°, 589 nm, c=0.38 g/100 ml, methanol

LC-MS (Method 1): R$_t$=2.30 min; MS (ESIpos): m/z=606/608 [M+H]$^+$ $^1$H-NMR (400 MHz, DMSO-d6) δ [ppm]: 1.234 (0.46), 1.341 (0.42), 1.353 (0.63), 1.371 (2.44), 1.609 (14.42), 1.790 (9.61), 1.896 (1.69), 1.906 (1.59), 1.927 (2.08), 1.942 (1.89), 1.957 (1.81), 1.974 (2.47), 1.987 (1.58), 1.998 (2.65), 2.038 (1.46), 2.053 (2.67), 2.076 (2.81), 2.094 (1.80), 2.114 (3.37), 2.151 (11.17), 3.504 (11.21), 3.518 (16.00), 3.533 (11.08), 3.608 (1.66), 3.622 (1.72), 3.704 (1.75), 3.720 (1.56), 7.367 (0.82), 7.462 (2.06), 7.481 (4.17), 7.499 (2.61), 7.536 (5.40), 7.558 (10.42), 7.599 (5.89), 7.604 (5.66), 7.621 (2.99), 7.626 (2.99), 7.688 (1.66), 7.707 (4.67), 7.721 (8.20), 7.737 (9.48), 7.752 (2.35), 8.740 (2.22), 8.755 (4.42), 8.770 (2.21).

Example 123

5-[({6-Bromo-2-[3-fluoropiperidin-1-yl]-3-methylquinolin-4-yl}carbonyl)amino]-4-[2-(trifluoromethyl)phenyl]pentanoic acid (Diastereomer Mixture)

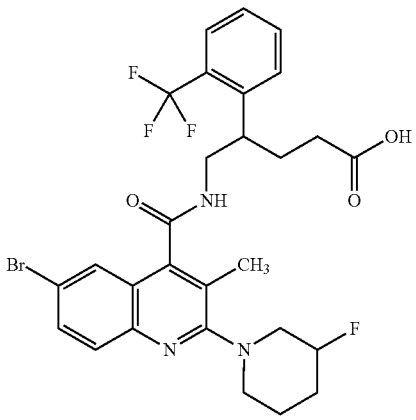 [SMILES: Cc1c(N2CCCC(F)C2)nc2ccc(Br)cc2c1C(=O)NCC(CCC(=O)O)c1ccccc1C(F)(F)F]

To a solution of tert-butyl 5-[({6-bromo-2-[3-fluoropiperidin-1-yl]-3-methylquinolin-4-yl}carbonyl)amino]-4-[2-(trifluoromethyl)phenyl]pentanoate (85 mg, 128 μmol, diastereomer mixture, Example 138A) in dichloromethane (1.5 ml) was added TFA (200 μl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 55 mg (100% purity, 71% of theory) of the title compound were obtained.

LC-MS (Method 1): R$_t$=2.12 min; MS (ESIpos): m/z=610/612 [M+H]$^+$ $^1$H-NMR (400 MHz, DMSO-d6) δ [ppm]: 1.652 (1.93), 1.773 (0.54), 1.812 (1.78), 1.829 (1.51), 1.908 (4.68), 1.928 (4.50), 1.943 (3.34), 1.952 (3.13), 1.982 (3.45), 1.994 (2.44), 2.006 (3.39), 2.041 (1.73), 2.057 (2.96), 2.080 (3.00), 2.097 (1.82), 2.116 (3.20), 2.140 (2.39), 2.178 (14.18), 3.084 (1.27), 3.114 (2.24), 3.170 (2.37), 3.186 (2.31), 3.214 (1.29), 3.317 (12.17), 3.395 (2.33), 3.428 (1.26), 3.452 (2.01), 3.480 (1.30), 3.613 (1.25), 3.628 (1.89), 3.644 (2.09), 3.707 (1.99), 4.824 (1.57), 4.945 (1.58), 7.465 (2.95), 7.484 (4.87), 7.502 (3.00), 7.658 (2.05), 7.681 (16.00), 7.688 (10.91), 7.710 (6.16), 7.725 (10.19), 7.741 (8.20), 7.755 (2.49), 8.772 (2.36), 8.787 (4.50), 8.801 (2.20), 12.043 (0.89).

Example 124

5-[({6-Bromo-2-[3-ethylpiperidin-1-yl]-3-methylquinolin-4-yl}carbonyl)amino]-4-[2-(trifluoromethyl)phenyl]pentanoic acid (Diastereomer Mixture)

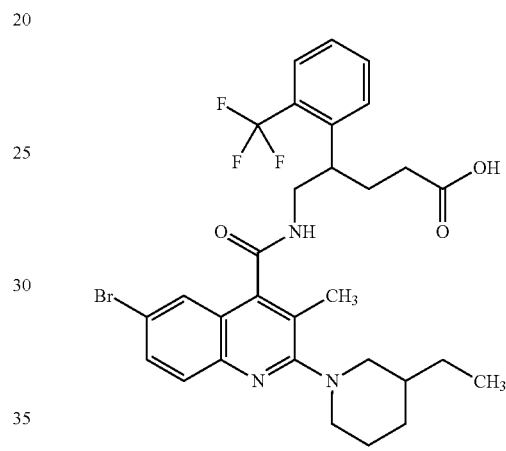

To a solution of tert-butyl 5-[({6-bromo-2-[3-ethylpiperidin-1-yl]-3-methylquinolin-4-yl}carbonyl)amino]-4-[2-(trifluoromethyl)phenyl]pentanoate (85 mg, 126 μmol, diastereomer mixture, Example 139A) in dichloromethane (1.5 ml) was added TFA (190 μl, 2.5 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 45 mg (100% purity, 58% of theory) of the title compound were obtained.

LC-MS (Method 1): R$_t$=2.48 min; MS (ESIpos): m/z=620/622 [M+H]$^+$ $^1$H-NMR (400 MHz, DMSO-d6) δ [ppm]: 0.895 (6.54), 0.913 (16.00), 0.932 (8.08), 1.042 (0.48), 1.070 (1.30), 1.092 (1.32), 1.099 (1.35), 1.121 (0.59), 1.131 (0.54), 1.245 (1.03), 1.262 (2.36), 1.279 (3.38), 1.296 (2.77), 1.310 (1.63), 1.570 (1.54), 1.578 (1.49), 1.596 (1.25), 1.611 (1.37), 1.642 (1.23), 1.752 (1.86), 1.785 (1.25), 1.853 (1.69), 1.892 (2.33), 1.926 (1.42), 1.939 (1.34), 1.948 (1.17), 1.961 (1.05), 1.978 (1.80), 1.991 (1.10), 2.002 (2.03), 2.019 (0.80), 2.041 (1.16), 2.056 (2.01), 2.079 (2.14), 2.097 (1.54), 2.115 (3.36), 2.133 (4.50), 2.159 (7.40), 2.417 (0.90), 2.443 (1.33), 2.474 (0.85), 2.721 (1.01), 2.749 (1.83), 2.778 (1.01), 3.513 (2.86), 3.534 (2.38), 3.614 (1.11), 3.628 (1.30), 3.701 (0.98), 3.717 (1.62), 3.734 (1.43), 3.751 (0.99), 3.767 (0.53), 7.462 (1.95), 7.481 (3.47), 7.499 (2.11), 7.635 (0.82), 7.657 (15.46), 7.686 (1.56), 7.707 (3.81), 7.723 (5.27), 7.738 (7.56), 7.756 (1.73), 8.753 (1.67), 8.768 (3.28), 8.782 (1.65), 12.055 (0.48).

Example 125

5-[({6-Bromo-3-methyl-2-[3-methylpiperidin-1-yl]quinolin-4-yl}carbonyl)amino]-4-[2-(trifluoromethyl)phenyl]pentanoic acid (Diastereomer Mixture)

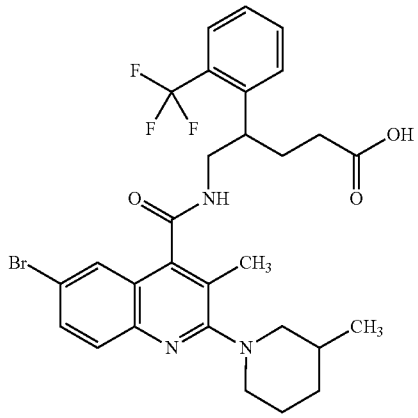 [SMILES: Cc1c(N2CCCC(C)C2)nc2ccc(Br)cc2c1C(=O)NCC(CCC(=O)O)c1ccccc1C(F)(F)F]

To a solution of tert-butyl 5-[({6-bromo-3-methyl-2-[3-methylpiperidin-1-yl]quinolin-4-yl}carbonyl)amino]-4-[2-(trifluoromethyl)phenyl]pentanoate (85 mg, 128 µmol, diastereomer mixture, Example 140A) in dichloromethane (1.5 ml) was added TFA (200 µl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 66 mg (100% purity, 85% of theory) of the title compound were obtained.

LC-MS (Method 1): $R_t$=2.36 min; MS (ESIpos): m/z=606/608 [M+H]$^+$ $^1$H-NMR (400 MHz, DMSO-d6) δ [ppm]: 0.961 (11.43), 0.977 (11.69), 1.119 (1.33), 1.142 (1.37), 1.170 (0.55), 1.668 (1.15), 1.698 (1.36), 1.772 (2.38), 1.805 (2.36), 1.831 (3.01), 1.861 (1.82), 1.931 (1.31), 1.942 (1.22), 1.963 (1.52), 1.977 (1.40), 1.995 (1.27), 2.012 (1.97), 2.025 (1.20), 2.036 (2.22), 2.045 (1.32), 2.073 (1.16), 2.088 (2.19), 2.112 (2.28), 2.129 (1.30), 2.148 (2.41), 2.202 (9.83), 2.362 (0.23), 2.401 (0.17), 2.472 (1.26), 2.724 (1.08), 2.753 (1.97), 2.781 (1.07), 3.488 (2.15), 3.514 (3.81), 3.543 (1.91), 3.647 (1.13), 3.663 (1.43), 3.678 (1.25), 3.745 (1.32), 7.468 (0.77), 7.498 (1.91), 7.517 (3.49), 7.535 (2.12), 7.670 (0.83), 7.692 (16.00), 7.721 (1.57), 7.742 (3.68), 7.758 (7.71), 7.770 (5.90), 7.795 (1.69), 8.809 (3.31), 8.824 (1.65), 12.057 (0.39).

Example 126

(+/−)-5-({[6-Bromo-3-methyl-2-(piperidin-1-yl)quinolin-4-yl]carbonyl}amino)-4-[2-(trifluoromethoxy)phenyl]pentanoic acid (Racemate)

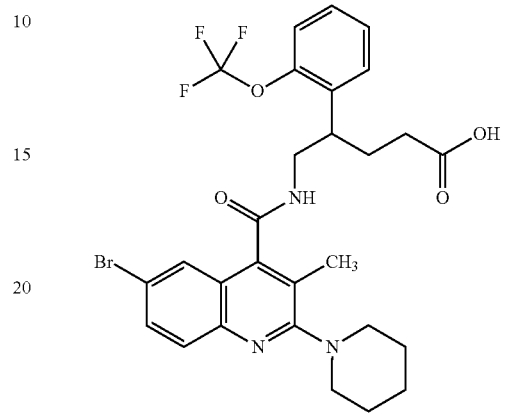

To a solution of (+/−)-tert-butyl 5-({[6-bromo-3-methyl-2-(piperidin-1-yl)quinolin-4-yl]carbonyl}-amino)-4-[2-(trifluoromethoxy)phenyl]pentanoate (85 mg, 128 µmol, racemate, Example 141A) in dichloromethane (1.5 ml) was added TFA (200 µl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 58 mg (100% purity, 75% of theory) of the title compound were obtained.

LC-MS (Method 1): $R_t$=2.28 min; MS (ESIpos): m/z=608/610 [M+H]$^+$ $^1$H-NMR (400 MHz, DMSO-d6) δ [ppm]: 1.609 (5.45), 1.674 (10.79), 1.802 (1.40), 1.816 (1.97), 1.826 (1.94), 1.836 (2.70), 1.860 (2.03), 1.888 (0.49), 2.034 (0.85), 2.048 (3.13), 2.062 (3.86), 2.074 (15.09), 2.105 (2.80), 2.141 (13.35), 2.223 (0.46), 3.142 (14.21), 3.358 (1.72), 3.378 (2.31), 3.389 (2.71), 3.405 (2.55), 3.585 (0.80), 3.600 (1.32), 3.618 (2.89), 3.634 (3.97), 3.644 (3.21), 3.659 (3.20), 3.677 (2.34), 3.693 (1.16), 3.711 (0.65), 7.362 (4.71), 7.366 (4.18), 7.380 (1.52), 7.386 (2.11), 7.401 (8.29), 7.411 (6.88), 7.418 (6.54), 7.423 (7.52), 7.436 (2.09), 7.462 (1.58), 7.548 (5.03), 7.554 (3.43), 7.561 (4.22), 7.572 (3.66), 7.630 (2.79), 7.652 (16.00), 7.658 (11.38), 7.663 (9.59), 7.680 (1.69), 7.685 (1.88), 8.732 (2.66), 8.746 (5.24), 8.761 (2.61), 12.069 (0.60).

Example 127

(−)-5-({[6-Bromo-3-methyl-2-(piperidin-1-yl)quinolin-4-yl]carbonyl}amino)-4-[2-(trifluoromethoxy)phenyl]pentanoic acid (Enantiomer 1)

To a solution of (−)-tert-butyl 5-({[6-bromo-3-methyl-2-(piperidin-1-yl)quinolin-4-yl]carbonyl}amino)-4-[2-(trifluoromethoxy)phenyl]pentanoate (90 mg, 135 µmol, enantiomer 1, Example 142A) in dichloromethane (1.0 ml) was added TFA (230 µl, 3.0 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 50 mg (100% purity, 61% of theory) of the title compound were obtained.

$[\alpha]_D^{20}=-18.0°$, 589 nm, c=0.49 g/100 ml, methanol

LC-MS (Method 1): $R_t$=2.29 min; MS (ESIpos): m/z=608/610 [M+H]$^+$ $^1$H-NMR (400 MHz, DMSO-d6) δ [ppm]: 1.609 (5.83), 1.674 (11.45), 1.803 (1.47), 1.817 (2.13), 1.826 (2.21), 1.837 (2.80), 1.861 (2.09), 1.888 (0.51), 2.051 (3.70), 2.077 (16.00), 2.107 (3.39), 2.140 (13.75), 2.222 (0.47), 3.142 (14.84), 3.390 (2.52), 3.405 (2.42), 3.585 (0.89), 3.600 (1.48), 3.618 (3.15), 3.634 (4.30), 3.648 (3.40), 3.659 (3.41), 3.677 (2.42), 3.693 (1.19), 3.711 (0.64), 7.358 (3.80), 7.362 (4.85), 7.366 (4.34), 7.381 (1.93), 7.387 (2.65), 7.401 (8.69), 7.412 (7.29), 7.418 (6.79), 7.424 (7.60), 7.436 (2.21), 7.443 (1.73), 7.458 (1.58), 7.549 (5.35), 7.554 (3.69), 7.561 (4.42), 7.572 (3.74), 7.630 (3.18), 7.651 (15.85), 7.658 (11.08), 7.663 (9.30), 7.680 (1.75), 7.685 (1.89), 8.729 (2.97), 8.744 (5.43), 8.758 (2.65), 12.048 (9.94).

Example 128

(+)-5-({[6-Bromo-3-methyl-2-(piperidin-1-yl)quinolin-4-yl]carbonyl}amino)-4-[2-(trifluoromethoxy)phenyl]pentanoic acid (Enantiomer 2)

To a solution of (+)-tert-butyl 5-({[6-bromo-3-methyl-2-(piperidin-1-yl)quinolin-4-yl]carbonyl}-amino)-4-[2-(trifluoromethoxy)phenyl]pentanoate (80 mg, 120 µmol, enantiomer 2, Example 143A) in dichloromethane (930 µl) was added TFA (200 µl, 2.6 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 45 mg (100% purity, 62% of theory) of the title compound were obtained.

$[\alpha]_D^{20}=+18.6°$, 589 nm, c=0.42 g/100 ml, methanol

LC-MS (Method 1): $R_t$=2.29 min; MS (ESIpos): m/z=608/610 [M+H]$^+$ $^1$H-NMR (400 MHz, DMSO-d6) δ [ppm]: 1.609 (5.47), 1.674 (10.78), 1.802 (1.28), 1.815 (1.94), 1.825 (1.99), 1.836 (2.69), 1.860 (2.04), 1.887 (0.50), 2.049 (3.08), 2.075 (15.31), 2.105 (2.79), 2.140 (13.35), 2.222 (0.46), 2.327 (0.57), 2.670 (0.58), 3.142 (14.18), 3.390 (2.48), 3.403 (2.39), 3.585 (0.80), 3.599 (1.32), 3.617 (2.90), 3.633 (3.99), 3.659 (3.26), 3.676 (2.36), 3.693 (1.16), 3.709 (0.65), 7.362 (4.65), 7.380 (1.46), 7.387 (2.06), 7.401 (8.36), 7.412 (6.83), 7.418 (6.44), 7.424 (7.64), 7.436 (2.15), 7.460 (1.59), 7.548 (5.00), 7.561 (4.22), 7.572 (3.68), 7.629 (2.93), 7.651 (16.00), 7.658 (10.68), 7.662 (9.54), 7.680 (1.74), 7.685 (1.95), 8.729 (2.66), 8.744 (5.30), 8.758 (2.62), 12.050 (3.04).

Example 129

(+/−)-5-({[6-Bromo-3-methyl-2-(pyrrolidin-1-yl)quinolin-4-yl]carbonyl}amino)-4-[2-(trifluoromethoxy)phenyl]pentanoic acid (Racemate)

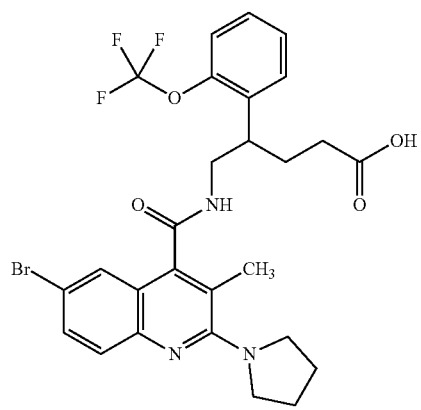 [SMILES: Cc1c(N2CCCC2)nc2ccc(Br)cc2c1C(=O)NCC(CCC(=O)O)c1ccccc1OC(F)(F)F]

To a solution of (+/−)-tert-butyl 5-({[6-bromo-3-methyl-2-(pyrrolidin-1-yl)quinolin-4-yl]carbonyl}-amino)-4-[2-(trifluoromethoxy)phenyl]pentanoate (85 mg, 131 µmol, racemate, Example 144A) in dichloromethane (1.5 ml) was added TFA (200 µl, 2.6 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 53 mg (100% purity, 68% of theory) of the title compound were obtained.

LC-MS (Method 1): $R_t$=1.60 min; MS (ESIpos): m/z=594/596 [M+H]$^+$ $^1$H-NMR (400 MHz, DMSO-d6) δ [ppm]: −0.008 (1.22), 0.008 (1.27), 1.803 (0.93), 1.816 (1.30), 1.825 (1.46), 1.837 (2.26), 1.875 (10.81), 2.032 (0.74), 2.046 (2.32), 2.056 (1.86), 2.073 (10.27), 2.081 (6.67), 2.103 (1.93), 2.115 (1.46), 2.125 (1.55), 2.161 (4.17), 3.315 (16.00), 3.356 (0.63), 3.386 (1.60), 3.401 (1.57), 3.613 (2.82), 3.628 (1.60), 3.643 (1.41), 3.660 (1.95), 3.677 (1.62), 3.694 (0.98), 3.712 (0.55), 7.337 (1.93), 7.341 (2.10), 7.346 (2.33), 7.351 (2.89), 7.356 (3.69), 7.360 (3.24), 7.375 (1.47), 7.381 (1.74), 7.398 (5.84), 7.407 (4.63), 7.415 (4.68), 7.432 (1.15), 7.473 (5.13), 7.495 (8.79), 7.549 (6.82), 7.555 (6.12), 7.571 (4.26), 7.577 (2.97), 8.680 (1.74), 8.695 (3.33), 8.709 (1.70), 12.049 (1.68).

Example 130

(−)-5-({[6-Bromo-3-methyl-2-(pyrrolidin-1-yl)quinolin-4-yl]carbonyl}amino)-4-[2-(trifluoromethoxy)phenyl]pentanoic acid (Enantiomer 1)

To a solution of (−)-tert-butyl 5-({[6-bromo-3-methyl-2-(pyrrolidin-1-yl)quinolin-4-yl]carbonyl}-amino)-4-[2-(trifluoromethoxy)phenyl]pentanoate (140 mg, 215 µmol, enantiomer 1, Example 145A) in dichloromethane (1.7 ml) was added TFA (360 µl, 4.7 mmol), and the mixture was left to stand at RT for 22 h. The mixture was then concentrated and repeatedly dichloromethane was added and the mixture was concentrated again. The residue was purified by preparative HPLC (Method 6). The combined target fractions were concentrated, and the residue was lyophilized. 97 mg (100% purity, 76% of theory) of the title compound were obtained.

[α]$_D^{20}$=−16.7°, 589 nm, c=0.41 g/100 ml, methanol
LC-MS (Method 1): R$_t$=1.58 min; MS (ESIpos): m/z=594/596 [M+H]$^+$ $^1$H-NMR (400 MHz, DMSO-d6) δ [ppm]: 1.825 (0.44), 1.836 (0.68), 1.875 (3.31), 2.046 (0.70), 2.074 (2.84), 2.103 (0.59), 2.116 (0.44), 2.125 (0.47), 2.162 (1.28), 3.313 (16.00), 3.386 (0.48), 3.401 (0.47), 3.612 (0.87), 3.628 (0.48), 3.643 (0.43), 3.660 (0.59), 3.677 (0.50), 7.346 (0.74), 7.355 (1.15), 7.359 (1.03), 7.375 (0.46), 7.381 (0.54), 7.398 (1.81), 7.407 (1.42), 7.415 (1.45), 7.473 (1.56), 7.495 (2.67), 7.549 (2.09), 7.555 (1.90), 7.571 (1.31), 7.577 (0.92), 8.679 (0.54), 8.694 (1.03), 8.709 (0.52), 12.043 (2.77).

Example 131

(+)-5-({[6-Bromo-3-methyl-2-(pyrrolidin-1-yl)quinolin-4-yl]carbonyl}amino)-4-[2-(trifluoromethoxy)phenyl]pentanoic acid (Enantiomer 2)

To a solution of (+)-tert-butyl 5-({[6-bromo-3-methyl-2-(pyrrolidin-1-yl)quinolin-4-yl]carbonyl}-amino)-4-[2-(trifluoromethoxy)phenyl]pentanoate (130 mg, 200 μmol, enantiomer 2, Example 146A) in dichloromethane (1.5 ml) was added TFA (340 μl, 4.4 mmol), and the mixture was left to stand at RT for 22 h. The mixture was then concentrated and repeatedly dichloromethane was added and the mixture was concentrated again. The residue was purified by preparative HPLC (Method 6). The combined target fractions were concentrated, and the residue was lyophilized. 94 mg (100% purity, 79% of theory) of the title compound were obtained.

[α]$_D^{20}$=+48.5°, 589 nm, c=0.41 g/100 ml, methanol
LC-MS (Method 1): R$_t$=1.58 min; MS (ESIpos): m/z=594/596 [M+H]$^+$ $^1$H-NMR (400 MHz, DMSO-d6) δ [ppm]: −0.008 (3.65), 1.815 (2.03), 1.825 (2.29), 1.836 (3.45), 1.879 (16.00), 2.007 (0.46), 2.032 (1.10), 2.046 (3.63), 2.055 (2.83), 2.074 (14.77), 2.102 (2.92), 2.124 (2.33), 2.163 (6.20), 2.327 (0.57), 2.669 (0.50), 3.385 (2.83), 3.401 (2.67), 3.581 (11.94), 3.612 (5.50), 3.628 (2.90), 3.644 (2.39), 3.661 (3.14), 3.678 (2.59), 3.694 (1.61), 3.712 (0.91), 7.346 (3.62), 7.356 (5.66), 7.375 (2.23), 7.381 (2.65), 7.398 (9.07), 7.407 (7.10), 7.416 (7.30), 7.433 (1.86), 7.482 (2.36), 7.504 (3.73), 7.546 (6.03), 7.559 (7.96), 7.569 (5.48), 7.578 (3.09), 8.685 (2.29), 8.699 (4.21), 8.713 (2.32), 12.044 (3.05).

Example 132

(+/−)-5-({[6-Bromo-2-(3,3-difluoropiperidin-1-yl)-3-methylquinolin-4-yl]carbonyl}amino)-4-[2-(trifluoromethoxy)phenyl]pentanoic acid (Racemate)

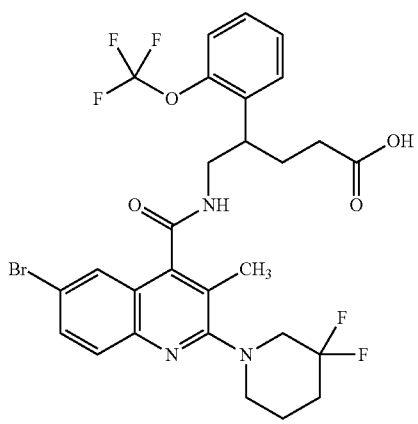 [SMILES: Cc1c(N2CCCC(F)(F)C2)nc2ccc(Br)cc2c1C(=O)NCC(CCC(=O)O)c1ccccc1OC(F)(F)F]

To a solution of (+/−)-tert-butyl 5-({[6-bromo-2-(3,3-difluoropiperidin-1-yl)-3-methylquinolin-4-yl]carbonyl}amino)-4-[2-(trifluoromethoxy)phenyl]pentanoate (85 mg, 121 μmol, racemate, Example 147A) in dichloromethane (1.5 ml) was added TFA (190 μl, 2.4 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 56 mg (100% purity, 72% of theory) of the title compound were obtained.

LC-MS (Method 1): R$_t$=2.21 min; MS (ESIpos): m/z=644/646 [M+H]$^+$ $^1$H-NMR (400 MHz, DMSO-d6) δ [ppm]: 1.805 (1.11), 1.818 (1.77), 1.828 (1.91), 1.839 (2.54), 1.887 (5.28), 2.050 (4.05), 2.077 (16.00), 2.115 (4.22), 2.159 (11.45), 2.245 (0.46), 3.174 (6.42), 3.360 (1.50), 3.391 (2.46), 3.406 (2.34), 3.456 (3.91), 3.485 (7.30), 3.513 (3.66), 3.595 (0.77), 3.610 (1.24), 3.628 (2.53), 3.644 (3.42), 3.657 (3.10), 3.672 (2.69), 3.689 (1.99), 3.705 (1.05), 3.722 (0.56), 7.363 (4.21), 7.382 (1.32), 7.388 (1.84), 7.403 (7.29), 7.414 (6.03), 7.421 (5.78), 7.425 (6.39), 7.438 (1.46), 7.495 (1.18), 7.553 (4.60), 7.566 (3.87), 7.576 (3.35), 7.680 (2.13), 7.702 (14.18), 7.707 (10.77), 7.712 (8.50), 7.729 (1.33), 7.734 (1.48), 8.743 (2.48), 8.758 (4.81), 8.772 (2.40), 12.069 (0.56).

Example 133

(−)-5-({[6-Bromo-2-(3,3-difluoropiperidin-1-yl)-3-methylquinolin-4-yl]carbonyl}amino)-4-[2-(trifluoromethoxy)phenyl]pentanoic acid (Enantiomer 1)

To a solution of (−)-tert-butyl 5-({[6-bromo-2-(3,3-difluoropiperidin-1-yl)-3-methylquinolin-4-yl]carbonyl}amino)-4-[2-(trifluoromethoxy)phenyl]pentanoate (115 mg, 164 μmol, enantiomer 1, Example 148A) in dichloromethane (1.3 ml) was added TFA (280 μl, 3.6 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 92 mg (100% purity, 86% of theory) of the title compound were obtained.

[α]$_D^{20}$=−15.9°, 589 nm, c=0.39 g/100 ml, methanol
LC-MS (Method 2): R$_t$=1.17 min; MS (ESIpos): m/z=644/646 [M+H]$^+$ $^1$H-NMR (400 MHz, DMSO-d6) δ [ppm]: 1.806 (0.97), 1.818 (1.67), 1.829 (1.78), 1.840 (2.38), 1.887 (4.81), 2.054 (3.60), 2.080 (16.00), 2.093 (6.95), 2.115 (3.93), 2.159 (10.72), 2.245 (0.45), 3.174 (5.85), 3.362 (0.96), 3.392 (2.07), 3.407 (2.04), 3.456 (3.60), 3.485 (6.81), 3.513 (3.40), 3.595 (0.68), 3.611 (1.12), 3.628 (2.37), 3.644 (3.21), 3.658 (2.83), 3.671 (2.52), 3.689 (1.85), 3.704 (0.96), 3.722 (0.52), 7.364 (4.04), 7.368 (3.55), 7.383 (1.21), 7.389 (1.74), 7.404 (6.92), 7.414 (5.86), 7.421 (5.49), 7.426 (6.17), 7.439 (1.40), 7.494 (1.13), 7.554 (4.44), 7.559 (3.07), 7.566 (3.66), 7.577 (3.23), 7.680 (2.15), 7.702 (14.00), 7.707 (10.50), 7.712 (8.41), 7.730 (1.33), 7.734 (1.49), 8.741 (2.35), 8.755 (4.60), 8.770 (2.27), 12.052 (2.47).

Example 134

(+)-5-({[6-Bromo-2-(3,3-difluoropiperidin-1-yl)-3-methylquinolin-4-yl]carbonyl}amino)-4-[2-(trifluoromethoxy)phenyl]pentanoic acid (Enantiomer 2)

To a solution of (+)-tert-butyl 5-({[6-bromo-2-(3,3-difluoropiperidin-1-yl)-3-methylquinolin-4-yl]

carbonyl}amino)-4-[2-(trifluoromethoxy)phenyl]pentanoate (105 mg, 150 µmol, enantiomer 2, Example 149A) in dichloromethane (1.2 ml) was added TFA (250 µl, 3.3 mmol), and the mixture was left to stand at RT for 22 h. The mixture was then concentrated and repeatedly dichloromethane was added and the mixture was concentrated again. The residue was purified by preparative HPLC (Method 7). The combined target fractions were concentrated, and the residue was lyophilized. 81 mg (99% purity, 83% of theory) of the title compound were obtained.

$[\alpha]_D^{20}$=+17.2°, 589 nm, c=0.42 g/100 ml, methanol

LC-MS (Method 2): $R_t$=1.17 min; MS (ESIpos): m/z=644/646 $[M+H]^+$ $^1$H-NMR (400 MHz, DMSO-d6) δ [ppm]: −0.008 (1.53), 0.008 (1.48), 1.806 (1.02), 1.819 (1.71), 1.829 (1.81), 1.840 (2.41), 1.887 (4.81), 2.053 (3.70), 2.079 (16.00), 2.093 (6.81), 2.116 (3.90), 2.159 (10.73), 2.245 (0.44), 3.174 (5.91), 3.392 (2.02), 3.406 (1.98), 3.456 (3.65), 3.485 (6.90), 3.513 (3.41), 3.595 (0.67), 3.610 (1.11), 3.628 (2.38), 3.644 (3.22), 3.658 (2.82), 3.672 (2.49), 3.689 (1.85), 3.704 (0.95), 3.722 (0.52), 7.354 (2.52), 7.359 (3.13), 7.364 (4.16), 7.368 (3.61), 7.382 (1.24), 7.389 (1.78), 7.404 (7.08), 7.414 (6.10), 7.421 (5.65), 7.426 (6.34), 7.439 (1.47), 7.496 (1.14), 7.554 (4.57), 7.559 (3.07), 7.566 (3.74), 7.577 (3.32), 7.680 (2.29), 7.702 (14.75), 7.707 (10.95), 7.712 (8.88), 7.729 (1.44), 7.734 (1.59), 8.741 (2.36), 8.756 (4.69), 8.770 (2.33), 12.055 (2.70).

Example 135

(+/−)-5-({[2-(Azepan-1-yl)-6-bromo-3-methylquinolin-4-yl]carbonyl}amino)-4-[2-(trifluoromethoxy)phenyl]pentanoic acid (Racemate)

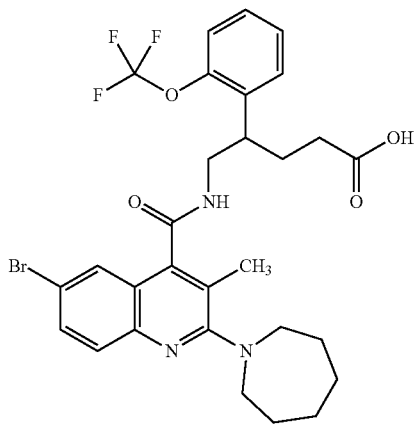 [SMILES: Cc1c(N2CCCCCC2)nc2ccc(Br)cc2c1C(=O)NCC(CCC(=O)O)c1ccccc1OC(F)(F)F]

To a solution of (+/−)-tert-butyl 5-({[2-(azepan-1-yl)-6-bromo-3-methylquinolin-4-yl]carbonyl}-amino)-4-[2-(trifluoromethoxy)phenyl]pentanoate (85 mg, 125 µmol, racemate, Example 150A) in dichloromethane (1.1 ml) was added TFA (210 µl, 2.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 52 mg (100% purity, 67% of theory) of the title compound were obtained.

LC-MS (Method 1): $R_t$=2.34 min; MS (ESIpos): m/z=622/624 $[M+H]^+$ $^1$H-NMR (400 MHz, DMSO-d6) δ [ppm]: 1.234 (0.73), 1.605 (14.46), 1.784 (9.83), 1.835 (2.54), 1.859 (1.84), 1.886 (0.52), 2.032 (0.83), 2.046 (2.81), 2.073 (13.10), 2.124 (8.68), 2.215 (0.46), 2.327 (0.46), 2.669 (0.49), 3.357 (1.19), 3.387 (2.23), 3.402 (2.13), 3.494 (11.26), 3.509 (16.00), 3.523 (10.92), 3.571 (0.90), 3.586 (1.30), 3.604 (2.18), 3.618 (2.63), 3.635 (1.81), 3.662 (2.15), 3.679 (1.80), 7.358 (4.37), 7.385 (2.48), 7.399 (7.73), 7.410 (6.56), 7.417 (6.14), 7.421 (6.49), 7.434 (1.57), 7.531 (6.00), 7.553 (13.64), 7.562 (4.00), 7.573 (3.14), 7.597 (6.11), 7.602 (5.59), 7.619 (3.18), 7.625 (3.00), 8.702 (2.26), 8.717 (4.27), 8.731 (2.14), 12.058 (0.97).

Example 136

(−)-5-({[2-(Azepan-1-yl)-6-bromo-3-methylquinolin-4-yl]carbonyl}amino)-4-[2-(trifluoromethoxy)phenyl]pentanoic acid (Enantiomer 1)

To a solution of (−)-tert-butyl 5-({[2-(azepan-1-yl)-6-bromo-3-methylquinolin-4-yl]carbonyl}amino)-4-[2-(trifluoromethoxy)phenyl]pentanoate (145 mg, 214 µmol, enantiomer 1, Example 151A) in dichloromethane (1.6 ml) was added TFA (360 µl, 4.7 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 75 mg (100% purity, 56% of theory) of the title compound were obtained.

$[\alpha]_D^{20}$=−16.5°, 589 nm, c=0.35 g/100 ml, methanol

LC-MS (Method 1): $R_t$=2.34 min; MS (ESIpos): m/z=622/624 $[M+H]^+$ $^1$H-NMR (400 MHz, DMSO-d6) δ [ppm]: −0.008 (1.64), 0.008 (2.00), 1.371 (0.52), 1.605 (14.32), 1.613 (12.24), 1.784 (9.58), 1.824 (2.16), 1.836 (2.49), 1.860 (1.82), 1.887 (0.48), 2.032 (0.82), 2.046 (2.82), 2.061 (3.46), 2.073 (12.90), 2.079 (9.89), 2.124 (8.41), 2.215 (0.43), 3.388 (2.27), 3.404 (2.15), 3.495 (11.59), 3.509 (16.00), 3.524 (11.30), 3.571 (0.87), 3.586 (1.27), 3.604 (2.17), 3.619 (2.60), 3.635 (1.74), 3.645 (1.58), 3.663 (2.15), 3.679 (1.76), 3.694 (1.07), 3.714 (0.57), 7.353 (3.36), 7.358 (4.32), 7.362 (3.85), 7.378 (1.75), 7.385 (2.43), 7.399 (7.64), 7.410 (6.64), 7.417 (6.07), 7.421 (6.62), 7.435 (1.61), 7.532 (6.31), 7.554 (14.24), 7.562 (4.07), 7.573 (3.33), 7.597 (6.38), 7.603 (5.95), 7.620 (3.35), 7.625 (3.23), 8.704 (2.31), 8.718 (4.42), 8.732 (2.22), 12.060 (0.53).

Example 137

(+)-5-({[2-(Azepan-1-yl)-6-bromo-3-methylquinolin-4-yl]carbonyl}amino)-4-[2-(trifluoromethoxy)phenyl]pentanoic acid (Enantiomer 2)

To a solution of (+)-tert-butyl 5-({[2-(azepan-1-yl)-6-bromo-3-methylquinolin-4-yl]carbonyl}amino)-4-[2-(trifluoromethoxy)phenyl]pentanoate (140 mg, 206 µmol, enantiomer 2, Example 152A) in dichloromethane (1.6 ml) was added TFA (350 µl, 4.5 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 88 mg (100% purity, 68% of theory) of the title compound were obtained.

[α]$_D^{20}$=+16.9°, 589 nm, c=0.44 g/100 ml, methanol
LC-MS (Method 1): R$_t$=2.34 min; MS (ESIpos): m/z=622/624 [M+H]$^+$
$^1$H-NMR (400 MHz, DMSO-d6) δ [ppm]: 1.606 (14.31), 1.784 (9.86), 1.837 (2.55), 1.861 (1.79), 1.888 (0.53), 2.049 (2.72), 2.076 (13.15), 2.125 (8.84), 2.215 (0.47), 2.328 (0.42), 2.670 (0.44), 3.390 (2.07), 3.403 (2.07), 3.495 (10.87), 3.510 (16.00), 3.524 (10.86), 3.572 (0.92), 3.587 (1.31), 3.605 (2.21), 3.620 (2.66), 3.637 (1.81), 3.664 (2.19), 3.680 (1.85), 7.359 (4.31), 7.385 (2.45), 7.400 (7.84), 7.410 (6.35), 7.422 (6.61), 7.435 (1.62), 7.532 (5.57), 7.554 (13.16), 7.563 (3.91), 7.574 (3.13), 7.598 (5.67), 7.603 (5.52), 7.620 (2.99), 7.625 (3.00), 8.701 (2.25), 8.716 (4.35), 8.730 (2.19), 12.046 (2.47).

Example 138

5-[({6-Bromo-2-[3-fluoropiperidin-1-yl]-3-methylquinolin-4-yl}carbonyl)amino]-4-[2-(trifluoromethoxy)phenyl]pentanoic acid (Diastereomer Mixture)

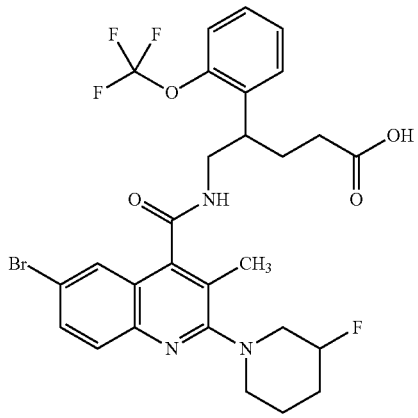

To a solution of tert-butyl 5-[({6-bromo-2-[3-fluoropiperidin-1-yl]-3-methylquinolin-4-yl}carbonyl)amino]-4-[2-(trifluoromethoxy)phenyl]pentanoate (85 mg, 125 μmol, diastereomer mixture, Example 153A) in dichloromethane (1.1 ml) was added TFA (210 μl, 2.7 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 55 mg (100% purity, 71% of theory) of the title compound were obtained.
LC-MS (Method 1): R$_t$=2.18 min; MS (ESIpos): m/z=626/628 [M+H]$^+$
$^1$H-NMR (400 MHz, DMSO-d6) δ [ppm]: −0.008 (2.06), 0.008 (2.52), 1.236 (0.83), 1.646 (1.98), 1.768 (0.68), 1.815 (3.36), 1.826 (3.43), 1.837 (3.81), 1.861 (2.67), 1.902 (3.30), 1.922 (2.78), 1.953 (1.96), 1.987 (1.15), 2.010 (0.72), 2.050 (2.99), 2.077 (14.97), 2.104 (2.52), 2.153 (12.67), 2.328 (0.48), 2.670 (0.45), 3.074 (1.28), 3.104 (2.25), 3.163 (2.42), 3.176 (2.36), 3.208 (1.25), 3.350 (2.24), 3.387 (4.28), 3.411 (3.01), 3.438 (2.24), 3.472 (1.37), 3.590 (0.69), 3.605 (1.17), 3.622 (2.52), 3.639 (3.61), 3.652 (3.10), 3.680 (1.90), 4.820 (1.66), 4.939 (1.69), 7.362 (4.58), 7.366 (4.02), 7.381 (1.37), 7.387 (1.93), 7.402 (7.98), 7.412 (6.54), 7.419 (6.20), 7.424 (7.11), 7.437 (1.74), 7.474 (1.39), 7.551 (4.96), 7.563 (4.09), 7.574 (3.61), 7.654 (2.68), 7.675 (16.00), 7.681 (11.09), 7.686 (9.41), 7.704 (1.75), 7.708 (1.85), 8.736 (2.62), 8.750 (5.19), 8.765 (2.57), 12.057 (1.66).

Example 139

5-[({6-Bromo-2-[3-ethylpiperidin-1-yl]-3-methylquinolin-4-yl}carbonyl)amino]-4-[2-(trifluoromethoxy)phenyl]pentanoic acid (Diastereomer Mixture)

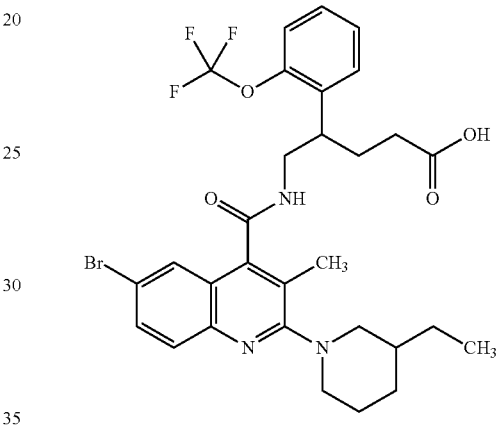

To a solution of tert-butyl 5-[({6-bromo-2-[3-ethylpiperidin-1-yl]-3-methylquinolin-4-yl}carbonyl)amino]-4-[2-(trifluoromethoxy)phenyl]pentanoate (85 mg, 123 μmol, diastereomer mixture, Example 154A) in dichloromethane (1.5 ml) was added TFA (190 μl, 2.5 mmol), and the mixture was stirred at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 60 mg (100% purity, 77% of theory) of the title compound were obtained.
LC-MS (Method 1): R$_t$=2.52 min; MS (ESIpos): m/z=636/638 [M+H]$^+$
$^1$H-NMR (400 MHz, DMSO-d6) δ [ppm]: 0.892 (6.52), 0.911 (16.00), 0.930 (8.01), 1.039 (0.62), 1.059 (1.34), 1.067 (1.35), 1.090 (1.31), 1.097 (1.32), 1.119 (0.60), 1.128 (0.53), 1.242 (1.02), 1.260 (2.47), 1.277 (3.35), 1.295 (2.40), 1.564 (1.51), 1.573 (1.45), 1.590 (1.24), 1.601 (1.32), 1.635 (1.16), 1.749 (1.81), 1.782 (1.45), 1.801 (0.96), 1.814 (1.34), 1.825 (1.40), 1.837 (2.34), 1.858 (2.39), 1.884 (1.66), 2.051 (2.07), 2.078 (10.33), 2.109 (4.06), 2.135 (5.81), 2.409 (0.86), 2.435 (1.21), 2.464 (0.70), 2.715 (0.95), 2.745 (1.75), 2.775 (0.94), 3.363 (0.67), 3.393 (1.53), 3.406 (1.51), 3.495 (2.71), 3.525 (2.53), 3.585 (0.64), 3.600 (1.01), 3.618 (1.79), 3.633 (2.24), 3.649 (1.67), 3.660 (1.23), 3.677 (1.52), 3.695 (1.19), 7.357 (2.77), 7.385 (1.24), 7.400 (5.23), 7.410 (4.34), 7.421 (4.73), 7.435 (1.32), 7.456 (0.83), 7.554 (2.88), 7.566 (2.50), 7.576 (2.07), 7.631 (1.14), 7.654 (12.66), 7.682 (0.77), 8.718 (1.71), 8.733 (3.25), 8.747 (1.66), 12.046 (0.84).

Example 140

5-[({6-Bromo-3-methyl-2-[3-methylpiperidin-1-yl]quinolin-4-yl}carbonyl)amino]-4-[2-(trifluoromethoxy)phenyl]pentanoic acid (Diastereomer Mixture)

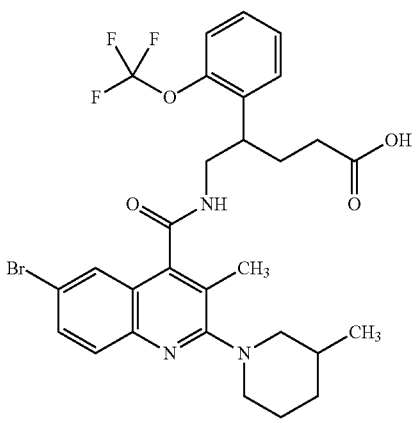 [SMILES: Cc1c(N2CCCC(C)C2)nc2ccc(Br)cc2c1C(=O)NCC(CCC(=O)O)c1ccccc1OC(F)(F)F]

To a solution of tert-butyl 5-[({6-bromo-3-methyl-2-[3-methylpiperidin-1-yl]quinolin-4-yl}carbonyl)amino]-4-[2-(trifluoromethoxy)phenyl]pentanoate (85 mg, 125 µmol, diastereomer mixture, Example 155A) in dichloromethane (1.1 ml) was added TFA (210 µl, 2.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 56 mg (100% purity, 71% of theory) of the title compound were obtained.

LC-MS (Method 1): $R_t$=2.42 min; MS (ESIpos): m/z=622/624 [M+H]$^+$ $^1$H-NMR (400 MHz, DMSO-d6) δ [ppm]: 0.923 (14.04), 0.939 (14.42), 1.054 (0.58), 1.080 (1.68), 1.109 (1.75), 1.132 (0.71), 1.235 (0.89), 1.628 (1.42), 1.658 (1.67), 1.685 (0.79), 1.733 (3.00), 1.766 (3.19), 1.800 (3.96), 1.816 (3.37), 1.825 (3.80), 1.835 (3.76), 1.860 (1.79), 1.888 (0.45), 2.050 (2.61), 2.076 (13.15), 2.106 (2.82), 2.140 (8.43), 2.433 (1.30), 2.458 (2.15), 2.684 (1.32), 2.713 (2.46), 2.742 (1.32), 3.358 (0.97), 3.389 (2.11), 3.404 (2.09), 3.440 (2.69), 3.469 (4.76), 3.500 (2.26), 3.598 (1.01), 3.617 (1.92), 3.631 (2.43), 3.647 (2.54), 3.665 (2.40), 3.682 (1.87), 3.698 (1.04), 3.716 (0.56), 7.361 (3.79), 7.387 (1.64), 7.400 (6.96), 7.412 (5.56), 7.423 (6.36), 7.436 (1.82), 7.550 (4.02), 7.563 (3.50), 7.573 (2.95), 7.631 (1.47), 7.654 (16.00), 7.682 (1.06), 8.720 (2.23), 8.735 (4.29), 8.749 (2.17), 12.048 (3.54).

Example 141

(+/−)-5-({[6-Bromo-3-methyl-2-(piperidin-1-yl)quinolin-4-yl]carbonyl}amino)-4-(2-chloro-3-fluorophenyl)pentanoic acid (Racemate)

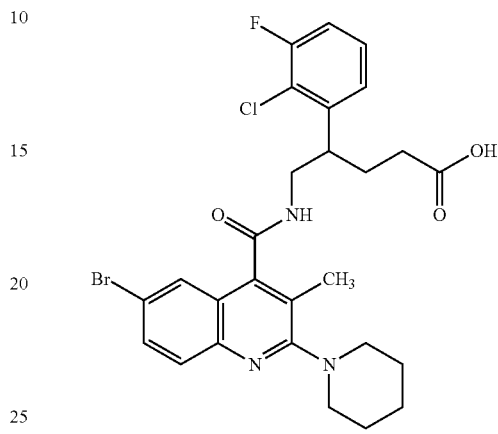

To a solution of (+/−)-tert-butyl 5-({[6-bromo-3-methyl-2-(piperidin-1-yl)quinolin-4-yl]carbonyl}-amino)-4-(2-chloro-3-fluorophenyl)pentanoate (172 mg, 272 µmol, racemate, Example 156A) in dichloromethane (4.0 ml) was added TFA (310 µl, 4.1 mmol), and the mixture was stirred at RT for 18 h. Subsequently, TFA (155 µl, 2.05 mmol) was added again, and the mixture was stirred at RT for 26 h. This was followed by concentration of the mixture, and repeated additions of dichloromethane followed by concentration again. The residue was purified by preparative HPLC (Method 6). The combined target fractions were concentrated, and the residue was lyophilized. 143 mg (100% purity, 91% of theory) of the title compound were obtained.

LC-MS (Method 1): $R_t$=2.19 min; MS (ESIpos): m/z=576/578 [M+H]$^+$ $^1$H-NMR (400 MHz, DMSO-d6) δ [ppm]: 1.606 (4.25), 1.672 (8.45), 1.790 (0.50), 1.806 (0.96), 1.824 (1.50), 1.845 (1.97), 1.867 (1.12), 1.883 (0.52), 2.020 (0.49), 2.039 (1.16), 2.063 (3.60), 2.075 (1.70), 2.090 (4.80), 2.100 (8.16), 2.130 (16.00), 2.165 (1.21), 2.328 (0.48), 2.366 (0.44), 2.669 (0.52), 2.709 (0.44), 3.135 (11.08), 3.616 (1.87), 3.697 (3.00), 7.288 (1.68), 7.309 (3.78), 7.331 (2.61), 7.344 (2.90), 7.363 (4.95), 7.396 (2.49), 7.411 (2.98), 7.416 (3.42), 7.430 (3.39), 7.450 (1.62), 7.624 (2.09), 7.646 (11.69), 7.653 (7.79), 7.658 (6.74), 7.675 (1.30), 7.680 (1.47), 8.718 (2.07), 8.732 (4.17), 8.746 (2.03), 12.059 (0.63).

Separation of the Enantiomers:

The title compound (125 mg) was dissolved in methanol (20 ml) and separated into the enantiomers by means of preparative SFC on chiral phase (see Examples 142 and 143) [column: Daicel Chiralcel OX-H, 5 µm, 250 mm×20 mm; flow rate: 80 ml/min; detection: 210 nm; temperature: 40° C.; injection: 1.0 ml; eluent: 17% ethanol/83% carbon dioxide; run time 13 min, isocratic]. The combined target fractions were each concentrated, and the respective residue was lyophilized.

Example 142

(−)-5-({[6-Bromo-3-methyl-2-(piperidin-1-yl)quino-lin-4-yl]carbonyl}amino)-4-(2-chloro-3-fluorophe-nyl)pentanoic acid (Enantiomer 1)

In the enantiomer separation described in Example 141, 43 mg (100% purity, ee>99%) of the title compound were obtained as the enantiomer that eluted earlier.

$[\alpha]_D^{20}$=−13.8°, 589 nm, c=0.37 g/100 ml, methanol

LC-MS (Method 1): $R_t$=2.20 min; MS (ESIpos): m/z=576/578 [M+H]$^+$ $^1$H-NMR (400 MHz, DMSO-d6) δ [ppm]: −0.008 (2.03), 0.008 (2.00), 1.596 (3.88), 1.605 (4.29), 1.671 (8.19), 1.792 (0.54), 1.807 (1.05), 1.826 (1.62), 1.833 (1.58), 1.846 (2.10), 1.868 (1.23), 1.884 (0.62), 2.021 (0.60), 2.040 (1.29), 2.064 (3.77), 2.077 (1.88), 2.091 (4.95), 2.101 (8.41), 2.131 (16.00), 2.166 (1.27), 2.182 (0.56), 3.121 (7.95), 3.134 (10.68), 3.617 (1.89), 3.644 (1.14), 3.699 (2.96), 7.289 (1.83), 7.309 (3.92), 7.332 (2.80), 7.346 (2.97), 7.364 (5.02), 7.397 (2.62), 7.411 (3.07), 7.416 (3.55), 7.430 (3.51), 7.450 (1.68), 7.624 (2.18), 7.645 (11.92), 7.652 (7.95), 7.657 (7.09), 7.674 (1.32), 7.679 (1.53), 8.719 (2.03), 8.733 (4.07), 8.747 (2.01), 12.066 (5.30).

Example 143

(+)-5-({[6-Bromo-3-methyl-2-(piperidin-1-yl)quino-lin-4-yl]carbonyl}amino)-4-(2-chloro-3-fluorophe-nyl)pentanoic acid (Enantiomer 2)

In the enantiomer separation described in Example 141, 37 mg (100% purity, ee 95%) of the title compound were obtained as the enantiomer that eluted later.

$[\alpha]_D^{20}$=+13.4°, 589 nm, c=0.35 g/100 ml, methanol

LC-MS (Method 1): $R_t$=2.20 min; MS (ESIpos): m/z=576/578 [M+H]$^+$ $^1$H-NMR (400 MHz, DMSO-d6) δ [ppm]: 1.605 (4.31), 1.671 (8.37), 1.793 (0.53), 1.808 (1.01), 1.827 (1.61), 1.834 (1.61), 1.847 (2.06), 1.869 (1.22), 1.885 (0.62), 2.023 (0.56), 2.041 (1.26), 2.065 (3.63), 2.077 (1.87), 2.092 (4.86), 2.102 (8.13), 2.131 (16.00), 2.167 (1.31), 2.183 (0.60), 3.134 (10.81), 3.618 (1.95), 3.644 (1.18), 3.699 (3.03), 7.288 (1.74), 7.309 (3.75), 7.331 (2.65), 7.346 (2.89), 7.364 (4.84), 7.397 (2.46), 7.411 (3.00), 7.416 (3.41), 7.430 (3.37), 7.450 (1.67), 7.624 (1.92), 7.646 (10.90), 7.652 (7.58), 7.657 (6.58), 7.675 (1.19), 7.679 (1.36), 8.719 (1.99), 8.734 (3.94), 8.748 (1.97), 12.068 (3.84).

Example 144

(+/−)-5-({[6-Bromo-3-methyl-2-(piperidin-1-yl)qui-nolin-4-yl]carbonyl}amino)-4-(6-chloro-2,3-difluo-rophenyl)pentanoic acid (Racemate)

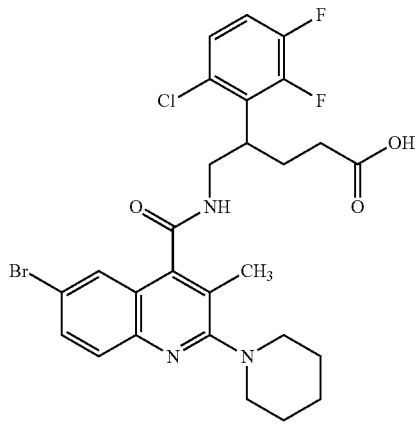

To a solution of (+/−)-tert-butyl 5-({[6-bromo-3-methyl-2-(piperidin-1-yl)quinolin-4-yl]carbonyl}-amino)-4-(6-chloro-2,3-difluorophenyl)pentanoate (123 mg, 189 μmol, racemate, Example 157A) in dichloromethane (3 ml) was added TFA (220 μl, 2.8 mmol), and the mixture was stirred at RT for 18 h. Subsequently, TFA (110 μl, 1.4 mmol) was added again, and the mixture was stirred at RT for 26 h. This was followed by concentration of the mixture, and repeated additions of dichloromethane followed by concentration again. The residue was purified by preparative HPLC (Method 6). The combined target fractions were concentrated, and the residue was lyophilized. 124 mg (94% purity, 103% of theory) of the title compound were obtained.

LC-MS (Method 1): $R_t$=2.22 min; MS (ESIpos): m/z=594/596 [M+H]$^+$ $^1$H-NMR (400 MHz, DMSO-d6) δ [ppm]: −0.023 (0.44), −0.008 (2.46), 0.008 (2.14), 1.234 (0.89), 1.367 (4.68), 1.606 (2.38), 1.656 (4.36), 1.671 (4.64), 1.979 (0.61), 2.073 (2.70), 2.101 (1.76), 2.128 (2.50), 2.144 (16.00), 2.187 (0.81), 2.327 (0.46), 2.332 (0.40), 2.347 (0.61), 2.366 (0.85), 2.670 (0.52), 2.710 (0.85), 3.135 (6.17), 3.734 (0.97), 3.770 (1.43), 7.376 (1.80), 7.389 (2.16), 7.412 (1.47), 7.433 (1.39), 7.456 (0.69), 7.626 (1.67), 7.648 (6.98), 7.658 (4.62), 7.663 (4.00), 7.680 (1.01), 7.685 (1.05), 8.807 (1.03), 8.822 (2.00), 8.835 (0.99).

Separation of the Enantiomers:

The title compound (110 mg) was dissolved in methanol (15 ml) and separated into the enantiomers by means of preparative SFC on chiral phase (see Examples 145 and 146) [column: Daicel Chiralpak AD, 5 μm, 250 mm×20 mm; flow rate: 80 ml/min; detection: 210 nm; temperature: 40° C.; injection: 2.0 ml; eluent: 30% isopropanol/70% carbon dioxide; run time 7 min, isocratic]. The combined target fractions were each concentrated, and the respective residue was lyophilized.

Example 145

(−)-5-({[6-Bromo-3-methyl-2-(piperidin-1-yl)quinolin-4-yl]carbonyl}amino)-4-(6-chloro-2,3-difluorophenyl)pentanoic acid (Enantiomer 1)

In the enantiomer separation described in Example 144, 43 mg (100% purity, ee>99%) of the title compound were obtained as the enantiomer that eluted earlier.

$[\alpha]_D^{20}$=−31.8°, 589 nm, c=0.41 g/100 ml, methanol
LC-MS (Method 2): $R_t$=1.13 min; MS (ESIpos): m/z=594/596 [M+H]$^+$
$^1$H-NMR (400 MHz, DMSO-d6) δ [ppm]: 0.069 (0.50), 1.367 (3.93), 1.606 (2.74), 1.671 (5.29), 1.983 (0.77), 2.065 (1.26), 2.076 (1.30), 2.095 (1.33), 2.110 (1.94), 2.144 (16.00), 2.172 (2.18), 2.195 (0.93), 2.434 (0.58), 3.135 (6.96), 3.738 (1.19), 3.771 (1.70), 7.377 (2.00), 7.389 (2.43), 7.412 (1.72), 7.434 (1.70), 7.456 (1.02), 7.486 (0.51), 7.626 (1.66), 7.648 (6.84), 7.658 (4.26), 7.663 (4.01), 7.681 (0.93), 7.685 (1.02), 8.803 (1.17), 8.817 (2.27), 8.831 (1.13).

Example 146

(+)-5-({[6-Bromo-3-methyl-2-(piperidin-1-yl)quinolin-4-yl]carbonyl}amino)-4-(6-chloro-2,3-difluorophenyl)pentanoic acid (Enantiomer 2)

In the enantiomer separation described in Example 144, 31 mg (98% purity, ee>99%) of the title compound were obtained as the enantiomer that eluted later.

$[\alpha]_D^{20}$=+34.1°, 589 nm, c=0.40 g/100 ml, methanol
LC-MS (Method 2): $R_t$=1.14 min; MS (ESIpos): m/z=594/596 [M+H]$^+$
$^1$H-NMR (400 MHz, DMSO-d6) δ [ppm]: −0.008 (1.37), 0.008 (0.74), 1.368 (0.77), 1.596 (2.49), 1.606 (2.69), 1.671 (5.00), 1.982 (0.72), 2.067 (1.07), 2.079 (1.22), 2.097 (1.31), 2.116 (2.21), 2.145 (16.00), 2.178 (2.09), 2.200 (0.82), 3.122 (5.17), 3.135 (6.49), 3.739 (1.21), 3.771 (1.63), 7.355 (0.86), 7.378 (2.03), 7.390 (2.38), 7.413 (1.64), 7.435 (1.43), 7.457 (0.74), 7.627 (1.88), 7.649 (7.16), 7.659 (4.59), 7.664 (4.01), 7.681 (1.00), 7.686 (1.02), 8.802 (1.22), 8.816 (2.19), 8.830 (1.05).

Example 147

(+/−)-5-({[6-Bromo-3-methyl-2-(piperidin-1-yl)quinolin-4-yl]carbonyl}amino)-4-(5-fluoro-2-methylphenyl)pentanoic acid (Racemate)

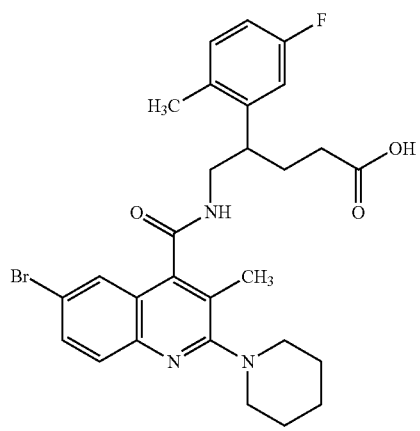 [SMILES: Cc1ccc(F)cc1C(CCC(=O)O)CNC(=O)c1c(C)c(N2CCCCC2)nc2ccc(Br)cc12]

To a solution of (+/−)-tert-butyl 5-({[6-bromo-3-methyl-2-(piperidin-1-yl)quinolin-4-yl]carbonyl}amino)-4-(5-fluoro-2-methylphenyl)pentanoate (185 mg, 302 μmol, racemate, Example 158A) in dichloromethane (4 ml) was added TFA (350 μl, 4.5 mmol), and the mixture was stirred at RT for 18 h. The mixture was then concentrated and repeatedly dichloromethane was added and the mixture was concentrated again. The residue was purified by preparative HPLC (Method 6). The combined target fractions were concentrated, and the residue was lyophilized. 149 mg (100% purity, 89% of theory) of the title compound were obtained.

LC-MS (Method 1): $R_t$=2.21 min; MS (ESIpos): m/z=556/558 [M+H]$^+$
$^1$H-NMR (400 MHz, DMSO-d6) δ [ppm]: −0.008 (2.37), 0.008 (2.26), 1.606 (3.10), 1.670 (6.11), 1.739 (0.41), 1.756 (0.83), 1.772 (0.96), 1.797 (1.23), 1.828 (0.55), 1.993 (0.96), 2.006 (1.24), 2.023 (1.21), 2.043 (1.30), 2.063 (4.89), 2.079 (5.98), 2.100 (10.78), 2.293 (16.00), 2.327 (0.60), 2.669 (0.46), 3.135 (8.13), 3.460 (1.02), 3.473 (1.34), 3.493 (1.53), 3.507 (1.68), 3.521 (1.03), 3.653 (1.00), 3.672 (1.51), 3.690 (1.34), 3.705 (1.15), 3.725 (0.70), 6.921 (1.05), 6.928 (1.22), 6.942 (2.27), 6.949 (2.54), 6.963 (1.30), 6.970 (1.35), 7.132 (2.32), 7.139 (2.36), 7.159 (2.39), 7.166 (2.29), 7.197 (2.30), 7.213 (2.66), 7.218 (2.51), 7.234 (2.07), 7.439 (1.06), 7.626 (1.65), 7.648 (9.38), 7.654 (6.97), 7.659 (5.99), 7.676 (1.07), 7.681 (1.21), 8.711 (1.47), 8.726 (2.38), 8.740 (1.48).

Separation of the Enantiomers:

The title compound (135 mg) was dissolved in methanol (20 ml) and separated into the enantiomers by means of preparative SFC on chiral phase (see Examples 148 and 149) [column: Daicel Chiralcel OX-H, 5 μm, 250 mm×20 mm; flow rate: 80 ml/min; detection: 210 nm; temperature: 40° C.; injection: 2.0 ml; eluent: 30% ethanol/70% carbon dioxide; run time 8 min, isocratic]. The combined target fractions were each concentrated, and the respective residue was lyophilized.

Example 148

(−)-5-({[6-Bromo-3-methyl-2-(piperidin-1-yl)quinolin-4-yl]carbonyl}amino)-4-(5-fluoro-2-methylphenyl)pentanoic acid (Enantiomer 1)

In the enantiomer separation described in Example 147, 57 mg (100% purity, ee>99%) of the title compound were obtained as the enantiomer that eluted earlier.

$[\alpha]_D^{20}$=−13.8°, 589 nm, c=0.49 g/100 ml, methanol
LC-MS (Method 2): $R_t$=1.12 min; MS (ESIpos): m/z=556/558 [M−H]$^+$
$^1$H-NMR (400 MHz, DMSO-d6) δ [ppm]: 1.609 (3.14), 1.673 (6.11), 1.746 (0.41), 1.764 (0.84), 1.780 (1.02), 1.788 (1.06), 1.798 (1.19), 1.803 (1.18), 1.818 (1.00), 1.836 (0.56), 1.980 (0.44), 1.999 (1.06), 2.012 (1.31), 2.030 (1.30), 2.049 (1.40), 2.062 (1.59), 2.075 (5.10), 2.091 (7.94), 2.103 (10.32), 2.294 (16.00), 3.147 (7.87), 3.320 (1.45), 3.432 (0.41), 3.450 (0.52), 3.463 (1.20), 3.476 (1.60), 3.496 (1.88), 3.510 (2.09), 3.524 (1.47), 3.656 (1.37), 3.674 (1.84), 3.693 (1.62), 3.708 (1.41), 3.727 (0.90), 6.924 (1.07), 6.930 (1.25), 6.945 (2.28), 6.951 (2.50), 6.966 (1.28), 6.972 (1.33), 7.137 (2.34), 7.144 (2.41), 7.164 (2.39), 7.171 (2.32), 7.200 (2.34), 7.215 (2.65), 7.220 (2.47), 7.236 (2.02), 7.444 (1.01), 7.638

(1.21), 7.660 (9.17), 7.664 (7.93), 7.669 (5.88), 7.686 (0.75), 7.691 (0.88), 8.714 (1.52), 8.729 (2.41), 8.743 (1.46).

Example 149

(+)-5-({[6-Bromo-3-methyl-2-(piperidin-1-yl)quinolin-4-yl]carbonyl}amino)-4-(5-fluoro-2-methylphenyl)pentanoic acid (Enantiomer 2)

In the enantiomer separation described in Example 147, 51 mg (100% purity, ee 96%) of the title compound were obtained as the enantiomer that eluted later.

$[\alpha]_D^{20}$=+13.4°, 589 nm, c=0.37 g/100 ml, methanol
LC-MS (Method 2): $R_t$=1.13 min; MS (ESIpos): m/z=556/558 [M+H]$^+$
$^1$H-NMR (400 MHz, DMSO-d6) δ [ppm]: −0.008 (1.34), 0.008 (1.21), 1.030 (0.40), 1.046 (0.41), 1.609 (3.05), 1.673 (5.95), 1.745 (0.41), 1.763 (0.85), 1.779 (1.01), 1.787 (1.04), 1.797 (1.17), 1.803 (1.15), 1.820 (1.02), 1.835 (0.58), 1.979 (0.43), 1.999 (1.03), 2.012 (1.29), 2.030 (1.29), 2.049 (1.38), 2.062 (1.54), 2.075 (5.05), 2.091 (7.75), 2.103 (10.14), 2.294 (16.00), 3.149 (7.64), 3.319 (1.39), 3.450 (0.41), 3.463 (1.08), 3.476 (1.46), 3.496 (1.72), 3.510 (1.90), 3.524 (1.28), 3.656 (1.43), 3.674 (1.91), 3.693 (1.69), 3.708 (1.48), 3.727 (0.98), 6.923 (1.08), 6.930 (1.25), 6.944 (2.29), 6.951 (2.50), 6.965 (1.28), 6.972 (1.31), 7.137 (2.34), 7.143 (2.38), 7.164 (2.38), 7.170 (2.30), 7.199 (2.38), 7.215 (2.66), 7.220 (2.45), 7.236 (2.05), 7.443 (0.99), 7.640 (1.11), 7.662 (9.23), 7.669 (5.86), 7.687 (0.70), 7.692 (0.82), 8.715 (1.52), 8.730 (2.36), 8.744 (1.44).

Example 150

(+/−)-5-({[6-Bromo-2-(3,3-difluoropiperidin-1-yl)-3-methylquinolin-4-yl]carbonyl}amino)-4-(5-fluoro-2-methylphenyl)pentanoic acid (Racemate)

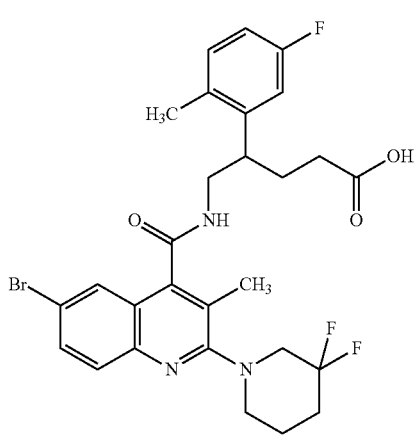 [SMILES: Cc1ccc(F)cc1C(CCC(=O)O)CNC(=O)c1c(C)c(N2CCCC(F)(F)C2)nc2ccc(Br)cc12]

To a solution of (+/−)-tert-butyl 5-({[6-bromo-2-(3,3-difluoropiperidin-1-yl)-3-methylquinolin-4-yl]carbonyl}amino)-4-(5-fluoro-2-methylphenyl)pentanoate (263 mg, 406 μmol, racemate, Example 159A) in dichloromethane (4 ml) was added TFA (620 μl, 8.1 mmol), and the mixture was stirred at RT for 18 h. The mixture was then concentrated and repeatedly dichloromethane was added and the mixture was concentrated again. The residue was purified by preparative HPLC (Method 6). The combined target fractions were concentrated, and the residue was lyophilized. 211 mg (100% purity, 88% of theory) of the title compound were obtained.

LC-MS (Method 1): $R_t$=2.17 min; MS (ESIpos): m/z=592/594 [M+H]$^+$
$^1$H-NMR (400 MHz, DMSO-d6) δ [ppm]: −0.008 (2.15), 0.008 (1.52), 1.763 (0.87), 1.779 (1.10), 1.787 (1.11), 1.796 (1.27), 1.802 (1.23), 1.820 (1.00), 1.835 (0.72), 1.880 (3.31), 1.976 (0.53), 1.996 (1.11), 2.009 (1.35), 2.027 (1.46), 2.046 (2.40), 2.071 (6.38), 2.087 (8.11), 2.117 (10.60), 2.292 (16.00), 2.322 (0.52), 2.327 (0.56), 2.524 (1.64), 3.164 (4.06), 3.449 (2.71), 3.479 (5.41), 3.505 (3.74), 3.518 (2.18), 3.533 (1.13), 3.665 (1.08), 3.683 (1.64), 3.702 (1.40), 3.716 (1.20), 3.736 (0.71), 6.924 (1.18), 6.931 (1.33), 6.945 (2.41), 6.952 (2.57), 6.966 (1.34), 6.973 (1.35), 7.141 (2.55), 7.147 (2.54), 7.167 (2.57), 7.174 (2.42), 7.200 (2.58), 7.215 (2.84), 7.221 (2.58), 7.237 (2.16), 7.476 (0.90), 7.678 (1.75), 7.699 (10.07), 7.704 (7.52), 7.709 (6.08), 7.727 (0.97), 7.731 (1.10), 8.722 (1.71), 8.736 (2.53), 8.751 (1.53).

Example 151

(+/−)-5-({[6-Bromo-3-methyl-2-(piperidin-1-yl)quinolin-4-yl]carbonyl}amino)-4-(2-chloro-3,6-difluorophenyl)pentanoic acid (Racemate)

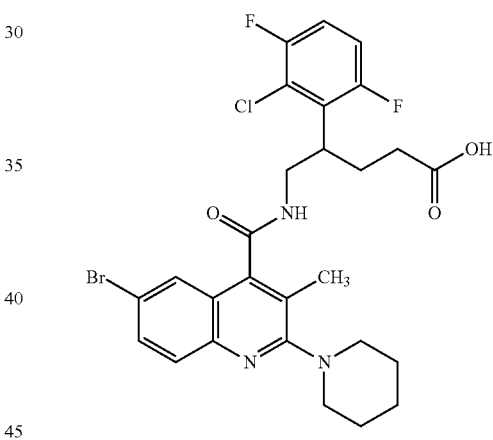

To a solution of (+/−)-tert-butyl 5-({[6-bromo-3-methyl-2-(piperidin-1-yl)quinolin-4-yl]carbonyl}-amino)-4-(2-chloro-3,6-difluorophenyl)pentanoate (269 mg, 413 μmol, racemate, Example 160A) in dichloromethane (5 ml) was added TFA (480 μl, 6.2 mmol), and the mixture was stirred at RT for 18 h. Subsequently, TFA (240 μl, 3.1 mmol) was added again, and the mixture was stirred at RT for a further 24 h. This was followed by concentration of the mixture, and repeated additions of dichloromethane followed by concentration again. The residue was purified by preparative HPLC (Method 6). The combined target fractions were concentrated, and the residue was lyophilized. 221 mg (100% purity, 90% of theory) of the title compound were obtained.

LC-MS (Method 1): $R_t$=2.19 min; MS (ESIpos): m/z=594/596 [M+H]$^+$
$^1$H-NMR (400 MHz, DMSO-d6) δ [ppm]: −0.008 (2.84), 0.008 (2.84), 1.606 (3.28), 1.673 (6.38), 1.980 (0.76), 2.073 (2.12), 2.095 (2.56), 2.122 (4.17), 2.143 (16.00), 2.172 (1.53), 2.194 (0.58), 2.327 (0.55), 2.366 (0.54), 2.669 (0.59), 2.710 (0.57), 3.137 (8.46), 3.722 (1.94), 7.267 (0.88), 7.278 (1.02), 7.290 (1.81), 7.301 (1.87), 7.316 (1.43), 7.327 (1.33), 7.389 (1.13), 7.400 (1.34), 7.410 (1.91), 7.421 (1.92), 7.433 (1.20), 7.444 (1.12), 7.629 (2.29), 7.650 (9.72), 7.660 (6.52), 7.665 (5.84), 7.683 (1.37), 7.687 (1.47), 8.821 (2.50).

Separation of the Enantiomers:

The title compound (200 mg) was dissolved in methanol (20 ml) and separated into the enantiomers by means of preparative SFC on chiral phase (see Examples 152 and 153) [column: Daicel Chiralcel OJ-H, 5 µm, 250 mm×20 mm; flow rate: 80 ml/min; detection: 210 nm; temperature: 40° C.; injection: 0.5 ml; eluent: 17% methanol/83% carbon dioxide; run time 5 min, isocratic]. The combined target fractions were each concentrated, and the respective residue was lyophilized.

Example 152

(−)-5-({[6-Bromo-3-methyl-2-(piperidin-1-yl)quinolin-4-yl]carbonyl}amino)-4-(2-chloro-3,6-difluorophenyl)pentanoic acid (Enantiomer 1)

In the enantiomer separation described in Example 151, 70 mg (99% purity, ee>99%) of the title compound were obtained as the enantiomer that eluted earlier.

$[\alpha]_D^{20}$=−35.9°, 589 nm, c=0.45 g/100 ml, methanol

LC-MS (Method 2): $R_t$=1.12 min; MS (ESIpos): m/z=594/596 [M+H]$^+$ $^1$H-NMR (400 MHz, DMSO-d6) δ [ppm]: −0.008 (0.78), 0.008 (0.73), 1.597 (2.64), 1.607 (2.93), 1.673 (5.58), 1.980 (0.71), 2.073 (1.02), 2.082 (1.14), 2.089 (1.23), 2.103 (2.10), 2.144 (16.00), 2.161 (3.72), 2.179 (1.26), 2.201 (0.46), 3.125 (5.49), 3.137 (7.35), 3.726 (1.72), 7.268 (0.79), 7.279 (0.89), 7.291 (1.58), 7.302 (1.63), 7.317 (1.24), 7.328 (1.14), 7.390 (1.02), 7.401 (1.20), 7.411 (1.67), 7.422 (1.65), 7.433 (1.05), 7.445 (0.95), 7.629 (1.92), 7.651 (8.28), 7.661 (5.32), 7.665 (4.77), 7.683 (1.12), 7.688 (1.20), 8.804 (1.22), 8.819 (2.19), 12.101 (1.08).

Example 153

(+)-5-({[6-Bromo-3-methyl-2-(piperidin-1-yl)quinolin-4-yl]carbonyl}amino)-4-(2-chloro-3,6-difluorophenyl)pentanoic acid (Enantiomer 2)

In the enantiomer separation described in Example 151, 67 mg (98% purity, ee 99%) of the title compound were obtained as the enantiomer that eluted later.

$[\alpha]_D^{20}$=+36.3°, 589 nm, c=0.38 g/100 ml, methanol

LC-MS (Method 2): $R_t$=1.13 min; MS (ESIpos): m/z=594/596 [M+H]$^+$ $^1$H-NMR (400 MHz, DMSO-d6) δ [ppm]: −0.008 (1.16), 0.008 (1.02), 1.607 (2.99), 1.673 (5.69), 1.980 (0.73), 2.102 (2.13), 2.144 (16.00), 2.159 (3.78), 2.178 (1.27), 2.201 (0.47), 3.125 (5.63), 3.137 (7.50), 3.725 (1.78), 7.268 (0.83), 7.279 (0.95), 7.291 (1.66), 7.302 (1.69), 7.317 (1.28), 7.328 (1.17), 7.390 (1.09), 7.401 (1.28), 7.411 (1.75), 7.422 (1.72), 7.433 (1.10), 7.445 (0.99), 7.629 (2.00), 7.651 (8.50), 7.661 (5.45), 7.666 (4.83), 7.683 (1.13), 7.688 (1.20), 8.804 (1.26), 8.818 (2.23), 12.101 (0.71).

Example 154

(+/−)-5-({[6-Bromo-3-methyl-2-(pyrrolidin-1-yl)quinolin-4-yl]carbonyl}amino)-4-(2-chloro-3,6-difluorophenyl)pentanoic acid (Racemate)

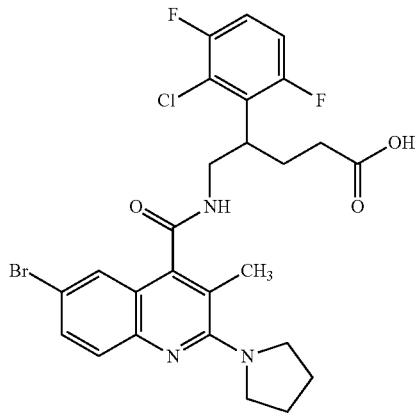 [SMILES: Cc1c(N2CCCC2)nc2ccc(Br)cc2c1C(=O)NCC(CCC(=O)O)c1c(F)ccc(F)c1Cl]

To a solution of (+/−)-tert-butyl 5-({[6-bromo-3-methyl-2-(pyrrolidin-1-yl)quinolin-4-yl]carbonyl}-amino)-4-(2-chloro-3,6-difluorophenyl)pentanoate (84 mg, 131 µmol, racemate, Example 161A) in dichloromethane (1.1 ml) was added TFA (220 µl, 2.9 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 24 mg (100% purity, 32% of theory) of the title compound were obtained.

LC-MS (Method 1): $R_t$=1.46 min; MS (ESIpos): m/z=580/582 [M+H]$^+$ $^1$H-NMR (400 MHz, DMSO-d6) δ [ppm]: 0.854 (0.47), 1.236 (2.28), 1.271 (0.43), 1.873 (16.00), 1.969 (1.55), 2.091 (4.87), 2.118 (6.28), 2.131 (8.95), 2.169 (15.24), 2.327 (0.58), 2.342 (0.50), 2.670 (0.47), 3.317 (4.55), 3.713 (4.24), 7.261 (1.77), 7.273 (2.08), 7.285 (3.43), 7.296 (3.55), 7.311 (2.67), 7.322 (2.43), 7.382 (2.28), 7.392 (2.69), 7.403 (3.45), 7.413 (3.29), 7.436 (1.69), 7.471 (8.63), 7.493 (14.06), 7.551 (7.71), 7.556 (7.15), 7.573 (4.50), 7.579 (4.32), 8.756 (2.66), 8.770 (4.44).

Example 155

(+/−)-5-({[6-Bromo-2-(3,3-difluoropiperidin-1-yl)-3-methylquinolin-4-yl]carbonyl}amino)-4-(2-chloro-3,6-difluorophenyl)pentanoic acid (Racemate)

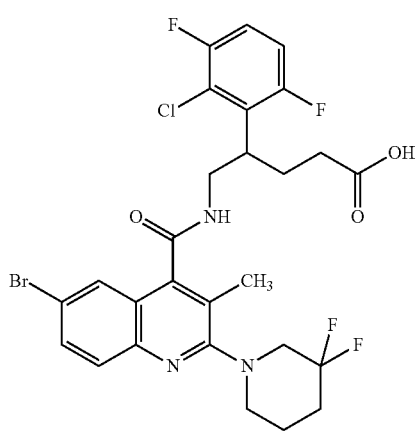 [SMILES: Cc1c(N2CCCC(F)(F)C2)nc2ccc(Br)cc2c1C(=O)NCC(CCC(=O)O)c1c(F)ccc(F)c1Cl]

To a solution of (+/−)-tert-butyl 5-({[6-bromo-2-(3,3-difluoropiperidin-1-yl)-3-methylquinolin-4-yl]carbonyl}amino)-4-(2-chloro-3,6-difluorophenyl)pentanoate (68 mg, 83% purity, 82.2 µmol, racemate, Example 162A) in dichloromethane (690 µl) was added TFA (140 µl, 1.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 35 mg (100% purity, 67% of theory) of the title compound were obtained.

LC-MS (Method 1): $R_t$=2.14 min; MS (ESIpos): m/z=630/632 [M+H]$^+$ $^1$H-NMR (400 MHz, DMSO-d6) δ [ppm]: −0.008 (1.30), 0.008 (1.39), 1.236 (0.67), 1.885 (2.91), 1.980 (0.64), 2.082 (2.77), 2.100 (3.27), 2.106 (3.21), 2.134 (4.76), 2.147 (4.55), 2.165 (16.00), 3.170 (3.69), 3.451 (2.24), 3.480 (4.31), 3.509 (2.17), 3.736 (1.60), 7.271 (0.76), 7.282 (0.86), 7.295 (1.56), 7.305 (1.62), 7.320 (1.22), 7.331 (1.11), 7.392 (0.94), 7.403 (1.13), 7.414 (1.56), 7.425 (1.52), 7.436 (0.92), 7.447 (0.78), 7.680 (1.80), 7.702 (8.65), 7.710 (5.87), 7.715 (5.09), 7.733 (1.08), 7.738 (1.16), 8.818 (1.29), 8.833 (2.32), 12.100 (1.60).

Example 156

5-[({6-Bromo-2-[3-fluoropiperidin-1-yl]-3-methylquinolin-4-yl}carbonyl)amino]-4-(2-chloro-3,6-difluorophenyl)pentanoic acid (Diastereomer Mixture)

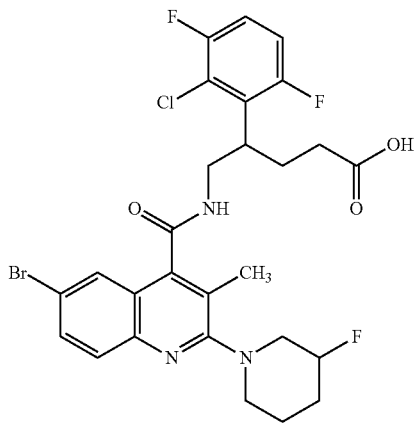

To a solution of tert-butyl 5-[({6-bromo-2-[3-fluoropiperidin-1-yl]-3-methylquinolin-4-yl}carbonyl)amino]-4-(2-chloro-3,6-difluorophenyl)pentanoate (85 mg, 127 µmol, diastereomer mixture, Example 163A) in dichloromethane (1.1 ml) was added TFA (220 µl, 2.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 51 mg (100% purity, 65% of theory) of the title compound were obtained.

LC-MS (Method 1): $R_t$=2.09 min; MS (ESIpos): m/z=612/614 [M+H]$^+$ $^1$H-NMR (400 MHz, DMSO-d6) δ [ppm]: −0.008 (1.33), 1.235 (0.52), 1.647 (1.14), 1.808 (1.08), 1.901 (1.96), 1.921 (1.82), 1.953 (1.67), 1.984 (1.23), 2.099 (2.21), 2.127 (3.58), 2.139 (4.40), 2.157 (16.00), 2.198 (0.59), 3.100 (1.31), 3.166 (1.35), 3.174 (1.35), 3.381 (1.62), 3.413 (0.83), 3.438 (1.26), 3.467 (0.80), 3.728 (1.77), 4.820 (0.94), 4.938 (0.95), 7.268 (0.78), 7.279 (0.90), 7.292 (1.63), 7.303 (1.69), 7.318 (1.28), 7.329 (1.18), 7.390 (0.96), 7.411 (1.63), 7.422 (1.63), 7.445 (0.87), 7.653 (1.94), 7.676 (8.85), 7.684 (5.74), 7.689 (5.25), 7.706 (1.15), 7.711 (1.24), 8.814 (1.27), 8.828 (2.28).

Example 157

5-[({6-Bromo-3-methyl-2-[3-methylpiperidin-1-yl]quinolin-4-yl}carbonyl)amino]-4-(2-chloro-3,6-difluorophenyl)pentanoic acid (Diastereomer Mixture)

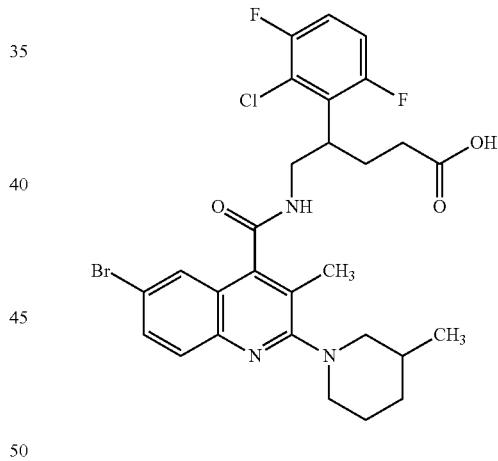

To a solution of tert-butyl 5-[({6-bromo-3-methyl-2-[3-methylpiperidin-1-yl]quinolin-4-yl}carbonyl)amino]-4-(2-chloro-3,6-difluorophenyl)pentanoate (85 mg, 128 µmol, diastereomer mixture, Example 164A) in dichloromethane (1.1 ml) was added TFA (220 µl, 2.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 53 mg (100% purity, 69% of theory) of the title compound were obtained.

LC-MS (Method 1): $R_t$=2.33 min; MS (ESIpos): m/z=608/610 [M+H]$^+$

¹H-NMR (400 MHz, DMSO-d6) δ [ppm]: 0.922 (10.55), 0.938 (10.81), 1.051 (0.41), 1.080 (1.22), 1.108 (1.27), 1.131 (0.52), 1.235 (0.49), 1.630 (0.96), 1.657 (1.13), 1.732 (2.16), 1.765 (2.08), 1.793 (2.57), 1.824 (1.63), 1.983 (0.80), 2.104 (2.45), 2.145 (16.00), 2.161 (4.62), 2.179 (1.52), 2.203 (0.55), 2.461 (1.21), 2.679 (0.77), 2.711 (1.36), 2.741 (0.72), 3.436 (1.83), 3.464 (3.30), 3.493 (1.55), 3.725 (1.98), 7.268 (0.89), 7.279 (1.01), 7.292 (1.83), 7.303 (1.89), 7.317 (1.40), 7.329 (1.28), 7.390 (1.15), 7.401 (1.39), 7.412 (1.93), 7.423 (1.91), 7.433 (1.23), 7.445 (1.09), 7.632 (1.57), 7.654 (9.91), 7.658 (7.43), 7.663 (5.90), 7.681 (0.88), 7.685 (1.00), 8.796 (1.39), 8.811 (2.45), 12.100 (2.08).

Example 158

5-[({6-Bromo-2-[3-ethylpiperidin-1-yl]-3-methylquinolin-4-yl}carbonyl)amino]-4-(2-chloro-3,6-difluorophenyl)pentanoic acid (Diastereomer Mixture)

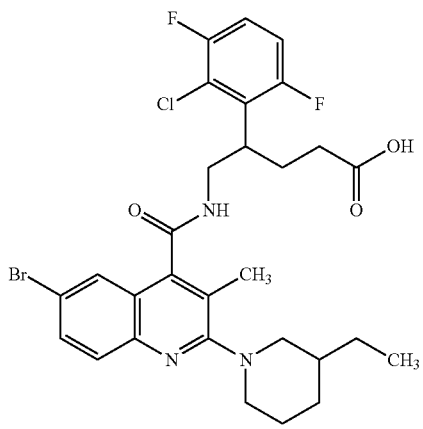 [SMILES: CCC1CCCN(c2nc3ccc(Br)cc3c(C(=O)NCC(CCC(=O)O)c3c(F)ccc(F)c3Cl)c2C)C1]

To a solution of tert-butyl 5-[({6-bromo-2-[3-ethylpiperidin-1-yl]-3-methylquinolin-4-yl}carbonyl)amino]-4-(2-chloro-3,6-difluorophenyl)pentanoate (85 mg, 125 µmol, diastereomer mixture, Example 165A) in dichloromethane (1.1 ml) was added TFA (210 µl, 2.8 mmol), and the mixture was left to stand at RT for 18 h. The mixture was then concentrated and repeatedly dichloromethane was added and the mixture was concentrated again. The residue was purified by preparative HPLC (Method 7). The combined target fractions were concentrated, and the residue was lyophilized. 59 mg (100% purity, 76% of theory) of the title compound were obtained.

LC-MS (Method 1): R$_t$=2.44 min; MS (ESIpos): m/z=622/624 [M+H]⁺

¹H-NMR (400 MHz, DMSO-d6) δ [ppm]: 0.008 (2.12), 0.891 (5.97), 0.910 (13.55), 0.928 (7.25), 1.038 (0.57), 1.066 (1.50), 1.088 (1.54), 1.096 (1.54), 1.117 (0.72), 1.241 (1.46), 1.259 (3.18), 1.277 (4.17), 1.294 (2.81), 1.566 (1.70), 1.600 (1.55), 1.633 (1.32), 1.748 (2.11), 1.781 (1.43), 1.847 (1.75), 1.878 (1.71), 1.972 (0.97), 2.067 (1.41), 2.104 (3.81), 2.136 (16.00), 2.162 (4.53), 2.181 (1.63), 2.203 (0.64), 2.327 (0.43), 2.423 (1.35), 2.670 (0.43), 2.745 (1.52), 3.488 (3.26), 3.518 (3.03), 3.725 (2.52), 7.266 (1.04), 7.277 (1.19), 7.290 (2.16), 7.300 (2.21), 7.315 (1.62), 7.326 (1.46), 7.386 (1.42), 7.397 (1.68), 7.408 (2.33), 7.419 (2.32), 7.429 (1.44), 7.441 (1.30), 7.631 (1.77), 7.653 (11.15), 7.684 (1.03), 8.794 (1.74), 8.809 (3.01), 12.096 (8.21).

Example 159

(+/−)-5-({[2-(Azepan-1-yl)-6-bromo-3-methylquinolin-4-yl]carbonyl}amino)-4-(2-chloro-3,6-difluorophenyl)pentanoic acid (Racemate)

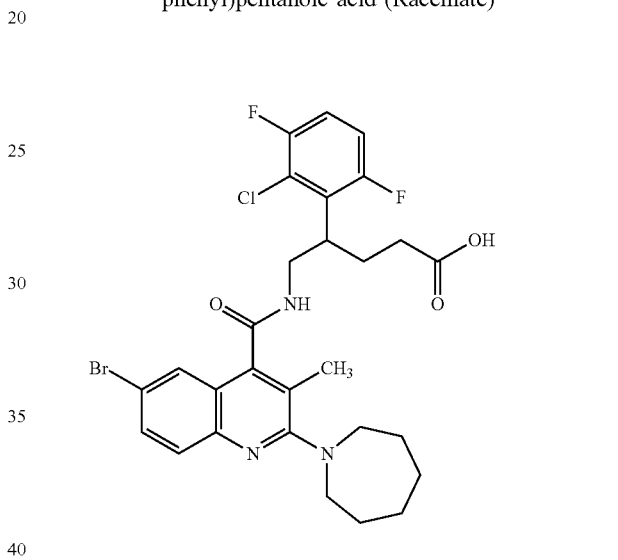

To a solution of (+/−)-tert-butyl 5-({[2-(azepan-1-yl)-6-bromo-3-methylquinolin-4-yl]carbonyl}-amino)-4-(2-chloro-3,6-difluorophenyl)pentanoate (85 mg, 128 µmol, racemate, Example 166A) in dichloromethane (1.1 ml) was added TFA (210 µl, 2.8 mmol), and the mixture was left to stand at RT for 3.5 h. The mixture was then concentrated and repeatedly dichloromethane was added and the mixture was concentrated again. The residue was purified by preparative HPLC (Method 7). The combined target fractions were concentrated, and the residue was lyophilized. 54 mg (100% purity, 69% of theory) of the title compound were obtained.

LC-MS (Method 1): R$_t$=2.22 min; MS (ESIpos): m/z=608/610 [M+H]⁺

¹H-NMR (400 MHz, DMSO-d6) δ [ppm]: 1.603 (11.39), 1.781 (7.18), 1.972 (0.89), 2.104 (2.93), 2.134 (16.00), 2.161 (4.26), 2.179 (1.62), 2.202 (0.64), 3.492 (8.81), 3.506 (13.30), 3.521 (8.69), 3.722 (2.42), 7.267 (1.00), 7.278 (1.15), 7.291 (2.00), 7.301 (2.10), 7.316 (1.57), 7.327 (1.47), 7.388 (1.42), 7.400 (1.68), 7.410 (2.19), 7.421 (2.12), 7.444 (1.08), 7.531 (4.68), 7.553 (8.36), 7.600 (4.67), 7.606 (4.40), 7.622 (2.52), 7.628 (2.47), 8.792 (2.66), 12.101 (1.23).

Example 160

(+/−)-5-({[6-Bromo-3-methyl-2-(piperidin-1-yl)quinolin-4-yl]carbonyl}amino)-4-[2-fluoro-6-(trifluoromethyl)phenyl]pentanoic acid (Racemate)

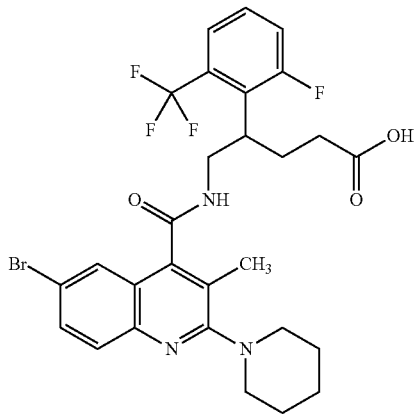 [SMILES: Cc1c(N2CCCCC2)nc2ccc(Br)cc2c1C(=O)NCC(CCC(=O)O)c1c(F)cccc1C(F)(F)F]

To a solution of (+/−)-tert-butyl 5-({[6-bromo-3-methyl-2-(piperidin-1-yl)quinolin-4-yl]carbonyl}-amino)-4-[2-fluoro-6-(trifluoromethyl)phenyl]pentanoate (55 mg, 82.5 μmol, racemate, Example 167A) in dichloromethane (1.1 ml) was added TFA (610 μl, 8.3 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 45 mg (100% purity, 89% of theory) of the title compound were obtained.

LC-MS (Method 1): $R_t$=2.21 min; MS (ESIpos): m/z=610/612 [M+H]$^+$ $^1$H-NMR (400 MHz, DMSO-d6) δ [ppm]: −0.149 (1.21), −0.008 (15.78), 0.008 (11.37), 0.146 (1.24), 1.234 (1.30), 1.340 (0.44), 1.611 (5.24), 1.677 (10.32), 2.017 (1.79), 2.030 (3.50), 2.060 (4.14), 2.092 (2.65), 2.121 (5.79), 2.136 (5.10), 2.167 (15.23), 2.268 (0.63), 2.327 (1.41), 2.366 (0.44), 2.670 (1.41), 3.148 (13.24), 3.703 (1.54), 3.873 (1.46), 7.383 (0.58), 7.562 (5.88), 7.571 (5.05), 7.577 (4.94), 7.587 (4.08), 7.595 (8.17), 7.626 (5.79), 7.652 (16.00), 7.658 (11.67), 7.663 (9.57), 7.680 (1.57), 7.685 (1.77), 8.808 (2.37), 8.824 (4.50), 8.839 (2.21), 12.075 (1.49).

$^1$H-NMR (400 MHz, DMSO-d6) δ [ppm]: 12.08 (br. s, 1H), 8.82 (t, 1H), 7.74-7.51 (m, 5H), 7.38 (br. s, 1H), 3.87 (br. s, 1H), 3.70 (br. s, 1H), 3.33-3.27 (1H, concealed, tentative), 3.20-3.10 (m, 4H), 2.25-1.95 (m, 7H), 1.70-1.55 (m, 6H).

Example 161

(−)-5-({[6-Bromo-3-methyl-2-(piperidin-1-yl)quinolin-4-yl]carbonyl}amino)-4-[2-fluoro-6-(trifluoromethyl)phenyl]pentanoic acid (Enantiomer 1)

To a solution of tert-butyl 5-({[6-bromo-3-methyl-2-(piperidin-1-yl)quinolin-4-yl]carbonyl}amino)-4-[2-fluoro-6-(trifluoromethyl)phenyl]pentanoate (85 mg, 128 μmol, enantiomer 1, Example 168A) in dichloromethane (1.7 ml) was added TFA (950 μl, 13 mmol), and the mixture was stirred at RT for 1 h. Subsequently, the mixture was concentrated and the residue was taken up in DMSO and purified by means of preparative HPLC (Method 20). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 63 mg (98% purity, 79% of theory) of the title compound were obtained.

$[α]_D^{20}$=−40.1°, 589 nm, c=0.38 g/100 ml, methanol

LC-MS (Method 1): $R_t$=2.24 min; MS (ESIpos): m/z=610/612 [M+H]$^+$ $^1$H-NMR (400 MHz, DMSO-d6) δ [ppm]: −0.149 (0.84), 0.146 (0.81), 1.612 (5.48), 1.678 (10.55), 2.019 (1.74), 2.031 (3.64), 2.062 (4.46), 2.084 (2.72), 2.122 (6.02), 2.137 (5.09), 2.167 (16.00), 2.268 (0.57), 2.327 (1.29), 2.366 (0.72), 2.670 (1.38), 2.710 (0.81), 3.149 (13.62), 3.162 (14.23), 3.174 (7.58), 3.511 (0.50), 3.694 (1.67), 3.877 (1.54), 4.076 (1.83), 4.089 (1.77), 7.370 (0.63), 7.563 (5.36), 7.577 (5.14), 7.595 (7.85), 7.627 (5.54), 7.652 (14.78), 7.684 (1.70), 8.806 (2.22), 8.821 (4.53), 8.836 (2.38), 12.061 (1.47).

Example 162

(+)-5-({[6-Bromo-3-methyl-2-(piperidin-1-yl)quinolin-4-yl]carbonyl}amino)-4-[2-fluoro-6-(trifluoromethyl)phenyl]pentanoic acid (Enantiomer 2)

To a solution of tert-butyl 5-({[6-bromo-3-methyl-2-(piperidin-1-yl)quinolin-4-yl]carbonyl}amino)-4-[2-fluoro-6-(trifluoromethyl)phenyl]pentanoate (93 mg, 140 μmol, enantiomer 2, Example 169A) in dichloromethane (1.9 ml) was added TFA (1.0 ml, 14 mmol), and the mixture was stirred at RT for 1 h. Subsequently, the mixture was concentrated and the residue was taken up in DMSO and purified by means of preparative HPLC (Method 20). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 68 mg (98% purity, 78% of theory) of the title compound were obtained.

$[α]_D^{20}$=+45.9°, 589 nm, c=0.45 g/100 ml, methanol

LC-MS (Method 1): $R_t$=2.21 min; MS (ESIpos): m/z=610/612 [M+H]$^+$ $^1$H-NMR (400 MHz, DMSO-d6) δ [ppm]: −0.149 (0.70), −0.008 (5.63), 0.008 (5.76), 0.146 (0.70), 1.613 (4.93), 1.679 (9.47), 2.019 (1.64), 2.032 (3.34), 2.062 (4.01), 2.093 (2.39), 2.122 (5.44), 2.137 (4.54), 2.167 (14.53), 2.268 (0.52), 2.327 (1.02), 2.366 (0.57), 2.670 (1.02), 2.710 (0.56), 3.149 (12.27), 3.162 (10.30), 3.174 (4.19), 3.707 (1.42), 3.876 (1.33), 4.075 (0.66), 4.089 (0.66), 7.370 (0.56), 7.563 (5.67), 7.572 (4.77), 7.578 (4.68), 7.587 (3.90), 7.596 (8.06), 7.626 (5.40), 7.653 (16.00), 7.658 (11.01), 7.663 (9.24), 7.681 (1.51), 7.685 (1.70), 8.807 (2.26), 8.822 (4.55), 8.837 (2.29), 12.062 (1.62).

Example 163

(+/−)-5-({[6-Bromo-3-methyl-2-(pyrrolidin-1-yl)quinolin-4-yl]carbonyl}amino)-4-[2-fluoro-6-(trifluoromethyl)phenyl]pentanoic acid (Racemate)

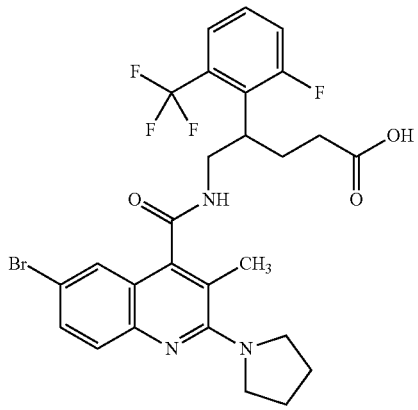 [SMILES: Cc1c(N2CCCC2)nc2ccc(Br)cc2c1C(=O)NCC(CCC(=O)O)c1c(F)cccc1C(F)(F)F]

To a solution of (+/−)-tert-butyl 5-({[6-bromo-3-methyl-2-(pyrrolidin-1-yl)quinolin-4-yl]carbonyl}-amino)-4-[2-fluoro-6-(trifluoromethyl)phenyl]pentanoate (55 mg, 84.3 μmol, racemate, Example 170A) in dichloromethane (1.1 ml) was added TFA (630 μl, 8.4 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 41 mg (100% purity, 82% of theory) of the title compound were obtained.

LC-MS (Method 1): $R_t$=1.51 min; MS (ESIpos): m/z=596/598 [M+H]$^+$ $^1$H-NMR (400 MHz, DMSO-d6) δ [ppm]: −0.149 (1.17), −0.008 (10.78), 0.008 (13.42), 0.146 (1.33), 1.879 (16.00), 2.012 (2.39), 2.026 (3.42), 2.056 (4.94), 2.085 (2.81), 2.118 (5.81), 2.125 (5.56), 2.154 (6.67), 2.171 (6.97), 2.328 (2.11), 2.366 (0.53), 2.669 (1.75), 3.581 (11.19), 3.895 (1.53), 7.474 (8.50), 7.496 (14.53), 7.549 (8.83), 7.555 (10.11), 7.571 (10.28), 7.577 (8.56), 7.592 (8.33), 7.617 (5.47), 7.629 (3.89), 7.640 (2.44), 8.139 (1.83), 8.748 (2.86), 8.763 (5.56), 8.778 (2.81), 12.088 (1.00).

$^1$H-NMR (400 MHz, DMSO-d6) δ [ppm]: 12.09 (br. s, 1H), 8.76 (t, 1H), 7.72-7.52 (m, 4H), 7.51-7.39 (m, 1H), 7.28 (br. s, 1H), 3.90 (br. s, 1H), 3.73-3.49 (m, 5H), 3.33-2.26 (1H, concealed, tentative), 2.27-1.95 (m, 7H), 1.82-1.83 (m, 4H).

Example 164

(+)-5-({[6-Bromo-3-methyl-2-(pyrrolidin-1-yl)quinolin-4-yl]carbonyl}amino)-4-[2-fluoro-6-(trifluoromethyl)phenyl]pentanoic acid (Enantiomer 1)

To a solution of tert-butyl 5-({[6-bromo-3-methyl-2-(pyrrolidin-1-yl)quinolin-4-yl]carbonyl}amino)-4-[2-fluoro-6-(trifluoromethyl)phenyl]pentanoate (75 mg, 115 μmol, enantiomer 1, Example 171A) in dichloromethane (1.5 ml) was added TFA (850 μl, 11 mmol), and the mixture was stirred at RT for 1 h. Subsequently, the mixture was concentrated and the residue was taken up in DMSO and purified by means of preparative HPLC (Method 22). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 55 mg (99% purity, 79% of theory) of the title compound were obtained.

$[α]_D^{20}$=+38.1°, 589 nm, c=0.35 g/100 ml, methanol

LC-MS (Method 1): $R_t$=1.54 min; MS (ESIpos): m/z=596/598 [M+H]$^+$ $^1$H-NMR (400 MHz, DMSO-d6) δ [ppm]: −0.149 (1.69), −0.008 (13.12), 0.146 (1.65), 1.880 (16.00), 2.012 (2.46), 2.027 (3.61), 2.056 (5.18), 2.089 (2.95), 2.118 (5.99), 2.125 (5.83), 2.154 (6.79), 2.176 (6.98), 2.328 (2.53), 2.366 (1.42), 2.670 (2.30), 2.710 (1.50), 2.998 (0.42), 3.071 (2.07), 3.169 (2.76), 3.581 (11.20), 3.926 (2.19), 4.072 (0.42), 4.154 (3.65), 7.431 (0.58), 7.474 (7.60), 7.497 (13.47), 7.549 (8.02), 7.555 (9.63), 7.571 (10.24), 7.577 (8.75), 7.592 (8.71), 7.617 (5.83), 7.629 (4.34), 7.676 (1.96), 8.136 (1.23), 8.748 (2.95), 8.763 (5.76), 8.779 (2.88), 12.062 (1.73).

Example 165

(−)-5-({[6-Bromo-3-methyl-2-(pyrrolidin-1-yl)quinolin-4-yl]carbonyl}amino)-4-[2-fluoro-6-(trifluoromethyl)phenyl]pentanoic acid (Enantiomer 2)

To a solution of tert-butyl 5-({[6-bromo-3-methyl-2-(pyrrolidin-1-yl)quinolin-4-yl]carbonyl}amino)-4-[2-fluoro-6-(trifluoromethyl)phenyl]pentanoate (79 mg, 121 μmol, enantiomer 2, Example 172A) in dichloromethane (1.6 ml) was added TFA (900 μl, 12 mmol), and the mixture was stirred at RT for 1 h. Subsequently, the mixture was concentrated and the residue was taken up in DMSO and purified by means of preparative HPLC (Method 21). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 49 mg (97% purity, 66% of theory) of the title compound were obtained.

$[α]_D^{20}$=−41.4°, 589 nm, c=0.35 g/100 ml, methanol

LC-MS (Method 1): $R_t$=1.53 min; MS (ESIpos): m/z=596/598 [M+H]$^+$ $^1$H-NMR (400 MHz, DMSO-d6) δ [ppm]: −0.150 (1.29), −0.008 (10.93), 0.008 (10.93), 0.146 (1.33), 1.879 (16.00), 2.012 (2.80), 2.026 (3.87), 2.056 (5.56), 2.092 (3.20), 2.118 (6.40), 2.124 (6.22), 2.153 (6.98), 2.171 (7.07), 2.293 (0.58), 2.327 (2.18), 2.366 (0.98), 2.669 (2.22), 2.709 (1.29), 3.162 (0.62), 3.174 (0.71), 3.210 (0.58), 3.472 (0.93), 3.580 (11.02), 3.897 (1.87), 7.393 (0.58), 7.409 (0.62), 7.432 (0.89), 7.474 (6.98), 7.496 (12.49), 7.549 (7.78), 7.555 (9.56), 7.571 (10.22), 7.592 (8.93), 7.617 (5.91), 7.628 (4.44), 7.640 (2.89), 8.748 (3.11), 8.763 (5.69), 8.778 (2.89), 9.693 (0.44), 12.054 (6.53).

Example 166

(+/−)-5-({[6-Bromo-2-(3,3-difluoropiperidin-1-yl)-3-methylquinolin-4-yl]carbonyl}amino)-4-[2-fluoro-6-(trifluoromethyl)phenyl]pentanoic acid (Racemate)

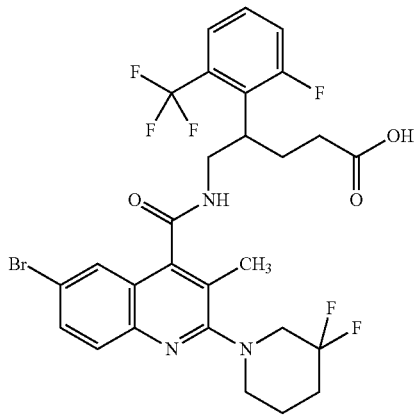 [SMILES: Cc1c(N2CCCC(F)(F)C2)nc2ccc(Br)cc2c1C(=O)NCC(CCC(=O)O)c1c(F)cccc1C(F)(F)F]

To a solution of (+/−)-tert-butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (55 mg, 78.3 µmol, racemate, Example 173A) in dichloromethane (1.0 ml) was added TFA (580 µl, 7.8 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 50 mg (100% purity, 99% of theory) of the title compound were obtained.

LC-MS (Method 1): $R_t$=2.16 min; MS (ESIpos): m/z=646/648 [M+H]$^+$ $^1$H-NMR (400 MHz, DMSO-d6) δ [ppm]: −0.149 (0.66), −0.008 (8.90), 0.008 (6.39), 0.146 (0.64), 1.890 (5.53), 2.037 (4.19), 2.067 (7.01), 2.087 (6.21), 2.099 (6.24), 2.122 (8.03), 2.137 (6.44), 2.155 (5.81), 2.188 (14.73), 2.293 (0.54), 2.327 (0.78), 2.670 (0.80), 3.175 (6.37), 3.186 (5.71), 3.462 (4.30), 3.491 (7.92), 3.520 (3.94), 3.699 (1.55), 3.891 (1.37), 7.420 (0.55), 7.566 (5.81), 7.575 (5.24), 7.581 (5.08), 7.591 (4.30), 7.599 (7.83), 7.628 (5.37), 7.638 (3.85), 7.652 (2.57), 7.681 (2.59), 7.704 (16.00), 7.707 (13.15), 7.712 (9.58), 7.730 (1.41), 7.734 (1.57), 8.820 (2.64), 8.835 (4.85), 8.850 (2.43), 12.072 (2.23).

$^1$H-NMR (400 MHz, DMSO-d$_6$): δ [ppm]=12.07 (br. s, 1H), 8.84 (t, 1H), 7.77-7.52 (m, 5H), 7.52-7.17 (m, 1H), 4.01-3.81 (m, 1H), 3.81-3.61 (m, 1H), 3.49 (t, 2H), 3.25-3.10 (m, 2H), 2.30-1.99 (m, 10H), 1.89 (br. s, 2H).

Example 167

(−)-5-({[6-Bromo-2-(3,3-difluoropiperidin-1-yl)-3-methylquinolin-4-yl]carbonyl}amino)-4-[2-fluoro-6-(trifluoromethyl)phenyl]pentanoic acid (Enantiomer 1)

To a solution of tert-butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (91 mg, 130 µmol, enantiomer 1, Example 174A) in dichloromethane (1.7 ml) was added TFA (960 µl, 13 mmol), and the mixture was stirred at RT for 1 h. Subsequently, the mixture was concentrated and the residue was taken up in DMSO and purified by means of preparative HPLC (Method 19). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 61 mg (97% purity, 71% of theory) of the title compound were obtained.

$[α]_D^{20}$=−40.8°, 589 nm, c=0.34 g/100 ml, methanol

LC-MS (Method 1): $R_t$=2.16 min; MS (ESIpos): m/z=646/648 [M+H]$^+$ $^1$H-NMR (400 MHz, DMSO-d6) δ [ppm]: −0.149 (0.45), 0.146 (0.47), 1.891 (5.64), 2.038 (4.28), 2.068 (7.20), 2.088 (6.27), 2.099 (6.42), 2.123 (8.16), 2.137 (6.54), 2.155 (5.94), 2.189 (15.09), 2.293 (0.57), 2.328 (0.70), 2.366 (0.41), 2.670 (0.67), 2.710 (0.41), 3.163 (11.92), 3.175 (14.69), 3.462 (4.32), 3.491 (8.03), 3.520 (4.01), 3.703 (1.56), 3.895 (1.38), 4.063 (1.08), 4.076 (2.53), 4.089 (2.43), 4.102 (0.90), 7.422 (0.55), 7.566 (5.90), 7.575 (5.37), 7.581 (5.29), 7.591 (4.40), 7.599 (7.94), 7.628 (5.40), 7.638 (3.92), 7.651 (2.59), 7.681 (2.56), 7.703 (16.00), 7.712 (9.63), 7.730 (1.32), 7.734 (1.55), 8.819 (2.73), 8.834 (5.02), 8.849 (2.47), 12.066 (3.48).

Example 168

(+)-5-({[6-Bromo-2-(3,3-difluoropiperidin-1-yl)-3-methylquinolin-4-yl]carbonyl}amino)-4-[2-fluoro-6-(trifluoromethyl)phenyl]pentanoic acid (Enantiomer 2)

To a solution of tert-butyl 5-({[6-bromo-2-(3,3-difluoropiperidin-1-yl)-3-methylquinolin-4-yl]carbonyl}amino)-4-[2-fluoro-6-(trifluoromethyl)phenyl]pentanoate (93 mg, 132 µmol, enantiomer 2, Example 175A) in dichloromethane (1.8 ml) was added TFA (980 µl, 13 mmol), and the mixture was stirred at RT for 1 h. Subsequently, the mixture was concentrated and the residue was taken up in DMSO and purified by means of preparative HPLC (Method 19). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 61 mg (98% purity, 70% of theory) of the title compound were obtained.

$[α]_D^{20}$=−40.8°, 589 nm, c=0.34 g/100 ml, methanol

LC-MS (Method 1): $R_t$=2.16 min; MS (ESIpos): m/z=646/648 [M+H]$^+$ $^1$H-NMR (400 MHz, DMSO-d6) δ [ppm]: −0.149 (1.31), 0.146 (1.38), 1.890 (5.50), 2.034 (3.86), 2.067 (6.68), 2.086 (6.14), 2.097 (5.80), 2.121 (8.32), 2.136 (6.41), 2.153 (5.43), 2.188 (15.23), 2.292 (0.50), 2.327 (1.78), 2.366 (1.11), 2.670 (2.05), 2.710 (1.21), 3.162 (12.11), 3.175 (15.19), 3.462 (4.33), 3.491 (8.18), 3.519 (4.13), 3.708 (1.54), 3.894 (1.44), 4.063 (0.97), 4.074 (2.62), 4.088 (2.65), 4.100 (1.01), 7.424 (0.57), 7.566 (5.47), 7.575 (5.03), 7.599 (8.02), 7.628 (5.27), 7.638 (3.89), 7.651 (2.58), 7.680 (2.11), 7.703 (16.00), 7.734 (1.61), 8.821 (2.28), 8.837 (4.46), 8.851 (2.38), 12.068 (1.31).

Example 169

5-[({6-Bromo-2-[3-fluoropiperidin-1-yl]-3-methylquinolin-4-yl}carbonyl)amino]-4-[2-fluoro-6-(trifluoromethyl)phenyl]pentanoic acid (Diastereomer Mixture)

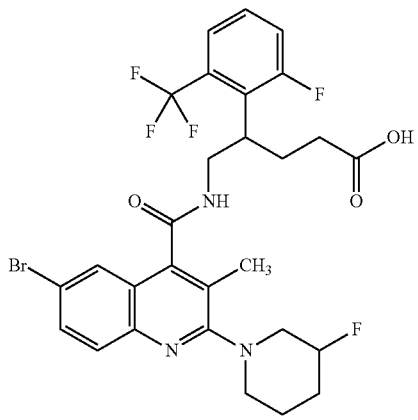 [SMILES: Cc1c(N2CCCC(F)C2)nc2ccc(Br)cc2c1C(=O)NCC(CCC(=O)O)c1c(F)cccc1C(F)(F)F]

To a solution of tert-butyl 5-[({6-bromo-2-[3-fluoropiperidin-1-yl]-3-methylquinolin-4-yl}carbonyl)amino]-4-[2-fluoro-6-(trifluoromethyl)phenyl]pentanoate (55 mg, 80.3 µmol, diastereomer mixture, Example 176A) in dichloromethane (1.1 ml) was added TFA (600 µl, 8.0 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 43 mg (100% purity, 85% of theory) of the title compound were obtained.

LC-MS (Method 1): $R_t$=2.11 min; MS (ESIpos): m/z=628/630 [M+H]$^+$ $^1$H-NMR (400 MHz, DMSO-d6) δ [ppm]: −0.149 (1.05), −0.008 (8.09), 0.008 (9.08), 0.146 (1.02), 1.654 (2.10), 1.811 (1.98), 1.907 (3.49), 1.927 (3.06), 1.957 (2.29), 2.002 (1.61), 2.021 (2.10), 2.035 (4.08), 2.065 (5.07), 2.087 (3.12), 2.123 (6.15), 2.137 (4.76), 2.156 (5.44), 2.181 (16.00), 2.286 (0.59), 2.328 (1.33), 2.670 (1.36), 3.118 (2.38), 3.178 (2.53), 3.356 (2.47), 3.392 (2.47), 3.424 (1.42), 3.449 (2.29), 3.482 (1.45), 3.705 (1.67), 3.888 (1.51), 4.827 (1.70), 4.939 (1.76), 7.417 (0.65), 7.565 (6.15), 7.573 (5.50), 7.589 (4.36), 7.597 (8.93), 7.627 (5.93), 7.636 (4.26), 7.652 (3.37), 7.677 (15.14), 7.708 (1.64), 8.815 (2.44), 8.829 (4.76), 8.844 (2.44), 12.073 (2.35).

$^1$H-NMR (400 MHz, DMSO-d$_6$): δ [ppm]=12.07 (br. s, 1H), 8.83 (t, 1H), 7.73-7.54 (m, 5H), 7.52-7.26 (m, 1H), 4.88 (br. d, 1H), 4.00-3.80 (m, 1H), 3.77-3.60 (m, 1H), 3.52-3.33 (m, 3H, partially hidden, tentative), 3.25-3.03 (m, 2H), 2.26-1.72 (m, 10H), 1.70-1.57 (m, 1H).

Example 170

5-[({6-Bromo-2-[3-ethylpiperidin-1-yl]-3-methylquinolin-4-yl}carbonyl)amino]-4-[2-fluoro-6-(trifluoromethyl)phenyl]pentanoic acid (Diastereomer Mixture)

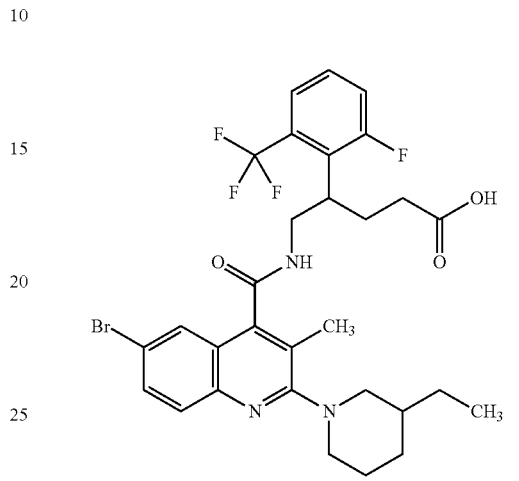

To a solution of tert-butyl 5-[({6-bromo-2-[3-ethylpiperidin-1-yl]-3-methylquinolin-4-yl}carbonyl)amino]-4-[2-fluoro-6-(trifluoromethyl)phenyl]pentanoate (57 mg, 82 µmol, diastereomer mixture, Example 177A) in dichloromethane (1.1 ml) was added TFA (610 µl, 8.2 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 51 mg (100% purity, 97% of theory) of the title compound were obtained.

LC-MS (Method 1): $R_t$=2.46 min; MS (ESIpos): m/z=638 [M+H]$^+$ $^1$H-NMR (400 MHz, DMSO-d6) δ [ppm]: −0.149 (1.26), −0.008 (16.00), 0.008 (10.04), 0.146 (1.32), 0.896 (5.78), 0.914 (13.57), 0.933 (6.59), 1.071 (1.05), 1.092 (1.14), 1.263 (2.01), 1.280 (2.73), 1.290 (2.22), 1.308 (1.53), 1.574 (1.32), 1.640 (1.02), 1.753 (1.53), 1.853 (1.32), 1.882 (1.20), 2.031 (1.92), 2.062 (2.58), 2.086 (1.74), 2.122 (3.69), 2.137 (4.58), 2.162 (6.14), 2.327 (1.44), 2.669 (1.38), 2.710 (0.81), 2.739 (1.05), 3.512 (2.52), 3.688 (0.84), 3.900 (0.84), 7.563 (3.09), 7.573 (2.85), 7.595 (4.28), 7.626 (2.67), 7.654 (9.32), 7.657 (9.41), 7.680 (0.60), 8.813 (2.10), 12.069 (1.14).

$^1$H-NMR (400 MHz, DMSO-d$_6$): δ [ppm]=12.07 (br. s, 1H), 8.81 (t, 1H), 7.70-7.52 (m, 5H), 7.51-7.19 (br. m, 1H), 3.99-3.82 (m, 1H), 3.76-3.62 (m, 1H), 3.58-3.45 (m, 2H), 2.84-2.69 (m, 1H), 2.50-2.37 (m, 1H, partially hidden), 2.24-1.99 (m, 8H), 1.93-1.82 (m, 1H), 1.82-1.71 (m, 1H), 1.70-1.49 (m, 2H), 1.38-1.20 (m, 2H), 1.08 (br. q, 1H), 0.91 (t, 3H).

Example 171

(+/−)-5-({[6-Bromo-3-methyl-2-(piperidin-1-yl)quinolin-4-yl]carbonyl}amino)-4-(2,3,6-trichlorophenyl)pentanoic acid (Racemate)

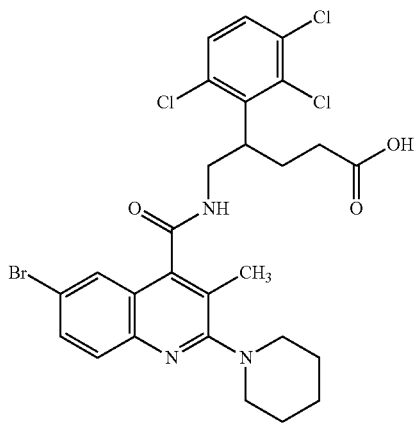 [SMILES: Cc1c(N2CCCCC2)nc2ccc(Br)cc2c1C(=O)NCC(CCC(=O)O)c1c(Cl)ccc(Cl)c1Cl]

To a solution of (+/−)-tert-butyl 5-({[6-bromo-3-methyl-2-(piperidin-1-yl)quinolin-4-yl]carbonyl}-amino)-4-(2,3,6-trichlorophenyl)pentanoate (55 mg, 80.4 µmol, racemate, Example 178A) in dichloromethane (1.1 ml) was added TFA (600 µl, 8.0 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 49 mg (100% purity, 97% of theory) of the title compound were obtained.

LC-MS (Method 1): $R_t$=2.34 min; MS (ESIpos): m/z=626/628/630 [M+H]$^+$ $^1$H-NMR (400 MHz, DMSO-d6) δ [ppm]: −0.149 (1.91), −0.008 (16.00), 0.008 (14.22), 0.146 (1.95), 1.234 (0.51), 1.610 (3.52), 1.675 (6.66), 2.071 (1.40), 2.085 (1.95), 2.099 (2.63), 2.120 (3.18), 2.136 (7.09), 2.155 (3.52), 2.169 (14.39), 2.180 (3.35), 2.203 (1.49), 2.282 (1.40), 2.327 (2.55), 2.366 (0.42), 2.670 (2.04), 2.710 (0.55), 3.140 (8.79), 3.807 (1.23), 4.065 (1.99), 7.476 (2.50), 7.498 (3.56), 7.533 (3.18), 7.555 (5.43), 7.596 (3.78), 7.617 (2.59), 7.630 (1.74), 7.635 (1.61), 7.652 (6.24), 7.657 (5.90), 7.661 (4.63), 7.667 (5.94), 7.672 (3.01), 7.689 (1.57), 8.813 (2.25), 12.108 (1.10).

$^1$H-NMR (400 MHz, DMSO-d6) δ [ppm]: 12.10 (br. s, 1H), 8.92-8.69 (m, 1H), 7.77-7.39 (m, 5H), 4.20-3.92 (m, 2H), 3.90-3.75 (m, 1H), 3.14 (br. s, 4H), 2.32-2.22 (m, 1H), 2.21-2.01 (m, 6H), 1.67 (br. s, 4H), 1.65-1.55 (m, 2H).

Example 172

(+)-5-({[6-Bromo-3-methyl-2-(piperidin-1-yl)quinolin-4-yl]carbonyl}amino)-4-(2,3,6-trichlorophenyl) pentanoic acid (Enantiomer 1)

To a solution of tert-butyl 5-({[6-bromo-3-methyl-2-(piperidin-1-yl)quinolin-4-yl]carbonyl}amino)-4-(2,3,6-trichlorophenyl)pentanoate (92 mg, 95% purity, 128 µmol, enantiomer 1, Example 179A) in dichloromethane (1.1 ml) under argon was added TFA (960 µl, 13 mmol), and the mixture was stirred at RT for 2 h. Subsequently, the mixture was concentrated and the residue was dissolved in DMSO and purified by means of preparative HPLC (Method 15). The combined target fractions were concentrated, and the residue was dried under reduced pressure. 68 mg (100% purity, 85% of theory) of the title compound were obtained.

$[α]_D^{20}$=+31.4°, 589 nm, c=0.37 g/100 ml, methanol

LC-MS (Method 1): $R_t$=2.36 min; MS (ESIpos): m/z=626/628/630 [M+H]$^+$ $^1$H-NMR (400 MHz, DMSO-d6) δ [ppm]: −0.149 (1.92), −0.008 (15.84), 0.146 (1.96), 1.609 (3.95), 1.676 (7.70), 2.075 (1.68), 2.101 (3.23), 2.122 (4.27), 2.136 (8.34), 2.169 (16.00), 2.183 (3.27), 2.206 (1.56), 2.230 (0.76), 2.282 (1.56), 2.327 (2.91), 2.366 (1.52), 2.669 (2.31), 2.710 (1.52), 3.143 (10.13), 3.808 (1.44), 4.057 (2.19), 7.477 (2.67), 7.498 (3.91), 7.533 (3.47), 7.555 (5.79), 7.597 (4.27), 7.618 (2.99), 7.631 (1.76), 7.654 (6.46), 7.658 (6.34), 7.668 (6.30), 7.691 (1.52), 8.808 (2.79), 12.101 (0.48).

Example 173

(−)-5-({[6-Bromo-3-methyl-2-(piperidin-1-yl)quinolin-4-yl]carbonyl}amino)-4-(2,3,6-trichlorophenyl) pentanoic acid (Enantiomer 2)

To a solution of tert-butyl 5-({[6-bromo-3-methyl-2-(piperidin-1-yl)quinolin-4-yl]carbonyl}amino)-4-(2,3,6-trichlorophenyl)pentanoate (96 mg, 95% purity, 133 µmol, enantiomer 2, Example 180A) in dichloromethane (1.1 ml) under argon was added TFA (1.0 ml, 13 mmol), and the mixture was stirred at RT for 2 h. Subsequently, the mixture was concentrated and the residue was dissolved in DMSO and purified by means of preparative HPLC (Method 15). The combined target fractions were concentrated, and the residue was dried under reduced pressure. 62 mg (100% purity, 74% of theory) of the title compound were obtained.

$[α]_D^{20}$=−28.8°, 589 nm, c=0.35 g/100 ml, methanol

LC-MS (Method 1): $R_t$=2.36 min; MS (ESIpos): m/z=626/628/630 [M+H]$^+$ $^1$H-NMR (400 MHz, DMSO-d6) δ [ppm]: −0.149 (1.14), 0.147 (1.14), 1.607 (4.08), 1.675 (8.11), 2.072 (1.61), 2.086 (2.39), 2.099 (3.19), 2.120 (4.11), 2.136 (8.64), 2.156 (4.33), 2.169 (16.00), 2.181 (3.50), 2.203 (1.67), 2.282 (1.64), 2.327 (2.25), 2.367 (1.03), 2.669 (1.69), 2.710 (1.14), 3.141 (10.56), 3.807 (1.42), 4.054 (2.42), 7.476 (2.58), 7.497 (3.81), 7.533 (3.39), 7.555 (5.50), 7.598 (4.42), 7.618 (3.11), 7.629 (2.06), 7.651 (6.64), 7.656 (6.81), 7.666 (6.50), 7.688 (1.56), 8.810 (2.67), 12.111 (1.14).

Example 174

(+/−)-5-({[6-Bromo-3-methyl-2-(pyrrolidin-1-yl)quinolin-4-yl]carbonyl}amino)-4-(2,3,6-trichlorophenyl)pentanoic acid (Racemate)

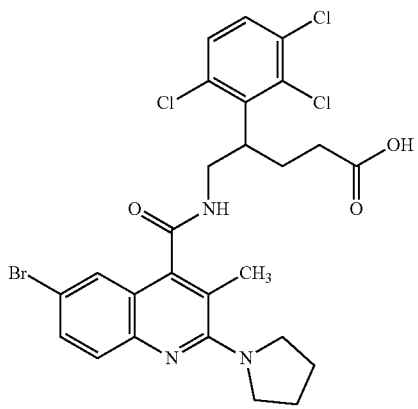 [SMILES: Cc1c(N2CCCC2)nc2ccc(Br)cc2c1C(=O)NCC(CCC(=O)O)c1c(Cl)ccc(Cl)c1Cl]

To a solution of (+/−)-tert-butyl 5-({[6-bromo-3-methyl-2-(pyrrolidin-1-yl)quinolin-4-yl]carbonyl}-amino)-4-(2,3,6-trichlorophenyl)pentanoate (55 mg, 82.1 μmol, racemate, Example 181A) in dichloromethane (1.1 ml) was added TFA (610 μl, 8.2 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 41 mg (100% purity, 81% of theory) of the title compound were obtained.

LC-MS (Method 1): $R_t$=1.66 min; MS (ESIpos): m/z=612/614/616 [M+H]$^+$ $^1$H-NMR (400 MHz, DMSO-d6) δ [ppm]: −0.150 (1.74), −0.008 (16.00), 0.146 (1.82), 1.875 (15.55), 2.070 (2.64), 2.097 (4.97), 2.118 (5.12), 2.158 (8.72), 2.194 (15.11), 2.277 (2.23), 2.327 (2.78), 2.669 (2.04), 3.573 (11.14), 3.784 (2.12), 4.068 (3.34), 7.472 (8.09), 7.494 (13.07), 7.499 (8.76), 7.522 (4.64), 7.544 (8.24), 7.552 (5.31), 7.558 (7.39), 7.580 (5.16), 7.590 (5.79), 7.611 (3.56), 8.146 (2.26), 8.757 (4.08).

$^1$H-NMR (400 MHz, DMSO-d6) δ [ppm]: 12.06 (br. s, 1H), 8.76 (br. s, 1H), 7.73-7.15 (m, 5H), 4.23-3.92 (m, 2H), 3.92-3.69 (m, 1H), 3.57 (br. s, 4H), 2.39-2.02 (m, 7H), 1.88 (br. s, 4H).

Example 175

(+)-5-({[6-Bromo-3-methyl-2-(piperidin-1-yl)quinolin-4-yl]carbonyl}amino)-4-(2,3,6-trichlorophenyl)pentanoic acid (Enantiomer 1)

To a solution of tert-butyl 5-({[6-bromo-3-methyl-2-(pyrrolidin-1-yl)quinolin-4-yl]carbonyl}amino)-4-(2,3,6-trichlorophenyl)pentanoate (92 mg, 97% purity, 133 μmol, enantiomer 1, Example 182A) in dichloromethane (1.1 ml) under argon was added TFA (990 μl, 13 mmol), and the mixture was stirred at RT for 2 h. Subsequently, the mixture was concentrated and the residue was dissolved in DMSO and purified by means of preparative HPLC (Method 15). The combined target fractions were concentrated, and the residue was dried under reduced pressure. 48 mg (100% purity, 59% of theory) of the title compound were obtained.

[α]$_D^{20}$=+31.4°, 589 nm, c=0.37 g/100 ml, methanol

LC-MS (Method 1): $R_t$=1.63 min; MS (ESIpos): m/z=612/614/616 [M+H]$^+$ $^1$H-NMR (400 MHz, DMSO-d6) δ [ppm]: −0.149 (1.80), −0.008 (15.65), 0.008 (16.00), 0.147 (1.97), 1.875 (15.71), 2.067 (2.90), 2.096 (4.93), 2.108 (5.22), 2.157 (8.64), 2.194 (15.19), 2.276 (2.38), 2.327 (4.81), 2.366 (1.62), 2.669 (3.59), 2.710 (1.39), 3.576 (11.13), 3.785 (2.09), 4.057 (3.36), 7.472 (9.10), 7.494 (14.03), 7.500 (8.93), 7.523 (5.28), 7.544 (9.28), 7.552 (5.74), 7.558 (7.71), 7.580 (5.22), 7.590 (5.97), 7.611 (3.59), 8.206 (1.74), 8.759 (4.00), 12.141 (0.93).

Example 176

(−)-5-({[6-Bromo-3-methyl-2-(piperidin-1-yl)quinolin-4-yl]carbonyl}amino)-4-(2,3,6-trichlorophenyl)pentanoic acid formate (Enantiomer 2)

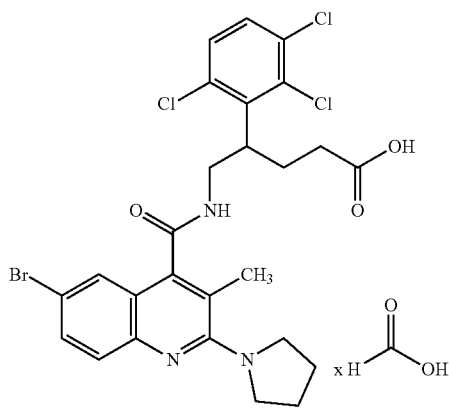

To a solution of tert-butyl 5-({[6-bromo-3-methyl-2-(pyrrolidin-1-yl)quinolin-4-yl]carbonyl}amino)-4-(2,3,6-trichlorophenyl)pentanoate (98 mg, 94% purity, 138 μmol, enantiomer 2, Example 183A) in dichloromethane (1.2 ml) under argon was added TFA (1.0 ml, 14 mmol), and the mixture was stirred at RT for 2 h. Subsequently, the mixture was concentrated and the residue was dissolved in DMSO and purified by means of preparative HPLC (Method 15). The combined target fractions were concentrated, and the residue was dried under reduced pressure. 51 mg (100% purity, 56% of theory) of the title compound were obtained.

[α]$_D^{20}$=−29.4°, 589 nm, c=0.36 g/100 ml, methanol

LC-MS (Method 1): $R_t$=1.65 min; MS (ESIpos): m/z=612/614/616 [M+H]$^+$ $^1$H-NMR (400 MHz, DMSO-d6) δ [ppm]: −0.149 (0.68), −0.008 (6.08), 0.008 (5.30), 0.146 (0.67), 1.876 (7.64), 2.070 (1.42), 2.085 (1.86), 2.097 (2.48), 2.110 (2.55), 2.118 (2.55), 2.131 (2.05), 2.159 (4.35), 2.194 (7.61), 2.231 (0.86), 2.281 (1.11), 2.305 (1.13), 2.327 (1.39), 2.366 (0.65), 2.670 (0.99), 2.674 (0.75), 2.710 (0.62), 3.143 (0.56), 3.574 (5.49), 3.769 (0.86), 3.785 (1.00), 3.800 (1.07), 4.034 (1.42), 4.069 (1.66), 4.085 (0.92), 4.102 (0.67), 7.472 (4.33), 7.477 (2.93), 7.495 (7.02), 7.500 (4.41), 7.523 (2.67), 7.544 (4.63), 7.552 (2.80), 7.558 (3.90), 7.564 (1.99), 7.574 (1.77), 7.580 (2.63), 7.590 (2.85), 7.612 (1.83), 8.145 (16.00), 8.757 (2.02).

Example 177

(+/−)-5-({[6-Bromo-2-(3,3-difluoropiperidin-1-yl)-3-methylquinolin-4-yl]carbonyl}amino)-4-(2,3,6-trichlorophenyl)pentanoic acid (Racemate)

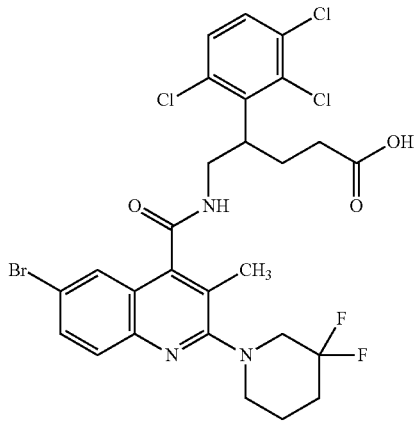 [SMILES: Cc1c(N2CCCC(F)(F)C2)nc2ccc(Br)cc2c1C(=O)NCC(CCC(=O)O)c1c(Cl)ccc(Cl)c1Cl]

To a solution of (+/−)-tert-butyl 5-({[6-bromo-2-(3,3-difluoropiperidin-1-yl)-3-methylquinolin-4-yl]carbonyl}amino)-4-(2,3,6-trichlorophenyl)pentanoate (56 mg, 77.8 μmol, racemate, Example 184A) in dichloromethane (1.0 ml) was added TFA (580 μl, 7.8 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 48 mg (100% purity, 93% of theory) of the title compound were obtained.

LC-MS (Method 1): $R_t$=2.25 min; MS (ESIpos): m/z=662/664/666 [M+H]$^+$ $^1$H-NMR (400 MHz, DMSO-d6) δ [ppm]: 1.885 (3.71), 2.103 (4.93), 2.116 (5.04), 2.135 (3.96), 2.159 (9.28), 2.188 (16.00), 2.307 (1.63), 2.328 (1.61), 2.670 (1.01), 3.174 (4.63), 3.453 (2.74), 3.483 (5.27), 3.511 (2.65), 3.819 (1.27), 4.071 (2.16), 7.479 (2.26), 7.501 (3.20), 7.535 (3.02), 7.556 (5.36), 7.599 (4.05), 7.620 (2.74), 7.681 (1.38), 7.703 (6.38), 7.709 (6.79), 7.716 (6.35), 7.739 (1.34), 8.822 (2.49), 12.109 (1.24).

$^1$H-NMR (400 MHz, DMSO-d$_6$): δ [ppm]=12.10 (br. s, 1H), 8.95-8.67 (m, 1H), 7.78-7.66 (m, 2H), 7.65-7.47 (m, 3H), 4.17-3.96 (m, 2H), 3.92-3.76 (m, 1H), 3.48 (br. t, 2H), 3.17 (br. s, 2H), 2.19 (s, 9H), 1.94-1.82 (m, 2H).

Example 178

(+)-5-({[6-Bromo-2-(3,3-difluoropiperidin-1-yl)-3-methylquinolin-4-yl]carbonyl}amino)-4-(2,3,6-trichlorophenyl)pentanoic acid (Enantiomer 1)

To a solution of tert-butyl 5-({[6-bromo-2-(3,3-difluoropiperidin-1-yl)-3-methylquinolin-4-yl]carbonyl}amino)-4-(2,3,6-trichlorophenyl)pentanoate (79 mg, 95% purity, 104 μmol, enantiomer 1, Example 185A) in dichloromethane (890 μl) was added TFA (780 μl, 10 mmol), and the mixture was stirred at RT for 1 h. Subsequently, the mixture was concentrated and the residue was taken up in DMSO and purified by means of preparative HPLC (Method 19). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 49 mg (98% purity, 69% of theory) of the title compound were obtained.

$[α]_D^{20}$=+30.4°, 589 nm, c=0.35 g/100 ml, methanol

LC-MS (Method 1): $R_t$=2.28 min; MS (ESIpos): m/z=662/664/666 [M+H]$^+$ $^1$H-NMR (400 MHz, DMSO-d6) δ [ppm]: −0.149 (0.91), 0.146 (0.82), 1.886 (3.76), 2.102 (4.96), 2.117 (5.16), 2.136 (4.03), 2.158 (9.41), 2.188 (16.00), 2.229 (0.82), 2.307 (1.69), 2.328 (1.71), 2.366 (0.74), 2.669 (1.07), 2.710 (0.60), 3.162 (13.82), 3.175 (14.53), 3.453 (2.72), 3.483 (5.34), 3.512 (2.63), 3.819 (1.31), 3.833 (1.23), 4.062 (2.91), 4.076 (4.18), 4.088 (3.40), 7.479 (2.31), 7.500 (3.29), 7.534 (2.87), 7.556 (5.16), 7.598 (4.34), 7.620 (2.89), 7.685 (1.49), 7.703 (6.67), 7.709 (7.06), 7.716 (6.21), 7.738 (1.33), 8.822 (2.47), 12.100 (1.47).

Example 179

(−)-5-({[6-Bromo-2-(3,3-difluoropiperidin-1-yl)-3-methylquinolin-4-yl]carbonyl}amino)-4-(2,3,6-trichlorophenyl)pentanoic acid (Enantiomer 2)

To a solution of tert-butyl 5-({[6-bromo-2-(3,3-difluoropiperidin-1-yl)-3-methylquinolin-4-yl]carbonyl}amino)-4-(2,3,6-trichlorophenyl)pentanoate (100 mg, 97% purity, 134 μmol, enantiomer 2, Example 186A) in dichloromethane (1.2 ml) was added TFA (1.0 ml, 13 mmol), and the mixture was stirred at RT for 1 h. Subsequently, the mixture was concentrated and the residue was taken up in DMSO and purified by means of preparative HPLC (Method 19). The combined target fractions were concentrated, and the respective residues were lyophilized. Subsequently, the lyophilizates were taken up in methanol and combined, and the mixture was left to dry under ambient conditions. After subsequent drying of the residue under reduced pressure, 49 mg (98% purity, 69% of theory) of the title compound were obtained.

$[α]_D^{20}$=−26.7°, 589 nm, c=0.36 g/100 ml, methanol

LC-MS (Method 1): $R_t$=2.25 min; MS (ESIpos): m/z=662/664/666 [M+H]$^+$ $^1$H-NMR (400 MHz, DMSO-d6) δ [ppm]: −0.149 (0.65), −0.008 (5.21), 0.008 (3.92), 0.146 (0.56), 1.884 (3.63), 2.065 (2.12), 2.078 (3.31), 2.103 (4.75), 2.117 (4.92), 2.136 (3.88), 2.158 (9.19), 2.188 (16.00), 2.206 (1.67), 2.229 (0.81), 2.279 (1.29), 2.307 (1.58), 2.327 (1.60), 2.366 (0.65), 2.670 (1.04), 2.710 (0.56), 3.162 (6.10), 3.175 (6.79), 3.453 (2.73), 3.482 (5.23), 3.511 (2.58), 3.802 (0.90), 3.817 (1.25), 3.833 (1.21), 4.048 (1.81), 4.074 (2.58), 4.106 (0.85), 7.479 (2.23), 7.500 (3.19), 7.535 (2.83), 7.556 (5.19), 7.598 (4.19), 7.620 (2.79), 7.680 (1.40), 7.685 (1.35), 7.703 (6.46), 7.709 (6.79), 7.716 (6.08), 7.738 (1.33), 8.821 (2.46), 12.100 (2.10).

Example 180

5-[({6-Bromo-2-[3-fluoropiperidin-1-yl]-3-methylquinolin-4-yl}carbonyl)amino]-4-(2,3,6-trichlorophenyl)pentanoic acid (Diastereomer Mixture)

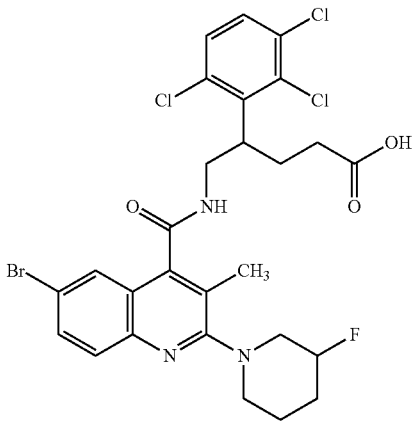 [SMILES: Cc1c(N2CCCC(F)C2)nc2ccc(Br)cc2c1C(=O)NCC(CCC(=O)O)c1c(Cl)ccc(Cl)c1Cl]

To a solution of tert-butyl 5-[({6-bromo-2-[3-fluoropiperidin-1-yl]-3-methylquinolin-4-yl}carbonyl)amino]-4-(2,3,6-trichlorophenyl)pentanoate (55 mg, 78.4 µmol, diastereomer mixture, Example 187A) in dichloromethane (1.0 ml) was added TFA (580 µl, 7.8 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 46 mg (100% purity, 91% of theory) of the title compound were obtained.

LC-MS (Method 1): $R_t$=2.22 min; MS (ESIpos): m/z=644/646/648 [M+H]$^+$ $^1$H-NMR (400 MHz, DMSO-d6) δ [ppm]: −0.149 (1.84), −0.008 (16.00), 0.008 (15.66), 0.146 (1.80), 1.234 (0.68), 1.641 (1.24), 1.811 (1.24), 1.903 (1.88), 2.072 (1.33), 2.100 (2.40), 2.112 (2.70), 2.153 (7.06), 2.182 (12.62), 2.306 (1.37), 2.327 (2.52), 2.366 (0.81), 2.669 (1.84), 2.709 (0.64), 3.105 (1.33), 3.171 (1.45), 3.385 (1.37), 3.441 (1.16), 3.472 (0.68), 3.832 (0.98), 4.060 (1.71), 4.819 (0.98), 4.940 (0.94), 7.477 (2.05), 7.499 (2.82), 7.533 (2.87), 7.555 (4.96), 7.597 (3.17), 7.617 (2.10), 7.654 (1.33), 7.676 (5.48), 7.680 (5.18), 7.690 (5.39), 7.712 (1.28), 8.819 (1.97), 12.102 (0.98).

Example 181

5-[({6-Bromo-2-[3-ethylpiperidin-1-yl]-3-methylquinolin-4-yl}carbonyl)amino]-4-(2,3,6-trichlorophenyl)pentanoic acid (Diastereomer Mixture)

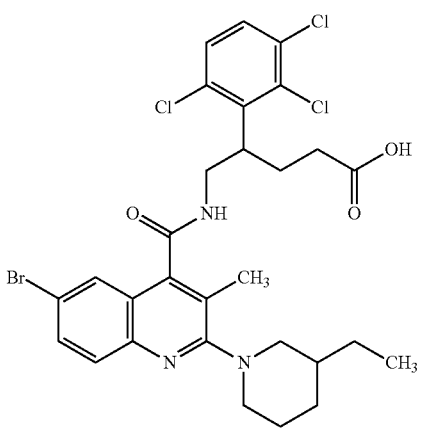 [SMILES: CCC1CCCN(c2nc3ccc(Br)cc3c(C(=O)NCC(CCC(=O)O)c3c(Cl)ccc(Cl)c3Cl)c2C)C1]

To a solution of tert-butyl 5-[({6-bromo-2-[3-ethylpiperidin-1-yl]-3-methylquinolin-4-yl}carbonyl)amino]-4-(2,3,6-trichlorophenyl)pentanoate (55 mg, 77.3 µmol, diastereomer mixture, Example 188A) in dichloromethane (1.0 ml) was added TFA (570 µl, 7.7 mmol), and the mixture was stirred at RT for 1.5 h. Subsequently, the mixture was concentrated and the residue was dissolved in DMSO and purified by means of preparative HPLC (Method 15). The combined target fractions were concentrated, and the residue was dried under reduced pressure. 45 mg (100% purity, 89% of theory) of the title compound were obtained.

LC-MS (Method 1): $R_t$=2.58 min; MS (ESIpos): m/z=654/656/658 [M+H]$^+$ $^1$H-NMR (400 MHz, DMSO-d6) δ [ppm]: −0.149 (1.89), −0.008 (16.00), 0.008 (15.48), 0.146 (1.85), 0.893 (5.12), 0.912 (12.22), 0.930 (6.41), 1.068 (1.29), 1.092 (1.25), 1.261 (2.41), 1.279 (3.14), 1.571 (1.42), 1.640 (1.20), 1.751 (1.76), 1.850 (1.42), 1.880 (1.46), 2.073 (1.46), 2.127 (5.85), 2.154 (11.44), 2.159 (9.81), 2.184 (2.37), 2.206 (1.29), 2.230 (0.82), 2.276 (1.38), 2.327 (2.37), 2.366 (0.77), 2.426 (1.25), 2.669 (2.11), 2.710 (1.12), 2.754 (1.16), 3.493 (2.80), 3.523 (2.62), 3.819 (1.08), 4.047 (1.76), 4.080 (1.76), 7.475 (2.58), 7.497 (3.74), 7.527 (3.35), 7.549 (5.59), 7.590 (3.44), 7.596 (3.61), 7.612 (2.37), 7.632 (1.25), 7.658 (8.82), 7.663 (6.24), 7.684 (1.03), 8.802 (2.06), 12.107 (1.38).

Example 182

(+/−)-5-({[6-Bromo-3-methyl-2-(piperidin-1-yl)quinolin-4-yl]carbonyl}amino)-4-[2-(difluoromethoxy)-6-fluorophenyl]pentanoic acid (Racemate)

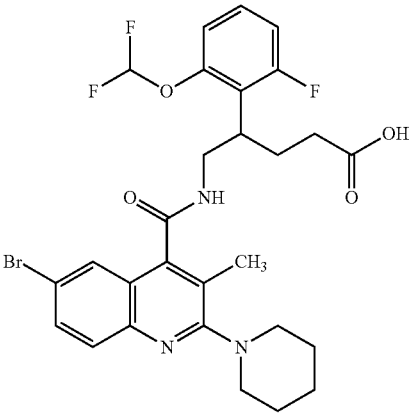 [SMILES: Cc1c(N2CCCCC2)nc2ccc(Br)cc2c1C(=O)NCC(CCC(=O)O)c1c(F)cccc1OC(F)F]

To a solution of (+/−)-tert-butyl 5-({[6-bromo-3-methyl-2-(piperidin-1-yl)quinolin-4-yl]carbonyl}-amino)-4-[2-(difluoromethoxy)-6-fluorophenyl]pentanoate (85 mg, 128 µmol, racemate, Example 189A) in dichloromethane (1.1 ml) was added TFA (220 µl, 2.8 mmol), and the mixture was left to stand at RT for 3.5 h. The mixture was then concentrated and repeatedly dichloromethane was added and the mixture was concentrated again. The residue was purified by preparative HPLC (Method 7). The combined target fractions were concentrated, and the residue was lyophilized. 52 mg (100% purity, 67% of theory) of the title compound were obtained.

LC-MS (Method 1): $R_t$=2.16 min; MS (ESIpos): m/z=608/610 [M+H]$^+$ $^1$H-NMR (400 MHz, DMSO-d6) δ [ppm]: −0.008 (1.21), 1.608 (4.52), 1.673 (8.82), 1.908 (0.41), 1.924 (0.72), 1.941

(1.34), 1.963 (1.75), 1.986 (1.24), 2.004 (0.65), 2.036 (1.55), 2.055 (3.62), 2.093 (8.19), 2.134 (16.00), 3.139 (11.63), 3.534 (1.87), 3.665 (0.84), 3.680 (1.39), 3.697 (2.25), 3.713 (2.67), 3.728 (1.44), 3.745 (1.52), 3.762 (2.00), 3.781 (1.70), 3.794 (1.07), 3.815 (0.62), 7.020 (4.00), 7.041 (4.62), 7.050 (3.53), 7.091 (2.63), 7.114 (4.09), 7.138 (2.96), 7.234 (5.54), 7.359 (1.55), 7.380 (3.08), 7.397 (3.02), 7.418 (4.11), 7.478 (0.95), 7.628 (2.91), 7.650 (13.17), 7.659 (8.54), 7.664 (7.65), 7.681 (1.71), 7.686 (1.86), 8.775 (2.20), 8.790 (4.37), 8.805 (2.16), 12.045 (0.54).

Example 183

(−)-5-({[6-Bromo-3-methyl-2-(piperidin-1-yl)quinolin-4-yl]carbonyl}amino)-4-[2-(difluoromethoxy)-6-fluorophenyl]pentanoic acid (Enantiomer 1)

To a solution of (−)-tert-butyl 5-({[6-bromo-3-methyl-2-(piperidin-1-yl)quinolin-4-yl]carbonyl}amino)-4-[2-(difluoromethoxy)-6-fluorophenyl]pentanoate (180 mg, 271 µmol, enantiomer 1, Example 190A) in dichloromethane (2.1 ml) was added TFA (460 µl, 6.0 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 121 mg (100% purity, 73% of theory) of the title compound were obtained.

$[\alpha]_D^{20}$=−30.4°, 589 nm, c=0.33 g/100 ml, methanol
LC-MS (Method 1): $R_t$=2.15 min; MS (ESIpos): m/z=608/610 [M+H]$^+$
$^1$H-NMR (400 MHz, DMSO-d6) δ [ppm]: −0.008 (1.66), 1.608 (4.73), 1.673 (9.37), 1.921 (0.69), 1.939 (1.41), 1.959 (1.86), 1.984 (1.30), 2.003 (0.64), 2.034 (1.58), 2.050 (3.83), 2.087 (8.86), 2.133 (16.00), 2.327 (0.43), 2.670 (0.46), 3.137 (12.32), 3.532 (1.88), 3.663 (0.85), 3.678 (1.42), 3.696 (2.33), 3.711 (2.76), 3.726 (1.49), 3.744 (1.58), 3.761 (2.09), 3.780 (1.82), 3.793 (1.14), 3.814 (0.67), 7.020 (4.17), 7.040 (4.81), 7.049 (3.58), 7.091 (2.74), 7.113 (4.27), 7.138 (3.06), 7.233 (5.70), 7.359 (1.62), 7.379 (3.26), 7.396 (3.13), 7.417 (4.27), 7.474 (1.00), 7.626 (3.16), 7.648 (13.68), 7.658 (8.84), 7.662 (8.24), 7.680 (1.79), 7.685 (2.02), 8.776 (2.26), 8.791 (4.44), 8.805 (2.18), 12.067 (0.62).

Example 184

(+)-5-({[6-Bromo-3-methyl-2-(piperidin-1-yl)quinolin-4-yl]carbonyl}amino)-4-[2-(difluoromethoxy)-6-fluorophenyl]pentanoic acid (Enantiomer 2)

To a solution of (+)-tert-butyl 5-({[6-bromo-3-methyl-2-(piperidin-1-yl)quinolin-4-yl]carbonyl}-amino)-4-[2-(difluoromethoxy)-6-fluorophenyl]pentanoate (145 mg, 218 µmol, enantiomer 2, Example 191A) in dichloromethane (1.7 ml) was added TFA (370 µl, 4.8 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized. 95 mg (100% purity, 72% of theory) of the title compound were obtained.

$[\alpha]_D^{20}$=+29.9°, 589 nm, c=0.30 g/100 ml, methanol
LC-MS (Method 1): $R_t$=2.15 min; MS (ESIpos): m/z=608/610 [M+H]$^+$
$^1$H-NMR (400 MHz, DMSO-d6) δ [ppm]: 0.070 (0.53), 1.608 (4.56), 1.673 (9.01), 1.921 (0.70), 1.939 (1.37), 1.959 (1.76), 1.984 (1.24), 2.000 (0.64), 2.034 (1.52), 2.052 (3.62), 2.090 (8.27), 2.133 (16.00), 2.669 (0.44), 3.137 (11.85), 3.532 (1.81), 3.664 (0.80), 3.678 (1.36), 3.696 (2.21), 3.712 (2.64), 3.727 (1.46), 3.744 (1.54), 3.763 (2.00), 3.781 (1.73), 3.815 (0.63), 7.020 (4.01), 7.041 (4.64), 7.049 (3.41), 7.091 (2.61), 7.114 (4.15), 7.138 (2.97), 7.234 (5.33), 7.359 (1.49), 7.380 (3.11), 7.397 (2.99), 7.417 (4.01), 7.474 (0.98), 7.626 (2.92), 7.648 (12.70), 7.658 (7.83), 7.662 (7.47), 7.680 (1.63), 7.684 (1.80), 8.775 (2.16), 8.789 (4.27), 8.804 (2.14), 12.053 (1.06).

Example 185

(−)-5-[({6-Bromo-2-[3-fluoropiperidin-1-yl]-3-methylquinolin-4-yl}carbonyl)amino]-4-(2-chlorophenyl)pentanoic acid (Diastereomer 1)

[For structural formula see Example 78 (diastereomer mixture)]

To a solution of (−)-tert-butyl 5-[({6-bromo-2-[3-fluoropiperidin-1-yl]-3-methylquinolin-4-yl}carbonyl)amino]-4-(2-chlorophenyl)pentanoate (470 mg, 742 µmol, diastereomer 1, Example 192A) in dichloromethane (13 ml) was added TFA (1.3 ml, 16 mmol), and the mixture was left to stand at RT for 16 h. The mixture was then concentrated and repeatedly dichloromethane was added and the mixture was concentrated again. The residue was purified by preparative HPLC (Method 32). The combined target fractions were concentrated, and the residue was lyophilized from acetonitrile/water. 372 mg (100% purity, 68% of theory) of the title compound were obtained.

$[\alpha]_D^{20}$=−9.3°, 589 nm, c=0.35 g/100 ml, methanol
LC-MS (Method 1): $R_t$=2.06 min; MS (ESIpos): m/z=576/578 [M+H]$^+$
$^1$H-NMR (500 MHz, DMSO-d6) δ [ppm]: −0.007 (1.49), 0.006 (1.24), 1.640 (2.13), 1.775 (0.87), 1.793 (2.38), 1.801 (2.71), 1.818 (3.92), 1.835 (3.85), 1.853 (2.01), 1.906 (3.85), 1.916 (2.80), 1.923 (3.08), 1.944 (1.86), 1.966 (1.19), 1.973 (1.24), 1.990 (0.72), 2.022 (0.95), 2.032 (1.71), 2.049 (6.03), 2.070 (5.11), 2.077 (5.53), 2.094 (4.64), 2.117 (3.43), 2.134 (7.30), 2.146 (15.75), 3.067 (1.67), 3.087 (2.43), 3.161 (2.60), 3.175 (2.56), 3.196 (1.61), 3.281 (1.64), 3.295 (2.57), 3.307 (3.21), 3.320 (3.36), 3.335 (2.14), 3.389 (2.50), 3.410 (1.66), 3.415 (1.66), 3.436 (2.25), 3.457 (1.57), 3.595 (2.39), 4.829 (1.80), 4.919 (1.56), 4.925 (1.81), 4.931 (1.50), 7.259 (2.37), 7.273 (4.84), 7.287 (3.20), 7.289 (3.16), 7.358 (3.08), 7.373 (5.30), 7.387 (2.77), 7.443 (8.03), 7.445 (8.07), 7.459 (6.96), 7.461 (6.79), 7.482 (6.24), 7.485 (6.43), 7.498 (5.40), 7.500 (5.27), 7.651 (4.10), 7.669 (16.00), 7.676 (11.40), 7.680 (9.95), 7.694 (2.38), 7.698 (2.47), 8.720 (3.02), 8.731 (5.62), 8.743 (2.74).

Example 186

(−)-5-[({6-Bromo-2-[3-fluoropiperidin-1-yl]-3-methylquinolin-4-yl}carbonyl)amino]-4-(2-chlorophenyl)pentanoic acid (Diastereomer 2)

To a solution of (−)-tert-butyl 5-[({6-bromo-2-[3-fluoropiperidin-1-yl]-3-methylquinolin-4-yl}carbonyl)amino]-4-(2-chlorophenyl)pentanoate (420 mg, 664 µmol, diastereomer 2, Example 193A) in dichloromethane (12 ml) was added TFA (1.1 ml, 15 mmol), and the mixture was left to stand at RT for 16 h. The mixture was then concentrated and repeatedly dichloromethane was added and the mixture was concentrated again. The residue was purified by preparative HPLC (Method 32). The combined target fractions were concentrated, and the residue was lyophilized from acetonitrile/water. 331 mg (100% purity, 86% of theory) of the title compound were obtained.

$[\alpha]_D^{20} = -16.5°$, 589 nm, c=0.43 g/100 ml, methanol

LC-MS (Method 1): $R_t$=2.06 min; MS (ESIpos): m/z=576/578 [M+H]$^+$ $^1$H-NMR (500 MHz, DMSO-d6) δ [ppm]: −0.007 (1.47), 0.007 (1.09), 1.644 (1.88), 1.650 (1.80), 1.772 (0.62), 1.791 (2.00), 1.799 (2.22), 1.815 (3.30), 1.833 (3.44), 1.851 (1.68), 1.905 (3.34), 1.922 (2.59), 1.943 (1.35), 1.949 (1.32), 1.967 (1.01), 1.975 (1.02), 1.983 (0.67), 1.991 (0.54), 2.019 (0.68), 2.029 (1.29), 2.038 (1.58), 2.046 (5.27), 2.066 (4.31), 2.073 (4.72), 2.090 (4.20), 2.113 (2.61), 2.130 (5.56), 2.144 (12.88), 2.518 (0.57), 2.522 (0.43), 3.073 (1.31), 3.094 (2.18), 3.108 (1.92), 3.150 (2.24), 3.163 (2.22), 3.185 (1.32), 3.282 (1.40), 3.297 (2.20), 3.309 (2.83), 3.322 (3.01), 3.337 (1.88), 3.385 (2.32), 3.406 (1.51), 3.411 (1.50), 3.427 (2.03), 3.432 (2.11), 3.453 (1.48), 3.592 (2.08), 3.651 (1.20), 3.665 (2.13), 3.676 (2.72), 3.686 (2.31), 4.820 (1.33), 4.826 (1.57), 4.915 (1.34), 4.921 (1.57), 4.927 (1.30), 7.257 (1.94), 7.260 (2.01), 7.273 (4.31), 7.288 (2.95), 7.290 (2.80), 7.359 (2.64), 7.374 (4.73), 7.388 (2.45), 7.442 (8.34), 7.445 (7.88), 7.458 (7.21), 7.461 (6.59), 7.482 (5.70), 7.484 (5.71), 7.497 (4.85), 7.651 (3.74), 7.668 (16.00), 7.675 (11.47), 7.679 (9.85), 7.693 (2.33), 7.697 (2.46), 8.720 (2.73), 8.732 (5.23), 8.743 (2.55).

Example 187

(+)-5-[({6-Bromo-2-[3-fluoropiperidin-1-yl]-3-methylquinolin-4-yl}carbonyl)amino]-4-(2-chlorophenyl)pentanoic acid (Diastereomer 3)

To a solution of (+)-tert-butyl 5-[({6-bromo-2-[3-fluoropiperidin-1-yl]-3-methylquinolin-4-yl}carbonyl)amino]-4-(2-chlorophenyl)pentanoate (580 mg, 916 μmol, diastereomer 3, Example 194A) in dichloromethane (8 ml) was added TFA (1.4 ml, 18 mmol), and the mixture was left to stand at RT for 18 h. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 470 mg (100% purity, ee>99%, 89% of theory) of the title compound were obtained.

$[\alpha]_D^{20} = +10.0°$, 589 nm, c=0.37 g/100 ml, methanol

LC-MS (Method 1): $R_t$=2.09 min; MS (ESIpos): m/z=576/578 [M+H]$^+$ $^1$H-NMR (400 MHz, DMSO-d6) δ [ppm]: −0.008 (3.12), 0.008 (2.34), 1.641 (1.61), 1.793 (1.81), 1.811 (2.86), 1.835 (3.14), 1.858 (1.83), 1.898 (2.57), 1.917 (2.18), 1.948 (1.57), 1.982 (0.97), 2.012 (0.69), 2.045 (4.00), 2.079 (4.65), 2.088 (4.76), 2.143 (16.00), 2.327 (0.60), 2.366 (0.43), 2.670 (0.60), 3.060 (1.10), 3.093 (1.78), 3.158 (1.92), 3.175 (1.84), 3.202 (1.07), 3.380 (1.98), 3.406 (1.07), 3.438 (1.66), 3.464 (1.06), 3.594 (1.82), 3.680 (3.53), 4.817 (1.32), 4.937 (1.32), 7.256 (1.68), 7.274 (3.88), 7.291 (2.78), 7.356 (2.33), 7.374 (4.34), 7.392 (2.23), 7.441 (6.24), 7.444 (5.85), 7.461 (5.31), 7.464 (4.93), 7.484 (5.31), 7.500 (4.60), 7.647 (2.38), 7.668 (13.37), 7.675 (9.32), 7.680 (8.01), 7.698 (1.56), 7.702 (1.76), 8.716 (2.06), 8.730 (4.24), 8.745 (2.04), 12.062 (0.71).

Example 188

(+)-5-[({6-Bromo-2-[3-fluoropiperidin-1-yl]-3-methylquinolin-4-yl}carbonyl)amino]-4-(2-chlorophenyl)pentanoic acid (Diastereomer 4)

To a solution of (+)-tert-butyl 5-[({6-bromo-2-[3-fluoropiperidin-1-yl]-3-methylquinolin-4-yl}carbonyl)amino]-4-(2-chlorophenyl)pentanoate (609 mg, 962 μmol, diastereomer 4, Example 195A) in dichloromethane (8 ml) was added TFA (1.5 ml, 19 mmol), and the mixture was left to stand at RT for 18 h. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 485 mg (100% purity, ee>95%, 87% of theory) of the title compound were obtained.

LC-MS (Method 1): $R_t$=2.09 min; MS (ESIpos): m/z=576/578 [M+H]$^+$ $^1$H-NMR (400 MHz, DMSO-d6) δ [ppm]: 1.646 (1.83), 1.765 (0.56), 1.792 (1.99), 1.811 (3.13), 1.819 (2.79), 1.834 (3.36), 1.858 (2.09), 1.901 (2.96), 1.921 (2.38), 1.948 (1.57), 1.983 (1.04), 2.011 (0.79), 2.045 (4.41), 2.080 (5.20), 2.088 (5.48), 2.101 (2.64), 2.142 (16.00), 2.218 (0.42), 2.327 (0.45), 2.366 (0.42), 2.670 (0.47), 2.710 (0.44), 3.068 (1.11), 3.100 (2.08), 3.147 (2.16), 3.162 (2.10), 3.190 (1.11), 3.376 (2.35), 3.409 (1.20), 3.433 (1.91), 3.461 (1.20), 3.593 (2.05), 3.645 (1.01), 3.664 (2.25), 3.678 (3.47), 4.814 (1.44), 4.934 (1.43), 7.257 (1.79), 7.275 (4.15), 7.293 (2.91), 7.357 (2.52), 7.375 (4.58), 7.394 (2.42), 7.441 (6.19), 7.444 (6.08), 7.461 (5.32), 7.464 (5.20), 7.484 (5.92), 7.501 (4.82), 7.646 (2.35), 7.668 (13.36), 7.675 (9.12), 7.679 (7.80), 7.697 (1.46), 7.702 (1.63), 8.716 (2.26), 8.730 (4.52), 8.744 (2.19), 12.050 (0.58).

Example 189

(+)-5-[({6-Bromo-2-[3-fluoropiperidin-1-yl]-3-methylquinolin-4-yl}carbonyl)amino]-4-[2-(trifluoromethyl)phenyl]pentanoic acid (Diastereomer 1)

[For structural formula see Example 123 (diastereomer mixture)]

To a solution of (+)-tert-butyl 5-[({6-bromo-2-[3-fluoropiperidin-1-yl]-3-methylquinolin-4-yl}carbonyl)amino]-4-[2-(trifluoromethyl)phenyl]pentanoate (60 mg, 90 μmol, diastereomer 1, Example 196A) in dichloromethane (690 μl) was added TFA (150 μl, 2.0 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 43 mg (100% purity, 77% of theory) of the title compound were obtained.

$[\alpha]_D^{20} = +15.8°$, 589 nm, c=0.29 g/100 ml, methanol

LC-MS (Method 1): $R_t$=2.11 min; MS (ESIpos): m/z=610/612 [M+H]$^+$ $^1$H-NMR (400 MHz, DMSO-d6) δ [ppm]: −0.008 (2.36), 0.069 (0.58), 1.652 (1.85), 1.773 (0.52), 1.812 (1.73), 1.905 (4.46), 1.925 (4.44), 1.935 (3.90), 1.957 (3.44), 1.974 (3.09), 1.987 (2.33), 1.998 (3.21), 2.036 (1.48), 2.051 (2.71), 2.074 (2.78), 2.092 (1.69), 2.110 (2.91), 2.135 (2.12), 2.177 (14.09), 2.328 (0.51), 2.670 (0.49), 3.113 (2.20), 3.169 (2.39), 3.187 (2.31), 3.213 (1.42), 3.320 (11.51), 3.394 (2.51), 3.420 (1.33), 3.452 (2.05), 3.479 (1.32), 3.627 (1.84), 3.643 (2.09), 3.702 (2.12), 3.718 (1.77), 3.733 (1.19), 4.824 (1.57), 4.944 (1.56), 7.463 (2.86), 7.482 (4.75), 7.500 (2.94), 7.658 (1.91), 7.680 (16.00), 7.687 (11.53), 7.706 (5.71), 7.724 (10.67), 7.733 (7.57), 7.741 (6.70), 8.778 (2.25), 8.793 (4.51), 8.808 (2.24).

Example 190

(+)-5-[({6-Bromo-2-[3-fluoropiperidin-1-yl]-3-methylquinolin-4-yl}carbonyl)amino]-4-[2-(trifluoromethyl)phenyl]pentanoic acid (Diastereomer 2)

To a solution of (+)-tert-butyl 5-[({6-bromo-2-[3-fluoropiperidin-1-yl]-3-methylquinolin-4-yl}carbonyl)amino]-4-[2-(trifluoromethyl)phenyl]pentanoate (60 mg, 90 μmol, diastereomer 2, Example 197A) in dichloromethane (690 μl) was added TFA (150 μl, 2.0 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 38 mg (100% purity, 70% of theory) of the title compound were obtained.
$[\alpha]_D^{20}$=+21.1°, 589 nm, c=0.29 g/100 ml, methanol
LC-MS (Method 1): $R_t$=2.11 min; MS (ESIpos): m/z=610/612 [M+H]$^+$
$^1$H-NMR (400 MHz, DMSO-d6) δ [ppm]: 0.069 (0.92), 1.651 (1.87), 1.771 (0.52), 1.811 (1.72), 1.903 (4.20), 1.923 (4.35), 1.952 (3.26), 1.968 (3.32), 1.981 (2.34), 1.992 (3.53), 2.030 (1.48), 2.046 (2.71), 2.069 (2.78), 2.086 (1.60), 2.105 (2.86), 2.131 (2.09), 2.177 (13.12), 2.327 (0.52), 2.670 (0.49), 3.083 (1.26), 3.114 (2.23), 3.169 (2.41), 3.184 (2.37), 3.212 (1.51), 3.309 (7.64), 3.322 (8.73), 3.338 (7.32), 3.395 (2.74), 3.420 (1.48), 3.452 (2.14), 3.479 (1.38), 3.605 (1.26), 3.622 (1.90), 3.639 (2.06), 3.708 (2.01), 3.724 (1.76), 3.741 (1.22), 4.824 (1.52), 4.944 (1.52), 7.463 (2.71), 7.482 (4.63), 7.500 (2.86), 7.657 (1.95), 7.679 (16.00), 7.686 (11.33), 7.708 (5.90), 7.723 (10.09), 7.734 (7.42), 7.739 (7.24), 8.784 (2.18), 8.799 (4.37), 8.813 (2.19).

Example 191

5-[({6-Bromo-2-[3-fluoropiperidin-1-yl]-3-methylquinolin-4-yl}carbonyl)amino]-4-[2-(trifluoromethyl)phenyl]pentanoic acid (Diastereomer 3)

Reaction and Separation of the Mixed Fraction from Example 196A (Peak 1):

The mixed fraction (peak 1) described in Example 196A was dissolved in dichloromethane (1.5 ml), TFA (340 μl, 4.4 mmol) was added, and the mixture was left to stand at RT for 24 h. The mixture was then concentrated and repeatedly dichloromethane was added and the mixture was concentrated again. The residue was purified by preparative HPLC (Method 7). The product-containing fractions were collected (loss of substance occurred here), combined and concentrated, and the residue was lyophilized from acetonitrile/water. 45 mg (100% purity) of 5-[({6-bromo-2-[3-fluoropiperidin-1-yl]-3-methylquinolin-4-yl}carbonyl)amino]-4-[2-(trifluoromethyl)phenyl]pentanoic acid (diastereomer mixture) were obtained.

14 mg of this diastereomer mixture were dissolved in a mixture (8 ml) of acetonitrile and methanol, and purified by means of preparative SFC on chiral phase (see Examples 191 and 192) [column: Daicel Chiralcel OD-H, 5 μm, 250 mm×20 mm; flow rate: 80 ml/min; injection: 2.0 ml; temperature 40° C., UV detection 210 nm, eluent: 80% carbon dioxide/20% ethanol; run time 6.5 min, isocratic]. The combined target fractions were each concentrated, and each residue was lyophilized.

(−)-5-[({6-Bromo-2-[3-fluoropiperidin-1-yl]-3-methylquinolin-4-yl}carbonyl)amino]-4-[2-(trifluoromethyl)phenyl]pentanoic acid (Diastereomer 3)

In the diastereomer separation described, 3 mg (100% purity) of the title compound were obtained as the diastereomer that eluted first.
LC-MS (Method 1): $R_t$=2.12 min; MS (ESIpos): m/z=610/612 [M+H]$^+$
$^1$H-NMR (500 MHz, DMSO-d6) δ [ppm]: −0.007 (0.29), 0.006 (0.25), 0.069 (0.38), 0.843 (0.31), 1.033 (0.89), 1.045 (0.90), 1.236 (0.47), 1.296 (0.21), 1.483 (0.16), 1.498 (0.17), 1.652 (1.74), 1.813 (1.61), 1.829 (1.36), 1.907 (4.05), 1.914 (4.49), 1.924 (3.83), 1.947 (2.99), 1.965 (2.07), 1.979 (3.03), 1.989 (2.09), 1.998 (2.78), 2.007 (1.91), 2.045 (1.72), 2.057 (2.46), 2.076 (2.68), 2.090 (1.44), 2.107 (2.78), 2.118 (1.61), 2.133 (2.08), 2.177 (10.18), 2.215 (0.82), 2.359 (0.30), 2.363 (0.36), 2.432 (1.68), 2.637 (0.45), 2.640 (0.34), 3.087 (1.24), 3.106 (1.94), 3.173 (2.21), 3.188 (2.24), 3.208 (1.55), 3.229 (3.57), 3.396 (3.72), 3.422 (2.39), 3.448 (2.66), 3.469 (1.89), 3.604 (1.48), 3.614 (1.57), 3.629 (1.80), 3.642 (1.90), 3.705 (1.90), 3.717 (1.73), 3.922 (0.24), 3.933 (0.24), 3.962 (0.30), 3.985 (0.27), 4.836 (1.52), 4.923 (1.82), 4.931 (1.65), 4.938 (1.32), 7.467 (2.66), 7.483 (4.72), 7.497 (2.92), 7.662 (3.02), 7.679 (16.00), 7.685 (12.54), 7.689 (11.15), 7.703 (3.21), 7.707 (6.31), 7.724 (9.33), 7.735 (6.85), 7.740 (6.75), 7.749 (2.78), 7.826 (0.92), 8.777 (2.43), 8.789 (4.78), 8.801 (2.35).

Example 192

5-[({6-Bromo-2-[3-fluoropiperidin-1-yl]-3-methylquinolin-4-yl}carbonyl)amino]-4-[2-(trifluoromethyl)phenyl]pentanoic acid (Diastereomer 4)

In the diastereomer separation described in Example 191, 3 mg (100% purity) of the title compound were obtained as the diastereomer that eluted second.
LC-MS Method 1): $R_t$=2.12 min; MS (ESIpos): m/z=610/612 [M+H]$^+$
$^1$H-NMR (400 MHz, DMSO-d6) δ [ppm]: −0.150 (0.03), 0.145 (0.03), 1.199 (0.06), 1.313 (0.08), 1.324 (0.10), 1.359 (16.00), 1.515 (0.07), 1.606 (1.36), 1.786 (0.95), 1.829 (0.23), 1.856 (0.12), 2.014 (0.07), 2.033 (0.27), 2.044 (0.29), 2.065 (1.27), 2.089 (0.32), 2.096 (0.28), 2.128 (0.72), 2.327 (0.04), 2.669 (0.04), 3.369 (0.20), 3.386 (0.20), 3.496 (1.10), 3.511 (1.53), 3.525 (1.08), 3.602 (0.20), 3.618 (0.27), 3.630 (0.26), 3.645 (0.24), 3.663 (0.18), 7.358 (0.39), 7.384 (0.20), 7.397 (0.78), 7.408 (0.64), 7.414 (0.61), 7.420 (0.72), 7.432 (0.19), 7.534 (0.65), 7.546 (0.46), 7.556 (1.45), 7.569 (0.34), 7.600 (0.62), 7.606 (0.59), 7.623 (0.33), 7.628 (0.32), 8.703 (0.21), 8.718 (0.40), 8.732 (0.20).

Example 193

(+)-5-[({6-Bromo-2-[3-ethylpiperidin-1-yl]-3-methylquinolin-4-yl}carbonyl)amino]-4-[2-(trifluoromethyl)phenyl]pentanoic acid (Diastereomer 1)

[For structural formula see Example 124 (diastereomer mixture)]

To a solution of (+)-tert-butyl 5-[({6-bromo-2-[3-ethylpiperidin-1-yl]-3-methylquinolin-4-yl}carbonyl)amino]-4-[2-(trifluoromethyl)phenyl]pentanoate (45 mg, 67 μmol, diastereomer 1, Example 198A) in dichloromethane (510 μl) was added TFA (110 µl, 1.5 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 33 mg (100% purity, 81% of theory) of the title compound were obtained.

$[\alpha]_D^{20}$=+11.5°, 436 nm, c=0.44 g/100 ml, methanol
LC-MS (Method 2): $R_t$=1.28 min; MS (ESIpos): m/z=620/622 [M+H]$^+$
$^1$H-NMR (400 MHz, DMSO-d6) δ [ppm]: 0.895 (1.56), 0.913 (3.64), 0.932 (1.85), 1.263 (0.63), 1.281 (0.82), 1.298 (0.59), 1.571 (0.42), 1.753 (0.48), 1.887 (0.65), 1.921 (0.41), 1.965 (0.46), 1.989 (0.49), 2.049 (0.52), 2.072 (0.57), 2.089 (0.48), 2.130 (1.77), 2.434 (0.42), 2.501 (16.00), 2.749 (0.48), 3.511 (0.75), 3.532 (0.62), 3.716 (0.46), 3.732 (0.40), 7.459 (0.53), 7.479 (0.88), 7.497 (0.53), 7.657 (3.86), 7.685 (0.50), 7.706 (0.96), 7.715 (1.30), 7.735 (2.15), 7.754 (0.48), 8.778 (0.74).

Example 194

(−)-5-[({6-Bromo-2-[3-ethylpiperidin-1-yl]-3-methylquinolin-4-yl}carbonyl)amino]-4-[2-(trifluoromethyl)phenyl]pentanoic acid (Diastereomer 2)

To a solution of (−)-tert-butyl 5-[({6-bromo-2-[3-ethylpiperidin-1-yl]-3-methylquinolin-4-yl}carbonyl)amino]-4-[2-(trifluoromethyl)phenyl]pentanoate (40 mg, 59 µmol, diastereomer 2, Example 199A) in dichloromethane (450 µl) was added TFA (100 µl, 1.3 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 33 mg (100% purity, 81% of theory) of the title compound were obtained.

$[\alpha]_D^{20}$=−42.9°, 589 nm, c=0.34 g/100 ml, methanol
LC-MS (Method 2): $R_t$=1.28 min; MS (ESIpos): m/z=620/622 [M+H]$^+$
$^1$H-NMR (400 MHz, DMSO-d6) δ [ppm]: 0.146 (0.17), 0.896 (6.44), 0.915 (16.00), 0.934 (7.90), 1.060 (0.48), 1.087 (1.16), 1.113 (1.24), 1.139 (0.55), 1.234 (0.82), 1.247 (1.07), 1.264 (2.26), 1.281 (3.55), 1.299 (3.26), 1.315 (1.91), 1.333 (0.76), 1.578 (1.42), 1.618 (1.33), 1.651 (1.17), 1.763 (1.74), 1.797 (1.17), 1.858 (1.58), 1.895 (2.34), 1.927 (1.27), 1.945 (1.22), 1.967 (0.98), 1.985 (1.74), 1.997 (1.06), 2.008 (2.11), 2.025 (0.80), 2.041 (1.12), 2.057 (2.00), 2.080 (2.04), 2.097 (1.20), 2.110 (2.27), 2.165 (10.84), 2.328 (0.56), 2.367 (0.30), 2.671 (0.47), 2.711 (0.25), 2.779 (0.72), 2.809 (1.32), 3.326 (1.42), 3.546 (2.56), 3.577 (2.59), 3.618 (1.37), 3.634 (1.42), 3.724 (1.28), 4.333 (0.69), 7.415 (0.63), 7.465 (1.66), 7.484 (3.16), 7.502 (2.03), 7.706 (10.33), 7.724 (6.22), 7.741 (8.10), 7.758 (1.71), 8.778 (1.46), 8.792 (2.81), 8.807 (1.49).

Example 195

5-[({6-Bromo-2-[3-ethylpiperidin-1-yl]-3-methylquinolin-4-yl}carbonyl)amino]-4-[2-(trifluoromethyl)phenyl]pentanoic acid (Diastereomer 3)

To a solution of (−)-tert-butyl 5-[({6-bromo-2-[3-ethylpiperidin-1-yl]-3-methylquinolin-4-yl}carbonyl)amino]-4-[2-(trifluoromethyl)phenyl]pentanoate (55 mg, 81 µmol, diastereomer 3, Example 200A) in dichloromethane (625 µl) was added TFA (138 µl, 1.78 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 33 mg (100% purity, 81% of theory) of the title compound were obtained.

LC-MS (Method 2): $R_t$=1.28 min; MS (ESIpos): m/z=620/622 [M+H]$^+$
$^1$H-NMR (400 MHz, DMSO-d6) δ [ppm]: 0.896 (6.71), 0.915 (16.00), 0.933 (7.95), 1.060 (0.50), 1.089 (1.32), 1.118 (1.37), 1.140 (0.62), 1.233 (0.74), 1.248 (1.12), 1.265 (2.52), 1.275 (2.32), 1.283 (3.35), 1.292 (2.79), 1.301 (2.42), 1.310 (1.90), 1.344 (0.28), 1.580 (1.69), 1.606 (1.47), 1.616 (1.53), 1.648 (1.30), 1.678 (0.58), 1.763 (1.92), 1.796 (1.31), 1.856 (1.82), 1.895 (2.61), 1.920 (1.46), 1.927 (1.46), 1.943 (1.42), 1.965 (1.14), 1.982 (1.98), 1.995 (1.20), 2.006 (2.34), 2.023 (1.04), 2.044 (1.28), 2.059 (2.27), 2.082 (2.50), 2.137 (6.50), 2.328 (0.40), 2.367 (0.31), 2.671 (0.37), 2.711 (0.24), 2.784 (0.87), 2.812 (1.60), 2.840 (0.89), 3.324 (1.56), 3.545 (2.89), 3.576 (2.80), 3.609 (1.15), 3.626 (1.48), 3.643 (1.56), 3.708 (1.13), 3.725 (1.89), 3.742 (1.68), 3.759 (1.21), 3.775 (0.66), 4.374 (0.60), 7.465 (2.03), 7.483 (3.62), 7.502 (2.29), 7.690 (1.98), 7.710 (13.25), 7.728 (4.42), 7.739 (8.10), 7.761 (2.15), 8.780 (1.62), 8.795 (3.23), 8.809 (1.68).

Example 196

(+)-5-[({6-Bromo-2-[3-ethylpiperidin-1-yl]-3-methylquinolin-4-yl}carbonyl)amino]-4-[2-(trifluoromethyl)phenyl]pentanoic acid (Diastereomer 4)

To a solution of (−)-tert-butyl 5-[({6-bromo-2-[3-ethylpiperidin-1-yl]-3-methylquinolin-4-yl}carbonyl)amino]-4-[2-(trifluoromethyl)phenyl]pentanoate (45 mg, 67 µmol, diastereomer 4, Example 201A) in dichloromethane (512 µl) was added TFA (113 µl, 1.46 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 22 mg (100% purity, 54% of theory) of the title compound were obtained.

$[\alpha]_D^{20}$=+36.5°, 589 nm, c=0.44 g/100 ml, methanol
LC-MS (Method 2): $R_t$=1.28 min; MS (ESIpos): m/z=620/622 [M+H]$^+$
$^1$H-NMR (400 MHz, DMSO-d6) δ [ppm]: 0.895 (6.49), 0.914 (16.00), 0.933 (7.87), 1.045 (0.48), 1.074 (1.22), 1.097 (1.27), 1.126 (0.56), 1.245 (1.11), 1.262 (2.28), 1.279 (3.44), 1.296 (3.11), 1.312 (1.94), 1.330 (0.77), 1.572 (1.42), 1.615 (1.37), 1.644 (1.20), 1.755 (1.80), 1.788 (1.19), 1.853 (1.63), 1.894 (2.29), 1.926 (1.31), 1.942 (1.33), 1.965 (1.02), 1.982 (1.75), 1.994 (1.19), 2.006 (2.13), 2.024 (0.84), 2.041 (1.16), 2.056 (2.06), 2.079 (2.04), 2.097 (1.29), 2.110 (2.32), 2.159 (11.74), 2.328 (0.58), 2.367 (0.41), 2.429 (1.18), 2.458 (1.97), 2.670 (0.49), 2.710 (0.42), 2.733 (0.86), 2.759 (1.56), 2.790 (0.85), 3.325 (1.61), 3.522 (5.03), 3.543 (4.60), 3.595 (2.21), 3.614 (2.34), 3.631 (2.17), 3.716 (1.56), 7.414 (0.69), 7.464 (1.69), 7.483 (3.14), 7.501 (1.93), 7.643 (0.61), 7.665 (14.63), 7.690 (1.70), 7.709 (3.46), 7.723 (6.19), 7.740 (7.10), 7.756 (1.65), 8.756 (1.60), 8.770 (3.12), 8.785 (1.58).

Example 197

(+)-5-[({6-Bromo-3-methyl-2-[3-methylpiperidin-1-yl]quinolin-4-yl}carbonyl)amino]-4-[2-(trifluoromethyl)phenyl]pentanoic acid (Diastereomer 1)

[For structural formula see Example 125 (diastereomer mixture)]

To a solution of (+)-tert-butyl 5-[({6-bromo-3-methyl-2-[3-methylpiperidin-1-yl]quinolin-4-yl}carbonyl)amino]-4-[2-(trifluoromethyl)phenyl]pentanoate (70 mg, 106 μmol, diastereomer 1, Example 202A) in dichloromethane (810 μl) was added TFA (180 μl, 2.32 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 45 mg (100% purity, 70% of theory) of the title compound were obtained.

$[\alpha]_D^{20}$=+22.2°, 589 nm, c=0.27 g/100 ml, methanol

LC-MS (Method 1): $R_t$=2.34 min; MS (ESIpos): m/z=606/608 [M+H]$^+$ $^1$H-NMR (400 MHz, DMSO-d6) δ [ppm]: −0.149 (0.18), −0.008 (1.58), 0.008 (1.81), 0.069 (0.44), 0.146 (0.19), 0.927 (10.77), 0.943 (10.98), 0.984 (0.16), 1.056 (0.36), 1.084 (1.12), 1.114 (1.17), 1.135 (0.48), 1.235 (0.33), 1.633 (0.97), 1.663 (1.14), 1.691 (0.56), 1.737 (2.00), 1.771 (1.99), 1.797 (2.53), 1.827 (1.55), 1.893 (1.08), 1.902 (1.01), 1.924 (1.40), 1.938 (1.28), 1.952 (1.21), 1.968 (1.64), 1.981 (0.97), 1.992 (1.83), 2.001 (1.10), 2.032 (0.90), 2.047 (1.77), 2.071 (1.84), 2.088 (1.01), 2.108 (1.88), 2.162 (8.48), 2.328 (0.30), 2.367 (0.19), 2.436 (1.04), 2.465 (1.69), 2.670 (0.37), 2.691 (0.96), 2.718 (1.71), 2.747 (0.94), 3.452 (1.85), 3.479 (3.26), 3.508 (1.63), 3.608 (0.78), 3.625 (1.19), 3.641 (1.32), 3.696 (1.34), 3.712 (1.15), 3.729 (0.76), 7.435 (0.73), 7.462 (1.67), 7.481 (2.99), 7.499 (1.81), 7.636 (0.90), 7.657 (16.00), 7.661 (8.05), 7.684 (1.57), 7.707 (3.18), 7.722 (6.86), 7.732 (4.91), 7.739 (4.39), 8.766 (1.46), 8.781 (2.92), 8.795 (1.44), 12.101 (0.17).

Example 198

(+)-5-[({6-Bromo-3-methyl-2-[3-methylpiperidin-1-yl]quinolin-4-yl}carbonyl)amino]-4-[2-(trifluoromethyl)phenyl]pentanoic acid (Diastereomer 2)

To a solution of (+)-tert-butyl 5-[({6-bromo-3-methyl-2-[3-methylpiperidin-1-yl]quinolin-4-yl}carbonyl)amino]-4-[2-(trifluoromethyl)phenyl]pentanoate (70 mg, 106 μmol, diastereomer 2, Example 203A) in dichloromethane (810 μl) was added TFA (180 μl, 2.3 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 47 mg (100% purity, 73% of theory) of the title compound were obtained.

$[\alpha]_D^{20}$=+11.7°, 589 nm, c=0.29 g/100 ml, methanol

LC-MS (Method 1): $R_t$=2.34 min; MS (ESIpos): m/z=606/608 [M+H]$^+$ $^1$H-NMR (400 MHz, DMSO-d6) δ [ppm]: −0.008 (1.27), 0.008 (1.49), 0.069 (0.30), 0.146 (0.17), 0.928 (11.12), 0.944 (11.35), 1.059 (0.37), 1.085 (1.15), 1.115 (1.18), 1.136 (0.47), 1.235 (0.19), 1.635 (0.98), 1.665 (1.19), 1.695 (0.56), 1.737 (2.01), 1.771 (1.99), 1.797 (2.48), 1.828 (1.54), 1.897 (1.09), 1.907 (1.03), 1.927 (1.25), 1.942 (1.18), 1.961 (1.04), 1.978 (1.67), 1.990 (1.02), 2.002 (1.92), 2.011 (1.17), 2.039 (1.00), 2.053 (1.87), 2.076 (1.89), 2.094 (1.09), 2.113 (1.91), 2.168 (10.24), 2.328 (0.43), 2.366 (0.20), 2.438 (1.20), 2.468 (1.84), 2.670 (0.48), 2.689 (0.90), 2.718 (1.63), 2.746 (0.89), 3.452 (1.81), 3.480 (3.20), 3.508 (1.54), 3.612 (1.12), 3.629 (1.22), 3.707 (1.17), 3.723 (1.04), 7.424 (0.65), 7.465 (1.63), 7.483 (2.97), 7.501 (1.79), 7.636 (0.89), 7.658 (16.00), 7.662 (7.92), 7.685 (1.30), 7.709 (3.20), 7.724 (6.78), 7.735 (4.84), 7.741 (4.46), 8.760 (1.53), 8.775 (3.04), 8.789 (1.47), 12.012 (0.45).

Example 199

(−)-5-[({6-Bromo-3-methyl-2-[3-methylpiperidin-1-yl]quinolin-4-yl}carbonyl)amino]-4-[2-(trifluoromethyl)phenyl]pentanoic acid (Diastereomer 3)

Reaction and Separation of the Mixed Fraction from Example 202A (Peak 1):

The mixed fraction (peak 1) described in Example 202A was dissolved in dichloromethane (1.8 ml), TFA (390 μl, 5.05 mmol) was added, and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 106 mg (100% purity) of 5-[({6-bromo-3-methyl-2-[3-methylpiperidin-1-yl]quinolin-4-yl}carbonyl)amino]-4-[2-(trifluoromethyl)phenyl]pentanoic acid (diastereomer mixture) were obtained.

78 mg of this diastereomer mixture were dissolved in a mixture (8 ml) of acetonitrile and methanol, and purified by means of preparative SFC on chiral phase (see Examples 199 and 200) [column: Daicel Chiralcel OD-H, 5 μm, 250 mm×20 mm; flow rate: 80 ml/min; injection: 2.0 ml; temperature 40° C., UV detection 210 nm, eluent: 80% carbon dioxide/20% ethanol; run time 6.5 min, isocratic]. The combined target fractions were each concentrated, and each residue was lyophilized.

(−)-5-[({6-Bromo-3-methyl-2-[3-methylpiperidin-1-yl]quinolin-4-yl}carbonyl)amino]-4-[2-(trifluoromethyl)phenyl]pentanoic acid (Diastereomer 3)

In the diastereomer separation described, 24 mg (100% purity, ee>99%) of the title compound were obtained as the diastereomer that eluted first.

LC-MS (Method 2): $R_t$=1.22 min; MS (ESIpos): m/z=606/608 [M+H]$^+$ $^1$H-NMR (400 MHz, DMSO-d6) δ [ppm]: −0.008 (0.79), 0.008 (0.76), 0.069 (0.28), 0.927 (10.81), 0.943 (10.94), 1.056 (0.42), 1.084 (1.13), 1.108 (1.18), 1.136 (0.48), 1.237 (0.16), 1.633 (1.00), 1.663 (1.16), 1.737 (2.02), 1.744 (1.93), 1.772 (2.02), 1.797 (2.51), 1.828 (1.59), 1.898 (1.22), 1.909 (1.22), 1.929 (1.37), 1.942 (1.31), 1.963 (1.20), 1.979 (1.84), 1.992 (1.24), 2.004 (2.13), 2.012 (1.20), 2.040 (1.15), 2.055 (2.08), 2.079 (2.19), 2.096 (1.33), 2.114 (2.35), 2.162 (8.78), 2.328 (0.42), 2.366 (0.31), 2.436 (1.08), 2.466 (1.74), 2.670 (0.48), 2.691 (0.94), 2.718 (1.67), 2.747 (0.93), 3.452 (1.70), 3.479 (3.15), 3.509 (1.53), 3.628 (1.16), 3.644 (1.35), 3.697 (1.39), 3.713 (1.17), 7.432 (0.80), 7.464 (1.77), 7.483 (3.21), 7.502 (1.99), 7.636 (0.94), 7.658 (16.00), 7.662 (7.86), 7.685 (1.53), 7.709 (3.51), 7.724 (6.91), 7.740 (5.40), 7.754 (1.76), 8.756 (1.54), 8.770 (3.12), 8.785 (1.54), 12.030 (2.34).

Example 200

(−)-5-[({6-Bromo-3-methyl-2-[3-methylpiperidin-1-yl]quinolin-4-yl}carbonyl)amino]-4-[2-(trifluoromethyl)phenyl]pentanoic acid (Diastereomer 4)

In the diastereomer separation described in Example 199, 23 mg (100% purity, ee>99%) of the title compound were obtained as the diastereomer that eluted second.

LC-MS (Method 2): $R_t$=1.22 min; MS (ESIpos): m/z=606/608 [M+H]$^+$ $^1$H-NMR (400 MHz, DMSO-d6) δ [ppm]: 0.008 (0.84), 0.069 (0.29), 0.928 (11.23), 0.944 (11.35), 1.085 (1.20), 1.115 (1.22), 1.136 (0.52), 1.634 (1.04), 1.665 (1.28), 1.692 (0.64), 1.737 (2.13), 1.771 (2.10), 1.797 (2.59), 1.828 (1.65), 1.897 (1.30), 1.909 (1.29), 1.929 (1.44), 1.943 (1.42), 1.963 (1.22), 1.980 (1.93), 1.993 (1.27), 2.004 (2.23), 2.014 (1.33), 2.040 (1.25), 2.055 (2.17), 2.078 (2.26), 2.096 (1.43), 2.114 (2.23), 2.168 (10.68), 2.255 (0.24), 2.328 (0.50), 2.367 (0.27), 2.438 (1.21), 2.469 (1.90), 2.670 (0.59), 2.690 (0.94), 2.718 (1.67), 2.746 (0.93), 3.453 (1.89), 3.480 (3.27), 3.509 (1.63), 3.613 (1.27), 3.630 (1.33), 3.708 (1.29), 3.724 (1.16), 7.425 (0.71), 7.465 (1.79), 7.484 (3.29), 7.502 (2.08), 7.636 (0.78), 7.658 (16.00), 7.662 (8.26), 7.690 (1.53), 7.709 (3.65), 7.725 (7.44), 7.735 (5.58), 7.742 (5.23), 8.758 (1.60), 8.773 (3.25), 8.788 (1.62), 12.029 (2.27).

Example 201

(−)-5-[({6-Bromo-2-[3-fluoropiperidin-1-yl]-3-methylquinolin-4-yl}carbonyl)amino]-4-[2-(trifluoromethoxy)phenyl]pentanoic acid (Diastereomer 1)

[For structural formula see Example 138 (diastereomer mixture)]

To a solution of (−)-tert-butyl 5-[({6-bromo-2-[3-fluoropiperidin-1-yl]-3-methylquinolin-4-yl}carbonyl)amino]-4-[2-(trifluoromethoxy)phenyl]pentanoate (70 mg, 101 µmol, diastereomer 1, Example 204A) in dichloromethane (1.8 ml) was added TFA (172 µl, 2.23 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 40 mg (100% purity, 62% of theory) of the title compound were obtained.

$[α]_D^{20}$=−20.0°, 589 nm, c=0.33 g/100 ml, methanol

LC-MS (Method 1): $R_t$=2.15 min; MS (ESIpos): m/z=626/628 [M+H]$^+$ $^1$H-NMR (500 MHz, DMSO-d6) δ [ppm]: −0.007 (1.74), 0.006 (1.29), 0.117 (0.17), 1.234 (0.48), 1.358 (0.18), 1.647 (2.01), 1.777 (0.83), 1.794 (1.85), 1.807 (3.28), 1.815 (3.49), 1.825 (3.10), 1.833 (3.74), 1.851 (2.21), 1.910 (3.53), 1.926 (2.82), 1.948 (1.55), 1.970 (1.09), 1.978 (1.12), 1.995 (0.62), 2.010 (0.51), 2.031 (1.08), 2.042 (2.73), 2.068 (9.82), 2.072 (8.73), 2.093 (2.44), 2.106 (1.59), 2.153 (8.47), 2.242 (0.33), 2.358 (0.31), 2.362 (0.41), 2.519 (0.94), 2.523 (0.70), 2.632 (0.31), 2.636 (0.41), 2.639 (0.31), 3.079 (1.46), 3.100 (2.29), 3.163 (2.39), 3.177 (2.41), 3.198 (1.53), 3.292 (1.73), 3.305 (2.59), 3.318 (3.24), 3.331 (3.42), 3.345 (2.27), 3.390 (4.35), 3.395 (4.39), 3.415 (2.52), 3.441 (2.30), 3.463 (1.61), 3.594 (1.07), 3.605 (1.65), 3.620 (2.70), 3.632 (3.18), 3.645 (1.99), 3.656 (1.71), 3.670 (2.44), 3.684 (2.05), 3.696 (1.26), 3.711 (0.70), 4.831 (1.64), 4.920 (1.40), 4.926 (1.64), 4.932 (1.37), 7.343 (2.70), 7.347 (2.74), 7.351 (2.93), 7.355 (3.78), 7.359 (4.72), 7.362 (3.77), 7.384 (1.38), 7.389 (2.08), 7.399 (6.05), 7.403 (8.73), 7.410 (7.42), 7.417 (7.35), 7.431 (1.78), 7.468 (0.96), 7.550 (4.55), 7.554 (3.30), 7.562 (3.39), 7.569 (3.42), 7.657 (3.58), 7.674 (16.00), 7.681 (10.84), 7.685 (9.37), 7.699 (2.17), 7.703 (2.30), 8.746 (2.70), 8.757 (4.94), 8.769 (2.51).

Example 202

(−)-5-[({6-Bromo-2-[3-fluoropiperidin-1-yl]-3-methylquinolin-4-yl}carbonyl)amino]-4-[2-(trifluoromethoxy)phenyl]pentanoic acid (Diastereomer 2)

To a solution of (−)-tert-butyl 5-[({6-bromo-2-[3-fluoropiperidin-1-yl]-3-methylquinolin-4-yl}carbonyl)amino]-4-[2-(trifluoromethoxy)phenyl]pentanoate (70 mg, 103 µmol, diastereomer 2, Example 205A) in dichloromethane (1.8 ml) was added TFA (174 µl, 2.26 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 37 mg (100% purity, 58% of theory) of the title compound were obtained.

$[α]_D^{20}$=−14.2°, 589 nm, c=0.33 g/100 ml, methanol

LC-MS (Method 1): $R_t$=2.15 min; MS (ESIpos): m/z=626/628 [M+H]$^+$ $^1$H-NMR (500 MHz, DMSO-d6) δ [ppm]: −0.120 (0.23), −0.007 (2.56), 0.006 (1.91), 0.070 (0.24), 0.117 (0.21), 1.234 (0.27), 1.249 (0.18), 1.365 (0.16), 1.646 (1.97), 1.779 (0.86), 1.795 (1.89), 1.809 (3.39), 1.818 (3.31), 1.827 (3.12), 1.835 (3.65), 1.854 (2.25), 1.910 (3.52), 1.920 (2.49), 1.927 (2.86), 1.949 (1.66), 1.970 (1.11), 1.978 (1.13), 2.017 (0.45), 2.048 (2.62), 2.070 (10.21), 2.096 (2.46), 2.154 (9.21), 2.240 (0.34), 2.362 (0.39), 2.519 (0.85), 2.523 (0.58), 2.636 (0.37), 3.078 (1.46), 3.098 (2.24), 3.167 (2.44), 3.181 (2.44), 3.202 (1.56), 3.290 (1.92), 3.304 (2.85), 3.316 (3.52), 3.329 (3.62), 3.343 (2.38), 3.395 (4.37), 3.416 (2.57), 3.442 (2.19), 3.464 (1.51), 3.599 (0.89), 3.611 (1.41), 3.625 (2.70), 3.638 (3.40), 3.650 (3.29), 3.664 (2.72), 3.678 (2.12), 3.690 (1.14), 3.705 (0.62), 4.826 (1.45), 4.832 (1.71), 4.921 (1.45), 4.927 (1.72), 4.933 (1.42), 7.345 (2.69), 7.348 (2.70), 7.352 (2.89), 7.356 (3.79), 7.360 (4.70), 7.363 (3.78), 7.384 (1.46), 7.389 (2.13), 7.399 (6.05), 7.403 (8.97), 7.410 (7.38), 7.417 (7.59), 7.431 (1.73), 7.480 (0.99), 7.551 (4.79), 7.555 (3.42), 7.563 (3.46), 7.570 (3.57), 7.658 (3.77), 7.675 (16.00), 7.682 (10.74), 7.686 (9.28), 7.700 (2.17), 7.704 (2.26), 8.743 (2.56), 8.755 (4.81), 8.766 (2.44), 12.171 (0.19).

Example 203

(+)-5-[({6-Bromo-2-[3-fluoropiperidin-1-yl]-3-methylquinolin-4-yl}carbonyl)amino]-4-[2-(trifluoromethoxy)phenyl]pentanoic acid (Diastereomer 3)

To a solution of (+)-tert-butyl 5-[({6-bromo-2-[3-fluoropiperidin-1-yl]-3-methylquinolin-4-yl}carbonyl)amino]-4-[2-(trifluoromethoxy)phenyl]pentanoate (64 mg, 92 µmol, diastereomer 3, Example 206A) in dichloromethane (1.62 ml) was added TFA (156 µl, 2.02 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 38 mg (100% purity, 65% of theory) of the title compound were obtained.

[α]$_D^{20}$=+14.9°, 589 nm, c=0.32 g/100 ml, methanol
LC-MS (Method 1): R$_t$=2.15 min; MS (ESIpos): m/z=626/628 [M+H]$^+$
$^1$H-NMR (500 MHz, DMSO-d6) δ [ppm]: −0.007 (1.72), 0.006 (1.14), 0.070 (0.25), 1.233 (0.53), 1.333 (0.22), 1.353 (0.39), 1.371 (0.25), 1.646 (2.02), 1.779 (0.85), 1.795 (1.93), 1.809 (3.59), 1.819 (3.45), 1.827 (3.18), 1.835 (3.82), 1.854 (2.40), 1.911 (3.61), 1.920 (2.55), 1.927 (2.93), 1.949 (1.71), 1.971 (1.13), 1.978 (1.15), 2.015 (0.49), 2.036 (1.12), 2.047 (2.88), 2.069 (10.49), 2.096 (2.64), 2.111 (1.57), 2.154 (9.53), 2.241 (0.34), 2.362 (0.36), 2.519 (0.74), 2.522 (0.54), 2.636 (0.34), 3.078 (1.52), 3.099 (2.33), 3.167 (2.56), 3.181 (2.58), 3.202 (1.69), 3.289 (1.77), 3.303 (2.69), 3.316 (3.34), 3.329 (3.53), 3.343 (2.33), 3.395 (4.62), 3.416 (2.75), 3.442 (2.37), 3.464 (1.65), 3.599 (0.94), 3.611 (1.50), 3.625 (2.85), 3.638 (3.63), 3.650 (3.47), 3.664 (2.87), 3.678 (2.24), 3.690 (1.23), 3.705 (0.71), 4.832 (1.74), 4.921 (1.49), 4.927 (1.76), 4.933 (1.46), 7.345 (2.68), 7.348 (2.69), 7.352 (2.86), 7.357 (3.85), 7.360 (4.78), 7.384 (1.37), 7.389 (2.04), 7.399 (6.17), 7.403 (9.14), 7.410 (7.53), 7.417 (7.95), 7.431 (1.82), 7.481 (1.02), 7.551 (5.06), 7.555 (3.52), 7.563 (3.66), 7.570 (3.84), 7.658 (3.63), 7.675 (16.00), 7.683 (10.62), 7.686 (9.13), 7.700 (2.21), 7.704 (2.30), 8.744 (2.82), 8.756 (5.44), 8.767 (2.75).

Example 204

(+)-5-[({6-Bromo-2-[3-fluoropiperidin-1-yl]-3-methylquinolin-4-yl}carbonyl)amino]-4-[2-(trifluoromethoxy)phenyl]pentanoic acid (Diastereomer 4)

To a solution of (+)-tert-butyl 5-[({6-bromo-2-[3-fluoropiperidin-1-yl]-3-methylquinolin-4-yl}carbonyl)amino]-4-[2-(trifluoromethoxy)phenyl]pentanoate (64 mg, 94 µmol, diastereomer 4, Example 207A) in dichloromethane (1.66 ml) was added TFA (159 µl, 2.06 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 31 mg (100% purity, 53% of theory) of the title compound were obtained.
[α]$_D^{20}$=+20.0°, 589 nm, c=0.35 g/100 ml, methanol
LC-MS (Method 1): R$_t$=2.15 min; MS (ESIpos): m/z=626/628 [M+H]$^+$
$^1$H-NMR (500 MHz, DMSO-d6) δ [ppm]: −0.120 (0.20), −0.007 (2.68), 0.006 (1.93), 0.117 (0.20), 1.131 (3.23), 1.235 (0.50), 1.353 (0.28), 1.386 (0.19), 1.646 (2.21), 1.778 (0.95), 1.795 (2.07), 1.807 (3.59), 1.816 (3.73), 1.825 (3.47), 1.833 (4.07), 1.852 (2.39), 1.910 (3.89), 1.926 (3.11), 1.947 (1.73), 1.971 (1.24), 1.978 (1.26), 2.047 (2.74), 2.068 (11.03), 2.093 (2.58), 2.153 (9.32), 2.242 (0.35), 2.362 (0.50), 2.636 (0.46), 3.080 (1.61), 3.099 (2.52), 3.163 (2.63), 3.176 (2.67), 3.198 (1.69), 3.291 (2.30), 3.305 (3.33), 3.318 (4.05), 3.331 (4.17), 3.345 (2.80), 3.390 (4.88), 3.415 (2.76), 3.441 (2.48), 3.462 (1.70), 3.594 (1.14), 3.605 (1.76), 3.620 (2.90), 3.632 (3.47), 3.645 (2.18), 3.656 (1.95), 3.670 (2.71), 3.683 (2.24), 3.696 (1.38), 3.711 (0.77), 4.254 (0.23), 4.265 (0.19), 4.831 (1.80), 4.926 (1.80), 7.213 (0.24), 7.286 (0.23), 7.302 (0.26), 7.344 (2.98), 7.347 (3.03), 7.351 (3.22), 7.355 (4.05), 7.359 (4.92), 7.389 (2.26), 7.400 (6.52), 7.403 (9.12), 7.411 (7.68), 7.418 (7.84), 7.432 (1.90), 7.473 (1.07), 7.551 (4.79), 7.562 (3.74), 7.569 (3.59), 7.657 (3.65), 7.674 (16.00), 7.681 (10.76), 7.685 (9.35), 7.699 (2.19), 7.703 (2.29), 8.745 (2.59), 8.756 (4.66), 8.768 (2.45), 12.196 (0.18).

Example 205

(+)-5-[({6-Bromo-2-[3-ethylpiperidin-1-yl]-3-methylquinolin-4-yl}carbonyl)amino]-4-[2-(trifluoromethoxy)phenyl]pentanoic acid (Diastereomer 1)

[For structural formula see Example 139 (diastereomer mixture)]
To a solution of (+)-tert-butyl 5-[({6-bromo-2-[3-ethylpiperidin-1-yl]-3-methylquinolin-4-yl}carbonyl)amino]-4-[2-(trifluoromethoxy)phenyl]pentanoate (45 mg, 65 µmol, diastereomer 1, Example 208A) in dichloromethane (0.5 ml) was added TFA (110 µl, 1.43 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 38 mg (100% purity, 92% of theory) of the title compound were obtained.
[α]$_D^{20}$=+12.7°, 436 nm, c=0.30 g/100 ml, methanol
LC-MS (Method 2): R$_t$=1.31 min; MS (ESIpos): m/z=636/638 [M+H]$^+$
$^1$H-NMR (400 MHz, DMSO-d6) δ [ppm]: 0.893 (6.77), 0.911 (16.00), 0.930 (8.24), 1.045 (0.61), 1.067 (1.37), 1.102 (1.47), 1.140 (0.77), 1.242 (1.36), 1.260 (2.97), 1.278 (3.89), 1.296 (2.68), 1.567 (1.79), 1.603 (1.66), 1.636 (1.39), 1.753 (2.05), 1.785 (1.75), 1.812 (1.58), 1.836 (2.59), 1.857 (2.73), 1.882 (1.90), 1.909 (1.96), 2.051 (2.59), 2.077 (12.08), 2.111 (7.17), 2.229 (0.46), 2.246 (0.53), 2.327 (0.72), 2.675 (0.63), 2.739 (1.08), 2.769 (1.95), 2.799 (1.06), 3.390 (1.88), 3.510 (3.52), 3.540 (3.41), 3.567 (1.51), 3.584 (1.48), 3.599 (1.93), 3.617 (2.79), 3.633 (3.32), 3.648 (2.34), 3.661 (2.48), 3.678 (3.22), 3.696 (2.83), 3.711 (2.05), 3.731 (1.49), 7.355 (3.26), 7.385 (1.48), 7.397 (5.85), 7.409 (4.92), 7.420 (5.18), 7.476 (1.21), 7.555 (3.56), 7.567 (3.02), 7.578 (2.59), 7.674 (15.79), 8.734 (1.88), 8.749 (3.42), 8.763 (1.76).

Example 206

5-[({6-Bromo-2-[3-ethylpiperidin-1-yl]-3-methylquinolin-4-yl}carbonyl)amino]-4-[2-(trifluoromethoxy)phenyl]pentanoic acid (Diastereomer 2)

To a solution of (−)-tert-butyl 5-[({6-bromo-2-[3-ethylpiperidin-1-yl]-3-methylquinolin-4-yl}carbonyl)amino]-4-[2-(trifluoromethoxy)phenyl]pentanoate (30 mg, 43 µmol, diastereomer 2, Example 209A) in dichloromethane (330 µl) was added TFA (73 µl, 950 µmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 14 mg (100% purity, 50% of theory) of the title compound were obtained.
LC-MS (Method 2): R$_t$=1.31 min; MS (ESIpos): m/z=636/638 [M+H]$^+$
$^1$H-NMR (400 MHz, DMSO-d6) δ [ppm]: 0.069 (0.21), 0.894 (6.49), 0.913 (16.00), 0.931 (8.01), 1.086 (1.30), 1.114 (1.33), 1.138 (0.60), 1.245 (1.15), 1.262 (2.51), 1.280 (3.24), 1.291 (2.89), 1.298 (2.89), 1.309 (1.93), 1.574 (1.48), 1.614 (1.40), 1.645 (1.26), 1.760 (1.81), 1.792 (1.65), 1.815 (1.52), 1.838 (1.92), 1.858 (2.48), 1.885 (1.73), 1.909 (0.69), 2.054 (2.32), 2.079 (10.90), 2.141 (9.25), 2.328 (0.48), 2.367 (0.29), 2.671 (0.47), 2.710 (0.27), 2.803 (1.31), 3.406 (1.46), 3.536 (2.86), 3.566 (2.69), 3.603 (1.12), 3.621 (1.93), 3.637 (2.39), 3.653 (1.91), 3.675 (1.73), 3.691 (1.41), 4.286 (0.64), 7.358 (2.99), 7.387 (1.36), 7.401 (5.34), 7.412 (4.79), 7.419 (4.47), 7.424 (5.17), 7.437 (1.59), 7.554 (3.13), 7.566 (2.68), 7.577 (2.30), 7.702 (8.48), 8.747 (1.57), 8.762 (2.93).

Example 207

(−)-5-[({6-Bromo-2-[3-ethylpiperidin-1-yl]-3-methylquinolin-4-yl}carbonyl)amino]-4-[2-(trifluoromethoxy)phenyl]pentanoic acid (Diastereomer 3)

To a solution of (−)-tert-butyl 5-[({6-bromo-2-[3-ethylpiperidin-1-yl]-3-methylquinolin-4-yl}carbonyl)amino]-4-[2-(trifluoromethoxy)phenyl]pentanoate (45 mg, 65 µmol, diastereomer 3, Example 210A) in dichloromethane (0.5 ml) was added TFA (110 µl, 1.43 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 22 mg (100% purity, 53% of theory) of the title compound were obtained.

$[\alpha]_D^{20}$=−10.6°, 436 nm, c=0.35 g/100 ml, methanol
LC-MS (Method 2): $R_t$=1.31 min; MS (ESIpos): m/z=636/638 [M+H]$^+$
$^1$H-NMR (400 MHz, DMSO-d6) δ [ppm]: 0.893 (6.49), 0.912 (16.00), 0.930 (7.83), 1.069 (1.16), 1.098 (1.20), 1.121 (0.54), 1.243 (1.11), 1.260 (2.52), 1.278 (3.35), 1.296 (2.24), 1.564 (1.46), 1.602 (1.36), 1.634 (1.14), 1.751 (1.72), 1.784 (1.42), 1.814 (1.24), 1.825 (1.32), 1.836 (2.15), 1.857 (2.26), 1.883 (1.55), 2.050 (2.20), 2.077 (10.21), 2.109 (5.78), 2.328 (0.41), 2.367 (0.34), 2.404 (0.80), 2.430 (1.31), 2.458 (0.96), 2.670 (0.35), 2.723 (0.91), 2.755 (1.66), 2.783 (0.94), 3.409 (2.32), 3.498 (3.72), 3.528 (3.05), 3.584 (0.97), 3.599 (1.25), 3.617 (1.88), 3.633 (2.25), 3.648 (1.36), 3.660 (1.49), 3.677 (1.98), 3.696 (1.66), 3.712 (0.97), 3.730 (0.63), 7.355 (2.78), 7.384 (1.19), 7.399 (4.88), 7.410 (4.38), 7.417 (3.92), 7.421 (4.57), 7.434 (1.17), 7.472 (0.98), 7.555 (3.27), 7.560 (2.08), 7.567 (2.60), 7.578 (2.44), 7.637 (1.08), 7.660 (13.23), 7.665 (7.07), 7.683 (0.77), 7.688 (0.90), 8.722 (1.55), 8.736 (2.95), 8.750 (1.56), 12.021 (0.18).

Example 208

(+)-5-[({6-Bromo-2-[3-ethylpiperidin-1-yl]-3-methylquinolin-4-yl}carbonyl)amino]-4-[2-(trifluoromethoxy)phenyl]pentanoic acid (Diastereomer 4)

To a solution of (+)-tert-butyl 5-[({6-bromo-2-[3-ethylpiperidin-1-yl]-3-methylquinolin-4-yl}carbonyl)amino]-4-[2-(trifluoromethoxy)phenyl]pentanoate (50 mg, 72 µmol, diastereomer 4, Example 211A) in dichloromethane (550 µl) was added TFA (122 µl, 1.60 mmol), and the mixture was left to stand at RT for 24 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 29 mg (100% purity, 64% of theory) of the title compound were obtained.

$[\alpha]_D^{20}$=+33.2°, 589 nm, c=0.33 g/100 ml, methanol
LC-MS (Method 2): $R_t$=1.31 min; MS (ESIpos): m/z=636/638 [M+H]$^+$
$^1$H-NMR (400 MHz, DMSO-d6) δ [ppm]: 0.893 (2.80), 0.911 (6.69), 0.930 (3.44), 1.040 (0.22), 1.068 (0.60), 1.098 (0.62), 1.120 (0.28), 1.242 (0.50), 1.260 (1.07), 1.277 (1.46), 1.288 (1.30), 1.306 (0.89), 1.323 (0.36), 1.565 (0.68), 1.608 (0.66), 1.638 (0.61), 1.669 (0.27), 1.749 (0.86), 1.783 (0.69), 1.813 (0.64), 1.825 (0.64), 1.837 (1.03), 1.857 (1.17), 1.883 (0.79), 2.052 (0.97), 2.078 (4.80), 2.104 (0.89), 2.134 (4.71), 2.408 (0.49), 2.436 (0.80), 2.501 (16.00), 2.711 (0.49), 2.743 (0.82), 2.772 (0.45), 3.391 (0.71), 3.405 (0.71), 3.495 (1.33), 3.525 (1.23), 3.585 (0.29), 3.600 (0.45), 3.618 (0.88), 3.633 (1.10), 3.650 (1.01), 3.668 (0.85), 3.686 (0.68), 3.702 (0.37), 3.721 (0.20), 7.357 (1.35), 7.385 (0.60), 7.400 (2.46), 7.410 (2.05), 7.422 (2.29), 7.435 (0.73), 7.551 (1.40), 7.564 (1.20), 7.574 (1.03), 7.630 (0.49), 7.653 (5.71), 7.681 (0.35), 8.718 (0.80), 8.733 (1.55), 8.747 (0.78), 12.050 (0.93).

Example 209

(−)-5-[({6-Bromo-3-methyl-2-[3-methylpiperidin-1-yl]quinolin-4-yl}carbonyl)amino]-4-[2-(trifluoromethoxy)phenyl]pentanoic acid (Diastereomer 1)

[For structural formula see Example 140 (diastereomer mixture)]

To a solution of tert-butyl 5-[({6-bromo-3-methyl-2-[3-methylpiperidin-1-yl]quinolin-4-yl}carbonyl)amino]-4-[2-(trifluoromethoxy)phenyl]pentanoate (55 mg, 81 µmol, diastereomer 1, Example 212A) in dichloromethane (620 µl) was added TFA (140 µl, 1.78 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 31 mg (100% purity, 62% of theory) of the title compound were obtained.

$[\alpha]_D^{20}$=−10.3°, 589 nm, c=0.32 g/100 ml, methanol
LC-MS (Method 1): $R_t$=2.38 min; MS (ESIpos): m/z=622/624 [M+H]$^+$
$^1$H-NMR (600 MHz, DMSO-d6) δ [ppm]: 0.926 (16.00), 0.936 (15.61), 1.064 (0.58), 1.078 (1.42), 1.084 (1.41), 1.097 (1.41), 1.102 (1.47), 1.117 (0.60), 1.123 (0.56), 1.231 (0.22), 1.613 (0.50), 1.634 (1.34), 1.654 (1.48), 1.675 (0.64), 1.735 (2.32), 1.740 (2.10), 1.757 (2.38), 1.782 (1.39), 1.798 (2.50), 1.805 (2.60), 1.814 (2.76), 1.821 (2.68), 1.828 (2.74), 1.844 (1.25), 1.863 (0.27), 2.010 (0.25), 2.020 (0.39), 2.037 (0.85), 2.046 (2.13), 2.064 (6.16), 2.069 (7.11), 2.090 (2.07), 2.101 (1.52), 2.140 (3.50), 2.223 (0.26), 2.388 (0.21), 2.438 (1.09), 2.457 (1.74), 2.476 (1.11), 2.616 (0.17), 2.685 (0.84), 2.703 (1.42), 2.722 (0.81), 3.446 (3.21), 3.470 (3.69), 3.495 (2.02), 3.599 (1.21), 3.611 (1.68), 3.621 (1.82), 3.671 (1.25), 7.349 (2.25), 7.362 (3.62), 7.394 (1.37), 7.407 (4.92), 7.413 (4.94), 7.419 (5.18), 7.432 (1.39), 7.556 (3.06), 7.567 (2.56), 7.572 (2.44), 7.641 (2.35), 7.655 (10.60), 7.661 (6.80), 7.665 (6.00), 7.676 (1.43), 7.679 (1.49), 8.756 (2.07), 8.765 (3.88), 8.775 (2.04).

Example 210

(−)-5-[({6-Bromo-3-methyl-2-[3-methylpiperidin-1-yl]quinolin-4-yl}carbonyl)amino]-4-[2-(trifluoromethoxy)phenyl]pentanoic acid (Diastereomer 2)

To a solution of tert-butyl 5-[({6-bromo-3-methyl-2-[3-methylpiperidin-1-yl]quinolin-4-yl}carbonyl)amino]-4-[2-

(trifluoromethoxy)phenyl]pentanoate (54 mg, 80 µmol, diastereomer 2, Example 213A) in dichloromethane (612 µl) was added TFA (135 µl, 1.75 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 32 mg (100% purity, 65% of theory) of the title compound were obtained.

$[\alpha]_D^{20}$=−21.8°, 589 nm, c=0.36 g/100 ml, methanol
LC-MS (Method 1): $R_t$=2.38 min; MS (ESIpos): m/z=622/624 [M+H]$^+$
$^1$H-NMR (600 MHz, DMSO-d6) δ [ppm]: 0.924 (16.00), 0.935 (15.74), 1.056 (0.52), 1.063 (0.63), 1.076 (1.57), 1.082 (1.58), 1.096 (1.60), 1.100 (1.67), 1.115 (0.68), 1.121 (0.63), 1.231 (0.24), 1.630 (1.33), 1.650 (1.46), 1.736 (2.56), 1.741 (2.31), 1.758 (2.71), 1.777 (1.77), 1.783 (1.70), 1.803 (3.04), 1.812 (3.22), 1.820 (3.18), 1.827 (3.32), 1.843 (1.39), 1.861 (0.33), 1.912 (0.18), 2.015 (0.47), 2.033 (1.03), 2.042 (2.40), 2.060 (6.59), 2.068 (7.94), 2.088 (2.88), 2.098 (2.41), 2.128 (2.87), 2.183 (1.04), 2.203 (0.44), 2.388 (0.27), 2.448 (1.37), 2.616 (0.22), 2.689 (1.13), 2.707 (2.01), 2.727 (1.10), 3.444 (3.52), 3.470 (3.91), 3.494 (2.73), 3.596 (0.97), 3.606 (1.40), 3.617 (1.98), 3.627 (2.24), 3.637 (1.42), 3.668 (1.72), 3.679 (1.54), 7.349 (2.52), 7.361 (4.01), 7.393 (1.55), 7.406 (5.60), 7.412 (5.50), 7.418 (5.79), 7.431 (1.52), 7.482 (0.41), 7.539 (0.39), 7.557 (3.59), 7.568 (2.93), 7.572 (2.82), 7.640 (3.18), 7.655 (13.58), 7.661 (7.95), 7.665 (7.00), 7.676 (1.83), 7.679 (1.86), 7.691 (0.24), 7.694 (0.24), 8.756 (1.89), 8.765 (3.35), 8.774 (1.84).

Example 211

(+)-5-[({6-Bromo-3-methyl-2-[3-methylpiperidin-1-yl]quinolin-4-yl}carbonyl)amino]-4-[2-(trifluoromethoxy)phenyl]pentanoic acid (Diastereomer 3)

To a solution of tert-butyl 5-[({6-bromo-3-methyl-2-[3-methylpiperidin-1-yl]quinolin-4-yl}carbonyl)amino]-4-[2-(trifluoromethoxy)phenyl]pentanoate (43 mg, 63 µmol, diastereomer 3, Example 214A) in dichloromethane (490 µl) was added TFA (107 µl, 1.39 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 32 mg (100% purity, 65% of theory) of the title compound were obtained.

$[\alpha]_D^{20}$=+28.2°, 589 nm, c=0.32 g/100 ml, methanol
LC-MS (Method 1): $R_t$=2.38 min; MS (ESIpos): m/z=622/624 [M+H]$^+$
$^1$H-NMR (600 MHz, DMSO-d6) δ [ppm]: 0.926 (16.00), 0.937 (15.62), 1.073 (0.62), 1.087 (1.54), 1.092 (1.54), 1.111 (1.60), 1.126 (0.64), 1.132 (0.60), 1.232 (0.37), 1.635 (1.27), 1.654 (1.37), 1.742 (2.59), 1.747 (2.38), 1.753 (1.94), 1.764 (2.85), 1.770 (2.57), 1.782 (1.70), 1.788 (1.71), 1.802 (2.90), 1.810 (2.73), 1.825 (3.13), 1.832 (3.13), 1.848 (1.67), 1.866 (0.40), 2.030 (0.47), 2.048 (1.13), 2.057 (2.98), 2.075 (10.52), 2.082 (8.56), 2.096 (3.00), 2.104 (2.18), 2.110 (2.35), 2.128 (2.72), 2.216 (0.36), 2.389 (0.23), 2.478 (1.40), 2.617 (0.18), 2.720 (1.08), 2.739 (1.95), 2.759 (1.06), 3.394 (1.70), 3.466 (1.91), 3.496 (2.75), 3.518 (2.09), 3.611 (1.33), 3.623 (1.95), 3.633 (2.23), 3.643 (1.46), 3.673 (1.78), 3.684 (1.62), 4.021 (3.98), 7.351 (2.40), 7.361 (3.19), 7.364 (4.04), 7.396 (1.42), 7.405 (3.71), 7.410 (5.53), 7.415 (5.55), 7.422 (5.89), 7.434 (1.58), 7.562 (3.71), 7.573 (3.06), 7.577 (3.13), 7.662 (2.25), 7.677 (12.80), 7.681 (8.38), 7.684 (7.38), 7.696 (1.44), 7.699 (1.60), 8.763 (1.83), 8.773 (3.46), 8.783 (1.97).

Example 212

(+)-5-[({6-Bromo-3-methyl-2-[3-methylpiperidin-1-yl]quinolin-4-yl}carbonyl)amino]-4-[2-(trifluoromethoxy)phenyl]pentanoic acid (Diastereomer 4)

To a solution of tert-butyl 5-[({6-bromo-3-methyl-2-[3-methylpiperidin-1-yl]quinolin-4-yl}carbonyl)amino]-4-[2-(trifluoromethoxy)phenyl]pentanoate (53 mg, 78 µmol, diastereomer 4, Example 215A) in dichloromethane (600 µl) was added TFA (132 µl, 1.72 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 26 mg (100% purity, 53% of theory) of the title compound were obtained.

$[\alpha]_D^{20}$=+11.8°, 589 nm, c=0.34 g/100 ml, methanol
LC-MS (Method 1): $R_t$=2.38 min; MS (ESIpos): m/z=622/624 [M+H]$^+$
$^1$H-NMR (600 MHz, DMSO-d6) δ [ppm]: 0.925 (16.00), 0.936 (15.89), 1.064 (0.59), 1.078 (1.47), 1.083 (1.49), 1.097 (1.49), 1.102 (1.57), 1.116 (0.65), 1.123 (0.61), 1.230 (0.21), 1.613 (0.51), 1.634 (1.38), 1.655 (1.54), 1.675 (0.66), 1.735 (2.39), 1.740 (2.19), 1.757 (2.49), 1.781 (1.46), 1.798 (2.63), 1.804 (2.79), 1.813 (2.92), 1.821 (2.88), 1.828 (2.98), 1.843 (1.28), 1.862 (0.30), 2.018 (0.36), 2.035 (0.83), 2.044 (2.11), 2.063 (6.09), 2.068 (7.27), 2.086 (2.04), 2.089 (2.21), 2.099 (1.65), 2.140 (3.69), 2.222 (0.30), 2.388 (0.20), 2.438 (1.12), 2.457 (1.81), 2.476 (1.13), 2.616 (0.20), 2.684 (0.89), 2.704 (1.50), 2.722 (0.88), 3.447 (3.51), 3.470 (3.99), 3.495 (2.22), 3.599 (1.31), 3.610 (1.79), 3.620 (1.95), 3.670 (1.33), 7.349 (2.41), 7.361 (3.73), 7.393 (1.49), 7.407 (5.12), 7.412 (5.06), 7.419 (5.28), 7.431 (1.38), 7.556 (3.17), 7.567 (2.64), 7.571 (2.47), 7.640 (2.43), 7.655 (10.78), 7.661 (6.89), 7.664 (6.03), 7.676 (1.37), 7.679 (1.44), 8.756 (2.16), 8.766 (3.93), 8.776 (2.02).

Example 213

(−)-5-({[6-Bromo-2-(3,3-difluoropiperidin-1-yl)-3-methylquinolin-4-yl]carbonyl}amino)-4-(5-fluoro-2-methylphenyl)pentanoic acid (Enantiomer 1)

[For structural formula see Example 150 (racemate)]
Separation of the Enantiomers from Example 150:
(+/−)-5-({[6-Bromo-2-(3,3-difluoropiperidin-1-yl)-3-methylquinolin-4-yl]carbonyl}amino)-4-(5-fluoro-2-methylphenyl)pentanoic acid (racemate, 183 mg, 309 µmol, Example 150) was separated into the enantiomers by means of preparative SFC on chiral phase (see Examples 213 and 214) [column: Daicel Chiralcel OX-H, 5 µm, 250 mm×20 mm; flow rate: 60 ml/min; UV detection: 230 nm, temperature: 25° C.; eluent: 80% carbon dioxide/20% ethanol; isocratic]. The combined target fractions were each concentrated at 30° C./30 mbar.

(−)-5-({[6-Bromo-2-(3,3-difluoropiperidin-1-yl)-3-methylquinolin-4-yl]carbonyl}amino)-4-(5-fluoro-2-methylphenyl)pentanoic acid (Enantiomer 1)

In the enantiomer separation described, 90 mg (>99% purity, ee>97%) of the title compound were obtained as the enantiomer that eluted earlier.

[α]$_D^{20}$=−10.8°, 589 nm, c=0.46 g/100 ml, methanol
LC-MS (Method 2): R$_t$=1.12 min; MS (ESIpos): m/z=592/594 [M+H]$^+$
$^1$H-NMR (400 MHz, DMSO-d6) δ [ppm]: −0.149 (0.17), 0.069 (0.30), 0.146 (0.19), 1.235 (0.96), 1.745 (0.36), 1.763 (0.84), 1.779 (1.06), 1.797 (1.31), 1.819 (1.05), 1.835 (0.71), 1.880 (3.50), 1.976 (0.55), 1.997 (1.12), 2.009 (1.39), 2.028 (1.49), 2.046 (2.35), 2.072 (5.97), 2.088 (7.64), 2.117 (11.26), 2.293 (16.00), 2.366 (0.29), 2.670 (0.41), 2.710 (0.21), 3.165 (4.29), 3.450 (2.65), 3.479 (5.58), 3.506 (3.83), 3.533 (1.13), 3.665 (1.00), 3.683 (1.61), 3.702 (1.43), 3.717 (1.21), 3.736 (0.69), 6.930 (1.26), 6.945 (2.35), 6.951 (2.51), 6.966 (1.32), 6.972 (1.35), 7.141 (2.38), 7.147 (2.44), 7.168 (2.44), 7.174 (2.35), 7.200 (2.42), 7.216 (2.84), 7.237 (2.08), 7.479 (1.02), 7.677 (1.46), 7.699 (9.77), 7.708 (5.87), 7.731 (0.97), 8.722 (1.64), 8.736 (2.62), 8.749 (1.57), 12.074 (0.51).

Example 214

(+)-5-({[6-Bromo-2-(3,3-difluoropiperidin-1-yl)-3-methylquinolin-4-yl]carbonyl}amino)-4-(5-fluoro-2-methylphenyl)pentanoic acid (Enantiomer 2)

In the enantiomer separation described in Example 213, 91 mg (>99% purity, ee>95%) of the title compound were obtained as the enantiomer that eluted later.
[α]$_D^{20}$=+15.6°, 589 nm, c=0.46 g/100 ml, methanol
LC-MS (Method 2): R$_t$=1.12 min; MS (ESIpos): m/z=592/594 [M+H]$^+$
$^1$H-NMR (400 MHz, DMSO-d6) δ [ppm]: −0.149 (0.22), 0.069 (0.40), 0.146 (0.25), 0.854 (0.28), 1.236 (1.91), 1.743 (0.33), 1.761 (0.79), 1.776 (1.03), 1.795 (1.26), 1.817 (1.00), 1.833 (0.64), 1.880 (3.52), 1.974 (0.55), 1.995 (1.09), 2.008 (1.35), 2.025 (1.40), 2.044 (2.36), 2.067 (5.71), 2.083 (7.36), 2.117 (11.16), 2.292 (16.00), 2.327 (0.76), 2.366 (0.39), 2.669 (0.53), 2.710 (0.36), 3.164 (4.38), 3.449 (2.80), 3.479 (5.80), 3.506 (3.89), 3.532 (1.17), 3.665 (1.03), 3.683 (1.64), 3.701 (1.45), 3.717 (1.24), 3.736 (0.71), 6.924 (1.15), 6.930 (1.27), 6.945 (2.41), 6.951 (2.58), 6.966 (1.37), 6.972 (1.37), 7.140 (2.43), 7.146 (2.46), 7.167 (2.48), 7.173 (2.37), 7.199 (2.53), 7.215 (2.93), 7.220 (2.73), 7.236 (2.18), 7.477 (1.00), 7.677 (1.54), 7.699 (10.24), 7.704 (7.44), 7.708 (5.90), 7.727 (0.92), 7.731 (1.00), 8.724 (1.65), 8.737 (2.63), 8.752 (1.58), 12.098 (0.31).

Example 215

(+)-5-({[6-Bromo-3-methyl-2-(pyrrolidin-1-yl)quinolin-4-yl]carbonyl}amino)-4-(2-chloro-3,6-difluorophenyl)pentanoic acid (Enantiomer 1)

[For structural formula see Example 154 (racemate)]
To a mixture of (+/−)-tert-butyl 5-{[(6-bromo-2-chloro-3-methylquinolin-4-yl)carbonyl]amino}-4-(2-chloro-3,6-difluorophenyl)pentanoate (301 mg, 500 μmol, Example 48A) in NMP (2.0 ml) was added pyrrolidine (125 μl, 1.50 mmol), and the mixture was stirred at 110° C. for 2 h. After cooling to RT, the mixture was admixed with ethyl acetate (100 ml) and washed once with water (100 ml). The aqueous phase was extracted once with ethyl acetate (100 ml). The combined organic phases were washed once with saturated sodium chloride solution, dried over sodium sulfate, filtered and concentrated, and the residue was purified by preparative HPLC (Method 33). The combined target fractions were concentrated, and the residue was lyophilized from acetonitrile/water. The title compound was obtained directly (without isolation of the tert-butyl ester and a subsequent hydrolysis step), since the reactant used was apparently already in partly hydrolysed form. 27 mg (100% purity, 9% of theory) of the title compound were obtained.
[α]$_D^{20}$=+25.1°, 589 nm, c=0.37 g/100 ml, methanol
LC-MS (Method 1): R$_t$=1.45 min; MS (ESIpos): m/z=580/582 [M+H]$^+$
$^1$H-NMR (400 MHz, DMSO-d6) δ [ppm]: −0.008 (1.81), 1.020 (0.81), 1.029 (0.43), 1.036 (0.81), 1.245 (0.78), 1.261 (0.79), 1.277 (0.42), 1.402 (0.68), 1.838 (0.86), 1.898 (16.00), 1.938 (2.12), 2.066 (2.00), 2.077 (2.29), 2.102 (4.07), 2.129 (6.46), 2.142 (7.04), 2.159 (7.73), 2.178 (7.47), 2.196 (11.68), 2.328 (0.69), 2.367 (0.78), 2.667 (0.96), 2.686 (1.84), 2.695 (8.17), 2.710 (0.72), 3.285 (2.20), 3.303 (3.04), 3.321 (2.14), 3.718 (7.64), 3.816 (7.02), 7.266 (1.61), 7.277 (1.87), 7.290 (3.14), 7.301 (3.22), 7.315 (2.42), 7.326 (2.20), 7.386 (2.00), 7.407 (3.05), 7.418 (2.99), 7.566 (1.86), 7.588 (3.77), 7.615 (5.18), 7.635 (2.29), 8.817 (3.70).

Example 216

(−)-5-({[6-Bromo-3-methyl-2-(pyrrolidin-1-yl)quinolin-4-yl]carbonyl}amino)-4-(2-chloro-3,6-difluorophenyl)pentanoic acid (Enantiomer 2)

To a mixture of (−)-tert-butyl 5-{[(6-bromo-2-chloro-3-methylquinolin-4-yl)carbonyl]amino}-4-(2-chloro-3,6-difluorophenyl)pentanoate (301 mg, 500 μmol, Example 49A) in NMP (2.0 ml) was added pyrrolidine (125 μl, 1.50 mmol), and the mixture was stirred at 110° C. for 2 h. After cooling to RT, the mixture was admixed with ethyl acetate (100 ml) and washed once with water (100 ml). The aqueous phase was extracted once with ethyl acetate (100 ml). The combined organic phases were washed once with saturated sodium chloride solution, dried over sodium sulfate, filtered and concentrated, and the residue was purified by preparative HPLC (Method 33). The combined target fractions were concentrated, and the residue was lyophilized from acetonitrile/water. The title compound was obtained directly (without isolation of the tert-butyl ester and a subsequent hydrolysis step), since the reactant used was apparently already in partly hydrolysed form. 15 mg (100% purity, 5% of theory) of the title compound were obtained.
[α]$_D^{20}$=−26.9°, 589 nm, c=0.32 g/100 ml, methanol
LC-MS (Method 1): R$_t$=1.45 min; MS (ESIpos): m/z=580/582 [M+H]$^+$
$^1$H-NMR (400 MHz, DMSO-d6) δ [ppm]: −0.024 (3.21), 0.853 (0.68), 1.120 (0.42), 1.135 (0.88), 1.150 (0.46), 1.234 (8.39), 1.606 (0.89), 1.667 (1.32), 1.689 (2.77), 1.713 (2.12), 1.872 (16.00), 1.919 (2.19), 1.938 (1.34), 1.987 (2.25), 2.174 (10.50), 2.227 (1.01), 2.248 (0.88), 2.328 (0.52), 2.346 (0.56), 2.366 (0.42), 2.670 (0.49), 2.694 (6.62), 2.710 (0.54), 3.285 (4.71), 3.303 (8.01), 3.526 (6.69), 3.571 (9.55), 3.653 (3.61), 3.822 (1.24), 7.226 (1.39), 7.236 (1.65), 7.249 (2.96), 7.258 (3.79), 7.274 (2.59), 7.279 (2.66), 7.285 (2.57), 7.336 (2.05), 7.348 (2.38), 7.358 (3.09), 7.369 (2.96), 7.391 (1.71), 7.466 (7.59), 7.488 (12.49), 7.544 (6.80), 7.549 (6.31), 7.566 (3.94), 7.571 (3.80), 7.589 (0.63), 7.615 (0.53), 8.526 (0.60), 8.859 (0.49), 8.938 (3.00).

Example 217

(+)-5-({[6-Bromo-2-(3,3-difluoropiperidin-1-yl)-3-methylquinolin-4-yl]carbonyl}amino)-4-(2-chloro-3,6-difluorophenyl)pentanoic acid (Enantiomer 1)

[For structural formula see Example 155 (racemate)]
To a solution of (+)-tert-butyl 5-({[6-bromo-2-(3,3-difluoropiperidin-1-yl)-3-methylquinolin-4-yl]carbonyl}amino)-4-(2-chloro-3,6-difluorophenyl)pentanoate (70 mg, 99 μmol, enantiomer 1, Example 216A) in dichloromethane (1.8 ml) was added TFA (169 μl, 2.19 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 18 mg (100% purity, 28% of theory) of the title compound were obtained.

$[\alpha]_D^{20}$=+33.1°, 589 nm, c=0.31 g/100 ml, methanol

LC-MS (Method 1): $R_t$=2.11 min; MS (ESIpos): m/z=630/632 [M+H]$^+$ $^1$H-NMR (500 MHz, DMSO-d6) δ [ppm]: −0.007 (1.41), 0.006 (1.38), 0.071 (0.81), 1.235 (0.63), 1.353 (0.24), 1.361 (0.68), 1.885 (4.28), 1.969 (0.95), 2.070 (2.84), 2.097 (5.30), 2.111 (4.98), 2.122 (5.25), 2.165 (16.00), 2.292 (0.18), 2.304 (0.18), 2.362 (0.41), 2.523 (0.97), 2.636 (0.39), 3.170 (5.56), 3.317 (1.07), 3.457 (3.41), 3.480 (6.14), 3.503 (3.20), 3.727 (2.01), 7.274 (1.01), 7.283 (1.19), 7.293 (2.09), 7.302 (2.18), 7.313 (1.54), 7.322 (1.36), 7.411 (2.06), 7.419 (2.03), 7.683 (3.35), 7.701 (12.28), 7.711 (8.00), 7.715 (7.27), 7.728 (2.00), 7.732 (2.13), 8.838 (2.94).

Example 218

(−)-5-({[6-Bromo-2-(3,3-difluoropiperidin-1-yl)-3-methylquinolin-4-yl]carbonyl}amino)-4-(2-chloro-3,6-difluorophenyl)pentanoic acid (Enantiomer 2)

To a solution of (−)-tert-butyl 5-({[6-bromo-2-(3,3-difluoropiperidin-1-yl)-3-methylquinolin-4-yl]carbonyl}amino)-4-(2-chloro-3,6-difluorophenyl)pentanoate (70 mg, 102 µmol, enantiomer 2, Example 217A) in dichloromethane (1.8 ml) was added TFA (173 µl, 2.24 mmol), and the mixture was left to stand at RT for 16 h. The mixture was then concentrated and repeatedly dichloromethane was added and the mixture was concentrated again. The residue was purified by preparative HPLC (Method 7). The combined target fractions were concentrated, and the residue was lyophilized from acetonitrile/water. 27 mg (100% purity, 42% of theory) of the title compound were obtained.

$[\alpha]_D^{20}$=−33.8°, 589 nm, c=0.34 g/100 ml, methanol

LC-MS (Method 1): $R_t$=2.11 min; MS (ESIpos): m/z=630/632 [M+H]$^+$ $^1$H-NMR (500 MHz, DMSO-d6) δ [ppm]: −0.120 (0.21), −0.007 (2.56), 0.006 (1.56), 0.069 (0.21), 0.117 (0.20), 1.234 (0.54), 1.353 (0.21), 1.361 (0.19), 1.370 (0.20), 1.885 (4.23), 1.967 (0.93), 2.069 (2.85), 2.084 (4.22), 2.094 (5.84), 2.114 (4.95), 2.127 (5.76), 2.164 (16.00), 2.304 (0.18), 2.358 (0.39), 2.362 (0.50), 2.519 (1.30), 2.522 (0.91), 2.635 (0.48), 3.169 (5.45), 3.314 (1.22), 3.457 (3.35), 3.480 (6.01), 3.503 (3.07), 3.730 (1.95), 7.274 (1.09), 7.283 (1.25), 7.293 (2.14), 7.302 (2.17), 7.313 (1.56), 7.322 (1.38), 7.411 (2.05), 7.419 (1.97), 7.683 (3.38), 7.701 (12.40), 7.710 (8.28), 7.715 (7.26), 7.728 (2.01), 7.732 (2.08), 8.826 (1.80), 8.837 (3.09).

Example 219

(+)-5-({[2-(Azepan-1-yl)-6-bromo-3-methylquinolin-4-yl]carbonyl}amino)-4-(2-chloro-3,6-difluorophenyl)pentanoic acid (Enantiomer 1)

[For structural formula see Example 159 (racemate)]

To a solution of tert-butyl 5-({[2-(azepan-1-yl)-6-bromo-3-methylquinolin-4-yl]carbonyl}amino)-4-(2-chloro-3,6-difluorophenyl)pentanoate (35 mg, 49 µmol, enantiomer 1, Example 218A) in dichloromethane (378 µl) was added TFA (83 µl, 1.08 mmol), and the mixture was left to stand at RT for four days. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 15 mg (100% purity, 51% of theory) of the title compound were obtained.

$[\alpha]_D^{20}$=+31.4°, 589 nm, c=0.38 g/100 ml, methanol

LC-MS (Method 1): $R_t$=2.21 min; MS (ESIpos): m/z=608/610 [M+H]$^+$ $^1$H-NMR (400 MHz, DMSO-d6) δ [ppm]: −0.150 (0.18), 1.234 (0.71), 1.259 (0.35), 1.298 (0.28), 1.360 (1.00), 1.602 (13.68), 1.781 (8.50), 1.891 (0.92), 1.965 (1.10), 2.071 (3.58), 2.107 (7.74), 2.133 (15.66), 2.272 (0.34), 2.327 (0.34), 2.366 (0.31), 2.669 (0.32), 2.710 (0.31), 3.318 (2.40), 3.491 (10.92), 3.505 (16.00), 3.520 (10.56), 3.711 (2.90), 7.262 (1.06), 7.273 (1.27), 7.285 (2.29), 7.296 (2.42), 7.311 (1.84), 7.322 (1.74), 7.384 (1.63), 7.395 (1.94), 7.405 (2.60), 7.416 (2.58), 7.438 (1.37), 7.529 (5.55), 7.551 (10.09), 7.599 (5.55), 7.604 (5.36), 7.621 (3.13), 7.626 (3.13), 8.804 (3.10).

Example 220

5-({[2-(Azepan-1-yl)-6-bromo-3-methylquinolin-4-yl]carbonyl}amino)-4-(2-chloro-3,6-difluorophenyl)pentanoic acid (Enantiomer 2)

To a solution of tert-butyl 5-({[2-(azepan-1-yl)-6-bromo-3-methylquinolin-4-yl]carbonyl}amino)-4-(2-chloro-3,6-difluorophenyl)pentanoate (28 mg, 39 µmol, enantiomer 2, Example 219A) in dichloromethane (300 µl) was added TFA (66 µl, 858 µmol), and the mixture was left to stand at RT for 4 days. The mixture was then concentrated and repeatedly dichloromethane was added and the mixture was concentrated again. The residue was purified by preparative HPLC (Method 6). The combined target fractions were concentrated, and the residue was lyophilized from acetonitrile/water. 9 mg (100% purity, 39% of theory) of the title compound were obtained.

LC-MS (Method 1): $R_t$=2.21 min; MS (ESIpos): m/z=608/610 [M+H]$^+$ $^1$H-NMR (400 MHz, DMSO-d6) δ [ppm]: 1.235 (0.90), 1.259 (0.51), 1.298 (0.35), 1.360 (0.94), 1.602 (13.49), 1.781 (8.38), 1.880 (2.79), 1.946 (1.09), 2.055 (3.52), 2.085 (6.46), 2.132 (15.36), 2.274 (0.37), 2.326 (0.42), 2.366 (0.38), 2.669 (0.41), 2.710 (0.34), 3.320 (1.46), 3.490 (10.99), 3.505 (16.00), 3.519 (10.58), 3.703 (2.91), 7.259 (1.22), 7.270 (1.40), 7.282 (2.43), 7.293 (2.56), 7.308 (1.90), 7.319 (1.76), 7.401 (2.69), 7.412 (2.69), 7.528 (6.05), 7.551 (10.65), 7.598 (5.94), 7.603 (5.52), 7.620 (3.18), 7.625 (3.14), 8.810 (3.11).

Example 221

5-[({6-Bromo-2-[3-fluoropiperidin-1-yl]-3-methylquinolin-4-yl}carbonyl)amino]-4-(2,3,6-trichlorophenyl)pentanoic acid (Diastereomer 1)

[For structural formula see Example 180 (diastereomer mixture)]

To a solution of tert-butyl 5-[({6-bromo-2-[3-fluoropiperidin-1-yl]-3-methylquinolin-4-yl}carbonyl)amino]-4-(2,3,6-trichlorophenyl)pentanoate (14 mg, 20 µmol, diastereomer 1, Example 220A) in dichloromethane (153 µl) was added TFA (34 µl, 439 µmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 7 mg (100% purity, 51% of theory) of the title compound were obtained.

LC-MS (Method 1): $R_t$=2.20 min; MS (ESIpos): m/z=644/646/648 [M+H]$^+$ $^1$H-NMR (600 MHz, DMSO-d6) δ [ppm]: −0.024 (0.18), 0.852 (0.29), 0.923 (0.20), 1.232 (1.22), 1.369 (0.28), 1.648 (2.02), 1.723 (1.34), 1.809 (1.91), 1.910 (3.93), 1.924 (3.45), 2.040 (1.60), 2.154 (4.33), 2.183 (8.36), 2.299 (0.27), 2.388 (0.31), 2.618 (0.25), 2.695 (0.22), 3.097 (2.45), 3.164 (2.36), 3.330 (5.54), 3.413 (16.00), 3.765 (1.57), 4.002 (1.26), 4.100 (1.07), 4.839 (1.36), 4.919 (1.34), 7.459 (1.70), 7.473 (1.94), 7.519 (2.29), 7.533 (3.23), 7.573 (2.41), 7.658 (2.35), 7.673 (5.57), 7.689 (4.72), 7.704 (1.81), 8.972 (1.67).

Example 222

5-[({6-Bromo-2-[3-fluoropiperidin-1-yl]-3-methylquinolin-4-yl}carbonyl)amino]-4-(2,3,6-trichlorophenyl)pentanoic acid (Diastereomer 2)

To a solution of tert-butyl 5-[({6-bromo-2-[3-fluoropiperidin-1-yl]-3-methylquinolin-4-yl}carbonyl)amino]-4-(2,3,6-trichlorophenyl)pentanoate (17 mg, 24 µmol, diastereomer 2, Example 220A) in dichloromethane (186 µl) was added TFA (41 µl, 533 µmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 7 mg (100% purity, 51% of theory) of the title compound were obtained.

LC-MS (Method 1): $R_t$=2.20 min; MS (ESIpos): m/z=644/646/648 [M+H]$^+$ $^1$H-NMR (600 MHz, DMSO-d6) δ [ppm]: 0.854 (0.19), 1.233 (0.77), 1.645 (1.59), 1.817 (1.51), 1.912 (2.83), 1.925 (2.37), 1.945 (1.40), 1.968 (0.93), 2.060 (0.51), 2.073 (1.19), 2.083 (1.71), 2.097 (3.37), 2.108 (3.12), 2.114 (3.29), 2.128 (2.50), 2.151 (3.80), 2.160 (4.09), 2.184 (16.00), 2.197 (2.28), 2.214 (0.72), 2.290 (1.68), 2.301 (1.57), 2.389 (0.24), 2.617 (0.24), 3.086 (1.75), 3.180 (1.65), 3.192 (1.74), 3.326 (1.77), 3.336 (1.90), 3.395 (1.70), 3.415 (1.17), 3.434 (1.69), 3.453 (1.22), 3.805 (3.40), 3.816 (3.99), 3.826 (4.27), 3.835 (4.43), 3.912 (6.65), 4.040 (3.28), 4.055 (3.16), 4.064 (3.35), 4.073 (3.57), 4.079 (3.71), 4.088 (2.70), 4.098 (2.22), 4.113 (1.56), 4.846 (1.43), 4.925 (1.41), 7.486 (1.89), 7.501 (2.34), 7.543 (2.74), 7.558 (4.14), 7.605 (2.65), 7.619 (2.28), 7.666 (2.31), 7.671 (2.15), 7.680 (6.02), 7.686 (5.41), 7.694 (3.96), 7.697 (4.31), 7.703 (3.05), 7.709 (1.79), 7.712 (1.82), 7.718 (1.29), 8.838 (2.29), 8.848 (2.59).

Example 223

5-[({6-Bromo-2-[3-fluoropiperidin-1-yl]-3-methylquinolin-4-yl}carbonyl)amino]-4-(2,3,6-trichlorophenyl)pentanoic acid (Diastereomer 3)

To a solution of tert-butyl 5-[({6-bromo-2-[3-fluoropiperidin-1-yl]-3-methylquinolin-4-yl}carbonyl)amino]-4-(2,3,6-trichlorophenyl)pentanoate (32 mg, 46 µmol, diastereomer 3, Example 220A) in dichloromethane (351 µl) was added TFA (77 µl, 1.0 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 15 mg (100% purity, 52% of theory) of the title compound were obtained.

LC-MS (Method 1): $R_t$=2.20 min; MS (ESIpos): m/z=644/646/648 [M+H]$^+$ $^1$H-NMR (600 MHz, DMSO-d6) δ [ppm]: 1.232 (0.37), 1.244 (0.46), 1.255 (0.44), 1.259 (0.38), 1.270 (0.31), 1.646 (1.40), 1.817 (1.34), 1.912 (2.53), 1.926 (2.11), 1.944 (1.31), 1.968 (0.82), 2.009 (0.20), 2.060 (0.58), 2.074 (1.12), 2.083 (1.63), 2.097 (3.20), 2.109 (2.88), 2.114 (3.11), 2.129 (2.31), 2.151 (3.35), 2.160 (3.84), 2.184 (16.00), 2.197 (2.11), 2.214 (0.68), 2.289 (1.54), 2.301 (1.44), 2.306 (1.31), 2.389 (0.24), 2.617 (0.21), 3.074 (1.12), 3.089 (1.58), 3.185 (1.49), 3.197 (1.59), 3.214 (1.04), 3.320 (1.20), 3.330 (1.56), 3.340 (1.66), 3.351 (0.95), 3.398 (1.52), 3.420 (1.00), 3.437 (1.49), 3.456 (1.05), 3.806 (1.52), 3.817 (1.72), 3.827 (1.71), 3.834 (1.57), 4.040 (4.13), 4.049 (4.31), 4.056 (4.60), 4.064 (5.06), 4.071 (5.46), 4.079 (5.82), 4.088 (5.09), 4.099 (4.83), 4.113 (4.27), 4.847 (1.34), 4.926 (1.33), 7.028 (0.27), 7.113 (0.32), 7.198 (0.28), 7.486 (1.95), 7.501 (2.41), 7.543 (3.07), 7.558 (4.54), 7.605 (2.56), 7.619 (2.13), 7.668 (2.51), 7.674 (2.27), 7.683 (6.65), 7.689 (5.63), 7.696 (4.24), 7.700 (4.26), 7.702 (3.33), 7.706 (2.72), 7.711 (1.61), 7.715 (1.64), 7.717 (1.20), 7.721 (1.08), 8.835 (2.19), 8.846 (2.41), 9.683 (0.16).

Example 224

5-[({6-Bromo-2-[3-fluoropiperidin-1-yl]-3-methylquinolin-4-yl}carbonyl)amino]-4-(2,3,6-trichlorophenyl)pentanoic acid (Diastereomer 4)

To a solution of tert-butyl 5-[({6-bromo-2-[3-fluoropiperidin-1-yl]-3-methylquinolin-4-yl}carbonyl)amino]-4-(2,3,6-trichlorophenyl)pentanoate (27 mg, 38 µmol, diastereomer 4, Example 220A) in dichloromethane (296 µl) was added TFA (65 µl, 846 µmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized from acetonitrile/water. 9 mg (100% purity, 36% of theory) of the title compound were obtained.

LC-MS (Method 1): $R_t$=2.20 min; MS (ESIpos): m/z=644/646/648 [M+H]$^+$ $^1$H-NMR (600 MHz, DMSO-d6) δ [ppm]: 0.841 (0.19), 0.853 (0.24), 0.913 (0.21), 1.231 (0.86), 1.552 (0.61), 1.648 (2.28), 1.674 (0.65), 1.812 (2.09), 1.825 (1.79), 1.910 (4.02), 1.924 (2.87), 1.947 (1.51), 1.970 (1.30), 2.061 (1.95), 2.076 (2.56), 2.083 (3.02), 2.096 (3.15), 2.109 (2.63), 2.121 (2.60), 2.145 (5.67), 2.166 (4.32), 2.180 (16.00), 2.278 (1.99), 2.389 (0.46), 2.616 (0.26), 3.077 (1.94), 3.093 (2.84), 3.174 (2.89), 3.427 (5.68), 3.449 (3.64), 3.783 (0.87), 3.791 (1.60), 3.802 (1.66), 3.812 (1.93), 3.822 (1.47), 4.054 (1.96), 4.062 (1.76), 4.070 (1.68), 4.077 (1.98), 4.088 (1.51), 4.099 (1.29), 4.109 (1.07), 4.124 (0.59), 4.839 (1.68), 4.919 (1.66), 7.484 (2.30), 7.498 (2.76), 7.539 (4.21), 7.554 (6.01), 7.603 (3.12), 7.617 (2.69), 7.662 (3.82), 7.667 (2.96), 7.677 (9.70), 7.682 (7.07), 7.690 (6.12), 7.694 (6.22), 7.700 (3.79), 7.705 (2.38), 7.709 (2.46), 7.715 (1.52), 8.837 (2.65), 8.846 (3.25).

Example 225

5-[({6-Bromo-2-[3-ethylpiperidin-1-yl]-3-methylquinolin-4-yl}carbonyl)amino]-4-(2,5-difluorophenyl)pentanoic acid (Diastereomer Mixture)

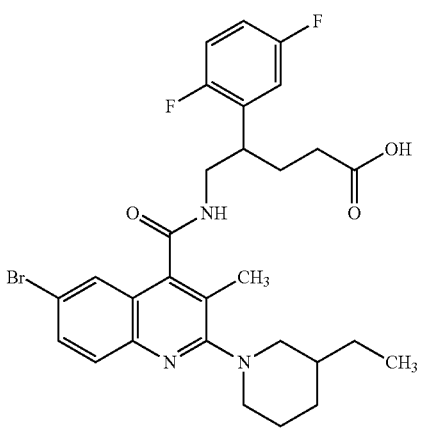 [SMILES: CCC1CCCN(c2nc3ccc(Br)cc3c(C(=O)NCC(CCC(=O)O)c3cc(F)ccc3F)c2C)C1]

tert-Butyl 5-[({6-bromo-2-(3-ethylpiperidin-1-yl]-3-methylquinolin-4-yl}carbonyl)amino]-4-(2,5-difluorophenyl)pentanoate (diastereomer mixture, 56 mg, 86.9 µmol, Example 227A) was dissolved in dichloromethane (1.2 ml). At RT, TFA (650 µl, 8.7 mmol) was added and the mixture was stirred at RT for 90 min. The volatile components were removed on a rotary evaporator. The residue was dissolved in a little DMSO and purified by means of preparative HPLC (Method 15). The target fractions were concentrated by rotary evaporation together, and the residue was dried under reduced pressure. 48 mg (100% purity, 94% of theory) of the title compound were obtained.

LC-MS (Method 1): $R_t$=2.37 min; MS (ESIpos): m/z=588/590 [M+H]$^+$ $^1$H-NMR (400 MHz, DMSO-d6) δ [ppm]: −0.008 (3.01), 0.890 (6.60), 0.908 (16.00), 0.927 (8.11), 1.035 (0.56), 1.064 (1.36), 1.093 (1.40), 1.116 (0.62), 1.238 (1.14), 1.256 (2.65), 1.275 (3.54), 1.292 (2.47), 1.560 (1.54), 1.602 (1.47), 1.632 (1.31), 1.747 (1.98), 1.786 (1.98), 1.809 (1.45), 1.842 (1.85), 1.877 (1.52), 2.002 (1.18), 2.015 (1.54), 2.034 (1.67), 2.054 (1.89), 2.063 (1.63), 2.108 (12.92), 2.119 (6.84), 2.139 (2.27), 2.160 (0.71), 2.327 (0.67), 2.422 (1.36), 2.670 (0.80), 2.709 (1.23), 2.737 (1.87), 2.766 (1.05), 3.481 (2.87), 3.513 (2.74), 3.616 (1.09), 3.634 (1.63), 3.649 (2.32), 3.662 (1.38), 3.677 (1.11), 3.696 (1.45), 7.122 (2.01), 7.143 (1.43), 7.198 (1.72), 7.209 (1.78), 7.221 (2.79), 7.232 (2.72), 7.244 (1.31), 7.256 (1.20), 7.291 (1.65), 7.300 (2.36), 7.315 (1.65), 7.426 (0.71), 7.624 (1.40), 7.647 (11.57), 7.654 (6.46), 7.677 (1.03), 8.729 (2.85), 12.061 (5.15).

Example 226

(−)-5-[({6-Bromo-2-[3-ethylpiperidin-1-yl]-3-methylquinolin-4-yl}carbonyl)amino]-4-(2,5-difluorophenyl)pentanoic acid (mixture of two diastereomers)

To a solution of tert-butyl 5-[({6-bromo-2-[3-ethylpiperidin-1-yl]-3-methylquinolin-4-yl}carbonyl)amino]-4-(2,5-difluorophenyl)pentanoate (118 mg, 183 µmol, mixture of two diastereomers, Example 228A) in dichloromethane (1.4 ml) was added TFA (310 µl, 4.03 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 88 mg (100% purity, 81% of theory) of the title compound were obtained.

$[α]_D^{20}$=−32.2°, 589 nm, c=0.46 g/100 ml, methanol

LC-MS (Method 1): $R_t$=2.35 min; MS (ESIpos): m/z=588/590 [M+H]$^+$ $^1$H-NMR (600 MHz, DMSO-d6) δ [ppm]: −0.021 (1.21), 0.839 (0.16), 0.851 (0.32), 0.862 (0.18), 0.895 (7.27), 0.907 (16.00), 0.919 (8.17), 1.036 (0.49), 1.042 (0.58), 1.057 (1.40), 1.062 (1.43), 1.076 (1.48), 1.081 (1.49), 1.096 (0.64), 1.103 (0.57), 1.227 (2.36), 1.245 (1.25), 1.257 (2.57), 1.269 (3.67), 1.280 (3.10), 1.292 (1.60), 1.551 (1.33), 1.556 (1.48), 1.574 (0.99), 1.585 (0.77), 1.606 (1.26), 1.627 (1.34), 1.647 (0.55), 1.748 (2.00), 1.769 (1.82), 1.775 (1.61), 1.791 (1.33), 1.805 (1.44), 1.814 (1.08), 1.829 (0.61), 1.853 (1.68), 1.870 (1.64), 1.997 (0.58), 2.010 (1.28), 2.018 (1.73), 2.032 (1.83), 2.041 (1.27), 2.053 (1.10), 2.064 (1.27), 2.073 (1.48), 2.078 (1.64), 2.091 (4.12), 2.104 (7.92), 2.116 (7.21), 2.130 (3.21), 2.144 (1.34), 2.157 (0.68), 2.414 (0.84), 2.714 (0.86), 2.733 (1.45), 2.752 (0.82), 3.494 (3.60), 3.510 (2.68), 3.627 (1.33), 3.637 (1.69), 3.640 (1.59), 3.649 (2.00), 3.709 (1.15), 7.127 (1.84), 7.140 (1.20), 7.211 (1.72), 7.219 (1.85), 7.226 (2.96), 7.234 (2.92), 7.242 (1.44), 7.250 (1.30), 7.301 (1.79), 7.309 (2.30), 7.317 (1.78), 7.448 (0.24), 7.635 (2.37), 7.649 (9.88), 7.657 (5.87), 7.672 (1.32), 8.744 (1.47), 8.754 (2.67).

Example 227

(+)-5-[({6-Bromo-2-[3-ethylpiperidin-1-yl]-3-methylquinolin-4-yl}carbonyl)amino]-4-(2,5-difluorophenyl)pentanoic acid (Diastereomer 1)

To a solution of tert-butyl 5-[({6-bromo-2-[3-ethylpiperidin-1-yl]-3-methylquinolin-4-yl}carbonyl)amino]-4-(2,5-difluorophenyl)pentanoate (37 mg, 57 µmol, diastereomer 1, Example 229A) in dichloromethane (442 µl) was added TFA (97 µl, 1.26 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 20 mg (100% purity, 60% of theory) of the title compound were obtained.

$[α]_D^{20}$=+17.1°, 589 nm, c=0.31 g/100 ml, methanol

LC-MS (Method 1): $R_t$=2.38 min; MS (ESIpos): m/z=588/590 [M+H]$^+$ $^1$H-NMR (600 MHz, DMSO-d6) δ [ppm]: −0.021 (1.57), 0.839 (0.20), 0.851 (0.40), 0.862 (0.20), 0.895 (6.95), 0.908 (16.00), 0.920 (7.91), 1.036 (0.39), 1.042 (0.45), 1.057 (1.08), 1.062 (1.11), 1.076 (1.14), 1.081 (1.15), 1.096 (0.50), 1.103 (0.45), 1.228 (3.22), 1.245 (1.13), 1.256 (2.13), 1.268 (3.04), 1.280 (2.59), 1.292 (1.39), 1.539 (0.79), 1.545 (0.94), 1.550 (1.07), 1.557 (1.21), 1.562 (1.04), 1.574 (0.82), 1.605 (0.92), 1.626 (0.99), 1.646 (0.43), 1.747 (1.60), 1.752 (1.34), 1.764 (1.31), 1.769 (1.42), 1.774 (1.36), 1.787 (1.08), 1.796 (1.06), 1.802 (1.15), 1.811 (0.88), 1.817 (0.65), 1.826 (0.52), 1.854 (1.30), 1.862 (0.90), 1.870 (1.27), 1.993 (0.47), 2.006 (1.01), 2.014 (1.35), 2.027 (1.49), 2.036 (0.99), 2.041 (1.03), 2.053 (1.23), 2.062 (1.16), 2.079 (2.91), 2.094 (4.55), 2.108 (4.56), 2.121 (2.74), 2.135 (1.28), 2.148 (0.71), 2.417 (0.69), 2.695 (0.28), 2.713 (0.72), 2.733 (1.24), 2.752 (0.70), 3.478 (2.03), 3.495 (3.09), 3.511 (2.04), 3.612 (0.89), 3.621 (1.38), 3.634 (1.50), 3.643 (1.98), 3.652 (1.12), 3.709 (1.00), 7.125 (1.33), 7.209 (1.28), 7.217 (1.39), 7.225 (2.20), 7.232 (2.18), 7.240 (1.10), 7.247 (0.98), 7.290 (1.07), 7.295 (1.34), 7.299 (1.42), 7.305 (1.91), 7.310 (1.40), 7.314 (1.34), 7.320 (1.05),

Example 228

(+)-5-[({6-Bromo-2-[3-ethylpiperidin-1-yl]-3-methylquinolin-4-yl}carbonyl)amino]-4-(2,5-difluorophenyl)pentanoic acid (Diastereomer 2)

To a solution of tert-butyl 5-[({6-bromo-2-[3-ethylpiperidin-1-yl]-3-methylquinolin-4-yl}carbonyl)amino]-4-(2,5-difluorophenyl)pentanoate (43 mg, 67 µmol, diastereomer 2, Example 230A) in dichloromethane (513 µl) was added TFA (113 µl, 1.47 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 25 mg (100% purity, 63% of theory) of the title compound were obtained.

$[\alpha]_D^{20}$=+47.3°, 589 nm, c=0.32 g/100 ml, methanol
LC-MS (Method 1): $R_t$=2.38 min; MS (ESIpos): m/z=588/590 [M+H]$^+$ $^1$H-NMR (600 MHz, DMSO-d6) δ [ppm]: −0.022 (1.15), 0.852 (0.27), 0.895 (6.90), 0.907 (16.00), 0.919 (7.82), 1.037 (0.38), 1.043 (0.44), 1.058 (1.06), 1.063 (1.08), 1.077 (1.11), 1.083 (1.12), 1.097 (0.50), 1.104 (0.44), 1.230 (2.23), 1.247 (0.91), 1.258 (1.89), 1.270 (2.65), 1.281 (2.16), 1.290 (1.20), 1.557 (1.06), 1.586 (0.60), 1.606 (1.01), 1.628 (1.08), 1.648 (0.45), 1.750 (1.53), 1.755 (1.31), 1.760 (1.16), 1.771 (1.65), 1.783 (1.27), 1.791 (1.07), 1.799 (1.12), 1.807 (0.84), 1.813 (0.64), 1.822 (0.50), 1.855 (1.27), 1.871 (1.24), 1.990 (0.41), 2.003 (0.94), 2.012 (1.23), 2.025 (1.35), 2.034 (0.86), 2.038 (0.86), 2.046 (0.75), 2.055 (0.78), 2.064 (0.82), 2.082 (2.33), 2.095 (4.70), 2.108 (7.35), 2.121 (2.98), 2.135 (1.06), 2.148 (0.51), 2.412 (0.62), 2.730 (0.98), 3.491 (2.76), 3.509 (2.34), 3.614 (0.80), 3.623 (1.33), 3.636 (1.50), 3.645 (2.05), 3.654 (1.10), 3.701 (0.84), 7.126 (1.43), 7.140 (0.93), 7.210 (1.32), 7.217 (1.42), 7.225 (2.26), 7.233 (2.23), 7.240 (1.11), 7.248 (1.00), 7.292 (1.09), 7.297 (1.34), 7.301 (1.40), 7.307 (1.90), 7.313 (1.37), 7.317 (1.32), 7.322 (1.04), 7.632 (1.89), 7.647 (7.35), 7.654 (4.76), 7.658 (4.23), 7.669 (1.08), 7.672 (1.12), 7.499 (0.20), 7.634 (2.33), 7.649 (9.46), 7.656 (5.17), 7.659 (4.64), 7.671 (1.16), 7.674 (1.22), 8.745 (1.67), 8.755 (2.75), 8.764 (1.62).

Example 229

(+/−)-5-({[6-Bromo-2-(3,3-difluoropiperidin-1-yl)-3-methylquinolin-4-yl]carbonyl}amino)-4-(2-methylphenyl)pentanoic acid (Racemate)

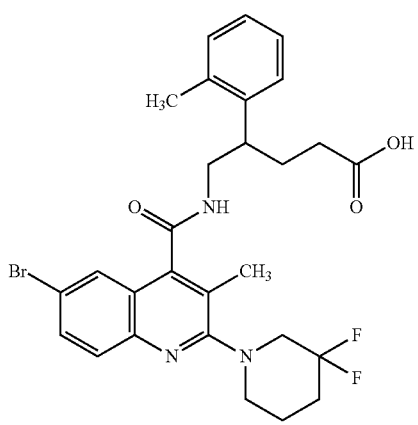 [SMILES: Cc1ccccc1C(CCC(=O)O)CNC(=O)c1c(C)c(N2CCCC(F)(F)C2)nc2ccc(Br)cc12]

To (+/−)-5-{[(6-bromo-2-chloro-3-methylquinolin-4-yl)carbonyl]amino}-4-(2-methylphenyl)pentanoic acid (racemate, 500 mg, 86% purity, 0.88 mmol, Example 234A) and 3,3-difluoropiperidine hydrochloride (804 mg, 5.10 mmol) in NMP (2.6 ml) was added DIPEA (2.1 ml, 12 mmol), and the mixture was stirred at 120° C. for 4 days. Subsequently, the mixture was cooled to RT and the reaction mixture was added to 1 M hydrochloric acid. The mixture was extracted with dichloromethane, and the organic phase was dried over sodium sulfate and concentrated on a rotary evaporator. The residue was prepurified by column chromatography (Isolera, KP-Sil, eluent: dichloromethane/methanol, gradient: 0-40% methanol) and then repurified by means of preparative HPLC (Method 27). 212 mg (99% purity, 42% of theory) of the title compound were obtained.

LC-MS (Method 26): $R_t$=0.80 min; MS (ESIpos): m/z=574/576 [M+H]$^+$ $^1$H-NMR (400 MHz, CHLOROFORM-d) δ [ppm]: 1.262 (1.33), 1.935 (1.64), 1.950 (1.86), 1.957 (1.72), 1.967 (1.54), 1.974 (1.08), 1.985 (0.60), 1.991 (0.70), 2.009 (0.48), 2.022 (0.57), 2.039 (0.67), 2.055 (1.10), 2.071 (1.05), 2.087 (0.88), 2.106 (0.65), 2.121 (0.52), 2.142 (0.63), 2.155 (0.73), 2.173 (0.67), 2.190 (0.41), 2.208 (0.49), 2.212 (0.57), 2.244 (16.00), 2.277 (2.20), 2.295 (3.73), 2.315 (1.53), 2.366 (15.79), 2.389 (2.69), 2.628 (2.33), 3.127 (1.35), 3.138 (1.70), 3.389 (0.46), 3.396 (0.53), 3.402 (0.53), 3.410 (0.81), 3.433 (1.79), 3.447 (0.50), 3.461 (2.58), 3.489 (1.35), 3.677 (0.49), 3.690 (0.54), 3.699 (0.48), 3.711 (1.03), 3.725 (0.66), 3.732 (0.61), 3.746 (0.54), 3.933 (0.69), 3.949 (1.16), 3.965 (0.97), 3.982 (0.92), 3.998 (0.46), 5.949 (0.59), 5.963 (1.00), 5.977 (0.56), 7.114 (0.46), 7.122 (0.56), 7.127 (0.44), 7.133 (1.21), 7.142 (1.42), 7.154 (1.65), 7.167 (2.44), 7.185 (0.96), 7.193 (0.71), 7.199 (0.74), 7.204 (0.97), 7.208 (0.67), 7.219 (2.04), 7.223 (3.71), 7.231 (3.85), 7.234 (3.60), 7.602 (1.21), 7.607 (1.30), 7.624 (2.59), 7.629 (2.96), 7.659 (4.47), 7.682 (2.17), 7.692 (3.39), 7.697 (2.97).

Separation of the Enantiomers:

The title compound (197 mg) was dissolved in dichloromethane/methanol (1:1, 3.3 ml) and separated into the enantiomers by means of preparative HPLC on chiral phase (see Examples 230 and 231) [column: Daicel Chiralpak IA, 5 µm, 250 mm×30 mm; flow rate: 50 ml/min; detection: UV 254 nm; injection: 0.3 ml; eluent: hexane+0.1% by volume of TFA (80%)/isopropanol (20%), isocratic]. The combined target fractions were each concentrated, and the respective residue was lyophilized.

Example 230

(−)-5-({[6-Bromo-2-(3,3-difluoropiperidin-1-yl)-3-methylquinolin-4-yl]carbonyl}amino)-4-(2-methylphenyl)pentanoic acid (Enantiomer 1)

In the enantiomer separation described in Example 229, 71 mg (98% purity, ee>99%) of the title compound were obtained as the enantiomer that eluted earlier.
$[\alpha]_D^{20}$=−5.0°, 589 nm, c=0.34 g/100 ml, methanol

Example 231

(+)-5-({[6-Bromo-2-(3,3-difluoropiperidin-1-yl)-3-methylquinolin-4-yl]carbonyl}amino)-4-(2-methylphenyl)pentanoic acid (Enantiomer 2)

In the enantiomer separation described in Example 229, 85 mg (88% purity, ee 87%) of the title compound were obtained as the enantiomer that eluted later.
$[\alpha]_D^{20}$=+7.8°, 589 nm, c=0.28 g/100 ml, methanol

Example 232

(+/−)-5-({[6-Bromo-3-methyl-2-(pyrrolidin-1-yl)quinolin-4-yl]carbonyl}amino)-4-(2-methylphenyl)pentanoic acid (Racemate)

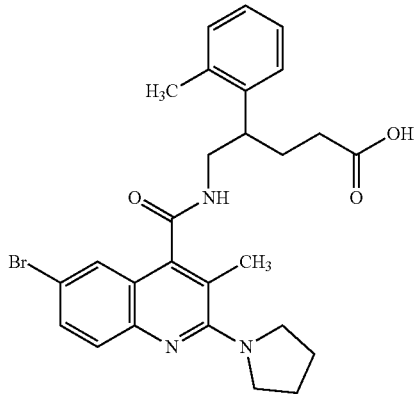 [SMILES: Cc1ccccc1C(CCC(=O)O)CNC(=O)c1c(C)c(N2CCCC2)nc2ccc(Br)cc12]

(+/−)-5-{[(6-Bromo-2-chloro-3-methylquinolin-4-yl)carbonyl]amino}-4-(2-methylphenyl)pentanoic acid (racemate, 500 mg, 86% purity, 0.88 mmol, Example 234A) was stirred in pyrrolidine (3.0 ml, 2.2 mmol) at 100° C. for 2 h. After cooling to RT, the reaction mixture was added to 1 M hydrochloric acid, and the mixture was extracted with dichloromethane. The organic phase was dried over sodium sulfate and concentrated on a rotary evaporator. The residue was prepurified by column chromatography (Isolera, KP-Sil, eluent: dichloromethane/methanol, gradient: 0-40% methanol) and repurified by means of preparative HPLC (Method 27). 375 mg (99% purity, 80% of theory) of the title compound were obtained.

LC-MS (Method 26): $R_t$=0.77 min; MS (ESIpos): m/z=524/526 [M+H]$^+$ $^1$H-NMR (400 MHz, CHLOROFORM-d) δ [ppm]: 0.084 (0.46), 0.087 (0.42), 0.838 (0.57), 0.850 (0.55), 0.871 (0.52), 0.888 (0.83), 1.184 (0.44), 1.217 (0.82), 1.262 (7.00), 1.391 (0.53), 1.918 (2.72), 1.927 (3.16), 1.935 (8.00), 1.942 (3.26), 1.951 (3.35), 1.968 (1.08), 1.977 (0.98), 1.987 (0.95), 1.993 (0.93), 2.012 (0.96), 2.028 (0.87), 2.037 (0.70), 2.049 (0.87), 2.054 (0.66), 2.063 (0.63), 2.075 (0.71), 2.090 (0.74), 2.102 (0.46), 2.108 (0.41), 2.118 (0.55), 2.123 (0.58), 2.147 (0.43), 2.166 (0.78), 2.179 (0.93), 2.186 (0.64), 2.199 (0.90), 2.224 (15.03), 2.282 (0.60), 2.301 (2.74), 2.320 (3.62), 2.339 (1.34), 2.368 (16.00), 2.385 (1.42), 2.392 (11.83), 2.518 (0.66), 2.535 (0.58), 2.545 (0.67), 2.560 (1.05), 2.567 (0.84), 2.574 (0.82), 2.582 (0.76), 2.629 (3.84), 3.246 (0.40), 3.258 (0.54), 3.266 (0.45), 3.273 (0.42), 3.284 (0.50), 3.292 (0.49), 3.297 (0.85), 3.325 (1.15), 3.352 (0.62), 3.401 (0.45), 3.410 (0.84), 3.421 (1.22), 3.431 (0.88), 3.436 (0.94), 3.448 (0.68), 3.459 (0.48), 3.586 (2.41), 3.602 (6.38), 3.618 (2.37), 3.671 (0.54), 3.684 (0.58), 3.693 (0.54), 3.705 (0.95), 3.718 (0.69), 3.727 (0.59), 3.741 (0.56), 3.933 (0.55), 3.949 (0.98), 3.966 (0.89), 3.983 (0.81), 3.999 (0.42), 5.785 (0.65), 7.006 (0.54), 7.114 (0.46), 7.121 (0.50), 7.128 (0.52), 7.133 (1.29), 7.141 (1.26), 7.146 (1.19), 7.154 (1.89), 7.166 (2.94), 7.181 (1.44), 7.193 (2.67), 7.198 (2.32), 7.207 (4.20), 7.221 (2.42), 7.229 (3.00), 7.235 (4.04), 7.238 (3.76), 7.249 (0.51), 7.507 (5.43), 7.528 (0.70), 7.576 (2.43), 7.579 (3.98).

Separation of the Enantiomers:

The title compound (360 mg) was dissolved in DMSO/dichloromethane/methanol (1:1:1, 6 ml) and separated into the enantiomers by means of preparative SFC on a chiral phase (see Examples 233 and 234) [column: Chiralpak IG, 5 µm, 250 mm×30 mm; flow rate: 100 ml/min; detection: MWD 220 nm; injection: 1.0 ml; eluent: 28% methanol/72% carbon dioxide, isocratic]. The combined target fractions were each concentrated, and the respective residue was lyophilized.

Example 233

(+)-5-({[6-Bromo-3-methyl-2-(pyrrolidin-1-yl)quinolin-4-yl]carbonyl}amino)-4-(2-methylphenyl)pentanoic acid (Enantiomer 1)

In the enantiomer separation described in Example 232, 190 mg (98% purity, ee 98%) of the title compound were obtained as the enantiomer that eluted earlier.

$[α]_D^{20}$=+12.7°, 589 nm, c=0.27 g/100 ml, methanol

Example 234

(−)-5-({[6-Bromo-3-methyl-2-(pyrrolidin-1-yl)quinolin-4-yl]carbonyl}amino)-4-(2-methylphenyl)pentanoic acid (Enantiomer 2)

In the enantiomer separation described in Example 232, 135 mg (96% purity, ee 96%) of the title compound were obtained as the enantiomer that eluted later.

$[α]_D^{20}$=−4.43°, 589 nm, c=0.35 g/100 ml, methanol

Example 235

(+)-5-({[6-Bromo-3-methyl-2-(piperidin-1-yl)quinolin-4-yl]carbonyl}amino)-4-(2-methoxyphenyl)pentanoic acid (Enantiomer 1)

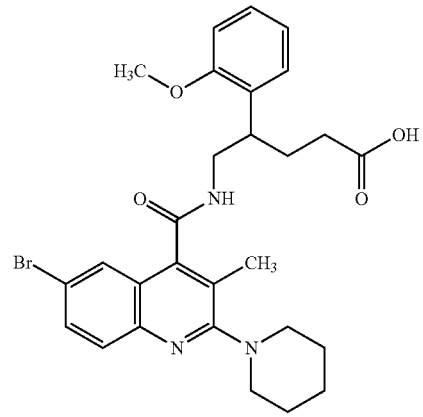 [SMILES: COc1ccccc1C(CCC(=O)O)CNC(=O)c1c(C)c(N2CCCCC2)nc2ccc(Br)cc12]

A mixture of 5-{[(6-bromo-2-chloro-3-methylquinolin-4-yl)carbonyl]amino}-4-(2-methoxyphenyl)pentanoic acid (Enantiomer 1, 200 mg, 85% purity, 336 µmol, Example 241A) and piperidine (5.0 ml) was stirred at 100° C. for 2 h After cooling to RT, the reaction mixture was added to 1 M hydrochloric acid and extracted with dichloromethane. The organic phase was dried over sodium sulfate and concentrated. The crude product was purified by preparative HPLC (Method 28). 160 mg (99% purity, 85% of theory) of the title compound were obtained.

[α]$_D^{20}$=+4.73°, 589 nm, c=0.36 g/100 ml, chloroform
LC-MS (Method 25): R$_t$=1.29 min; MS (ESIpos): m/z=554/556 [M+H]$^+$ $^1$H-NMR (400 MHz, CHLOROFORM-d) δ [ppm]: 1.643 (1.02), 1.653 (1.13), 1.711 (2.01), 1.721 (2.28), 2.018 (0.40), 2.031 (0.46), 2.039 (0.46), 2.054 (0.43), 2.131 (0.52), 2.144 (0.65), 2.151 (0.45), 2.165 (0.67), 2.189 (8.51), 2.279 (0.84), 2.293 (1.56), 2.299 (0.99), 2.313 (1.58), 2.323 (0.57), 2.334 (0.69), 3.173 (2.55), 3.447 (0.48), 3.460 (0.61), 3.472 (0.51), 3.551 (0.42), 3.709 (0.51), 3.740 (16.00), 3.815 (0.58), 3.828 (0.51), 3.838 (0.46), 3.852 (0.42), 3.931 (0.47), 3.946 (0.87), 3.960 (0.54), 3.979 (0.58), 5.824 (0.55), 6.845 (1.50), 6.865 (1.54), 6.958 (0.68), 6.960 (0.70), 6.979 (1.59), 6.995 (0.95), 6.998 (0.90), 7.210 (1.95), 7.212 (1.90), 7.230 (2.18), 7.251 (0.81), 7.255 (0.63), 7.561 (0.88), 7.566 (1.02), 7.583 (1.45), 7.589 (1.81), 7.630 (2.05), 7.635 (1.95), 7.664 (0.46).

Example 236

(−)-5-({[6-Bromo-3-methyl-2-(piperidin-1-yl)quinolin-4-yl]carbonyl}amino)-4-(2-methoxyphenyl)pentanoic acid (Enantiomer 2)

A mixture of 5-{[(6-bromo-2-chloro-3-methylquinolin-4-yl)carbonyl]amino}-4-(2-methoxyphenyl)pentanoic acid (Enantiomer 2, 200 mg, 87% purity, 344 μmol, Example 242A) and piperidine (5.0 ml) was stirred at 100° C. for 1.5 h After cooling to RT, the reaction mixture was added to 1 M hydrochloric acid and extracted with dichloromethane. The organic phase was dried over sodium sulfate and concentrated. The crude product was purified by preparative HPLC (Method 28). 166 mg (99% purity, 86% of theory) of the title compound were obtained.

[α]$_D^{20}$=−2.58°, 589 nm, c=0.8 g/100 ml, chloroform.
LC-MS (Method 25): R$_t$=1.35 min; MS (ESIpos): m/z=554/556 [M+H]$^+$ $^1$H-NMR (400 MHz, CHLOROFORM-d) δ [ppm]: 1.036 (0.66), 1.194 (0.73), 1.261 (0.62), 1.276 (16.00), 1.282 (1.00), 1.295 (0.60), 1.610 (0.44), 1.623 (0.62), 1.638 (0.83), 1.650 (0.82), 1.707 (1.46), 1.717 (1.68), 1.745 (0.88), 1.760 (0.72), 2.179 (6.04), 2.225 (0.48), 2.238 (0.80), 2.258 (0.82), 2.299 (0.42), 2.995 (0.57), 3.009 (0.76), 3.023 (0.54), 3.148 (1.64), 3.162 (2.07), 3.173 (1.50), 3.439 (0.43), 3.729 (11.07), 3.791 (0.41), 3.924 (0.61), 3.957 (0.41), 5.978 (0.72), 6.832 (0.97), 6.853 (1.08), 6.942 (0.51), 6.945 (0.50), 6.962 (1.06), 6.963 (1.09), 6.980 (0.68), 6.982 (0.65), 7.199 (2.09), 7.218 (2.39), 7.235 (0.57), 7.552 (0.71), 7.557 (0.73), 7.574 (1.23), 7.579 (1.51), 7.625 (2.89), 7.628 (1.65), 7.634 (1.32), 7.646 (1.30).

Example 237

(+)-5-({[6-Bromo-3-methyl-2-(pyrrolidin-1-yl)quinolin-4-yl]carbonyl}amino)-4-(2-methoxyphenyl)pentanoic acid (Enantiomer 1)

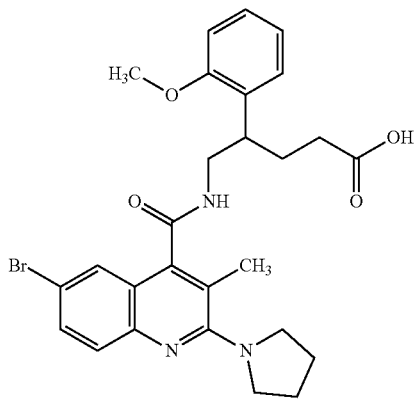 [SMILES: COc1ccccc1C(CCC(=O)O)CNC(=O)c1c(C)c(N2CCCC2)nc2ccc(Br)cc12]

A mixture of 5-{[(6-bromo-2-chloro-3-methylquinolin-4-yl)carbonyl]amino}-4-(2-methoxyphenyl)pentanoic acid (Enantiomer 1, 200 mg, 85% purity, 336 μmol, Example 241A) and pyrrolidine (1.5 ml) was stirred at 100° C. for 2 h. After cooling to RT, the reaction mixture was added to 1 M hydrochloric acid and extracted with dichloromethane. The organic phase was dried over sodium sulfate and concentrated. The crude product was purified by preparative HPLC (Method 28). 65 mg (99% purity, 35% of theory) of the title compound were obtained.

[α]$_D^{20}$=+5.19°, 589 nm, c=0.24 g/100 ml, chloroform
LC-MS (Method 25): R$_t$=0.85 min; MS (ESIpos): m/z=540/542 [M+H]$^+$ $^1$H-NMR (400 MHz, CHLOROFORM-d) δ [ppm]: 1.914 (1.96), 1.923 (2.41), 1.930 (5.41), 1.937 (2.38), 1.946 (2.04), 1.962 (0.41), 1.973 (0.52), 1.993 (0.40), 2.007 (0.47), 2.015 (0.41), 2.019 (0.50), 2.028 (0.51), 2.032 (0.50), 2.043 (0.45), 2.126 (0.75), 2.150 (4.86), 2.172 (0.56), 2.179 (0.40), 2.239 (0.55), 2.272 (0.92), 2.285 (1.36), 2.292 (1.07), 2.304 (1.54), 2.324 (0.67), 2.374 (0.50), 2.635 (2.71), 3.462 (0.51), 3.475 (0.63), 3.487 (0.53), 3.566 (1.94), 3.577 (2.68), 3.583 (4.90), 3.599 (1.79), 3.717 (0.65), 3.741 (16.00), 3.753 (0.68), 3.828 (0.47), 3.841 (0.44), 3.896 (0.41), 3.911 (0.69), 3.926 (0.48), 6.082 (0.69), 6.847 (1.55), 6.867 (1.61), 6.954 (0.76), 6.956 (0.75), 6.974 (1.66), 6.991 (1.01), 6.993 (0.94), 7.211 (3.38), 7.230 (3.74), 7.249 (0.85), 7.253 (0.61), 7.408 (0.72), 7.430 (1.91), 7.450 (1.96), 7.456 (2.06), 7.473 (0.66), 7.478 (0.82), 7.528 (1.65).

Example 238

(−)-5-({[6-Bromo-3-methyl-2-(pyrrolidin-1-yl)quinolin-4-yl]carbonyl}amino)-4-(2-methoxyphenyl) pentanoic acid (Enantiomer 2)

A mixture of 5-{[(6-bromo-2-chloro-3-methylquinolin-4-yl)carbonyl]amino}-4-(2-methoxyphenyl)pentanoic acid (Enantiomer 2, 127 mg, 87% purity, 218 μmol, Example 242A) and pyrrolidine (1.0 ml) was stirred at 100° C. for 1.5 h After cooling to RT, the reaction mixture was added to 1 M hydrochloric acid and extracted with dichloromethane. The organic phase was dried over sodium sulfate and concentrated. The crude product was purified by preparative HPLC (Method 28). 24 mg (99% purity, 20% of theory) of the title compound were obtained.

To determine the optical rotation, a sample of the title compound was dissolved in dichloromethane and washed with water. The organic phase was concentrated and the residue was dried and dissolved in chloroform for the measurement of optical rotation.

[α]$_D^{20}$=−2.0°, 589 nm, c=0.33 g/100 ml, chloroform
LC-MS (Method 25): R$_t$=0.85 min; MS (ESIpos): m/z=540/542 [M+H]$^+$ $^1$H-NMR (400 MHz, CHLOROFORM-d) δ [ppm]: 1.260 (1.06), 1.649 (2.69), 1.790 (1.96), 1.911 (2.71), 1.928 (7.02), 1.944 (3.21), 1.978 (0.87), 1.998 (0.87), 2.016 (0.86), 2.035 (0.46), 2.085 (0.76), 2.099 (0.91), 2.118 (0.91), 2.139 (0.64), 2.171 (6.76), 2.220 (1.98), 2.238 (1.97), 2.257 (0.91), 3.028 (2.58), 3.042 (3.03), 3.056 (2.57), 3.423 (0.94), 3.435 (1.21), 3.448 (1.02), 3.568 (3.20), 3.584 (7.25), 3.665 (0.70), 3.727 (16.00), 3.767 (0.91), 3.786 (1.16), 3.799 (1.04), 3.822 (0.82), 3.884 (0.81), 3.899 (1.23), 3.913 (0.97), 3.931 (0.85), 6.149 (1.09), 6.827 (1.86), 6.848 (2.18), 6.935 (1.01), 6.953 (2.11), 6.971 (1.26), 7.192 (1.35), 7.206 (3.26), 7.225 (2.36), 7.452 (0.52), 7.476 (4.64), 7.504 (0.56), 7.551 (2.52).

Example 239

(+)-5-({[2-(Azepan-1-yl)-6-bromo-3-methylquinolin-4-yl]carbonyl}amino)-4-(2-methoxyphenyl)pentanoic acid (Enantiomer 1)

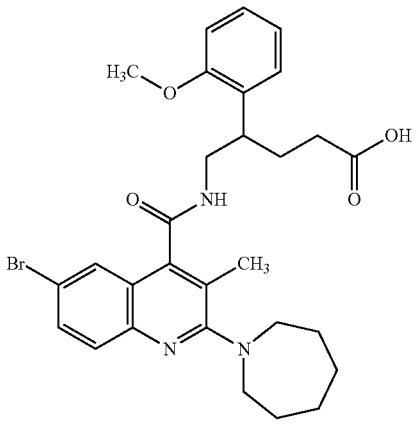 [SMILES: COc1ccccc1C(CCC(=O)O)CNC(=O)c1c(C)c(N2CCCCCC2)nc2ccc(Br)cc12]

A mixture of 5-{[(6-bromo-2-chloro-3-methylquinolin-4-yl)carbonyl]amino}-4-(2-methoxyphenyl)pentanoic acid (Enantiomer 1, 200 mg, 85% purity, 336 μmol, Example 241A) and azepane (1.5 ml) was stirred at 100° C. for 2 h After cooling to RT, the reaction mixture was added to 1 M hydrochloric acid and extracted with dichloromethane. The organic phase was dried over sodium sulfate and concentrated. The crude product was purified by preparative HPLC (Method 28). 65 mg (99% purity, 34% of theory) of the title compound were obtained.

To determine the optical rotation, a sample of the title compound was dissolved in dichloromethane and washed with water. The organic phase was concentrated and the residue was dried and dissolved in methanol for the measurement of optical rotation.

$[\alpha]_D^{20}$=+11.0°, 589 nm, c=0.47 g/100 ml, methanol.

LC-MS (Method 25): $R_t$=1.26 min; MS (ESIpos): m/z=568/570 [M+H]$^+$ $^1$H-NMR (400 MHz, CHLOROFORM-d) δ [ppm]: 1.261 (0.55), 1.654 (1.36), 1.660 (2.71), 1.669 (3.59), 1.677 (3.06), 1.684 (2.08), 1.815 (2.31), 2.019 (0.45), 2.032 (0.49), 2.041 (0.52), 2.055 (0.47), 2.066 (0.43), 2.130 (0.58), 2.144 (0.76), 2.151 (0.58), 2.171 (7.20), 2.278 (0.94), 2.292 (1.65), 2.299 (1.06), 2.313 (1.86), 2.332 (0.76), 2.632 (0.59), 3.446 (0.53), 3.459 (0.68), 3.471 (0.60), 3.495 (2.65), 3.509 (3.27), 3.524 (2.42), 3.563 (0.58), 3.715 (0.51), 3.739 (16.00), 3.808 (0.60), 3.821 (0.53), 3.831 (0.48), 3.845 (0.45), 3.922 (0.49), 3.936 (0.88), 3.951 (0.55), 3.969 (0.59), 5.825 (0.48), 6.843 (1.57), 6.863 (1.56), 6.956 (0.77), 6.958 (0.74), 6.977 (1.60), 6.993 (1.04), 7.210 (2.73), 7.229 (3.12), 7.249 (0.85), 7.253 (0.63), 7.523 (0.48), 7.528 (0.63), 7.545 (1.76), 7.549 (1.96), 7.561 (0.89), 7.590 (1.96).

Example 240

(−)-5-({[2-(Azepan-1-yl)-6-bromo-3-methylquinolin-4-yl]carbonyl}amino)-4-(2-methoxyphenyl)pentanoic acid (Enantiomer 2)

A mixture of 5-{[(6-bromo-2-chloro-3-methylquinolin-4-yl)carbonyl]amino}-4-(2-methoxyphenyl)pentanoic acid (Enantiomer 2, 70 mg, 87% purity, 120 μmol, Example 242A) and azepane (0.5 ml) was stirred at 100° C. for 1.5 h After cooling to RT, the reaction mixture was added to 1 M hydrochloric acid and extracted with dichloromethane. The organic phase was dried over sodium sulfate and concentrated. The crude product was purified by preparative HPLC (Method 28). 58 mg (99% purity, 84% of theory) of the title compound were obtained.

To determine the optical rotation, a sample of the title compound was dissolved in dichloromethane and washed with water. The organic phase was concentrated and the residue was dried and dissolved in methanol for the measurement of optical rotation.

$[\alpha]_D^{20}$=−8.8°, 589 nm, c=0.40 g/100 ml, methanol.

LC-MS (Method 25): $R_t$=1.38 min; MS (ESIpos): m/z=568/570 [M+H]$^+$ $^1$H-NMR (400 MHz, CHLOROFORM-d) δ [ppm]: 1.287 (0.66), 1.430 (0.60), 1.435 (0.60), 1.440 (0.59), 1.447 (0.68), 1.451 (0.68), 1.459 (0.66), 1.464 (0.82), 1.475 (0.64), 1.480 (0.66), 1.487 (0.79), 1.589 (0.72), 1.620 (0.90), 1.671 (2.26), 1.676 (2.27), 1.681 (2.15), 1.688 (2.69), 1.692 (2.40), 1.700 (2.08), 1.706 (2.52), 1.710 (2.46), 1.715 (1.42), 1.722 (1.23), 1.728 (1.45), 1.739 (0.58), 1.746 (0.66), 2.074 (9.60), 2.080 (9.89), 2.088 (10.03), 2.225 (8.25), 2.392 (1.01), 2.413 (1.28), 2.427 (1.51), 2.449 (1.17), 2.463 (0.78), 2.508 (1.34), 2.523 (1.47), 2.542 (1.59), 2.562 (3.91), 2.583 (5.23), 2.597 (6.79), 2.607 (4.51), 2.618 (6.43), 2.636 (2.19), 2.653 (2.10), 2.673 (1.04), 3.403 (1.36), 3.408 (1.53), 3.413 (1.92), 3.427 (2.90), 3.432 (3.63), 3.437 (4.40), 3.442 (4.50), 3.448 (3.86), 3.453 (4.66), 3.460 (4.20), 3.467 (3.15), 3.476 (2.60), 3.481 (1.25), 3.488 (1.49), 3.852 (1.68), 3.879 (2.23), 3.885 (2.31), 3.915 (6.23), 3.930 (6.53), 3.944 (4.69), 3.966 (2.11), 4.116 (4.77), 4.120 (4.83), 4.126 (4.65), 4.133 (5.54), 4.136 (5.90), 4.139 (5.58), 4.144 (5.35), 4.150 (8.43), 4.154 (7.75), 4.160 (4.77), 4.166 (5.01), 4.173 (7.65), 4.188 (0.85), 4.202 (1.00), 4.223 (0.87), 4.324 (0.95), 4.338 (1.27), 4.358 (1.14), 4.372 (0.79), 6.547 (1.48), 7.235 (1.36), 7.251 (1.79), 7.292 (1.11), 7.347 (1.00), 7.364 (1.59), 7.382 (2.13), 7.400 (1.78), 7.420 (0.70), 7.580 (0.44), 7.585 (0.42), 7.599 (1.69), 7.604 (1.77), 7.609 (1.76), 7.620 (2.87), 7.628 (2.62), 7.635 (3.96), 7.660 (12.32), 7.664 (11.67), 7.670 (10.66), 7.677 (12.09), 7.680 (12.39), 7.683 (11.15), 7.688 (11.09), 7.694 (15.57), 7.699 (14.56), 7.702 (2.63), 7.704 (10.36), 7.710 (10.63), 7.715 (12.08), 7.717 (16.00), 7.931 (0.88), 7.936 (1.58), 7.942 (1.97), 7.948 (2.49), 7.954 (2.68), 7.960 (2.75), 7.965 (3.65), 7.970 (3.52), 7.981 (3.59), 7.988 (3.08), 7.995 (3.43), 8.001 (3.64), 8.015 (1.81), 8.031 (2.10), 8.049 (1.69).

Example 241

(+/−)-5-({[6-Bromo-3-methyl-2-(piperidin-1-yl)quinolin-4-yl]carbonyl}amino)-4-(2,6-dichlorophenyl)pentanoic acid (Racemate)

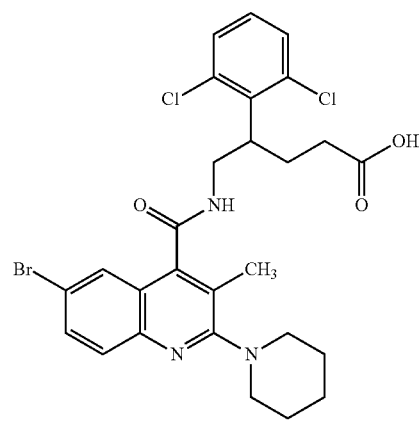 [SMILES: Cc1c(N2CCCCC2)nc2ccc(Br)cc2c1C(=O)NCC(CCC(=O)O)c1c(Cl)cccc1Cl]

Method A:

(+/−)-5-{[(6-Bromo-2-chloro-3-methylquinolin-4-yl)carbonyl]amino}-4-(2,6-dichlorophenyl)pentanoic acid (racemate, 45.0 mg, 72% purity, 59.5 µmol, Example 246A) and piperidine (1.0 ml, 180 µmol) were stirred at 100° C. for 1.5 h.

Method B:

(+/−)-5-{[(6-Bromo-2-chloro-3-methylquinolin-4-yl)carbonyl]amino}-4-(2,6-dichlorophenyl)pentanoic acid (racemate, 123 mg, 72% purity, 163 µmol, Example 246A) and piperidine (50 µl, 500 µmol) were stirred in 1-butanol (6 ml) at 100° C. for 8 h.

The combined reaction mixtures from method A and method B were added to 1 M hydrochloric acid and extracted with dichloromethane. The organic phase was dried over sodium sulfate and concentrated on a rotary evaporator. The crude product was purified by means of preparative HPLC (Chromatorex C-18, 10 µm, 125 mm×30 mm, eluent A: water+0.1% formic acid, eluent B: acetonitrile; gradient: 50-95% B). 69 mg (97% purity, 50% of theory) of the title compound were obtained.

LC-MS (Method 25): $R_t$=1.39 min; MS (ESIpos): m/z=592/594/596 $[M+H]^+$ $^1$H-NMR (400 MHz, CHLOROFORM-d) δ [ppm]: 0.959 (0.56), 1.185 (1.50), 1.200 (2.54), 1.205 (0.61), 1.219 (0.63), 1.370 (12.44), 1.561 (0.53), 1.604 (1.80), 1.614 (1.57), 1.650 (3.36), 1.659 (3.52), 2.069 (0.76), 2.079 (0.72), 2.085 (0.73), 2.088 (0.75), 2.102 (1.06), 2.113 (0.71), 2.121 (0.58), 2.133 (1.46), 2.158 (16.00), 2.172 (1.46), 2.187 (1.38), 2.205 (1.47), 2.223 (1.78), 2.242 (1.01), 2.264 (0.61), 2.283 (0.41), 2.287 (0.43), 2.307 (0.42), 2.313 (0.79), 2.317 (0.72), 2.336 (0.48), 2.353 (0.58), 2.366 (0.61), 2.378 (0.60), 2.390 (0.61), 2.534 (1.04), 2.931 (0.65), 3.214 (4.22), 3.783 (3.91), 3.991 (0.77), 4.006 (0.82), 4.019 (1.17), 4.033 (1.38), 4.045 (0.93), 4.059 (0.85), 4.072 (0.85), 4.083 (0.65), 4.090 (0.95), 4.107 (0.60), 4.118 (0.79), 4.133 (0.70), 6.816 (0.42), 6.836 (0.47), 7.049 (1.92), 7.070 (4.35), 7.089 (2.79), 7.219 (2.59), 7.222 (3.11), 7.239 (2.35), 7.242 (2.40), 7.261 (0.43), 7.273 (2.98), 7.277 (2.73), 7.294 (2.59), 7.297 (2.53), 7.317 (0.41), 7.527 (1.62), 7.532 (1.85), 7.549 (2.11), 7.554 (2.61), 7.587 (2.49), 7.636 (3.49), 7.658 (2.29).

Example 242

(+/−)-5-({[6-Bromo-3-methyl-2-(piperidin-1-yl)quinolin-4-yl]carbonyl}amino)-4-(2-methylphenyl)pentanoic acid (Racemate)

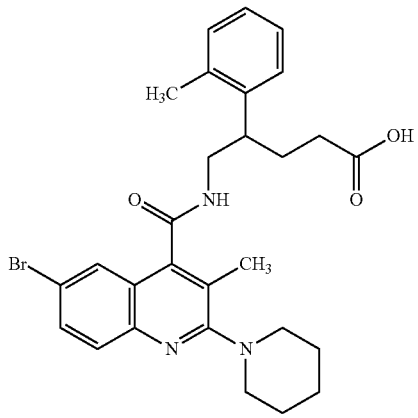 [SMILES: Cc1ccccc1C(CCC(=O)O)CNC(=O)c1c(C)c(N2CCCCC2)nc2ccc(Br)cc12]

(+/−)-5-{[(6-Bromo-2-chloro-3-methylquinolin-4-yl)carbonyl]amino}-4-(2-methylphenyl)pentanoic acid (racemate, 500 mg, 86% purity, 0.88 mmol, Example 234A) and piperidine (3.0 ml, 2.2 mmol) were stirred at 100° C. for 2 h. After cooling to RT, the reaction mixture was added to 1 M hydrochloric acid and extracted with dichloromethane. The organic phase was dried over sodium sulfate and concentrated. The crude product was prepurified by column chromatography (Isolera, KP-Sil, eluent: dichloromethane/methanol, gradient: 0-40% methanol) and repurified by means of preparative HPLC (Method 27). 330 mg (99% purity, 69% of theory) of the title compound were obtained.

LC-MS (Method 26): $R_t$=0.82 min; MS (ESIpos): m/z=538/540 $[M+H]^+$ $^1$H-NMR (400 MHz, CHLOROFORM-d) δ [ppm]: 1.565 (0.89), 1.577 (0.89), 1.660 (2.48), 1.672 (2.38), 1.689 (2.28), 1.704 (2.76), 1.716 (2.87), 1.885 (0.46), 1.907 (0.57), 1.913 (0.68), 1.920 (0.65), 1.942 (0.49), 2.079 (0.56), 2.092 (0.70), 2.111 (0.70), 2.130 (0.42), 2.180 (2.18), 2.198 (3.83), 2.207 (16.00), 2.218 (1.80), 2.262 (0.53), 2.356 (14.53), 2.391 (4.38), 2.874 (2.02), 2.888 (2.61), 2.902 (1.88), 3.145 (2.77), 3.159 (3.54), 3.169 (2.59), 3.316 (0.45), 3.343 (0.53), 3.352 (0.51), 3.369 (0.68), 3.382 (0.54), 3.652 (0.46), 3.665 (0.52), 3.673 (0.45), 3.685 (1.01), 3.698 (0.61), 3.706 (0.58), 3.720 (0.52), 3.913 (0.55), 3.929 (1.06), 3.945 (0.91), 3.962 (0.86), 3.979 (0.43), 6.165 (0.58), 6.179 (1.00), 6.193 (0.56), 7.087 (0.47), 7.091 (0.49), 7.107 (1.30), 7.111 (1.31), 7.122 (1.34), 7.126 (1.68), 7.141 (2.27), 7.155 (0.79), 7.178 (0.74), 7.183 (0.61), 7.190 (1.05), 7.197 (1.99), 7.202 (1.60), 7.205 (1.91), 7.217 (3.58), 7.221 (2.59), 7.237 (0.66), 7.554 (1.42), 7.559 (1.49), 7.577 (2.49), 7.582 (2.70), 7.628 (4.42), 7.650 (2.37), 7.664 (3.39), 7.669 (3.15).

Example 243

(+/−)-5-({[2-(Azepan-1-yl)-6-bromo-3-methylquinolin-4-yl]carbonyl}amino)-4-(2-methylphenyl)pentanoic acid (Racemate)

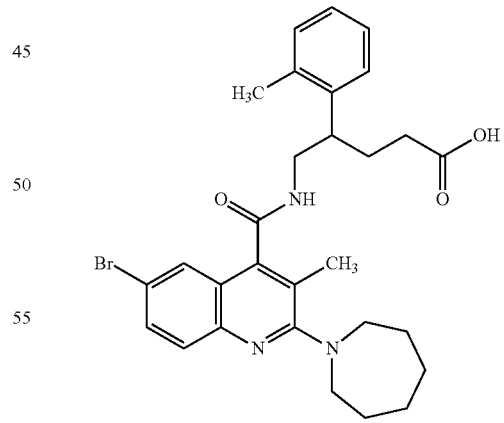

(+/−)-5-{[(6-Bromo-2-chloro-3-methylquinolin-4-yl)carbonyl]amino}-4-(2-methylphenyl)pentanoic acid (racemate, 500 mg, 86% purity, 0.88 mmol, Example 234A) and azepane (3.0 ml, 2.2 mmol) were stirred at 100° C. for 2 h. After cooling to RT, the reaction mixture was added to 1 M hydrochloric acid and extracted with dichloromethane. The organic phase was dried over sodium sulfate and concentrated. The crude product was purified by preparative HPLC (Method 27). 315 mg (99% purity, 64% of theory) of the title compound were obtained.

LC-MS (Method 26): $R_t$=0.87 min; MS (ESIpos): m/z=552/554 [M+H]$^+$ $^1$H-NMR (400 MHz, CHLOROFORM-d) δ [ppm]: 1.262 (0.44), 1.622 (0.65), 1.629 (1.23), 1.637 (1.69), 1.652 (2.55), 1.657 (3.68), 1.665 (4.74), 1.674 (4.04), 1.680 (2.70), 1.812 (3.00), 1.898 (0.58), 1.908 (0.52), 1.924 (0.51), 1.931 (0.58), 1.942 (0.65), 1.965 (0.57), 2.111 (0.66), 2.125 (0.74), 2.144 (0.71), 2.160 (0.48), 2.177 (0.48), 2.194 (16.00), 2.207 (0.84), 2.230 (2.25), 2.248 (3.63), 2.266 (1.71), 2.357 (15.85), 2.390 (2.68), 2.626 (1.58), 3.005 (1.99), 3.020 (1.81), 3.034 (1.87), 3.369 (0.52), 3.385 (0.72), 3.398 (0.58), 3.406 (0.49), 3.486 (4.69), 3.501 (5.26), 3.515 (4.60), 3.551 (0.41), 3.648 (0.50), 3.661 (0.57), 3.670 (0.49), 3.682 (1.07), 3.696 (0.67), 3.704 (0.61), 3.717 (0.56), 3.907 (0.61), 3.923 (1.16), 3.940 (1.00), 3.957 (0.93), 3.973 (0.47), 5.949 (0.63), 5.963 (1.10), 5.977 (0.62), 7.096 (0.45), 7.102 (0.49), 7.116 (1.30), 7.122 (1.17), 7.129 (1.28), 7.136 (1.72), 7.148 (2.58), 7.165 (0.88), 7.185 (0.51), 7.192 (0.68), 7.197 (0.67), 7.205 (2.43), 7.208 (2.22), 7.215 (2.91), 7.219 (3.74), 7.222 (3.61), 7.234 (0.49), 7.519 (0.65), 7.523 (0.61), 7.541 (3.29), 7.546 (3.86), 7.553 (5.15), 7.574 (0.96), 7.608 (0.42), 7.616 (3.08), 7.620 (2.89).

Example 244

(+/−)-5-({[6-Bromo-3-methyl-2-(piperidin-1-yl)quinolin-4-yl]carbonyl}amino)-4-(2,6-difluorophenyl) pentanoic acid (Racemate)

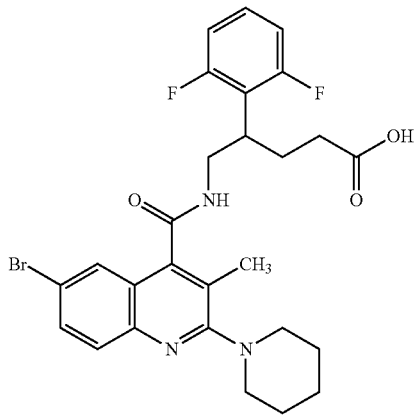 [SMILES: Cc1c(N2CCCCC2)nc2ccc(Br)cc2c1C(=O)NCC(CCC(=O)O)c1c(F)cccc1F]

Proceeding from (+/−)-tert-butyl 5-({[6-bromo-3-methyl-2-(piperidin-1-yl)quinolin-4-yl]carbonyl}amino)-4-(2,6-difluorophenyl)pentanoate (racemate, 55 mg, 89.2 μmol, Example 250A), the reaction with TFA and the purification of the product were effected as described for 5-[({6-bromo-2-[3-ethylpiperidin-1-yl]-3-methylquinolin-4-yl}carbonyl) amino]-4-(2,5-difluorophenyl)pentanoic acid (Example 225). 44 mg (100% purity, 88% of theory) of the title compound were obtained.

LC-MS (Method 1): $R_t$=2.10 min; MS (ESIpos): m/z=560/562 [M+H]$^+$ $^1$H-NMR (400 MHz, DMSO-d6) δ [ppm]: −0.149 (0.65), −0.008 (5.92), 0.008 (5.82), 0.146 (0.65), 1.607 (3.47), 1.671 (6.81), 1.873 (0.73), 1.888 (0.94), 1.905 (1.25), 2.051 (1.10), 2.065 (1.33), 2.082 (1.41), 2.101 (1.80), 2.116 (7.07), 2.135 (16.00), 2.327 (0.73), 2.669 (0.89), 3.133 (9.00), 3.489 (1.25), 3.677 (0.84), 3.695 (1.88), 3.710 (3.03), 3.724 (2.17), 7.057 (3.63), 7.079 (6.66), 7.102 (4.28), 7.322 (0.57), 7.340 (1.41), 7.359 (2.04), 7.378 (1.31), 7.396 (0.55), 7.468 (0.63), 7.623 (2.35), 7.645 (9.74), 7.656 (6.19), 7.661 (5.74), 7.678 (1.46), 7.683 (1.59), 8.798 (1.62), 8.813 (3.26), 8.827 (1.67), 12.078 (4.36).

Example 245

(+)-5-({[6-Bromo-3-methyl-2-(piperidin-1-yl)quinolin-4-yl]carbonyl}amino)-4-(2,6-difluorophenyl) pentanoic acid (Enantiomer 1)

tert-Butyl 5-({[6-bromo-3-methyl-2-(piperidin-1-yl)quinolin-4-yl]carbonyl}amino)-4-(2,6-difluorophenyl)pentanoate (Enantiomer 1, 85 mg, 138 μmol, Example 251A) was dissolved in dichloromethane (1.8 ml). At RT, TFA (1.0 ml, 14 mmol) was added and the mixture was stirred at RT for 1 h. The volatile components were removed on a rotary evaporator. The residue was dissolved in a little DMSO and purified by means of preparative HPLC (Method 31). The combined target fractions were concentrated and the residue was dried under reduced pressure. 64 mg (99% purity, 82% of theory) of the title compound were obtained.

$[\alpha]_D^{20}$=+40.8°, 589 nm, c=0.32 g/100 ml, methanol

LC-MS (Method 1): $R_t$=2.09 min; MS (ESIpos): m/z=560/562 [M+H]$^+$ $^1$H-NMR (400 MHz, DMSO-d6) δ [ppm]: −0.149 (0.63), 0.008 (3.76), 0.146 (0.46), 0.839 (0.69), 1.234 (0.67), 1.607 (3.61), 1.671 (6.99), 1.903 (1.28), 2.051 (1.15), 2.064 (1.45), 2.081 (1.45), 2.116 (7.35), 2.135 (16.00), 2.327 (1.49), 2.366 (0.97), 2.670 (1.49), 2.710 (0.92), 3.133 (9.28), 3.162 (1.97), 3.175 (1.74), 3.496 (1.22), 3.677 (0.82), 3.695 (1.89), 3.710 (3.13), 3.725 (2.14), 7.057 (3.84), 7.079 (7.06), 7.102 (4.58), 7.341 (1.47), 7.359 (2.10), 7.378 (1.36), 7.477 (0.67), 7.623 (2.54), 7.645 (10.62), 7.656 (6.64), 7.661 (6.07), 7.678 (1.72), 7.683 (1.72), 8.798 (1.66), 8.813 (3.38), 8.827 (1.76), 12.080 (2.94).

Example 246

(−)-5-({[6-Bromo-3-methyl-2-(piperidin-1-yl)quinolin-4-yl]carbonyl}amino)-4-(2,6-difluorophenyl) pentanoic acid (Enantiomer 2)

Proceeding from tert-butyl 5-({[6-bromo-3-methyl-2-(piperidin-1-yl)quinolin-4-yl]carbonyl}amino)-4-(2,6-difluorophenyl)pentanoate (Enantiomer 2, 63 mg, 102 μmol, Example 252A), the reaction and the purification of the product were effected as described for tert-butyl 5-({[6-bromo-3-methyl-2-(piperidin-1-yl)quinolin-4-yl] carbonyl}amino)-4-(2,6-difluorophenyl)pentanoate (Enantiomer 1, Example 245). 48 mg (100% purity, 84% of theory) of the title compound were obtained.

$[\alpha]_D^{20}$=−46.7°, 589 nm, c=0.30 g/100 ml, methanol

LC-MS (Method 1): $R_t$=2.09 min; MS (ESIpos): m/z=560/562 [M+H]$^+$ $^1$H-NMR (400 MHz, DMSO-d6) δ [ppm]: −0.149 (0.52), −0.008 (3.81), 0.008 (3.85), 0.146 (0.46), 1.606 (3.56), 1.671 (7.01), 1.902 (1.29), 2.050 (1.14), 2.063 (1.35), 2.081 (1.41), 2.115 (7.45), 2.135 (16.00), 2.327 (1.39), 2.366 (0.73), 2.669 (1.60), 2.710 (0.92), 3.133 (9.32), 3.493 (1.29), 3.676 (0.87), 3.694 (1.89), 3.710 (3.14), 3.724 (2.23), 7.057 (3.85), 7.079 (7.03), 7.101 (4.51), 7.340 (1.48), 7.359 (2.10), 7.379 (1.37), 7.396 (0.60), 7.470 (0.67), 7.623 (2.50), 7.645 (10.42), 7.656 (6.45), 7.661 (6.01), 7.678 (1.50), 7.683 (1.64), 8.798 (1.69), 8.813 (3.39), 8.828 (1.75), 12.083 (2.29).

Example 247

(+/−)-5-({[6-Bromo-3-methyl-2-(pyrrolidin-1-yl)quinolin-4-yl]carbonyl}amino)-4-(2,6-difluorophenyl)pentanoic acid hydrogenformate (Racemate)

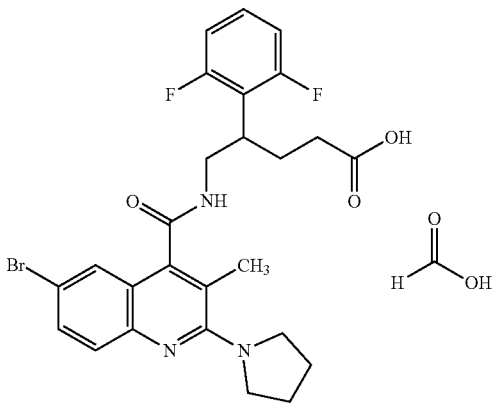 [SMILES: Cc1c(N2CCCC2)nc2ccc(Br)cc2c1C(=O)NCC(CCC(=O)O)c1c(F)cccc1F ; O=CO]

Proceeding from (+/−)-tert-butyl 5-({[6-bromo-3-methyl-2-(pyrrolidin-1-yl)quinolin-4-yl]carbonyl}-amino)-4-(2,6-difluorophenyl)pentanoate (racemate, 56 mg, 92.9 µmol, Example 253A), the reaction and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 20 mg (100% purity, 36% of theory) of the title compound were obtained (the formic acid present originated from the HPLC method).

LC-MS (Method 1): $R_t$=1.39 min; MS (ESIpos): m/z=546/548 [M+H]$^+$ $^1$H-NMR (400 MHz, DMSO-d6) δ [ppm]: −0.149 (1.79), 0.008 (16.00), 0.146 (1.79), 1.872 (13.83), 2.061 (1.98), 2.079 (2.02), 2.114 (8.78), 2.129 (7.73), 2.163 (9.28), 2.328 (2.17), 2.670 (2.10), 3.566 (8.93), 3.680 (2.52), 3.695 (3.53), 3.709 (2.80), 7.050 (5.01), 7.072 (9.09), 7.095 (5.79), 7.354 (2.87), 7.372 (2.14), 7.466 (7.03), 7.488 (11.61), 7.547 (6.21), 7.553 (5.86), 7.570 (3.77), 7.575 (3.61), 8.137 (14.49), 8.750 (2.29), 8.765 (4.50), 8.779 (2.29), 12.103 (0.50).

Example 248

5-({[6-Bromo-3-methyl-2-(pyrrolidin-1-yl)quinolin-4-yl]carbonyl}amino)-4-(2,6-difluorophenyl)pentanoic acid (Enantiomer 1)

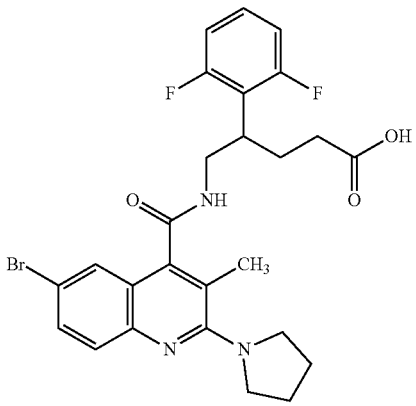 [SMILES: Cc1c(N2CCCC2)nc2ccc(Br)cc2c1C(=O)NCC(CCC(=O)O)c1c(F)cccc1F]

Proceeding from tert-butyl 5-({[6-bromo-3-methyl-2-(pyrrolidin-1-yl)quinolin-4-yl]carbonyl}amino)-4-(2,6-difluorophenyl)pentanoate (Enantiomer 1, 54 mg, 89.6 µmol, Example 254A), the reaction with TFA and the purification of the product were effected as described for (+)-5-({[6-bromo-3-methyl-2-(piperidin-1-yl)quinolin-4-yl]carbonyl}amino)-4-(2,6-difluorophenyl)pentanoic acid (Example 245). 20 mg (96% purity, 39% of theory) of the title compound were obtained.

LC-MS (Method 1): $R_t$=1.39 min; MS (ESIpos): m/z=546/548 [M+H]$^+$ $^1$H-NMR (400 MHz, DMSO-d6) δ [ppm]: −0.149 (1.41), 0.146 (1.22), 1.141 (5.31), 1.235 (3.97), 1.356 (1.09), 1.872 (13.06), 2.086 (16.00), 2.115 (9.79), 2.130 (8.19), 2.165 (8.58), 2.328 (3.90), 2.366 (2.69), 2.669 (4.54), 2.710 (3.14), 3.564 (8.13), 3.694 (3.65), 4.538 (0.83), 7.051 (4.99), 7.073 (8.96), 7.095 (5.44), 7.354 (3.14), 7.466 (6.53), 7.489 (10.50), 7.548 (5.63), 7.553 (5.31), 7.570 (3.39), 7.575 (3.14), 7.838 (0.96), 8.133 (5.63), 8.750 (2.43), 8.765 (4.10), 12.071 (1.73).

Example 249

(−)-5-({[6-Bromo-3-methyl-2-(pyrrolidin-1-yl)quinolin-4-yl]carbonyl}amino)-4-(2,6-difluorophenyl)pentanoic acid (Enantiomer 2)

Proceeding from tert-butyl 5-({[6-bromo-3-methyl-2-(pyrrolidin-1-yl)quinolin-4-yl]carbonyl}amino)-4-(2,6-difluorophenyl)pentanoate (Enantiomer 2, 47 mg, 78.0 µmol, Example 255A), the reaction with TFA and the purification of the product were effected as described for (+)-5-({[6-bromo-3-methyl-2-(piperidin-1-yl)quinolin-4-yl]carbonyl}amino)-4-(2,6-difluorophenyl)pentanoic acid (Example 245). 33 mg (96% purity, 74% of theory) of the title compound were obtained.

$[α]_D^{20}$=−41.1°, 589 nm, c=0.30 g/100 ml, methanol

LC-MS (Method 1): $R_t$=1.39 min; MS (ESIpos): m/z=546/548 [M+H]$^+$ $^1$H-NMR (400 MHz, DMSO-d6) δ [ppm]: −0.149 (1.73), 0.146 (1.64), 1.147 (0.95), 1.872 (16.00), 2.114 (10.29), 2.129 (9.25), 2.162 (10.64), 2.327 (5.88), 2.366 (2.34), 2.669 (5.71), 2.710 (2.51), 3.565 (9.95), 3.693 (3.98), 7.050 (5.79), 7.072 (10.81), 7.095 (6.40), 7.351 (3.11), 7.466 (8.13), 7.488 (13.15), 7.547 (6.83), 7.553 (6.66), 7.575 (4.15), 8.134 (10.90), 8.763 (4.84), 12.069 (1.38).

Example 250

(+/−)-5-({[6-Bromo-2-(3,3-difluoropiperidin-1-yl)-3-methylquinolin-4-yl]carbonyl}amino)-4-(2,6-difluorophenyl)pentanoic acid (Racemate)

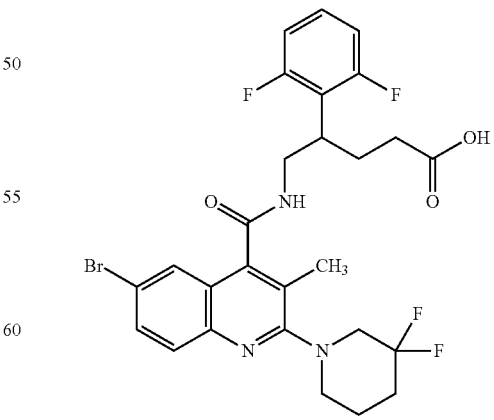

Proceeding from (+/−)-tert-butyl 5-({[6-bromo-2-(3,3-difluoropiperidin-1-yl)-3-methylquinolin-4-yl]carbonyl}amino)-4-(2,6-difluorophenyl)pentanoate (racemate, 55 mg, 84.3 µmol, Example 256A), the reaction with TFA and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 48 mg (100% purity, 95% of theory) of the title compound were obtained.

LC-MS (Method 1): $R_t$=2.07 min; MS (ESIpos): m/z=596/598 [M+H]$^+$ $^1$H-NMR (400 MHz, DMSO-d6) δ [ppm]: −0.149 (0.57), −0.008 (4.89), 0.146 (0.61), 1.234 (0.46), 1.890 (4.70), 2.064 (2.82), 2.082 (3.71), 2.101 (3.95), 2.118 (8.92), 2.134 (9.20), 2.155 (16.00), 2.327 (0.69), 2.670 (0.74), 3.165 (5.06), 3.448 (3.31), 3.477 (6.93), 3.505 (4.20), 3.686 (0.95), 3.704 (2.05), 3.719 (3.23), 3.733 (2.39), 7.059 (4.20), 7.081 (7.65), 7.104 (4.95), 7.324 (0.61), 7.343 (1.58), 7.361 (2.22), 7.379 (1.43), 7.398 (0.58), 7.511 (0.64), 7.674 (2.48), 7.696 (11.37), 7.705 (7.37), 7.710 (6.84), 7.728 (1.50), 7.732 (1.69), 8.814 (1.90), 8.828 (3.82), 8.842 (1.95), 12.091 (1.33).

Example 251

(+)-5-({[6-Bromo-2-(3,3-difluoropiperidin-1-yl)-3-methylquinolin-4-yl]carbonyl}amino)-4-(2,6-difluorophenyl)pentanoic acid (Enantiomer 1)

Proceeding from tert-butyl 5-({[6-bromo-3-methyl-2-(piperidin-1-yl)quinolin-4-yl]carbonyl}amino)-4-(2,6-difluorophenyl)pentanoate (Enantiomer 1, 82 mg, 126 μmol, Example 257A), the reaction with TFA was effected as described for (+)-5-({[6-bromo-3-methyl-2-(piperidin-1-yl)quinolin-4-yl]carbonyl}amino)-4-(2,6-difluorophenyl)pentanoic acid (Example 245). The product was purified by means of preparative HPLC (Method 19). 48 mg (98% purity, 63% of theory) of the title compound were obtained.

[α]$_D^{20}$=+44.1°, 589 nm, c=0.48 g/100 ml, methanol

LC-MS (Method 1): $R_t$=2.09 min; MS (ESIpos): m/z=596/598 [M+H]$^+$ $^1$H-NMR (400 MHz, DMSO-d6) δ [ppm]: −0.150 (0.59), 0.146 (0.64), 1.889 (4.78), 2.081 (3.71), 2.100 (3.95), 2.118 (8.73), 2.133 (9.08), 2.154 (16.00), 2.365 (0.46), 2.709 (0.55), 3.162 (10.75), 3.174 (9.58), 3.446 (3.22), 3.476 (6.83), 3.504 (4.20), 3.703 (2.08), 3.719 (3.25), 4.063 (0.59), 4.075 (1.40), 4.087 (1.37), 7.058 (3.98), 7.080 (7.57), 7.103 (4.68), 7.342 (1.63), 7.360 (2.24), 7.377 (1.44), 7.501 (0.70), 7.673 (2.24), 7.695 (10.13), 7.705 (6.46), 7.731 (1.48), 8.812 (1.86), 8.827 (3.59), 8.841 (1.87), 12.083 (1.83).

Example 252

(−)-5-({[6-Bromo-2-(3,3-difluoropiperidin-1-yl)-3-methylquinolin-4-yl]carbonyl}amino)-4-(2,6-difluorophenyl)pentanoic acid (Enantiomer 2)

Proceeding from tert-butyl 5-({[6-bromo-3-methyl-2-(piperidin-1-yl)quinolin-4-yl]carbonyl}amino)-4-(2,6-difluorophenyl)pentanoate (Enantiomer 2, 73 mg, 112 μmol, Example 258A), the reaction with TFA was effected as described for (+)-5-({[6-bromo-3-methyl-2-(piperidin-1-yl)quinolin-4-yl]carbonyl}amino)-4-(2,6-difluorophenyl)pentanoic acid (Example 245). The product was purified by means of preparative HPLC (Method 19). 40 mg (98% purity, 59% of theory) of the title compound were obtained.

[α]$_D^{20}$=−38.2°, 589 nm, c=0.37 g/100 ml, methanol

LC-MS (Method 1): $R_t$=2.06 min; MS (ESIpos): m/z=596/598 [M+H]$^+$ $^1$H-NMR (400 MHz, DMSO-d6) δ [ppm]: 1.890 (4.67), 2.065 (2.78), 2.082 (3.62), 2.101 (3.76), 2.119 (8.55), 2.135 (9.19), 2.155 (16.00), 2.327 (0.66), 2.670 (0.70), 2.710 (0.43), 3.162 (9.09), 3.175 (8.05), 3.447 (3.23), 3.476 (6.83), 3.504 (4.13), 3.687 (0.97), 3.703 (2.09), 3.719 (3.30), 3.734 (2.38), 4.062 (0.43), 4.075 (1.22), 4.088 (1.19), 4.102 (0.40), 7.059 (4.21), 7.081 (7.74), 7.104 (4.91), 7.323 (0.64), 7.342 (1.64), 7.361 (2.27), 7.378 (1.46), 7.398 (0.56), 7.511 (0.67), 7.674 (2.44), 7.696 (11.21), 7.705 (6.99), 7.710 (6.16), 7.728 (1.40), 7.732 (1.46), 8.812 (1.93), 8.827 (3.80), 8.841 (1.89), 12.081 (4.01).

Example 253

5-[({6-Bromo-2-(3-fluoropiperidin-1-yl)-3-methylquinolin-4-yl}carbonyl)amino]-4-(2,6-difluorophenyl)pentanoic acid (Diastereomer Mixture)

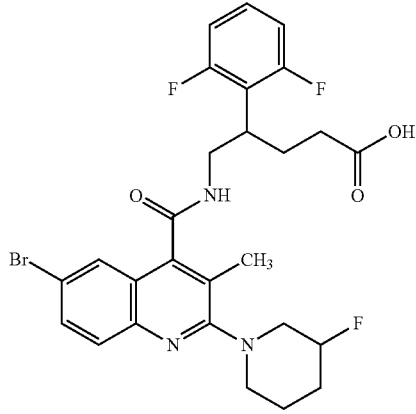 [SMILES: Cc1c(N2CCCC(F)C2)nc2ccc(Br)cc2c1C(=O)NCC(CCC(=O)O)c1c(F)cccc1F]

Proceeding from tert-butyl 5-[({6-bromo-2-(3-fluoropiperidin-1-yl)-3-methylquinolin-4-yl}carbonyl)amino]-4-(2,6-difluorophenyl)pentanoate (56 mg, 88 μmol, Example 259A), the reaction with TFA and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 44 mg (100% purity, 88% of theory) of the title compound were obtained.

LC-MS (Method 1): $R_t$=2.01 min; MS (ESIpos): m/z=578/580 [M+H]$^+$ $^1$H-NMR (400 MHz, DMSO-d6) δ [ppm]: −0.149 (1.03), −0.008 (8.38), 0.008 (8.14), 0.146 (0.93), 1.644 (1.51), 1.806 (1.39), 1.902 (3.86), 2.051 (1.37), 2.064 (1.63), 2.082 (1.68), 2.116 (7.76), 2.132 (8.29), 2.150 (16.00), 2.328 (1.27), 2.670 (1.27), 3.094 (1.82), 3.169 (1.75), 3.379 (1.96), 3.405 (1.08), 3.437 (1.77), 3.470 (1.84), 3.714 (2.97), 4.817 (1.29), 4.937 (1.20), 7.057 (4.38), 7.080 (7.98), 7.102 (5.17), 7.341 (1.68), 7.359 (2.32), 7.377 (1.49), 7.491 (0.77), 7.648 (2.80), 7.670 (11.98), 7.680 (7.57), 7.684 (7.16), 7.702 (1.77), 7.707 (1.80), 8.807 (1.82), 8.822 (3.74), 8.836 (1.96), 12.087 (1.51).

Example 254

5-[({6-Bromo-2-(3-ethylpiperidin-1-yl)-3-methylquinolin-4-yl}carbonyl)amino]-4-(2,6-difluorophenyl)pentanoic acid (Diastereomer Mixture)

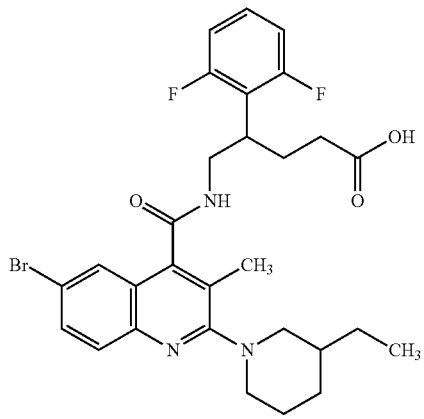 [SMILES: CCC1CCCN(c2nc3ccc(Br)cc3c(C(=O)NCC(CCC(=O)O)c3c(F)cccc3F)c2C)C1]

Proceeding from tert-butyl 5-[({6-bromo-2-(3-ethylpiperidin-1-yl)-3-methylquinolin-4-yl}carbonyl)amino]-4-(2,6-difluorophenyl)pentanoate (diastereomer mixture, 55 mg, 85.3 µmol, Example 260A), the reaction with TFA and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). This gave 48 mg (100% pure, 96% of theory) of the title compound.

LC-MS (Method 1): $R_t$=2.37 min; MS (ESIpos): m/z=588/590 [M+H]$^+$ $^1$H-NMR (400 MHz, DMSO-d6) δ [ppm]: −0.149 (0.62), −0.008 (5.31), 0.008 (4.88), 0.146 (0.62), 0.892 (5.28), 0.909 (12.18), 0.911 (12.13), 0.928 (6.42), 1.035 (0.46), 1.065 (1.21), 1.086 (1.24), 1.116 (0.56), 1.240 (1.12), 1.257 (2.48), 1.275 (3.28), 1.293 (2.31), 1.398 (0.50), 1.563 (1.35), 1.603 (1.26), 1.632 (1.09), 1.747 (1.69), 1.780 (1.17), 1.854 (1.61), 1.887 (2.01), 2.030 (0.44), 2.049 (1.06), 2.063 (1.30), 2.081 (1.38), 2.100 (1.76), 2.118 (8.16), 2.132 (16.00), 2.150 (2.62), 2.327 (0.62), 2.396 (0.74), 2.423 (1.15), 2.451 (0.74), 2.670 (0.71), 2.710 (0.96), 2.738 (1.43), 2.768 (0.80), 3.493 (3.67), 3.515 (2.99), 3.679 (0.74), 3.696 (1.61), 3.712 (2.60), 3.726 (1.88), 7.053 (3.55), 7.075 (6.48), 7.097 (4.26), 7.319 (0.53), 7.338 (1.33), 7.357 (1.92), 7.376 (1.26), 7.394 (0.56), 7.473 (0.53), 7.625 (1.61), 7.647 (9.98), 7.654 (6.34), 7.658 (5.28), 7.676 (0.99), 7.680 (1.02), 8.790 (1.48), 8.805 (2.94), 8.819 (1.52), 12.082 (1.72).

Example 255

(+/−)-5-({[6-Bromo-3-methyl-2-(piperidin-1-yl)quinolin-4-yl]carbonyl}amino)-4-(2,5-difluorophenyl)pentanoic acid (Racemate)

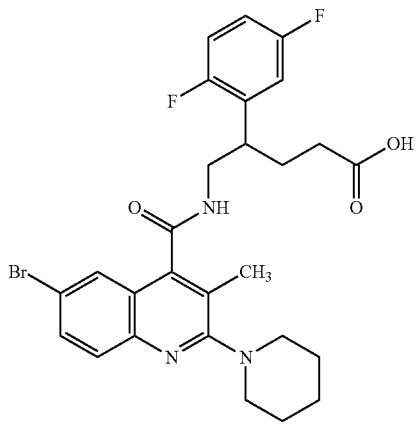 [SMILES: Cc1c(N2CCCCC2)nc2ccc(Br)cc2c1C(=O)NCC(CCC(=O)O)c1cc(F)ccc1F]

Proceeding from (+/−)-tert-butyl 5-({[6-bromo-3-methyl-2-(piperidin-1-yl)quinolin-4-yl]carbonyl}-amino)-4-(2,5-difluorophenyl)pentanoate (racemate, 56 mg, 90.8 µmol, Example 261A), the reaction with TFA (reaction time: 45 min) and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). This gave 49 mg (100% pure, 96% of theory) of the title compound.

LC-MS (Method 1): $R_t$=2.11 min; MS (ESIpos): m/z=560/562 [M+H]$^+$ $^1$H-NMR (400 MHz, DMSO-d6) δ [ppm]: −0.150 (0.88), 0.146 (0.88), 1.371 (0.59), 1.605 (4.49), 1.670 (8.78), 1.805 (1.66), 2.003 (1.56), 2.015 (2.05), 2.035 (1.95), 2.054 (2.24), 2.090 (5.07), 2.117 (16.00), 2.327 (1.76), 2.366 (0.54), 2.669 (1.95), 3.132 (11.56), 3.612 (1.46), 3.631 (2.10), 3.645 (3.02), 3.695 (1.76), 7.127 (2.54), 7.204 (2.05), 7.215 (2.24), 7.227 (3.32), 7.239 (3.32), 7.250 (1.61), 7.262 (1.46), 7.300 (3.12), 7.436 (1.02), 7.622 (2.54), 7.644 (12.63), 7.653 (8.44), 7.658 (7.66), 7.680 (1.76), 8.723 (2.15), 8.738 (3.90), 8.752 (2.10), 12.064 (1.46).

Example 256

(−)-5-({[6-Bromo-3-methyl-2-(piperidin-1-yl)quinolin-4-yl]carbonyl}amino)-4-(2,5-difluorophenyl)pentanoic acid (Enantiomer 1)

Proceeding from tert-butyl 5-({[6-bromo-3-methyl-2-(piperidin-1-yl)quinolin-4-yl]carbonyl}amino)-4-(2,5-difluorophenyl)pentanoate (Enantiomer 1, 81 mg, 131 µmol, Example 262A), the reaction with TFA was effected as described for (+)-5-({[6-bromo-3-methyl-2-(piperidin-1-yl)quinolin-4-yl]-carbonyl}amino)-4-(2,6-difluorophenyl)pentanoic acid (Example 245). The product was purified by means of preparative HPLC (Method 20). 40 mg (98% purity, 59% of theory) of the title compound were obtained.

$[\alpha]_D^{20}$=−28.8°, 589 nm, c=0.32 g/100 ml, methanol

LC-MS (Method 1): $R_t$=2.10 min; MS (ESIpos): m/z=560/562 [M+H]$^+$ $^1$H-NMR (400 MHz, DMSO-d6) δ [ppm]: −0.149 (1.04), 0.146 (0.87), 1.606 (4.57), 1.670 (8.65), 1.807 (1.78), 2.003 (1.72), 2.016 (2.23), 2.035 (2.23), 2.055 (2.53), 2.063 (2.20), 2.090 (5.31), 2.117 (16.00), 2.137 (3.69), 2.327 (1.78), 2.366 (1.04), 2.669 (1.65), 2.710 (0.81), 3.132 (11.40), 3.162 (5.70), 3.175 (5.54), 3.612 (1.49), 3.631 (2.07), 3.646 (2.98), 3.659 (1.68), 3.694 (1.65), 4.062 (0.52), 4.075 (1.49), 4.088 (1.43), 4.100 (0.49), 7.127 (2.49), 7.147 (1.68), 7.204 (2.23), 7.216 (2.36), 7.227 (3.47), 7.239 (3.43), 7.250 (1.65), 7.262 (1.59), 7.278 (1.78), 7.287 (2.11), 7.293 (2.17), 7.301 (3.01), 7.316 (2.11), 7.324 (1.68), 7.422 (0.94), 7.622 (2.66), 7.644 (12.70), 7.653 (7.90), 7.658 (7.13), 7.675 (1.46), 7.680 (1.68), 8.724 (2.17), 8.739 (3.92), 8.753 (2.14), 12.061 (2.36).

Example 257

(+)-5-({[6-Bromo-3-methyl-2-(piperidin-1-yl)quinolin-4-yl]carbonyl}amino)-4-(2,5-difluorophenyl)pentanoic acid (Enantiomer 2)

Proceeding from tert-butyl 5-({[6-bromo-3-methyl-2-(piperidin-1-yl)quinolin-4-yl]carbonyl}amino)-4-(2,5-difluorophenyl)pentanoate (Enantiomer 2, 90 mg, 146 µmol, Example 263A), the reaction with TFA was effected as described for (+)-5-({[6-bromo-3-methyl-2-(piperidin-1-yl)quinolin-4-yl]carbonyl}amino)-4-(2,6-difluorophenyl)pentanoic acid (Example 245). The product was purified by means of preparative HPLC (Method 20). 69 mg (97% purity, 82% of theory) of the title compound were obtained.

$[\alpha]_D^{20}$=+34.2°, 589 nm, c=0.33 g/100 ml, methanol

LC-MS (Method 1): $R_t$=2.11 min; MS (ESIpos): m/z=560/562 [M+H]$^+$ $^1$H-NMR (400 MHz, DMSO-d6) δ [ppm]: −0.149 (0.51), −0.008 (4.19), 0.008 (4.29), 0.146 (0.51), 1.605 (4.49), 1.670 (8.69), 1.750 (0.60), 1.773 (1.12), 1.785 (1.50), 1.808 (1.80), 1.984 (0.65), 2.003 (1.58), 2.016 (2.12), 2.035 (2.10), 2.055 (2.37), 2.063 (2.03), 2.091 (5.24), 2.117 (16.00), 2.137 (3.73), 2.157 (1.03), 2.327 (0.70), 2.366 (0.41), 2.670 (0.81), 2.710 (0.49), 3.132 (11.49), 3.162 (9.35), 3.175 (9.18), 3.195 (0.52), 3.599 (0.84), 3.612 (1.50), 3.632 (2.10), 3.645 (3.04), 3.659 (1.77), 3.675 (1.35), 3.694 (1.74), 3.712 (1.47), 4.062 (0.93), 4.075 (2.52), 4.088 (2.42), 4.101 (0.85), 7.105 (1.19), 7.127 (2.47), 7.136 (2.01), 7.147 (1.69), 7.204 (2.06), 7.215 (2.25), 7.227 (3.34), 7.239 (3.26), 7.250 (1.60), 7.262 (1.46), 7.278 (1.77), 7.286 (2.06), 7.292 (2.15), 7.301 (3.04), 7.310 (2.10), 7.316 (2.07), 7.324 (1.68), 7.422 (0.90), 7.622 (2.45), 7.644 (12.19), 7.653 (7.77), 7.657 (6.84), 7.675 (1.47), 7.680 (1.60), 8.724 (2.17), 8.739 (3.97), 8.753 (2.14), 12.060 (2.50).

Example 258

(+/−)-5-({[6-Bromo-3-methyl-2-(pyrrolidin-1-yl)quinolin-4-yl]carbonyl}amino)-4-(2,5-difluorophenyl)pentanoic acid (Racemate)

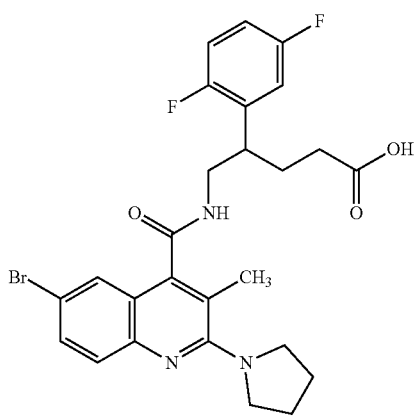 [SMILES: Cc1c(N2CCCC2)nc2ccc(Br)cc2c1C(=O)NCC(CCC(=O)O)c1cc(F)ccc1F]

Proceeding from (+/−)-tert-butyl 5-({[6-bromo-3-methyl-2-(pyrrolidin-1-yl)quinolin-4-yl]carbonyl}-amino)-4-(2,5-difluorophenyl)pentanoate (racemate, 55 mg, 91.3 μmol, Example 264A), the reaction with TFA and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 29 mg (100% purity, 58% of theory) of the title compound were obtained.

LC-MS (Method 1): $R_t$=1.41 min; MS (ESIpos): m/z=546/548 [M+H]$^+$ $^1$H-NMR (400 MHz, DMSO-d6) δ [ppm]: −0.149 (0.78), −0.008 (5.94), 0.008 (6.57), 0.146 (0.78), 1.235 (0.57), 1.750 (0.63), 1.773 (1.30), 1.786 (1.77), 1.806 (2.19), 1.830 (1.93), 1.871 (16.00), 1.981 (0.83), 2.001 (1.98), 2.013 (2.61), 2.033 (2.81), 2.052 (3.07), 2.060 (2.66), 2.088 (5.37), 2.102 (7.09), 2.118 (8.44), 2.138 (9.07), 2.323 (0.99), 2.327 (1.25), 2.332 (0.94), 2.665 (0.99), 2.670 (1.30), 2.674 (1.04), 2.710 (0.42), 3.566 (11.15), 3.597 (3.80), 3.617 (3.28), 3.631 (4.12), 3.644 (2.35), 3.688 (2.08), 7.099 (1.41), 7.120 (2.87), 7.140 (2.03), 7.196 (2.92), 7.208 (3.07), 7.219 (4.53), 7.231 (4.59), 7.242 (2.40), 7.254 (2.24), 7.271 (2.55), 7.279 (2.92), 7.285 (3.13), 7.294 (4.22), 7.303 (3.02), 7.309 (3.02), 7.317 (2.61), 7.465 (8.55), 7.488 (14.59), 7.544 (7.35), 7.549 (6.98), 7.566 (4.33), 7.571 (4.27), 8.133 (1.98), 8.678 (2.76), 8.693 (4.95), 8.707 (2.76), 12.057 (2.24).

Example 259

(+)-5-({[6-Bromo-3-methyl-2-(pyrrolidin-1-yl)quinolin-4-yl]carbonyl}amino)-4-(2,5-difluorophenyl)pentanoic acid (Enantiomer 1)

Proceeding from tert-butyl 5-({[6-bromo-3-methyl-2-(pyrrolidin-1-yl)quinolin-4-yl]carbonyl}amino)-4-(2,5-difluorophenyl)pentanoate (Enantiomer 1, 80 mg, 133 μmol, Example 265A), the reaction with TFA and the purification of the product were effected as described for (+)-5-({[6-bromo-3-methyl-2-(piperidin-1-yl)quinolin-4-yl]carbonyl}amino)-4-(2,6-difluorophenyl)pentanoic acid (Example 245). 59 mg (100% purity, 81% of theory) of the title compound were obtained.

$[α]_D^{20}$=+30.2°, 589 nm, c=0.30 g/100 ml, methanol

LC-MS (Method 1): $R_t$=1.42 min; MS (ESIpos): m/z=546/548 [M+H]$^+$ $^1$H-NMR (400 MHz, DMSO-d6) δ [ppm]: −0.149 (1.42), −0.008 (10.42), 0.008 (9.95), 0.146 (1.26), 1.148 (0.74), 1.806 (2.42), 1.871 (16.00), 2.001 (2.11), 2.013 (2.68), 2.033 (2.95), 2.052 (3.21), 2.060 (2.74), 2.088 (5.53), 2.101 (7.47), 2.118 (8.79), 2.137 (9.00), 2.327 (3.63), 2.332 (2.74), 2.366 (1.95), 2.669 (4.11), 2.710 (2.11), 3.169 (0.74), 3.566 (10.89), 3.617 (3.47), 3.631 (4.32), 3.645 (2.58), 3.685 (2.26), 7.119 (2.95), 7.196 (2.95), 7.207 (3.16), 7.219 (4.68), 7.231 (4.74), 7.242 (2.58), 7.254 (2.37), 7.271 (2.63), 7.285 (3.16), 7.294 (4.32), 7.303 (3.21), 7.317 (2.74), 7.466 (5.63), 7.488 (9.68), 7.544 (5.95), 7.550 (5.58), 7.567 (3.53), 7.572 (3.58), 7.834 (0.42), 8.133 (2.00), 8.679 (2.74), 8.693 (4.84), 8.707 (2.74), 12.057 (2.84), 12.732 (0.58).

Example 260

(−)-5-({[6-Bromo-3-methyl-2-(pyrrolidin-1-yl)quinolin-4-yl]carbonyl}amino)-4-(2,5-difluorophenyl)pentanoic acid (Enantiomer 2)

Proceeding from tert-butyl 5-({[6-bromo-3-methyl-2-(pyrrolidin-1-yl)quinolin-4-yl]carbonyl}amino)-4-(2,5-difluorophenyl)pentanoate (Enantiomer 2, 83 mg, 138 μmol, Example 266A), the reaction with TFA and the purification of the product were effected as described for (+)-5-({[6-bromo-3-methyl-2-(piperidin-1-yl)quinolin-4-yl]carbonyl}amino)-4-(2,6-difluorophenyl)pentanoic acid (Example 245). 56 mg (100% purity, 74% of theory) of the title compound were obtained.

$[α]_D^{20}$=−28.6°, 589 nm, c=0.30 g/100 ml, methanol

LC-MS (Method 1): $R_t$=1.42 min; MS (ESIpos): m/z=546/548 [M+H]$^+$ $^1$H-NMR (400 MHz, DMSO-d6) δ [ppm]: −0.149 (1.11), −0.008 (8.91), 0.008 (10.55), 0.146 (1.15), 1.147 (0.53), 1.806 (2.44), 1.871 (16.00), 2.001 (1.99), 2.013 (2.61), 2.033 (2.75), 2.052 (3.10), 2.088 (5.50), 2.102 (7.31), 2.118 (8.60), 2.138 (9.00), 2.327 (2.75), 2.366 (1.60), 2.669 (3.01), 2.710 (1.68), 3.207 (0.58), 3.565 (11.21), 3.617 (3.28), 3.631 (4.08), 3.644 (2.30), 3.686 (2.13), 7.120 (3.01), 7.196 (2.75), 7.208 (3.06), 7.219 (4.43), 7.231 (4.43), 7.242 (2.26), 7.254 (2.26), 7.271 (2.57), 7.285 (3.19), 7.294 (4.21), 7.303 (3.06), 7.317 (2.48), 7.465 (7.40), 7.487 (12.59), 7.544 (6.47), 7.549 (6.12), 7.566 (3.81), 7.571 (3.77), 8.132 (0.49), 8.678 (2.84), 8.693 (4.92), 8.707 (2.57), 12.055 (6.43).

Example 261

(+/−)-5-({[6-Bromo-2-(3,3-difluoropiperidin-1-yl)-3-methylquinolin-4-yl]carbonyl}amino)-4-(2,5-difluorophenyl)pentanoic acid (Racemate)

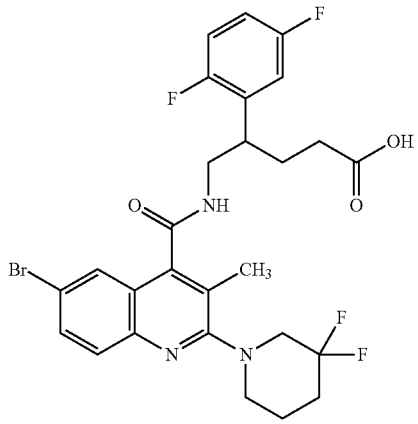 [SMILES: Cc1c(N2CCCC(F)(F)C2)nc2ccc(Br)cc2c1C(=O)NCC(CCC(=O)O)c1cc(F)ccc1F]

Proceeding from (+/−)-tert-butyl 5-({[6-bromo-2-(3,3-difluoropiperidin-1-yl)-3-methylquinolin-4-yl]carbonyl}amino)-4-(2,5-difluorophenyl)pentanoate (racemate, 55 mg, 84.3 µmol, Example 267A), the reaction with TFA (reaction time: 40 min) and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 47 mg (100% purity, 93% of theory) of the title compound were obtained.

LC-MS (Method 1): $R_t$=2.07 min; MS (ESIpos): m/z=596/598 [M+H]$^+$ $^1$H-NMR (400 MHz, DMSO-d6) δ [ppm]: −0.149 (0.53), −0.008 (4.53), 0.008 (4.37), 0.146 (0.53), 1.372 (1.58), 1.788 (1.68), 1.811 (1.95), 1.881 (5.11), 2.004 (1.84), 2.017 (2.37), 2.037 (2.95), 2.056 (4.21), 2.063 (3.89), 2.092 (8.63), 2.106 (8.47), 2.119 (10.53), 2.136 (15.47), 2.327 (1.53), 2.366 (0.42), 2.670 (1.63), 2.710 (0.53), 3.163 (6.42), 3.446 (4.05), 3.475 (7.63), 3.504 (3.84), 3.622 (1.68), 3.641 (2.42), 3.655 (3.42), 3.670 (2.00), 3.701 (1.79), 7.107 (1.21), 7.128 (2.79), 7.138 (2.26), 7.149 (1.95), 7.206 (2.53), 7.217 (2.74), 7.229 (4.11), 7.241 (4.16), 7.252 (2.00), 7.264 (1.84), 7.285 (2.05), 7.292 (2.42), 7.298 (2.58), 7.307 (3.58), 7.316 (2.42), 7.322 (2.47), 7.330 (2.16), 7.469 (0.89), 7.673 (2.89), 7.695 (16.00), 7.702 (10.95), 7.707 (9.63), 7.724 (1.95), 7.729 (2.11), 8.739 (2.53), 8.754 (4.79), 8.768 (2.58), 12.069 (1.58).

Example 262

(−)-5-({[6-Bromo-2-(3,3-difluoropiperidin-1-yl)-3-methylquinolin-4-yl]carbonyl}amino)-4-(2,5-difluorophenyl)pentanoic acid (Enantiomer 1)

Proceeding from tert-butyl 5-({[6-bromo-2-(3,3-difluoropiperidin-1-yl)-3-methylquinolin-4-yl]carbonyl}amino)-4-(2,5-difluorophenyl)pentanoate (Enantiomer 1, 55 mg, 84.3 µmol, Example 268A), the reaction with TFA was effected as described for (+)-5-({[6-bromo-3-methyl-2-(piperidin-1-yl)quinolin-4-yl]carbonyl}amino)-4-(2,6-difluorophenyl)pentanoic acid (Example 245). The product was purified by means of preparative HPLC (Method 20). 23 mg (98% purity, 35% of theory) of the title compound were obtained.

$[α]_D^{20}$=−30.7°, 589 nm, c=0.33 g/100 ml, methanol

LC-MS (Method 1): $R_t$=2.07 min; MS (ESIpos): m/z=596/598 [M+H]$^+$ $^1$H-NMR (400 MHz, DMSO-d6) δ [ppm]: −0.149 (0.99), −0.008 (12.44), 0.146 (0.96), 1.812 (2.13), 1.882 (5.42), 2.005 (2.03), 2.017 (2.55), 2.037 (3.26), 2.057 (4.72), 2.093 (9.47), 2.109 (9.62), 2.119 (11.50), 2.136 (16.00), 2.327 (1.24), 2.366 (0.72), 2.669 (1.46), 2.710 (0.82), 3.162 (13.03), 3.175 (11.43), 3.446 (4.30), 3.475 (7.79), 3.504 (3.88), 3.540 (0.67), 3.622 (1.83), 3.641 (2.65), 3.656 (3.59), 3.669 (2.28), 3.702 (2.08), 4.075 (1.63), 4.088 (1.58), 7.128 (2.97), 7.149 (2.05), 7.206 (2.52), 7.217 (2.72), 7.229 (4.06), 7.241 (4.03), 7.252 (2.05), 7.264 (1.85), 7.285 (2.23), 7.298 (2.74), 7.307 (3.66), 7.316 (2.60), 7.322 (2.57), 7.330 (2.08), 7.474 (1.04), 7.673 (2.99), 7.695 (15.06), 7.702 (10.51), 7.707 (9.15), 7.725 (1.76), 7.729 (1.98), 8.739 (2.72), 8.753 (4.77), 8.768 (2.62), 12.065 (1.78).

Example 263

(+)-5-({[6-Bromo-2-(3,3-difluoropiperidin-1-yl)-3-methylquinolin-4-yl]carbonyl}amino)-4-(2,5-difluorophenyl)pentanoic acid (Enantiomer 2)

Proceeding from tert-butyl 5-({[6-bromo-2-(3,3-difluoropiperidin-1-yl)-3-methylquinolin-4-yl]carbonyl}amino)-4-(2,5-difluorophenyl)pentanoate (Enantiomer 2, 71 mg, 95% purity, 103 µmol, Example 269A), the reaction with TFA was effected as described for (+)-5-({[6-bromo-3-methyl-2-(piperidin-1-yl)quinolin-4-yl]carbonyl}amino)-4-(2,6-difluorophenyl)pentanoic acid (Example 245). The product was purified by means of preparative HPLC (Method 20). 28 mg (99% purity, 45% of theory) of the title compound were obtained.

$[α]_D^{20}$=+34.0°, 589 nm, c=0.33 g/100 ml, methanol

LC-MS (Method 1): $R_t$=2.06 min; MS (ESIpos): m/z=596/598 [M+H]$^+$ $^1$H-NMR (400 MHz, DMSO-d6) δ [ppm]: −0.149 (0.62), 0.146 (0.69), 1.371 (0.58), 1.754 (0.65), 1.790 (1.79), 1.810 (2.06), 1.881 (5.45), 2.004 (1.92), 2.017 (2.47), 2.038 (3.17), 2.056 (4.63), 2.092 (9.35), 2.108 (9.58), 2.119 (11.35), 2.136 (16.00), 2.327 (0.91), 2.366 (0.44), 2.669 (1.00), 2.709 (0.49), 3.163 (7.70), 3.447 (4.16), 3.475 (7.62), 3.504 (3.78), 3.622 (1.83), 3.642 (2.58), 3.655 (3.47), 3.669 (2.14), 3.703 (1.99), 7.128 (2.87), 7.148 (1.86), 7.206 (2.42), 7.217 (2.60), 7.229 (3.79), 7.240 (3.68), 7.252 (1.83), 7.263 (1.66), 7.285 (2.14), 7.298 (2.63), 7.307 (3.52), 7.316 (2.47), 7.329 (1.86), 7.467 (0.96), 7.673 (2.87), 7.695 (14.19), 7.702 (9.23), 7.706 (8.04), 7.729 (1.64), 8.739 (2.76), 8.753 (4.69), 8.767 (2.46), 12.063 (1.15).

Example 264

5-[({6-Bromo-2-(3-fluoropiperidin-1-yl)-3-methylquinolin-4-yl}carbonyl)amino]-4-(2,5-difluorophenyl)pentanoic acid (Diastereomer Mixture)

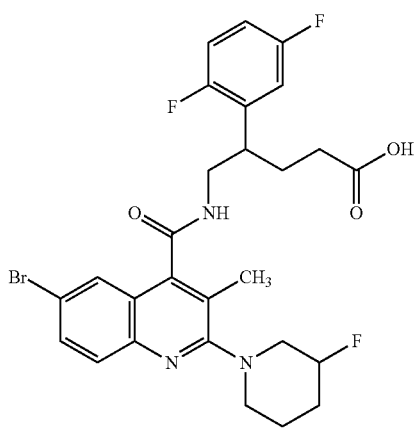 [SMILES: Cc1c(N2CCCC(F)C2)nc2ccc(Br)cc2c1C(=O)NCC(CCC(=O)O)c1cc(F)ccc1F]

Proceeding from tert-butyl 5-[({6-bromo-2-(3-fluoropiperidin-1-yl)-3-methylquinolin-4-yl}carbonyl)amino]-4-(2,5-difluorophenyl)pentanoate (diastereomer mixture, 55 mg, 86.7 µmol, Example 270A), the reaction with TFA and the purification of the product were effected as described for 5-[({6-bromo-2-[3-ethylpiperidin-1-yl]-3-methylquinolin-4-yl}carbonyl)amino]-4-(2,5-difluorophenyl)pentanoic acid (Example 225). 43 mg (100% purity, 86% of theory) of the title compound were obtained.

LC-MS (Method 1): $R_t$=2.02 min; MS (ESIpos): m/z=578/580 [M+H]$^+$ $^1$H-NMR (400 MHz, DMSO-d6) δ [ppm]: −0.149 (0.90), −0.008 (10.95), 0.008 (6.96), 0.017 (0.58), 0.146 (0.90), 1.643 (2.02), 1.806 (3.83), 1.899 (3.35), 1.948 (2.02), 1.983 (1.70), 2.003 (2.29), 2.016 (2.55), 2.035 (2.60), 2.055 (2.82), 2.063 (2.39), 2.091 (6.01), 2.105 (7.44), 2.128 (14.41), 2.327 (1.54), 2.523 (3.88), 2.665 (1.38), 2.670 (1.70), 2.711 (0.43), 3.094 (2.29), 3.153 (2.39), 3.170 (2.34), 3.369 (3.99), 3.401 (1.75), 3.434 (2.29), 3.460 (1.54), 3.540 (0.64), 3.618 (1.59), 3.636 (2.34), 3.650 (3.08), 3.700 (1.97), 4.817 (1.70), 4.935 (1.70), 7.127 (2.92), 7.147 (1.97), 7.204 (2.76), 7.216 (2.92), 7.227 (4.36), 7.239 (4.25), 7.251 (2.07), 7.262 (1.91), 7.281 (2.23), 7.289 (2.60), 7.295 (2.71), 7.304 (3.72), 7.313 (2.66), 7.319 (2.50), 7.327 (2.13), 7.450 (1.06), 7.647 (3.40), 7.669 (16.00), 7.676 (10.95), 7.681 (9.51), 7.699 (1.97), 7.704 (2.13), 8.732 (2.71), 8.747 (4.73), 8.761 (2.50), 12.068 (2.29).

Example 265

(−)-5-({[6-Bromo-2-(3,3-difluoropiperidin-1-yl)-3-methylquinolin-4-yl]carbonyl}amino)-4-(2,6-dichlorophenyl)pentanoic acid (Enantiomer 1)

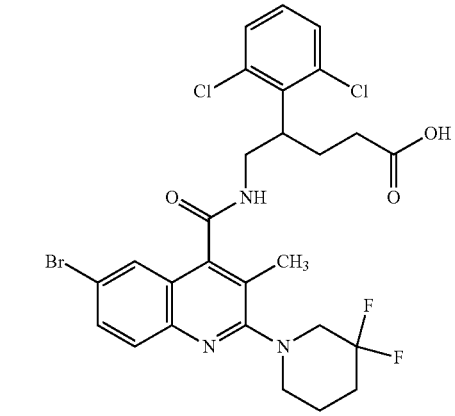 [SMILES: Cc1c(N2CCCC(F)(F)C2)nc2ccc(Br)cc2c1C(=O)NCC(CCC(=O)O)c1c(Cl)cccc1Cl]

A mixture of (+/−)-5-{[(6-bromo-2-chloro-3-methylquinolin-4-yl)carbonyl]amino}-4-(2,6-dichlorophenyl)pentanoic acid (racemate, 401 mg, 72% purity, 5 µmol, Example 246A), 3,3-difluoropiperidine hydrochloride (580 mg, 3.68 mmol) and DIPEA (1.5 ml, 8.8 mmol) in NMP (1.9 ml) was stirred at 120° C. for four days. After cooling to RT, the reaction mixture was added to 1 M hydrochloric acid and extracted with dichloromethane. The organic phase was dried over sodium sulfate and concentrated. The crude product was purified by column chromatography (Isolera, LiChroprep RP-18, eluent: water/acetonitrile, gradient: 20-100% acetonitrile). The product fraction (238 mg) was dissolved in dichloromethane/methanol (1:1, 5 ml) and separated into the enantiomers by means of preparative HPLC on chiral phase [column: Daicel Chiralpak IA, 5 µm, 250 mm×30 mm; flow rate: 50 ml/min; detection: UV 254 nm; injection: 1.0 ml; eluent: 70% hexane+0.1% by volume of trifluoroacetic acid/30% isopropanol, isocratic]. The combined target fractions were each concentrated, and the respective residue was lyophilized.

The title compound (52 mg, 98% purity, ee>99%) was obtained as the enantiomer that eluted earlier.

$[α]_D^{20}$=−10.2°, 589 nm, c=0.50 g/100 ml, chloroform

LC-MS (Method 25): $R_t$=1.37 min; MS (ESIpos): m/z=628/630/632 [M+H]$^+$ $^1$H-NMR (400 MHz, CHLOROFORM-d) δ [ppm]: 0.888 (0.45), 0.894 (0.47), 1.215 (0.47), 1.226 (1.52), 1.241 (1.34), 1.263 (2.42), 1.286 (1.77), 1.304 (0.89), 1.379 (4.12), 1.395 (4.07), 1.999 (2.53), 2.115 (1.08), 2.152 (2.73), 2.163 (3.07), 2.180 (2.45), 2.244 (0.69), 2.310 (16.00), 2.331 (2.78), 2.436 (0.45), 2.451 (0.79), 2.476 (0.98), 2.485 (0.84), 2.493 (0.84), 2.503 (1.20), 3.048 (0.51), 3.538 (2.47), 3.709 (1.54), 3.737 (2.47), 3.761 (1.32), 3.848 (0.43), 4.055 (0.46), 4.071 (0.96), 4.086 (1.16), 4.101 (1.99), 4.112 (1.96), 4.231 (0.65), 4.247 (0.86), 4.260 (1.13), 4.273 (0.87), 6.758 (1.37), 7.152 (2.35), 7.172 (5.73), 7.192 (3.52), 7.225 (0.51), 7.242 (0.74), 7.302 (0.56), 7.321 (3.36), 7.324 (3.85), 7.341 (3.30), 7.344 (3.50), 7.352 (0.95), 7.364 (4.49), 7.367 (3.81), 7.385 (3.43), 7.388 (2.99), 7.761 (2.77), 7.768 (3.04), 7.790 (2.66), 7.859 (2.44), 7.881 (1.58), 8.350 (0.78).

Example 266

(+)-5-({[6-Bromo-2-(3,3-difluoropiperidin-1-yl)-3-methylquinolin-4-yl]carbonyl}amino)-4-(2,6-dichlorophenyl)pentanoic acid (Enantiomer 2)

In the enantiomer separation described in Example 265, 50 mg (95% purity, ee 98%) of the title compound were obtained as the enantiomer that eluted later.

$[\alpha]_D^{20}$=+14.8°, 589 nm, c=0.50 g/100 ml, chloroform.

$^1$H-NMR (400 MHz, CHLOROFORM-d) δ [ppm]: 0.861 (0.55), 0.876 (0.59), 0.888 (0.89), 0.894 (0.86), 0.901 (0.64), 0.913 (0.48), 1.199 (0.55), 1.215 (0.70), 1.227 (1.84), 1.242 (1.70), 1.263 (4.61), 1.379 (3.69), 1.395 (3.79), 2.005 (2.59), 2.164 (2.71), 2.179 (2.35), 2.315 (16.00), 2.342 (2.09), 2.478 (1.02), 2.507 (1.24), 3.540 (2.34), 3.736 (2.05), 4.079 (1.03), 4.115 (2.36), 4.228 (0.74), 4.242 (0.88), 4.256 (1.23), 4.268 (0.91), 6.702 (1.37), 7.154 (2.59), 7.174 (6.12), 7.194 (3.69), 7.322 (3.68), 7.326 (4.24), 7.343 (3.18), 7.345 (3.19), 7.367 (4.49), 7.370 (3.96), 7.386 (3.70), 7.390 (3.25), 7.529 (0.51), 7.767 (3.80), 7.791 (3.05), 7.863 (2.27), 7.884 (1.87), 7.947 (0.79).

Example 267

(+)-5-[({6-Bromo-3-methyl-2-[($^2$H$_{10}$)piperidin-1-yl]quinolin-4-yl}carbonyl)amino]-4-(2-chlorophenyl)pentanoic acid (Enantiomer 1)

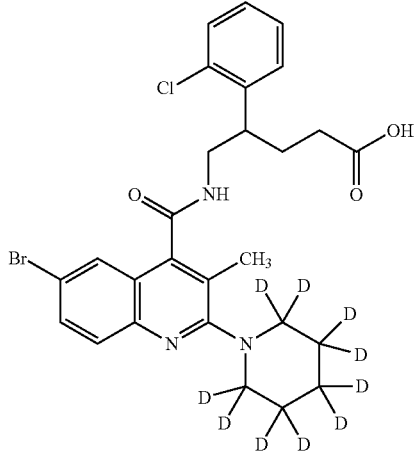 [SMILES: [2H]C1([2H])N(c2nc3ccc(Br)cc3c(C(=O)NCC(CCC(=O)O)c3ccccc3Cl)c2C)C([2H])([2H])C([2H])([2H])C([2H])([2H])C1([2H])[2H]]

To a solution of (+)-tert-butyl 5-[({6-bromo-3-methyl-2-[($^2$H$_{10}$)piperidin-1-yl]quinolin-4-yl}carbonyl)amino]-4-(2-chlorophenyl)pentanoate (262 mg, 419 µmol, enantiomer 1, Example 278A) in dichloromethane (3.2 ml) was added TFA (711 µl, 9.23 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 187 mg (100% purity, 79% of theory) of the title compound were obtained.

$[\alpha]_D^{20}$=+13.3°, 589 nm, c=0.38 g/100 ml, methanol

LC-MS (Method 1): R$_t$=2.15 min; MS (ESIpos): m/z=568/570 [M+H]$^+$ $^1$H-NMR (500 MHz, DMSO-d6) δ [ppm]: −0.021 (0.35), 1.232 (0.75), 1.540 (0.53), 1.613 (0.41), 1.792 (0.63), 1.800 (0.99), 1.818 (2.03), 1.835 (2.41), 1.853 (1.25), 1.873 (0.28), 2.024 (0.57), 2.036 (1.20), 2.041 (1.40), 2.052 (5.86), 2.074 (4.33), 2.081 (4.40), 2.097 (4.07), 2.127 (15.83), 2.154 (2.03), 2.196 (0.35), 2.363 (0.20), 2.636 (0.22), 3.078 (0.18), 3.086 (0.20), 3.593 (2.03), 3.674 (3.19), 7.258 (1.99), 7.261 (2.01), 7.274 (4.38), 7.288 (3.00), 7.291 (2.84), 7.359 (2.69), 7.374 (4.82), 7.388 (2.54), 7.443 (8.16), 7.446 (7.64), 7.459 (7.24), 7.462 (6.59), 7.480 (6.24), 7.482 (6.15), 7.496 (4.97), 7.623 (4.16), 7.640 (16.00), 7.650 (10.72), 7.654 (9.32), 7.667 (2.58), 7.671 (2.69), 8.710 (2.72), 8.721 (5.30), 8.733 (2.56), 12.042 (0.39).

Example 268

(−)-5-[({6-Bromo-3-methyl-2-[($^2$H$_{10}$)piperidin-1-yl]quinolin-4-yl}carbonyl)amino]-4-(2-chlorophenyl)pentanoic acid (Enantiomer 2)

To a solution of (−)-tert-butyl 5-[({6-bromo-3-methyl-2-[($^2$H$_{10}$)piperidin-1-yl]quinolin-4-yl}carbonyl)amino]-4-(2-chlorophenyl)pentanoate (244 mg, 391 µmol, enantiomer 2, Example 279A) in dichloromethane (3.0 ml) was added TFA (662 µl, 8.59 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 180 mg (100% purity, 81% of theory) of the title compound were obtained.

$[\alpha]_D^{20}$=−11.1°, 589 nm, c=0.40 g/100 ml, methanol

LC-MS (Method 1): R$_t$=2.17 min; MS (ESIpos): m/z=568/570 [M+H]$^+$ $^1$H-NMR (600 MHz, DMSO-d6) δ [ppm]: 1.538 (0.58), 1.611 (0.46), 1.799 (1.21), 1.814 (2.79), 1.828 (3.08), 1.843 (1.64), 2.028 (0.83), 2.043 (1.96), 2.053 (7.45), 2.071 (6.42), 2.076 (5.14), 2.087 (2.91), 2.092 (2.98), 2.099 (3.62), 2.125 (13.11), 2.131 (11.82), 2.148 (3.42), 2.195 (0.42), 2.386 (0.17), 2.613 (0.16), 3.074 (0.19), 3.081 (0.19), 3.592 (2.59), 3.673 (3.20), 7.263 (2.39), 7.276 (5.09), 7.288 (3.29), 7.363 (3.08), 7.376 (5.48), 7.388 (2.98), 7.448 (9.82), 7.461 (8.60), 7.488 (6.94), 7.500 (5.71), 7.626 (5.57), 7.641 (16.00), 7.654 (9.27), 7.656 (8.85), 7.668 (3.13), 7.671 (3.26), 8.734 (3.59), 8.744 (7.01), 8.753 (3.50), 12.078 (1.77).

Example 269

(−)-5-[({6-Bromo-3-methyl-2-[($^2$H$_{10}$)piperidin-1-yl]quinolin-4-yl}carbonyl)amino]-4-[2-(trifluoromethyl)phenyl]pentanoic acid (Enantiomer 1)

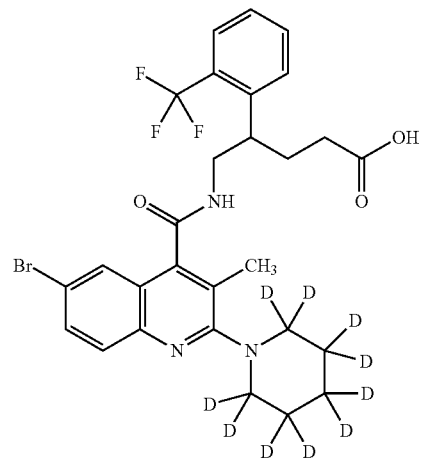 [SMILES: [2H]C1([2H])N(c2nc3ccc(Br)cc3c(C(=O)NCC(CCC(=O)O)c3ccccc3C(F)(F)F)c2C)C([2H])([2H])C([2H])([2H])C([2H])([2H])C1([2H])[2H]]

To a solution of (−)-tert-butyl 5-[({6-bromo-3-methyl-2-[($^2$H$_{10}$)piperidin-1-yl]quinolin-4-yl}carbonyl)amino]-4-[2-(trifluoromethyl)phenyl]pentanoate (231 mg, 352 µmol, enantiomer 1, Example 280A) in dichloromethane (2.7 ml) was added TFA (596 µl, 7.74 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 166 mg (100% purity, 79% of theory) of the title compound were obtained.

$[\alpha]_D^{20}$=−19.1°, 589 nm, c=0.31 g/100 ml, methanol

LC-MS (Method 1): R$_t$=2.18 min; MS (ESIpos): m/z=602/604 [M+H]$^+$ $^1$H-NMR (600 MHz, DMSO-d6) δ [ppm]: 0.005 (0.22), 1.229 (0.23), 1.546 (0.54), 1.620 (0.59), 1.876 (0.59), 1.885 (0.81), 1.892 (1.34), 1.900 (1.97), 1.907 (1.66), 1.915 (1.99), 1.923 (1.82), 1.939 (1.08), 1.953 (1.49), 1.962 (1.01), 1.969 (1.61), 1.980 (2.72), 1.989 (1.82), 1.996 (2.72), 2.005 (2.10), 2.047 (2.24), 2.058 (3.02), 2.063 (2.06), 2.074 (3.61), 2.078 (1.32), 2.085 (1.93), 2.101 (1.97), 2.116 (1.74), 2.125 (2.27), 2.139 (3.57), 2.162 (6.96), 2.191 (1.27), 2.388 (0.17), 2.616 (0.17), 3.096 (0.32), 3.633 (1.56), 3.707 (1.54), 7.471 (2.48), 7.484 (4.85), 7.497 (2.90), 7.639 (4.67), 7.654 (16.00), 7.662 (9.66), 7.666 (8.77), 7.677 (2.62), 7.680 (2.72), 7.698 (2.13), 7.711 (5.07), 7.724 (4.34), 7.729 (7.06), 7.741 (10.81), 7.753 (3.07), 8.793 (3.05), 8.803 (6.14), 8.813 (3.01), 12.085 (0.33).

Example 270

(+)-5-[({6-Bromo-3-methyl-2-[($^2$H$_{10}$)piperidin-1-yl]quinolin-4-yl}carbonyl)amino]-4-[2-(trifluoromethyl)phenyl]pentanoic acid (Enantiomer 2)

To a solution of (+)-tert-butyl 5-[({6-bromo-3-methyl-2-[($^2$H$_{10}$)piperidin-1-yl]quinolin-4-yl}carbonyl)amino]-4-[2-(trifluoromethyl)phenyl]pentanoate (204 mg, 310 µmol, enantiomer 2, Example 281A) in dichloromethane (2.4 ml) was added TFA (525 µl, 6.82 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 157 mg (100% purity, 84% of theory) of the title compound were obtained.

$[\alpha]_D^{20}$=+19.1°, 589 nm, c=0.45 g/100 ml, methanol

LC-MS (Method 1): R$_t$=2.23 min; MS (ESIpos): m/z=602/604 [M+H]$^+$ $^1$H-NMR (600 MHz, DMSO-d6) δ [ppm]: 1.546 (0.56), 1.620 (0.64), 1.877 (0.74), 1.892 (1.70), 1.900 (2.53), 1.907 (2.16), 1.915 (2.60), 1.923 (2.32), 1.939 (1.35), 1.954 (1.73), 1.963 (1.23), 1.970 (1.91), 1.981 (3.42), 1.990 (2.23), 1.997 (3.23), 2.006 (2.55), 2.048 (2.67), 2.059 (3.62), 2.074 (4.25), 2.086 (2.28), 2.101 (2.44), 2.117 (2.22), 2.126 (3.06), 2.162 (9.18), 2.387 (0.23), 2.614 (0.20), 3.096 (0.31), 3.632 (2.08), 3.705 (2.06), 7.472 (3.23), 7.484 (6.23), 7.497 (3.72), 7.638 (4.69), 7.653 (16.00), 7.663 (10.11), 7.679 (2.87), 7.698 (2.74), 7.711 (6.46), 7.729 (8.95), 7.742 (13.87), 7.753 (3.91), 8.792 (3.69), 8.802 (7.25), 8.812 (3.62), 12.063 (7.55).

Example 271

(+)-5-[({6-Bromo-3-methyl-2-[($^2$H$_{10}$)piperidin-1-yl]quinolin-4-yl}carbonyl)amino]-4-[2-(trifluoromethoxy)phenyl]pentanoic acid (Enantiomer 1)

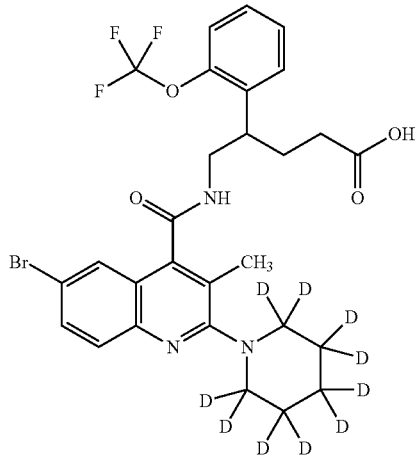 [SMILES: [2H]C1([2H])N(c2nc3ccc(Br)cc3c(C(=O)NCC(CCC(=O)O)c3ccccc3OC(F)(F)F)c2C)C([2H])([2H])C([2H])([2H])C([2H])([2H])C1([2H])[2H]]

To a solution of (+)-tert-butyl 5-[({6-bromo-3-methyl-2-[($^2$H$_{10}$)piperidin-1-yl]quinolin-4-yl}carbonyl)amino]-4-[2-(trifluoromethoxy)phenyl]pentanoate (181 mg, 268 µmol, enantiomer 1, Example 282A) in dichloromethane (2.1 ml) was added TFA (460 µl, 5.90 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 140 mg (100% purity, 84% of theory) of the title compound were obtained.

$[\alpha]_D^{20}$=+19.7°, 589 nm, c=0.33 g/100 ml, methanol

LC-MS (Method 1): R$_t$=2.28 min; MS (ESIpos): m/z=618/620 [M+H]$^+$ $^1$H-NMR (600 MHz, DMSO-d6) δ [ppm]: 1.231 (0.17), 1.543 (0.59), 1.615 (0.66), 1.788 (0.36), 1.799 (0.68), 1.812 (2.24), 1.819 (2.71), 1.826 (2.26), 1.834 (3.75), 1.849 (2.42), 1.867 (0.57), 2.031 (0.65), 2.048 (1.50), 2.057 (4.09), 2.077 (16.00), 2.098 (4.42), 2.105 (3.31), 2.111 (3.54), 2.135 (6.56), 2.219 (0.49), 2.388 (0.21), 2.616 (0.21), 3.089 (0.29), 3.393 (2.89), 3.403 (2.82), 3.599 (1.13), 3.609 (1.93), 3.620 (3.25), 3.631 (3.89), 3.641 (2.48), 3.664 (2.81), 3.674 (2.40), 7.282 (0.18), 7.352 (4.12), 7.364 (6.45), 7.394 (2.55), 7.408 (8.73), 7.414 (8.57), 7.421 (8.95), 7.433 (2.43), 7.559 (5.83), 7.569 (4.84), 7.573 (4.73), 7.634 (5.43), 7.649 (15.94), 7.661 (9.19), 7.664 (9.30), 7.679 (3.24), 8.756 (3.78), 8.765 (7.15), 8.775 (3.68), 12.083 (13.49).

Example 272

(−)-5-[({6-Bromo-3-methyl-2-[($^2$H$_{10}$)piperidin-1-yl]quinolin-4-yl}carbonyl)amino]-4-[2-(trifluoromethoxy)phenyl]pentanoic acid (Enantiomer 2)

To a solution of (−)-tert-butyl 5-[({6-bromo-3-methyl-2-[($^2$H$_{10}$)piperidin-1-yl]quinolin-4-yl}carbonyl)amino]-4-[2-

(trifluoromethoxy)phenyl]pentanoate (215 mg, 320 µmol, enantiomer 2, Example 283A) in dichloromethane (2.5 ml) was added TFA (540 µl, 7.03 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 166 mg (100% purity, 84% of theory) of the title compound were obtained.

$[\alpha]_D^{20}$=−17.5°, 589 nm, c=0.36 g/100 ml, methanol

LC-MS (Method 1): $R_t$=2.23 min; MS (ESIpos): m/z=618/620 [M+H]$^+$ $^1$H-NMR (600 MHz, DMSO-d6) δ [ppm]: 0.005 (0.31), 1.230 (0.24), 1.543 (0.56), 1.615 (0.58), 1.786 (0.29), 1.799 (0.52), 1.811 (1.78), 1.819 (2.11), 1.826 (1.75), 1.833 (2.88), 1.849 (2.02), 1.866 (0.46), 2.030 (0.51), 2.035 (0.44), 2.047 (1.22), 2.056 (3.38), 2.075 (11.92), 2.078 (11.58), 2.082 (10.29), 2.097 (3.39), 2.105 (2.47), 2.110 (2.68), 2.135 (4.84), 2.219 (0.43), 2.387 (0.17), 2.615 (0.17), 3.089 (0.30), 3.392 (2.55), 3.402 (2.34), 3.598 (0.88), 3.608 (1.48), 3.620 (2.50), 3.630 (2.95), 3.641 (1.87), 3.652 (1.45), 3.663 (2.07), 3.674 (1.76), 7.351 (3.20), 7.361 (4.27), 7.364 (5.30), 7.394 (2.04), 7.403 (5.07), 7.408 (6.93), 7.414 (7.35), 7.420 (7.47), 7.423 (5.23), 7.433 (1.99), 7.558 (4.77), 7.569 (3.85), 7.573 (3.74), 7.634 (5.48), 7.649 (16.00), 7.661 (8.72), 7.664 (8.01), 7.676 (2.81), 7.679 (2.85), 8.756 (3.09), 8.765 (5.88), 8.775 (3.00), 12.090 (0.88).

Example 273

(+)-5-[({6-Bromo-3-methyl-2-[($^2$H$_{10}$)piperidin-1-yl]quinolin-4-yl}carbonyl)amino]-4-(2-chloro-3,6-difluorophenyl)pentanoic acid (Enantiomer 1)

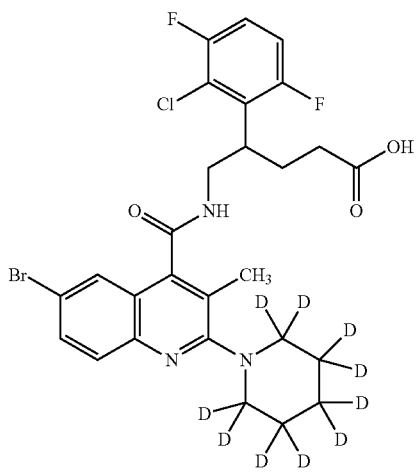 [SMILES: [2H]C1([2H])N(c2nc3ccc(Br)cc3c(C(=O)NCC(CCC(=O)O)c3c(F)ccc(F)c3Cl)c2C)C([2H])([2H])C([2H])([2H])C([2H])([2H])C1([2H])[2H]]

To a solution of (+)-tert-butyl 5-{[(6-bromo-2-chloro-3-methylquinolin-4-yl)carbonyl]amino}-4-(2-chloro-3,6-difluorophenyl)pentanoate (241 mg, 400 µmol, enantiomer 1, Example 48A) in NMP (1.6 ml) was added piperidine-D11 (120 µl, 1.20 mmol), and the mixture was stirred at 110° C. for 20 h. After cooling to RT, water (100 ml) was added to the mixture, which was extracted twice with ethyl acetate (80 ml each time). The combined organic phases were dried over sodium sulfate, filtered and concentrated, and the residue was purified by preparative HPLC (Method 32). The combined target fractions were concentrated, and the residue was lyophilized from acetonitrile/water. The title compound was obtained directly (without isolation of the corresponding tert-butyl ester). 32 mg (100% purity, 13% of theory) of the title compound were obtained.

$[\alpha]_D^{20}$=+37.3°, 589 nm, c=0.30 g/100 ml, methanol

LC-MS (Method 1): $R_t$=2.12 min; MS (ESIpos): m/z=604/606 [M+H]$^+$ $^1$H-NMR (600 MHz, DMSO-d6) δ [ppm]: −0.022 (0.32), 0.070 (0.18), 1.095 (0.19), 1.106 (0.18), 1.228 (1.01), 1.312 (0.88), 1.343 (0.85), 1.353 (0.90), 1.377 (0.85), 1.402 (0.51), 1.539 (0.67), 1.612 (0.55), 1.950 (1.96), 2.069 (4.94), 2.084 (5.40), 2.135 (16.00), 2.388 (0.38), 2.616 (0.42), 2.694 (0.48), 3.084 (0.84), 3.394 (4.23), 3.714 (4.00), 7.293 (3.51), 7.299 (3.54), 7.309 (2.55), 7.413 (3.39), 7.632 (6.05), 7.646 (14.75), 7.661 (9.57), 7.665 (8.43), 7.676 (3.85), 7.679 (3.58), 8.842 (4.13).

Example 274

(−)-5-[({6-Bromo-3-methyl-2-[($^2$H$_{10}$)piperidin-1-yl]quinolin-4-yl}carbonyl)amino]-4-(2-chloro-3,6-difluorophenyl)pentanoic acid (Enantiomer 2)

To a solution of (−)-tert-butyl 5-{[(6-bromo-2-chloro-3-methylquinolin-4-yl)carbonyl]amino}-4-(2-chloro-3,6-difluorophenyl)pentanoate (241 mg, 400 µmol, enantiomer 2, Example 49A) in NMP (1.6 ml) was added piperidine-D11 (120 µl, 1.20 mmol), and the mixture was stirred at 110° C. for 20 h. After cooling to RT, water (100 ml) was added to the mixture, which was extracted twice with ethyl acetate (80 ml each time). The combined organic phases were dried over sodium sulfate, filtered and concentrated, and the residue was purified by preparative HPLC (Method 32). The combined target fractions were concentrated, and the residue was lyophilized from acetonitrile/water. The title compound was obtained directly (without isolation of the corresponding tert-butyl ester). 42 mg (100% purity, 17% of theory) of the title compound were obtained.

$[\alpha]_D^{20}$=−29.2°, 589 nm, c=0.33 g/100 ml, methanol

LC-MS (Method 1): $R_t$=2.12 min; MS (ESIpos): m/z=604/606 [M+H]$^+$ $^1$H-NMR (600 MHz, DMSO-d6) δ [ppm]: −0.022 (0.18), 0.072 (0.21), 1.228 (1.00), 1.343 (0.66), 1.354 (0.71), 1.361 (0.75), 1.402 (0.20), 1.540 (0.68), 1.613 (0.55), 1.954 (1.87), 2.071 (4.75), 2.088 (5.11), 2.135 (16.00), 2.388 (0.30), 2.616 (0.35), 2.695 (0.50), 3.085 (0.78), 3.394 (3.81), 7.294 (3.41), 7.300 (3.44), 7.310 (2.45), 7.413 (3.29), 7.632 (6.00), 7.647 (14.77), 7.662 (9.74), 7.665 (8.27), 7.677 (3.79), 7.680 (3.41), 8.842 (4.09).

Example 275

(+)-5-[({6-Bromo-3-methyl-2-[($^2$H$_8$)pyrrolidin-1-yl]quinolin-4-yl}carbonyl)amino]-4-(2-chlorophenyl)pentanoic acid (Enantiomer 1)

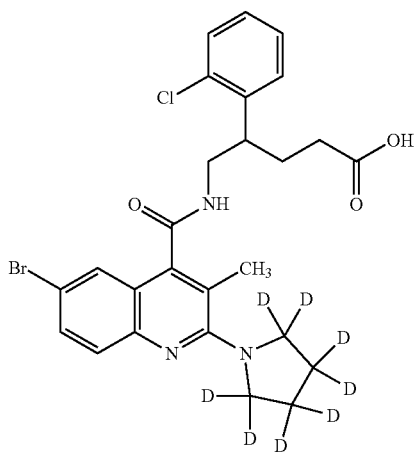 [SMILES: [2H]C1([2H])N(c2nc3ccc(Br)cc3c(C(=O)NCC(CCC(=O)O)c3ccccc3Cl)c2C)C([2H])([2H])C([2H])([2H])C1([2H])[2H]]

To a solution of (+)-tert-butyl 5-[({6-bromo-3-methyl-2-[($^2$H$_8$)pyrrolidin-1-yl]quinolin-4-yl}carbonyl)amino]-4-(2-chlorophenyl)pentanoate (232 mg, 380 µmol, enantiomer 1, Example 284A) in dichloromethane (2.9 ml) was added TFA (645 µl, 8.37 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 170 mg (100% purity, 81% of theory) of the title compound were obtained.

$[\alpha]_D^{20}$=+12.8°, 589 nm, c=0.38 g/100 ml, methanol

LC-MS (Method 1): R$_t$=1.42 min; MS (ESIpos): m/z=552/554 [M+H]$^+$ $^1$H-NMR (500 MHz, DMSO-d6) δ [ppm]: 1.232 (0.37), 1.792 (0.70), 1.800 (1.02), 1.818 (2.38), 1.835 (2.71), 1.853 (1.37), 2.022 (0.70), 2.032 (1.39), 2.041 (1.72), 2.049 (5.62), 2.070 (4.67), 2.072 (4.71), 2.076 (5.09), 2.093 (4.12), 2.117 (2.81), 2.134 (4.96), 2.155 (9.05), 2.237 (0.36), 2.284 (0.43), 2.362 (0.18), 2.636 (0.18), 3.587 (2.38), 3.654 (2.45), 7.254 (2.02), 7.269 (4.23), 7.283 (2.85), 7.355 (2.96), 7.370 (5.05), 7.384 (2.96), 7.436 (8.59), 7.439 (8.21), 7.452 (7.33), 7.455 (6.80), 7.468 (10.62), 7.475 (6.17), 7.477 (6.21), 7.486 (16.00), 7.490 (5.16), 7.543 (7.85), 7.548 (7.12), 7.561 (4.96), 7.566 (4.68), 8.663 (2.87), 8.674 (5.45), 8.686 (2.67).

Example 276

(−)-5-[({6-Bromo-3-methyl-2-[($^2$H$_8$)pyrrolidin-1-yl]quinolin-4-yl}carbonyl)amino]-4-(2-chlorophenyl)pentanoic acid (Enantiomer 2)

To a solution of (−)-tert-butyl 5-[({6-bromo-3-methyl-2-[($^2$H$_8$)pyrrolidin-1-yl]quinolin-4-yl}carbonyl)amino]-4-(2-chlorophenyl)pentanoate (236 mg, 388 µmol, enantiomer 2, Example 285A) in dichloromethane (3.0 ml) was added TFA (657 µl, 8.53 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 177 mg (100% purity, 83% of theory) of the title compound were obtained.

$[\alpha]_D^{20}$=−11.5°, 589 nm, c=0.48 g/100 ml, methanol

LC-MS (Method 1): R$_t$=1.43 min; MS (ESIpos): m/z=552/554 [M+H]$^+$ $^1$H-NMR (600 MHz, DMSO-d6) δ [ppm]: 1.800 (1.03), 1.815 (2.52), 1.829 (2.74), 1.845 (1.38), 2.027 (0.69), 2.035 (1.39), 2.051 (6.12), 2.069 (5.24), 2.088 (2.40), 2.099 (2.00), 2.117 (3.32), 2.132 (5.50), 2.148 (5.66), 2.238 (0.37), 2.283 (0.33), 3.585 (2.21), 3.651 (2.02), 7.258 (1.88), 7.270 (3.56), 7.282 (2.45), 7.360 (2.37), 7.372 (3.84), 7.384 (2.29), 7.441 (8.20), 7.455 (7.11), 7.469 (8.21), 7.484 (16.00), 7.495 (4.67), 7.548 (5.71), 7.551 (5.48), 7.562 (4.01), 7.565 (3.91), 8.686 (3.02), 8.695 (5.74), 8.704 (2.88), 12.077 (1.33).

Example 277

(−)-5-[({6-Bromo-3-methyl-2-[($^2$H$_8$)pyrrolidin-1-yl]quinolin-4-yl}carbonyl)amino]-4-[2-(trifluoromethyl)phenyl]pentanoic acid (Enantiomer 1)

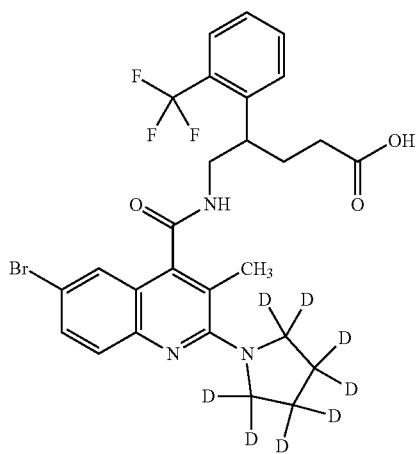 [SMILES: [2H]C1([2H])N(c2nc3ccc(Br)cc3c(C(=O)NCC(CCC(=O)O)c3ccccc3C(F)(F)F)c2C)C([2H])([2H])C([2H])([2H])C1([2H])[2H]]

To a solution of (−)-tert-butyl 5-[({6-bromo-3-methyl-2-[($^2$H$_8$)pyrrolidin-1-yl]quinolin-4-yl}carbonyl)amino]-4-[2-(trifluoromethyl)phenyl]pentanoate (200 mg, 311 µmol, enantiomer 1, Example 286A) in dichloromethane (2.4 ml) was added TFA (528 µl, 6.85 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 151 mg (100% purity, 83% of theory) of the title compound were obtained.

$[\alpha]_D^{20}$=−18.0°, 589 nm, c=0.30 g/100 ml, methanol

LC-MS (Method 1): R$_t$=1.51 min; MS (ESIpos): m/z=586/588 [M+H]$^+$ $^1$H-NMR (600 MHz, DMSO-d6) δ [ppm]: 1.829 (0.40), 1.874 (0.82), 1.883 (1.18), 1.890 (1.90), 1.898 (2.80), 1.905 (2.37), 1.913 (2.80), 1.920 (2.63), 1.937 (1.64), 1.946 (2.11), 1.955 (1.34), 1.962 (2.15), 1.972 (3.71), 1.981 (2.35), 1.989 (3.43), 1.997 (2.66), 2.049 (2.83), 2.059 (3.89), 2.075 (4.72), 2.086 (2.77), 2.102 (3.03), 2.113 (2.77), 2.121 (3.45), 2.135 (4.67), 2.145 (4.69), 2.159 (4.40), 2.169 (3.85), 2.178 (3.42), 2.278 (0.75), 2.387 (0.30), 2.615 (0.24), 3.598 (2.01), 3.722 (2.08), 7.247 (0.41), 7.394 (0.44), 7.467 (3.00), 7.480

(14.90), 7.495 (16.00), 7.555 (7.51), 7.558 (7.44), 7.570 (5.29), 7.573 (5.31), 7.696 (2.72), 7.709 (6.63), 7.722 (12.22), 7.736 (13.62), 7.751 (4.23), 8.737 (3.79), 8.746 (7.33), 8.756 (3.77), 12.063 (3.78).

Example 278

(+)-5-[({6-Bromo-3-methyl-2-[($^2$H$_8$)pyrrolidin-1-yl]quinolin-4-yl}carbonyl)amino]-4-[2-(trifluoromethyl)phenyl]pentanoic acid (Enantiomer 2)

To a solution of (+)-tert-butyl 5-[({6-bromo-3-methyl-2-[($^2$H$_8$)pyrrolidin-1-yl]quinolin-4-yl}carbonyl)amino]-4-[2-(trifluoromethyl)phenyl]pentanoate (184 mg, 287 µmol, enantiomer 2, Example 287A) in dichloromethane (2.2 ml) was added TFA (486 µl, 6.32 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 139 mg (100% purity, 82% of theory) of the title compound were obtained.

$[\alpha]_D^{20}$=+19.2°, 589 nm, c=0.30 g/100 ml, methanol

LC-MS (Method 1): R$_t$=1.47 min; MS (ESIpos): m/z=586/588 [M+H]$^+$ $^1$H-NMR (600 MHz, DMSO-d6) δ [ppm]: 0.005 (0.36), 1.232 (0.17), 1.830 (0.45), 1.876 (0.97), 1.884 (1.37), 1.891 (2.25), 1.899 (3.28), 1.907 (2.78), 1.914 (3.26), 1.922 (3.14), 1.938 (1.95), 1.948 (2.59), 1.957 (1.61), 1.964 (2.69), 1.975 (4.42), 1.983 (2.89), 1.991 (4.33), 1.999 (3.30), 2.050 (3.56), 2.061 (4.90), 2.066 (3.43), 2.077 (6.09), 2.088 (3.47), 2.104 (3.78), 2.114 (3.37), 2.122 (4.01), 2.136 (5.33), 2.147 (5.35), 2.152 (5.03), 2.161 (5.04), 2.170 (4.40), 2.180 (3.85), 2.281 (0.77), 2.387 (0.31), 2.616 (0.25), 3.325 (4.10), 3.601 (2.25), 3.724 (2.31), 7.118 (0.19), 7.247 (0.51), 7.396 (0.52), 7.467 (3.62), 7.483 (11.19), 7.498 (11.31), 7.557 (7.64), 7.561 (7.43), 7.572 (5.45), 7.575 (5.28), 7.696 (3.26), 7.709 (7.80), 7.722 (14.33), 7.737 (16.00), 7.751 (4.94), 8.739 (4.26), 8.748 (8.09), 8.758 (4.19), 12.062 (8.04).

Example 279

(+)-5-[({6-Bromo-3-methyl-2-[($^2$H$_8$)pyrrolidin-1-yl]quinolin-4-yl}carbonyl)amino]-4-[2-(trifluoromethyl)phenyl]pentanoic acid (Enantiomer 1)

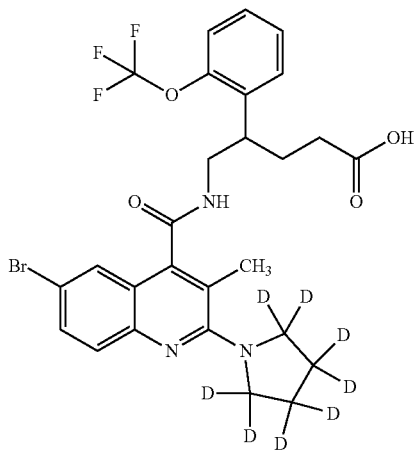 [SMILES: [2H]C1([2H])N(c2nc3ccc(Br)cc3c(C(=O)NCC(CCC(=O)O)c3ccccc3OC(F)(F)F)c2C)C([2H])([2H])C([2H])([2H])C1([2H])[2H]]

To a solution of (+)-tert-butyl 5-[({6-bromo-3-methyl-2-[($^2$H$_8$)pyrrolidin-1-yl]quinolin-4-yl}carbonyl)amino]-4-[2-(trifluoromethoxy)phenyl]pentanoate (221 mg, 335 µmol, enantiomer 1, Example 288A) in dichloromethane (2.6 ml) was added TFA (569 µl, 7.38 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 173 mg (100% purity, 86% of theory) of the title compound were obtained.

$[\alpha]_D^{20}$=+17.6°, 589 nm, c=0.44 g/100 ml, methanol

LC-MS (Method 1): R$_t$=1.52 min; MS (ESIpos): m/z=602/604 [M+H]$^+$ $^1$H-NMR (600 MHz, DMSO-d6) δ [ppm]: 0.005 (0.45), 1.232 (0.18), 1.371 (0.16), 1.785 (0.41), 1.797 (0.70), 1.809 (2.46), 1.817 (2.57), 1.824 (2.21), 1.832 (4.22), 1.847 (2.31), 1.863 (0.70), 2.025 (0.79), 2.043 (1.94), 2.052 (4.74), 2.057 (2.57), 2.062 (4.02), 2.070 (16.00), 2.077 (11.82), 2.080 (12.48), 2.095 (4.14), 2.099 (3.35), 2.110 (3.35), 2.128 (2.33), 2.154 (2.44), 2.299 (0.39), 2.387 (0.29), 2.521 (0.34), 2.615 (0.27), 3.388 (2.82), 3.539 (0.29), 3.576 (1.26), 3.586 (1.99), 3.597 (2.89), 3.608 (3.17), 3.618 (1.85), 3.665 (2.28), 3.675 (2.12), 7.279 (0.39), 7.342 (3.44), 7.345 (4.50), 7.355 (5.69), 7.357 (7.09), 7.360 (5.29), 7.389 (2.33), 7.404 (6.74), 7.409 (7.73), 7.417 (7.25), 7.429 (2.39), 7.478 (5.56), 7.492 (7.70), 7.555 (10.48), 7.566 (6.58), 7.570 (8.36), 8.707 (3.14), 8.716 (5.60), 8.726 (3.03), 12.080 (6.24).

Example 280

(−)-5-[({6-Bromo-3-methyl-2-[($^2$H$_8$)pyrrolidin-1-yl]quinolin-4-yl}carbonyl)amino]-4-[2-(trifluoromethyl)phenyl]pentanoic acid (Enantiomer 2)

To a solution of (−)-tert-butyl 5-[({6-bromo-3-methyl-2-[($^2$H$_8$)pyrrolidin-1-yl]quinolin-4-yl}carbonyl)amino]-4-[2-(trifluoromethoxy)phenyl]pentanoate (188 mg, 286 µmol, enantiomer 2, Example 289A) in dichloromethane (2.2 ml) was added TFA (484 µl, 6.28 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 140 mg (100% purity, 81% of theory) of the title compound were obtained.

$[\alpha]_D^{20}$=−14.4°, 589 nm, c=0.36 g/100 ml, methanol

LC-MS (Method 1): R$_t$=1.57 min; MS (ESIpos): m/z=602/604 [M+H]$^+$ $^1$H-NMR (600 MHz, DMSO-d6) δ [ppm]: 1.786 (0.41), 1.799 (0.79), 1.811 (2.56), 1.819 (2.97), 1.833 (4.47), 1.848 (2.43), 1.865 (0.72), 2.026 (0.76), 2.044 (1.92), 2.053 (4.55), 2.071 (16.00), 2.081 (13.66), 2.096 (4.73), 2.111 (3.63), 2.130 (2.70), 2.156 (2.87), 2.298 (0.47), 2.386 (0.22), 2.614 (0.20), 3.391 (3.10), 3.539 (0.31), 3.577 (1.37), 3.587 (2.26), 3.598 (3.23), 3.609 (3.59), 3.619 (2.09), 3.666 (2.65), 3.676 (2.45), 7.278 (0.44), 7.345 (4.72), 7.357 (7.31), 7.389 (2.62), 7.405 (7.34), 7.409 (8.25), 7.417 (7.84), 7.429 (2.59), 7.477 (8.39), 7.492 (11.72), 7.556 (12.90), 7.570 (9.71), 8.707 (3.63), 8.717 (6.58), 8.726 (3.55), 12.080 (13.05).

Example 281

(+)-5-[({6-Bromo-3-methyl-2-[($^2$H$_8$)pyrrolidin-1-yl]quinolin-4-yl}carbonyl)amino]-4-(2-chloro-3,6-difluorophenyl)pentanoic acid (Enantiomer 1)

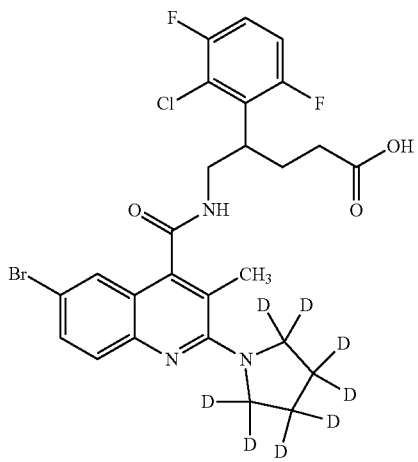 [SMILES: [2H]C1([2H])N(c2nc3ccc(Br)cc3c(C(=O)NCC(CCC(=O)O)c3c(F)ccc(F)c3Cl)c2C)C([2H])([2H])C([2H])([2H])C1([2H])[2H]]

Method A:

To a solution of tert-butyl 5-[({6-bromo-3-methyl-2-[($^2$H$_8$)pyrrolidin-1-yl]quinolin-4-yl}carbonyl)amino]-4-(2-chloro-3,6-difluorophenyl)pentanoate (38 mg, 59 μmol, enantiomer 1, Example 290A) in dichloromethane (1.0 ml) was added TFA (100 μl, 1.30 mmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 9 mg (100% purity, 25% of theory) of the title compound were obtained.

LC-MS (Method 1): R$_t$=1.43 min; MS (ESIpos): m/z=588/560 [M+H]$^+$ $^1$H-NMR (600 MHz, DMSO-d6) δ [ppm]: −0.022 (0.55), 1.232 (1.37), 1.825 (0.38), 1.966 (2.96), 2.072 (4.00), 2.079 (4.99), 2.092 (5.37), 2.105 (8.11), 2.128 (11.23), 2.139 (14.79), 2.151 (15.29), 2.160 (16.00), 2.171 (11.89), 2.341 (0.60), 2.387 (0.49), 2.616 (0.55), 3.440 (0.93), 3.536 (0.44), 3.708 (6.36), 7.301 (5.26), 7.415 (4.77), 7.478 (9.92), 7.493 (13.42), 7.560 (10.14), 7.562 (9.70), 7.574 (7.34), 7.577 (7.07), 7.649 (0.55), 8.792 (7.56), 12.132 (4.16).

Method B:

As described in Example 290A, proceeding from (+)-tert-butyl 5-{[(6-bromo-2-chloro-3-methylquinolin-4-yl)carbonyl]amino}-4-(2-chloro-3,6-difluorophenyl)pentanoate (241 mg, 400 μmol, Example 48A), the title compound was obtained directly (without isolating the corresponding tert-butyl ester) as fraction 1 (34 mg, 100% purity, 14% of theory).

[α]$_D^{20}$=+41.9°, 589 nm, c=0.32 g/100 ml, methanol

LC-MS (Method 1): R$_t$=1.43 min; MS (ESIpos): m/z=588/560 [M+H]$^+$ $^1$H-NMR (600 MHz, DMSO-d6) δ [ppm]: 0.071 (0.24), 1.085 (0.75), 1.232 (0.38), 1.357 (0.72), 1.368 (0.31), 1.825 (0.35), 1.956 (1.60), 2.081 (4.26), 2.098 (4.30), 2.157 (7.33), 2.338 (0.36), 2.387 (0.36), 2.615 (0.42), 3.703 (3.89), 7.297 (3.26), 7.410 (2.92), 7.473 (11.97), 7.488 (16.00), 7.555 (7.89), 7.559 (7.36), 7.570 (5.57), 7.573 (5.29), 8.792 (4.04).

Example 282

(−)-5-[({6-Bromo-3-methyl-2-[($^2$H$_8$)pyrrolidin-1-yl]quinolin-4-yl}carbonyl)amino]-4-(2-chloro-3,6-difluorophenyl)pentanoic acid (Enantiomer 2)

Method A:

To a solution of tert-butyl 5-[({6-bromo-3-methyl-2-[($^2$H$_8$)pyrrolidin-1-yl]quinolin-4-yl}carbonyl)amino]-4-(2-chloro-3,6-difluorophenyl)pentanoate (20 mg, 31 μmol, enantiomer 2, Example 291A) in dichloromethane (1.0 ml) was added TFA (52 μl, 682 μmol), and the mixture was left to stand at RT for 24 h. The mixture was then concentrated and repeatedly dichloromethane was added and the mixture was concentrated again. The residue was purified by preparative HPLC (Method 11). The combined target fractions were concentrated, and the residue was lyophilized. 7 mg (100% purity, 40% of theory) of the title compound were obtained.

LC-MS (Method 1): R$_t$=1.43 min; MS (ESIpos): m/z=588/590 [M+H]$^+$ $^1$H-NMR (600 MHz, DMSO-d6) δ [ppm]: −0.023 (0.78), 0.841 (0.28), 0.853 (0.58), 0.864 (0.25), 1.232 (2.98), 1.824 (0.24), 1.965 (1.80), 2.078 (2.77), 2.090 (3.00), 2.104 (4.61), 2.126 (5.66), 2.136 (7.73), 2.149 (8.42), 2.158 (9.21), 2.338 (0.40), 2.387 (0.34), 2.426 (0.43), 2.478 (0.57), 2.615 (0.40), 2.655 (0.45), 3.507 (0.69), 3.709 (3.84), 6.739 (0.25), 7.302 (3.16), 7.410 (2.83), 7.474 (11.76), 7.489 (16.00), 7.556 (7.66), 7.560 (7.21), 7.571 (5.50), 7.575 (5.26), 8.791 (4.57), 12.136 (0.40).

Method B:

As described in Example 291A, proceeding from (−)-tert-butyl 5-{[(6-bromo-2-chloro-3-methylquinolin-4-yl)carbonyl]amino}-4-(2-chloro-3,6-difluorophenyl)pentanoate (241 mg, 400 μmol, Example 49A), the title compound was obtained directly (without isolating the corresponding tert-butyl ester) as fraction 1 (55 mg, 100% purity, 23% of theory).

[α]$_D^{20}$=−35.2°, 589 nm, c=0.34 g/100 ml, methanol

LC-MS (Method 1): R$_t$=1.40 min; MS (ESIpos): m/z=588/590 [M+H]$^+$ $^1$H-NMR (600 MHz, DMSO-d6) δ [ppm]: 0.071 (0.17), 1.231 (0.19), 1.357 (0.26), 1.825 (0.27), 1.964 (1.63), 2.076 (2.62), 2.099 (4.96), 2.118 (4.75), 2.130 (5.92), 2.153 (8.09), 2.339 (0.43), 2.387 (0.35), 2.615 (0.33), 3.708 (3.65), 7.300 (3.01), 7.414 (2.67), 7.474 (11.71), 7.489 (16.00), 7.556 (7.50), 7.560 (7.17), 7.571 (5.41), 7.574 (5.25), 8.790 (4.30).

Example 283

(−)-5-({[6-Bromo-3-methyl-2-(pyrrolidin-1-yl)quinolin-4-yl]carbonyl}amino)-4-(2-chlorophenyl)pentanoic acid hydrochloride (Enantiomer 1)

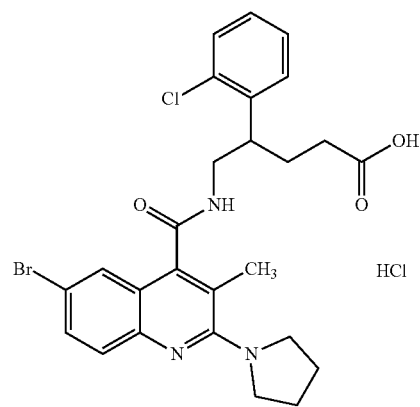 [SMILES: Cc1c(N2CCCC2)nc2ccc(Br)cc2c1C(=O)NCC(CCC(=O)O)c1ccccc1Cl ; Cl]

To prepare for the experiment, three different batches of (−)-5-({[6-bromo-3-methyl-2-(pyrrolidin-1-yl)quinolin-4-yl]carbonyl}amino)-4-(2-chlorophenyl)pentanoic acid (Enantiomer 1, totaling 1.386 g, 2.54 mmol, Example 34) were each dissolved in a few millilitres of methanol, the solutions were combined, and most of the methanol was removed again on a rotary evaporator. Subsequently, the residue was dissolved in dioxane (14 ml) and, at RT, a 4 M solution of hydrogen chloride in dioxane (3.2 ml, 12.72 mmol) was added dropwise. The mixture was allowed to stand at RT for 1 h. Thereafter, the solids formed were filtered off and dried under reduced pressure. Since, according to LC-MS, owing to the methanol used for preparation for the experiment, the methyl ester corresponding to the title compound had also formed, the residue was first purified by means of preparative HPLC (Method 32). The combined target fractions were concentrated, and the residue was dried under reduced pressure. The residue (960 mg) was subsequently dissolved in dioxane (10 ml) and, at RT, a 4 M solution of hydrogen chloride in dioxane (3.2 ml, 12.72 mmol) was added gradually, and the mixture was left to stand at RT for 2 h. Subsequently, the solids formed were filtered off, and the residue was lyophilized from acetonitrile/water. 603 mg (100% purity, 41% of theory) of the title compound were obtained.

$[\alpha]_D^{20}$=−17.0°, 589 nm, c=0.42 g/100 ml, methanol

LC-MS (Method 1): $R_t$=1.42 min; MS (ESIpos): m/z=544/546 [M+H]$^+$ $^1$H-NMR (500 MHz, DMSO-d6) δ [ppm]: 0.006 (0.51), 1.699 (0.22), 1.797 (0.88), 1.808 (1.38), 1.825 (2.64), 1.842 (2.97), 1.859 (1.76), 1.875 (0.81), 1.971 (16.00), 2.016 (1.20), 2.054 (6.83), 2.075 (5.25), 2.084 (4.69), 2.092 (3.14), 2.099 (3.96), 2.123 (3.41), 2.136 (3.36), 2.155 (1.81), 2.167 (1.04), 2.258 (3.04), 2.457 (0.43), 2.637 (0.27), 3.391 (1.40), 3.567 (9.59), 3.589 (5.02), 3.883 (6.69), 7.192 (0.27), 7.278 (3.55), 7.293 (2.99), 7.374 (3.48), 7.429 (0.87), 7.443 (9.54), 7.445 (8.90), 7.459 (7.85), 7.462 (7.11), 7.492 (5.89), 7.507 (4.80), 7.804 (2.56), 7.821 (2.63), 8.192 (0.78), 8.921 (3.10).

Example 284

(+)-5-({[6-Bromo-3-methyl-2-(pyrrolidin-1-yl)quinolin-4-yl]carbonyl}amino)-4-(2-chlorophenyl)pentanoic acid hydrochloride (Enantiomer 2)

Method A:

To a solution of (+)-5-({[6-bromo-3-methyl-2-(pyrrolidin-1-yl)quinolin-4-yl]carbonyl}amino)-4-(2-chlorophenyl)pentanoic acid (200 mg, 367 µmol, enantiomer 2, Example 35) in dioxane (2 ml) under argon was slowly added dropwise, at RT, a 4 M solution of hydrogen chloride in dioxane (460 µl, 1.89 mmol), and the mixture was stirred at RT for 16 h. Subsequently, the solids formed were filtered off and dried under reduced pressure. 195 mg (100% purity, 89% of theory) of the title compound were obtained.

Ion chromatography (Method 34): proportion by mass of chloride: 9.9% by weight (1.7 eq.)

LC-MS (Method 1): $R_t$=1.49 min; MS (ESIpos): m/z=544/546 [M+H]$^+$ $^1$H-NMR (500 MHz, DMSO-d6) δ [ppm]: −0.061 (0.36), −0.007 (1.38), 0.007 (0.75), 1.085 (0.25), 1.368 (1.02), 1.799 (0.66), 1.809 (1.07), 1.827 (2.10), 1.843 (2.36), 1.861 (1.33), 1.877 (0.54), 1.911 (0.37), 1.989 (13.81), 2.055 (5.55), 2.076 (4.32), 2.085 (3.94), 2.093 (2.67), 2.099 (2.82), 2.123 (2.59), 2.136 (2.33), 2.155 (1.09), 2.167 (0.49), 2.256 (2.66), 2.347 (2.35), 2.479 (0.87), 2.639 (0.16), 3.567 (16.00), 3.586 (1.74), 3.950 (5.56), 5.329 (0.39), 7.281 (2.32), 7.373 (2.16), 7.444 (8.14), 7.447 (7.62), 7.460 (6.83), 7.463 (6.17), 7.495 (3.99), 7.510 (3.54), 7.850 (3.33), 7.868 (3.51), 8.371 (2.22), 8.387 (2.08), 8.972 (2.46), 8.984 (4.49), 8.995 (2.33).

A portion of the title compound was then lyophilized from acetonitrile/water and analysed again: Ion chromatography (Method 34): proportion by mass of chloride: 4.6% by weight (0.8 eq.)

LC-MS (Method 1): $R_t$=1.47 min; MS (ESIpos): m/z=544/546 [M+H]$^+$ $^1$H-NMR (500 MHz, DMSO-d6) δ [ppm]: −0.061 (0.46), −0.007 (0.68), 0.007 (0.49), 1.086 (0.47), 1.143 (0.19), 1.368 (1.75), 1.795 (0.91), 1.806 (1.50), 1.824 (2.91), 1.840 (3.33), 1.858 (1.93), 1.874 (0.82), 1.962 (16.00), 2.015 (1.18), 2.053 (7.92), 2.074 (5.96), 2.082 (5.25), 2.091 (3.40), 2.098 (4.54), 2.118 (3.35), 2.123 (3.80), 2.135 (3.95), 2.153 (2.00), 2.165 (1.04), 2.248 (3.53), 2.363 (0.78), 2.637 (0.43), 3.679 (5.00), 3.839 (5.70), 7.277 (4.13), 7.292 (3.05), 7.361 (2.86), 7.375 (4.27), 7.389 (2.53), 7.442 (11.82), 7.445 (10.93), 7.458 (9.93), 7.461 (8.79), 7.491 (6.84), 7.506 (5.46), 7.786 (2.10), 8.063 (0.54), 8.875 (2.69).

Method B:

To a solution of (+)-5-({[6-bromo-3-methyl-2-(pyrrolidin-1-yl)quinolin-4-yl]carbonyl}amino)-4-(2-chlorophenyl)pentanoic acid (3.31 g, 6.08 mmol, enantiomer 2, Example 35) in dioxane (33 ml) was slowly added dropwise, at RT, a 4 M solution of hydrogen chloride in dioxane (7.6 ml, 30.37 mmol), and the mixture was left to stand at RT for 4 h. Subsequently, the solids formed were filtered off, taken up in water/acetonitrile and lyophilized to obtain a first lyophilizate. The filtrate was left to stand at RT overnight and the precipitate that formed overnight was filtered off. The precipitate obtained was combined with the above-described lyophilizate, and the mixture was taken up in water/acetonitrile and lyophilized to obtain a second lyophilizate. 3.21 g (100% purity, 91% of theory, ee 99%) of the title compound were obtained.

Ion chromatography (Method 34): proportion by mass of chloride: 4.8% by weight (0.9 eq.)

LC-MS (Method 1): $R_t$=1.47 min; MS (ESIpos): m/z=544/546 [M+H]$^+$ $^1$H-NMR (600 MHz, DMSO-d6) δ [ppm]: 0.005 (0.73), 1.799 (0.90), 1.808 (1.47), 1.823 (3.13), 1.837 (3.31), 1.851 (1.89), 1.865 (0.77), 1.974 (16.00), 2.021 (1.18), 2.045 (3.16), 2.056 (7.95), 2.074 (5.59), 2.081 (4.92), 2.088 (2.71), 2.097 (3.16), 2.119 (3.61), 2.133 (3.29), 2.148 (1.72), 2.159 (0.86), 2.235 (3.75), 2.335 (3.01), 3.389 (0.71), 3.567 (3.96), 3.589 (3.99), 3.897 (5.37), 7.286 (3.18), 7.376 (2.64), 7.448 (10.89), 7.449 (10.57), 7.461 (9.38), 7.463 (8.90), 7.500 (5.06), 7.512 (4.82), 7.824 (2.61), 7.834 (2.66), 8.266 (0.69), 8.970 (3.38).

Method C:

To a solution of (+)-tert-butyl 5-({[6-bromo-3-methyl-2-(pyrrolidin-1-yl)quinolin-4-yl]carbonyl}-amino)-4-(2-chlorophenyl)pentanoate (6.50 g, 10.82 mmol, enantiomer 1, Example 292A) in dioxane (70 ml) was slowly added dropwise, at RT, a 4 M solution of hydrogen chloride in dioxane (100 ml, 400 mmol), and the mixture was stirred at RT for 6 h. Another 4 M solution of hydrogen chloride in dioxane (40 ml, 40 mmol) was added dropwise, and the mixture was stirred at RT for a further 16 h. Since, according to HPLC, 1-2% reactant was still present, the mixture was treated with ultrasound for 1 h. Subsequently, diisopropyl ether (300 ml) was gradually added to the mixture, and the solids present were filtered off and washed successively with three portions of diisopropyl ether (50 ml each time) and then dried under reduced pressure at 60° C. 6.18 g (100% purity, 89% of theory) of the title compound were obtained.

LC-MS (Method 1): $R_t$=1.42 min; MS (ESIpos): m/z=544/546 [M+H]$^+$ $^1$H-NMR (500 MHz, DMSO-d6) δ [ppm]: −0.007 (1.43), 0.007 (0.81), 1.030 (1.11), 1.042 (1.11), 1.086 (0.20), 1.368 (1.75), 1.595 (0.60), 1.797 (0.87), 1.808 (1.42), 1.825 (2.76), 1.842 (3.11), 1.859 (1.78), 1.877 (0.74), 1.971 (16.00), 2.016 (1.24), 2.047 (3.15), 2.055 (7.39), 2.076 (5.65), 2.084 (5.03), 2.093 (3.33), 2.099 (4.13), 2.120 (3.19), 2.124 (3.52), 2.136 (3.47), 2.155 (1.73), 2.167 (0.87), 2.251 (3.11), 2.457 (0.39), 2.637 (0.21), 3.567 (3.96), 3.589 (2.60), 3.682 (3.45), 7.278 (3.61), 7.291 (2.86), 7.375 (3.60), 7.443 (10.86), 7.446 (9.79), 7.459 (9.09), 7.462 (7.90), 7.493 (6.15), 7.508 (5.00), 7.821 (2.31), 8.219 (0.58), 8.924 (2.84).

Example 285

(−)-Sodium 5-({[6-bromo-3-methyl-2-(pyrrolidin-1-yl)quinolin-4-yl]carbonyl}amino)-4-(2-chlorophenyl)pentanoate (Enantiomer 1)

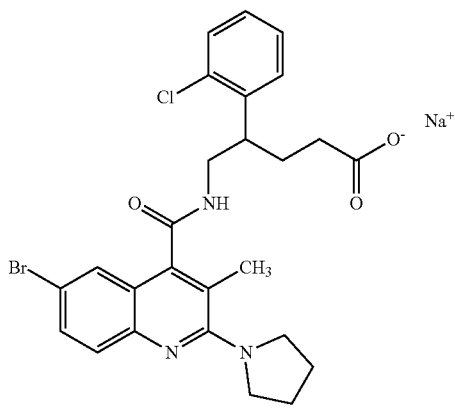 [SMILES: Cc1c(N2CCCC2)nc2ccc(Br)cc2c1C(=O)NCC(CCC(=O)[O-])c1ccccc1Cl ; [Na+]]

To a suspension of (−)-5-({[6-bromo-3-methyl-2-(pyrrolidin-1-yl)quinolin-4-yl]carbonyl}amino)-4-(2-chlorophenyl)pentanoic acid (125 mg, 229 mol, enantiomer 1, Example 34) in water (10 ml) was added, at RT, a 1 M aqueous sodium hydroxide solution (229 μl, 229 μmol). The mixture was treated with ultrasound and admixed with THF (2 ml), whereupon a solution formed. After stirring at RT for 1 h, the mixture was concentrated, and the residue was lyophilized from acetonitrile/water. 110 mg (98% purity, 83% of theory) of the title compound were obtained.

Ion chromatography (Method 34): proportion by mass of sodium: 3.5% by weight (0.9 eq)

$[α]_D^{20}$=−10.6°, 589 nm, c=0.36 g/100 ml, methanol

LC-MS (Method 1): $R_t$=1.45 min; MS (ESIpos): m/z=544/546 [M+H]$^+$ $^1$H-NMR (400 MHz, DMSO-d6) δ [ppm]: 1.355 (2.06), 1.695 (1.15), 1.707 (2.06), 1.729 (4.57), 1.738 (3.79), 1.753 (5.65), 1.768 (3.60), 1.782 (2.15), 1.807 (3.30), 1.833 (4.04), 1.872 (16.00), 1.916 (2.99), 1.933 (3.03), 2.178 (13.86), 2.256 (0.54), 2.267 (0.63), 2.710 (0.42), 3.465 (2.14), 3.480 (3.21), 3.497 (2.73), 3.514 (1.48), 3.572 (12.27), 3.618 (3.97), 7.215 (2.22), 7.233 (5.04), 7.251 (3.56), 7.325 (2.98), 7.343 (5.56), 7.361 (3.60), 7.407 (8.57), 7.426 (8.75), 7.438 (4.80), 7.462 (6.70), 7.484 (11.36), 7.536 (6.50), 7.541 (5.90), 7.558 (3.81), 7.564 (3.51), 9.051 (2.89).

Example 286

(+)-Sodium 5-({[6-bromo-3-methyl-2-(pyrrolidin-1-yl)quinolin-4-yl]carbonyl}amino)-4-(2-chlorophenyl)pentanoate (Enantiomer 2)

To a suspension of (+)-5-({[6-bromo-3-methyl-2-(pyrrolidin-1-yl)quinolin-4-yl]carbonyl}amino)-4-(2-chlorophenyl)pentanoic acid (125 mg, 229 μmol, enantiomer 2, Example 35) in water (10 ml) was added, at RT, a 1 M aqueous sodium hydroxide solution (229 μl, 229 μmol). The mixture was treated with ultrasound and admixed with THF (2 ml), whereupon a solution formed. After stirring at RT for 1 h, the mixture was concentrated, and the residue was lyophilized from acetonitrile/water. 129 mg (100% purity, 99% of theory, ee>99%) of the title compound were obtained.

Ion chromatography (Method 34): proportion by mass of sodium: 4.7% by weight (1.2 eq)

$[α]_D^{20}$=+11.4°, 589 nm, c=0.31 g/100 ml, methanol

LC-MS (Method 1): $R_t$=1.41 min; MS (ESIpos): m/z=544/546 [M+H]$^+$ $^1$H-NMR (600 MHz, DMSO-d6) δ [ppm]: 1.354 (3.55), 1.366 (1.65), 1.701 (1.24), 1.710 (2.34), 1.731 (5.80), 1.743 (5.24), 1.748 (5.40), 1.758 (4.03), 1.770 (2.04), 1.823 (4.25), 1.832 (3.64), 1.841 (6.72), 1.867 (15.69), 1.907 (3.02), 1.925 (3.71), 1.940 (2.01), 2.163 (6.98), 2.245 (0.69), 2.268 (0.64), 3.489 (4.06), 3.567 (10.12), 3.600 (5.64), 3.611 (4.58), 7.223 (2.64), 7.236 (5.49), 7.248 (3.68), 7.332 (3.31), 7.345 (5.80), 7.357 (3.71), 7.413 (10.88), 7.426 (16.00), 7.439 (6.16), 7.466 (11.09), 7.481 (15.50), 7.542 (7.81), 7.545 (7.58), 7.556 (5.65), 7.560 (5.53), 8.942 (3.81), 8.952 (7.12), 8.961 (3.87).

Example 287

(−)-Potassium 5-({[6-bromo-3-methyl-2-(pyrrolidin-1-yl)quinolin-4-yl]carbonyl}amino)-4-(2-chlorophenyl)pentanoate (Enantiomer 1)

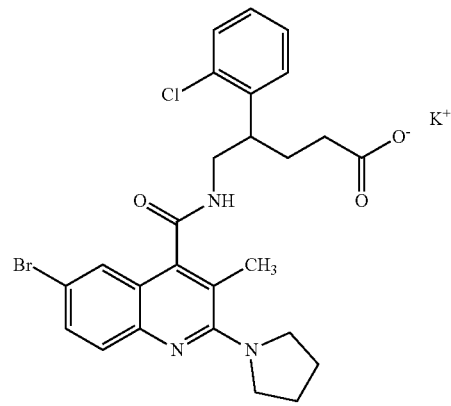 [SMILES: Cc1c(N2CCCC2)nc2ccc(Br)cc2c1C(=O)NCC(CCC(=O)[O-])c1ccccc1Cl ; [K+]]

To a suspension of (−)-5-({[6-bromo-3-methyl-2-(pyrrolidin-1-yl)quinolin-4-yl]carbonyl}amino)-4-(2-chlorophenyl)pentanoic acid (125 mg, 229 µmol, enantiomer 1, Example 34) in water (10 ml) was added, at RT, a 1 M potassium tert-butoxide solution (229 µl, 229 µmol). The mixture was treated with ultrasound and admixed with THF (2 ml), whereupon a solution formed. After stirring at RT for 1 h, the mixture was concentrated, and the residue was lyophilized from acetonitrile/water. 110 mg (98% purity, 81% of theory) of the title compound were obtained.

Ion chromatography (Method 34): proportion by mass of potassium: 6.9% by weight (1.0 eq)

$[α]_D^{20}$=−11.1°, 589 nm, c=0.50 g/100 ml, methanol

LC-MS (Method 1): $R_t$=1.45 min; MS (ESIpos): m/z=544/546 [M+H]$^+$ $^1$H-NMR (400 MHz, DMSO-d6) δ [ppm]: 1.299 (0.67), 1.612 (0.45), 1.694 (2.98), 1.717 (3.05), 1.730 (2.65), 1.758 (2.16), 1.782 (2.10), 1.794 (1.32), 1.863 (12.88), 1.947 (0.70), 2.184 (16.00), 2.227 (1.36), 2.237 (1.34), 2.709 (0.40), 3.552 (11.72), 3.597 (2.67), 3.617 (2.06), 3.650 (0.84), 7.054 (0.49), 7.137 (0.50), 7.181 (2.23), 7.200 (1.66), 7.223 (0.61), 7.289 (1.71), 7.307 (3.07), 7.325 (1.86), 7.361 (2.90), 7.381 (2.64), 7.403 (4.69), 7.420 (5.12), 7.442 (3.90), 7.482 (2.93), 7.503 (2.19).

Example 288

(+)-Potassium 5-({[6-bromo-3-methyl-2-(pyrrolidin-1-yl)quinolin-4-yl]carbonyl}amino)-4-(2-chlorophenyl)pentanoate (Enantiomer 2)

To a suspension of (+)-5-({[6-bromo-3-methyl-2-(pyrrolidin-1-yl)quinolin-4-yl]carbonyl}amino)-4-(2-chlorophenyl)pentanoic acid (125 mg, 229 µmol, enantiomer 2, Example 35) in water (10 ml) was added, at RT, a 1 M potassium tert-butoxide solution (229 µl, 229 µmol). The mixture was treated with ultrasound and admixed with THF (2 ml), whereupon a solution formed. After stirring at RT for 1 h, the mixture was concentrated, and the residue was lyophilized from acetonitrile/water. 137 mg (100% purity, "102%" of theory, ee>99%) of the title compound were obtained.

Ion chromatography (Method 34): proportion by mass of potassium: 5.8% by weight (0.9 eq)

$[α]_D^{20}$=+11.3°, 589 nm, c=0.31 g/100 ml, methanol

LC-MS (Method 1): $R_t$=1.41 min; MS (ESIpos): m/z=544/546 [M+H]$^+$ $^1$H-NMR (600 MHz, DMSO-d6) δ [ppm]: 1.109 (1.62), 1.354 (3.30), 1.366 (1.60), 1.683 (1.38), 1.692 (2.50), 1.707 (5.61), 1.712 (5.58), 1.724 (5.74), 1.733 (3.59), 1.748 (1.84), 1.758 (1.21), 1.764 (1.24), 1.781 (4.21), 1.790 (2.78), 1.798 (5.09), 1.808 (3.45), 1.825 (2.13), 1.870 (13.58), 1.916 (2.38), 2.182 (8.32), 2.263 (0.72), 3.438 (2.92), 3.450 (4.06), 3.461 (4.99), 3.472 (4.00), 3.574 (10.43), 7.221 (2.77), 7.233 (5.99), 7.246 (3.94), 7.330 (3.46), 7.342 (6.22), 7.354 (3.92), 7.410 (12.30), 7.417 (8.36), 7.423 (11.97), 7.469 (11.20), 7.483 (16.00), 7.543 (7.97), 7.546 (7.69), 7.557 (5.73), 7.561 (5.54), 9.146 (3.89), 9.155 (7.29), 9.164 (3.93).

Example 289

(+)-5-({[6-Bromo-2-(3,3-difluoropiperidin-1-yl)-3-methylquinolin-4-yl]carbonyl}amino)-4-(2-methoxyphenyl)pentanoic acid (Enantiomer 1)

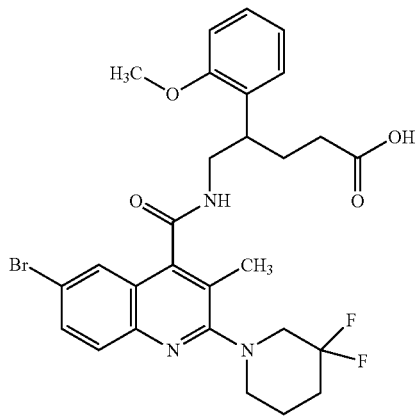 [SMILES: COc1ccccc1C(CCC(=O)O)CNC(=O)c1c(C)c(N2CCCC(F)(F)C2)nc2ccc(Br)cc12]

5-{[(6-Bromo-2-chloro-3-methylquinolin-4-yl)carbonyl]amino}-4-(2-methoxyphenyl)pentanoic acid (Enantiomer 1, 200 mg, 85% purity, 336 µmol, Example 241A), 3,3-difluoropiperidine hydrochloride (312 mg, 1.98 mmol) and DIPEA (830 µl, 4.7 mmol) in NMP (1.0 ml) were stirred at 120° C. for four days. After cooling to RT, the reaction mixture was added to 1 M hydrochloric acid and extracted with dichloromethane. The organic phase was dried over sodium sulfate and concentrated. The crude product was prepurified by column chromatography (Isolera, KP-Sil, eluent: dichloromethane/methanol, gradient: 0-40% methanol) and repurified by means of preparative HPLC (Method 27). 54 mg (99% purity, 27% of theory) were obtained.

$[α]_D^{20}$=+6.7°, 589 nm, c=0.50 g/100 ml, chloroform.

LC-MS (Method 26): $R_t$=0.80 min; MS (ESIpos): m/z=590/592 [M+H]$^+$ $^1$H-NMR (400 MHz, CHLOROFORM-d) δ [ppm]: 1.262 (0.43), 1.953 (1.11), 1.965 (0.97), 1.981 (0.52), 2.025 (0.71), 2.038 (0.82), 2.057 (1.02), 2.072 (1.08), 2.087 (0.84), 2.108 (0.48), 2.116 (0.44), 2.136 (0.57), 2.149 (0.66), 2.170 (0.63), 2.191 (1.16), 2.213 (7.96), 2.287 (0.88), 2.301 (1.65), 2.307 (1.08), 2.321 (1.76), 2.340 (0.84), 2.348 (0.58), 3.147 (1.27), 3.432 (1.19), 3.445 (0.50), 3.459 (2.36), 3.488 (1.21), 3.582 (0.42), 3.715 (0.43), 3.744 (16.00), 3.827 (0.57), 3.840 (0.51), 3.850 (0.47), 3.864 (0.42), 3.942 (0.56), 3.957 (0.88), 3.971 (0.57), 3.989 (0.59), 5.786 (0.50), 5.800 (1.00), 5.814 (0.52), 6.853 (1.55), 6.873 (1.58), 6.965 (0.71), 6.967 (0.71), 6.983 (1.56), 6.985 (1.54), 7.001 (0.96), 7.216 (1.85), 7.220 (1.39), 7.224 (0.68), 7.235 (1.67), 7.238 (1.56), 7.259 (0.89), 7.263 (0.94), 7.602 (0.82), 7.607 (0.89), 7.624 (1.77), 7.630 (2.19), 7.649 (0.42), 7.659 (3.62), 7.671 (2.06), 7.676 (1.81), 7.680 (1.92).

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms

CRTH2 chemoattractant receptor-homologous molecule expressed on T helper type 2 cells
DMEM Dulbecco's modified Eagle's medium
DMSO dimethyl sulfoxide
DP PGD2 receptor
$EC_{50}$ half-maximum effective concentration
em. emission
EP PGE2 receptor
ex. excitation
from Company (source)
FCS foetal calf serum
FP PGF2α receptor
HEPES 2-[4-(2-hydroxyethyl)piperazin-1-yl]ethanesulfonic acid
$IC_{50}$ half-maximum inhibitory concentration
IP PGI2 receptor
lit. literature (reference)
MES 2-(N-morpholino)ethanesulfonic acid
Pen/Strep penicillin/streptomycin
PGD2 prostaglandin D2
PGE2 prostaglandin E2
PGF2α prostaglandin F2α
PGI2 prostaglandin I2
TC tissue culture
TP thromboxane A2 receptor
Tris tris(hydroxymethyl)aminomethane
v/v volume to volume ratio (of a solution)
w/w weight to weight ratio (of a solution)

B-1. In Vitro Test of Inhibition of Human FP Receptor Activity

For the characterization of test substances in respect of FP antagonism, PGF2α-induced calcium flux in FP-expressing CHEM1 cells (Millipore, HTS093C) was used.

3000 cells in 30 µl of full medium [DMEM F12, 10% FCS, 1.35 mM sodium pyruvate, 20 mM HEPES, 4 mM GlutaMAX™, 2% sodium bicarbonate, 1% Pen/Strep, 1% 100× non-essential amino acids] are sown per well of a 384 multititre plate (from Greiner, TC plate, black with clear base) and incubated at 33° C., 5% $CO_2$ for 24 hours. Prior to the measurement, the medium is replaced by 30 µl of Fluo-8 AM loading buffer [calcium-free Tyrode (130 mM NaCl, 5 mM KCl, 20 mM HEPES, 1 mM $MgCl_2$, 4.8 mM $NaHCO_3$, pH 7.4), 2 mM $CaCl_2$, 6.3 mM Probenecid, 5 PM Fluo-8 AM, 0.0112% Pluronic®] and incubated at 37° C., 5% $CO_2$ for 30 minutes. The test substance is prepared in DMSO in various concentrations as a dose-response curve (starting concentration 10 mM, dilution factor 3.16) and prediluted 1:50 with calcium-free Tyrode, 2 mM $CaCl_2$, 0.002% SmartBlock (from CANDOR Bioscience GmbH). 10 µl of the prediluted substance solution are added to the Fluo-8-laden cells and incubated at 37° C., 5% $CO_2$ for 10 minutes. The FP receptor is activated by adding 40 µl of 2 nM (final concentration) PGF2α in calcium-free Tyrode, 2 mM $CaCl_2$, 0.002% SmartBlock, and the calcium flux is determined by measuring the fluorescence at ex. 470 nm/em. 525 nm in a fluorescence measuring instrument (FLIPR Tetra®, Molecular Devices) for 120 seconds.

Table 1 below lists the $IC_{50}$ values from this assay for individual working examples of the invention (some as mean values from multiple independent individual determinations):

TABLE 1

| Ex. No. | FP receptor activity $IC_{50}$ [µmol/l] |
|---|---|
| 1 | 0.026 |
| 2 | 0.023 |
| 3 | 0.092 |
| 4 | 0.17 |
| 5 | 0.0094 |
| 6 | 0.0078 |
| 7 | 0.0066 |
| 8 | 0.058 |
| 9 | 0.29 |
| 10 | 0.036 |
| 11 | 0.025 |
| 12 | 0.22 |
| 13 | 0.018 |
| 14 | 0.07 |
| 15 | 0.048 |
| 16 | 0.29 |
| 17 | 0.0041 |
| 18 | 0.08 |
| 19 | 0.13 |
| 20 | 0.49 |
| 21 | 0.23 |
| 22 | 0.0066 |
| 23 | 0.0053 |
| 24 | 0.0049 |
| 25 | 0.022 |
| 26 | 0.021 |
| 27 | 0.014 |
| 28 | 0.031 |
| 29 | 0.022 |
| 30 | 0.0087 |
| 31 | 0.029 |
| 32 | 0.048 |
| 33 | 0.032 |
| 34 | 0.0072 |
| 35 | 0.01 |
| 36 | 0.022 |
| 37 | 0.022 |
| 38 | 0.11 |
| 39 | 0.024 |
| 40 | 0.062 |
| 41 | 0.43 |
| 42 | 0.13 |
| 43 | 0.09 |
| 44 | 0.12 |
| 45 | 0.0047 |
| 46 | 0.0013 |
| 47 | 0.014 |
| 48 | 0.0012 |
| 49 | 0.014 |
| 50 | 0.003 |
| 51 | 0.013 |
| 52 | 0.0071 |
| 53 | 0.0057 |
| 54 | 0.85 |
| 55 | 0.11 |
| 56 | 0.33 |
| 57 | 0.00084 |
| 58 | 0.00052 |
| 59 | 0.011 |
| 60 | 0.0075 |
| 61 | 0.00083 |
| 62 | 0.11 |
| 63 | 0.0073 |
| 64 | 0.0098 |
| 65 | 0.11 |
| 66 | 0.012 |
| 67 | 0.0065 |
| 68 | 0.014 |
| 69 | 0.042 |
| 70 | 0.016 |
| 71 | 0.11 |
| 72 | 0.08 |
| 73 | 0.048 |
| 74 | 0.17 |
| 75 | 0.12 |
| 76 | 0.67 |

TABLE 1-continued

| Ex. No. | FP receptor activity IC$_{50}$ [μmol/l] |
|---|---|
| 77 | 0.066 |
| 78 | 0.0044 |
| 79 | 0.0078 |
| 80 | 0.098 |
| 81 | 0.18 |
| 82 | 0.0039 |
| 83 | 0.0064 |
| 84 | 0.028 |
| 85 | 0.59 |
| 86 | 0.33 |
| 87 | 0.55 |
| 88 | 0.88 |
| 89 | 0.35 |
| 90 | 0.059 |
| 91 | 0.0099 |
| 92 | 0.39 |
| 93 | 0.08 |
| 94 | 0.015 |
| 95 | 0.065 |
| 96 | 0.95 |
| 97 | 0.53 |
| 98 | 0.53 |
| 99 | 0.5 |
| 100 | 0.34 |
| 101 | 0.45 |
| 102 | 0.25 |
| 103 | 0.34 |
| 104 | 0.41 |
| 105 | 0.0054 |
| 106 | 0.004 |
| 107 | 0.005 |
| 108 | 0.36 |
| 109 | 0.86 |
| 110 | 0.024 |
| 111 | 0.0064 |
| 112 | 0.003 |
| 113 | 0.0099 |
| 114 | 0.014 |
| 115 | 0.029 |
| 116 | 0.0046 |
| 117 | 0.016 |
| 118 | 0.0085 |
| 119 | 0.014 |
| 120 | 0.011 |
| 121 | 0.0041 |
| 122 | 0.0067 |
| 123 | 0.013 |
| 124 | 0.0028 |
| 125 | 0.0052 |
| 126 | 0.0017 |
| 127 | 0.00079 |
| 128 | 0.0038 |
| 129 | 0.0061 |
| 130 | 0.0026 |
| 131 | 0.0098 |
| 132 | 0.0031 |
| 133 | 0.002 |
| 134 | 0.0049 |
| 135 | 0.003 |
| 136 | 0.0011 |
| 137 | 0.0038 |
| 138 | 0.003 |
| 139 | 0.0015 |
| 140 | 0.0023 |
| 141 | 0.0058 |
| 142 | 0.0043 |
| 143 | 0.0093 |
| 144 | 0.0022 |
| 145 | 0.0015 |
| 146 | 0.022 |
| 147 | 0.008 |
| 148 | 0.0045 |
| 149 | 0.013 |
| 150 | 0.022 |
| 151 | 0.0013 |
| 152 | 0.00063 |
| 153 | 0.027 |
| 154 | 0.0034 |
| 155 | 0.003 |
| 156 | 0.0025 |
| 157 | 0.0017 |
| 158 | 0.0016 |
| 159 | 0.0031 |
| 160 | 0.0053 |
| 161 | 0.0014 |
| 162 | 0.042 |
| 163 | 0.011 |
| 164 | 0.08 |
| 165 | 0.0029 |
| 166 | 0.0095 |
| 167 | 0.0037 |
| 168 | 0.09 |
| 169 | 0.0091 |
| 170 | 0.0027 |
| 171 | 0.0094 |
| 172 | 0.041 |
| 173 | 0.0022 |
| 174 | 0.011 |
| 175 | 0.16 |
| 176 | 0.0078 |
| 177 | 0.01 |
| 178 | 0.056 |
| 179 | 0.0023 |
| 180 | 0.014 |
| 181 | 0.0066 |
| 182 | 0.0029 |
| 183 | 0.0016 |
| 184 | 0.013 |
| 185 | 0.004 |
| 186 | 0.0086 |
| 187 | 0.024 |
| 188 | 0.0061 |
| 189 | 0.025 |
| 190 | 0.011 |
| 191 | 0.0041 |
| 192 | 0.0056 |
| 193 | 0.00062 |
| 194 | 0.011 |
| 195 | 0.077 |
| 196 | 0.0026 |
| 197 | 0.021 |
| 198 | 0.0037 |
| 199 | 0.0016 |
| 200 | 0.017 |
| 201 | 0.0027 |
| 202 | 0.0017 |
| 203 | 0.011 |
| 204 | 0.0026 |
| 205 | 0.00041 |
| 206 | 0.0095 |
| 207 | 0.022 |
| 208 | 0.0014 |
| 209 | 0.007 |
| 210 | 0.00068 |
| 211 | 0.017 |
| 212 | 0.0019 |
| 213 | 0.01 |
| 214 | 0.021 |
| 215 | 0.0039 |
| 216 | 0.0029 |
| 217 | 0.05 |
| 218 | 0.0012 |
| 219 | 0.029 |
| 220 | 0.00076 |
| 221 | 0.0084 |
| 222 | 0.003 |
| 223 | 0.14 |
| 224 | 0.038 |
| 225 | 0.0032 |
| 226 | 0.0018 |
| 227 | 0.057 |
| 228 | 0.0011 |

TABLE 1-continued

| Ex. No. | FP receptor activity IC$_{50}$ [µmol/l] |
|---|---|
| 229 | 0.013 |
| 230 | 0.012 |
| 231 | 0.039 |
| 232 | 0.018 |
| 233 | 0.084 |
| 234 | 0.0089 |
| 235 | 0.0014 |
| 236 | 0.011 |
| 237 | 0.0043 |
| 238 | 0.044 |
| 239 | 0.0014 |
| 240 | 0.016 |
| 241 | 0.012 |
| 242 | 0.0071 |
| 243 | 0.011 |
| 244 | 0.012 |
| 245 | 0.027 |
| 246 | 0.0031 |
| 247 | 0.055 |
| 248 | 0.12 |
| 249 | 0.0094 |
| 250 | 0.02 |
| 251 | 0.072 |
| 252 | 0.0094 |
| 253 | 0.025 |
| 254 | 0.0028 |
| 255 | 0.02 |
| 256 | 0.0084 |
| 257 | 0.015 |
| 258 | 0.08 |
| 259 | 0.055 |
| 260 | 0.029 |
| 261 | 0.028 |
| 262 | 0.018 |
| 263 | 0.028 |
| 264 | 0.03 |
| 265 | 0.013 |
| 266 | 0.037 |
| 267 | 0.0056 |
| 268 | 0.0031 |
| 269 | 0.0028 |
| 270 | 0.0033 |
| 271 | 0.0063 |
| 272 | 0.00085 |
| 273 | 0.03 |
| 274 | 0.00073 |
| 275 | 0.015 |
| 276 | 0.0097 |
| 277 | 0.034 |
| 278 | 0.034 |
| 279 | 0.011 |
| 280 | 0.0024 |
| 281 | 0.08 |
| 282 | 0.0019 |
| 283 | 0.0066 |
| 284 | 0.011 |
| 285 | 0.0053 |
| 286 | 0.013 |
| 287 | 0.0047 |
| 288 | 0.014 |
| 289 | 0.0024 |

B-2. In Vitro FP Receptor Binding Inhibition Test

For the FP receptor binding test, human recombinant prostanoid FP receptors, expressed in HEK293 cells, in modified MES buffer, pH 6.0, are used. This test is conducted commercially (at Eurofins Panlabs, catalog #268510). 80 µg of membrane are incubated with 1 nM [$^3$H]-PGF2α at 25° C. for 60 minutes. The amount of membrane protein can vary from batch to batch and is adjusted if required. Unspecific binding is determined in the presence of 1 µM cloprostenol. The membranes are filtered, washed and then analysed in order to determine the specific binding of [$^3$H]-PGF2α. Substances are tested for inhibitory activity at a concentration of 10 µM or in the form of a dose-response curve [lit.: Abramovitz et al., *J. Biol. Chem.* 1994, 269 (4): 2632].

B-3. In Vitro CRTH2 Receptor Binding Inhibition Test

For this test, human recombinant prostanoid CRTH2 receptors, expressed in CHO-K1 cells, in modified Tris-HCl buffer, pH 7.4, are used. This test is conducted commercially (at Eurofins Panlabs, catalog #268030). 4 µg of membrane are incubated with 1 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analysed in order to determine the specific binding of [$^3$H]-PGD2. Substances are tested for inhibitory activity at a concentration of 10 µM or in the form of a dose-response curve [lit.: Sugimoto et al., *J. Pharmacol. Exp. Ther.* 2003, 305 (1): 347].

B-4. In Vitro DP Receptor Binding Inhibition Test

For this test, human recombinant prostanoid DP receptors, expressed in Chem-1 cells, in modified HEPES buffer, pH 7.4, are used. This test is conducted commercially (at Eurofins Panlabs, catalog #268060). 10 µg of membrane are incubated with 2 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analysed in order to determine the specific binding of [$^3$H]-PGD2. Substances are tested for inhibitory activity at a concentration of 10 µM or in the form of a dose-response curve [lit.: Wright et al., *Br. J. Pharmacol.* 1998, 123 (7): 1317; Sharif et al., *Br. J. Pharmacol.* 2000, 131 (6): 1025].

B-5. In Vitro EP1 Receptor Binding Inhibition Test

For this test, human recombinant prostanoid EP1 receptors, expressed in HEK293 cells, in modified MES buffer, pH 6.0, are used. This test is conducted commercially (at Eurofins Panlabs, catalog #268110). 14 µg of membrane are incubated with 1 nM [$^3$H]-PGE2 at 25° C. for 60 minutes. The amount of membrane protein can vary from batch to batch and is adjusted if required. Unspecific binding is determined in the presence of 10 µM PGE2. The membranes are filtered, washed and then analysed in order to determine the specific binding of [$^3$H]-PGE2. Substances are tested for inhibitory activity at a concentration of 10 µM or in the form of a dose-response curve [lit.: Abramovitz et al., *Biochim. Biophys. Acta* 2000, 1483 (2): 285; Funk et al., *J. Biol. Chem.* 1993, 268 (35): 26767].

B-6. In Vitro EP2 Receptor Binding Inhibition Test

For this test, human recombinant prostanoid EP2 receptors, expressed in HEK293 cells, in modified MES/KOH buffer, pH 6.0, are used. This test is conducted commercially (at Eurofins Panlabs, catalog #268200). 25 mg/ml of membrane are incubated with 4 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analysed in order to determine the specific binding of [$^3$H]-PGE2. Substances are tested for inhibitory activity at a concentration of 10 µM or in the form of a dose-response curve [lit.: Bastien et al., *J. Biol. Chem.* 1994, 269 (16): 11873; Boie et al., *Eur. J. Pharmacol.* 1997, 340 (2-3): 227].

B-7. In Vitro EP3 Receptor Binding Inhibition Test

For this test, human recombinant prostanoid EP3 receptors, expressed in HEK293 cells, in modified MES buffer, pH 6.0, are used. This test is conducted commercially (at Eurofins Panlabs, catalog #268310). 3 µg of membrane are incubated with 0.5 nM [³H]-PGE2 at 25° C. for 120 minutes. The amount of membrane protein can vary from batch to batch and is adjusted if required. Unspecific binding is determined in the presence of 10 µM PGE2. The membranes are filtered, washed and then analysed in order to determine the specific binding of [³H]-PGE2. Substances are tested for inhibitory activity at a concentration of 10 µM or in the form of a dose-response curve [lit.: Schmidt et al., *Eur. J. Biochem.* 1995, 228 (1): 23].

B-8. In Vitro EP4 Receptor Binding Inhibition Test

For this test, human recombinant prostanoid EP4 receptors, expressed in Chem-1 cells, in modified MES buffer, pH 6.0, are used. This test is conducted commercially (at Eurofins Panlabs, catalog #268420). 3 µg of membrane are incubated with 1 nM [³H]-PGE2 at 25° C. for 120 minutes. The amount of membrane protein can vary from batch to batch and is adjusted if required. Unspecific binding is determined in the presence of 10 µM PGE2. The membranes are filtered, washed and then analysed in order to determine the specific binding of [³H]-PGE2. Substances are tested for inhibitory activity at a concentration of 10 µM or in the form of a dose-response curve [lit.: Davis et al., *Br. J. Pharmacol.* 2000, 130 (8): 1919].

B-9. In Vitro IP Receptor Binding Inhibition Test

For this test, human recombinant prostanoid IP receptors, expressed in HEK293 cells, in modified HEPES buffer, pH 6.0, are used. This test is conducted commercially (at Eurofins Panlabs, catalog #268600). 15 µg of membrane are incubated with 5 nM [³H]-iloprost at 25° C. for 60 minutes. The amount of membrane protein can vary from batch to batch and is adjusted if required. Unspecific binding is determined in the presence of 10 µM iloprost. The membranes are filtered, washed and then analysed in order to determine the specific binding of [³H]-iloprost. Substances are tested for inhibitory activity at a concentration of 10 µM or in the form of a dose-response curve [lit.: Armstrong et al., *Br. J. Pharmacol.* 1989, 97 (3): 657; Boie et al., *J. Biol. Chem.* 1994, 269 (16): 12173].

B-10. In Vitro TP Receptor Binding Inhibition Test

For this test, human recombinant prostanoid TP receptors, expressed in HEK-293 EBNA cells, in modified Tris/HCl buffer, pH 7.4, are used. This test is conducted commercially (at Eurofins Panlabs, catalog #285510). 18.4 µg of membrane are incubated with 5 nM [³H]-SQ-29 548 at 25° C. for 30 minutes. The amount of membrane protein can vary from batch to batch and is adjusted if required. Unspecific binding is determined in the presence of 1 µM SQ-29 548. The membranes are filtered, washed and then analysed in order to determine the specific binding of [³H]-SQ29 548. Substances are tested for inhibitory activity at a concentration of 10 µM or in the form of a dose-response curve [lit.: Saussy Jr. et al., *J. Biol. Chem.* 1986, 261: 3025; Hedberg et al., *J. Pharmacol. Exp. Ther.* 1988, 245: 786].

B-11. In Vitro Test for DP Agonism and Antagonism

For the characterization of test substances in respect of DP agonism and antagonism, PGD2-induced calcium flux in DP-expressing CHEM1 cells (Millipore, HTS091C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of DP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of DP antagonism, the DP receptor is activated in the FLIPR Tetra® by adding 20 µl of ~76 nM (2×$EC_{50}$, final concentration) PGD2 in, for example, calcium-free Tyrode/2 mM $CaCl_2$, and the calcium flux is determined by measuring the fluorescence at ex. 470 nm/em. 525 nm for 120 seconds [lit.: T. Matsuoka et al. (2000) *Science* 287: 2013-2017; S. Narumiya and G. A. Fitzgerald (2001) *J. Clin. Invest.* 108: 25-30].

B-12. In Vitro Test for EP1 Agonism and Antagonism

For the characterization of test substances in respect of EP1 agonism and antagonism, PGE2-induced calcium flux in EP1-expressing CHEM1 cells (Millipore, HTS099C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP1 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP1 antagonism, the EP1 receptor is activated in the FLIPR Tetra® by adding 20 µl of ~6 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: Y. Matsuoka et al. (2005) *Proc. Natl. Acad. Sci. USA* 102: 16066-16071; S. Narumiya and G. A. Fitzgerald (2001) *J. Clin. Invest.* 108: 25-30; K. Watanabe et al. (1999) *Cancer Res.* 59: 5093-5096].

B-13. In Vitro Test for EP2 Agonism and Antagonism

For the characterization of test substances in respect of EP2 agonism and antagonism, PGE2-induced calcium flux in EP2-expressing CHEM9 cells (Millipore, HTS185C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP2 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP2 antagonism, the EP2 receptor is activated in the FLIPR Tetra® by adding 20 µl of −22 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: C. R. Kennedy et al. (1999) *Nat. Med.* 5: 217-220; S. Narumiya and G. A. Fitzgerald (2001) *J. Clin. Invest.* 108: 25-30; N. Yang et al. (2003) *J. Clin. Invest.* 111: 727-735].

B-14. In Vitro Test for EP3 Agonism and Antagonism

For the characterization of test substances in respect of EP3 agonism and antagonism, PGE2-induced calcium flux in EP3 (splice variant 6)-expressing CHEM1 cells (Millipore, HTS092C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP3 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP3 antagonism, the EP3 receptor is activated in the FLIPR Tetra® by adding 20 µl of −2 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: M. Kotani et al. (1995) *Mol. Pharmacol.* 48: 869-879; M. Kotani et al. (1997) *Genomics* 40: 425-434; T. Kunikata et al. (2005) *Nat. Immunol.* 6: 524-531; S. Narumiya and G. A. Fitzgerald (2001) *J. Clin. Invest.* 108: 25-30; F. Ushikubi et al. (1998) *Nature* 395: 281-284].

B-15. In Vitro Test for EP4 Agonism and Antagonism

For the characterization of test substances in respect of EP4 agonism and antagonism, PGE2-induced calcium flux in EP4-expressing CHEM1 cells (Millipore, HTS142C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP4 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP4 antagonism, the EP4 receptor is activated in the FLIPR Tetra® by adding 20 µl of −26 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: S. Narumiya and G. A. Fitzgerald (2001) *J. Clin. Invest.* 108: 25-30; M. Nguyen et al. (1997) *Nature* 390: 78-81; K. Yoshida et al. (2002) *Proc. Natl. Acad. Sci. USA* 99: 4580-4585].

B-16. In Vitro Test for IP Agonism and Antagonism

For the characterization of test substances in respect of IP agonism and antagonism, iloprost-induced calcium flux in IP-expressing CHEM1 cells (Millipore, HTS131C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of IP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of IP antagonism, the IP receptor is activated in the FLIPR Tetra® by adding 20 µl of −106 nM (2×$EC_{50}$, final concentration) iloprost in, for example, calcium-free Tyrode/2 mM $CaCl_2$, and the calcium flux is determined by measuring the fluorescence at ex. 470 nm/em. 525 nm for 120 seconds [lit.: S. Narumiya et al. (1999) *Physiol. Rev.* 79: 1193-1226; T. Murata et al. (1997) *Nature* 388: 678-682; Y. Cheng et al. (2002) *Science* 296: 539-541; C. H. Xiao et al. (2001) *Circulation* 104: 2210-2215; G. A. Fitzgerald (2004) N. Engl. *J. Med.* 351: 1709-1711].

B-17. In Vitro Test for TP Agonism and Antagonism

For the characterization of test substances in respect of TP agonism and antagonism, U46619-induced calcium flux in TP-expressing CHEM1 cells (Millipore, HTS081C) was used: 3000 cells in 25 µl of plating medium [DMEM, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of TP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of TP antagonism, the TP receptor is activated in the FLIPR Tetra® by adding 20 µl of ~88 nM ($2\times EC_{50}$, final concentration) U46619 in, for example, calcium-free Tyrode/2 mM $CaCl_2$, and the calcium flux is determined by measuring the fluorescence at ex. 470 nm/em. 525 nm for 120 seconds [lit.: S. Ali et al. (1993) *J. Biol. Chem.* 268: 17397-17403; K. Hanasaki et al. (1989) *Biochem. Pharmacol.* 38: 2967-2976; M. Hirata et al. (1991) *Nature* 349: 617-620].

B-18. Animal Model of Bleomycin-Induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumours and Hodgkin- and Non-Hodgkin tumours. It is eliminated renally, has a half-life of about 3 hours and, as cytostatic, influences various phases of the division cycle [Lazo et al., *Cancer Chemother. Biol. Response Modif.* 15, 44-50 (1994)]. Its anti-neoplastic effect is based on an oxidatively damaging action on DNA [Hay et al., *Arch. Toxicol.* 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, a bronchio-alveolar lavage to determine the cell content and the pro-inflammatory and pro-fibrotic markers and measurements of lung function and a histological assessment of pulmonary fibrosis are carried out.

B-19. Animal Model of DQ12 Quartz-Induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-12 weeks. At the end of the study, a bronchio-alveolar lavage to determine the cell content and the pro-inflammatory and pro-fibrotic markers and measurements of lung function and a histological assessment of pulmonary fibrosis are carried out.

B-20. Animal Model of DQ12 Quartz-Induced Pulmonary Inflammation

In the mouse and the rat, intratracheal administration of DQ12 quartz leads to an inflammation in the lung [Shimbori et al., *Exp. Lung Res.* 36, 292-301 (2010)]. On the day of the instillation of DQ12 quartz or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchio-alveolar lavage to determine the cell content and the pro-inflammatory and pro-fibrotic markers is carried out.

B-21. Carbon Tetrachloride ($CCl_4$)-Induced Hepatic Fibrosis in Mice

Sixty C57BL/6J mice (Charles River, male, 8 weeks old) were randomized and divided equally into 4 groups (15 mice per group). Group 1 served as the untreated healthy control group, whereas groups 2-4 served as mice suffering from hepatic fibrosis. Hepatic fibrosis was induced by intraperitoneal injection of 50 µl $CCl_4$/olive oil suspension ($CCl_4$+olive oil, 1+9 v/v) three times per week (Monday, Wednesday and Friday) over the entire study period. $CCl_4$ is the oldest and most widely used substance for triggering toxically induced hepatic fibrosis (Starkel and Leclercq, *Best Pract. Res. Clin. Gastroenterol.* 2011, 25, 319-333). The $CCl_4$-treated mice of group 2 served as disease control and did not receive any further treatments, whereas the $CCl_4$-treated mice of group 3 were initially treated with vehicle and hence served as vehicle control. The $CCl_4$-treated mice of group 4 served as group treated with a compound of the formula (I). The oral treatment of group 3 with the vehicle solution and of group 4 with a compound of the formula (I) started on day 1 and was continued twice daily (in the morning and evening) over the complete study period of two weeks. At the end of the study, all animals were sacrificed under anaesthetic, and the livers were removed fixed in 4% buffered formaldehyde solution for the subsequent histological processing and analysis. For this purpose, liver samples for all animals were embedded in paraffin and 3 µm-thick paraffin sections were produced. Thereafter, all the sections were deparaffinized and stained with Picro-Sirius Red (Waldeck, Germany) to determine the liver fibrosis. Picro-Sirius Red staining is a histological technique for staining of collagen in tissue and hence of fibrosis. A Carl Zeiss microscope (Axio Observer) connected to a computer was used to scan the Picro-Sirius Red-stained liver sections for production of corresponding images. The sections were scanned with 20× enlargement and a light intensity of 4.8 V. The images thus produced were then converted to JPG format, and the red-stained area was quantified by means of ImageJ software (National Institute of Health, USA). The results are reported in % Sirius red per unit area.

The treatment with the compound from Example 284 led to a significant reduction in the progression of fibrosis (p<0.01; two-way ANOVA statistical analysis with Dunnett post-hoc test, mean±SD) in a 2-week study in mice with hepatic fibrosis (see Table 2).

TABLE 2

| Group | | Sirius red [% liver area] |
|---|---|---|
| 1 | Healthy control | 1.64 ± 0.34 |
| 2 | Untreated control (CCl4) | 4.37 ± 0.68 |
| 3 | Vehicle control (CCl4 + vehicle) | 4.29 ± 0.87 |
| 4 | Treated (CCl4 + 100 mg/kg Ex. 284) | 3.51 ± 0.65 |

B-22. Animal Model of Unilateral Ureteral Obstruction (UUO) in Mice (Renal Fibrosis)

Unilateral ureteral obstruction in mice and rats is a widely used animal model for interstitial renal fibrosis (Chevalier et al., Kidney Int. 2009, 75, 1145-1152). Permanent occlusion of the ureter leads, as a result of the sustained accumulation of the urine, to increased inflammatory cell infiltration into the interstitium, to tubular cell death and to irreversible loss of the renal parenchyma. After 5 to 7 days, owing to the elevated deposition of extracellular matrix proteins, interstitial fibrosis arises. Adult male C57Bl6J mice (Charles River Laboratories, Sulzfeld, Germany) having a weight of 20-22 g were anaesthetized with isoflurane, then, after opening up the abdominal cavity, a ureter was ligated and severed beneath the ligature. In the sham-operated control mice (SHAM), the abdominal cavity was merely opened up, but the ureter was not ligated. The treatment of the animals in the substance groups with the compound from Example 284 (10 and 30 mg/kg per os (po) twice daily (bid)) was commenced after the operation and continued for a further 10 days. 10 days after the UUO, the animals were anaesthetized and sacrificed by exsanguination. Thereafter, the kidneys were removed and renal fibrosis was assessed on the basis of the expression of pro-inflammatory and pro-fibrotic markers, and a histological assessment of the renal tissue. The results are shown in Tables 3 and 4.

UUO led to elevated gene expression of pro-inflammatory and pro-fibrotic genes (e.g.: αSMA, collagens, TGF-b, KC, MCP-1) in the obstructed kidneys. The treatment with the substance led to a dose-dependent reduction in the expression of SMA, Col1α1, Col4α1, TGF-1 and KC. The gene expression of Col3α1, CTGF, MCP-1, IL-6 and IL1-β was not affected by the treatment.

Histological staining showed an elevated αSMA and collagen (SR/FG) content in the UUO kidneys compared to SHAM-operated mice. The treatment with 60 [mg/kg] of the substance led to a significant reduction in the αSMA-positive area. The collagen content of the obstructed kidneys was not affected by the treatment.

B-23. Silica-Induced Pulmonary Fibrosis in Mice: Therapeutic Chronic 30-Day Study with FP Antagonists Adult female C57Bl6J mice (Charles River Laboratories, Sulzfeld, Germany) having a weight of 18-20 g were anaesthetized in a chamber with isoflurane (3% v/v) and treated intratracheally with 2.5 mg of crystalline DQ12 silica dissolved in 70 µL of sterile phosphate-buffered saline. Untreated control mice received the same volume of phosphate-buffered saline. On day 10 after the silica treatment, the animals in the substance groups were treated with the compound from Example 35 (10 and 30 mg/kg per os (po) twice daily (bid)) for 20 days. 30 days after the installation of silica, the animals were anaesthetized with an intraperitoneal injection of ketamine/medetomidine (50 mg/kg and

TABLE 3

Gene expression of proinflammatory and profibrotic markers in untreated and treated animals.

| Marker | SHAM | Placebo | Ex. 284 30 [mg/kg] | Ex. 284 60 [mg/kg] |
|---|---|---|---|---|
| αSMA | 18.71 ± 2.91 | 100.00 ± 38.62 | 72.97 ± 39.94 | 51.72 ± 21.33 |
| Col1α1 | 5.04 ± 0.83 | 100.00 ± 26.21 | 76.70 ± 36.22 | 38.90 ± 13.11 |
| Col3α1 | 4.82 ± 0.91 | 100.00 ± 18.34 | 103.74 ± 37.60 | 126.15 ± 46.51 |
| Col4α1 | 24.66 ± 1.56 | 100.00 ± 19.04 | 71.15 ± 20.20 | 45.97 ± 8.44 |
| CTGF | 16.43 ± 14.32 | 100.00 ± 27.67 | 105.67 ± 52.33 | 102.07 ± 26.99 |
| TGF-β | 21.68 ± 1.48 | 100.00 ± 23.90 | 67.57 ± 32.67 | 31.79 ± 9.06 |
| KC | 1.97 ± 0.31 | 100.00 ± 24.38 | 65.02 ± 15.98 | 50.69 ± 22.02 |
| MCP-1 | 3.40 ± 0.75 | 100.00 ± 35.65 | 93.98 ± 26.32 | 117.41 ± 38.15 |
| IL-6 | 0.52 ± 0.17 | 100.00 ± 141.69 | 207.04 ± 389.13 | 494.83 ± 850.76 |
| IL1-β | 8.62 ± 1.23 | 100.00 ± 51.64 | 81.91 ± 31.93 | 112.05 ± 71.38 | n = 10 animals/group. Averages ± SD. The gene expression values for the placebo group were set to 100%; the expressions for the other groups were calculated as the percentage by comparison with placebo group. αSMA = alpha smooth muscle actin; Col1α1 = alpha-1 type I collagen; Col3α1 = alpha-1 type III collagen; Col4α1 = alpha-1 type IV collagen; CTGF = connective tissue growth factor; TGF-β = transforming growth factor-β; KC = keratinocyte chemoattractant; MCP-1 = monocyte chemotactic protein 1; IL-6 = interleukin-6; IL1-β = interleukin-1β; SHAM = sham-operated control

TABLE 4

Immunohistochemically detectable αSMA staining and the histochemical staining of collagens (SR/FG)

| Marker | SHAM | Placebo | Ex. 284 30 [mg/kg] | Ex. 284 60 [mg/kg] |
|---|---|---|---|---|
| αSMA positive area [%] | 3.63 ± 0.62 | 29.03 ± 3.90 | 25.19 ± 3.23 | 22.28 ± 4.04 |
| SR/FG positive area [%] | 16.34 ± 3.64 | 40.01 ± 4.90 | 38.74 ± 9.12 | 34.66 ± 7.59 | n = 10 animals/group. Averages ± SD
αSMA = alpha smooth muscle actin; SR/FG = SiriusRed/FastGreen; SHAM = sham-operated control 0.33 mg/kg) combined with a subcutaneous injection of Temgesic (0.06 mg/kg) and sacrifice by exsanguination. Thereafter, the trachea was cannulated, and the animals' lungs were lavaged three times with 0.5 ml of ice-cold phosphate-buffered saline. Thereafter, the lungs were removed, weighed and shock-frozen in dry ice. After homogenization of the lung tissue, hydroxyproline was determined by means of HPLC [Paroni et al., Clin. Chem. 1992, 38, 407-411; column: Phenomenex Synergi Hydro RP 4 µm 80 A, 75×4.6 mm; gradient: eluent A: water (6 ml/l triethylamine, 3 ml/l acetic acid) pH 4.3; solvent B: acetonitrile; flow rate: 1.3 ml/min). The data are mean values±SEM of 8-12 animals per group. The statistical analysis was conducted with the unpaired Student's t test. P values<0.05 were considered to be significant. The results are shown in table 5.

TABLE 5

| Group | Hydroxyproline [ng/lung] |
|---|---|
| Healthy control | 1678 ± 60.49 (n = 8) |
| Silica-treated control | 2631 ± 85.31 (n = 12) |
| Silica + 10 mg/kg po bid of Ex. 284 | 2341 ± 54.99 (n = 12) |
| Silica + 30 mg/kg po bid of Ex. 284 | 2185 ± 86.79 (n = 12) |

The silica treatment, by comparison with the untreated control group, led to a significant increase in hydroxyproline, a marker of collagen accumulation and fibrosis in the lungs of the silica-treated animals. The treatment with the compound from Ex. 35 (10 and 30 mg/kg po bid) led to a significant reduction in the hydroxyproline formation and fibrosis in the treatment groups by comparison with the silica-treated control.

B-24. Effects of FP Antagonists on Mechanical Sensitivity (Peripheral, Mouse)

Mechanical allodynia is examined using the von Frey test on the injected and uninjected rear paws several times after the injection.

Mechanical allodynia is measured with 8 Semmes-Weinstein filaments (Stölting©; Wood Dale, Ill., USA) having different stiffness (0.04; 0.07; 0.16; 0.4; 1.0. 4.0 and 8.0 g) by the up-down method (Chaplan et al., *J. Neurosci. Meth.* 1994, 53, 56-63). Intact male ND4 mice (~30 g, 10 animals per group) are placed in individual acrylic chambers on a metal grid surface, and were allowed to get used to their environment for at least 15 minutes before the testing. Each filament is pressed with sufficient force at right angles to the underside of the paw, in order to cause slight bending against the paw, and is held for about 6 seconds or until a positive response is registered (paw quickly withdrawn). The testing is commenced with the 0.4 g filament. If the paw is not withdrawn, the next strongest stimulus is used. In the case that the paw is withdrawn, the next weakest stimulus is used. This process is repeated until up to 4 responses have been obtained after the initial change in response (no response after positive response or positive response after no response). If the animal does not react after the strongest filament has been reached or the animal reacts after the weakest filament has been reached, the test is stopped for this time point. The 50% paw response threshold is calculated using the following formula:

$$50\% \text{ Paw Response Threshold } (g) = \frac{10^{(Xf+k\delta)}}{10\,000}$$

Xf=value (in logarithmic units) of the last von Frey filament used k=table value for the pattern of positive/negative responses (see Chaplan et al., *J. Neurosci. Meth.* 1994, 53, 56-63, Annex 1, page 62)

δ=average difference (in logarithmic units) between the stimuli

The mean and standard deviation of the measurement value (SEM) is determined for each paw for each treatment group at each time point.

Group Design

| No. | Treatment | Dose (mg/kg) | Dose volume | Vehicle | Admin. | Day of treatment/frequency |
|---|---|---|---|---|---|---|
| 1 | fluprostenol | ~0.15 | 20 μL | 10% DMSO in PBS | IPL | Day 0, T = 0 |
|   | Vehicle | / | 5 mL/kg | DMSO/PEG400/H₂O (10/60/30) | PO | 3×, T = −2, 8, 22 h |
| 2 | fluprostenol | ~0.15 | 20 μL | 10% DMSO in PBS | IPL | Day 0, T = 0 |
|   | Test substance | tbd | 5 mL/kg | DMSO/PEG400/H₂O (10/60/30) | PO | 3×, T = −2, 8, 22 h |
| 3 | fluprostenol | ~1.5 | 20 μL | 10% DMSO in PBS | IPL | Day 0, T = 0 |
|   | Vehicle | / | 5 mL/kg | DMSO/PEG400/H₂O (10/60/30) | PO | 3×, T = −2, 8, 22 h |
| 4 | fluprostenol | ~1.5 | 20 μL | 10% DMSO in PBS | IPL | Day 0, T = 0 |
|   | Test substance | tbd | 5 mL/kg | DMSO/PEG400/H2O (10/60/30) | PO | 3×, T = −2, 8, 22 h |

IPL: intraplantary; PO: per os

In order to assess the analgesic effect of an FP antagonist on fluprostenol-induced mechanical sensitivity, the test substance is administered 2 hours before and 8 and 22 hours after the injection of fluprostenol. Ipsilateral and contralateral 50% paw response thresholds are examined prior to the administration of fluprostenol and 0.5, 2, 6 and 24 h after the administration.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. Compound of formula (I)

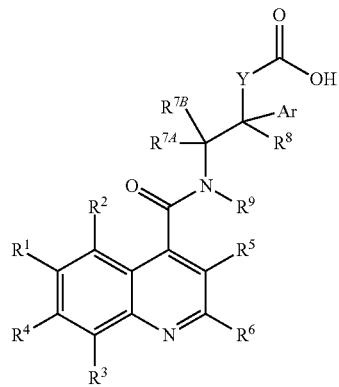

in which

Ar is phenyl or is pyridyl,
where phenyl may be up to tetrasubstituted and pyridyl up to disubstituted, in each case identically or differently, by fluorine, chlorine, by up to tri-fluorine-substituted ($C_1$-$C_4$)-alkyl, up to tetra-fluorine-substituted ($C_3$-$C_4$)-cycloalkyl, up to tri-fluorine-substituted ($C_1$-$C_2$)-alkoxy, or up to tri-fluorine-substituted ($C_1$-$C_2$)-alkylsulfanyl, or where two substituents of the phenyl or pyridyl group, if they are bonded to adjacent ring atoms, are optionally bonded to one another in such a way that they together form a methylenedioxy or ethylenedioxy group,
or
where phenyl may be up to pentasubstituted by fluorine, Y is a bond or a group of the formula $\#^1$—X—$(CR^{10A}R^{10B})_k$—$\#^2$ where
$\#^1$ is the attachment site to the carbon atom,
$\#^2$ is the attachment site to the carboxyl group, X is a bond, $CH_2$, —O—, —S(=O)$_m$— or —N($R^{11}$)—, in which
m is 0, 1 or 2 and
$R^{11}$ is hydrogen or methyl,
$R^{10A}$ and $R^{10B}$ are independently hydrogen, fluorine or methyl,
or
$R^{10A}$ and $R^{10B}$ together with the carbon atom to which they are bonded form a cyclopropyl group,
k is 1, 2, 3 or 4,
$R^1$ is halogen, up to penta-fluorine-substituted ($C_1$-$C_4$)-alkyl, up to tri-fluorine-substituted methoxy, (trifluoromethyl)sulfanyl, pentafluorosulfanyl, trimethylsilyl, ethynyl, cyclopropyl or cyclobutyl,
where cyclopropyl and cyclobutyl may be up to tetrasubstituted by fluorine,
$R^2$, $R^3$ and $R^4$ are independently hydrogen, halogen or up to tri-fluorine-substituted methyl,
$R^5$ is halogen, up to penta-fluorine-substituted ($C_1$-$C_4$)-alkyl, up to tri-fluorine-substituted methoxy, hydroxyl, methylsulfanyl, (trifluoromethyl)sulfanyl, cyano, ethenyl, cyclopropyl or cyclobutyl,
where cyclopropyl and cyclobutyl may be up to tetrasubstituted by fluorine,
$R^6$ is —$NR^{12}R^{13}$
in which
$R^{12}$ is hydrogen or ($C_1$-$C_3$)-alkyl, and
$R^{13}$ is ($C_1$-$C_4$)-alkyl or ($C_3$-$C_7$)-cycloalkyl,
in which ($C_3$-$C_7$)-cycloalkyl may be up to tetrasubstituted by fluorine and ($C_1$-$C_4$)-alkyl may be up to pentasubstituted by fluorine or monosubstituted by (C3-C6)-cycloalkyl, methoxy, trifluoromethoxy or phenyl,
in which phenyl may be up to trisubstituted by fluorine,
or
is a saturated or partially unsaturated, 4- to 8-membered monocyclic or 6- to 10-membered bicyclic heterocycle which is attached via a nitrogen atom and may contain one further, identical or different heteroatom from the group consisting of N, O, S, SO and $SO_2$ as ring member,
where the 4- to 8-membered monocyclic and 6- to 10-membered bicyclic heterocycle may each be substituted by 1 to 3 substituents independently selected from the group consisting of ($C_1$-$C_4$)-alkyl, hydroxyl, oxo, ($C_1$-$C_3$)-alkoxy, difluoromethoxy, trifluoromethoxy, cyano, amino, monomethylamino, dimethylamino, aminocarbonyl, monomethylaminocarbonyl, dimethylaminocarbonyl, and additionally up to tetrasubstituted by fluorine,
in which ($C_1$-$C_4$)-alkyl may be up to pentasubstituted by fluorine or monosubstituted by hydroxyl or methoxy,
$R^{7A}$ and $R^{7B}$ are independently hydrogen or methyl,
or
$R^{7A}$ and $R^{7B}$ together with the carbon atom to which they are bonded form a cyclopropyl group,
$R^8$ is hydrogen, fluorine, methyl, trifluoromethyl, ethyl or hydroxyl,
$R^9$ is hydrogen or methyl,
and/or an N-oxide, salt, solvate, salt of an N-oxide and/or a solvate of an N-oxide and/or salt thereof.

2. Compound of formula (I) according to claim 1 in which
Ar is phenyl,
where phenyl may be up to tetrasubstituted by fluorine or up to trisubstituted, identically or differently, by fluorine, chlorine, methyl, trifluoromethyl, difluoromethyl, methoxy, difluoromethoxy or trifluoromethoxy, Y is a bond or a group of the formula $\#^1-(CH_2)_n-\#^2$ where
$\#^1$ is the attachment site to the carbon atom,
$\#^2$ is the attachment site to the carboxyl group,
n is 1, 2 or 3,
$R^1$ is bromine or ethynyl,
$R^2$, $R^3$ and $R^4$ are each hydrogen,
$R^5$ is chlorine or methyl,
and
$R^6$ is $-NR^{12}R^{13}$
in which
$R^{12}$ is hydrogen or methyl, and
$R^{13}$ is (C1-C4)-alkyl,
  in which (C1-C4)-alkyl may be up to trisubstituted by fluorine or monosubstituted by phenyl,
or
is a saturated or partially unsaturated, 5- to 7-membered monocyclic or 7- to 10-membered bicyclic heterocycle which is attached via a nitrogen atom and may contain one further, identical or different heteroatom from the group consisting of N, O and S as ring member,
where the 5- to 7-membered monocyclic and 7- to 10-membered bicyclic heterocycle may each be substituted by 1 or 2 substituents independently selected from the group consisting of methyl, difluoromethyl, trifluoromethyl, ethyl, 2,2,2-trifluoroethyl, 2,2-difluoroethyl, isopropyl, and additionally up to tetrasubstituted by fluorine,
$R^{7A}$, $R^{7B}$, $R^8$ and $R^9$ are each hydrogen,
and/or a salt, solvate and/or solvate of a salt thereof.

3. Compound of formula (I) according to claim 1 in which
Ar is phenyl,
  where phenyl may be up to trisubstituted, identically or differently, by fluorine, chlorine, methyl, trifluoromethyl, difluoromethoxy or trifluoromethoxy,
Y is a group of the formula $\#^1-CH_2CH_2-\#^2$ where
$\#^1$ is the attachment site to the carbon atom,
$\#^2$ is the attachment site to the carboxyl group,
$R^1$ is bromine,
$R^2$, $R^3$, $R^4$ are each hydrogen,
$R^5$ is methyl,
$R^6$ is a group of the formula

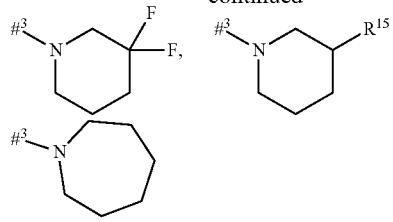

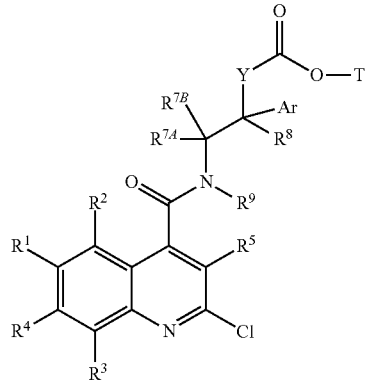

where
$\#^3$ is the attachment site to the rest of the molecule,
$R^{14}$ is fluorine or methyl,
$R^{15}$ is fluorine, methyl or ethyl,
$R^{7A}$, $R^{7B}$, $R^8$ and $R^9$ are each hydrogen,
and/or a salt, solvate and/or solvate of a salt thereof.

4. Process for preparing a compound of formula (I) as defined in claim 1, comprising
[A] reacting a compound of formula (II)

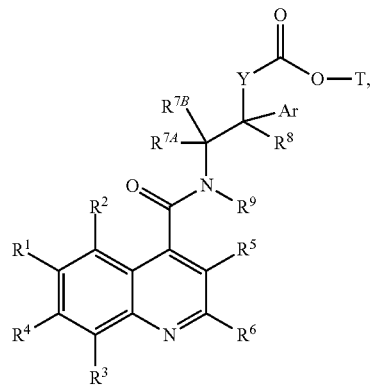

(II)

in which
T is an ester protecting group,
with an amine compound of formula (III)

$R^6-H$      (III), to obtain a compound of formula (IV)

(IV)

and

[B] detaching the ester radical T of the compound of formula (IV)

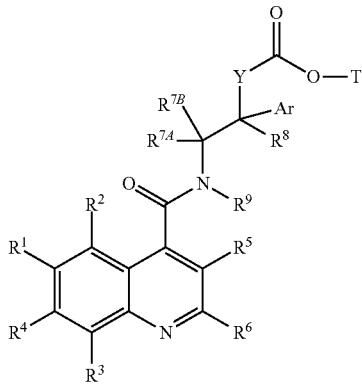

(IV)

in which
T is an ester protecting group,
to obtain the compound of formula (I)

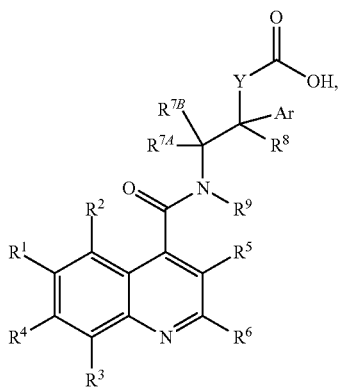

(I)

wherein the compound of formula (I) is optionally separated into enantiomers and/or diastereomers and/or converted with one or more appropriate (i) solvents and/or (ii) bases or acids to a solvate, salt and/or solvate of a salt thereof.

5. Compound as defined in claim 1 for treatment and/or prevention of diseases.

6. Compound as defined in claim 1 for use in a method for treatment and/or prevention of idiopathic pulmonary fibrosis, pulmonary hypertension, bronchiolitis obliterans syndrome, inflammatory and fibrotic skin and eye disorders and fibrotic disorders of the internal organs.

7. A product comprising a compound as defined in claim 1 for production of a medicament for treatment and/or prevention of idiopathic pulmonary fibrosis, pulmonary hypertension, bronchiolitis obliterans syndrome, inflammatory and fibrotic skin and eye disorders and fibrotic disorders of the internal organs.

8. Medicament comprising a compound as defined in claim 1 in combination with one or more inert, nontoxic, pharmaceutically suitable excipients.

9. Medicament comprising a compound as defined in claim 1 in combination with one or more further active ingredients selected from the group consisting of PDE 5 inhibitors, sGC activators, sGC stimulators, prostacyclin analogues, IP receptor agonists, endothelin antagonists, compounds that inhibit the signal transduction cascade and pirfenidone.

10. Medicament as claimed in claim 8 for treatment and/or prevention of idiopathic pulmonary fibrosis, pulmonary hypertension, bronchiolitis obliterans syndrome, inflammatory and fibrotic skin and eye disorders and fibrotic disorders of the internal organs.

11. Method for treatment and/or prevention of idiopathic pulmonary fibrosis, pulmonary hypertension, bronchiolitis obliterans syndrome, inflammatory and fibrotic skin and eye disorders and fibrotic disorders of the internal organs in humans and animals, said method comprising administering an effective amount of at least one compound as defined in claim 1.

12. The process for preparing a compound of formula (I) as defined in claim 4, wherein
T is $(C_1-C_4)$-alkyl.

* * * * *